United States Patent
Pierce et al.

(10) Patent No.: US 7,279,469 B2
(45) Date of Patent: Oct. 9, 2007

(54) DIAMINOTRIAZOLES USEFUL AS INHIBITORS OF PROTEIN KINASES

(75) Inventors: Albert C. Pierce, Cambridge, MA (US); Michael Amost, North Andover, MA (US); Robert J. Davies, Arlington, MA (US); Cornelia J. Forster, Pelham, NH (US); Vincent Galullo, South Grafton, MA (US); Ronald Grey, Jr., Cambridge, MA (US); Mark Ledeboer, Acton, MA (US); Shi-Kai Tian, Waltham, MA (US); Jinwang Xu, Framingham, MA (US); Hayley Binch, Harwell (GB); Brian Ledford, Attleboro, MA (US); David Messersmith, Somerville, MA (US); Suganthi Nanthakumar, Newton, MA (US); Andrew Jayaraj, Needham, MA (US); Greg Henkel, Carlsbad, CA (US); Francesco G. Salituro, Marlboro, MA (US); Jian Wang, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 206 days.

(21) Appl. No.: 10/715,111

(22) Filed: Nov. 17, 2003

(65) Prior Publication Data

US 2004/0214817 A1    Oct. 28, 2004

Related U.S. Application Data

(60) Provisional application No. 60/447,705, filed on Feb. 11, 2003, provisional application No. 60/426,681, filed on Nov. 15, 2002.

(51) Int. Cl.
| | |
|---|---|
| A61K 31/541 | (2006.01) |
| A61K 31/55 | (2006.01) |
| A61K 31/4196 | (2006.01) |
| A61K 31/5377 | (2006.01) |
| C07D 417/02 | (2006.01) |
| C07D 413/02 | (2006.01) |

(52) U.S. Cl. .............................. 514/217.09; 514/227.5; 514/235.8; 514/254.05; 514/326; 514/383; 544/60; 544/132; 544/366; 546/208; 548/264.8

(58) Field of Classification Search ............. 548/265.2, 548/266.2; 546/272.4; 544/124, 132; 514/383
See application file for complete search history.

(56) References Cited

U.S. PATENT DOCUMENTS

| 3,041,339 A * | 6/1962 | Tsujikawa et al. .......... 544/320 |
| 6,492,383 B1 * | 12/2002 | Munchhof et al. .......... 514/301 |
| 6,784,195 B2 * | 8/2004 | Hale et al. ................. 514/341 |

FOREIGN PATENT DOCUMENTS

| WO | WO 00/10563 A1 | 3/2000 |
| WO | WO 02/057240 A1 | 7/2002 |
| WO | WO 02/094814 A1 | 11/2002 |

OTHER PUBLICATIONS

Fromm et al. Ann., (1908), 356, 178-96. (STN search report included).*
STN search report of WO 9924440, Munchhoff et al.*
STN search report of U.S. Patent 3,041,339, Shirakawa et al.*

* cited by examiner

Primary Examiner—Kamal A. Saeed
Assistant Examiner—Yong Chu
(74) Attorney, Agent, or Firm—Daniel A. Pearson

(57) ABSTRACT

The present invention relates to inhibitors of protein kinases. The invention also provides pharmaceutical compositions comprising the compounds of the invention and methods of using the compositions in the treatment of various disorders.

15 Claims, No Drawings

DIAMINOTRIAZOLES USEFUL AS INHIBITORS OF PROTEIN KINASES

CROSS-REFERENCE TO RELATED APPLICATIONS

The present application claims priority under 35 U.S.C. §119 to U.S. Provisional Application No. 60/426,681, filed Nov. 15, 2002, entitled "Compositions Useful as Inhibitors of Protein Kinases, and 60/447,705, filed Feb. 11, 2003, entitled "Compositions Useful as Inhibitors of Protein Kinases", and the entire contents of each of these applications is hereby incorporated by reference.

TECHNICAL FIELD OF THE INVENTION

The present invention relates to inhibitors of protein kinases. The invention also provides pharmaceutical compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

A family of type III receptor tyrosine kinases including Flt3, c-Kit, PDGF-receptor and c-Fms play an important role in the maintenance, growth and development of hematopoietic and non-hematopoietic cells. [Scheijen, B, Griffin J D, *Oncogene*, 2002, 21, 3314-3333 and Reilly, J T, *British Journal of Haematology*, 2002, 116, 744-757]. FLT-3 and c-Kit regulate maintenance of stem cell/early progenitor pools as well the development of mature lymphoid and myeloid cells [Lyman, S, Jacobsen, S, *Blood*, 1998, 91, 1101-1134]. Both receptors contain an intrinsic kinase domain that is activated upon ligand-mediated dimerization of the receptors. Upon activation, the kinase domain induces autophosphorylation of the receptor as well as the phosphorylation of various cytoplasmic proteins that help propogate the activation signal leading to growth, differentiation and survival. Some of the downstream regulators of FLT-3 and c-Kit receptor signaling include, PLCγ, P13-kinase, Grb-2, SHIP and Src related kinases [Scheijen, B, Griffin J D, *Oncogene*, 2002, 21, 3314-3333]. Both receptor tyrosine kinases have been shown to play a role in a variety of hematopoietic and non-hematopoietic malignancies. Mutations that induce ligand independent activation of FLT-3 and c-Kit have been implicated acute-myelogenous leukemia (AML), acute lymphocytic leukemia (ALL), mastocytosis and gastrointestinal stromal tumor (GIST). These mutations include single amino acid changes in the kinase domain or internal tandem duplications, point mutations or in-frame deletions of the juxtamembrane region of the receptors. In addition to activating mutations, ligand dependent (autocrine or paracrine) stimulation of over-expressed wild-type FLT-3 or c-Kit can contribute to the malignant phenotype [Scheijen, B, Griffin J D, *Oncogene*, 2002, 21, 3314-3333].

c-fms encodes for macrophage colony stimulating factor receptor (M-CSF-1R) which is expressed predominately in the monocytes/macrophage lineage [Dai, X M et al., *Blood*, 2002, 99, 111-120]. MCSF-1R and its ligand regulate macrophage lineage growth and differentiation. Like the other family members, MCSF-1R contains an intrinsic kinase domain that is activated upon ligand-induced dimerization of the receptor. MCSF-1R is is also expressed in non-hematopoietic cells including mammary gland epithelial cells and neurons. Mutations in this receptor are potentially linked to myeloid leukemias and its expression is correlated with metastatic breast, ovarian and endometrial carcinomas [Reilly, J T, *British Journal of Haematology*, 2002, 116, 744-757 and Kacinski, B M, *Mol. Reprod and Devel.*, 1997, 46, 71-74]. Another possible indication for antagonists of MCSF-1R is osteoporosis [Teitelbaum, S, *Science* 2000, 289, 1504-1508.

PDGF-receptor (PDGFR) has two subunits—PDGFR-α and PDGRR-β, which can form homo or heterodimers upon ligand binding. There are several PDGF ligands: AB, BB, CC and DD. PDGFR is expressed on early stem cells, mast cells, myeloid cells, mesenchymal cells and smooth muscle cells [Scheijen, B, Griffin J D, *Oncogene*, 2002, 21, 3314-3333]. Only PDGFR-β has been implicated in myeloid leukemias—usually as a translocation partner with Tel, Huntingtin interacting protein (HIP1) or Rabaptin5. Recently it was shown that activation mutations in PDGFR-α kinase domain are in gastrointestinal stromal tumors (GIST) [Heinrich, M C et al., *Sciencexpress,* 2003]

Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active [Meijer, L., *Drug Resistance Updates* 2000, 3, 83-88].

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases [Nigg, E., *Nature Reviews* 2001, 2, 21-32; Flatt, P., Pietenpol, J., *Drug Metabolism Reviews* 2000, 32, 283-305].

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas [Flatt, P., Pietenpol, J., *Drug Metabolism Reviews* 2000, 32, 283-305]. The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy [Kaubisch, A., Schwartz, G., *The Cancer Journal* 2000, 6, 192-212].

CDKs, especially CDK2, also play a role in apoptosis and T-cell development. CDK2 has been identified as a key regulator of thymocyte apoptosis [Williams, O., et al, *European Journal of Immunology* 2000, 709-713]. Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegakovirus, herpes virus, and varicella-zoster virus [Meijer, L., *Drug Resistance Updates* 2000, 3, 83-88].

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 [Meijer, L., *Drug Resistance Updates,* 2000 3, 83-88].

Another kinase family of particular interest is the Src family of kinases. These kinases are implicated in cancer, immune system dysfunction and bone remodeling diseases. For general reviews, see Thomas and Brugge, *Annu. Rev. Cell Dev. Biol.* 1997, 13, 513; Lawrence and Niu, *Pharmacol. Ther.* 1998, 77, 81; Tatosyan and Mizenina, *Biochemistry* (Moscow) 2000, 65, 49; Boschelli et al., *Drugs of the Future* 2000, 25(7), 717, (2000).

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. *Biochemistry* (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., *Cell* 1992, 69, 551 and Soriano et al., *Cell* 1991, 64, 693.

Suppression of arthritic bone destruction has been achieved by the overexpression of CSK in rheumatoid synoviocytes and osteoclasts. Takayanagi et al., *J. Clin. Invest.* 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., *Drugs of the Future* 2000, 25(7), 717.

Src also plays a role in the replication of hepatitis B virus. The virally encoded transcription factor HBx activates Src in a step required for propagation of the virus. Klein et al., *EMBO J.* 1999, 18, 5019, and Klein et al., *Mol. Cell. Biol.* 1997, 17, 6427.

A number of studies have linked Src expression to cancers such as colon, breast, hepatic and pancreatic cancer, certain B-cell leukemias and lymphomas. Talamonti et al., *J. Clin. Invest.* 1993, 91, 53; Lutz et al., *Biochem. Biophys. Res.* 1998 243, 503; Rosen et al., *J. Biol. Chem.* 1986, 261, 13754; Bolen et al., *Proc. Natl. Acad. Sci. USA* 1987, 84, 2251; Masaki et al., *Hepatology* 1998, 27, 1257; Biscardi et al., *Adv. Cancer Res.* 1999, 76, 61; Lynch et al., *Leukemia,* 1993, 7, 1416. Furthermore, antisense Src expressed in ovarian and colon tumor cells has been shown to inhibit tumor growth. Wiener et al., *Clin. Cancer Res.,* 1999, 5, 2164; Staley et al., *Cell Growth Diff.,* 1997, 8, 269.

Other Src family kinases are also potential therapeutic targets. Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis. Molina et al., *Nature,* 1992, 357, 161. Hck, Fgr and Lyn have been identified as important mediators of integrin signaling in myeloid leukocytes. Lowell et al., *J. Leukoc. Biol.,* 1999, 65, 313. Inhibition of these kinase mediators may therefore be useful for treating inflammation. Boschelli et al., *Drugs of the Future* 2000, 25(7), 717.

Syk is a tyrosine kinase that plays a critical role in FcεRI mediated mast cell degranulation and eosiniphil activation. Accordingly, Syk kinase is implicated in various allergic disorders, in particular asthma. It has been shown that Syk binds to the phosphorylated gamma chain of the FcγRI receptor via N-terminal SH2 domains and is essential for downstream signaling [Taylor et al, *Mol. Cell. Biol.* 1995, 15, 4149].

Inhibition of eosinophil apoptosis has been proposed as key mechanisms for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al, *J Exp Med* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al, *Mol Cell Biol* 1998, 18, 4209]. It has also been reported that aerosolized Syk antisense suppresses Syk expression and mediator release from macrophages [Stenton et al, *J Immunology* 2000, 164, 3790].

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [*Frank Mol. Med.* 5, 432-456 (1999) & Seidel, et al, *Oncogene* 19, 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain ($\gamma_c$) and is activated by IL-2, IL-4, IL-7, IL-9, and IL-15. The proliferation and survival of murine mast cells induced by IL-4 and IL-9 have, in fact, been shown to be dependent on JAK3- and $\gamma_c$-signaling [Suzuki et al, *Blood* 96, 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, *Nature* 346, 274-276 (1990) & Galli, *N. Engl. J. Med.,* 328, 257-265 (1993)]. A crucial role for JAK3 in IgE receptor-mediated mast cell responses in vitro and in vivo has been established [Malaviya, et al, *Biochem. Biophys. Res. Commun.* 257, 807-813 (1999)]. In addition, the prevention of type I hypersensitivity reactions, including anaphylaxis, mediated by mast cell-activation through inhibition of JAK3 has also been reported [Malaviya et al, *J. Biol. Chem.* 274, 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, *Transpl. Proc.* 33, 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus Kinases (JAK 1 & 3) and that IL-4-associated JAK kinases are expressed in the RA synovium [Muller-Ladner, et al, *J. Immunol.* 164, 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This suggested that JAK3 plays a role in FALS [Trieu, et al, *Biochem. Biophys. Res. Commun.* 267, 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, *Clin. Cancer Res.* 5, 1569-1582 (1999)]. JAK3 specific compounds were shown to inhibit the clonogenic growth of JAK3-expressing cell lines DAUDI, RAMOS, LC1;19, NALM-6, MOLT-3 and HL-60.

In animal models, TEL/JAK2 fusion proteins have induced myeloproliferative disorders and in hematopoietic cell lines, introduction of TEL/JAK2 resulted in activation of STAT1, STAT3, STAT5, and cytokine-independent growth [Schwaller, et al, *EMBO J.* 17, 5321-5333 (1998)].

Inhibition of JAK 3 and TYK 2 abrogated tyrosine phosphorylation of STAT3, and inhibited cell growth of mycosis fungoides, a form of cutaneous T cell lymphoma. These results implicated JAK family kinases in the constitutively activated JAK/STAT pathway that is present in mycosis fungoides [Nielsen, et al, *Proc. Nat. Acad. Sci. U.S.A.* 94, 6764-6769 (1997)]. Similarly, STAT3, STAT5, JAK1 and JAK2 were demonstrated to be constitutively activated in mouse T cell lymphoma characterized initially by LCK over-expression, thus further implicating the JAK/STAT pathway in abnormal cell growth [Yu, et al, *J. Immunol.* 159, 5206-5210 (1997)]. In addition, IL-6-mediated STAT3 activation was blocked by an inhibitor of JAK, leading to sensitization of myeloma cells to apoptosis [Catlett-Falcone, et al, *Immunity* 10, 105-115 (1999)].

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature,* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell Biol.* 1996, 16, 5313-5327; Amano et al., *Science,* 1997, 275, 1308-1311; Ishizaki et al., *FEBS Lett.* 1997, 404, 118-124) and in downregulation of myosin phosphatase (Kimura et al., *Science,* 1996, 273, 245-248), platelet activation (Klages et al., *J. Cell. Biol.,* 1999, 144, 745-754), aortic smooth muscle contraction by various stimuli (Fu et al., *FEBS Lett.,* 1998, 440, 183-187), thrombin-induced responses of aortic smooth muscle cells (Seasholtz et al., *Cir. Res.,* 1999, 84, 1186-1193), hypertrophy of cardiomyocytes (Kuwahara et al., *FEBS Lett.,* 1999, 452, 314-318), bronchial smooth muscle contraction (Yoshii et al., *Am. J. Respir. Cell Mol. Biol.*, 1999, 20, 1190-1200), smooth muscle contraction and cytoskeletal reorganization of non-muscle cells (Fukata et al., *Trends in Pharm. Sci* 2001, 22, 32-39), activation of volume-regulated anion channels (Nilius et al., *J. Physiol.*, 1999, 516, 67-74), neurite retraction (Hirose et al., *J. Cell. Biol.*, 1998, 141, 1625-1636), neutrophil chemotaxis (Niggli, *FEBS Lett.*, 1999, 445, 69-72), wound healing (Nobes and Hall, *J. Cell. Biol.*, 1999, 144, 1235-1244), tumor invasion (Itoh et al., *Nat. Med.*, 1999, 5, 221-225) and cell transformation (Sahai et al., *Curr. Biol.*, 1999, 9, 136-145). More specifically, ROCK has been implicated in various diseases and disorders including hypertension (Satoh et al., *J. Clin. Invest.* 1994, 94, 1397-1403; Mukai et al., *FASEB J.* 2001, 15, 1062-1064; Uehata et al., *Nature* 1997, 389, 990-994; Masumoto et al., *Hypertension*, 2001, 38, 1307-1310), cerebral vasospasm (Sato et al., *Circ. Res.* 2000, 87, 195-200; Miyagi et al., *J. Neurosurg.* 2000, 93, 471-476; Tachibana et al., *Acta Neurochir (Wien)* 1999, 141, 13-19), coronary vasospasm (Shimokawa et al., *Jpn. Cir. J.* 2000, 64, 1-12; Kandabashi et al., *Circulation* 2000, 101, 1319-1323; Katsumata et al., *Circulation* 1997, 96, 4357-4363; Shimokawa et al., *Cardiovasc. Res.* 2001, 51, 169-177; Utsunomiya et al., *J. Pharmacol.* 2001, 134, 1724-1730; Masumoto et al., *Circulation* 2002, 105, 1545-1547), bronchial asthma (Chiba et al., *Comp. Biochem. Physiol. C Pharmacol. Toxicol. Endocrinol.* 1995, 11, 351-357; Chiba et al., *Br. J. Pharmacol.* 1999, 127, 597-600; Chiba et al., *Br. J. Pharmacol.* 2001, 133, 886-890; Iizuka et al., *Eur. J. Pharmacol.* 2000, 406, 273-279), preterm labor (Niro et al., *Biochem. Biophys. Res. Commun.* 1997, 230, 356-359; Tahara et al., *Endocrinology* 2002, 143, 920-929; Kupittayanant et al., *Pflugers Arch.* 2001, 443, 112-114), erectile dysfunction (Chitaley et al., *Nat. Med.* 2001, 7, 119-122; Mills et al., *J. Appl. Physiol.* 2001, 91, 1269-1273), glaucoma (Honjo et al., *Arch. Ophthalmol.* 2001, 1171-1178; Rao et al., *Invest. Ophthalmol. Vis. Sci.* 2001, 42, 1029-1037), vascular smooth muscle cell proliferation (Shimokawa et al., *Cardiovasc. Res.* 2001, 51, 169-177; Morishige et al., *Arterioscler. Thromb. Vasc. Biol.* 2001, 21, 548-554; Eto et al., *Am. J. Physiol. Heart Circ. Physiol.* 2000, 278, H1744-H1750; Sawada et al., *Circulation* 2000, 101, 2030-2023; Shibata et al., *Circulation* 2001, 103, 284-289), myocardial hypertrophy (Hoshijima et al., *J. Biol. Chem.* 1998, 273, 7725-77230; Sah et al., *J. Biol. Chem.* 1996, 271, 31185-31190; Kuwahara et al., *FEBS Lett.* 1999, 452, 314-318; Yanazume et al., *J. Biol. Chem.* 2002, 277, 8618-8625), malignoma (Itoh et al., *Nat. Med.* 1999, 5, 221-225; Genda et al., *Hepatology* 1999, 30, 1027-1036; Somlyo et al., *Biochem. Biophys. Res. Commun.* 2000, 269, 652-659), ischemia/reperfusion-induced injury (Ikeda et al., *J. of Surgical Res.* 2003, 109, 155-160; Miznuma et al. *Transplantation* 2003, 75, 579-586), endothelial dysfunction (Hernandez-Perera et al., *Circ. Res.* 2000, 87, 616-622; Laufs et al., *J. Biol. Chem.* 1998, 273, 24266-24271; Eto et al., *Circ. Res.* 2001, 89, 583-590), Crohn's Disease and colitis (Segain et al. *Gastroenterology* 2003, 124(5), 1180-1187), neurite outgrowth (Fournier et al. *J. Neurosci.* 2003, 23, 1416-1423), Raynaud's Disease (Shimokawa et al. *J. Cardiovasc. Pharmacol.* 2002, 39, 319-327), and atherosclerosis (Retzer et al. *FEBS Lett.* 2000, 466, 70-74; Ishibashi et al. *Biochim. Biophys. Acta* 2002, 1590, 123-130). Accordingly, the development of inhibitors of ROCK kinase would be useful as therapeutic agents for the treatment of disorders implicated in the ROCK kinase pathway.

ERK2 (extracellular signal regulated kinase) is a member of the mammalian mitogen-activated protein (MAP)1 kinase family. (MAP)1 kinases are serine/threonine kinases that mediate intracellular signal transduction pathways (Cobb and Goldsmith, *J. Biol. Chem.*, 1995, 270, 14843; Davis, *Mol. Reprod. Dev.* 1995, 42, 459) and are activated by mitogens and growth factors (Bokemeyer et al. *Kidney Int.* 1996, 49, 1187). Members of the MAP kinase family share sequence similarity and conserved structural domains, and, in addition to ERK2, include the JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., *Cell* 1994, 76, 1025; Han et al., *Science* 1994, 265, 808; Raingeaud et al., *J. Biol. Chem.* 1995, 270, 7420; Shapiro and Dinarello, *Proc. Natl. Acad. Sci. USA* 1995, 92, 12230). In contrast, ERKs are activated by mitogens and growth factors (Bokemeyer et al., *Kidney Int.* 1996, 49, 1187).

ERK2 is a widely distributed protein kinase that achieves maximum activity when both Thr183 and Tyr185 are phosphorylated by the upstream MAP kinase kinase, MEK1 (Anderson et al., *Nature* 1990, 343, 651; Crews et al., *Science* 1992, 258, 478). Upon activation, ERK2 phosphorylates many regulatory proteins, including the protein kinases Rsk90 (Bjorbaek et al., *J. Biol. Chem.* 1995, 270, 18848) and MAPKAP2 (Rouse et al., *Cell* 1994, 78, 1027), and transcription factors such as ATF2 (Raingeaud et al., *Mol. Cell Biol.* 1996, 16, 1247), Elk-1 (Raingeaud et al., *Mol. Cell Biol.* 1996, 16, 1247), c-Fos (Chen et al., *Proc. Natl. Acad. Sci. USA* 1993, 90, 10952), and c-Myc (Oliver et al., *Proc. Soc. Exp. Biol. Med.* 1995, 210, 162). ERK2 is also a downstream target of the Ras/Raf dependent pathways (Moodie et al., *Science* 1993, 260, 1658) and may help relay the signals from these potentially oncogenic proteins. ERK2 has been shown to play a role in the negative growth control of breast cancer cells (Frey and Mulder, *Cancer Res.* 1993, 57, 628) and hyperexpression of ERK2 in human breast cancer has been reported (Sivaraman et al., *J. Clin. Invest.* 1997, 99, 1478). Activated ERK2 has also been implicated in the proliferation of endothelin-stimulated airway smooth muscle cells, suggesting a role for this kinase in asthma (Whelchel et al., *Am. J. Respir. Cell Mol. Biol.* 1997, 16, 589).

Glycogen synthase kinase-3 (GSK-3) is a serine/threonine protein kinase comprised of $\alpha$ and $\beta$ isoforms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor $\beta$-catenin, the translation initiation factor eIF2B, as well as ATP citrate lyase, axin, heat shock factor-1, c-Jun, c-myc, c-myb, CREB, and CEPB$\alpha$. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al., *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., *Neuron,* 2003, 38, 547-554), and thus other β-amyloid-lowering strategies (e.g., the development of agents capable of inhibiting β-amyloid peptide) would be useful in the treatment of Alzherimer's disease and other psychotic and neurodegenerative disorders. Additionally, the neurofibrillary tangles contain hyperphosphorylated Tau protein, in which Tau is phosphorylated on abnormal sites, and thus agents capble of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of AD peptides through the inhibition of GSK-3 (Phiel et al. *Nature* 2003, 423, 435-439). Thus, the development of inhibitors of GSK-3 would be useful for the reduction of the formation of amyloid plaques and neurofibrillry tangles, the pathological hallmarks of Alzheimer's Disease, and would also be useful for the treament of other psychotic and neurodegenerative disorders.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is also associated with stroke [Wang et al., *Brain Res* 2000, 859, 381-5; Sasaki et al., *Neurol Res* 2001, 23, 588-92; Hashimoto et al., *J. Biol. Chem* 2002, 277, 32985-32991].

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes PKA, PKB (c-Akt), PKC, PRK1, 2, $p70^{S6K}$, and PDK.

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J. Neurosci.* 2000, 20, 2875-2886,)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.,* 1997, 17, 1595-1606,); (Hemmings, B. A., *Science,* 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.* 1992, 89, 9267-9271). It has also been found to be overexpressed in 12% of pancreatic cancers (Cheng, J. Q. et al., *Proc. Natl. Acad. Sci. U.S.A.* 1996, 93, 3636-3641). It was demonstrated that AKT-2 was overexpressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer* 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.* 1994, 5, 285-294). PKA is a tetrameric holoenzyme, which contains two catalytic subunits bound to a homo-dimeric regulatory subunit (which acts to inhibit the catalytic sub-units). On binding of cAMP (enzyme activation), the catalytic subunits dissociate from the regulatory subunits to yield the active serine/threonine kinase (McKnight, G. S. et al., *Recent Prog. Horm. Res.* 1988, 44, pp. 307). Three isoforms of the catalytic subunit (C-α, C-β and C-γ) have been reported to date (Beebe, S. J. et al., *J. Biol. Chem.* 1992, 267, 25505-25512) with the C-α subunit being the most extensively studied, primarily because of its elevated expression in primary and metastatic melanomas (Becker, D. et al., *Oncogene* 1990, 5, 1133). To date, strategies to modulate the activity of the C-α subunit involve the use of antibodies, molecules that block PKA activity by targeting regulatory dimers and antisense oligonucleotides expression.

The ribosomal protein kinases $p70^{S6K}$-1 and -2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). $p70^{S6K}$ dependent S6 phosphorylation is stimulated in response to a variety of hormones and growth factors primarily via the PI3K pathway (Coffer, P. J. et al., *Biochem. Biophys. Res. Commun,* 1994 198, 780-786), which may be under the regulation of mTOR, since rapamycin acts to inhibit $p70^{S6K}$ activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.,* 1998, 8, 69-81). The use of rapamycin and gene deletion studies of dp70S6K from Drosophila and $p70^{S6K}1$ from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, $R^{93}$-$R^{96}$). Many human cancers including prostate and NSCL have elevated PDK1 signaling pathway function resulting from a number of distinct genetic events such as PTEN mutations or overexpression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., *Cancer Res.,* 1997 57, 5221-5225), (Brognard, J. et al., *Cancer Res.,* 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer Ther.* 2002, 1, 707), colon [(*Neoplasia* 2001, 3, 278), (Arico, S. et al., *J. Biol. Chem.* 2002, 277, 27613-27621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biol.* 2000, 10, 1439-1442)].

Accordingly, there is a great need to develop inhibitors of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK protein kinases that are useful in treating various diseases or conditions associated with FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK activation, particularly given the inadequate treatments currently available for the majority of these disorders.

SUMMARY OF THE INVENTION

It has now been found that compounds of this invention, and pharmaceutically acceptable compositions thereof, are effective as inhibitors of FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK protein kinases. In certain embodiments, these compounds are effective as inhibitors of FLT-3, JAK-3, PDK-1, and/or SYK protein kinases. These compounds have the general formula I:

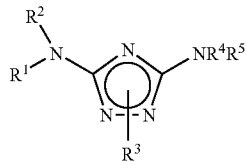

or a pharmaceutically acceptable salt thereof, wherein R$^1$, R$^2$, R$^3$, R$^4$, and R$^5$ are as defined below.

These compounds and pharmaceutical compositions thereof are useful for treating or preventing a variety of disorders, including, but not limited to, heart disease, diabetes, Alzheimer's disease, immunodeficiency disorders, inflammatory diseases, hypertension, allergic diseases, autoimmune diseases, destructive bone disorders such as osteoporosis, proliferative disorders, infectious diseases, immunologically-mediated diseases, and viral diseases. The compositions are also useful in methods for preventing cell death and hyperplasia and therefore may be used to treat or prevent reperfusion/ischemia in stroke, heart attacks, and organ hypoxia. The compositions are also useful in methods for preventing thrombin-induced platelet aggregation. The compositions are especially useful for disorders such as chronic myelogenous leukemia (CML), acute myeloid leukemia (AML), acute promyelocytic leukemia (APL), rheumatoid arthritis, asthma, osteoarthritis, ischemia, cancer (including, but not limited to, ovarian cancer, breast cancer and endometrial cancer), liver disease including hepatic ischemia, heart disease such as myocardial infarction and congestive heart failure, pathologic immune conditions involving T cell activation, and neurodegenerative disorders.

DETAILED DESCRIPTION OF THE INVENTION

1. General Description of Compounds of the Invention:
The present invention relates to a compound of formula I:

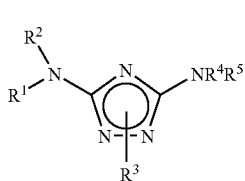

or a pharmaceutically acceptable salt thereof, wherein R$^1$ is hydrogen or Y—R', wherein Y is an optionally substituted C$_{1-6}$alkylidene chain wherein up to two methylene units are optionally and independently replaced with —O—, —S—, —NR—, —OCO—, —COO—, or —CO—;

each occurrence of R is independently hydrogen or an optionally substituted C$_{1-6}$ aliphatic group; and each occurrence of R' is independently hydrogen or an optionally substituted group selected from a C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

R$^2$ is -(T)$_n$Ar$^1$, or -(T)$_n$Cy$^1$, wherein T is an optionally substituted C$_{1-4}$ alkylidene chain wherein one methylene unit of T is optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; n is 0 or 1; Ar$^1$ is an optionally substituted aryl group selected from a 5-6 membered monocyclic or an 8-12 membered bicyclic ring having 0-5 heteroatoms independently selected from nitrogen, oxygen, or sulfur; and Cy$^1$ is an optionally substituted group selected from a 3-7-membered saturated or partially unsaturated monocyclic ring having 0-3 heteroatoms independently selected from nitrogen, oxygen, or sulfur, or an 8-12-membered saturated or partially unsaturated bicyclic ring system having 0-5 heteroatoms independently selected from nitrogen, oxygen, or sulfur, or R$^1$ and R$^2$, taken together with the nitrogen form an optionally substituted 5-8 membered monocyclic or 8-12 membered bicyclic saturated, partially unsaturated, or fully unsaturated ring having 0-3 additional heteroatoms independently selected from nitrogen, oxygen, or sulfur;

wherein Ar$^1$, Cy$^1$, or any ring formed by R$^1$ and R$^2$ taken together, are each independently optionally substituted with x independent occurrences of Q-R$^X$; wherein x is 0-5, Q is a bond or is a C$_1$-C$_6$ alkylidene chain wherein up to two methylene units of Q are optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^X$ is independently R', halogen, NO$_2$, CN, OR', SR', N(R')$_2$, NR'COR', NR'CONR'$_2$, NR'CO$_2$R', COR', CO$_2$R', OCOR', CON(R')$_2$, OCON(R')$_2$, SOR', SO$_2$R', SO$_2$N(R')$_2$, NR'SO$_2$R', NR'SO$_2$N(R')$_2$, COCOR', or COCH$_2$COR';

R$^3$ is bonded to the nitrogen atom in either the 1- or 2-position of the ring and is (L)$_m$Ar$^2$, or (L)$_m$Cy$^2$; wherein L is an optionally substituted C$_{1-4}$ alkylidene chain wherein one methylene unit of L is optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; m is 0 or 1; Ar$^2$ is an optionally substituted aryl group selected from a 5-6 membered monocyclic or an 8-12 membered bicyclic ring having 0-5 heteroatoms independently selected from nitrogen, oxygen, or sulfur; and Cy$^2$ is an optionally substituted group selected from a 3-7-membered saturated or partially unsaturated monocyclic ring having 0-3 heteroatoms independently selected from nitrogen, oxygen, or sulfur, or an 8-12-membered saturated or partially unsaturated bicyclic ring system having 0-5 heteroatoms independently selected from nitrogen, oxygen, or sulfur, wherein Ar$^2$ and Cy$^2$ are each independently optionally substituted with y occurrences of Z-R$^Y$; wherein y is 0-5, Z is a bond or is a C$_1$-C$_6$ alkylidene chain wherein up to two methylene units of Z are optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^Y$ is independently R', halogen, NO$_2$, CN, OR', SR', N(R')$_2$, NR'COR', NR'CONR'$_2$, NR'CO$_2$R', COR', CO$_2$R', OCOR', CON(R')$_2$, OCON(R')$_2$, SOR', SO$_2$R', SO$_2$N(R')$_2$, NR'OS$_2$R', NR'SO$_2$N(R')$_2$, COCOR', or COCH$_2$COR';

R$^4$ is hydrogen or C$_{1-6}$alkyl, provided that when R$^5$ is hydrogen, R$^4$ is also hydrogen;

R$^5$ is hydrogen; or R$^3$ and R$^5$, taken together form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur; and wherein any ring formed R$^3$ and R$^5$ taken together, is optionally substituted with up to five substituents selected from W—R$^W$; wherein W is a bond or is a C$_1$-C$_6$ alkylidene chain wherein up to two methylene units of W are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^W$ is independently R', halogen, NO$_2$, CN, OR', SR', N(R')$_2$, NR'COR', NR'CONR'$_2$, NR'CO$_2$R', COR', CO$_2$R', OCOR', CON(R')$_2$, OCON(R')$_2$, SOR', SO$_2$R', SO$_2$N(R')$_2$, NR'SO$_2$R', NR'SO$_2$N(R')$_2$, COCOR', or COCH$_2$COR'.

In certain embodiments, for compounds of formula I one or more or all of the following conditions apply:

a) when R$^3$ is unsubstituted phenyl, and R$^1$ is hydrogen, then R$^2$ is not:
  i) unsubstituted phenyl;
  ii) unsubstituted pyridyl;
  iii) benzyl substituted with o-OMe;
  iv) —(C=S)NH(C=O)phenyl; or v)
  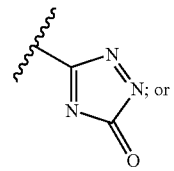

vi) —(C=S)NH-naphthyl or —(C=O)NH-naphthyl; or b) when R$^3$ is substituted or unsubstituted phenyl, then R$^2$ is not phenyl substituted in the para position with oxazole, thiazole, thiadiazole, oxadiazole, tetrazole, triazole, diazole, or pyrrole;

c) when R$^3$ is phenyl, pyridyl, pyrimidinedione, or cyclohexyl, and R$^1$ is hydrogen, then R$^2$ is not phenyl simultaneously substituted with one occurrence of OMe in the meta position, and one occurrence of oxazole in the para position;

d) when R$^3$ is 4-Cl phenyl, or 3,4-Cl-phenyl, then R$^2$ is not p-Cl phenyl;

e) when R$^3$ is unsubstituted pyrimidinyl, then R$^2$ is not unsubstituted phenyl, p-OMe substituted phenyl, p-OEt substituted phenyl or o-OMe substituted phenyl or when R$^3$ is 4-Me pyrimidinyl or 4,6-dimethylpyrimidinyl, then R$^2$ is not unsubstituted phenyl;

f) compounds of formula I exclude:

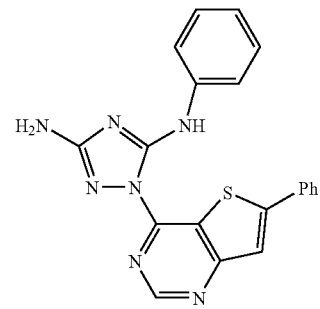

g) when R$^2$ is 3-pyridinyl and R$^1$ is hydrogen, then R$^3$ is not trimethoxybenzoyl;

h) when R$^3$ is optionally substituted phenyl and R$^1$ is hydrogen, then R$^2$ is not —(C=S)NH(C=O)phenyl, —(C=O)NHphenyl, —(C=S)NHphenyl, or —(C=O)CH$_2$(C=O)phenyl;

i) when R$^1$ is hydrogen, R$^2$ is unsubstituted benzyl, then R$^3$ is not thiadiazole substituted with optionally substituted phenyl;

j) when $R^1$ is hydrogen, $R^2$ is pyridyl, and $R^3$ is pyridyl, then $R^2$ is not substituted with one or more of $CF_3$, Me, OMe, Br, or Cl;
k) when $R^1$ is hydrogen, $R^2$ is pyridyl, then $R^3$ is not unsubstituted pyridyl, unsubstituted quinoline, unsubstituted phenyl, or unsubstituted isoquinoline;
l) when $R^1$ is hydrogen, and $R^2$ is unsubstituted quinoline, then $R^3$ is not unsubstituted pyridyl or unsubstituted quinoline
m) when $R^1$ is hydrogen, and $R^2$ is unsubstituted isoquinoline or unsubstituted naphthyl then $R^3$ is not unsubstituted pyridyl;
n) compounds of formula I exclude those compounds having the general structure:

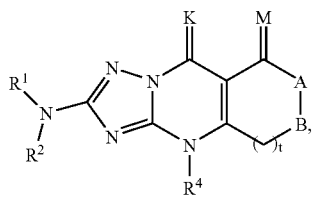

wherein $R^1$, $R^2$, and $R^3$ are as defined above, M and K are O or $H_2$, provided that K and M are different, A and B are each —$CH_2$—, —NH—, —N-alkyl-, N-aralkyl-, —$NCOR^a$, —$NCONHR^b$, or —$NCSNHR^b$, wherein $R^a$ is lower alkyl or aralkyl, and $R^b$ is straight or branched chain alkyl, aralkyl, or aryl which can either be unsubstituted or substituted with one or more alkyl and/or haloalkyl substituents;
o) compounds of formula I exclude those compounds having the general structure:

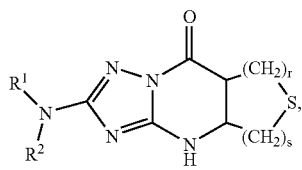

wherein $R^1$ and $R^2$ are as defined above, and r and s are each independently 0, 1, 2, 3, or 4, provided that the sum of s and r is at least 1;
p) compounds of formula I exclude any one or more of, or all of the following compounds:

i)
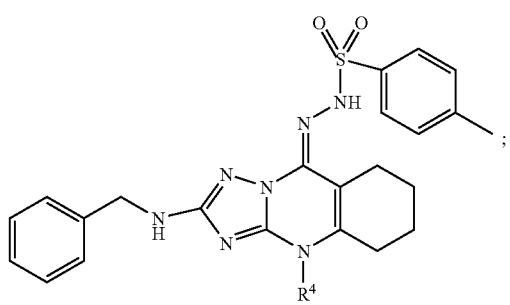

ii)
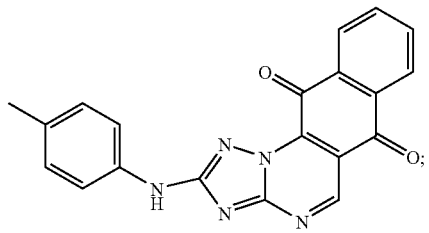

iii)
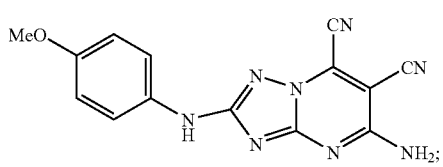

iv)
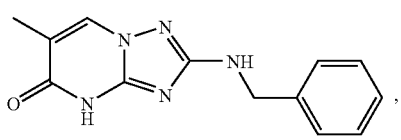

v)
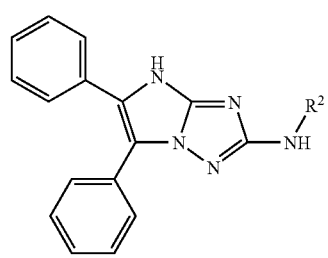

where $R^2$ is NH(CH)(Ph)C=O(Ph);

vi)
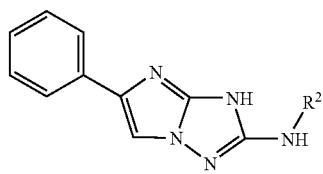

where $R^2$ is unsubstituted phenyl or phenyl substituted with OMe, Cl, or Me;

vii)
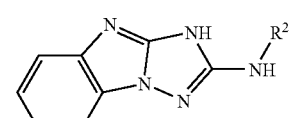

where $R^2$ is unsubstituted phenyl or phenyl substituted with OMe, Cl, Me, OMe, or $R^2$ is unsubstituted benzyl;

viii)

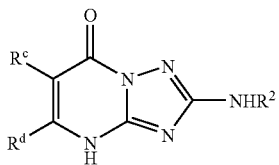

where $R^2$ is optionally substituted aralkyl, and $R^c$ and $R^d$ are each independently Me, hydrogen, $CH_2Cl$, or Cl;

ix)

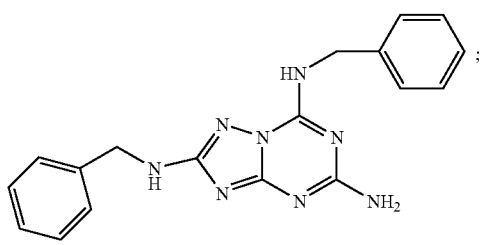

x)

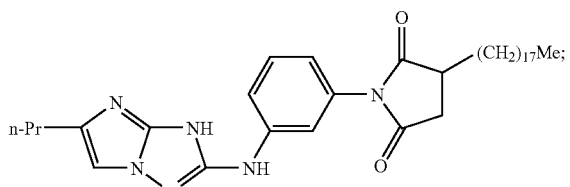

xi)

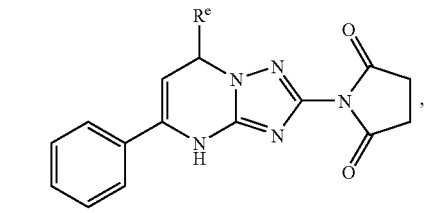

where $R^e$ is optionally substituted phenyl;

xii)

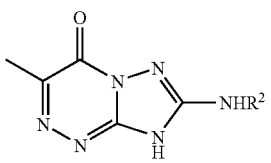

where $R^2$ is phenyl optionally substituted with Me, OMe, Br or Cl; or xiii)

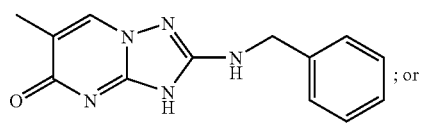

q) when $R^1$ is hydrogen, and $R^2$ is phenyl or optionally substituted phenyl, and m is 1, then L is not —CO—, —COCH$_2$—, or —COCH=CH—;

In certain other embodiments, for compounds of formula I, when $R^1$ is hydrogen, and $R^2$ is phenyl or optionally substituted phenyl, and m is 1, then L is not —CO—, —CS—, —CONR—, —CSNR—, —SO$_2$—, —SO$_2$NR—, —COSO$_2$—, or —CSSO$_2$—.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R^o$; —$OR^o$; —$SR^o$; phenyl (Ph) optionally substituted with $R^o$; —O(Ph) optionally substituted with $R^o$; —$(CH_2)_{1-2}$(Ph), optionally substituted with $R^o$; —CH=CH(Ph), optionally substituted with $R^o$; —$NO_2$; —CN; —$N(R^o)_2$; —$NR^oC(O)R^o$; —$NR^oC(S)R^o$; —$NR^oC(O)N(R^o)_2$; —$NR^oC(S)N(R^o)_2$; —$NR^oCO_2R^o$; —$NR^oNR^oC(O)R^o$; —$NR^oNR^oC(O)N(R^o)_2$; —$NR^oNR^oCO_2R^o$; —C(O)C(O)$R^o$; —C(O)$CH_2$C(O)$R^o$; —$CO_2R^o$; —C(O)$R^o$; —C(S)$R^o$; —C(O)N($R^o$)$_2$; —C(S)N($R^o$)$_2$; —OC(O)N($R^o$)$_2$; —OC(O)$R^o$; —C(O)N(O$R^o$)$R^o$; —C(NO$R^o$)$R^o$; —S(O)$_2R^o$; —S(O)$_3R^o$; —$SO_2$N($R^o$)$_2$; —S(O)$R^o$; —$NR^oSO_2$N($R^o$)$_2$; —$NR^oSO_2R^o$; —N(O$R^o$)$R^o$; —C(=NH)—N($R^o$)$_2$; —P(O)$_2R^o$; —PO($R^o$)$_2$; —OPO($R^o$)$_2$; —$(CH_2)_{0-2}$NHC(O)$R^o$; phenyl (Ph) optionally substituted with $R^o$; —O(Ph) optionally substituted with $R^o$; —$(CH_2)_{1-2}$(Ph), optionally substituted with $R^o$; or —CH=CH(Ph), optionally substituted with $R^o$; wherein each independent occurrence of $R^o$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^o$, on the same substituent or different substituents, taken together with the atom(s) to which each $R^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of $R^o$ are selected from $NH_2$, NH($C_{1-4}$aliphatic), N($C_{1-4}$aliphatic)$_2$, halogen, $C_{1-4}$aliphatic, OH, O($C_{1-4}$aliphatic), $NO_2$, CN, $CO_2H$, $CO_2$($C_{1-4}$aliphatic), O(halo$C_{1-4}$ aliphatic), or halo$C_{1-4}$ aliphatic, wherein each of the foregoing $C_{1-4}$aliphatic groups of $R^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic group.

Unless otherwise defined above and herein, optional substituents on the nitrogen of a non-aromatic heterocyclic ring are generally selected from —$R^+$, —N($R^+$)$_2$, —C(O)$R^+$, —$CO_2R^+$, —C(O)C(O)$R^+$, —C(O)$CH_2$C(O)$R^+$, —$SO_2R^+$, —$SO_2$N($R^+$)$_2$, —C(=S)N($R^{+1}$)$_2$, —C(=NH)—N($R^+$)$_2$, or —$NR^+SO_2R^+$; wherein $R^+$ is hydrogen, an optionally substituted $C_{1-6}$ aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R⁺ are selected from —$NH_2$, —$NH(C_{1-4}$ aliphatic), —$N(C_{1-4}$ aliphatic)$_2$, halogen, $C_{1-4}$ aliphatic, —OH, —$O(C_{1-4}$ aliphatic), —$NO_2$, —CN, —$CO_2H$, —$CO_2(C_{1-4}$ aliphatic), —O(halo $C_{1-4}$ aliphatic), or halo($C_{1-4}$ aliphatic), wherein each of the foregoing $C_{1-4}$aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R⁺, R, R' or any other variable similarly defined herein), are taken together with the atom(s) to which each variable is bound include, but are not limited to the following: a) two independent occurrences of R° (or R⁺, R, R' or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, R, R' or any other variable similarly defined herein) that are bound to different atoms and are taken together with both of those atoms to form a ring, for example where a phenyl group is substituted with two occurrences of OR°

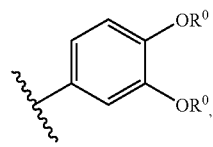

these two occurrences of R° are taken together with the oxygen atoms to which they are bound to form a fused 6-membered oxygen containing ring:

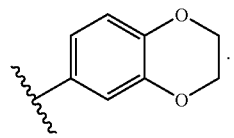

It will be appreciated that a variety of other rings can be formed when two independent occurrences of R° (or R⁺, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Compounds:

As described generally above for compounds of formula I, in certain embodiments, R² is -(T)$_n$Ar¹. In certain embodiments, Ar¹ is selected from one of the following groups:

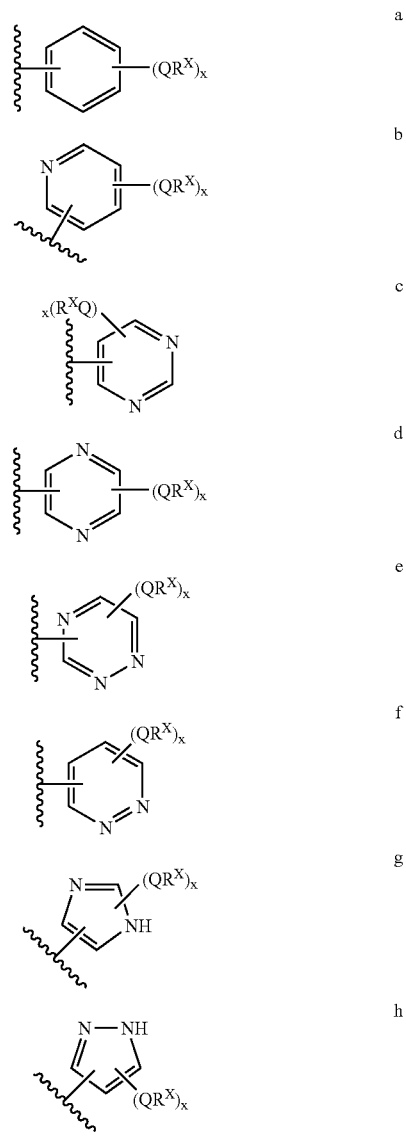

-continued
i 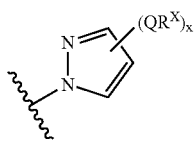
j 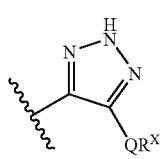
k 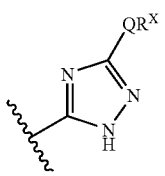
l 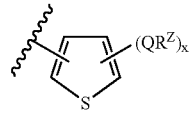
m 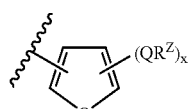
n 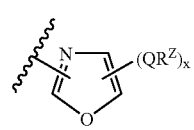
o 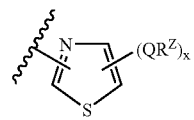
p 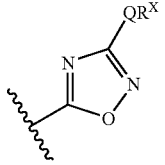
q 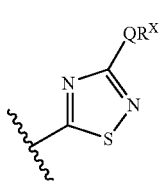
r 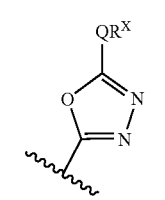
-continued
s 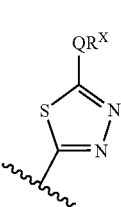
t 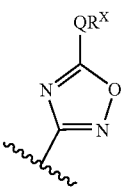
u 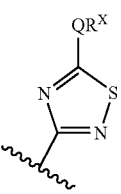
wherein Q and $R^X$ are as defined generally above and in classes and subclasses herein, and x is 0-5.
In other embodiments, $Ar^1$ is phenyl (a), pyridyl (b) (preferably attached in the 2-, 3-, or 4-position as shown by b-i, b-ii, and b-iii), pyrimidinyl (c) (preferably attached in the 2-, 4- or 5-position as shown by c-i, c-ii, and c-iii)
a 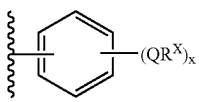
b-i 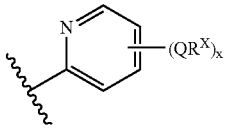
c-i 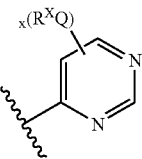
d 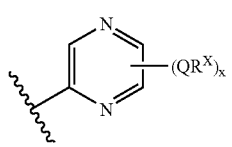
b-ii 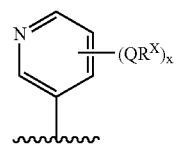

-continued

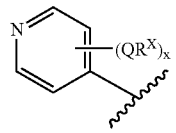
b-iii

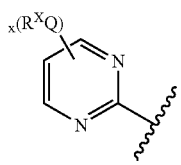
c-ii

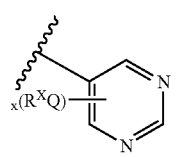
c-iii

In yet other embodiments R¹ is hydrogen, Ar¹ is phenyl (a), and compounds have the formula I-A or I-A':

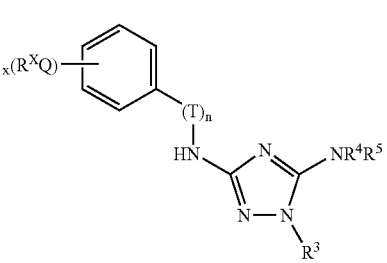
I-A

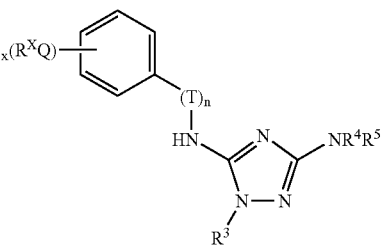
I-A'

In other embodiments, R² is -(T)$_n$Cy¹. In preferred embodiments, Cy¹ is selected from one of the following groups:

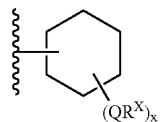
v

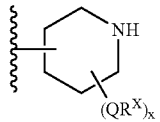
w

-continued

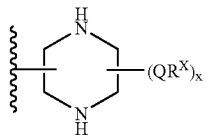
x

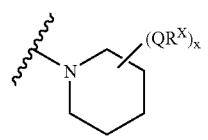
y

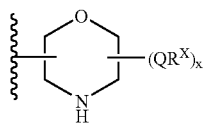
z

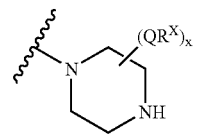
aa

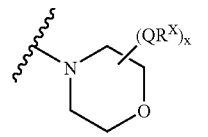
bb

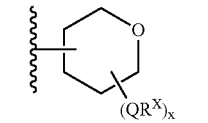
cc

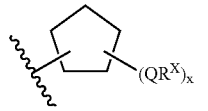
dd

ee

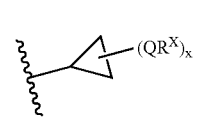
ff

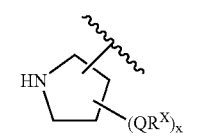
gg wherein any substituable carbon or nitrogen atom is optionally substituted with QR$^X$, and wherein Q and R$^X$ are as defined generally above and in classes and subclasses herein and x is 0-5.

In still other embodiments, Cy¹ is selected from one of the following groups:

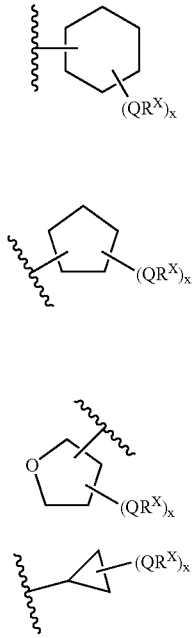

v dd ee ff

In other embodiments $R^1$ is hydrogen, $Cy^1$ is cyclohexyl (v), tetrahydrofuranyl (ee) (preferably attached in the 2-position), or cyclopropyl (ff), and compounds have one of the following formulas I-B, I-C, I-D, I-B', I-C', or I-D':

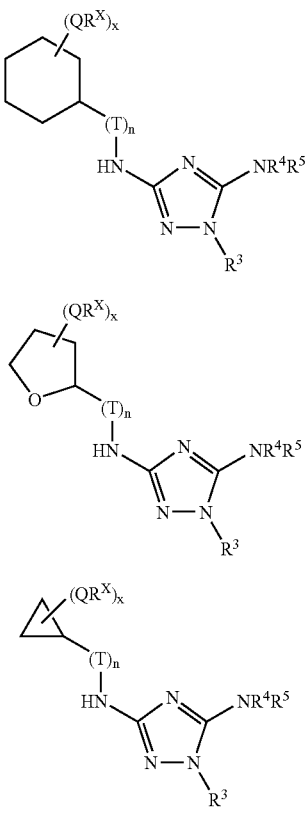

I-B

I-C

I-D

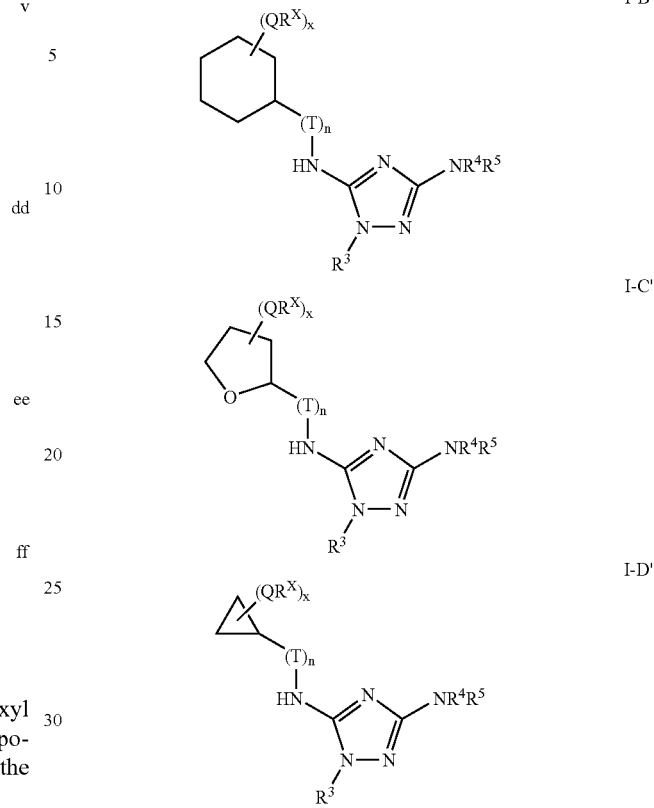

I-B'

I-C'

I-D'

In certain embodiments, $R^1$ is hydrogen, $C_{1-4}$alkyl, —CH$_2$OCOR', —CH$_2$OCOCHRNRR', COOR', —COCHROCOR', COR', —CO(CH$_2$)$_3$NHR', where R' is $C_{1-6}$alkyl, or alkyl-dioxolone. In most preferred embodiments, $R^1$ is hydrogen.

Exemplary T groups, when present, include CH$_2$ and —CH$_2$CH$_2$—. In certain other embodiments, n is 0 and T is absent.

As detailed above, $Ar^1$ or $Cy^1$ can be optionally substituted at one or more substitutable carbon or nitrogen atoms with up to 5 occurrences of $QR^X$. In certain embodiments, x is 0-3, and $Ar^1$ or $Cy^1$ are each independently substituted with 0-3 occurrences of $QR^X$. In still other embodiments, x is 0 and $Ar^1$ or $Cy^1$ are unsubstituted.

In some embodiments, $QR^X$ groups are each independently R', halogen, CN, NO$_2$—N(R')$_2$, —CH$_2$N(R')$_2$, —OR', —CH$_2$OR', —SR', —CH$_2$SR', —COOR', —NRCOR', —CON(R')$_2$, —SO$_2$N(R')$_2$, —CONR(CH$_2$)$_2$N(R')$_2$, —CONR(CH$_2$)$_3$N(R')$_2$, —CONR(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, or —O(CH$_2$)$_4$N(R')$_2$. In other embodiments, $QR^X$ groups are each independently Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, —O(CH$_2$)$_2$N-morpholino, —O(CH$_2$)$_3$N-morpholino, —O(CH$_2$)$_4$N-morpholino, —O(CH$_2$)$_2$N-piperazinyl, O(CH$_2$)$_3$N-piperizinyl, O(CH$_2$)$_4$N-piperizinyl, —NHCH(CH$_2$OH)phenyl, —CONH(CH$_2$)$_2$N-morpholino, —CONH(CH$_2$)$_2$N-piperazinyl, —CONH(CH$_2$)$_3$N-morpholino, —CONH(CH$_2$)$_3$N-piperazinyl, —CONH(CH$_2$)$_4$N-morpholino, —CONH(CH$_2$)$_4$N-piperazinyl, —SO$_2$NH(CH$_2$)$_2$N-morpholino, —SO$_2$NH(CH$_2$)$_2$N-piperazinyl, —SO$_2$NH(CH$_2$)$_3$N-morpholino, —SO$_2$NH(CH$_2$)$_3$N-piperazinyl, —SO$_2$NH(CH$_2$)$_4$N-morpholino, —SO$_2$NH(CH$_2$)$_4$N-piperazinyl, where each of the foregoing phenyl, morpholino, piperazinyl, or piperidinyl groups is optionally substituted, or an optionally substituted group selected from C$_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —COCH$_2$CN, or —COCH$_3$. Exemplary QR$^X$ groups also include those shown below in Table 1.

It will be appreciated that certain classes of compounds of general formula I are of special interest. In certain embodiments, the present invention provides monocyclic triazole compounds wherein R$^4$ and R$^5$ are each hydrogen and compounds have the general formula II or II':

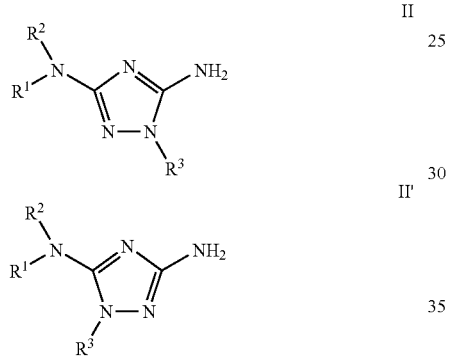

wherein R$^1$ and R$^2$ are defined generally above and in classes and subclasses herein;

R$^3$ is (L)$_m$Ar$^2$, or (L)$_m$Cy$^2$; wherein L is an optionally substituted C$_{1-4}$ alkylidene chain wherein one methylene unit of L is optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; m is 0 or 1; Ar$^2$ is an optionally substituted aryl group selected from a 5-6 membered monocyclic or an 8-12 membered bicyclic ring having 0-5 heteroatoms independently selected from nitrogen, oxygen, or sulfur; and Cy$^2$ is an optionally substituted group selected from a 3-7-membered saturated or partially unsaturated monocyclic ring having 0-3 heteroatoms independently selected from nitrogen, oxygen, or sulfur, or an 8-12-membered saturated or partially unsaturated bicyclic ring system having 0-5 heteroatoms independently selected from nitrogen, oxygen, or sulfur, wherein Ar$^2$ and Cy$^2$ are each independently optionally substituted with y occurrences of Z-R$^Y$; wherein y is 0-5, Z is a bond or is a C$_1$-C$_6$ alkylidene chain wherein up to two methylene units of Z are optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^Y$ is independently R', halogen, NO$_2$, CN, OR', SR', N(R')$_2$, NR'COR', NR'CONR'$_2$, NR'CO$_2$R', COR', CO$_2$R', OCOR', CON(R')$_2$, OCON(R')$_2$, SOR', SO$_2$R', SO$_2$N(R')$_2$, NR'SO$_2$R', NR'SO$_2$N(R')$_2$, COCOR', or COCH$_2$COR';

each occurrence of R is independently hydrogen or an optionally substituted C$_{1-6}$ aliphatic group; and each occurrence of R' is independently hydrogen or an optionally substituted group selected from a C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

In certain embodiments, for compounds of formula II described directly above, one or more or all of the following conditions apply:

a) when R$^3$ is unsubstituted phenyl, and R$^1$ is hydrogen, then R$^2$ is not:
   i) unsubstituted phenyl;
   ii) unsubstituted pyridyl;
   iii) benzyl substituted with o-OMe;
   iv) —(C═S)NH(C═O)phenyl; or

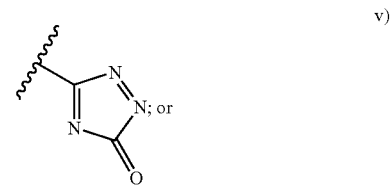

vi) —(C═S)NH-naphthyl or —(C═O)NH-naphthyl; or b) when R$^3$ is substituted or unsubstituted phenyl, then R$^2$ is not phenyl substituted in the para position with oxazole, thiazole, thiadiazole, oxadiazole, tetrazole, triazole, diazole, or pyrrole;

c) when R$^3$ is phenyl, pyridyl, pyrimidinedione, or cyclohexyl, and R$^1$ is hydrogen, then R$^2$ is not phenyl simultaneously substituted with one occurrence of OMe in the meta position, and one occurrence of oxazole in the para position;

d) when R$^3$ is 4-Cl phenyl, or 3,4-Cl-phenyl, then R$^2$ is not p-Cl phenyl;

e) when R$^3$ is unsubstituted pyrimidinyl, then R$^2$ is not unsubstituted phenyl, p-OMe substituted phenyl, p-OEt substituted phenyl or o-OMe substituted phenyl or when R$^3$ is 4-Me pyrimidinyl or 4,6-dimethylpyrimidinyl, then R$^2$ is not unsubstituted phenyl;

f) compounds of formula I exclude:

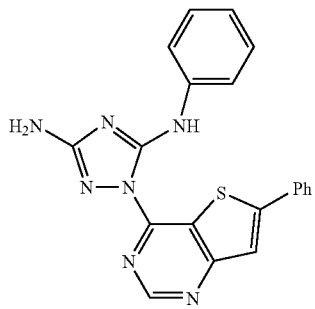

g) when $R^2$ is 3-pyridinyl and $R^1$ is hydrogen, then $R^3$ is not trimethoxybenzoyl;

h) when $R^3$ is optionally substituted phenyl and $R^1$ is hydrogen, then $R^2$ is not —(C=S)NH(C=O)phenyl, —(C=O)NHphenyl, —(C=S)NHphenyl, or —(C=O)CH$_2$(C=O)phenyl;

i) when $R^1$ is hydrogen, $R^2$ is unsubstituted benzyl, then $R^3$ is not thiadiazole substituted with optionally substituted phenyl;

j) when $R^1$ is hydrogen, $R^2$ is pyridyl, and $R^3$ is pyridyl, then $R^2$ is not substituted with one or more of CF$_3$, Me, OMe, Br, or Cl;

k) when $R^1$ is hydrogen, $R^2$ is pyridyl, then $R^3$ is not unsubstituted pyridyl, unsubstituted quinoline, unsubstituted phenyl, or unsubstituted isoquinoline;

l) when $R^1$ is hydrogen, and $R^2$ is unsubstituted quinoline, then $R^3$ is not unsubstituted pyridyl or unsubstituted quinoline m) when $R^1$ is hydrogen, and $R^2$ is unsubstituted isoquinoline or unsubstituted naphthyl then $R^3$ is not unsubstituted pyridyl; or n) when $R^1$ is hydrogen, and $R^2$ is phenyl or optionally substituted phenyl, and m is 1, then L is not —CO—, —COCH$_2$—, or —COCH=CH—;

In certain other embodiments, for compounds of formula I, when $R^1$ is hydrogen, and $R^2$ is phenyl or optionally substituted phenyl, and m is 1, then L is not —CO—, —CS—, —CONR—, —CSNR—, —SO$_2$—, —SO$_2$NR—, —COSO$_2$—, or —CSSO$_2$—.

As described generally above, in certain embodiments, $Ar^1$ is selected from any one of a through u depicted above (including certain subsets b-i, c-i, b-ii, b-iii, c-ii, or c-iii), and in certain other embodiments, $Cy^1$ is selected from any one of v through ff depicted above. It will be appreciated, however, that for compounds of formula II as described above, certain additional compounds are of special interest. For example, in certain exemplary embodiments, for compounds of general formula II or II' above, compounds of special interest include those compounds where $R^1$ is hydrogen, $Ar^1$ is optionally substituted phenyl, and $R^3$ is -(L)$_m$Ar$^2$ or (L)$_m$Cy$^2$, and compounds have the formula II-A-(i), II-A-(ii), II-A-(i)' or II-A-(ii)':

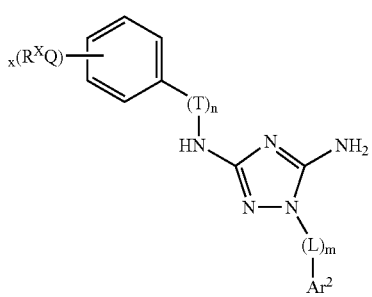

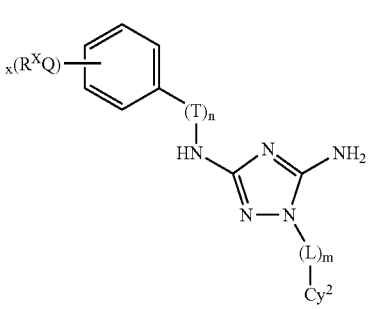

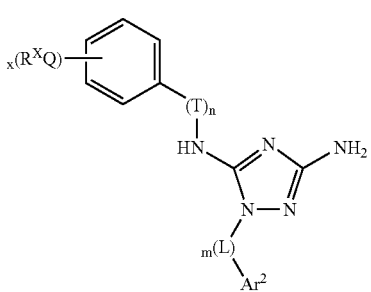

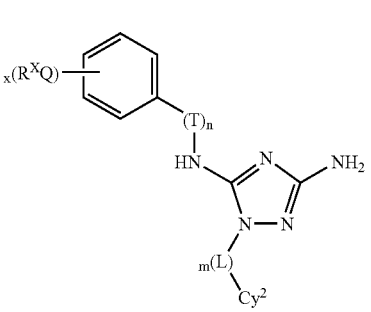

In some embodiments for compounds described directly above m and n are both 0.

In certain other exemplary embodiments, $R^1$ is hydrogen, $Cy^1$ is optionally substituted cyclohexyl, tetrahydrofuranyl, or cyclopropyl, and $R^3$ is -(L)$_m$Ar$^2$ or (L)$_m$Cy$^2$, and compounds have the formula II-B-(i), II-B-(ii), II-C-(i), II-C-(ii), II-D-(i), II-D-(ii), II-B-(i)', II-B-(ii)', II-C-(i)', II-C-(ii)', II-D-(i)' or II-D-(ii)':

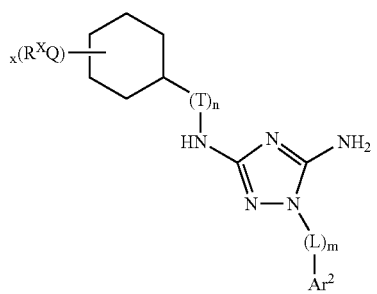 II-B-(i)
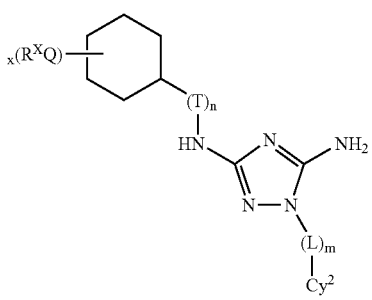 II-B-(ii)
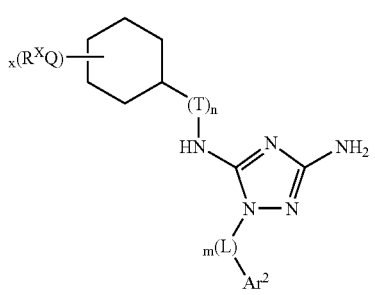 II-B-(i)'
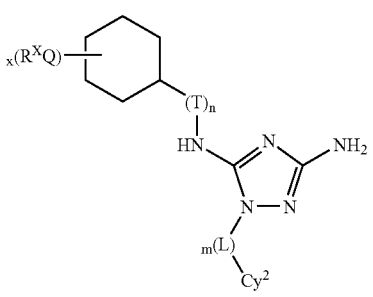 II-B-(ii)'
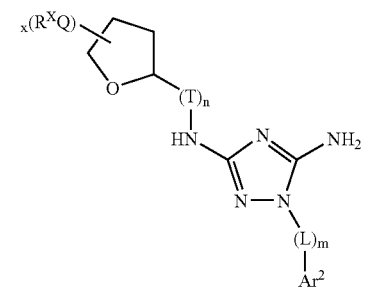 II-C-(i)
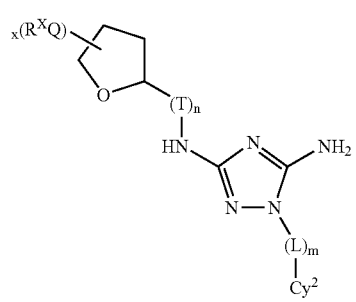 II-C-(ii)
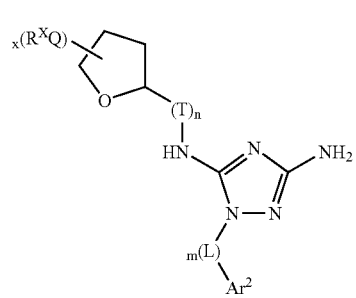 II-C-(i)'
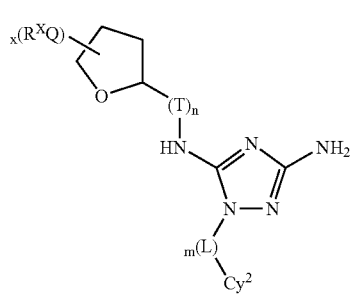 II-C-(ii)'
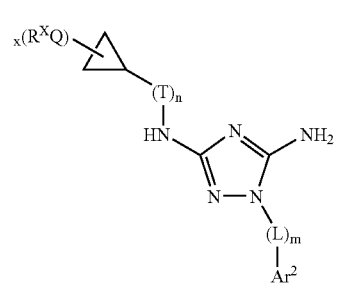 II-D-(i)
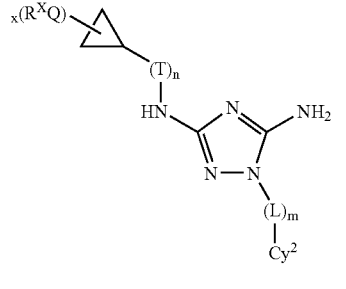 II-D-(ii)

-continued

II-D-(i)'

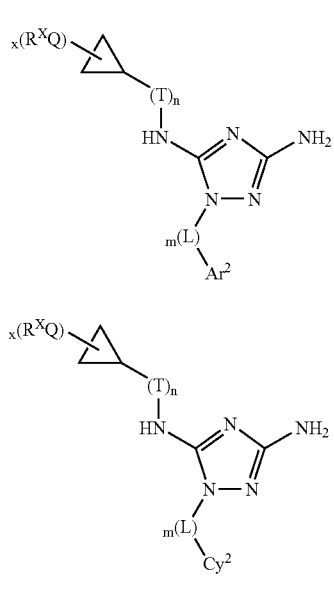

II-D-(ii)'

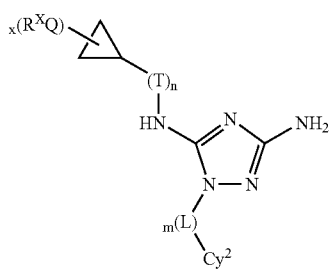

In some embodiments for compounds described directly above m and n are both 0.

In certain other embodiments, for compounds of general formula II, and subsets II-A-(i), II-B-(i), II-C-(i), II-D-(i), II-A-(i)', II-B-(i)', II-C-(i)', and II-D-(i)' described directly above, Ar² is selected from one of the following groups:

i
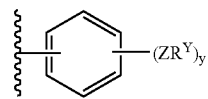

ii
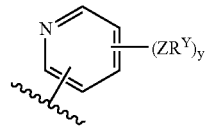

iii
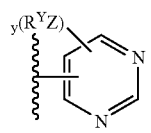

iv
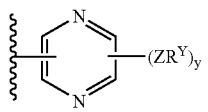

v
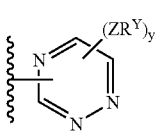

vii
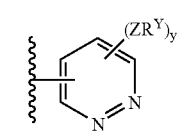

-continued viii
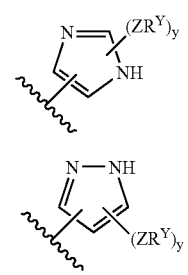

ix
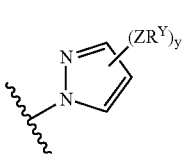

x
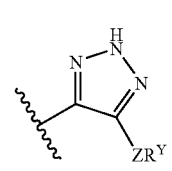

xi
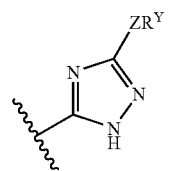

xii
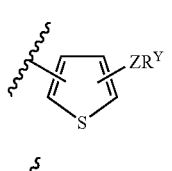

xiii
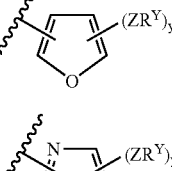

xiv
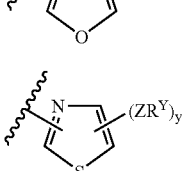

xv
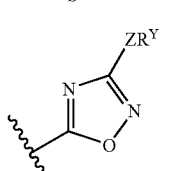

xvi
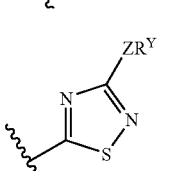

xvii
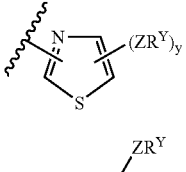

xviii
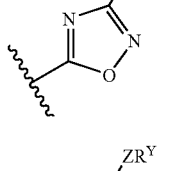

-continued
xix
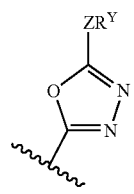
xx
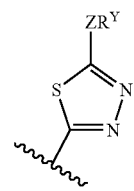
xxi
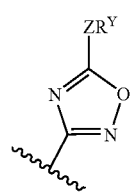
xxii
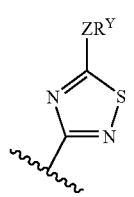
xxiii
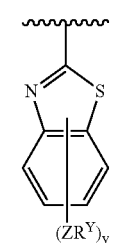
xxiv
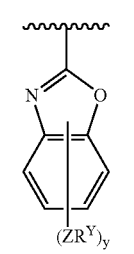
xxv
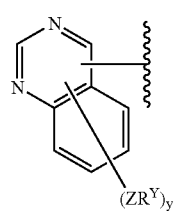
-continued
xxvi
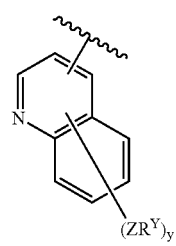
xxvii
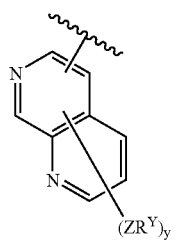
xxviii
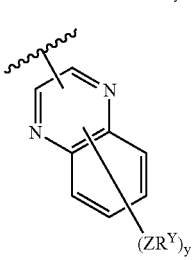
xxix
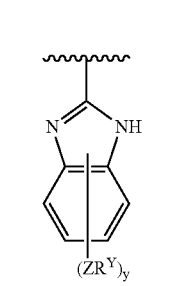
xxx
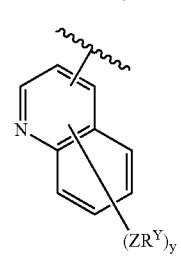
xxxi
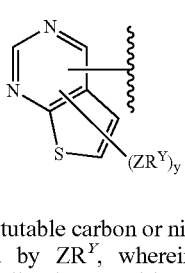
wherein any substitutable carbon or nitrogen atom is optionally substituted by $ZR^Y$, wherein Z and $R^Y$ are as described generally above and in classes and subclasses herein and y is 0-5.
In more preferred embodiments, $Ar^2$ is selected from one of the following groups:

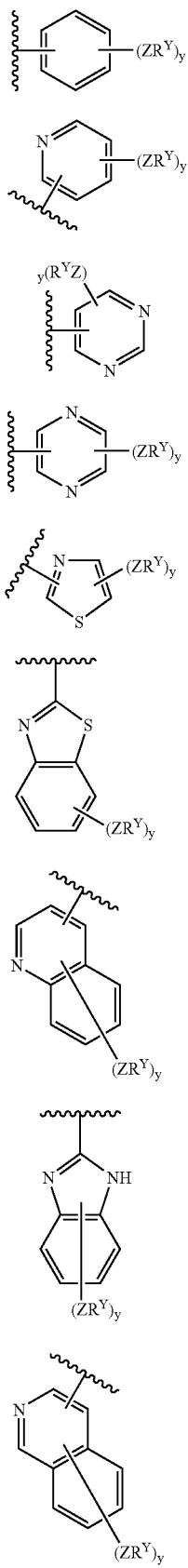
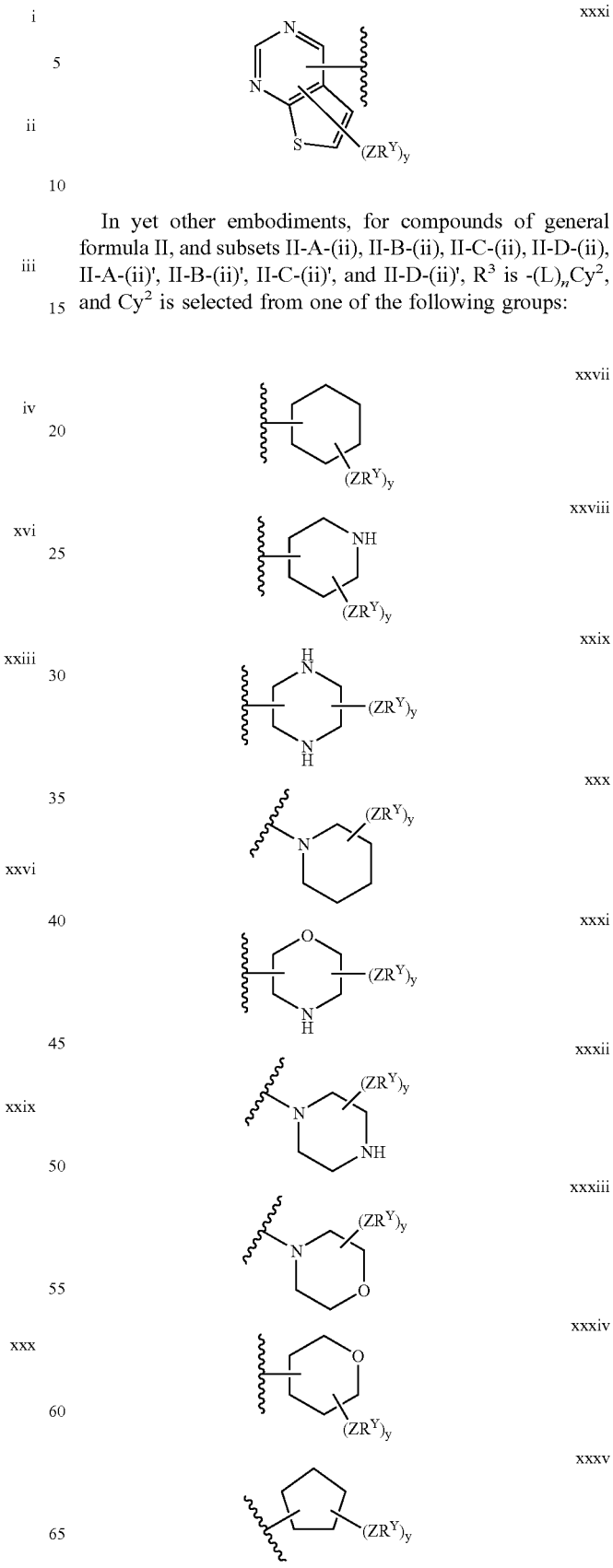
In yet other embodiments, for compounds of general formula II, and subsets II-A-(ii), II-B-(ii), II-C-(ii), II-D-(ii), II-A-(ii)', II-B-(ii)', II-C-(ii)', and II-D-(ii)', $R^3$ is $-(L)_n Cy^2$, and $Cy^2$ is selected from one of the following groups:

-continued

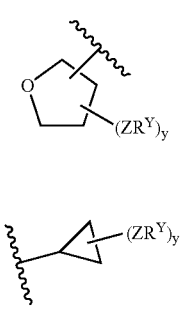
xxxvi

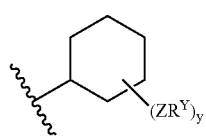
xxxvii wherein any substitutable carbon or nitrogen atom is optionally substituted by $ZR^Y$, wherein Z and $R^Y$ are as described generally above and in classes and subclasses herein and y is 0-5.

In still other embodiments, $Cy^2$ is selected from one of the following groups i-b or viii-b:

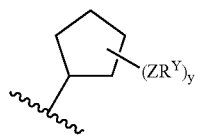
xxvii

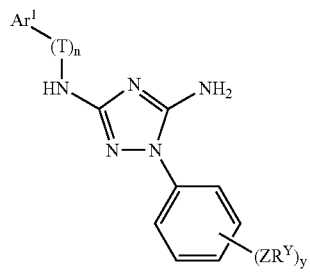
xxxv

In some embodiments, m is 1 and L is —O—, —NR—, or —CH$_2$—. In yet other embodiments, m is 0.

In certain other embodiments, for compounds of general formula II, $R^1$ and $R^2$ are as described generally above and in classes and subclasses herein, m is 0, and $Ar^2$ is optionally substituted phenyl, 2-pyridyl, 2-thiazolyl, 2-pyrimidinyl, 6-pyrimidinyl, 4-pyridyl, benzothiazolyl, or 2-quinolinyl, and compounds have one of the structures II-E-(i), II-E-(ii), II-F-(i) II-F-(ii), II-G-(i), II-G-(ii), II-G'-(i), II-G'-(ii), II-H-(i), II-H-(ii), II-I-(i), II-I-(ii), II-I'-(i), II-I'-(ii), II-J-(i), or II-J-(ii), II-E-(i)', II-E-(ii)', II-F-(i)', II-F-(ii)', II-G-(i)', II-G-(ii)', II-G'-(i)', II-G'-(ii)', II-H-(i)', II-H-(ii)', II-I-(i)', II-I-(ii)', II-I'-(i)', II-I'-(ii)', II-J-(i)', or II-J-(ii)':

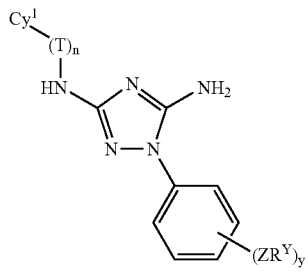
II-E-(i)

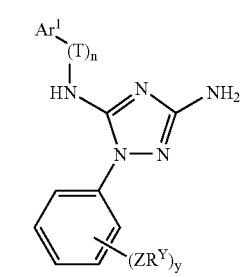
II-E-(ii)

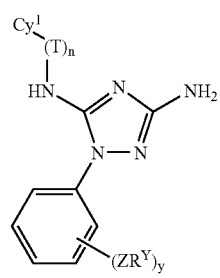
II-E-(i)'

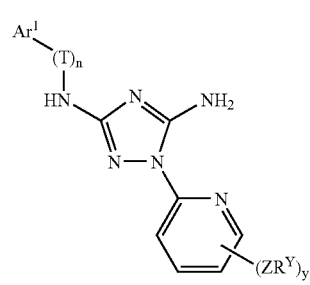
II-E-(ii)'

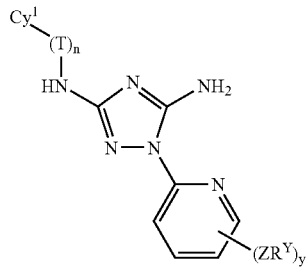
II-F-(i)

II-F-(ii)

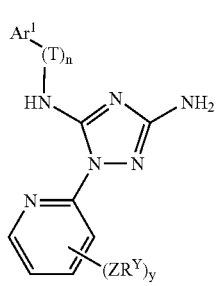 II-F-(i)'
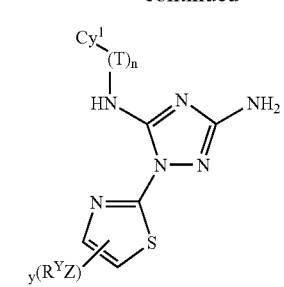 II-G-(ii)'
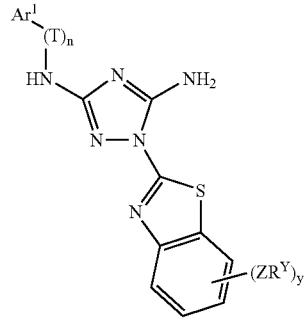 II-G'-(i)
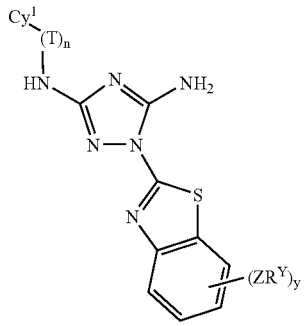 II-G'-(ii)
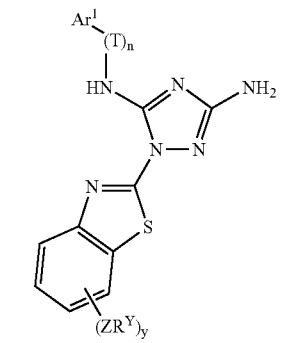 II-G'-(i)'
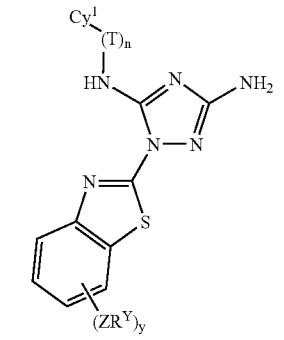 II-G'-(ii)'
II-F-(ii)'
II-G-(i)
II-G-(ii)
II-G-(i)'
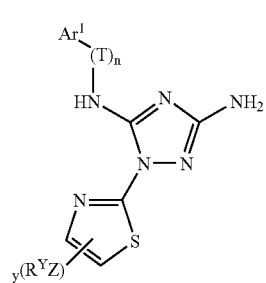

-continued
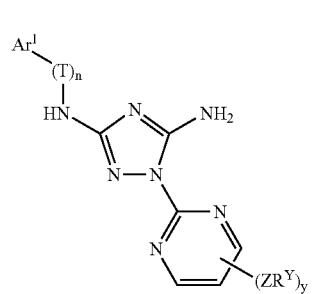
II-H-(i)
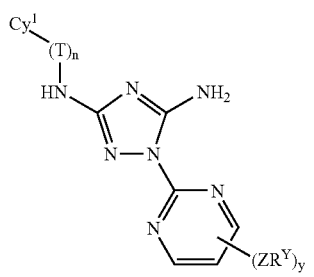
II-H-(ii)
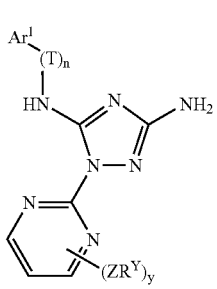
II-H-(i)'
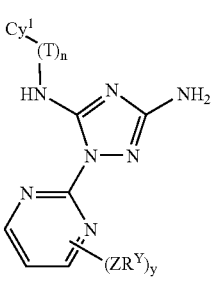
II-H-(ii)'
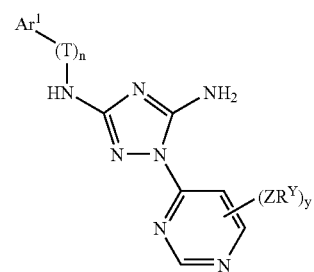
II-I-(i)
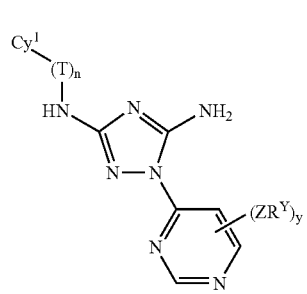
II-I-(ii)
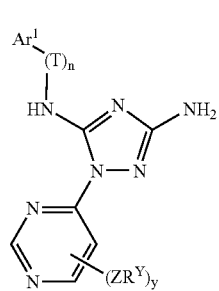
II-I-(i)'
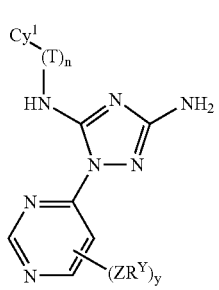
II-I-(ii)'
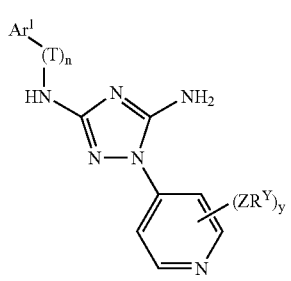
II-I'-(i)
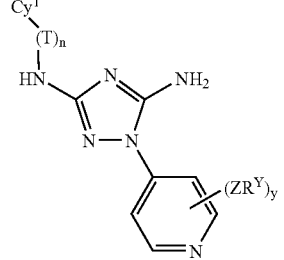
II-I'-(ii)

-continued
II-I'-(i)'
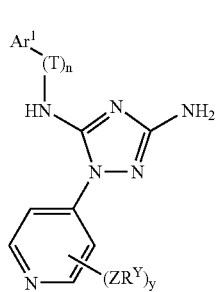
II-I'-(ii)'
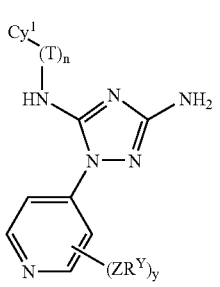
II-J-(i)
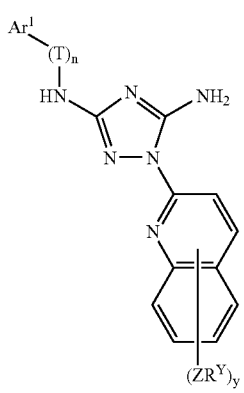
II-J-(ii)
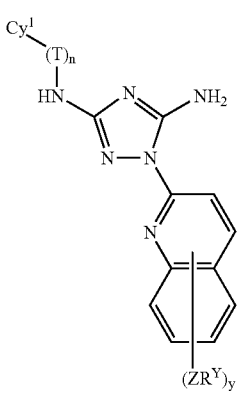
-continued
II-J-(i)'
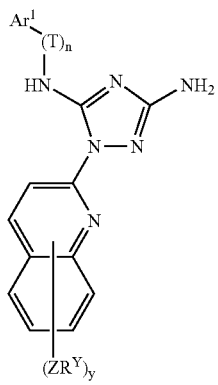
II-J-(ii)'
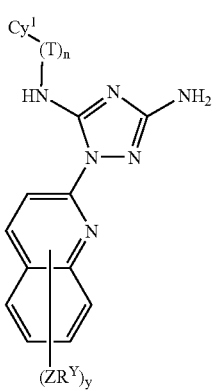
In still other preferred embodiments, $Cy^2$ is cyclohexyl and compounds have the formula II-K-(i), II-K-(ii), II-K-(i)' or II-K-(ii)':
II-K-(i)
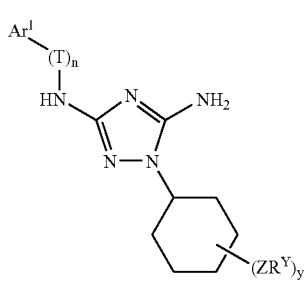
II-K-(ii)
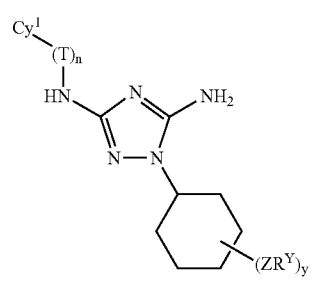

-continued

II-K-(i)'

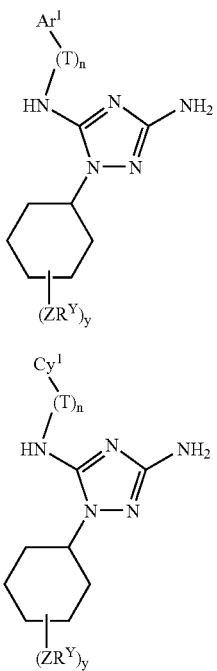

II-K-(ii)'

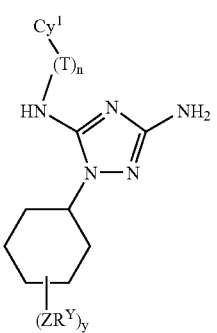

As detailed above, $Ar^2$ or $Cy^2$ can be optionally substituted at any substitutable carbon or nitrogen atom with up to 5 occurrences of $ZR^Y$. In certain preferred embodiments, y is 0-3 and thus $Ar^2$ or $Cy^2$ are each independently substituted with 0-3 occurrences of $ZR^Y$. In yet other preferred embodiments, y is 0 and $Ar^2$ or $Cy^2$ are unsubstituted.

In preferred embodiments, $ZR^Y$ groups are each independently R', halogen, CN, $NO_2$—$N(R')_2$, —$CH_2N(R')_2$, —OR', —$CH_2OR'$, —SR', —$CH_2SR'$, —COOR', —NRCOR', —$CON(R')_2$, —$SO_2N(R')_2$, —$CONR(CH_2)_2N(R')_2$, —$CONR(CH_2)_3N(R')_2$, —$CONR(CH_2)_4N(R')_2$, —$O(CH_2)_2OR'$, $O(CH_2)_3OR'$, $O(CH_2)_4OR'$, —$O(CH_2)_2N(R')_2$, —$O(CH_2)_3N(R')_2$, or —$O(CH_2)_4N(R')_2$. In other embodiments, $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, —$O(CH_2)_2$N-morpholino, —$O(CH_2)_3$N-morpholino, —$O(CH_2)_4$N-morpholino, —$O(CH_2)_2$N-piperazinyl, $O(CH_2)_3$N-piperizinyl, $O(CH_2)_4$N-piperizinyl, —$NHCH(CH_2OH)$phenyl, —$CONH(CH_2)_2$N-morpholino, —$CONH(CH_2)_2$N-piperazinyl, $CONH(CH_2)_3$N-morpholino, —$CONH(CH_2)_3$N-piperazinyl, —$CONH(CH_2)_4$N-morpholino, —$CONH(CH_2)_4$N-piperazinyl, —$SO_2NH(CH_2)_2$N-morpholino, —$SO_2NH(CH_2)_2$N-piperazinyl, —$SO_2NH(CH_2)_3$N-morpholino, —$SO_2NH(CH_2)_3$N-piperazinyl, —$SO_2NH(CH_2)_4$N-morpholino, —$SO_2NH(CH_2)_4$N-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —$COCH_2CN$, or —$COCH_3$. Exemplary $ZR^Y$ groups also include those shown below in Table 1.

It will be appreciated that certain subclasses of the foregoing compounds of formulas II, II-A-(i), II-A-(ii), II-B-(i), II-B-(ii), II-C-(i), II-C-(ii), II-D-(i), II-D-(ii), II-E-(i), II-E-(ii), II-F-(i), II-F-(ii), II-G-(i), II-G-(ii), II-G'-(i), II-G'-(ii), II-H-(i), II-H-(ii), II-I-(i), II-I-(ii), II-I'-(i), II-I'-(ii), II-J-(i), II-J-(ii), II-K-(i), II-K-(ii), II', II-A-(i)', II-A-(ii)', II-B-(i)', II-B-(ii)', II-C-(i)', II-C-(ii)', II-D-(i)', II-D-(ii)', II-E-(i)', II-E-(ii)', II-F-(i)', II-F-(ii)', II-G-(i)', II-G-(ii)', II-G'-(i)', II-G'-(ii)', II-H-(ii)', II-H-(i)', II-I-(i)', II-I-(ii)', II-I'-(i)', II-I'-(ii)', II-J-(i)', II-J-(ii)', II-K-(i)', and II-K-(ii)' are of particular interest.

For example, in certain preferred embodiments, for compounds of formulas II-A-(i), II-A-(ii), II-B-(i), II-B-(ii), II-C-(i), II-C-(ii), II-D-(i), II-D-(ii), II-A-(i)', II-A-(ii)', II-B-(i), II-B-(ii)', II-B-(ii)', II-C-(i)', II-C-(ii)', II-D-(i)', or II-D-(ii)' $Ar^2$ is phenyl, pyridyl, pyrimidinyl (more preferably 2- or 6-pyrimidinyl), quinolinyl, thiazolyl, or benzthiazolyl each optionally substituted with 0-3 occurrences of $ZR^Y$, and $Cy^2$ is cyclohexyl, optionally substituted with 0-3 occurrences of $ZR^Y$. In more preferred embodiments for compounds described above, n is 0, or n is 1 and T is $CH_2$; m is 0; x is 0-3; y is 0-3; and each occurrence of $QR^X$ or $ZR^Y$ is independently R', halogen, CN, $NO_2$—$N(R')_2$, —$CH_2N(R')_2$, —OR', —$CH_2OR'$, —SR', —$CH_2SR'$, —COOR', —NRCOR', —$CON(R')_2$, —$SO_2N(R')_2$, —$CONR(CH_2)_2N(R')_2$, —$CONR(CH_2)_3N(R')_2$, —$CONR(CH_2)_4N(R')_2$, —$O(CH_2)_2OR'$, $O(CH_2)_3OR'$, $O(CH_2)_4OR'$, —$O(CH_2)_2N(R')_2$, —$O(CH_2)_3N(R')_2$, or —$O(CH_2)_4N(R')_2$. In more preferred embodiments, $QR^X$ or $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, —$O(CH_2)_2$N-morpholino, —$O(CH_2)_3$N-morpholino, —$O(CH_2)_4$N-morpholino, —$O(CH_2)_2$N-piperazinyl, $O(CH_2)_3$N-piperizinyl, $O(CH_2)_4$N-piperizinyl, —$NHCH(CH_2OH)$phenyl, —$CONH(CH_2)_2$N-morpholino, —$CONH(CH_2)_2$N-piperazinyl, —$CONH(CH_2)_3$N-morpholino, —$CONH(CH_2)_3$N-piperazinyl, —$CONH(CH_2)_4$N-morpholino, —$CONH(CH_2)_4$N-piperazinyl, —$SO_2NH(CH_2)_2$N-morpholino, —$SO_2NH(CH_2)_2$N-piperazinyl, —$SO_2NH(CH_2)_3$N-morpholino, —$SO_2NH(CH_2)_3$N-piperazinyl, —$SO_2NH(CH_2)_4$N-morpholino, —$SO_2NH(CH_2)_4$N-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —$COCH_2CN$, or —$COCH_3$.

For compounds of formulas II-E-(i), II-E-(ii), II-F-(i), II-F-(ii), II-G-(i), II-G-(ii), II-G'-(i), II-G'-(ii), II-H-(i), II-H-(ii), II-I-(i), II-I-(ii), II-I'-(i), II-I'-(ii), II-J-(i), II-J-(ii), II-K-(i), II-K-(ii), II-E-(i)', II-E-(ii)', II-F-(i)', II-F-(ii)', II-G-(i)', II-G-(ii)', II-G'-(i)', II-G'-(ii)', II-H-(ii)', II-H-(i)', II-I-(i)', II-I-(ii)', II-I'-(i)', II-I'-(ii)', II-J-(i)', II-J-(ii)', II-K-(i)', or II-K-(ii)', $Ar^1$ is an optionally substituted group selected from phenyl, and $Cy^1$ is selected from cyclohexyl, furanyl, or cyclopropyl, optionally substituted with 0-3 occurrences of $QR^X$. In more preferred embodiments for compounds described above, n is 0, or n is 1 and T is $CH_2$; x is 0-3; y is 0-3; and each occurrence of $QR^X$ or $ZR^Y$ is independently R', halogen, CN, NO$_2$—N(R')$_2$, —CH$_2$N(R')$_2$, —OR', —CH$_2$OR', —SR', —CH$_2$SR', —COOR', —NRCOR', —CON(R')$_2$, —SO$_2$N(R')$_2$, —CONR(CH$_2$)$_2$N(R')$_2$, —CONR(CH$_2$)$_3$N(R')$_2$, —CONR(CH$_2$)$_4$N(R')$_2$, —O(CH$_2$)$_2$OR', O(CH$_2$)$_3$OR', O(CH$_2$)$_4$OR', —O(CH$_2$)$_2$N(R')$_2$, —O(CH$_2$)$_3$N(R')$_2$, or —O(CH$_2$)$_4$N(R')$_2$. In more preferred embodiments, QR$^X$ or ZR$^Y$ groups are each independently Cl, Br, F, CF$_3$, Me, Et, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, —O(CH$_2$)$_2$N-morpholino, —O(CH$_2$)$_3$N-morpholino, —O(CH$_2$)$_4$N-morpholino, —O(CH$_2$)$_2$N-piperazinyl, O(CH$_2$)$_3$N-piperizinyl, O(CH$_2$)$_4$N-piperizinyl, —NHCH(CH$_2$OH)phenyl, —CONH(CH$_2$)$_2$N-morpholino, —CONH(CH$_2$)$_2$N-piperazinyl, —CONH(CH$_2$)$_3$N-morpholino, —CONH(CH$_2$)$_3$N-piperazinyl, —CONH(CH$_2$)$_4$N-morpholino, —CONH(CH$_2$)$_4$N-piperazinyl, —SO$_2$NH(CH$_2$)$_2$N-morpholino, —SO$_2$NH(CH$_2$)$_2$N-piperazinyl, —SO$_2$NH(CH$_2$)$_3$N-morpholino, —SO$_2$NH(CH$_2$)$_3$N-piperazinyl, —SO$_2$NH(CH$_2$)$_4$N-morpholino, —SO$_2$NH(CH$_2$)$_4$N-piperazinyl, where each of the foregoing phenyl, morpholino, piperazinyl, or piperidinyl groups is optionally substituted, or an optionally substituted group selected from C$_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —COCH$_2$CN, or —COCH$_3$.

In still other embodiments, compounds are provided having one of the formulae:

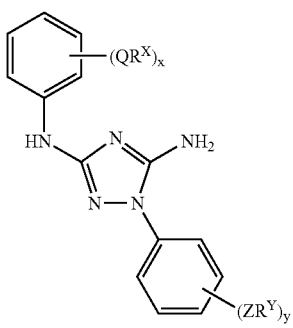

III

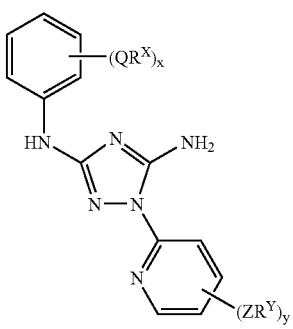

IV

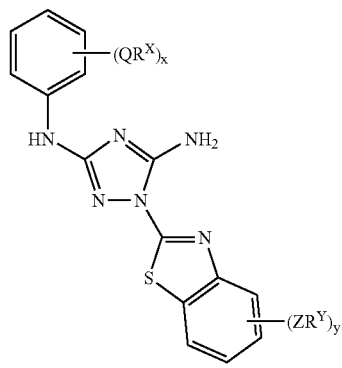

V

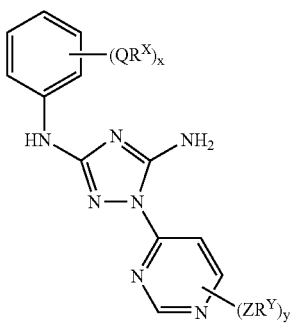

VI

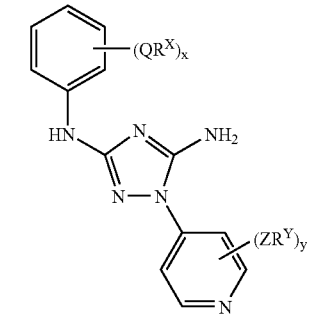

VII

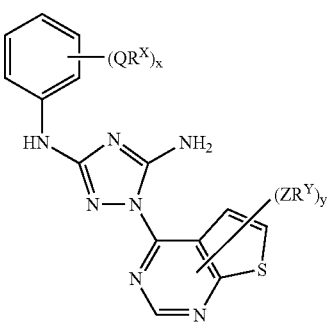

VIII

-continued

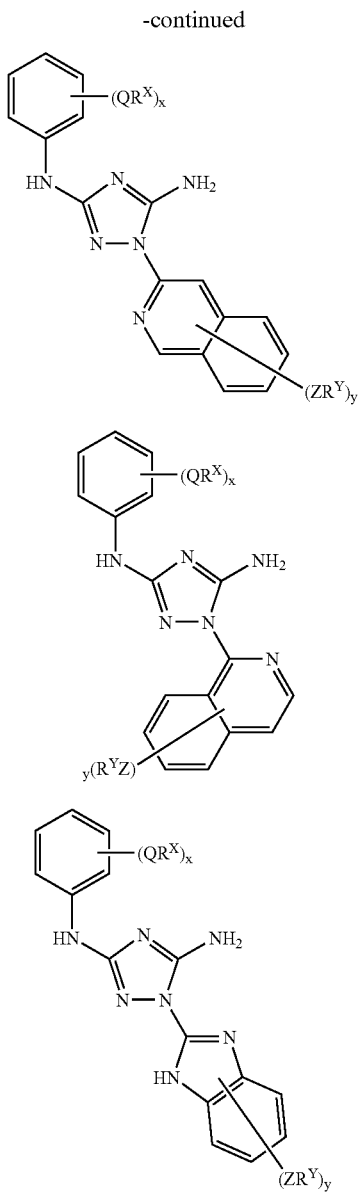

In certain preferred embodiments, for compounds of formulae III, IV, V, VI, VII, VIII, IX, X, or XI, x is 0-3; y is 0-3; and each occurrence of $QR^X$ or $ZR^Y$ is independently R', halogen, CN, $NO_2$—$N(R')_2$, —$CH_2N(R')_2$, —OR', —$CH_2OR'$, —SR', —$CH_2SR'$, —COOR', —NRCOR', —$CON(R')_2$, —$SO_2N(R')_2$, —$CONR(CH_2)_2N(R')_2$, —$CONR(CH_2)_3N(R')_2$, —$CONR(CH_2)_4N(R')_2$, —$O(CH_2)_2$ OR', $O(CH_2)_3OR'$, $O(CH_2)_4OR'$, —$O(CH_2)_2N(R')_2$, —$O(CH_2)_3N(R')_2$, or —$O(CH_2)_4N(R')_2$. In more preferred embodiments, $QR^X$ or $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, —$O(CH_2)_2$N-morpholino, —$O(CH_2)_3$N-morpholino, —$O(CH_2)_4$N-morpholino, —$O(CH_2)_2$N-piperazinyl, $O(CH_2)_3$N-piperizinyl, $O(CH_2)_4$N-piperizinyl, —$NHCH(CH_2OH)$phenyl, —$CONH(CH_2)_2$N-morpholino, —$CONH(CH_2)_2$N-piperazinyl, —$CONH(CH_2)_3$N-morpholino, —$CONH(CH_2)_3$N-piperazinyl, —$CONH(CH_2)_4$N-morpholino, —$CONH(CH_2)_4$N-piperazinyl, —$SO_2NH(CH_2)_2$N-morpholino, —$SO_2NH(CH_2)_2$N-piperazinyl, —$SO_2NH(CH_2)_3$N-morpholino, —$SO_2NH(CH_2)_3$N-piperazinyl, —$SO_2NH(CH_2)_4$N-morpholino, —$SO_2NH(CH_2)_4$N-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —$COCH_2CN$, or —$COCH_3$.

In still other embodiments, compounds of formulae III, VI, VIII, IX, X, and XI (including subsets thereof) are preferred as inhibitors of PDK-1.

In yet other embodiments, compounds of formulae VI and VII (including subsets thereof) are preferred as inhibitors of JAK-3. In certain preferred embodiments, compounds of formulae VI and VII useful as inhibitors of JAK-3 are substituted with at least one occurrence of $ZR^Y$, where $ZR^Y$ is N(R') and compounds have the structure:

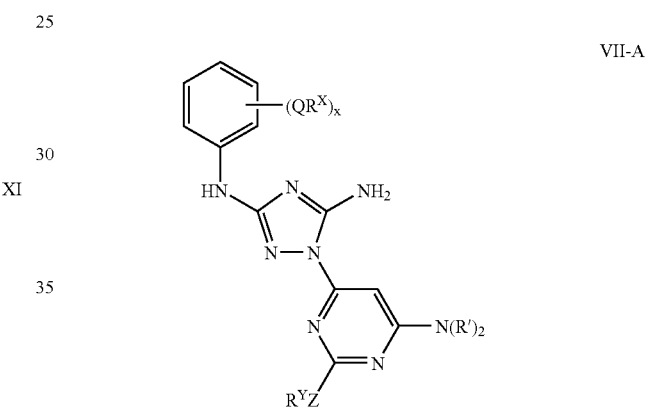

In still other embodiments, compounds of formulae III, IV, VI and VII (including subsets thereof) are preferred as inhibitors of FLT-3.

Certain other classes of special interest for compounds of formula I include bi- or tricyclic triazole compounds wherein:

$R^1$ and $R^2$ are as defined generally above and in classes and subclasses herein;

$R^4$ is hydrogen or $C_{1-6}$alkyl;

$R^3$ and $R^5$, taken together form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur;

$R^3$ and $R^5$, taken together form an optionally substituted group selected from a 5-7-membered saturated, partially unsaturated, or fully unsaturated monocyclic ring having 0-3 heteroatoms independently selected from nitrogen, oxygen, or sulfur, or an 8-10-membered saturated, partially unsaturated, or fully unsaturated bicyclic ring system having 0-3 heteroatoms independently selected from nitrogen, oxygen, or sulfur; and wherein any ring formed R³ and R⁵ taken together, is optionally substituted with up to five substituents selected from W—R$^W$; wherein W is a bond or is a $C_1$-$C_6$ alkylidene chain wherein up to two methylene units of W are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NR-CONR—, —OCONR—, —NRNR—, —NRSO$_2$NR—, —SO—, —SO$_2$—, —PO—, —PO$_2$—, or —POR—; and each occurrence of R$^W$ is independently R', halogen, NO$_2$, CN, OR', SR', N(R')$_2$, NR'COR', NR'CONR'$_2$, NR'CO$_2$R', COR', CO$_2$R', OCOR', CON(R')$_2$, OCON(R')$_2$, SOR', SO$_2$R', SO$_2$N(R')$_2$, NR'SO$_2$R', NR'SO$_2$N(R')$_2$, COCOR', or COCH$_2$COR'.

In certain embodiments, compounds described directly above include one of more of or all of the following limitations:

a) compounds of formula I exclude those compounds having the general structure:

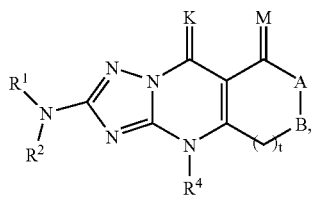

wherein R¹, R², and R³ are as defined above, M and K are O or H$_2$, provided that K and M are different, A and B are each —CH$_2$—, —NH—, —N-alkyl-, N-aralkyl-, —NCOR$^a$, —NCONHR$^b$, or —NCSNHR$^b$, wherein R$^a$ is lower alkyl or aralkyl, and R$^b$ is straight or branched chain alkyl, aralkyl, or aryl which can either be unsubstituted or substituted with one or more alkyl and/or haloalkyl substituents;

b) compounds of formula I exclude those compounds having the general structure:

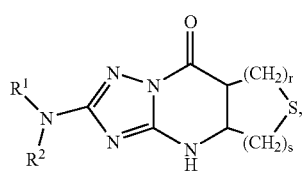

wherein R¹ and R² are as defined above, and r and s are each independently 0, 1, 2, 3, or 4, provided that the sum of s and r is at least 1;

c) compounds of formula I exclude any one or more of, or all of the following compounds:

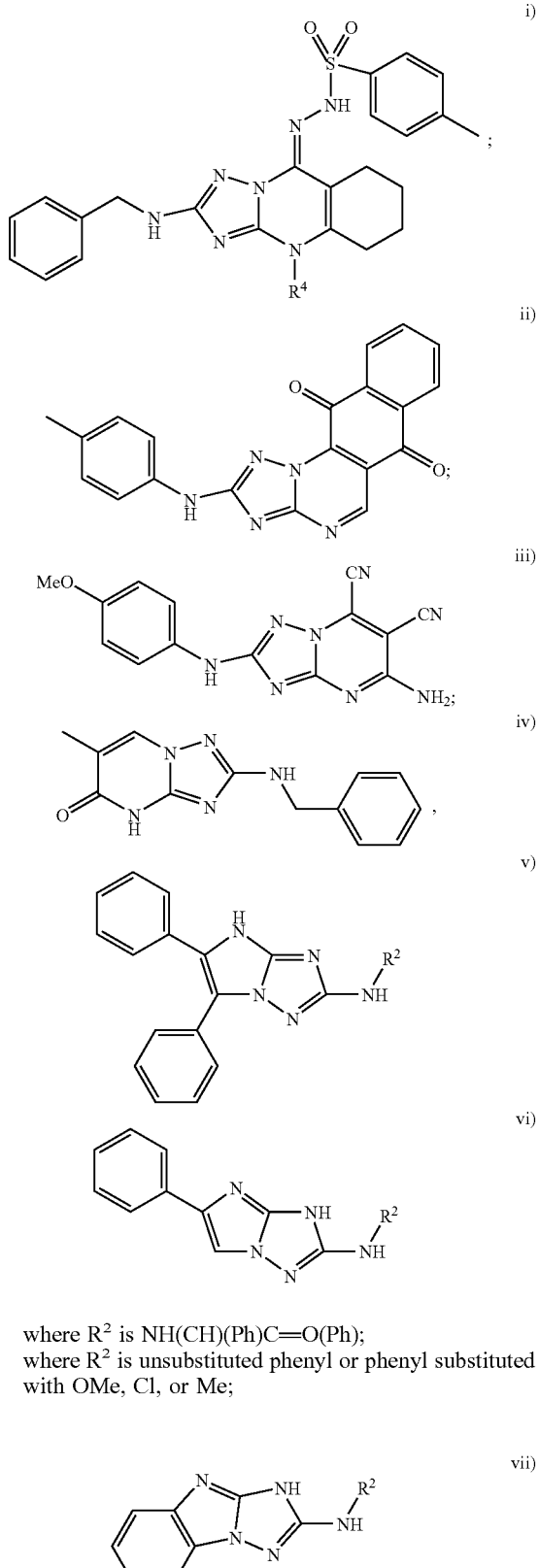

where R² is NH(CH)(Ph)C═O(Ph);
where R² is unsubstituted phenyl or phenyl substituted with OMe, Cl, or Me;

where R² is unsubstituted phenyl or phenyl substituted with OMe, Cl, Me, OMe, or R² is unsubstituted benzyl;

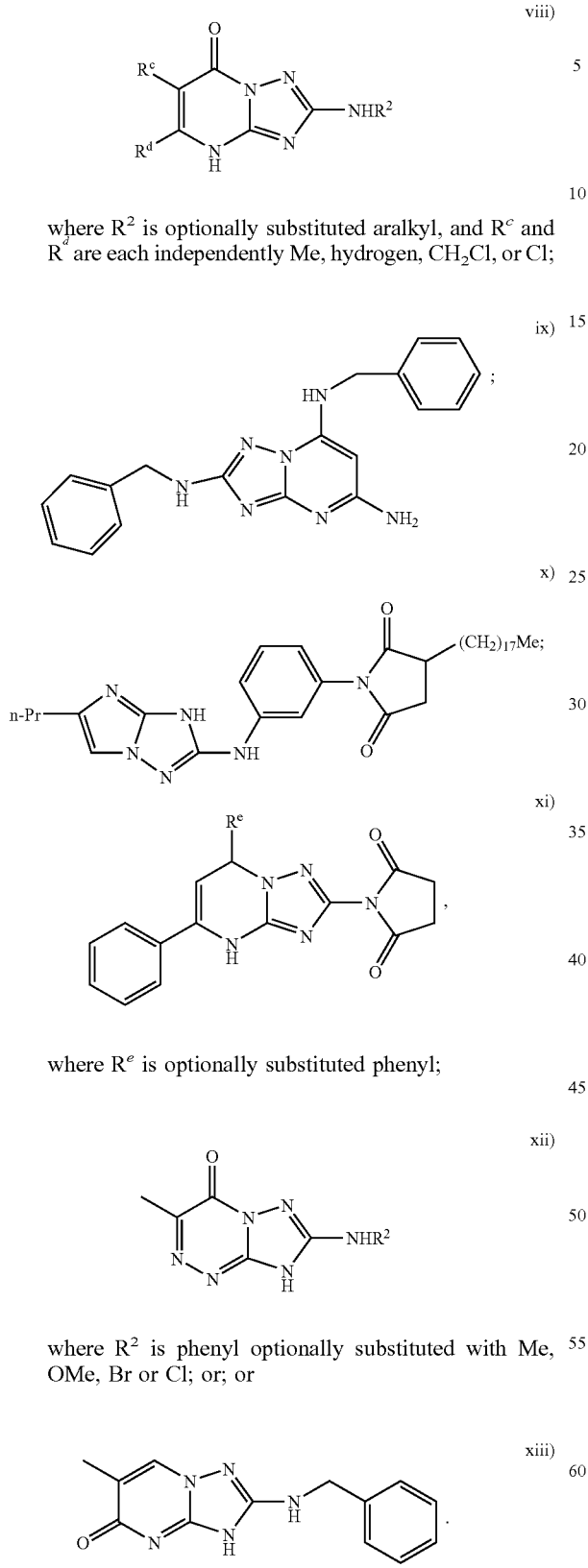
where R² is optionally substituted aralkyl, and R^c and R^d are each independently Me, hydrogen, CH₂Cl, or Cl;
where R^e is optionally substituted phenyl;
where R² is phenyl optionally substituted with Me, OMe, Br or Cl; or; or
In certain preferred embodiments, compounds have one of the following formulas:
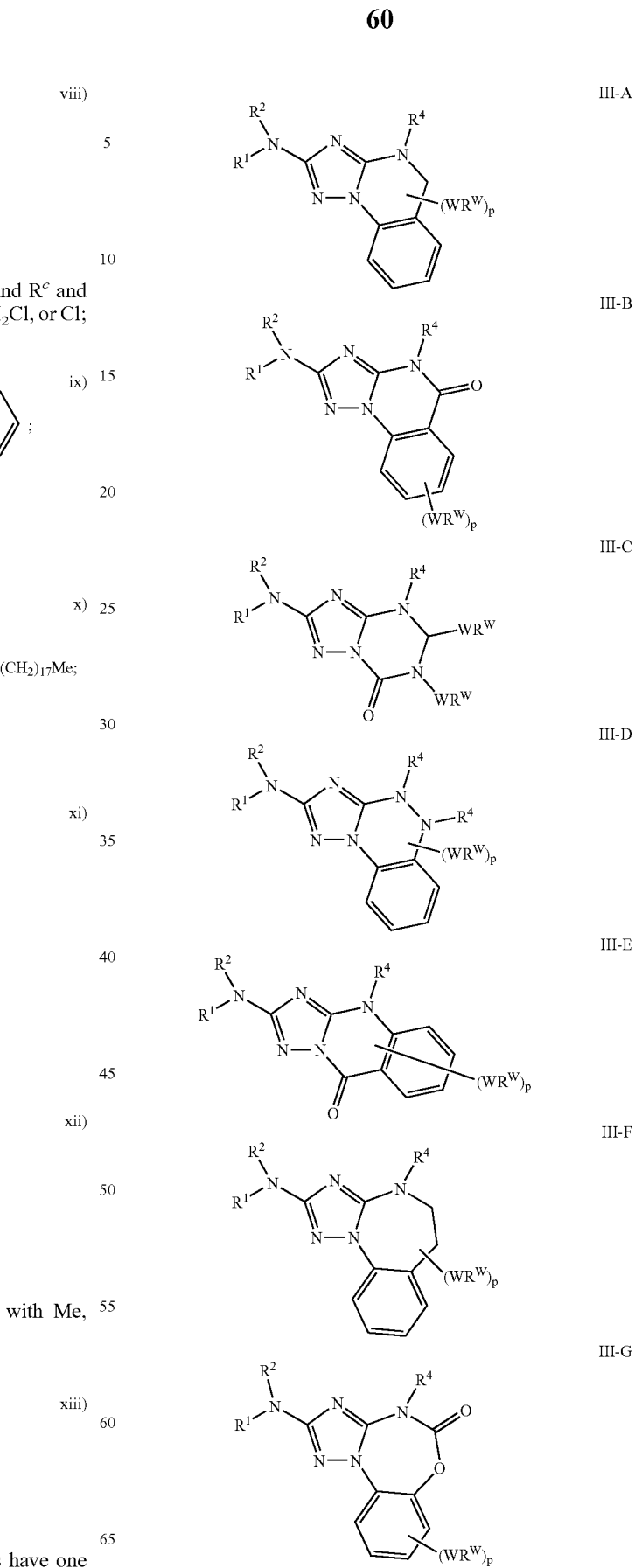

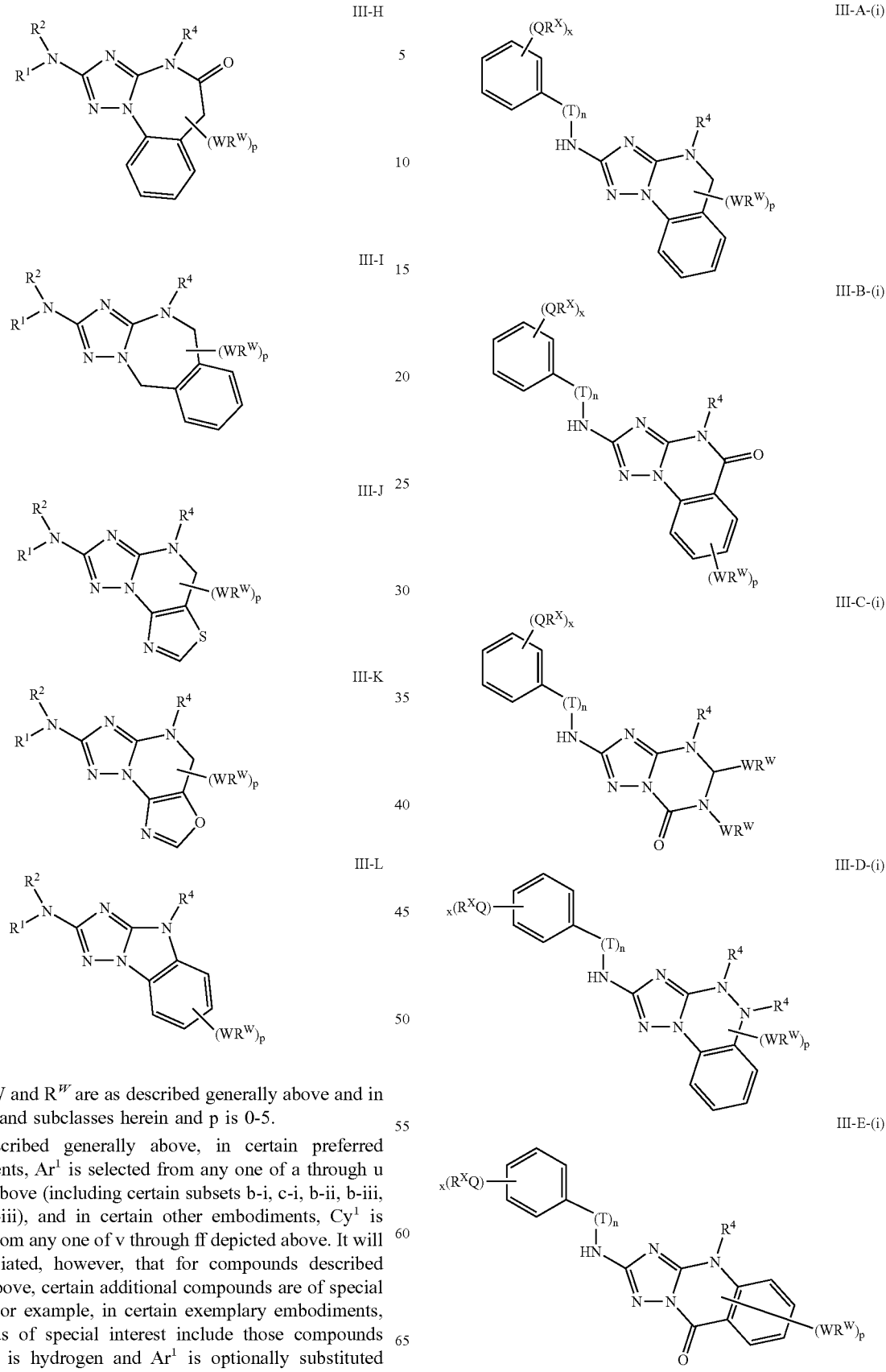

wherein W and $R^W$ are as described generally above and in classes and subclasses herein and p is 0-5.

As described generally above, in certain preferred embodiments, $Ar^1$ is selected from any one of a through u depicted above (including certain subsets b-i, c-i, b-ii, b-iii, c-ii, or c-iii), and in certain other embodiments, $Cy^1$ is selected from any one of v through ff depicted above. It will be appreciated, however, that for compounds described directly above, certain additional compounds are of special interest. For example, in certain exemplary embodiments, compounds of special interest include those compounds where $R^1$ is hydrogen and $Ar^1$ is optionally substituted phenyl.

-continued

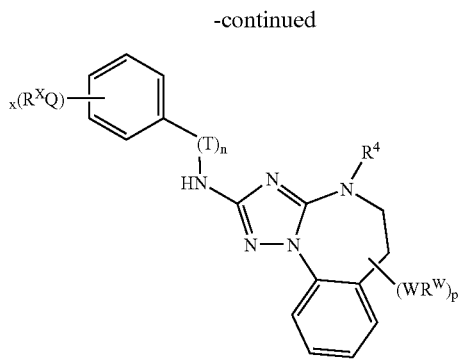

III-F-(i)

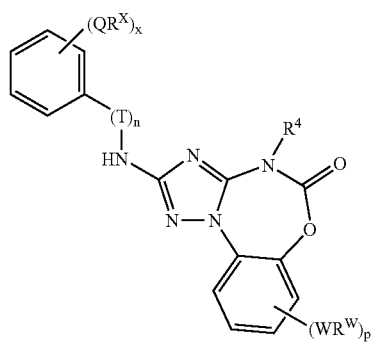

III-G-(i)

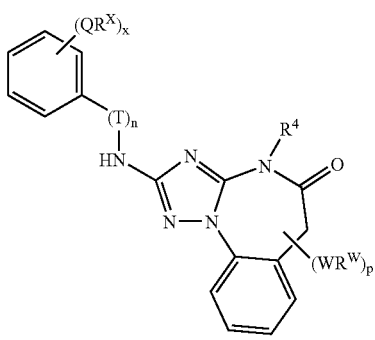

III-H-(i)

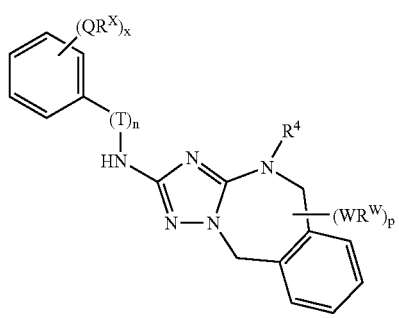

III-I-(i)

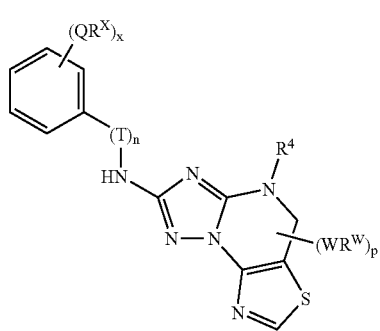

III-J-(i)

-continued

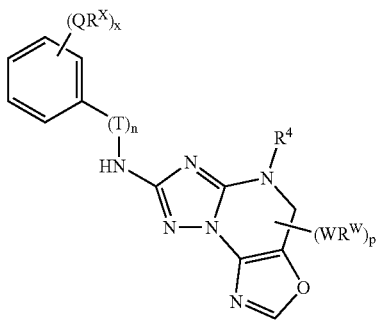

III-K-(i)

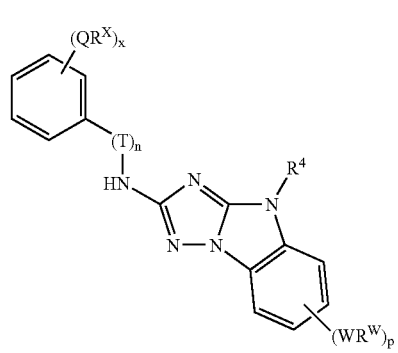

III-L-(i)

It will be appreciated that for compounds as described above, certain additional compounds are of special interest. For example, in certain other exemplary embodiments, compounds of special interest include those compounds where $R^1$ is hydrogen and $Ar^1$ is optionally substituted pyridyl.

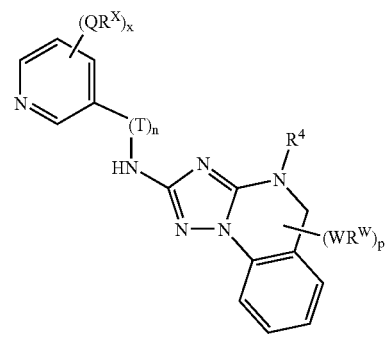

III-A-(ii)

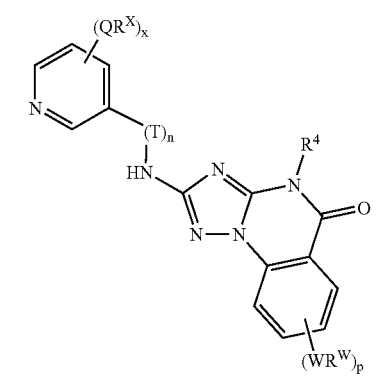

III-B-(ii)

-continued
III-C-(ii)
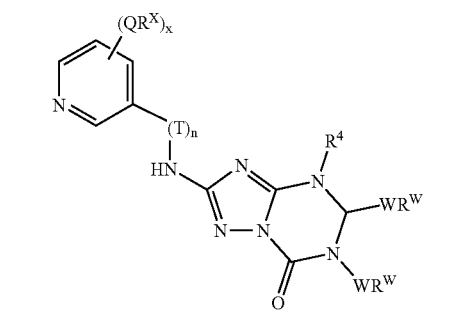
III-D-(ii)
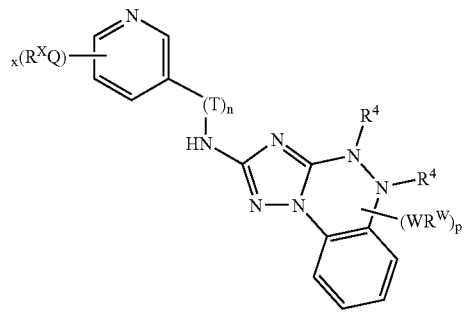
III-E-(ii)
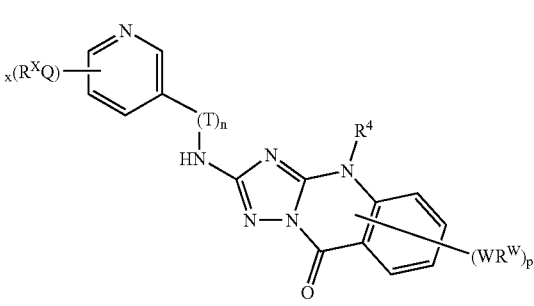
III-F-(ii)
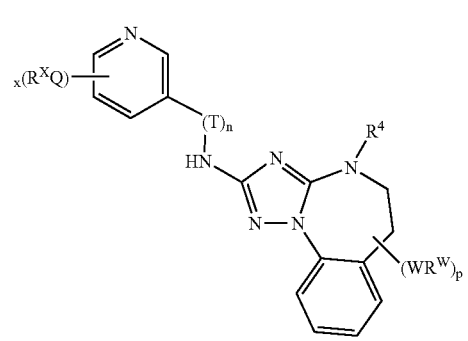
III-G-(ii)
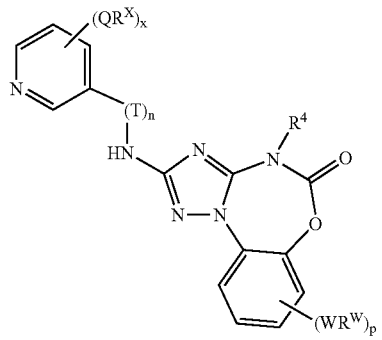
III-H-(ii)
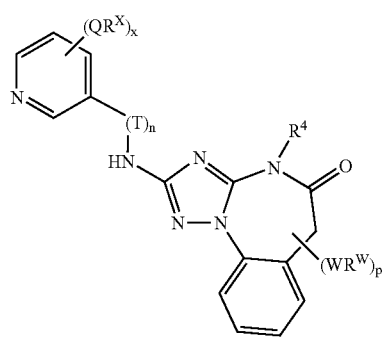
III-I-(ii)
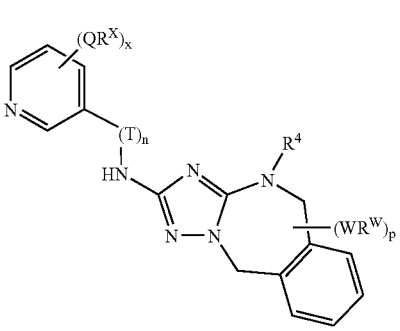
III-J-(ii)
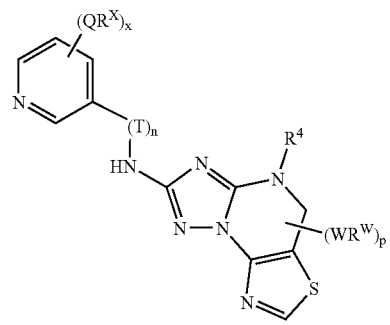
III-K-(ii)
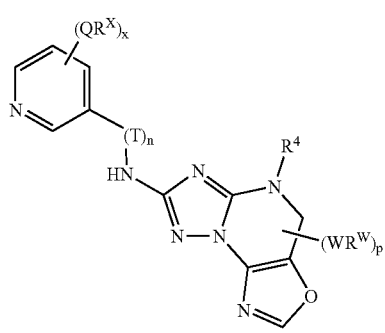

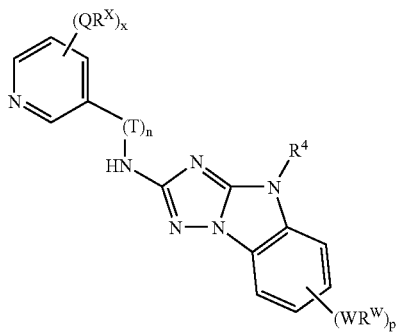

III-L-(ii)

It will be appreciated that for compounds as described above, certain additional compounds are of special interest. For example, in certain other exemplary embodiments, compounds of special interest include those compounds where $R^1$ is hydrogen and $Ar^1$ is optionally substituted cyclohexyl.

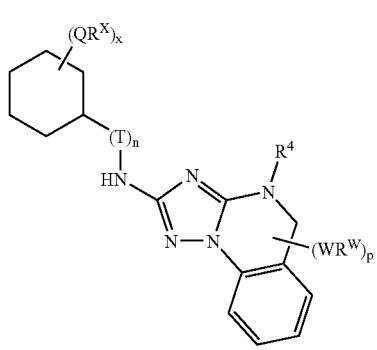

III-A-(iii)

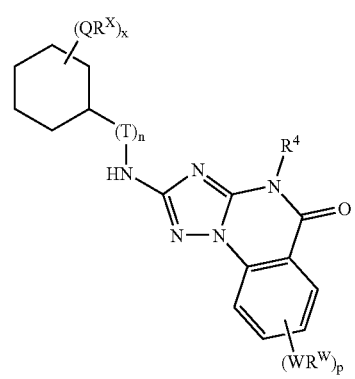

III-B-(iii)

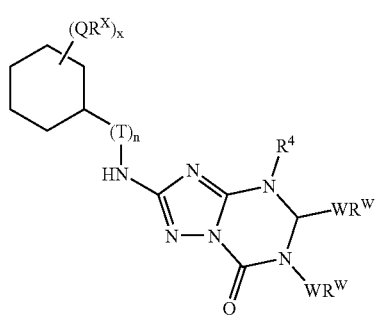

III-C-(iii)

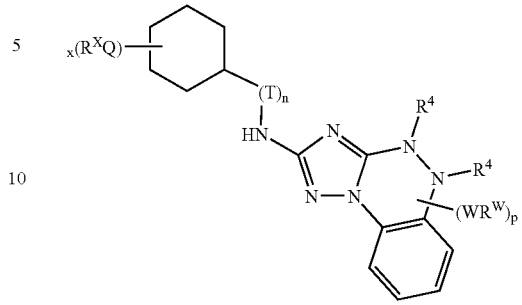

III-D-(iii), III-E-(iii), III-F-(iii)

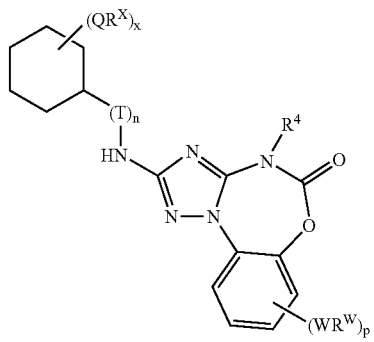

III-G-(iii)

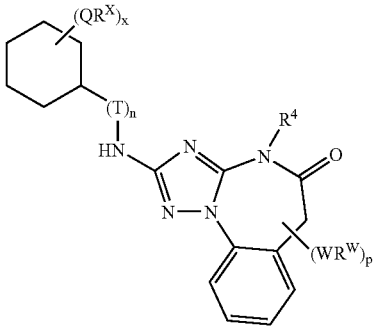

III-H-(iii)

-continued

III-I-(iii)
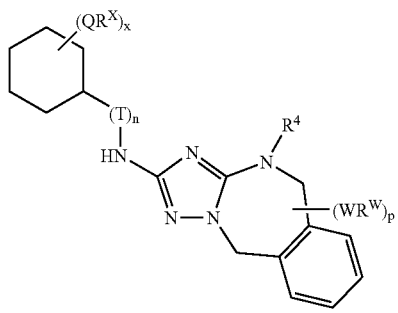

III-J-(iii)
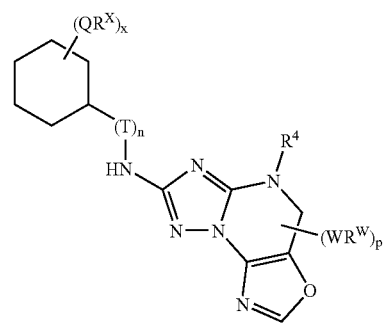

III-K-(iii)
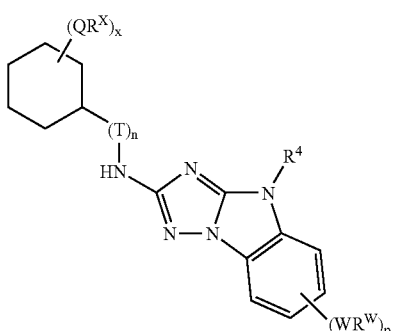

III-L-(iii)
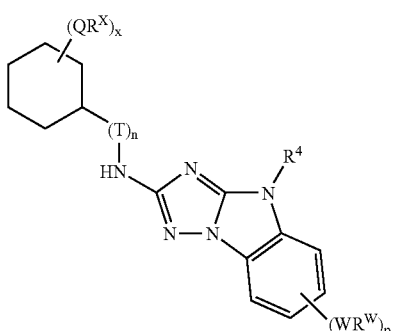

It will be appreciated that for compounds as described above, certain additional compounds are of special interest. For example, in still other exemplary embodiments, compounds of special interest include those compounds where $R^1$ is hydrogen and $Ar^1$ is optionally substituted tetrahydrofuryl.

III-A-(iv)
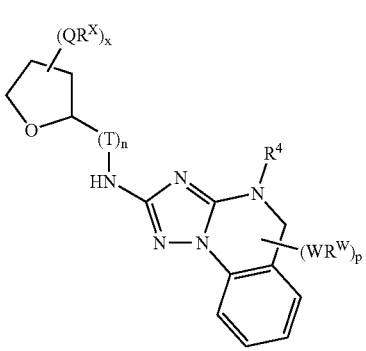

III-B-(iv)
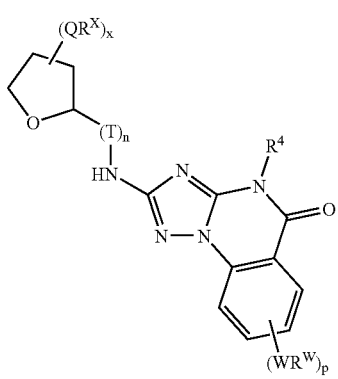

III-C-(iv)
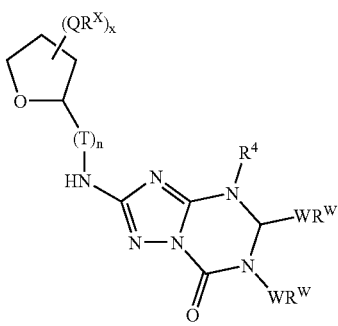

III-D-(iv)
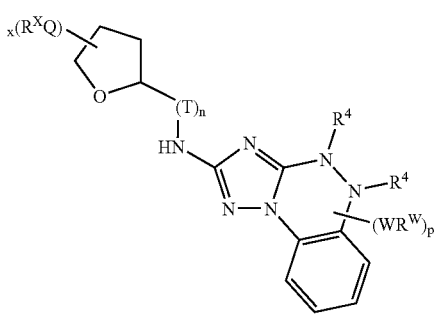

-continued

III-E-(iv)
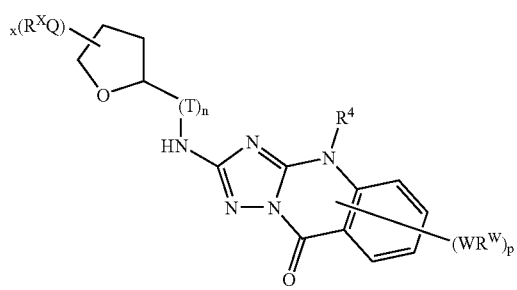

III-F-(iv)
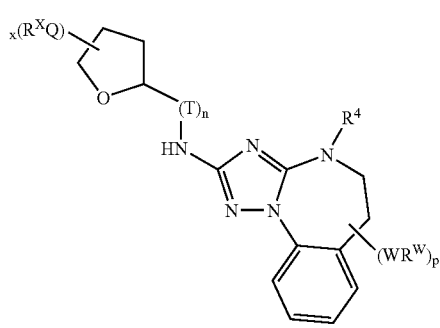

III-G-(iv)
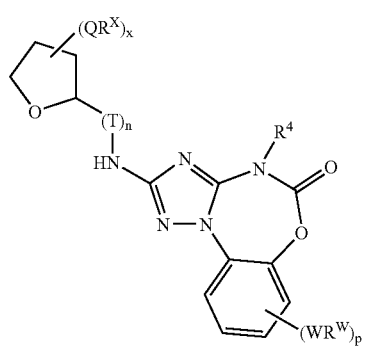

III-H-(iv)
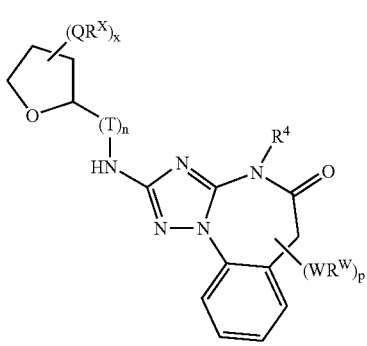

III-I-(iv)
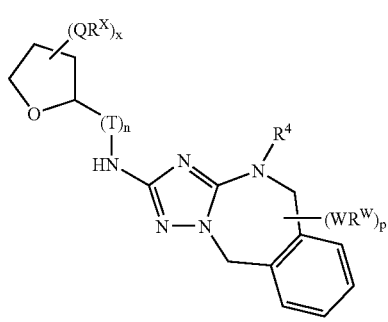

-continued

III-J-(iv)
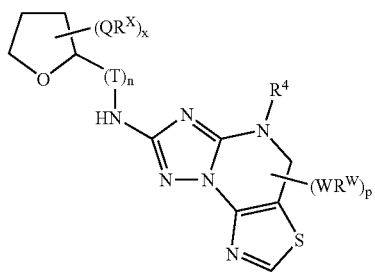

III-K-(iv)
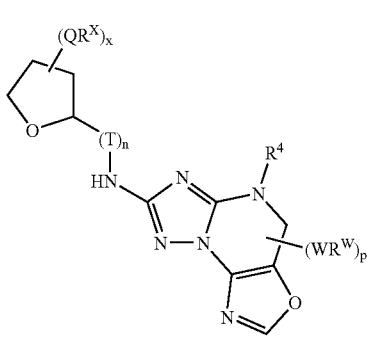

III-L-(iv)
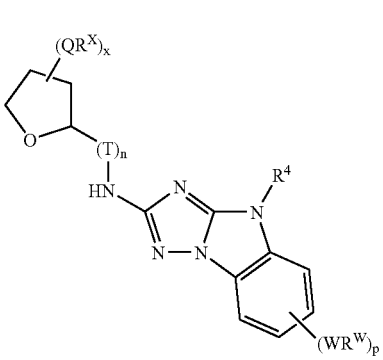

It will be appreciated that for compounds as described above, certain additional compounds are of special interest. For example, in yet other exemplary embodiments, compounds of special interest include those compounds where $R^1$ is hydrogen and $Ar^1$ is optionally substituted cyclopropyl.

III-A-(v)
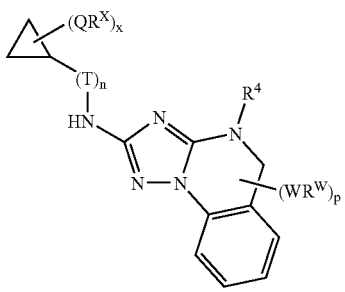

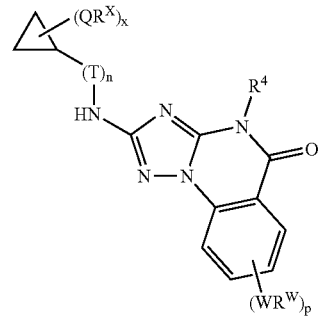
III-B-(v)
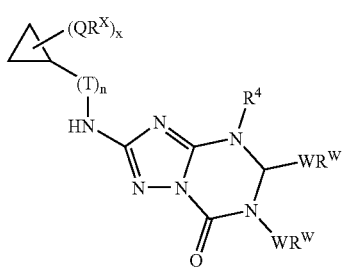
III-C-(v)
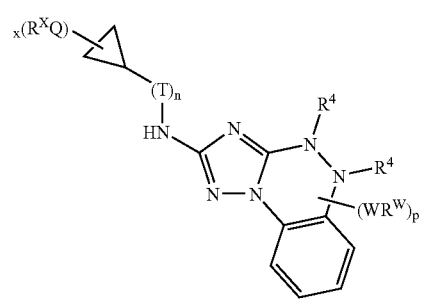
III-D-(v)
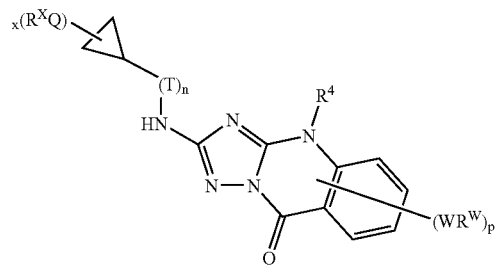
III-E-(v)
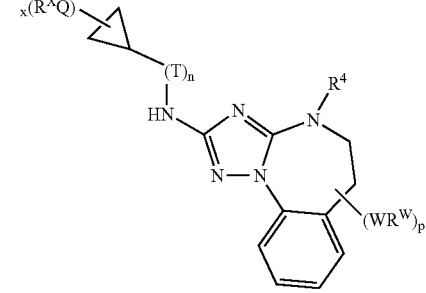
III-F-(v)
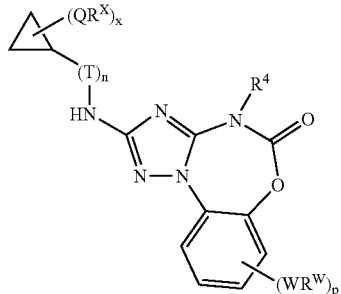
III-G-(v)
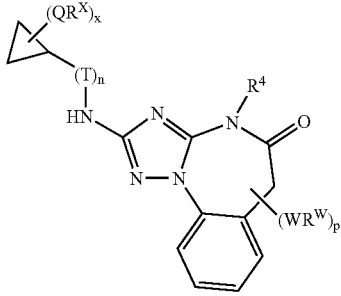
III-H-(v)
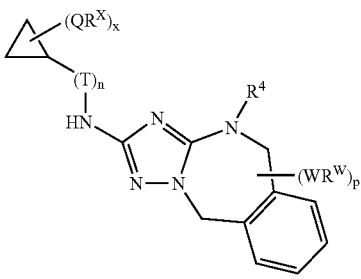
III-I-(v)
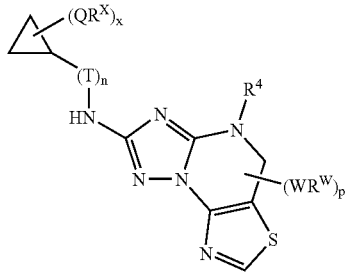
III-J-(v)
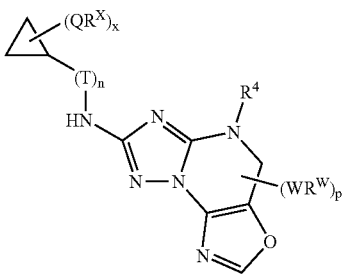
III-K-(v)

-continued

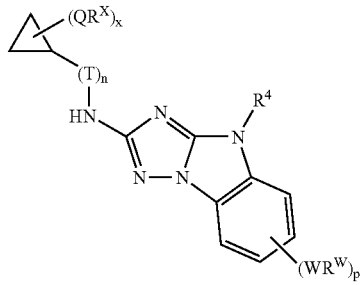

III-L-(v)

As detailed above, any ring formed by $R^3$ and $R^5$ taken together can be optionally substituted with up to 5 occurrences of $WR^W$. In certain preferred embodiments, p is 0-3. In still other preferred embodiments, p is 0 and the ring formed by $R^3$ and $R^5$ is unsubstituted.

In preferred embodiments, $WR^W$ groups are each independently R', halogen, CN, $NO_2$—$N(R')_2$, —$CH_2N(R')_2$, —OR', —$CH_2OR'$, —SR', —$CH_2SR'$, —COOR', —NRCOR', —$CON(R')_2$, —$SO_2N(R')_2$, —$CONR(CH_2)_2N(R')_2$, —$CONR(CH_2)_3N(R')_2$, —$CONR(CH_2)_4N(R')_2$, —$O(CH_2)_2OR'$, $O(CH_2)_3OR'$, $O(CH_2)_4OR'$, —$O(CH_2)_2N(R')_2$, —$O(CH_2)_3N(R')_2$, or —$O(CH_2)_4N(R')_2$. In other embodiments, $WR^W$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, —$O(CH_2)_2N$-morpholino, —$O(CH_2)_3N$-morpholino, —$O(CH_2)_4N$-morpholino, —$O(CH_2)_2N$-piperazinyl, $O(CH_2)_3N$-piperizinyl, $O(CH_2)_4N$-piperizinyl, —$NHCH(CH_2OH)$phenyl, —$CONH(CH_2)_2N$-morpholino, —$CONH(CH_2)_2N$-piperazinyl, —$CONH(CH_2)_3N$-morpholino, —$CONH(CH_2)_3N$-piperazinyl, —$CONH(CH_2)_4N$-morpholino, —$CONH(CH_2)_4N$-piperazinyl, —$SO_2NH(CH_2)_2N$-morpholino, —$SO_2NH(CH_2)_2N$-piperazinyl, —$SO_2NH(CH_2)_3N$-morpholino, —$SO_2NH(CH_2)_3N$-piperazinyl, —$SO_2NH(CH_2)_4N$-morpholino, —$SO_2NH(CH_2)_4N$-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —$COCH_2CN$, or —$COCH_3$. Exemplary $ZR^W$ groups also include those shown below in Table 1.

In more preferred embodiments for compounds described above, n is 0, or n is 1 and T is $CH_2$; p is 0-3; y is 0-3; and each occurrence of $WR^W$ or $ZR^Y$ is independently R', halogen, CN, $NO_2$—$N(R')_2$, —$CH_2N(R')_2$, —OR', —$CH_2OR'$, —SR', —$CH_2SR'$, —COOR', —NRCOR', —$CON(R')_2$, —$SO_2N(R')_2$, —$CONR(CH_2)_2N(R')_2$, —$CONR(CH_2)_3N(R')_2$, —$CONR(CH_2)_4N(R')_2$, —$O(CH_2)_2OR'$, $O(CH_2)_3OR'$, $O(CH_2)_4OR'$, —$O(CH_2)_2N(R')_2$, —$O(CH_2)_3N(R')_2$, or —$O(CH_2)_4N(R')_2$.

In more preferred embodiments, $WR^W$ or $ZR^Y$ groups are each independently Cl, Br, F, $CF_3$, Me, Et, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, methylenedioxy, ethylenedioxy, —$O(CH_2)_2N$-morpholino, —$O(CH_2)_3N$-morpholino, —$O(CH_2)_4N$-morpholino, —$O(CH_2)_2N$-piperazinyl, $O(CH_2)_3N$-piperizinyl, $O(CH_2)_4N$-piperizinyl, —$NHCH(CH_2OH)$phenyl, —$CONH(CH_2)_2N$-morpholino, —$CONH(CH_2)_2N$-piperazinyl, —$CONH(CH_2)_3N$-morpholino, —$CONH(CH_2)_3N$-piperazinyl, —$CONH(CH_2)_4N$-morpholino, —$CONH(CH_2)_4N$-piperazinyl, —$SO_2NH(CH_2)_2N$-morpholino, —$SO_2NH(CH_2)_2N$-piperazinyl, —$SO_2NH(CH_2)_3N$-morpholino, —$SO_2NH(CH_2)_3N$-piperazinyl, —$SO_2NH(CH_2)_4N$-morpholino, —$SO_2NH(CH_2)_4N$-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy. In some embodiments, the nitrogen atom of a piperidinyl or piperazinyl group is optionally substituted with —COR'. In certain other embodiments, the nitrogen atom of a piperidinyl or piperazinyl group is optionally substituted with —$COCH_2CN$, or —$COCH_3$.

In other preferred embodiments, $R^4$ is hydrogen or $C_{1-4}$alkyl. In more preferred embodiments, $R^4$ is hydrogen or methyl. In most preferred embodiments, $R^4$ is hydrogen.

Representative examples of compounds of formula I are set forth below in Table 1.

TABLE 1

Examples of Compounds of Formula I:

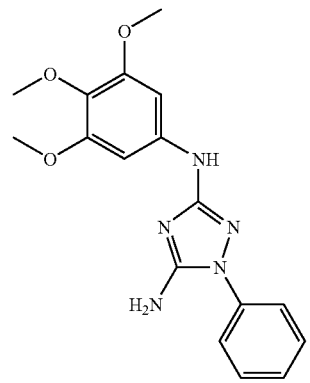

I-1

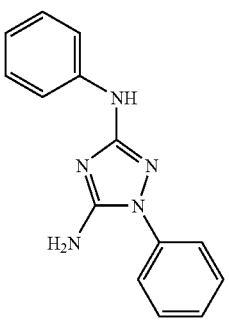

I-2

TABLE 1-continued
Examples of Compounds of Formula I:
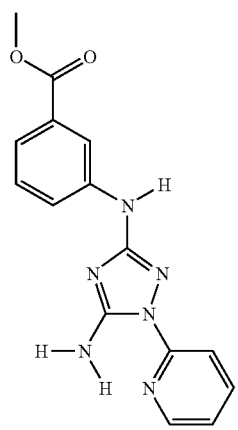
I-3
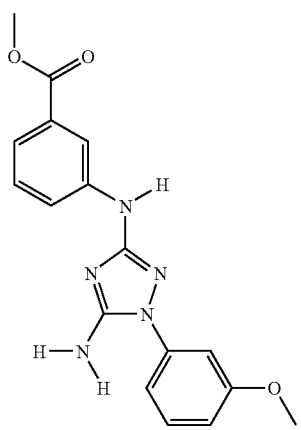
I-4
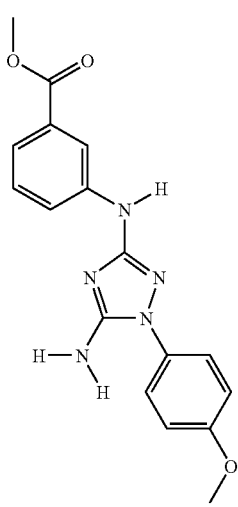
I-5
TABLE 1-continued
Examples of Compounds of Formula I:
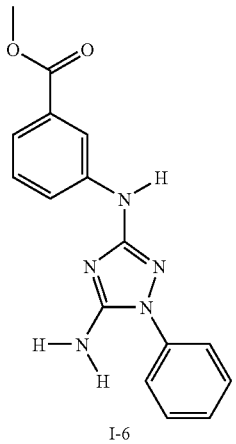
I-6
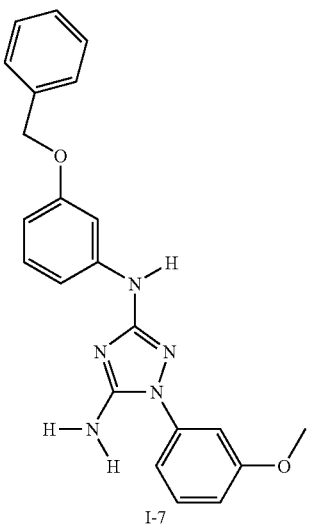
I-7
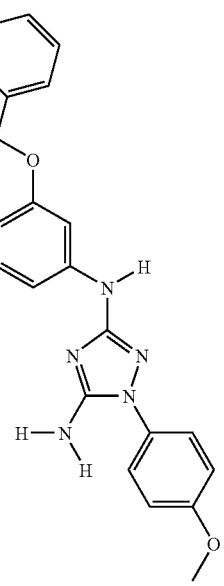
I-8

TABLE 1-continued
Examples of Compounds of Formula I:
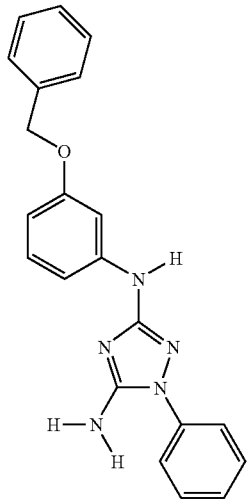
I-9
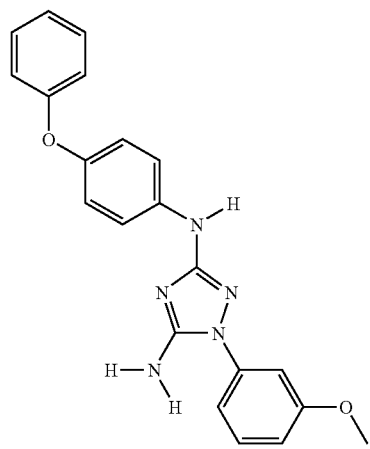
I-10
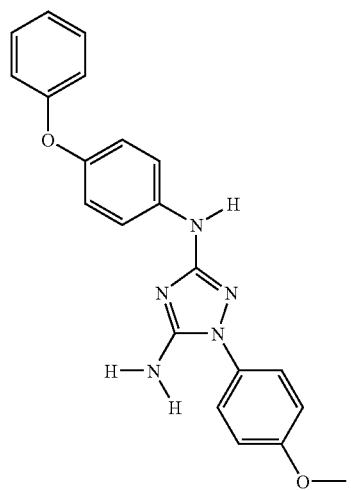
I-11
TABLE 1-continued
Examples of Compounds of Formula I:
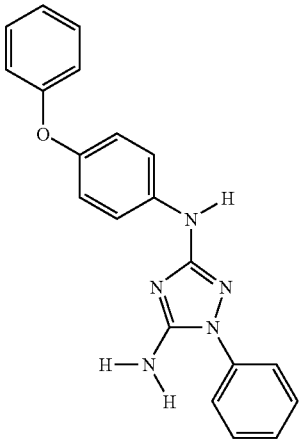
I-12
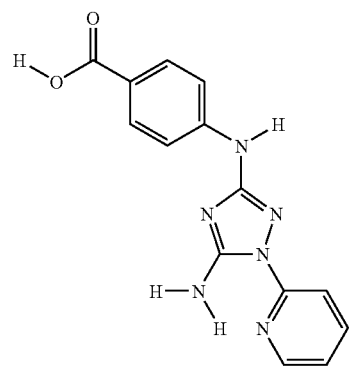
I-13
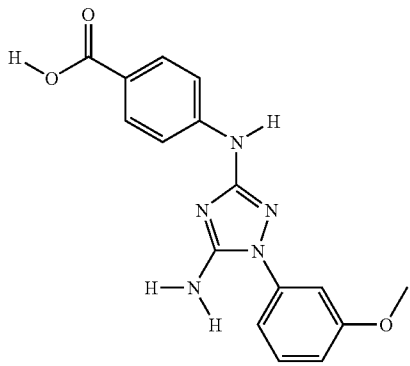
I-14

TABLE 1-continued
Examples of Compounds of Formula I:
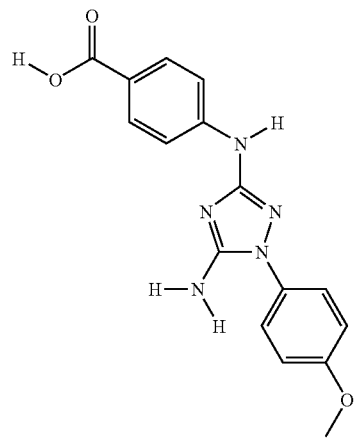
I-15
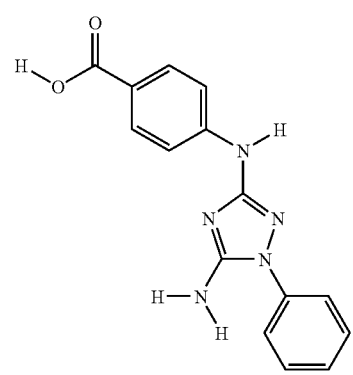
I-16
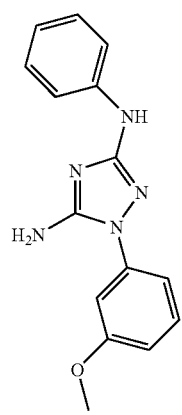
I-17
TABLE 1-continued
Examples of Compounds of Formula I:
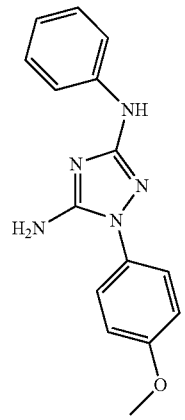
I-18
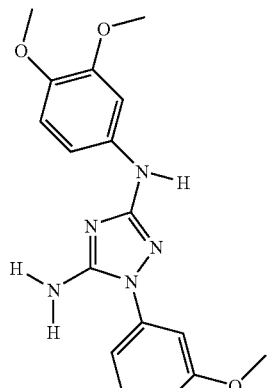
I-19
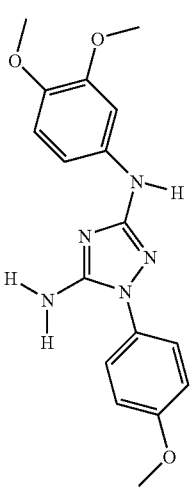
I-20

TABLE 1-continued
Examples of Compounds of Formula I:
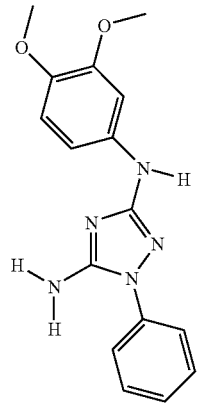
I-21
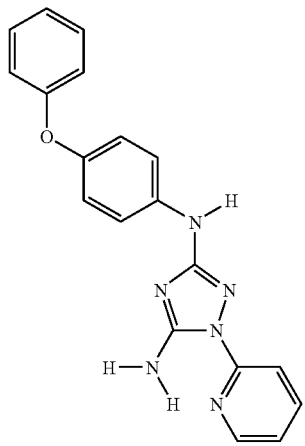
I-22
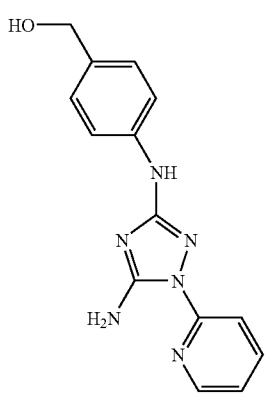
I-23
TABLE 1-continued
Examples of Compounds of Formula I:
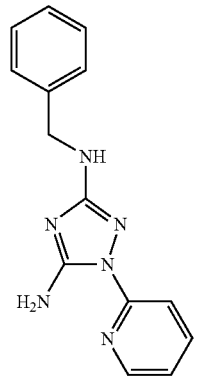
I-24
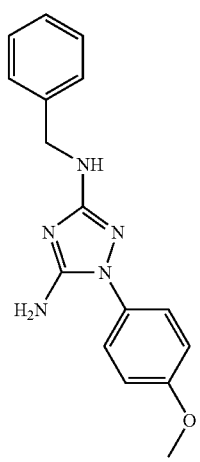
I-25
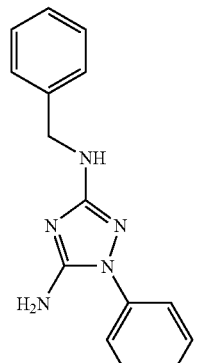
I-26

TABLE 1-continued
Examples of Compounds of Formula I:
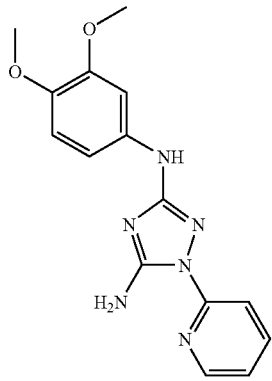
I-27
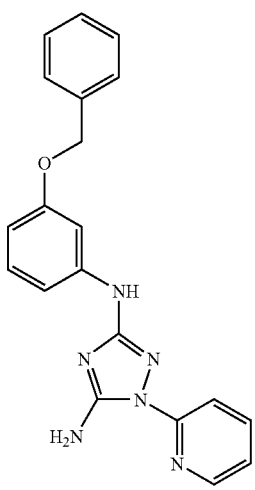
I-28
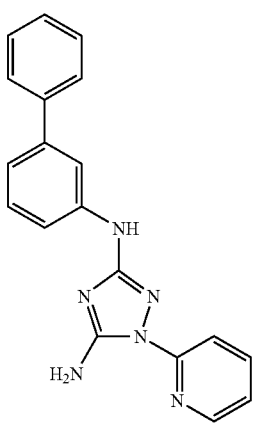
I-29
TABLE 1-continued
Examples of Compounds of Formula I:
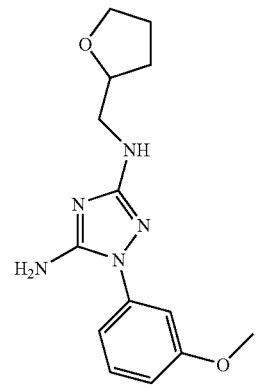
I-30
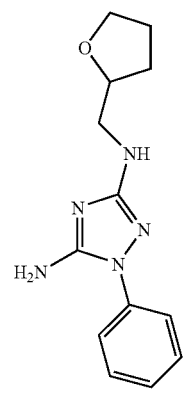
I-31
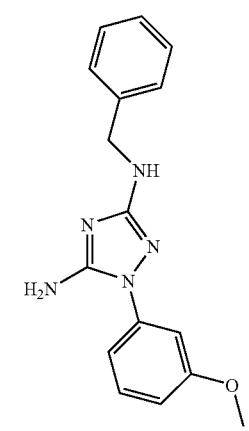
I-32

TABLE 1-continued
Examples of Compounds of Formula I:
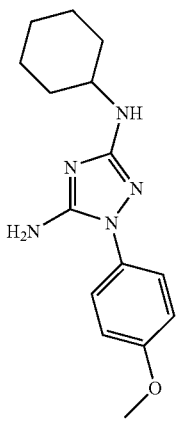
I-33
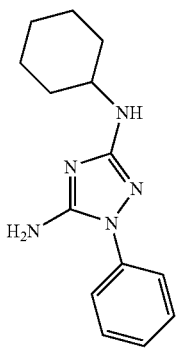
I-34
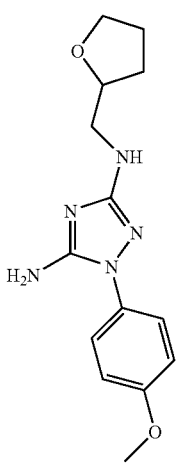
I-35
TABLE 1-continued
Examples of Compounds of Formula I:
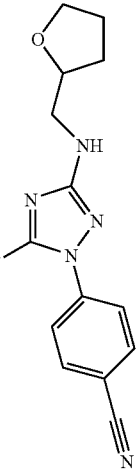
I-36
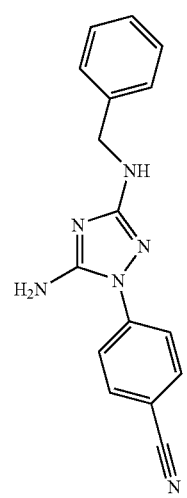
I-37
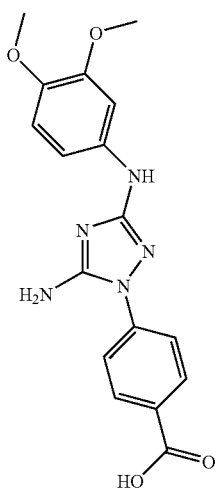
I-38

TABLE 1-continued
Examples of Compounds of Formula I:
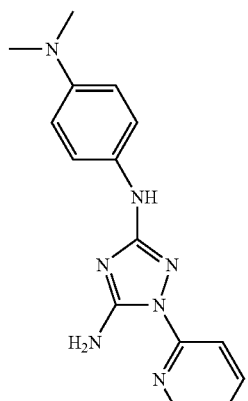
I-39
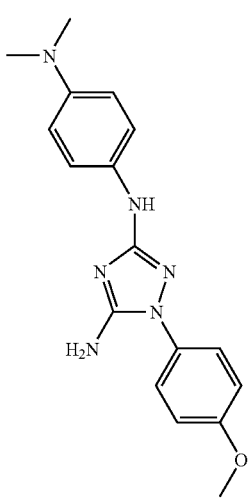
I-40
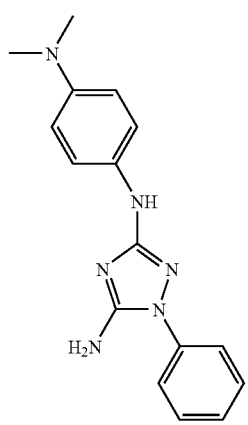
I-41
TABLE 1-continued
Examples of Compounds of Formula I:
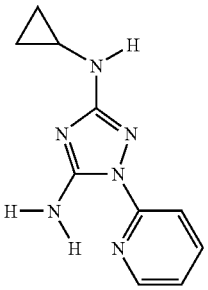
I-42
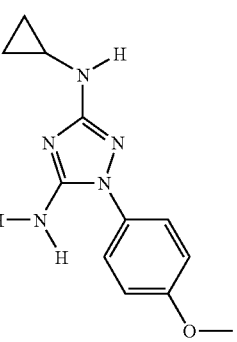
I-43
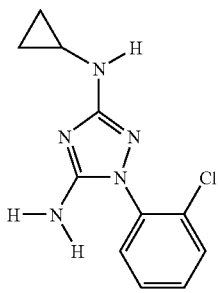
I-44
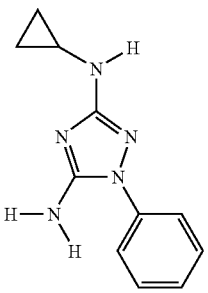
I-45

TABLE 1-continued
Examples of Compounds of Formula I:
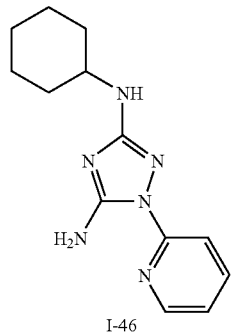
I-46
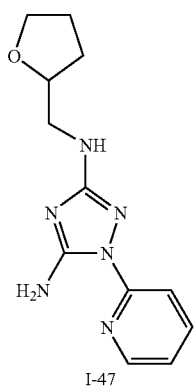
I-47
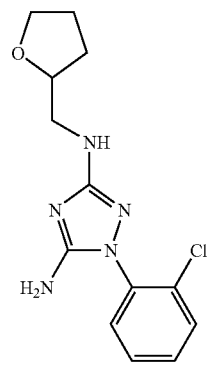
I-48
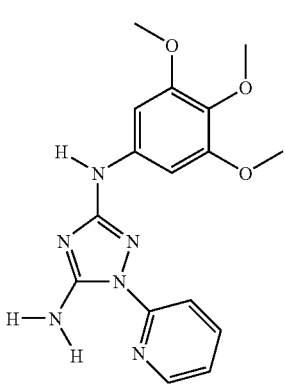
I-49
TABLE 1-continued
Examples of Compounds of Formula I:
I-50
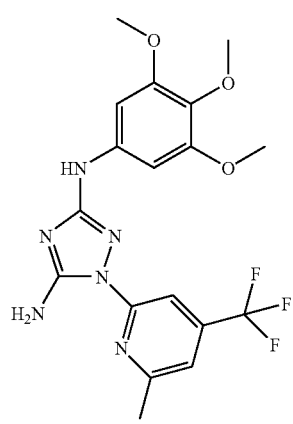
I-51
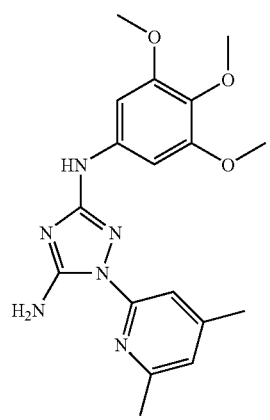
I-52

TABLE 1-continued
Examples of Compounds of Formula I:
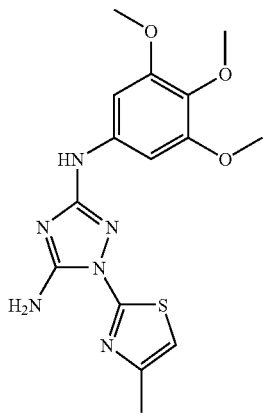
I-53
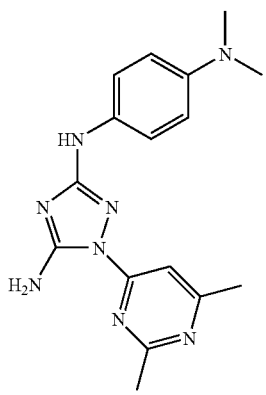
I-54
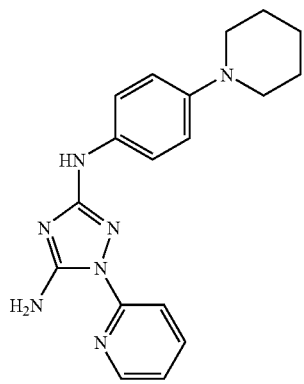
I-55
TABLE 1-continued
Examples of Compounds of Formula I:
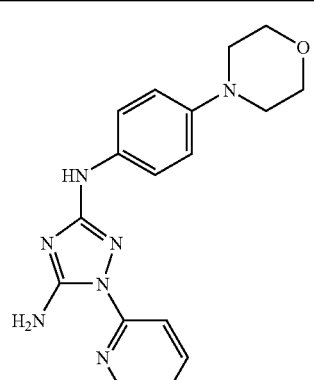
I-56
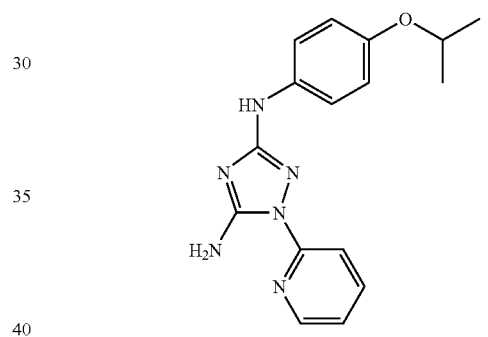
I-57
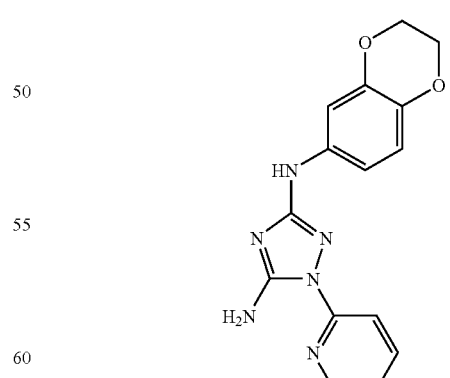
I-58

TABLE 1-continued

Examples of Compounds of Formula I:

I-59

I-60

I-61

I-62

I-63

I-64

I-65

I-66

TABLE 1-continued
Examples of Compounds of Formula I:
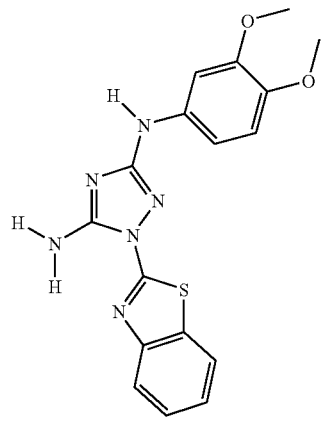
I-67
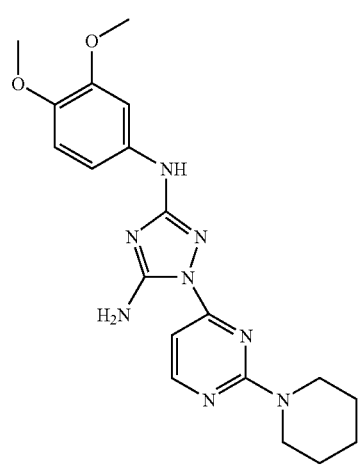
I-68
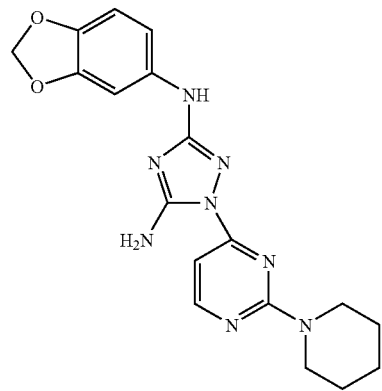
I-69
TABLE 1-continued
Examples of Compounds of Formula I:
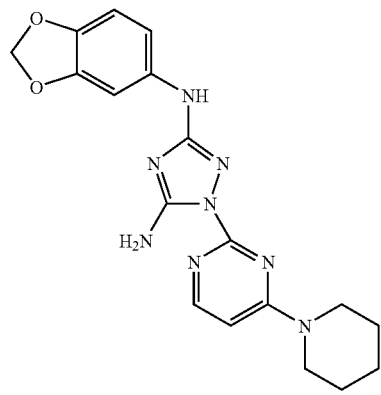
I-70
I-71
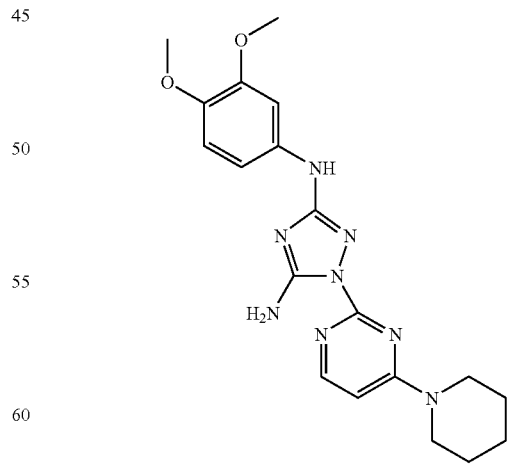
I-72

TABLE 1-continued
Examples of Compounds of Formula I:
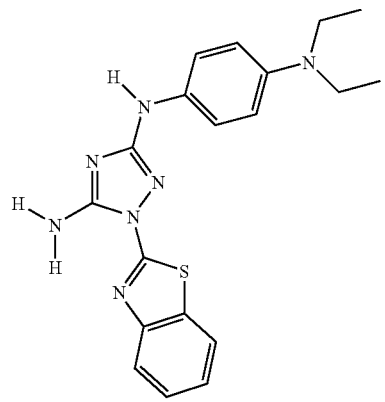
I-73
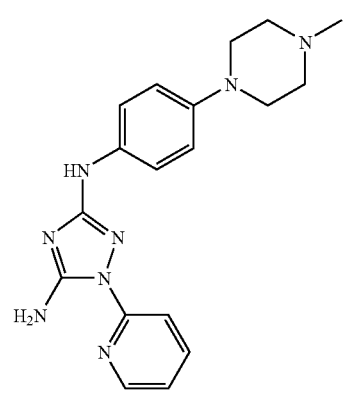
I-74
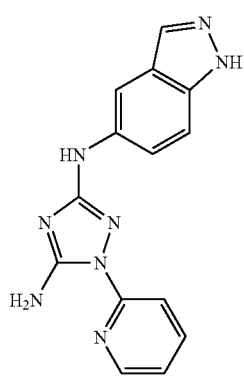
I-75
TABLE 1-continued
Examples of Compounds of Formula I:
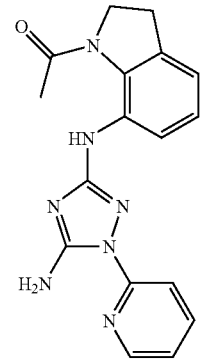
I-76
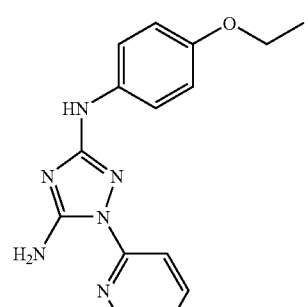
I-77
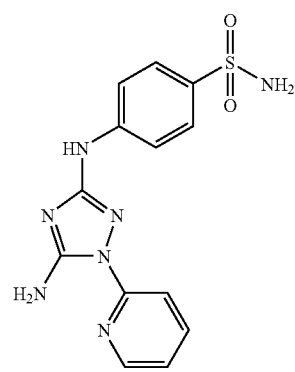
I-78
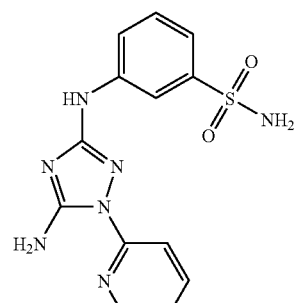
I-79

TABLE 1-continued
Examples of Compounds of Formula I:
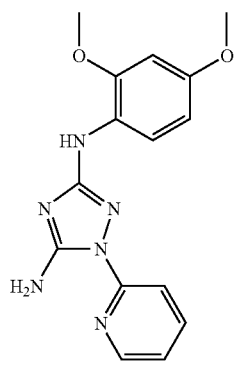
I-80
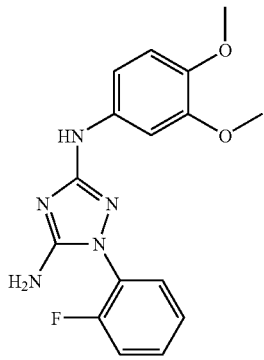
I-81
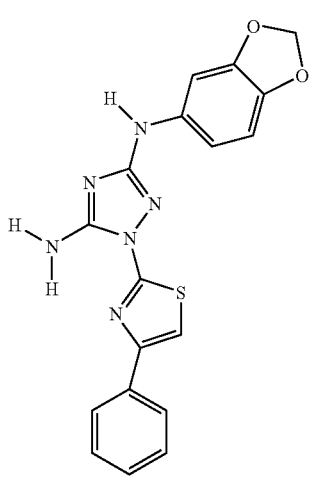
I-82
TABLE 1-continued
Examples of Compounds of Formula I:
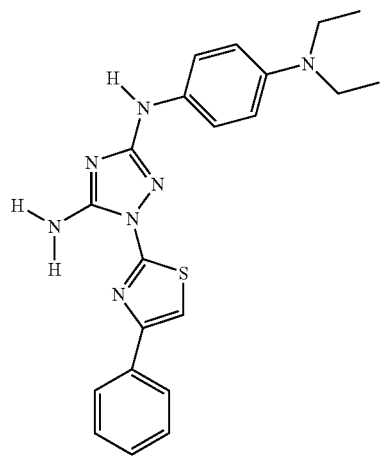
I-83
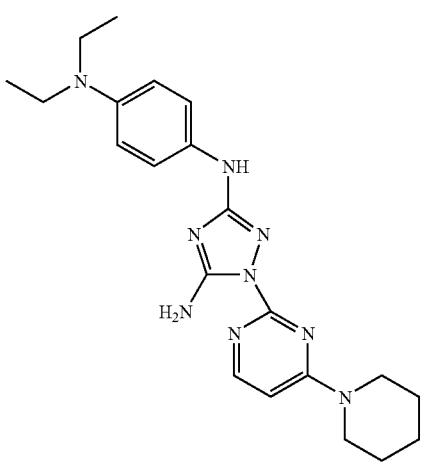
I-84
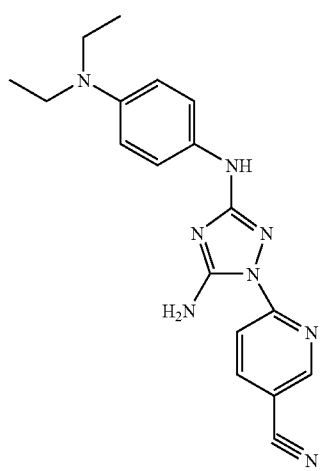
I-85

TABLE 1-continued
Examples of Compounds of Formula I:
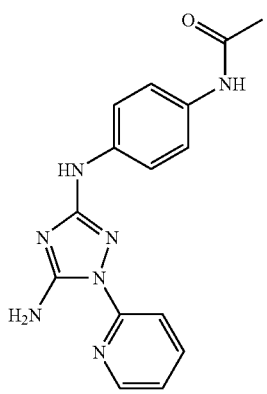
I-86
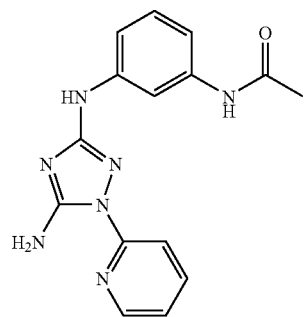
I-87
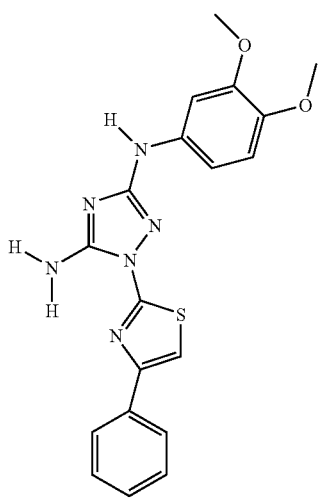
I-88
TABLE 1-continued
Examples of Compounds of Formula I:
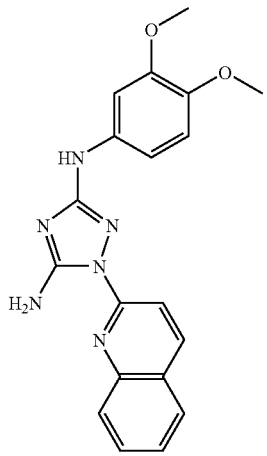
I-89
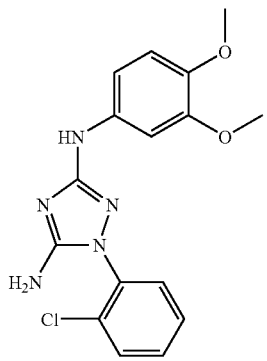
I-90
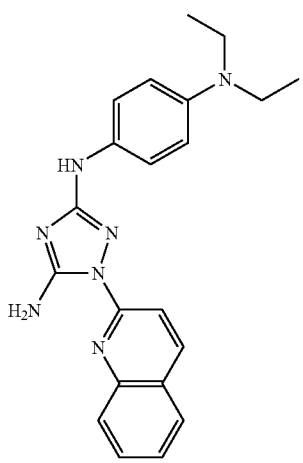
I-91

TABLE 1-continued
Examples of Compounds of Formula I:
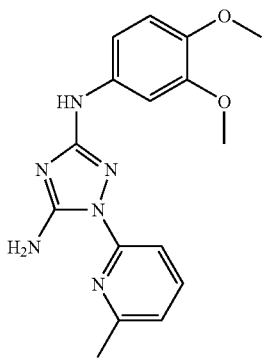
I-92
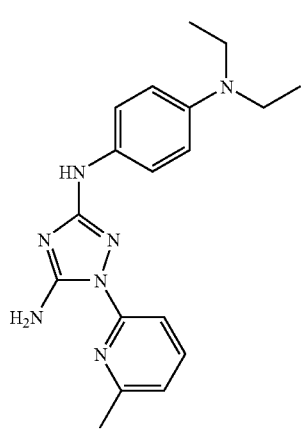
I-93
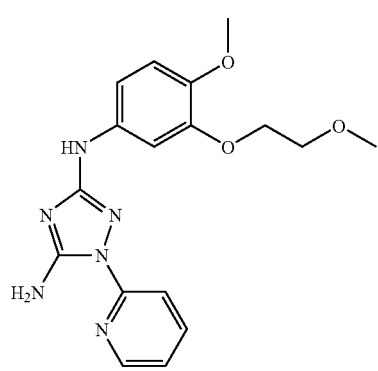
I-94
TABLE 1-continued
Examples of Compounds of Formula I:
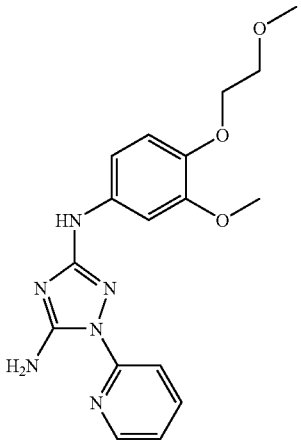
I-95
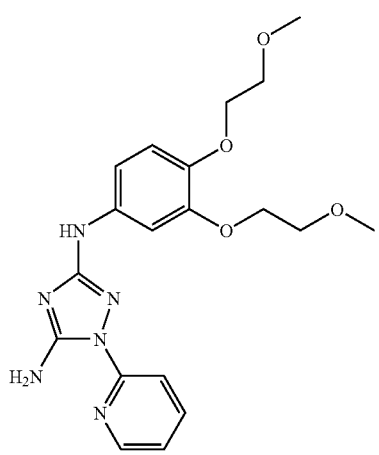
I-96
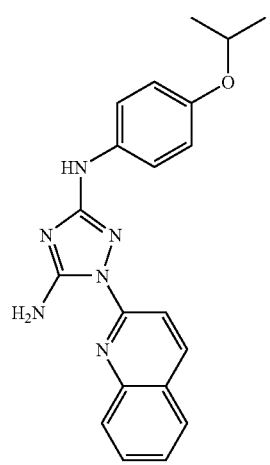
I-97

TABLE 1-continued
Examples of Compounds of Formula I:
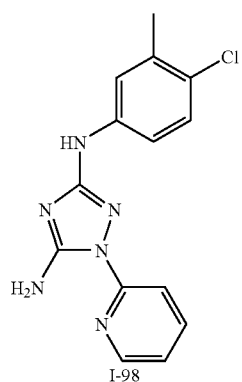
I-98
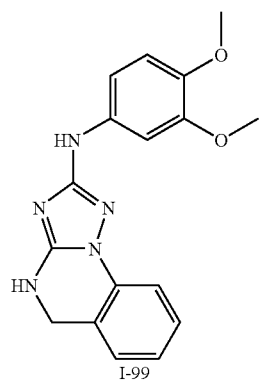
I-99
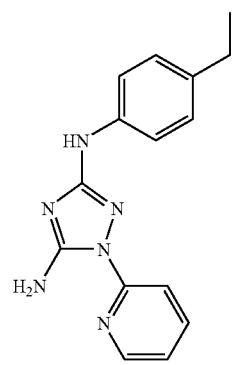
I-100
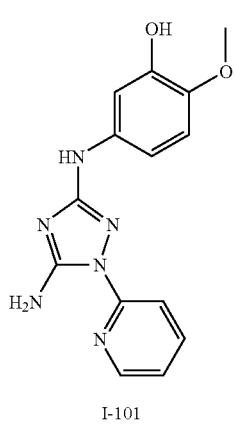
I-101
TABLE 1-continued
Examples of Compounds of Formula I:
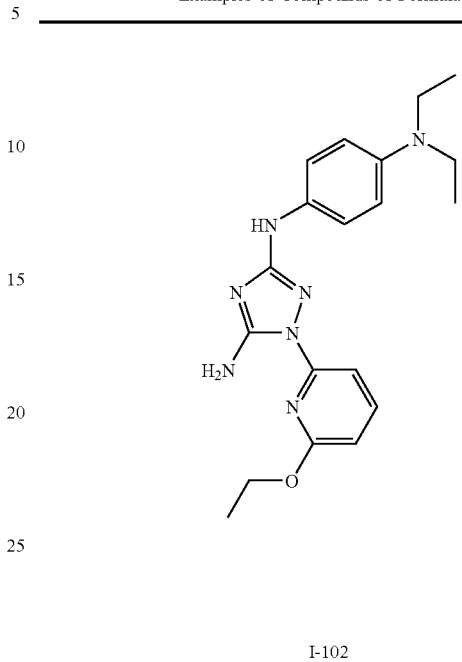
I-102
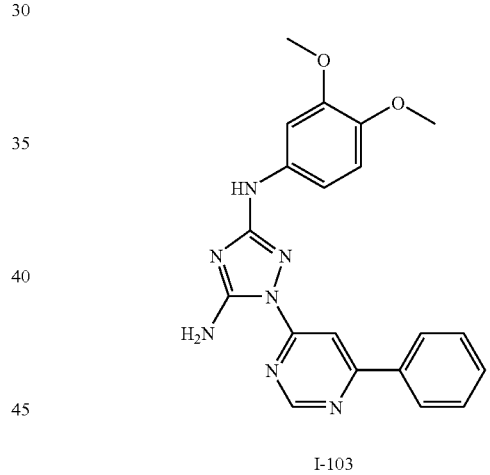
I-103
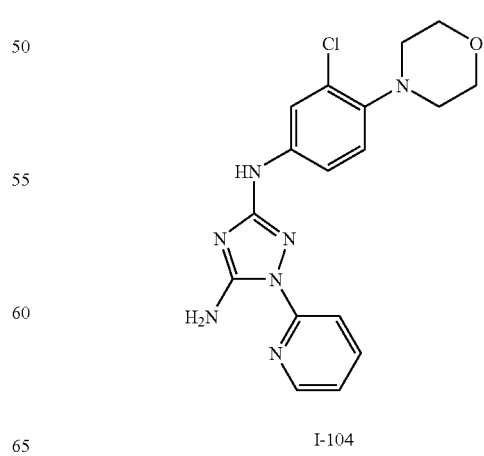
I-104

TABLE 1-continued
Examples of Compounds of Formula I:
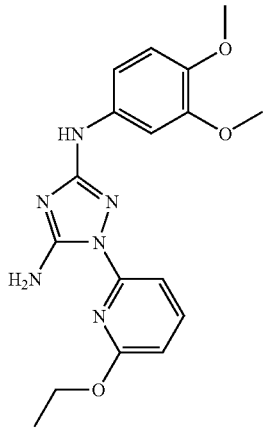
I-105
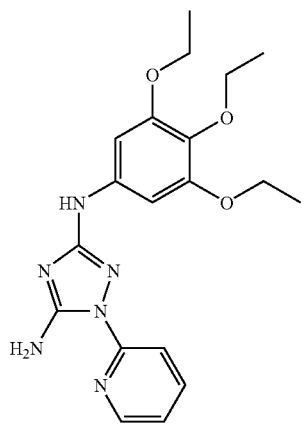
I-106
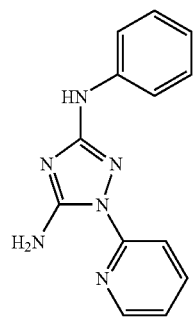
I-107
TABLE 1-continued
Examples of Compounds of Formula I:
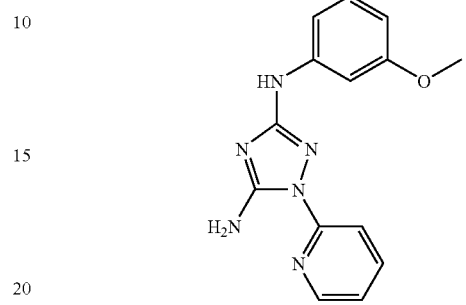
I-108
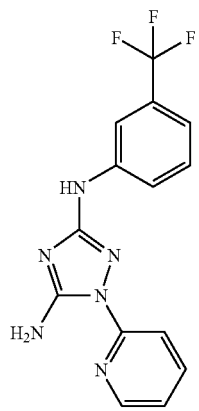
I-109
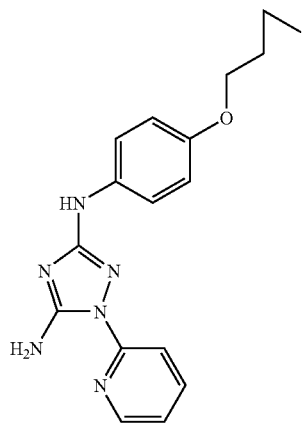
I-110

TABLE 1-continued
Examples of Compounds of Formula I:
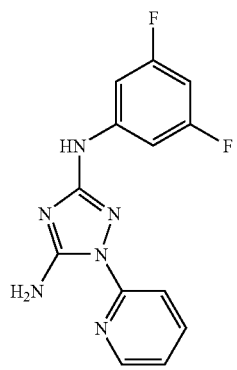
I-111
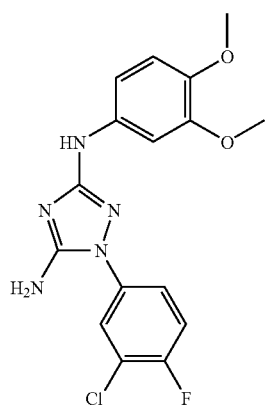
I-112
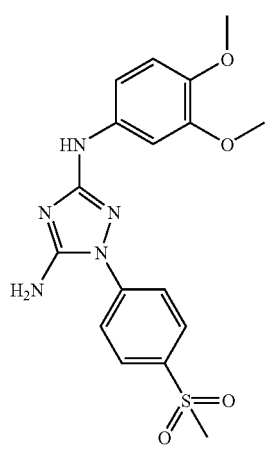
I-113
TABLE 1-continued
Examples of Compounds of Formula I:
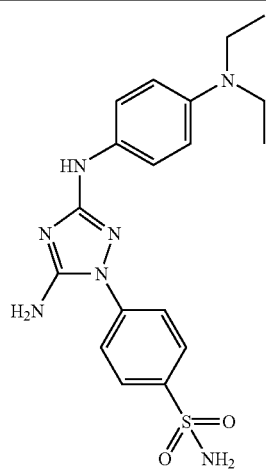
I-114
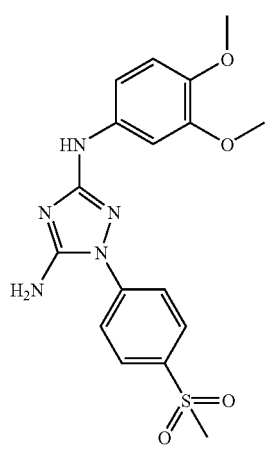
I-115

I-116

TABLE 1-continued
Examples of Compounds of Formula I:
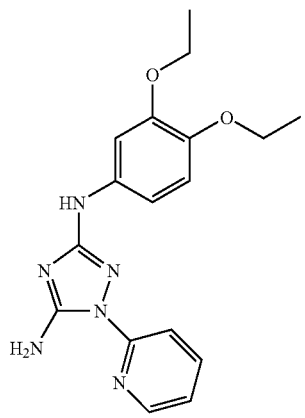
I-117
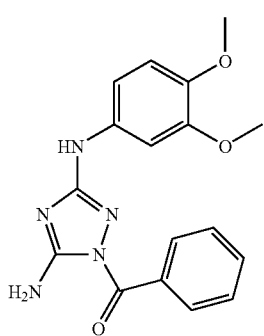
I-118
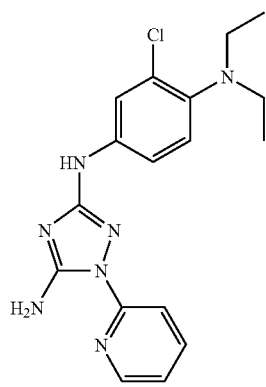
I-119
TABLE 1-continued
Examples of Compounds of Formula I:
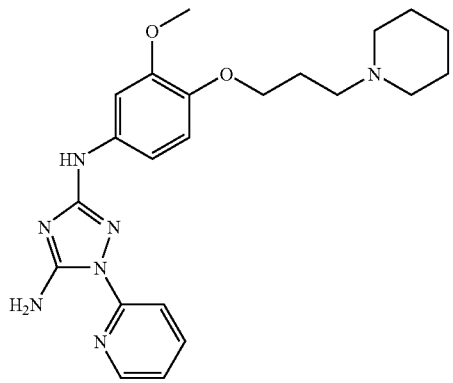
I-120
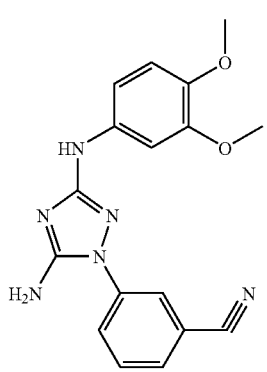
I-121
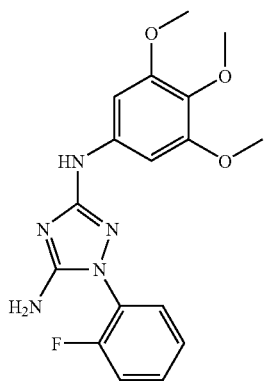
I-122

TABLE 1-continued
Examples of Compounds of Formula I:
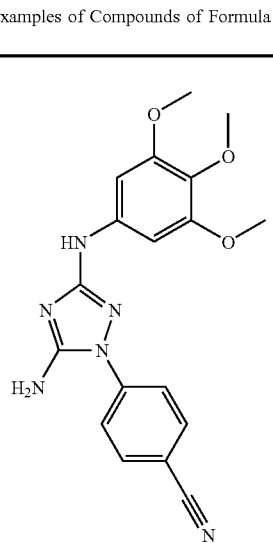
I-123
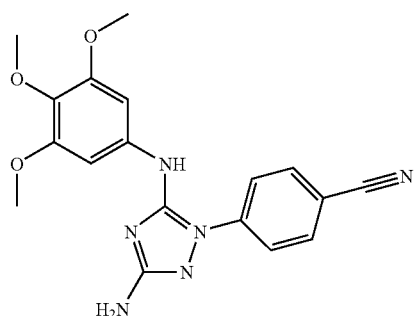
I-124
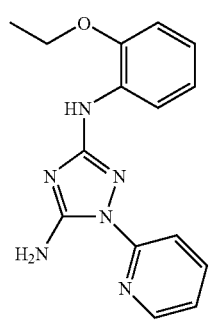
I-125
TABLE 1-continued
Examples of Compounds of Formula I:
I-126
I-127
I-128
I-129

TABLE 1-continued
Examples of Compounds of Formula I:
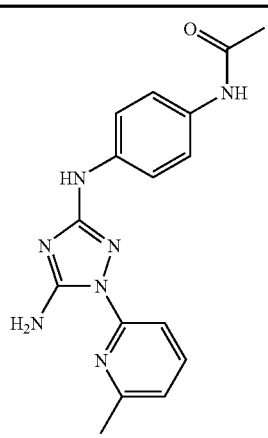
I-130
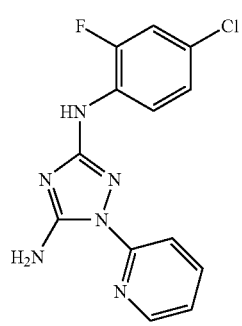
I-131
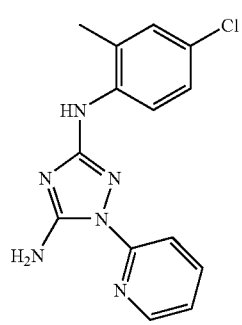
I-132
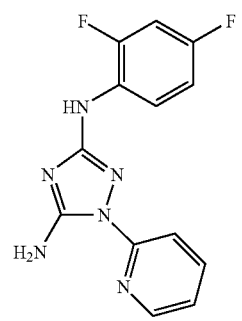
I-133
TABLE 1-continued
Examples of Compounds of Formula I:

I-134

I-135
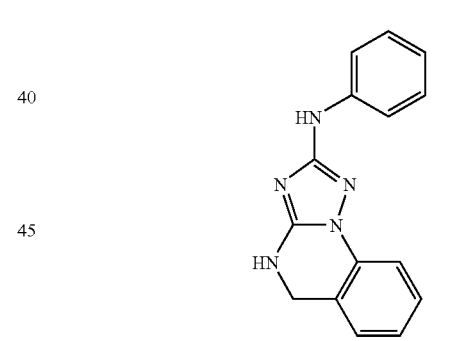
I-136
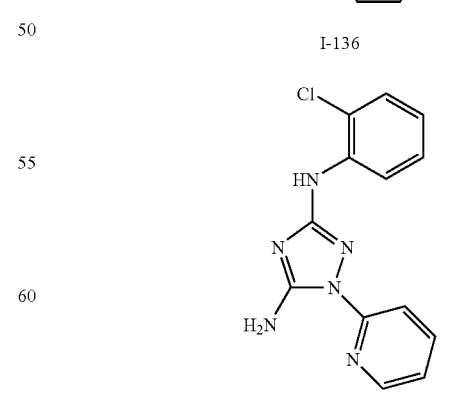
I-137

TABLE 1-continued
Examples of Compounds of Formula I:
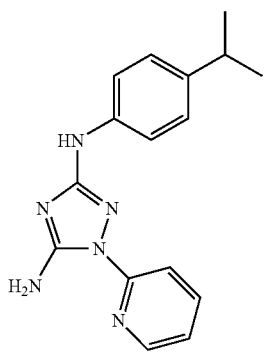
I-138
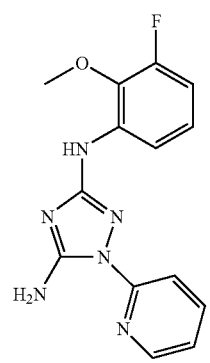
I-139
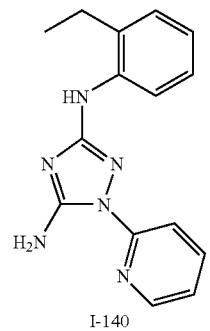
I-140
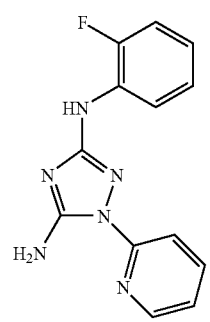
I-141
TABLE 1-continued
Examples of Compounds of Formula I:
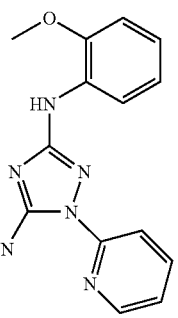
I-142
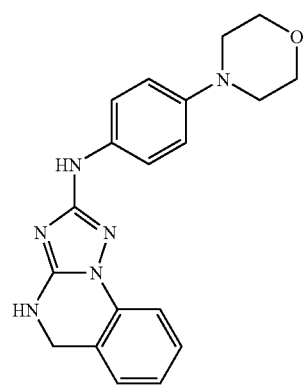
I-143
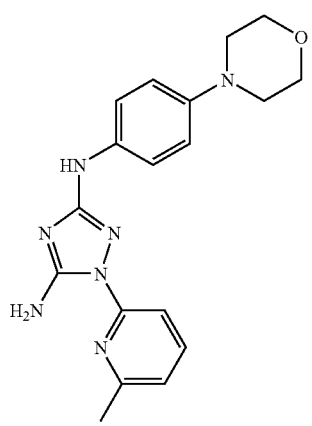
I-144

TABLE 1-continued
Examples of Compounds of Formula I:
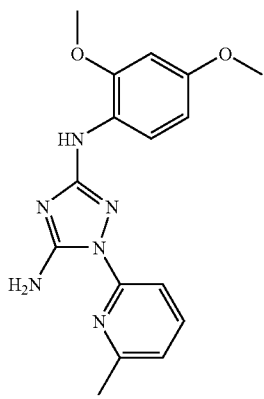
I-145
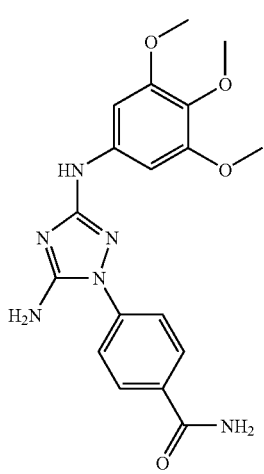
I-146
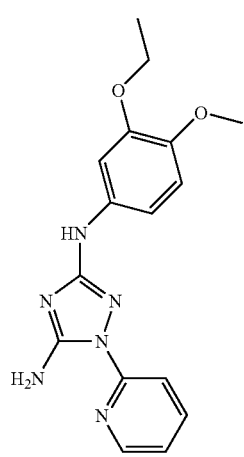
I-147
TABLE 1-continued
Examples of Compounds of Formula I:
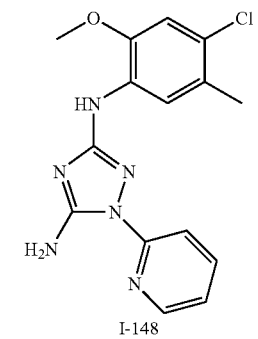
I-148
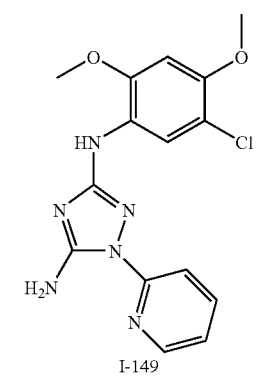
I-149
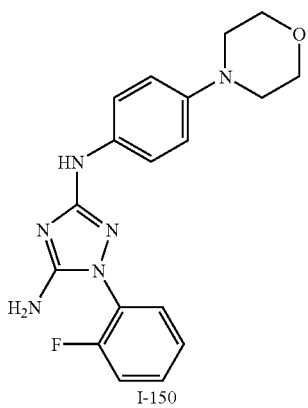
I-150
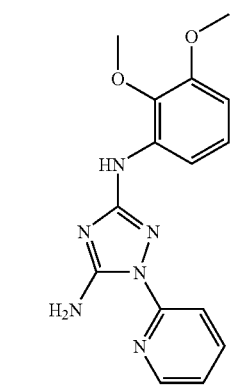
I-151

TABLE 1-continued
Examples of Compounds of Formula I:
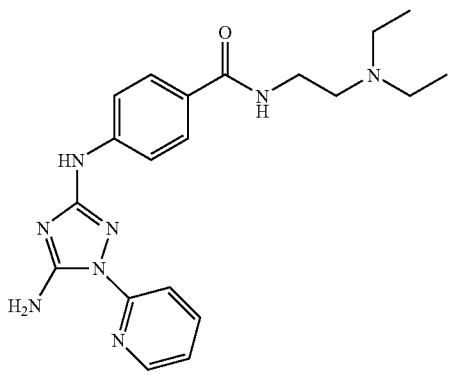
I-152
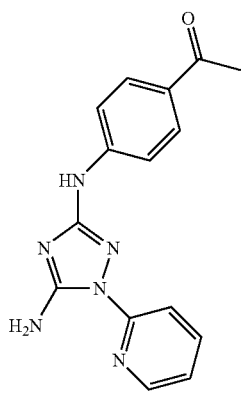
I-153
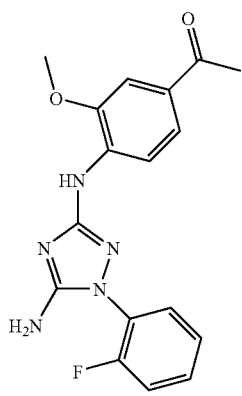
I-154
TABLE 1-continued
Examples of Compounds of Formula I:
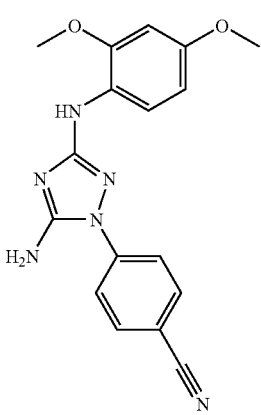
I-155
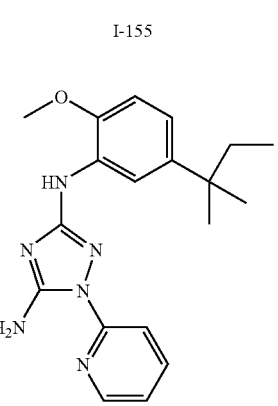
I-156
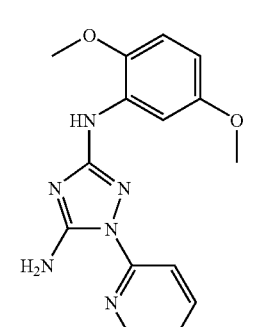
I-157

TABLE 1-continued
Examples of Compounds of Formula I:
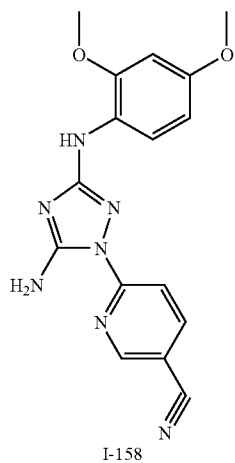
I-158
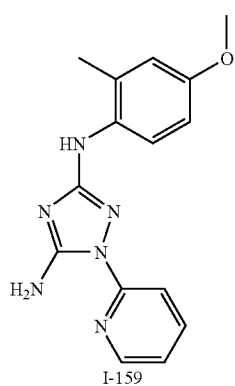
I-159
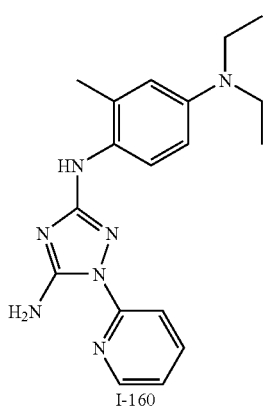
I-160
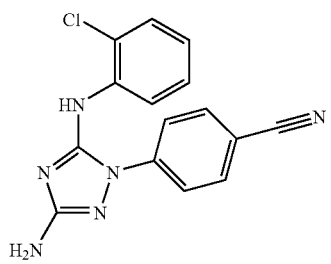
I-161
TABLE 1-continued
Examples of Compounds of Formula I:
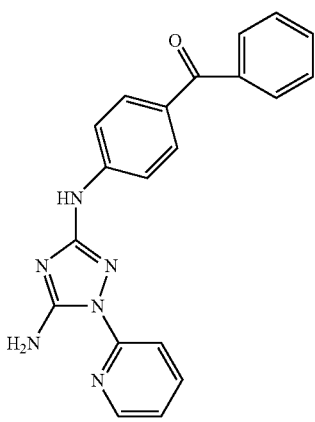
I-162
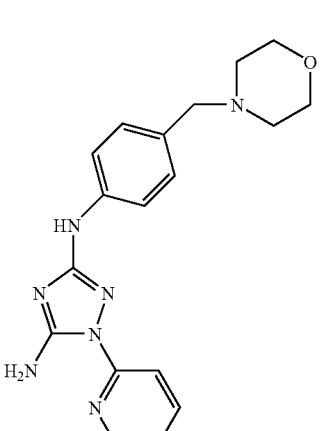
I-163
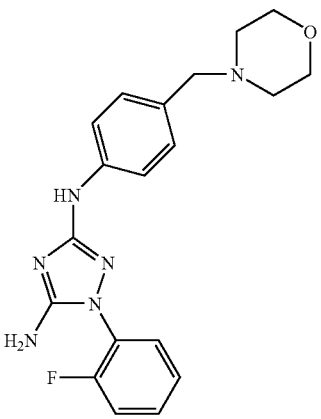
I-164

TABLE 1-continued
Examples of Compounds of Formula I:
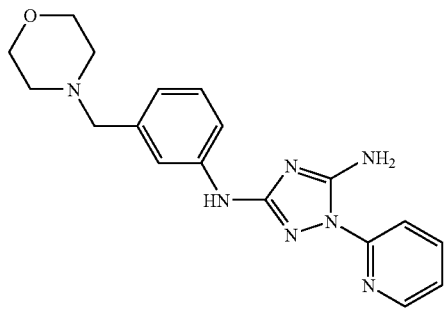
I-165
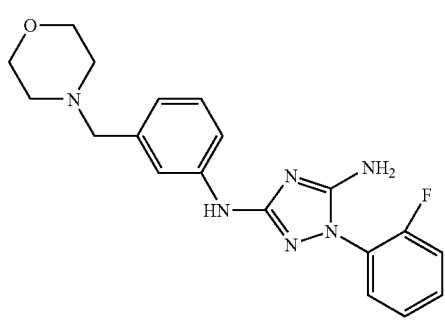
I-166
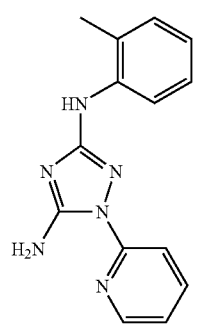
I-167
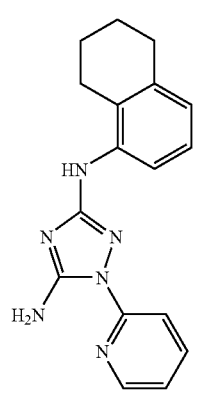
I-168
TABLE 1-continued
Examples of Compounds of Formula I:
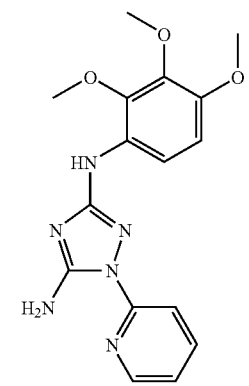
I-169
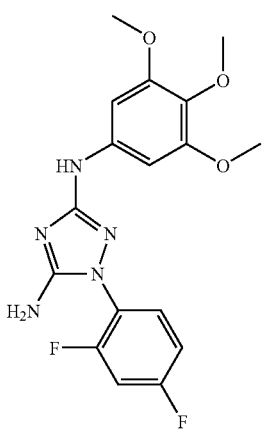
I-170
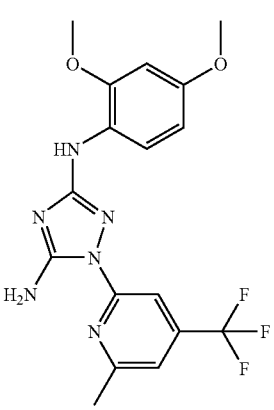
I-171

TABLE 1-continued
Examples of Compounds of Formula I:
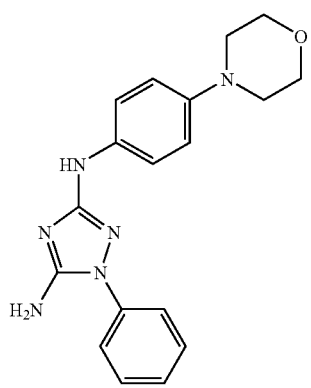
I-172
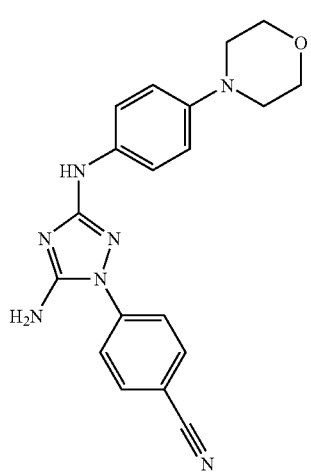
I-173
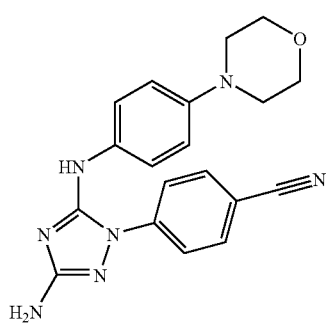
I-174
TABLE 1-continued
Examples of Compounds of Formula I:
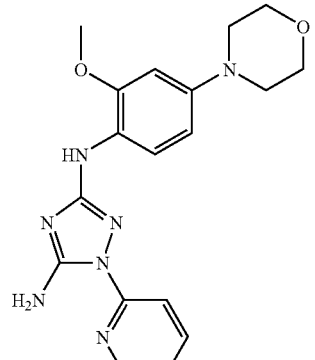
I-175
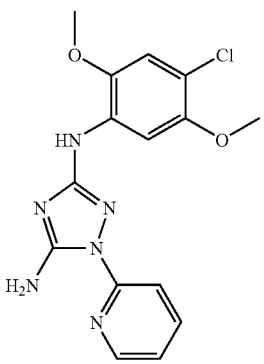
I-176
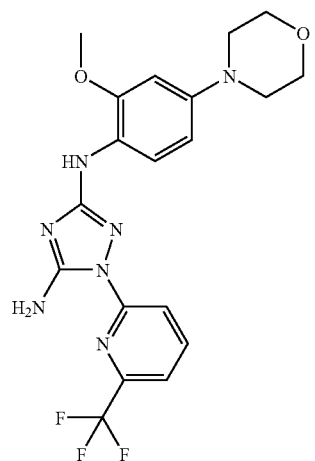
I-177

TABLE 1-continued
Examples of Compounds of Formula I:
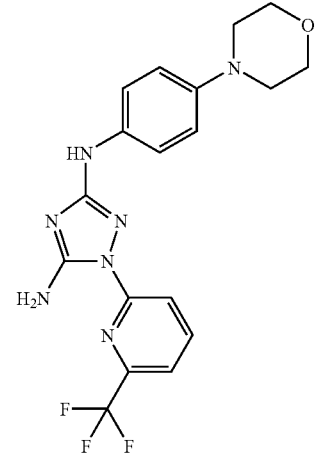
I-178
I-179
I-180
I-181
I-182
I-183

TABLE 1-continued
Examples of Compounds of Formula I:
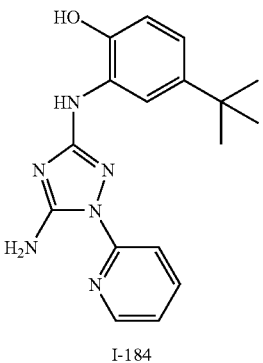
I-184
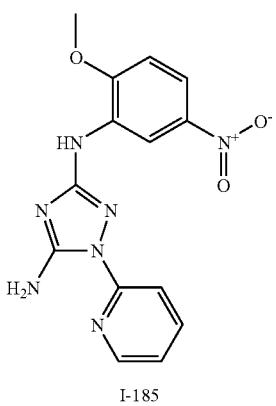
I-185
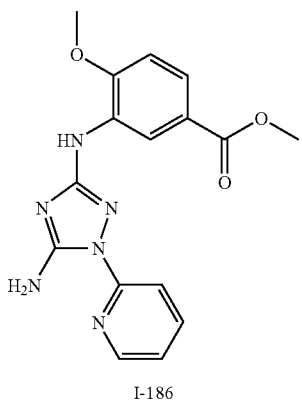
I-186
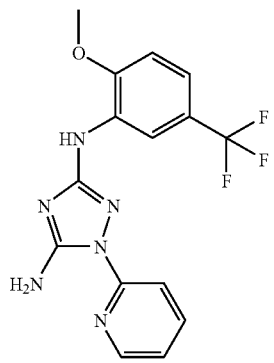
I-187
TABLE 1-continued
Examples of Compounds of Formula I:
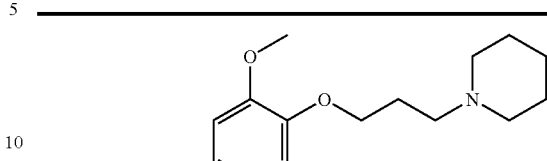
I-188
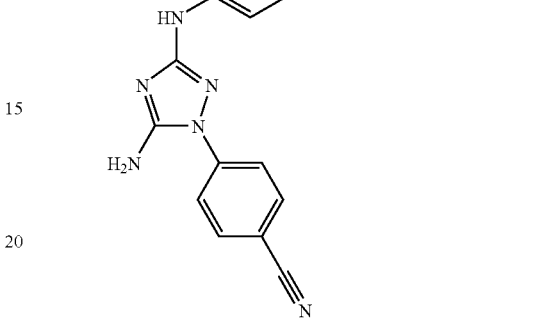
I-189
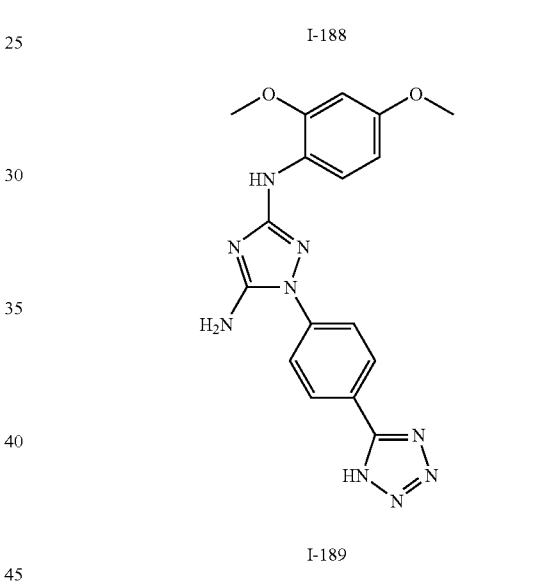
I-190

TABLE 1-continued
Examples of Compounds of Formula I:
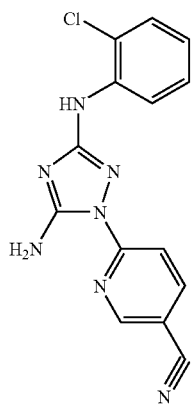
I-191
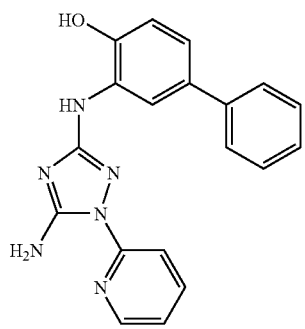
I-192
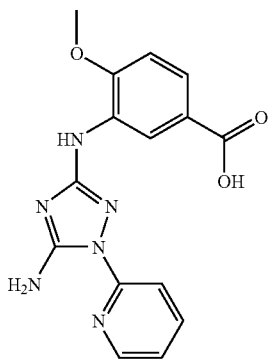
I-193
TABLE 1-continued
Examples of Compounds of Formula I:
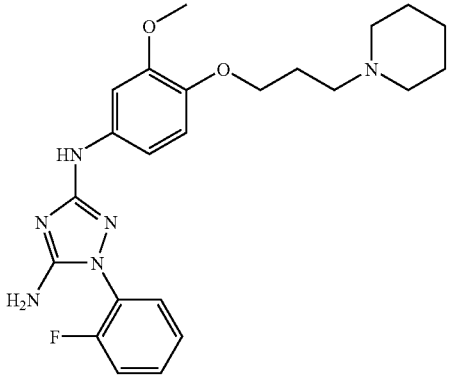
I-194
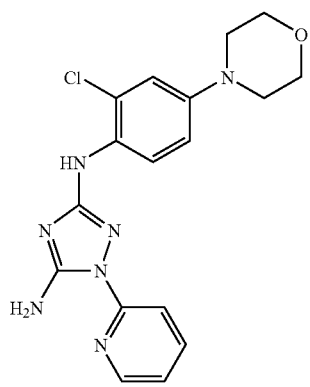
I-195
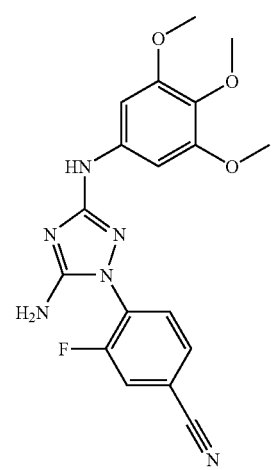
I-196

TABLE 1-continued
Examples of Compounds of Formula I:
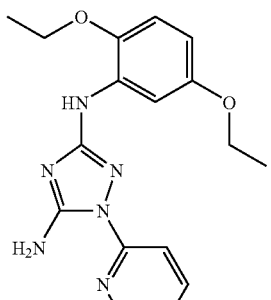
I-197
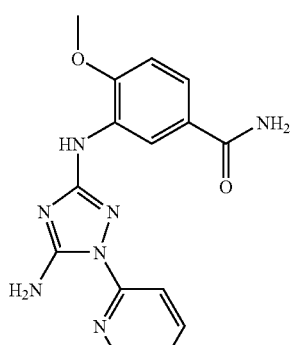
I-198
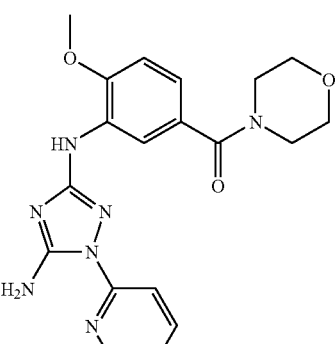
I-199
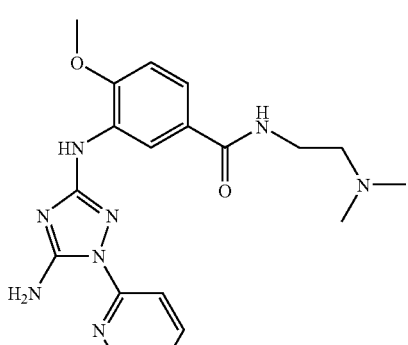
I-200
TABLE 1-continued
Examples of Compounds of Formula I:
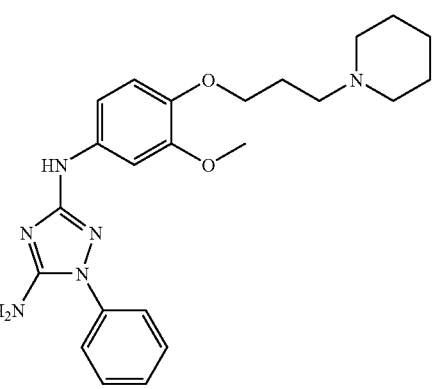
I-201
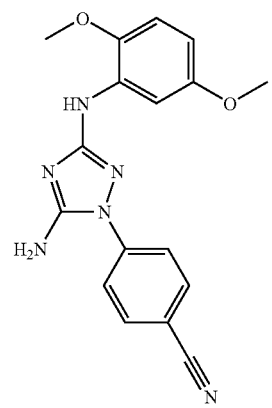
I-202
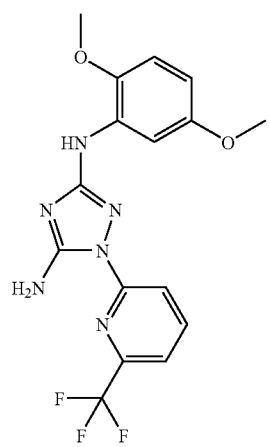
I-203

TABLE 1-continued
Examples of Compounds of Formula I:
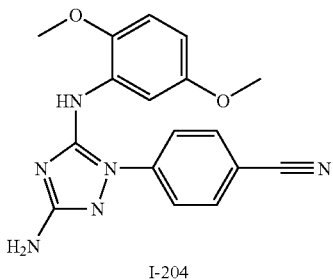
I-204
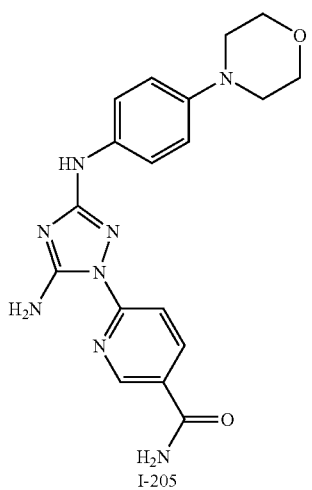
I-205
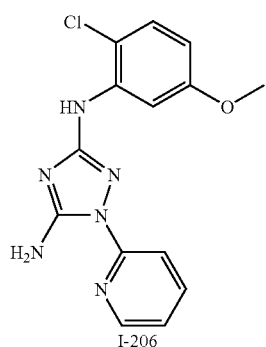
I-206
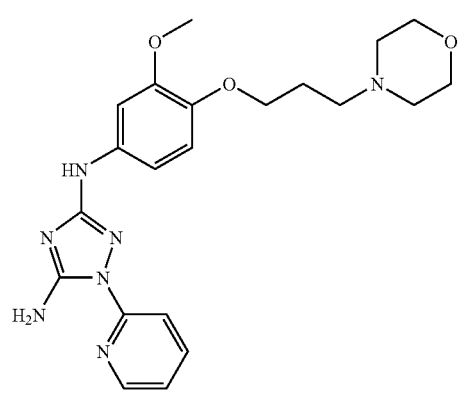
I-207
TABLE 1-continued
Examples of Compounds of Formula I:
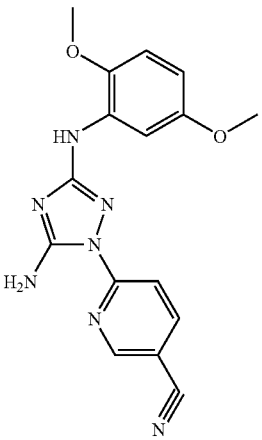
I-208
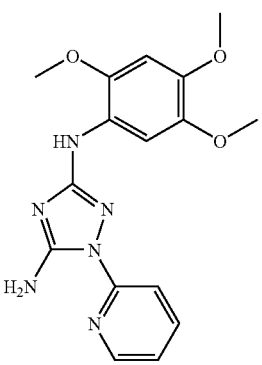
I-209
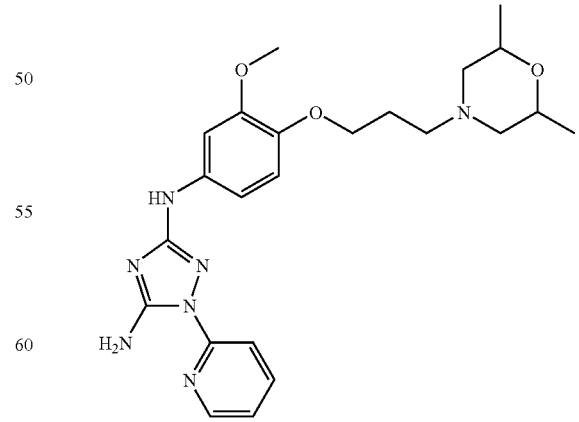
I-210

TABLE 1-continued
Examples of Compounds of Formula I:
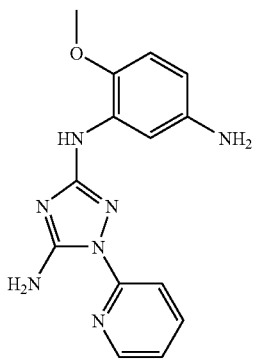
I-211
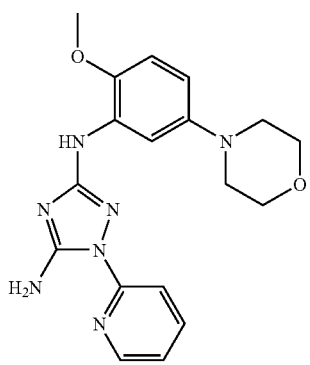
I-212
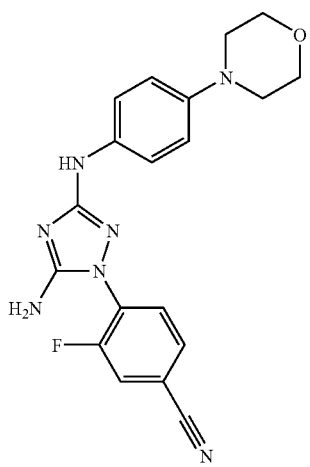
I-213
TABLE 1-continued
Examples of Compounds of Formula I:
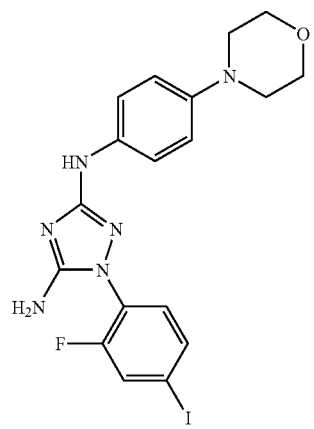
I-214
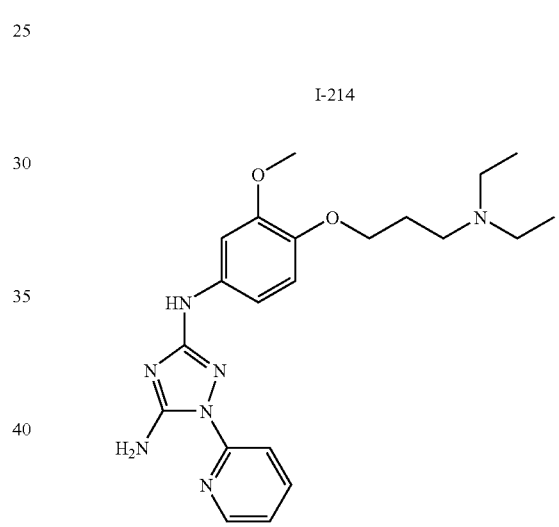
I-215
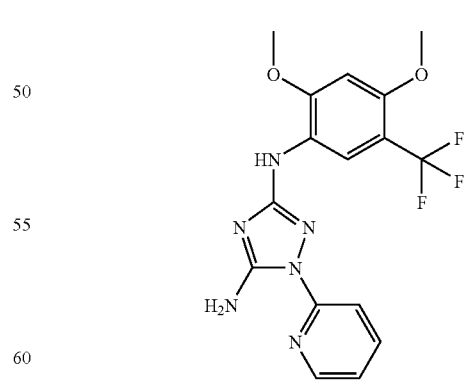
I-216

TABLE 1-continued
Examples of Compounds of Formula I:
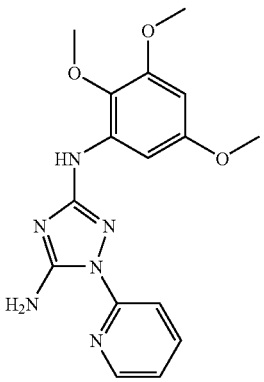
I-217
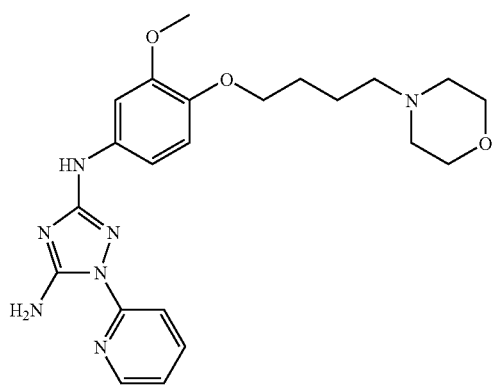
I-218
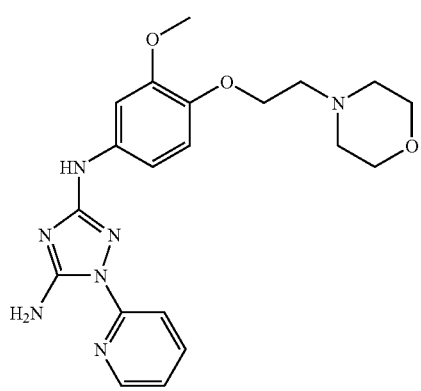
I-219
TABLE 1-continued
Examples of Compounds of Formula I:
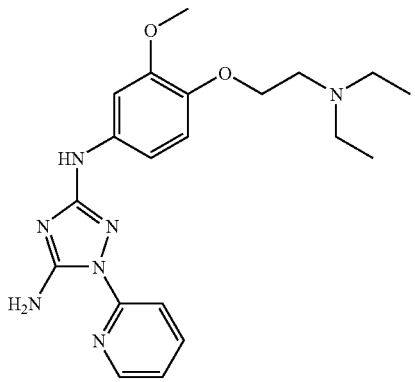
I-220
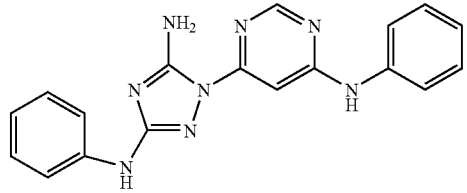
I-221
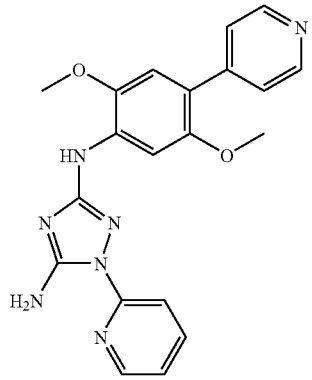
I-222
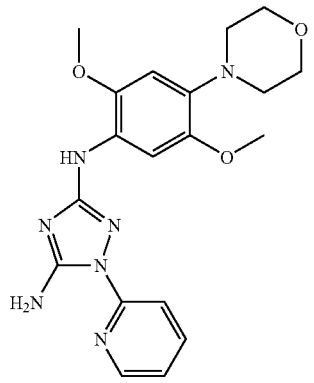
I-223

TABLE 1-continued
Examples of Compounds of Formula I:
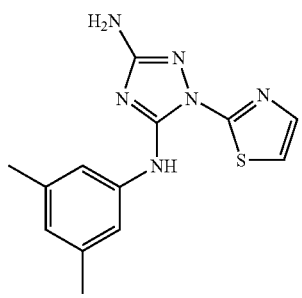
I-224
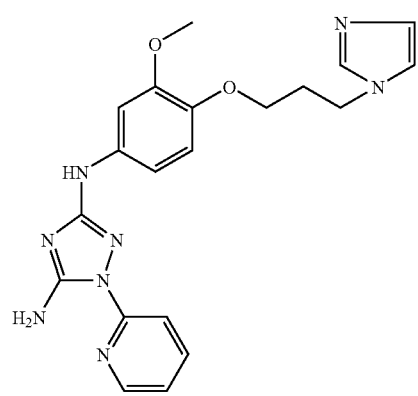
I-225
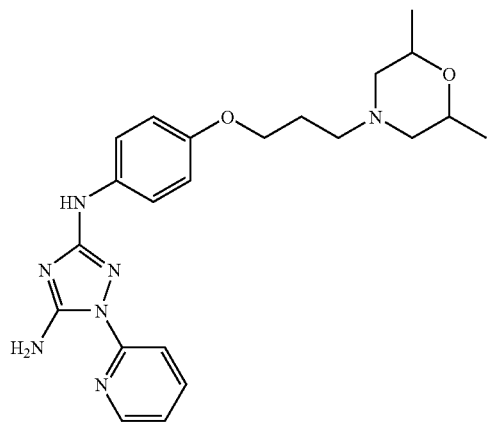
I-226
TABLE 1-continued
Examples of Compounds of Formula I:
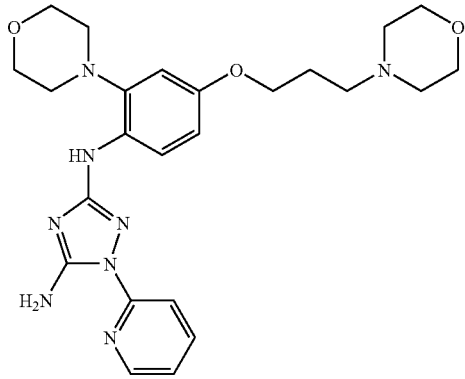
I-227
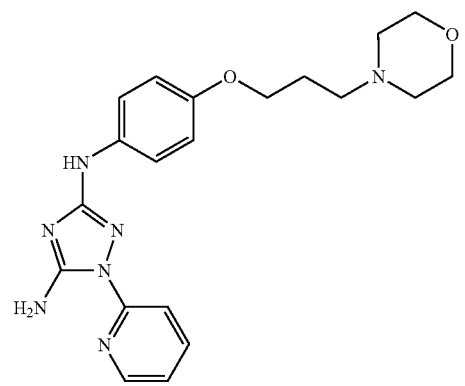
I-228
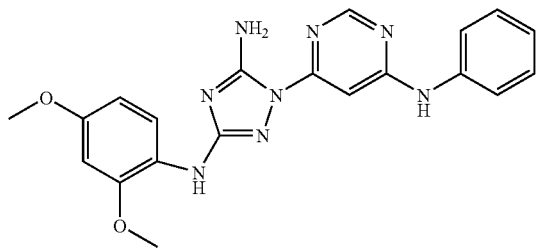
I-229
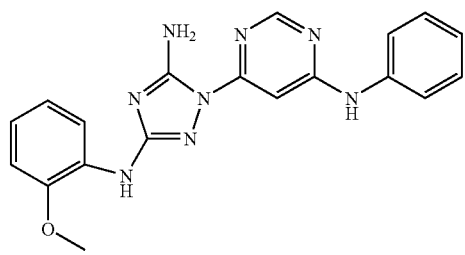
I-230

TABLE 1-continued
Examples of Compounds of Formula I:
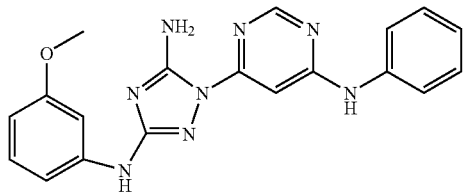
I-231
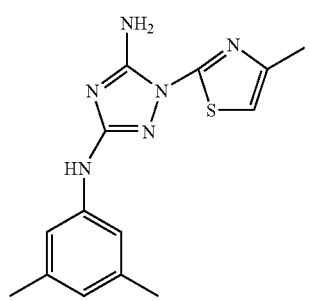
I-232
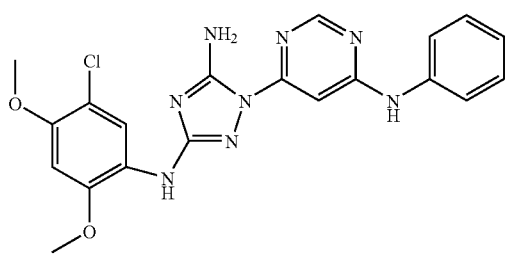
I-233
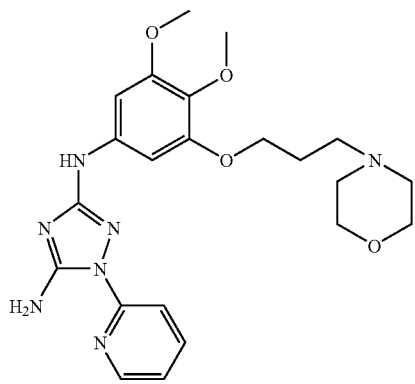
I-234
TABLE 1-continued
Examples of Compounds of Formula I:
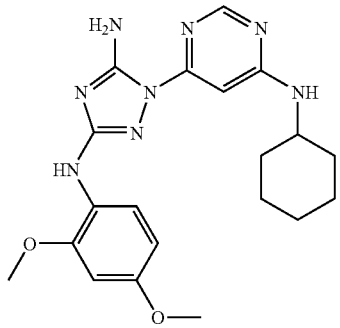
I-235
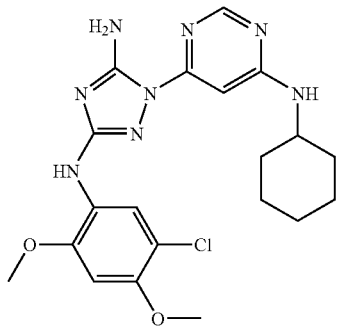
I-236
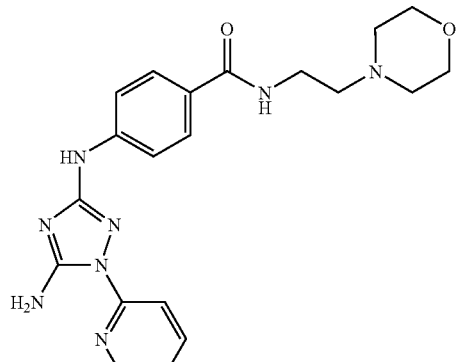
I-237

TABLE 1-continued
Examples of Compounds of Formula I:
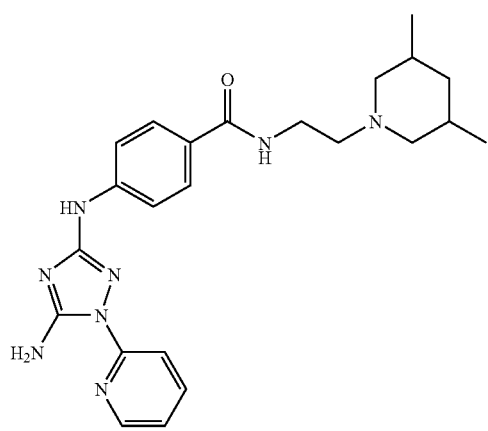
I-238
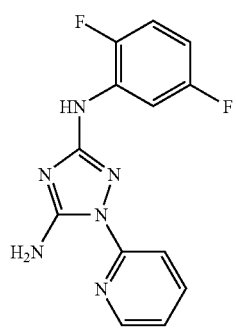
I-239
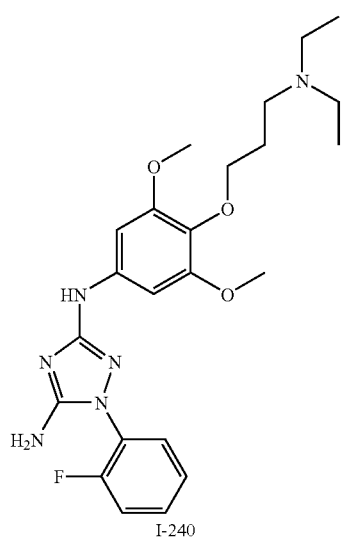
I-240
TABLE 1-continued
Examples of Compounds of Formula I:
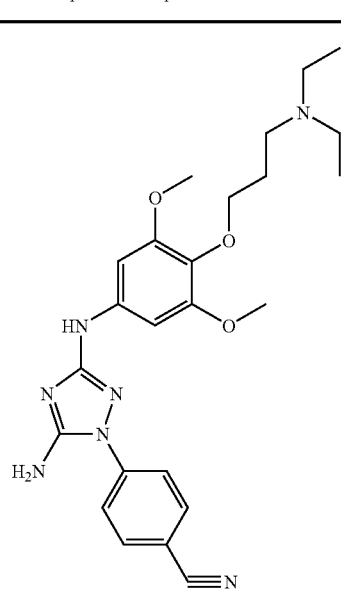
I-241
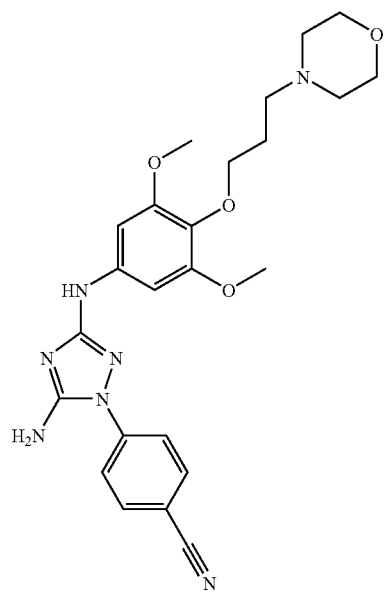
I-242

TABLE 1-continued
Examples of Compounds of Formula I:
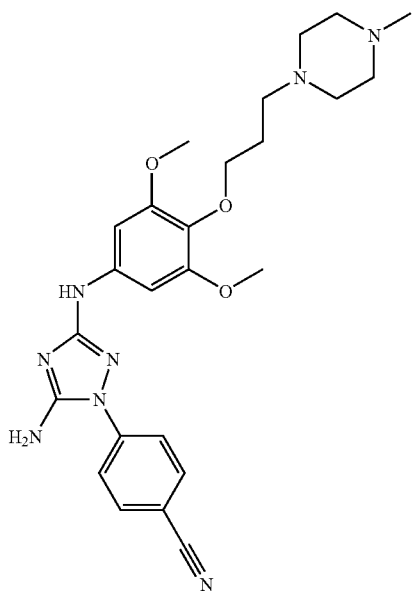
I-243
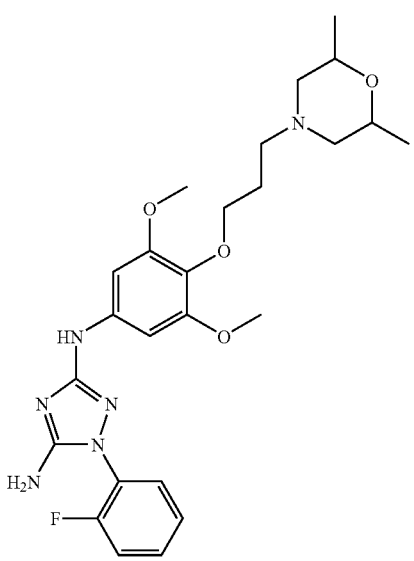
I-245
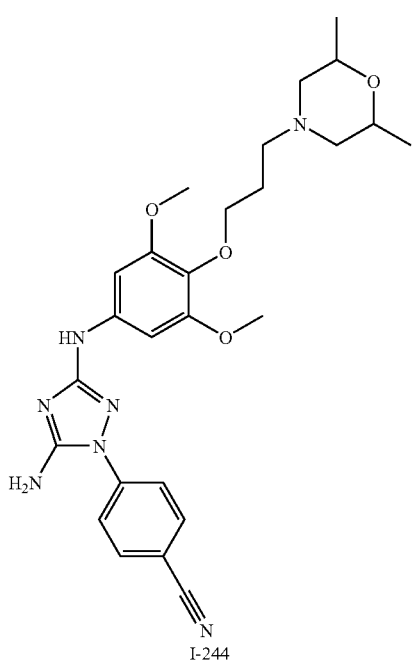
I-244
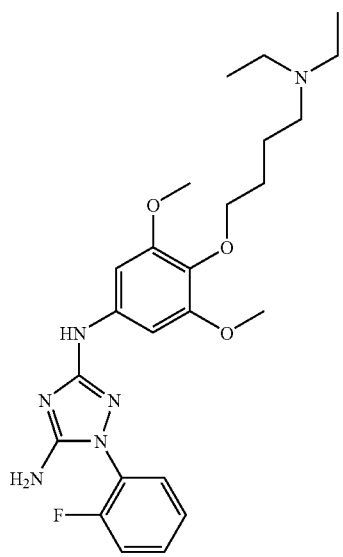
I-246

TABLE 1-continued
Examples of Compounds of Formula I:
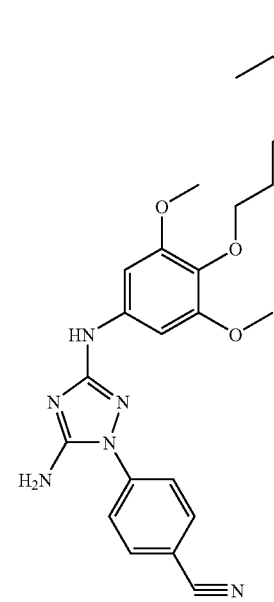
I-247
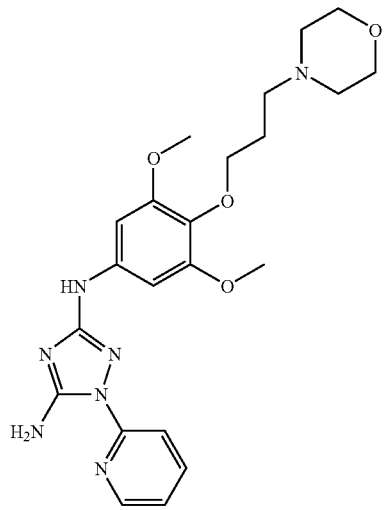
I-248
TABLE 1-continued
Examples of Compounds of Formula I:
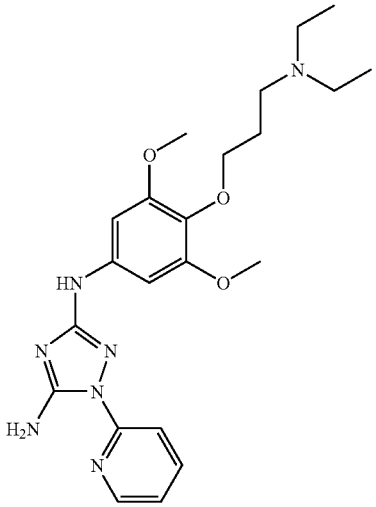
I-249
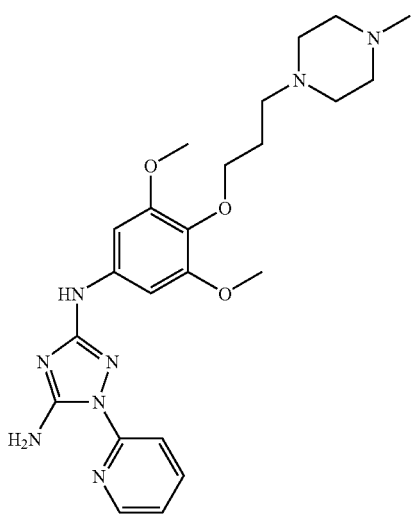
I-250
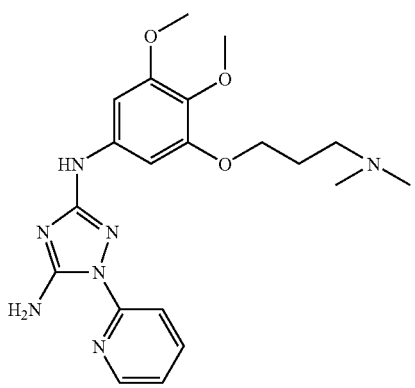
I-251

TABLE 1-continued
Examples of Compounds of Formula I:
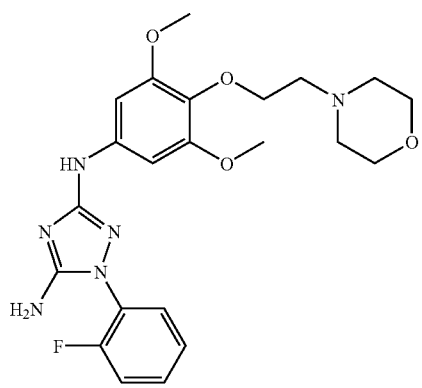
I-252
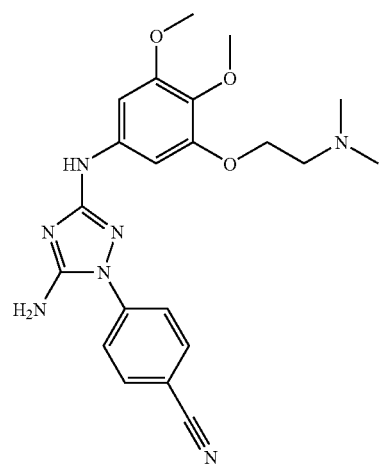
I-253
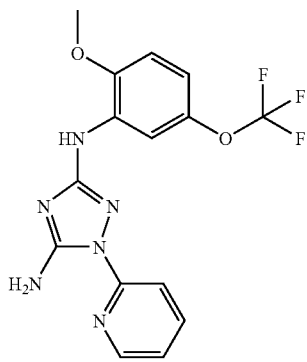
I-254
TABLE 1-continued
Examples of Compounds of Formula I:
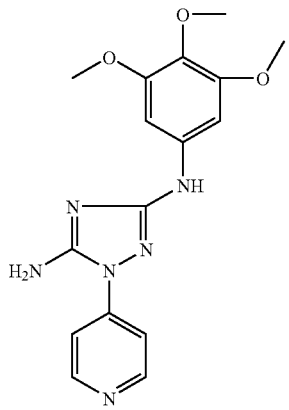
I-255
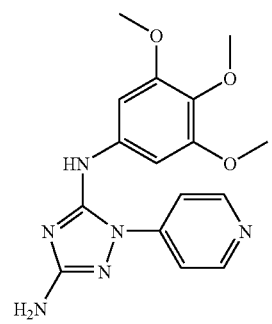
I-256
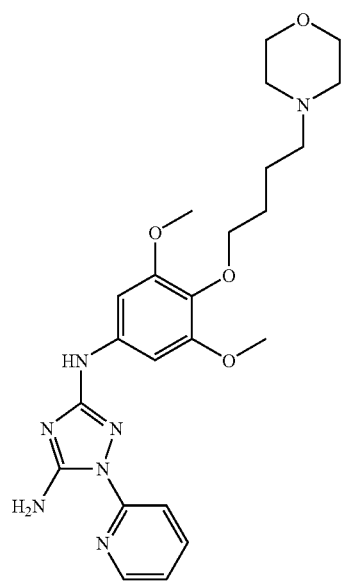
I-257

TABLE 1-continued
Examples of Compounds of Formula I:
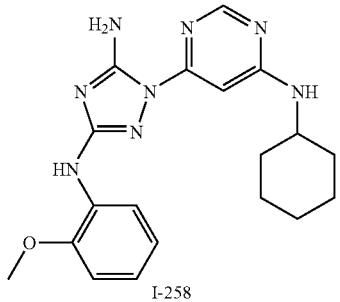
I-258
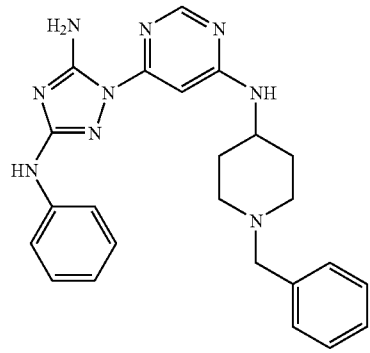
I-259
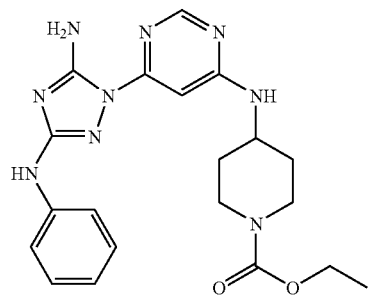
I-260
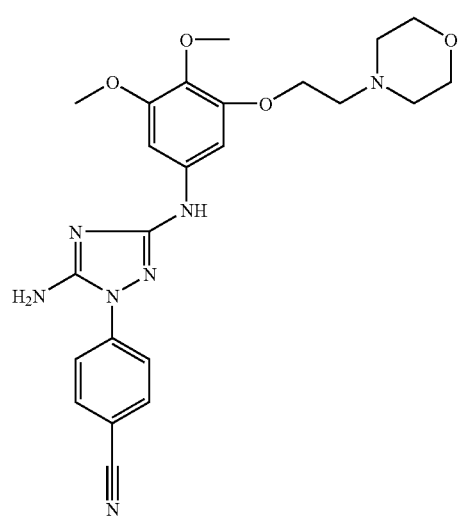
I-261
TABLE 1-continued
Examples of Compounds of Formula I:
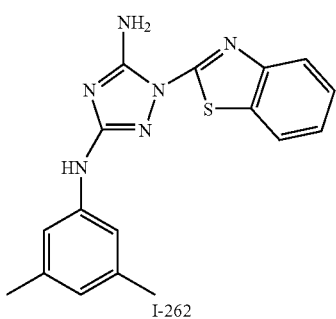
I-262
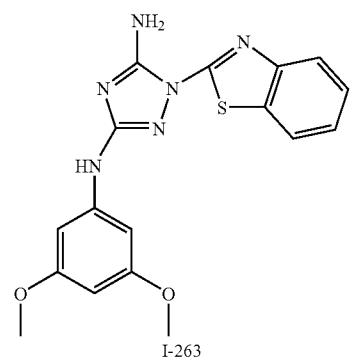
I-263
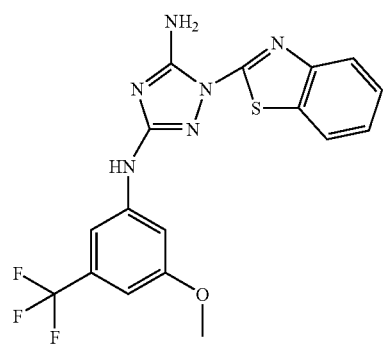
I-264
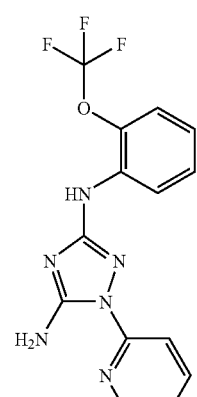
I-265

TABLE 1-continued
Examples of Compounds of Formula I:
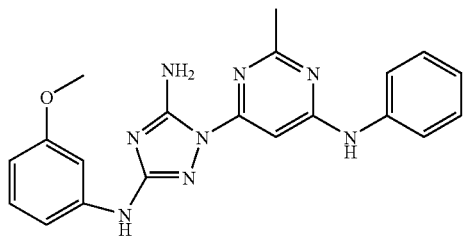
I-266
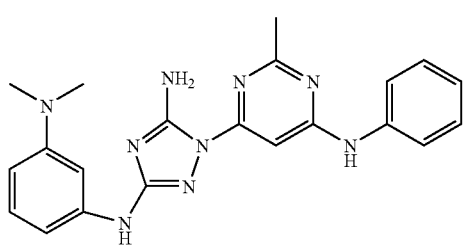
I-267
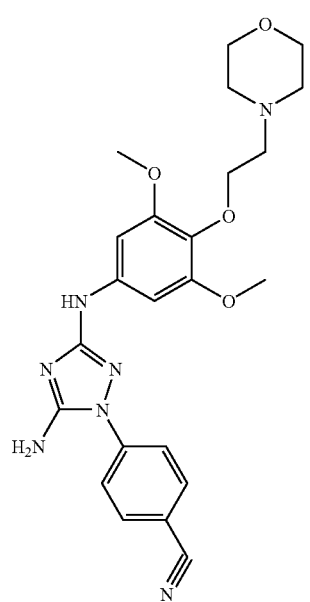
I-268
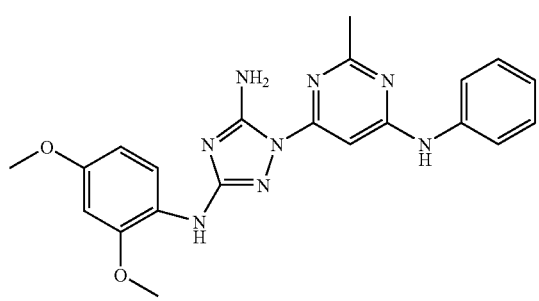
I-269
TABLE 1-continued
Examples of Compounds of Formula I:
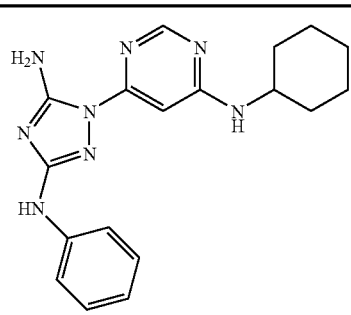
I-270
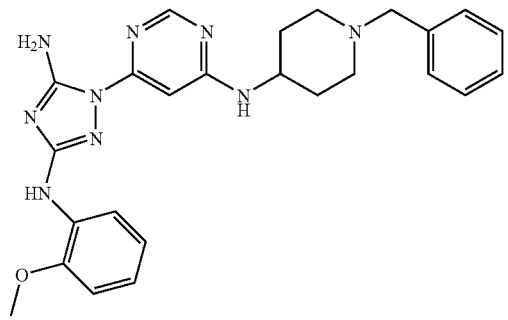
I-271
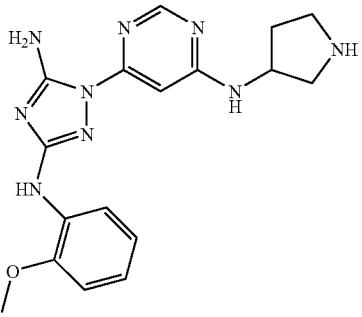
I-272
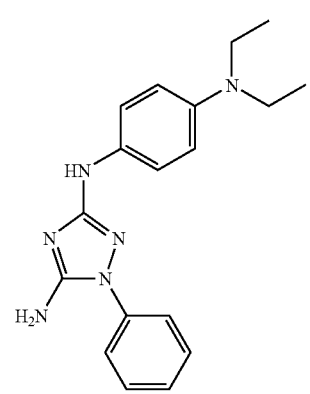
I-273

TABLE 1-continued
Examples of Compounds of Formula I:
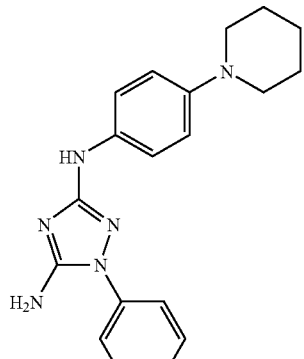
I-274
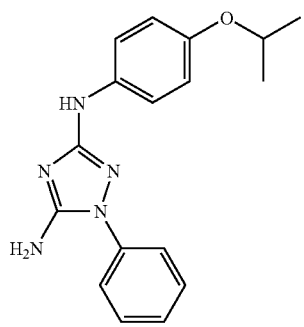
I-275
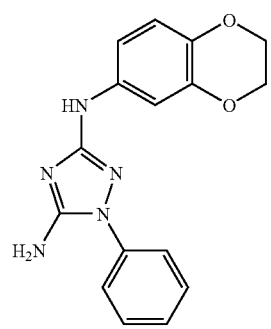
I-276
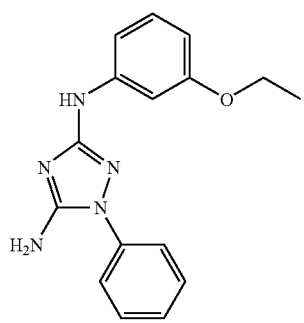
I-277
TABLE 1-continued
Examples of Compounds of Formula I:
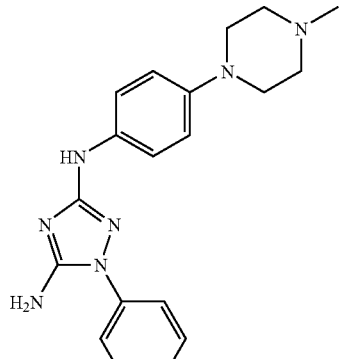
I-278
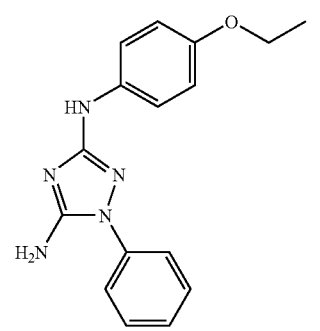
I-279
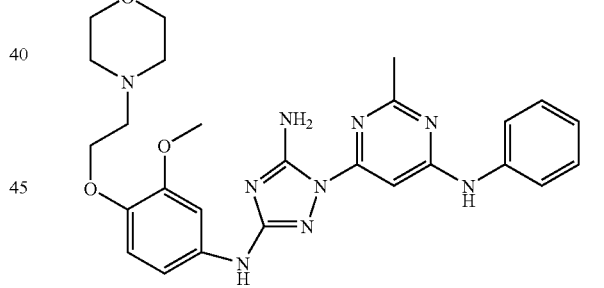
I-280
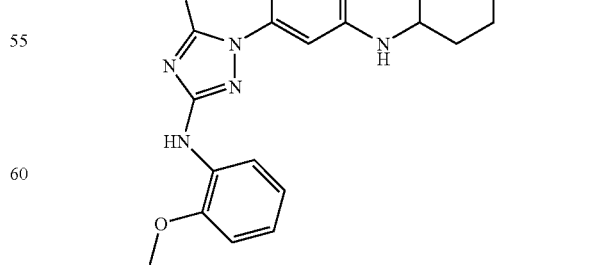
I-281

TABLE 1-continued
Examples of Compounds of Formula I:
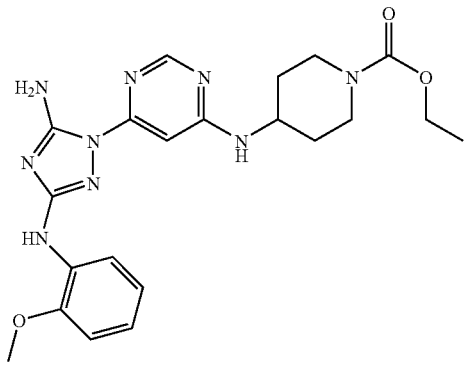
I-282
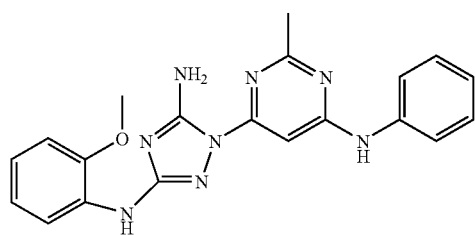
I-283
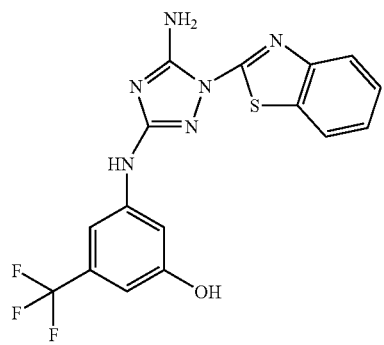
I-284
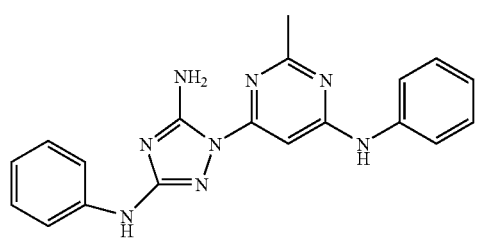
I-285
TABLE 1-continued
Examples of Compounds of Formula I:
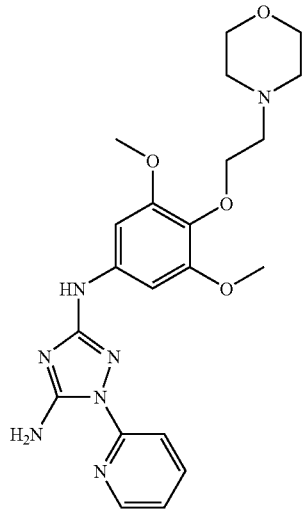
I-286
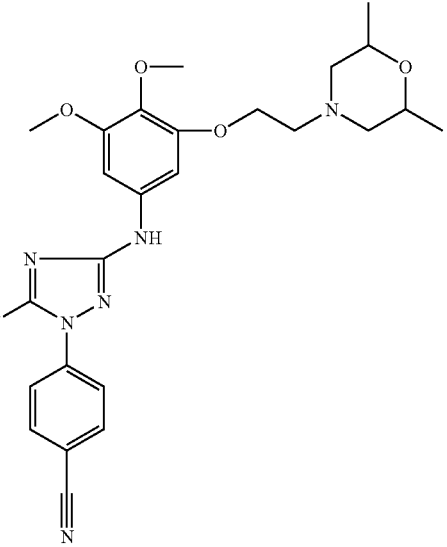
I-287
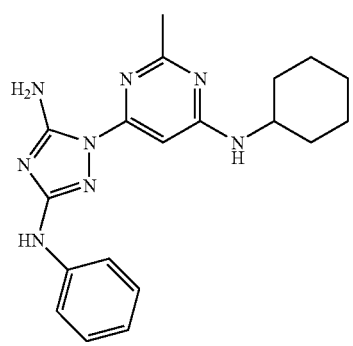
I-288

TABLE 1-continued
Examples of Compounds of Formula I:
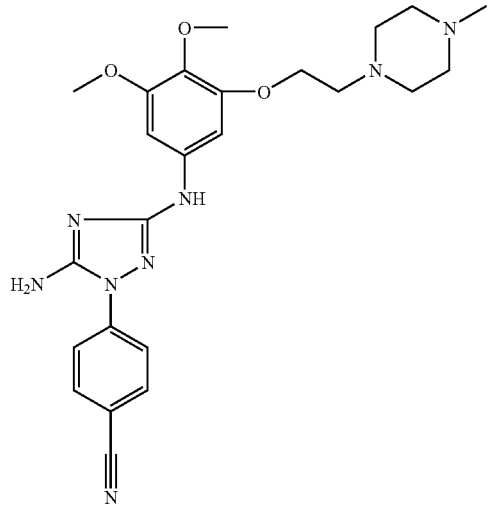
I-289
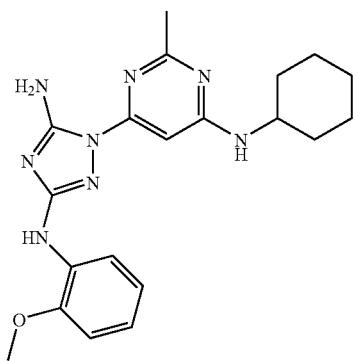
I-290
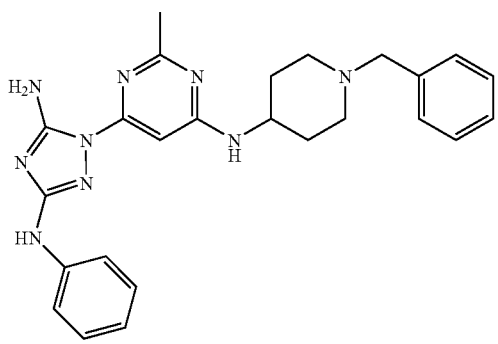
I-291
TABLE 1-continued
Examples of Compounds of Formula I:
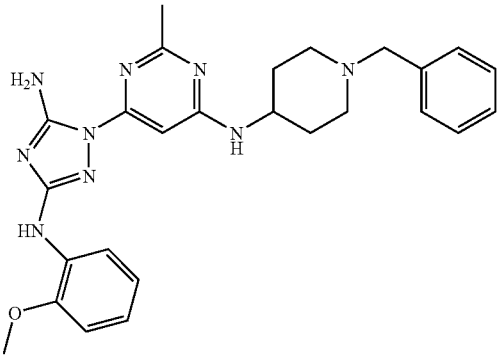
I-292
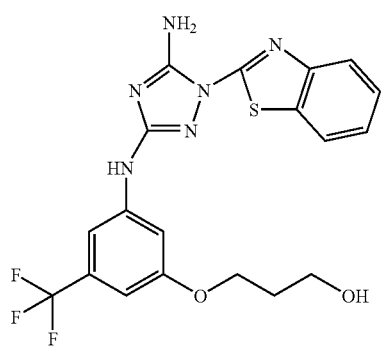
I-293
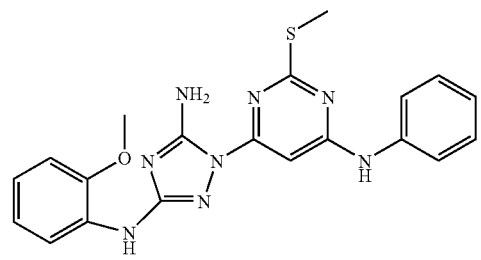
I-294
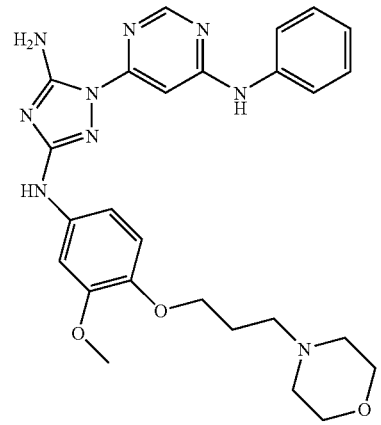
I-295

TABLE 1-continued
Examples of Compounds of Formula I:
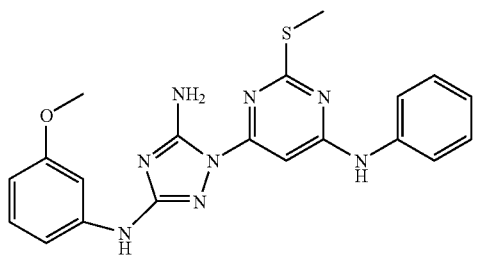
I-296
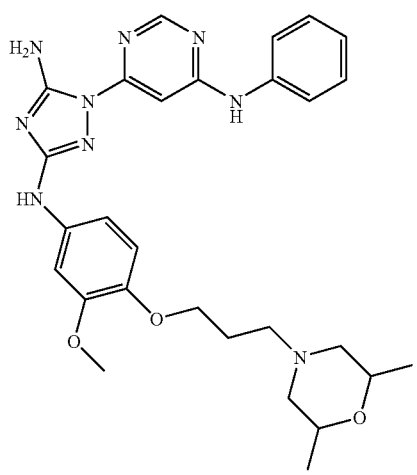
I-297
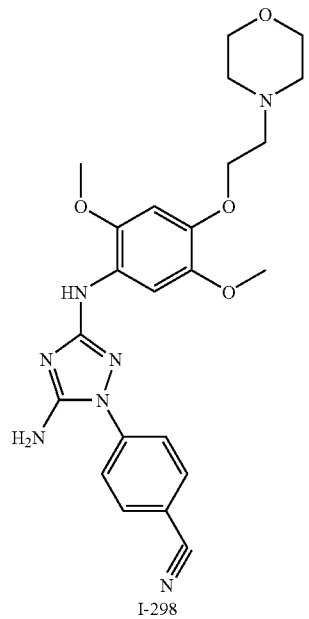
I-298
TABLE 1-continued
Examples of Compounds of Formula I:
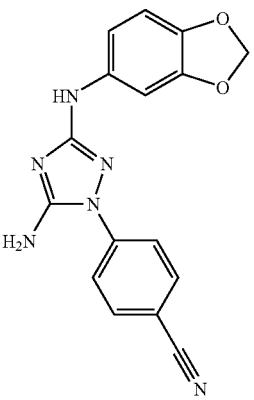
I-299
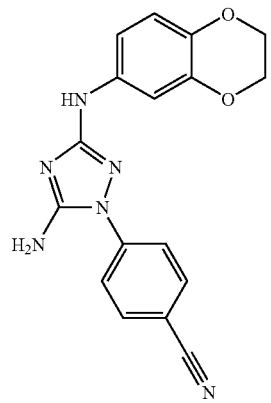
I-300
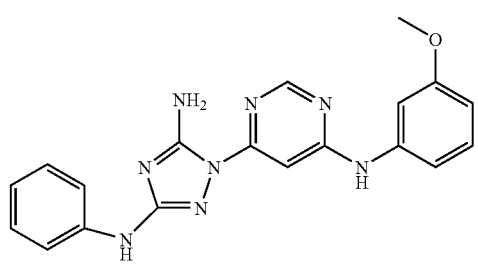
I-301

TABLE 1-continued
Examples of Compounds of Formula I:
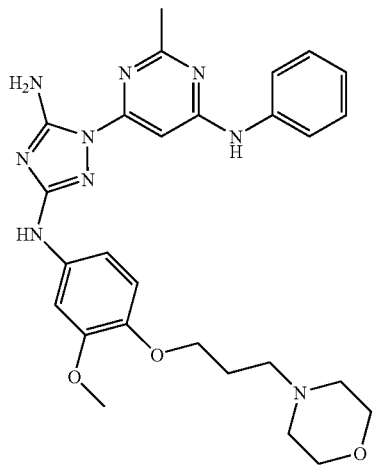
I-302
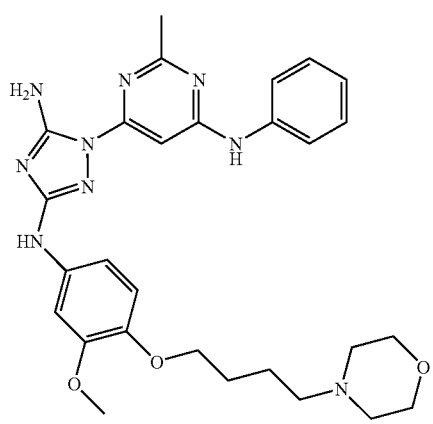
I-303
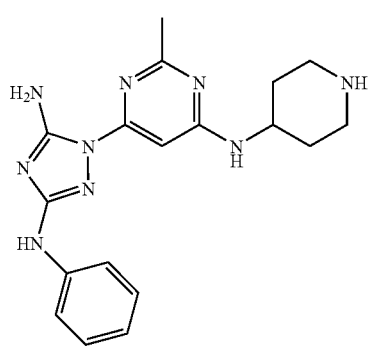
I-304
TABLE 1-continued
Examples of Compounds of Formula I:
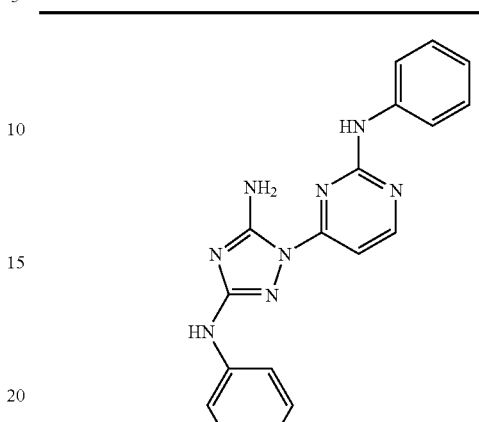
I-305
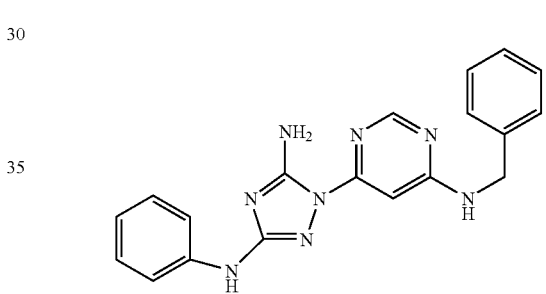
I-306
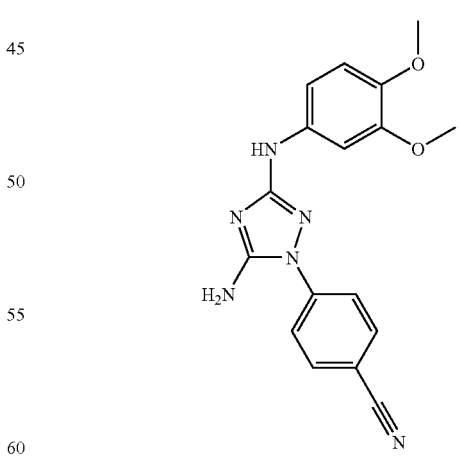
I-307

TABLE 1-continued
Examples of Compounds of Formula I:
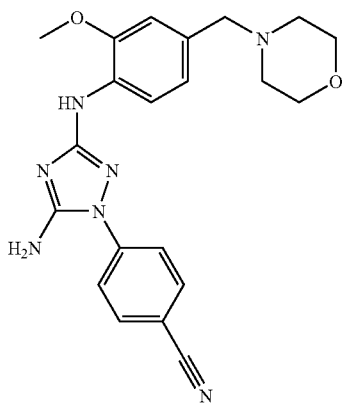
I-308
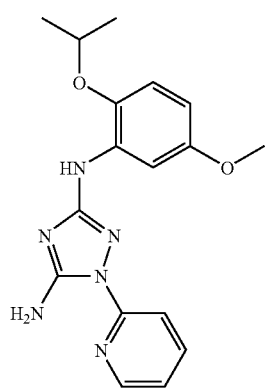
I-309
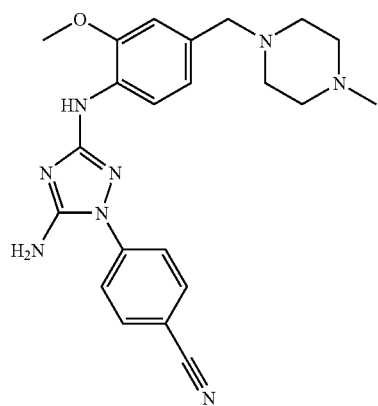
I-310
TABLE 1-continued
Examples of Compounds of Formula I:
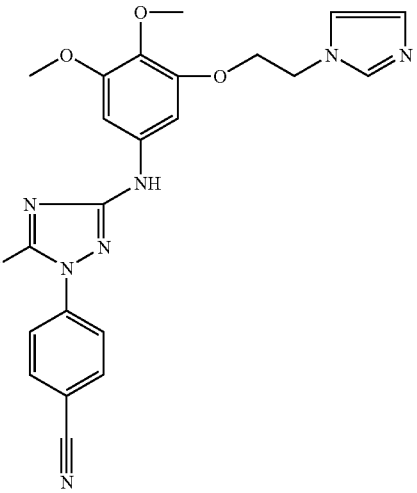
I-311
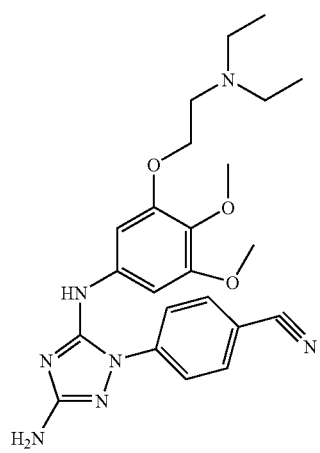
I-312
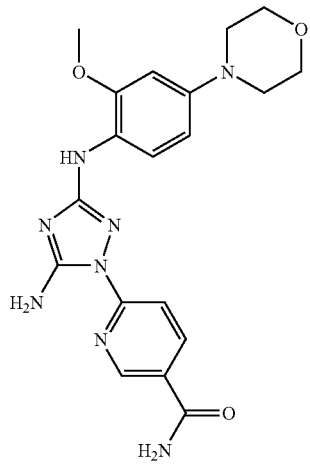
I-313

TABLE 1-continued
Examples of Compounds of Formula I:
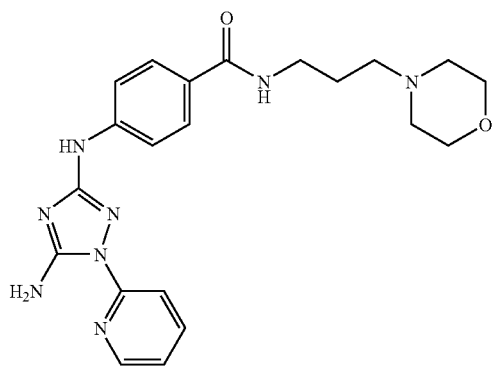
I-314
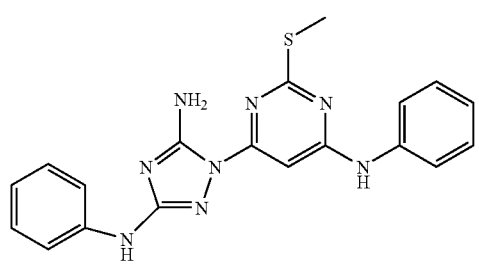
I-315
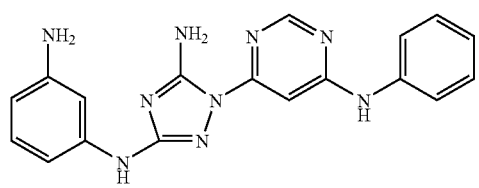
I-316
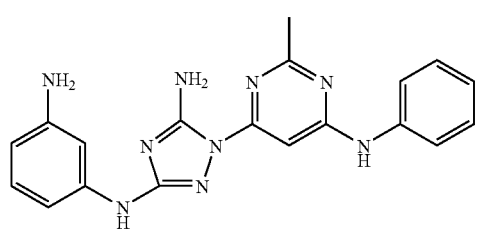
I-317
TABLE 1-continued
Examples of Compounds of Formula I:
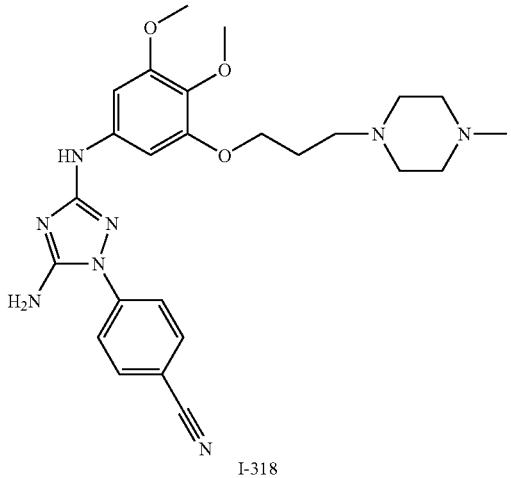
I-318
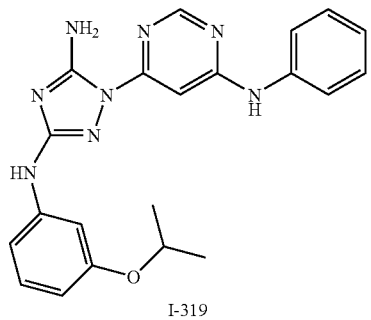
I-319
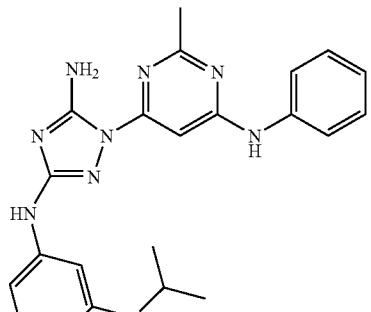
I-320
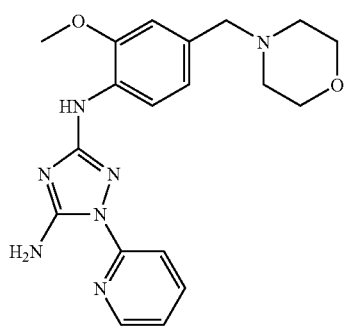
I-321

TABLE 1-continued
Examples of Compounds of Formula I:
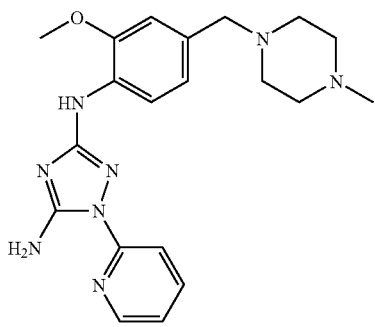
I-322
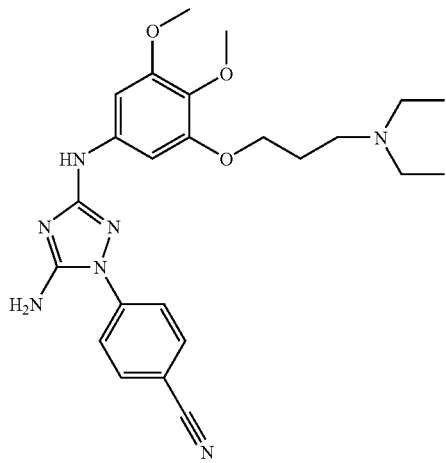
I-323
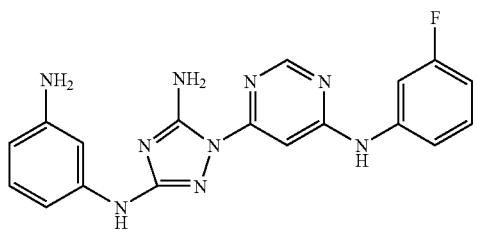
I-324
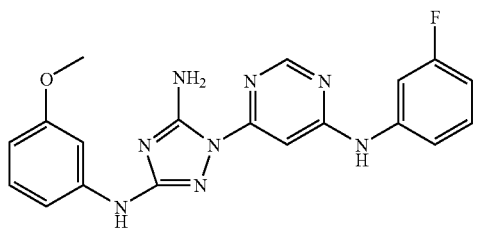
I-325
TABLE 1-continued
Examples of Compounds of Formula I:
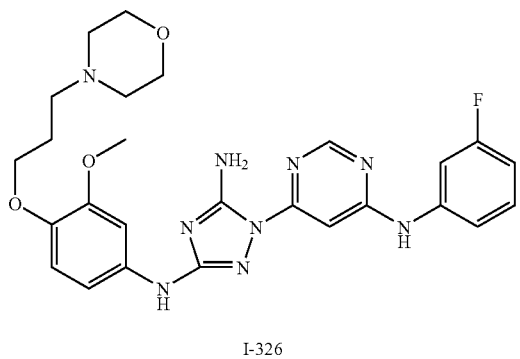
I-326
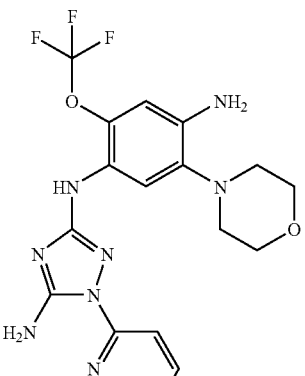
I-327
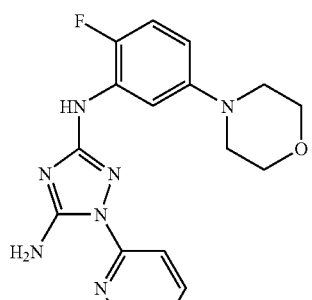
I-328
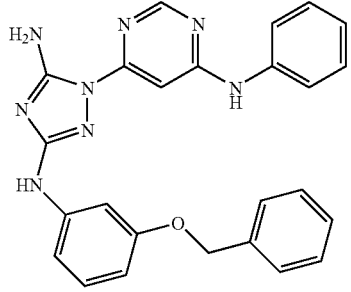
I-329

TABLE 1-continued
Examples of Compounds of Formula I:
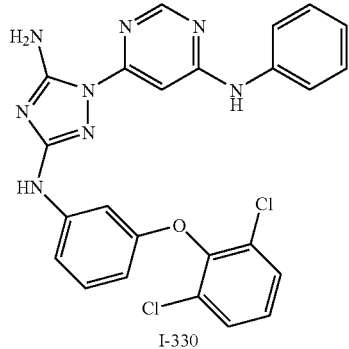
I-330
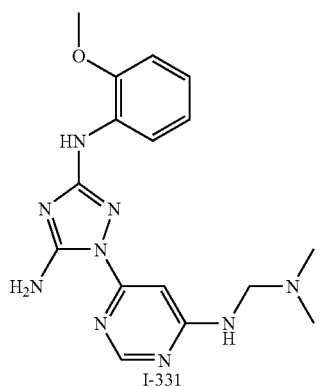
I-331
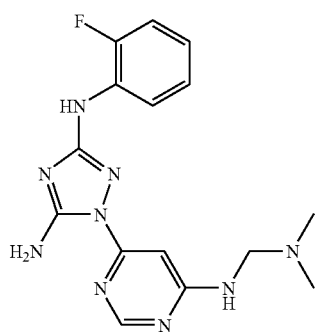
I-332
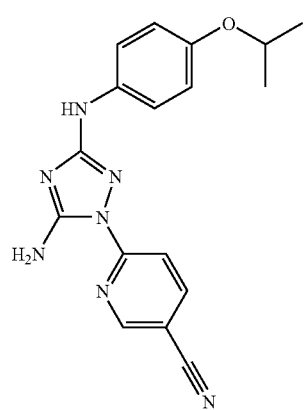
I-333
TABLE 1-continued
Examples of Compounds of Formula I:
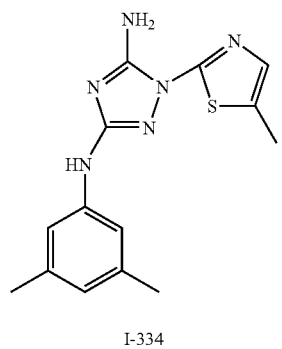
I-334
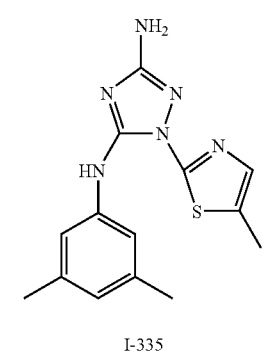
I-335
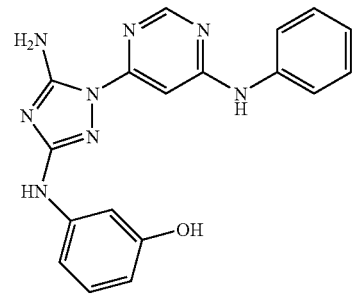
I-336
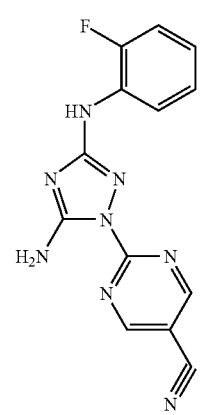
I-337

TABLE 1-continued
Examples of Compounds of Formula I:
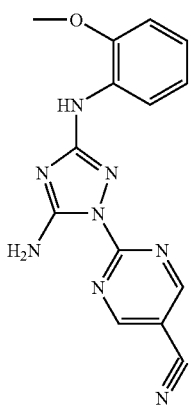
I-338
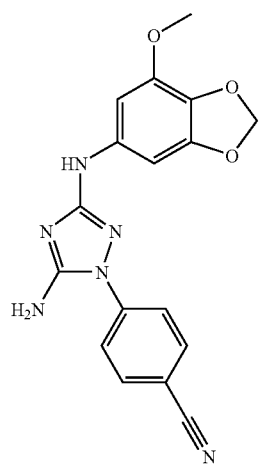
I-339
TABLE 1-continued
Examples of Compounds of Formula I:
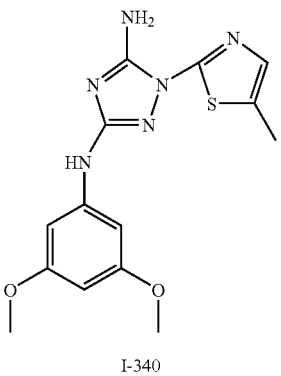
I-340
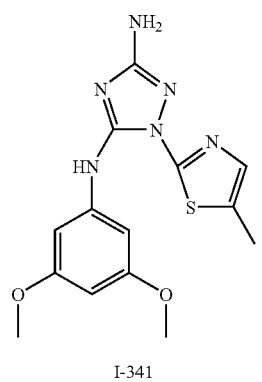
I-341
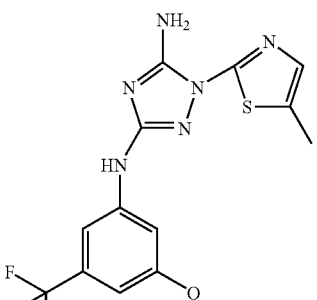
I-342
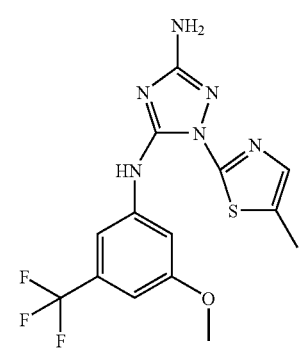
I-343

TABLE 1-continued
Examples of Compounds of Formula I:
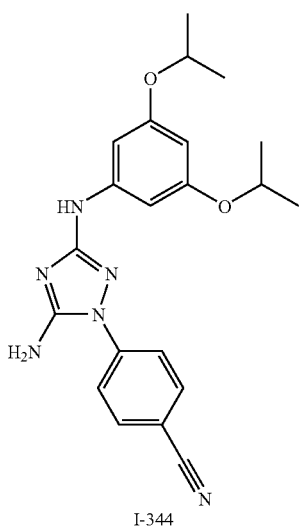
I-344
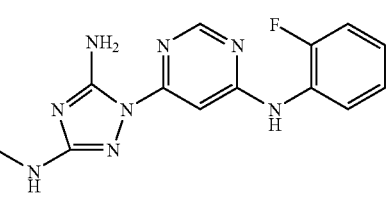
I-345
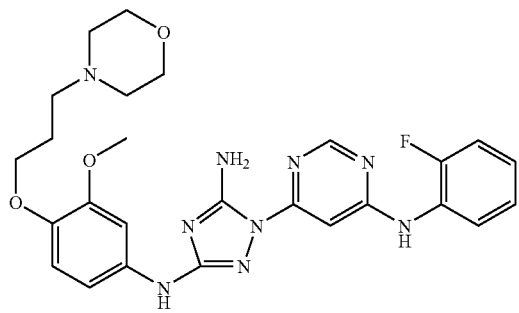
I-346
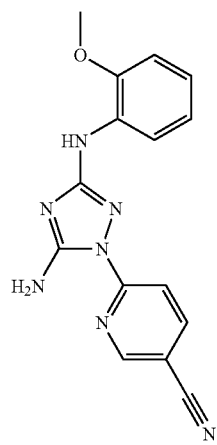
I-347
TABLE 1-continued
Examples of Compounds of Formula I:
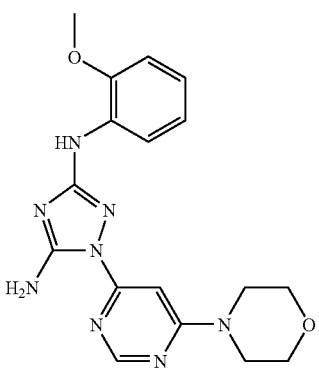
I-348
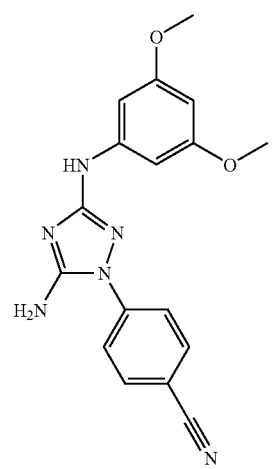
I-349
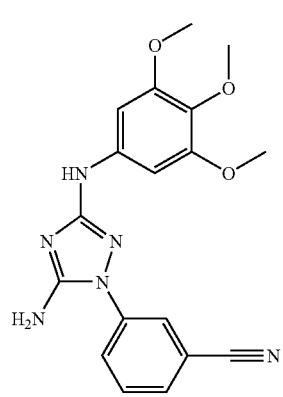
I-350

TABLE 1-continued
Examples of Compounds of Formula I:
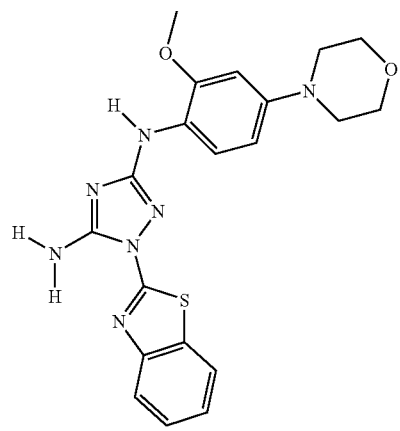
I-351
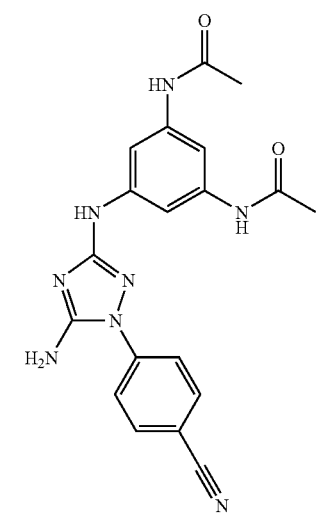
I-352
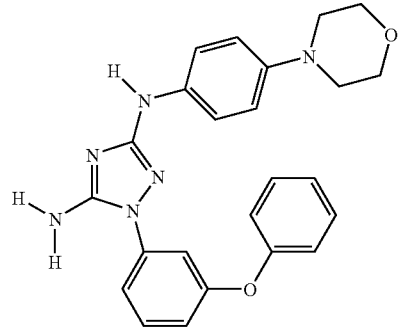
I-353
TABLE 1-continued
Examples of Compounds of Formula I:
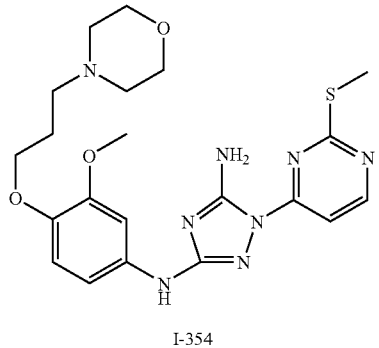
I-354
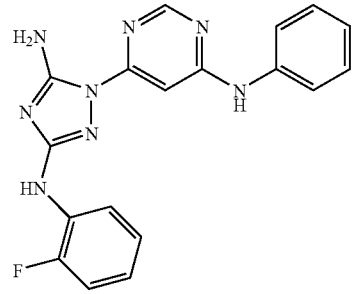
I-355
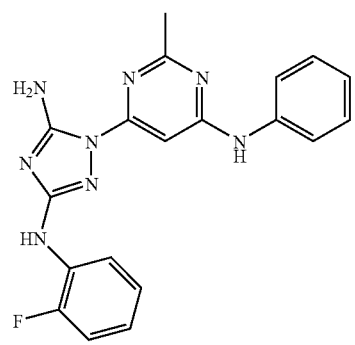
I-356
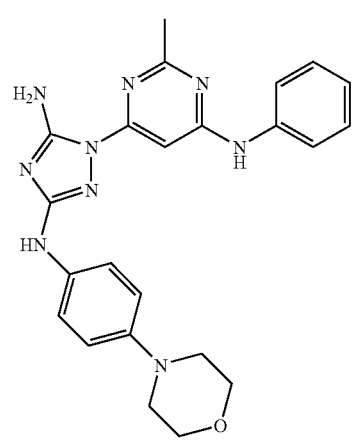
I-357

TABLE 1-continued
Examples of Compounds of Formula I:
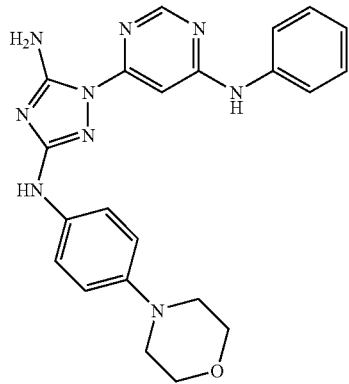
I-358
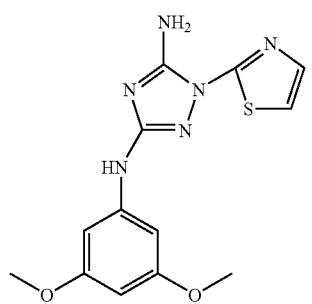
I-359
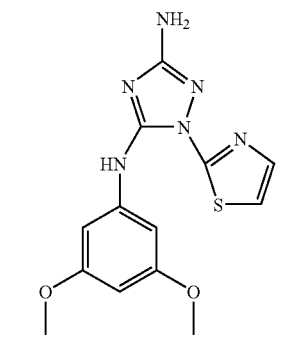
I-360
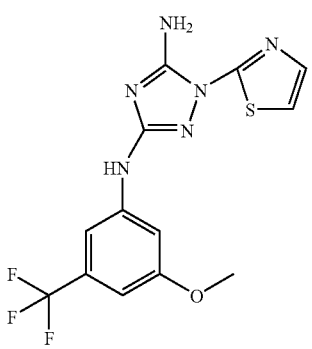
I-361
TABLE 1-continued
Examples of Compounds of Formula I:
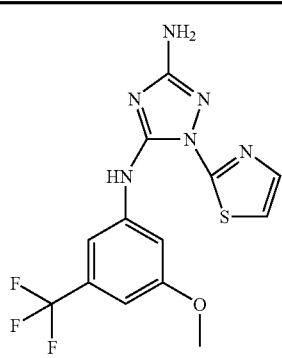
I-362
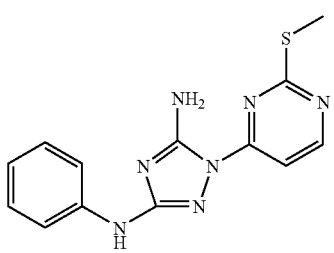
I-363
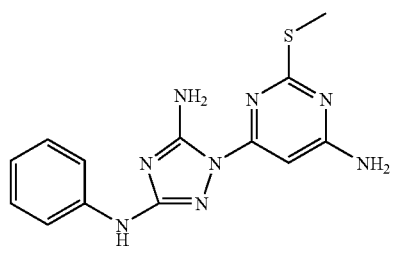
I-364
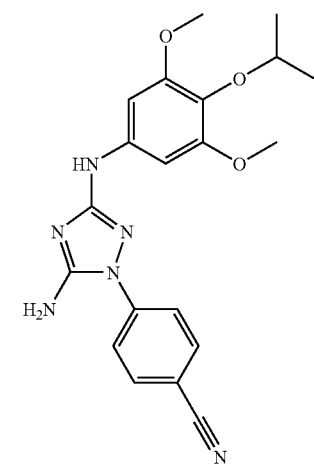
I-365

TABLE 1-continued
Examples of Compounds of Formula I:
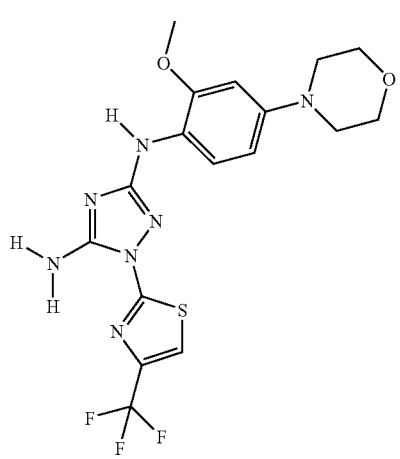
I-366
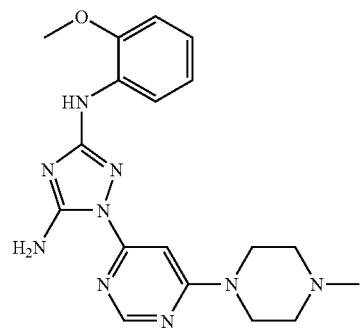
I-367
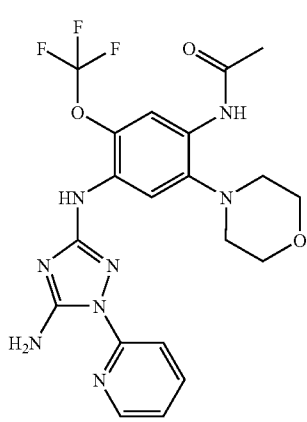
I-368
TABLE 1-continued
Examples of Compounds of Formula I:
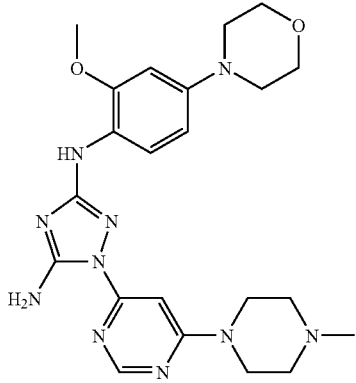
I-369
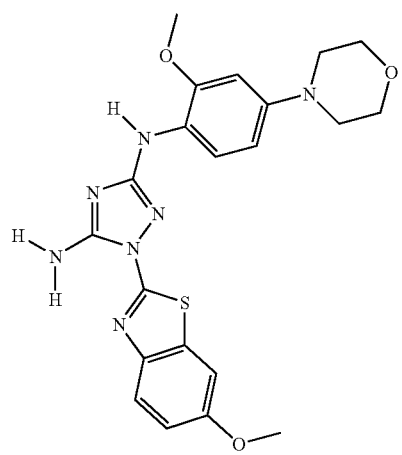
I-370
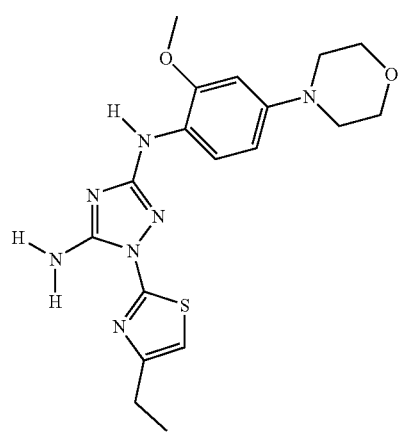
I-371

TABLE 1-continued
Examples of Compounds of Formula I:
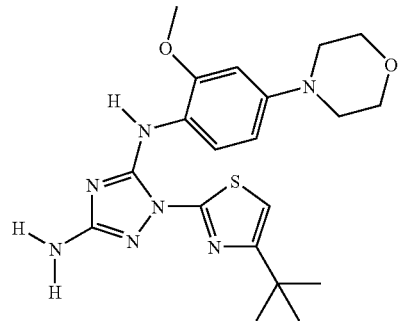
I-372
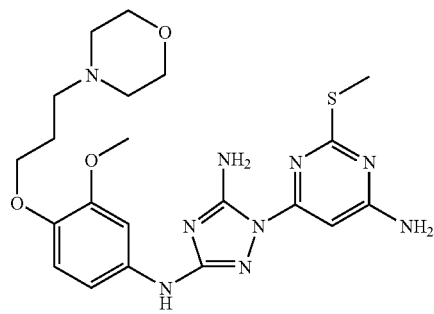
I-373
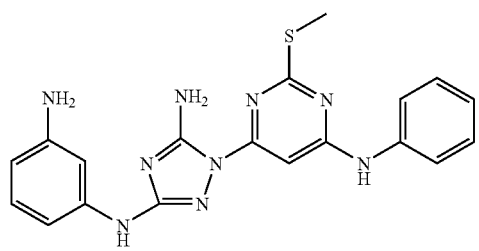
I-374
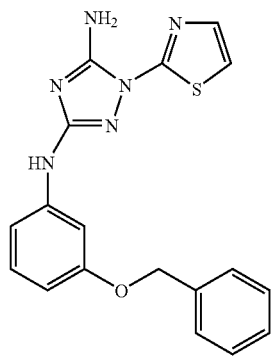
I-375
TABLE 1-continued
Examples of Compounds of Formula I:
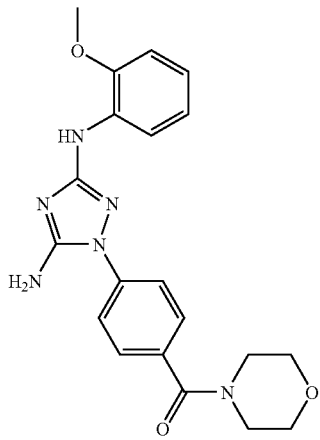
I-376
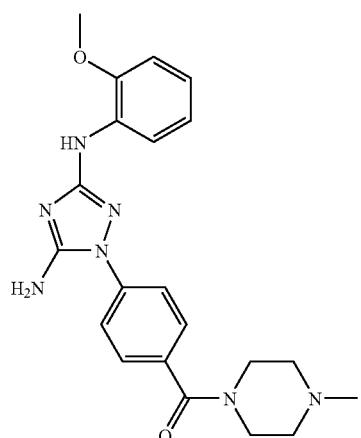
I-377
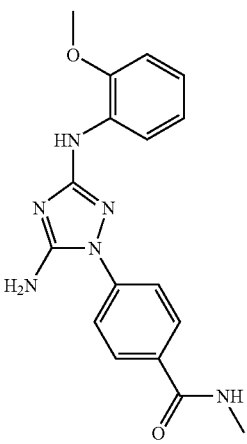
I-378

TABLE 1-continued
Examples of Compounds of Formula I:
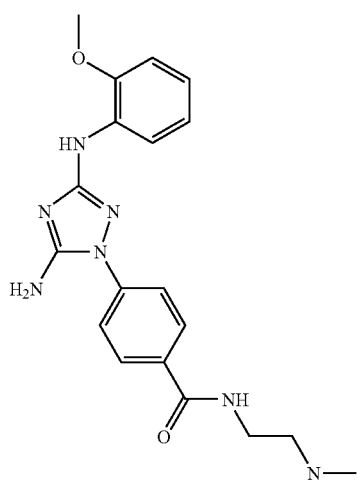
I-379
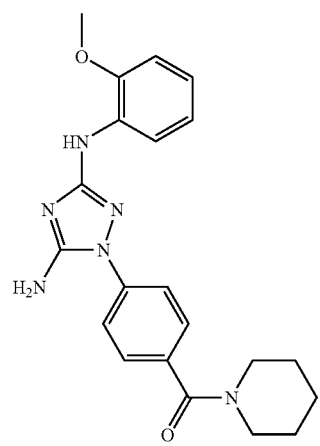
I-380
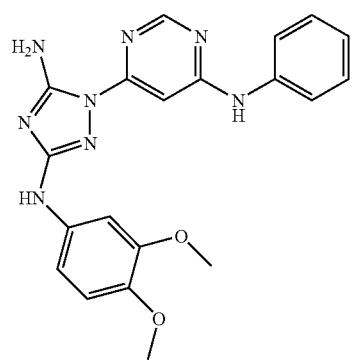
I-381
TABLE 1-continued
Examples of Compounds of Formula I:
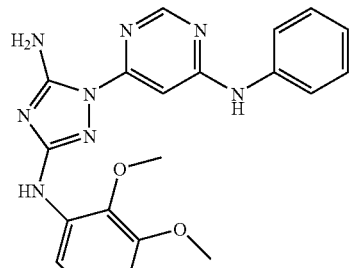
I-382
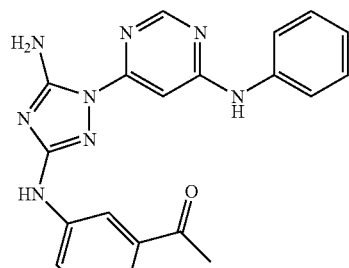
I-383
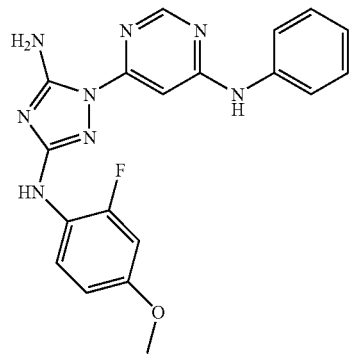
I-384
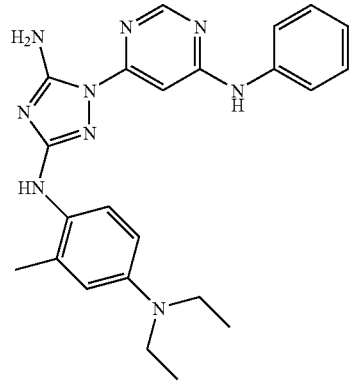
I-385

TABLE 1-continued
Examples of Compounds of Formula I:
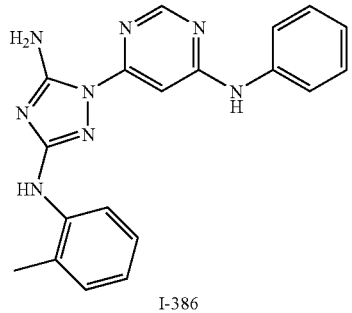
I-386
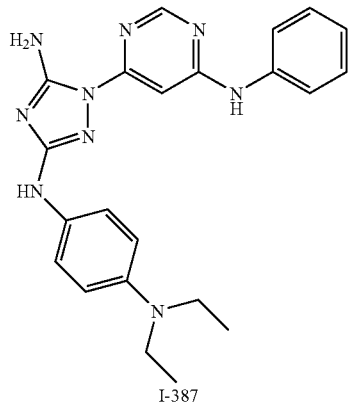
I-387
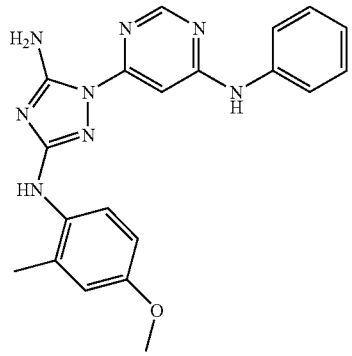
I-388
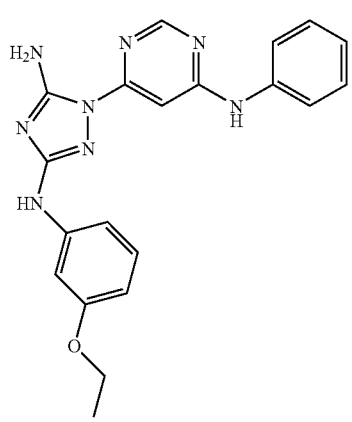
I-389
TABLE 1-continued
Examples of Compounds of Formula I:
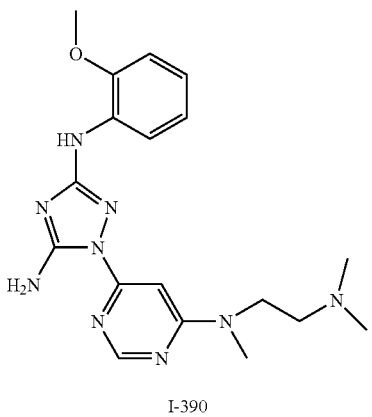
I-390
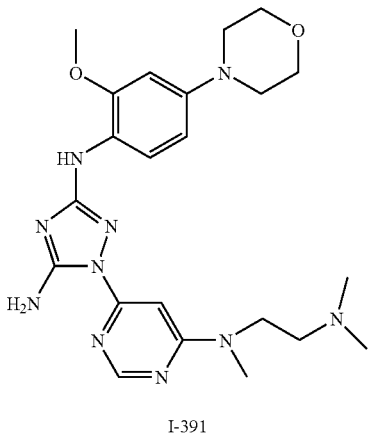
I-391
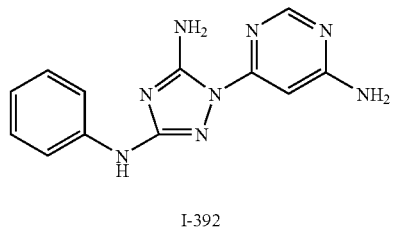
I-392
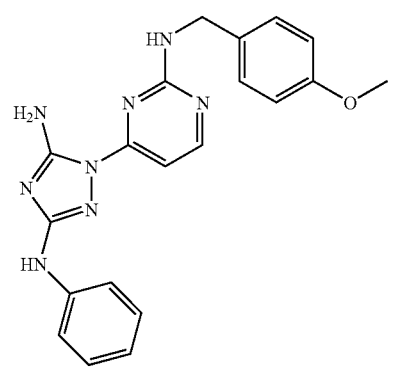
I-393

TABLE 1-continued
Examples of Compounds of Formula I:
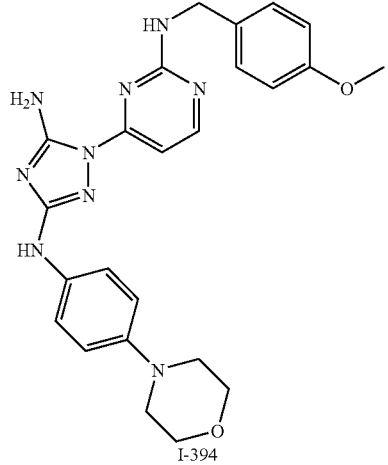
I-394
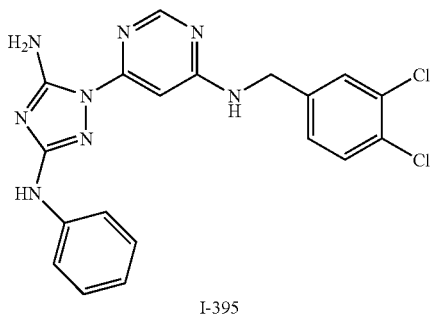
I-395
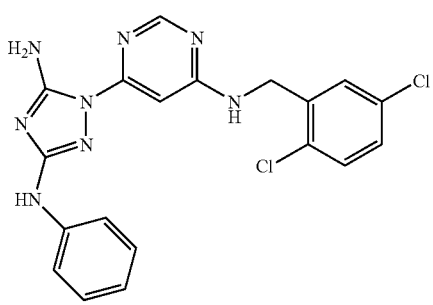
I-396
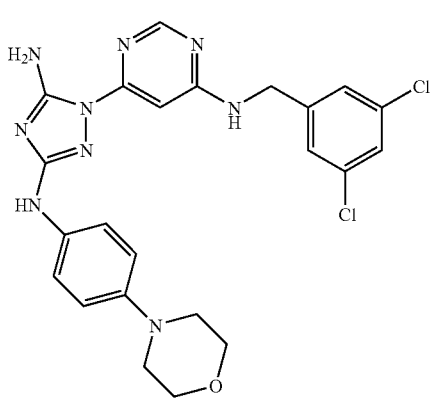
I-397
TABLE 1-continued
Examples of Compounds of Formula I:
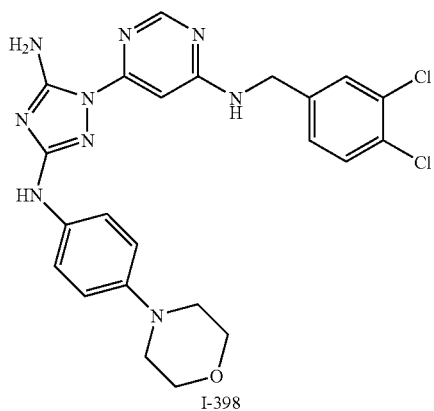
I-398
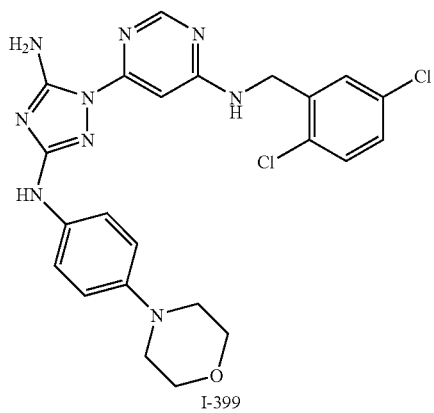
I-399
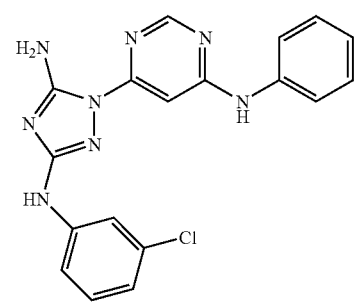
I-400
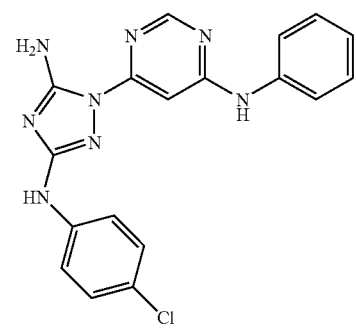
I-401

TABLE 1-continued
Examples of Compounds of Formula I:
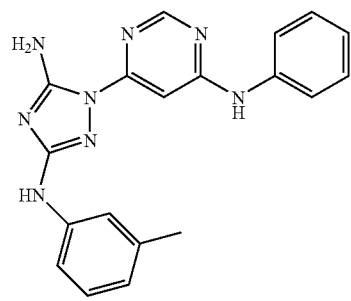
I-402
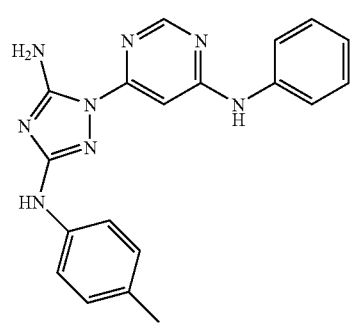
I-403
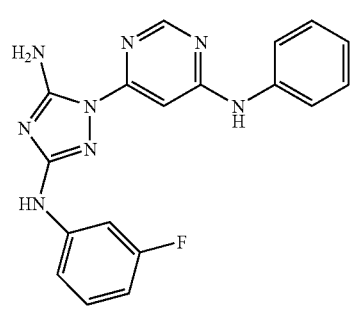
I-404
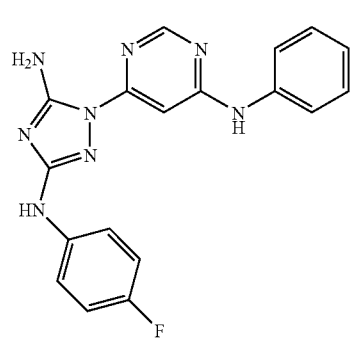
I-405
TABLE 1-continued
Examples of Compounds of Formula I:
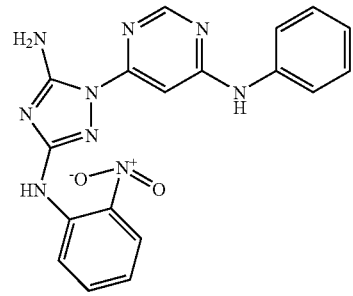
I-406
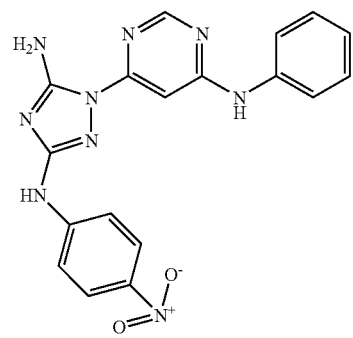
I-407
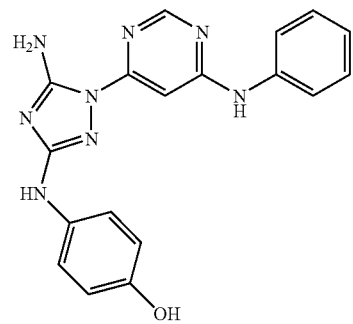
I-408
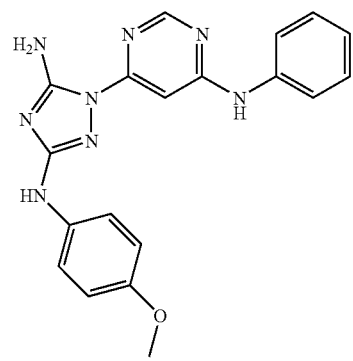
I-409

TABLE 1-continued
Examples of Compounds of Formula I:
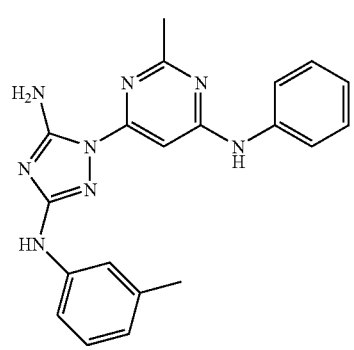
I-410
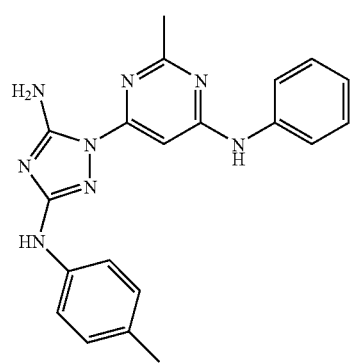
I-411
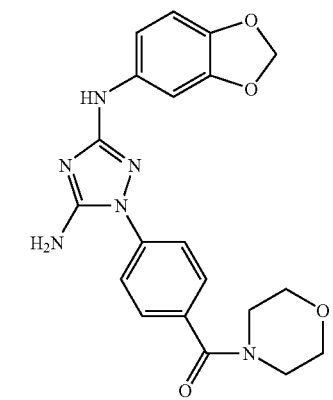
I-412
TABLE 1-continued
Examples of Compounds of Formula I:
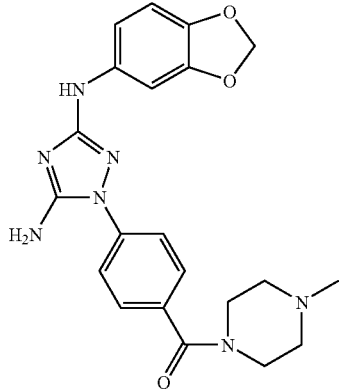
I-413
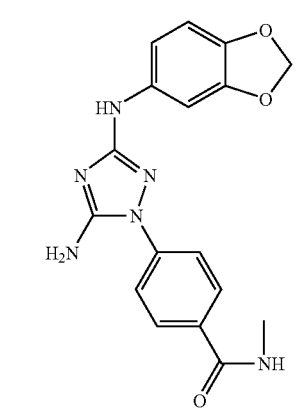
I-414
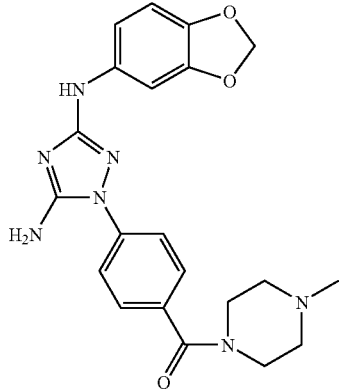
I-415

TABLE 1-continued
Examples of Compounds of Formula I:
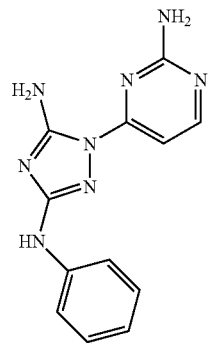
I-416
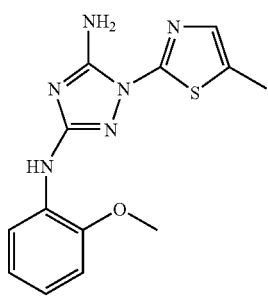
I-417
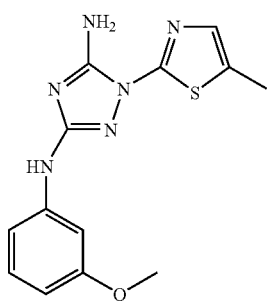
I-418
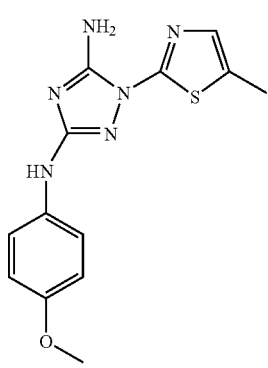
I-419
TABLE 1-continued
Examples of Compounds of Formula I:
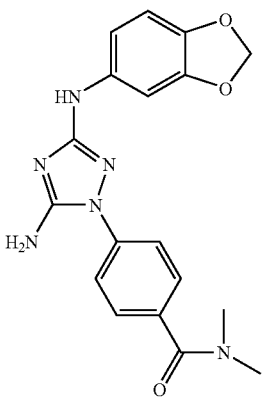
I-420
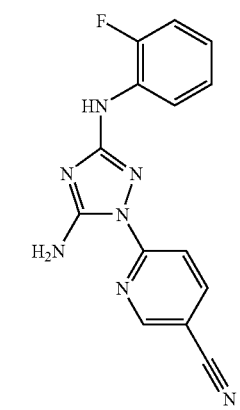
I-421
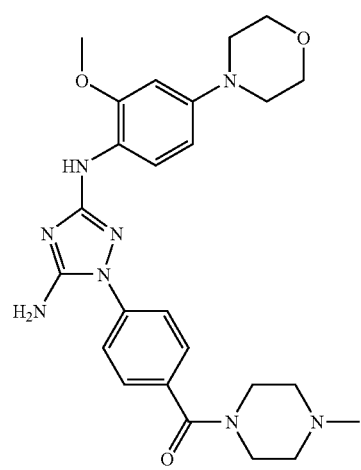
I-422

TABLE 1-continued
Examples of Compounds of Formula I:
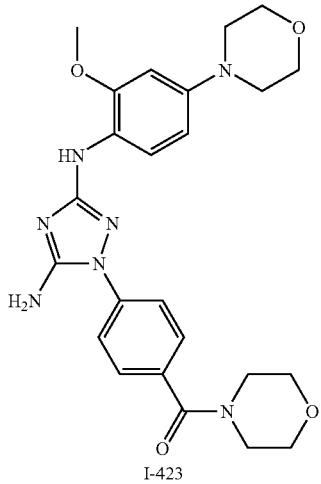
I-423
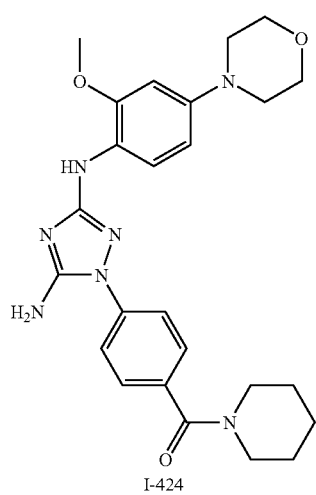
I-424
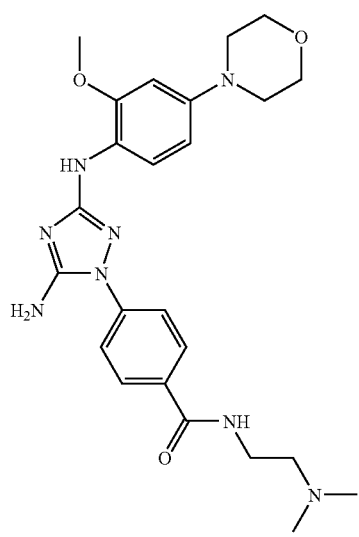
I-425
TABLE 1-continued
Examples of Compounds of Formula I:
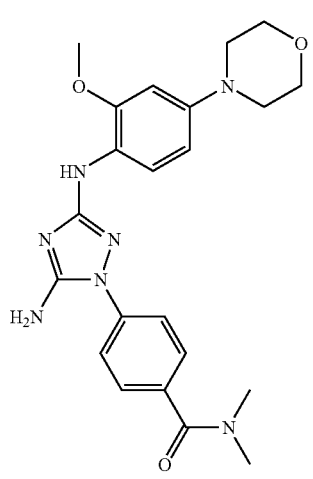
I-426
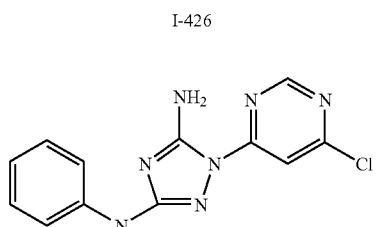
I-427
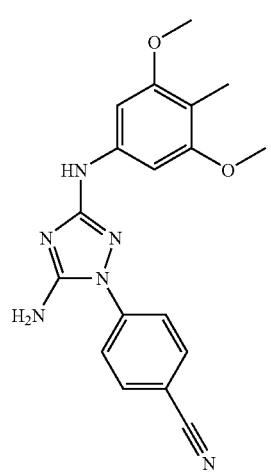
I-428

TABLE 1-continued
Examples of Compounds of Formula I:
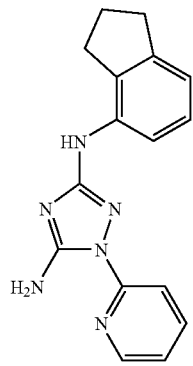
I-429
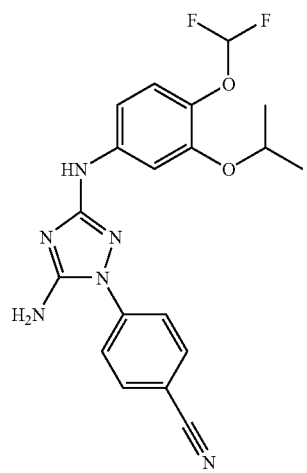
I-430
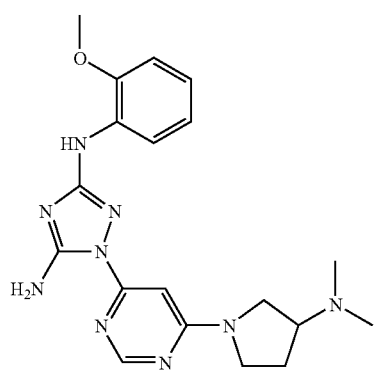
I-431
TABLE 1-continued
Examples of Compounds of Formula I:
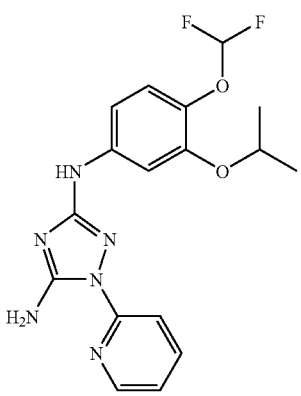
I-432
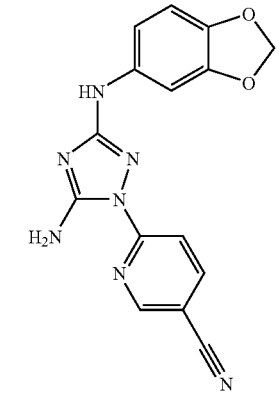
I-433
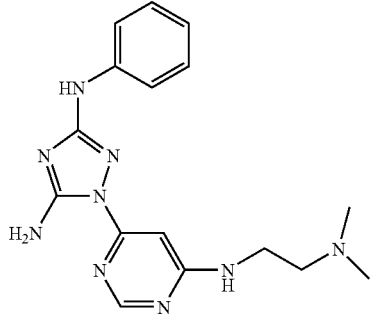
I-434

TABLE 1-continued
Examples of Compounds of Formula I:
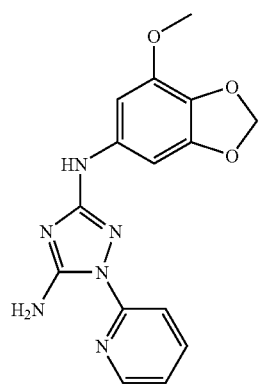
I-435
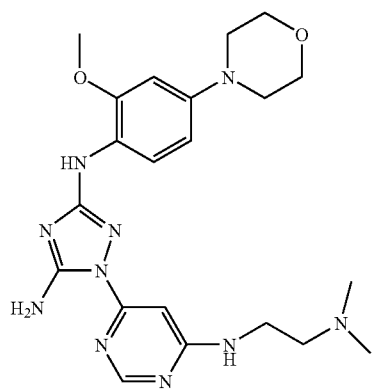
I-436
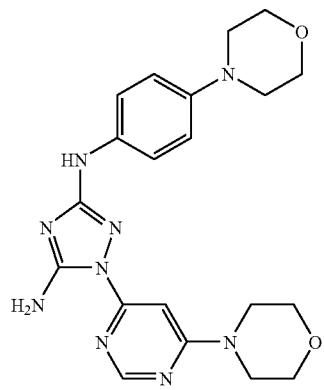
I-437
TABLE 1-continued
Examples of Compounds of Formula I:
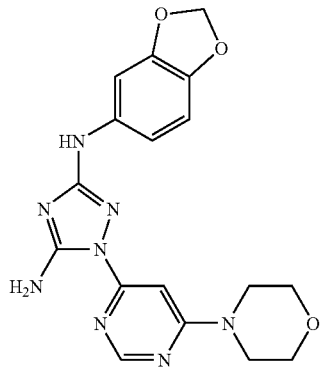
I-438
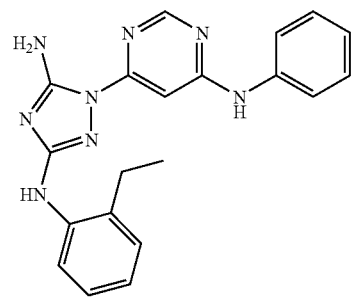
I-439
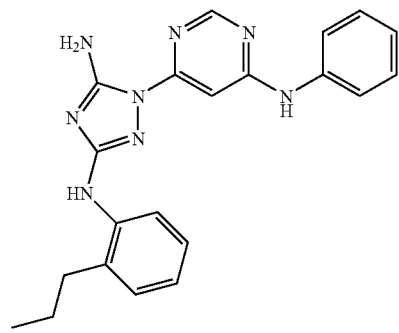
I-440
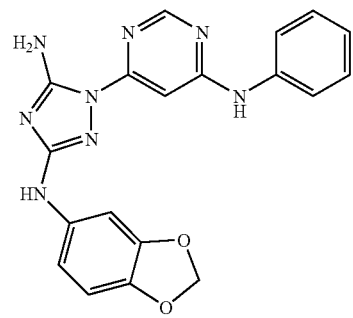
I-441

TABLE 1-continued
Examples of Compounds of Formula I:
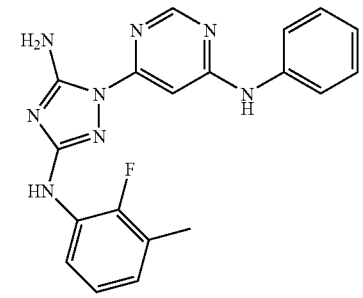
I-442
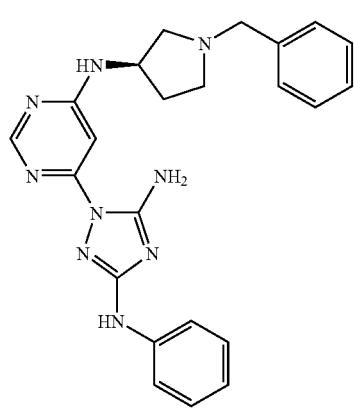
I-443
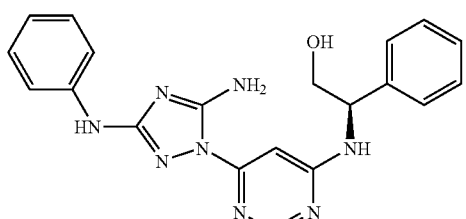
I-444
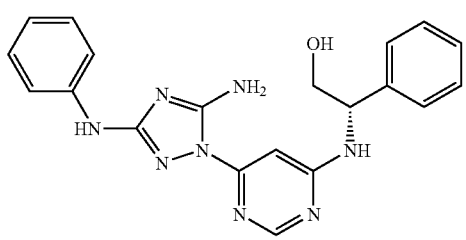
I-445
TABLE 1-continued
Examples of Compounds of Formula I:
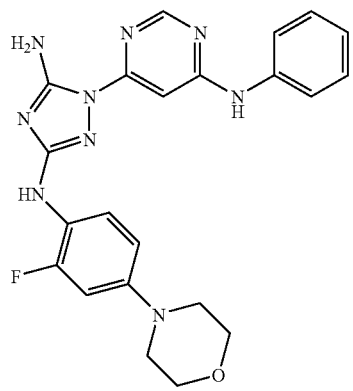
I-446
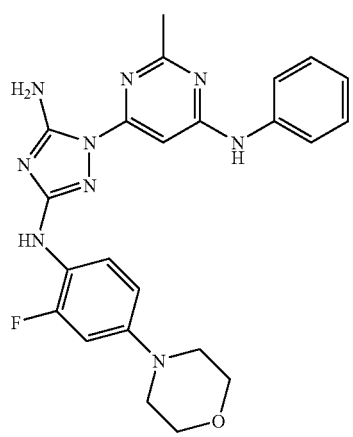
I-447
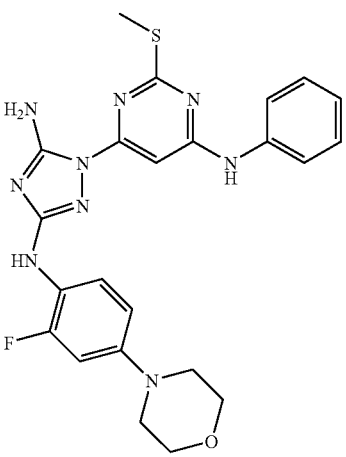
I-448

TABLE 1-continued
Examples of Compounds of Formula I:
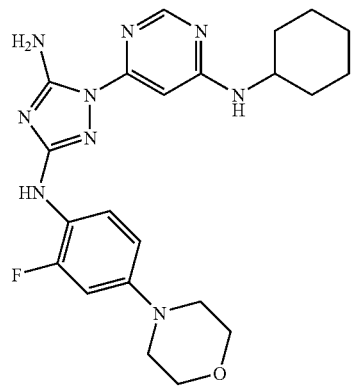
I-449
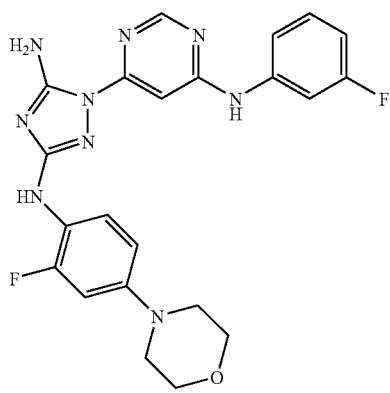
I-450
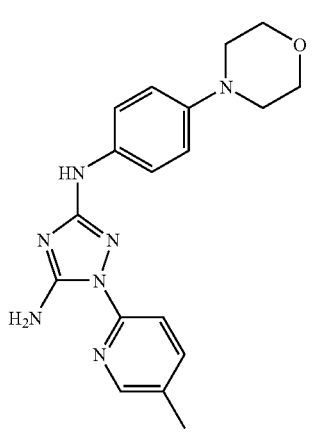
I-451
TABLE 1-continued
Examples of Compounds of Formula I:
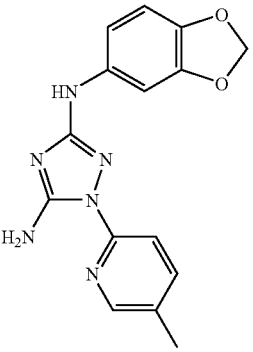
I-452
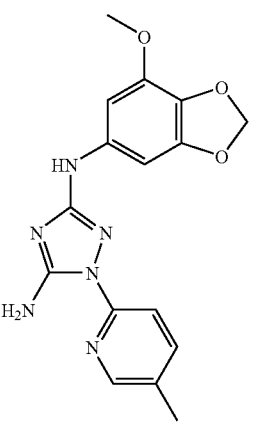
I-453
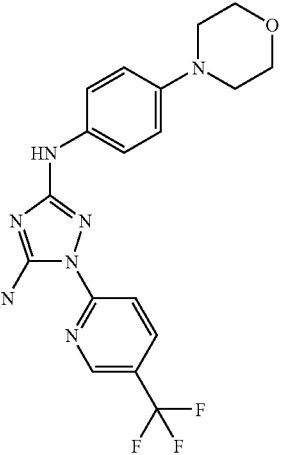
I-454

TABLE 1-continued

Examples of Compounds of Formula I:

I-455

I-456

I-457

I-458

I-459

I-460

I-461

I-462

TABLE 1-continued
Examples of Compounds of Formula I:
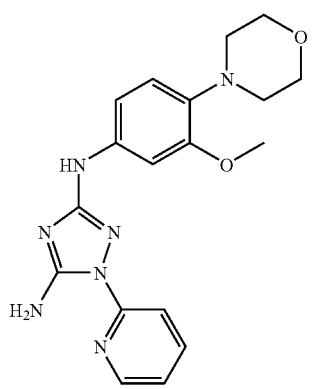
I-463
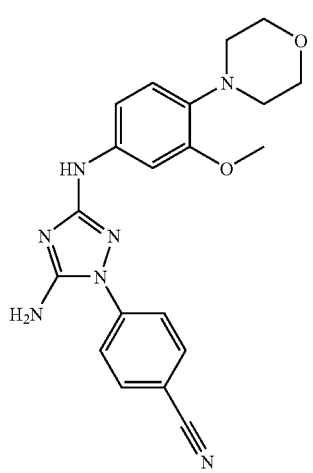
I-464
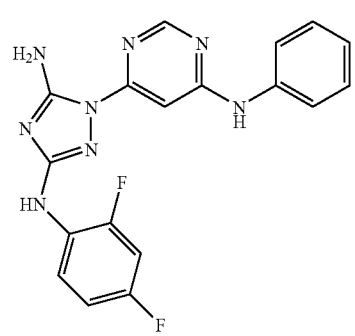
I-465
TABLE 1-continued
Examples of Compounds of Formula I:
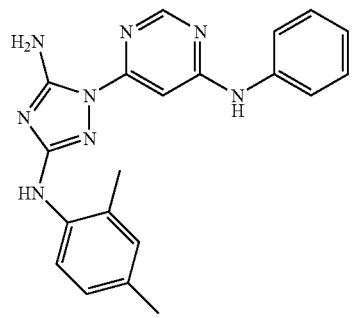
I-466
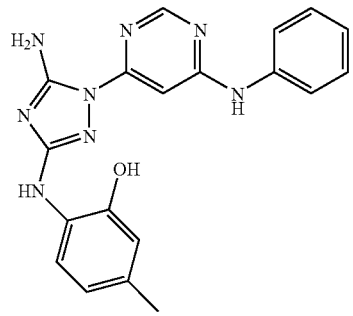
I-467
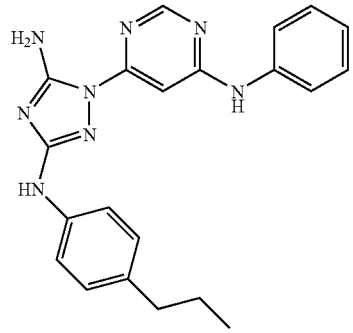
I-468
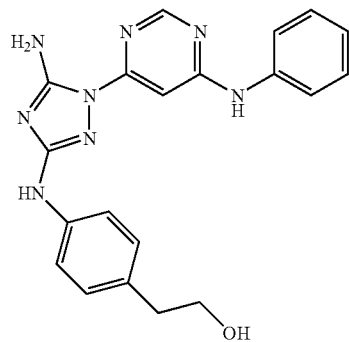
I-469

TABLE 1-continued
Examples of Compounds of Formula I:
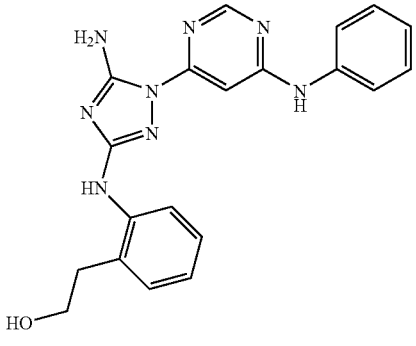
I-470
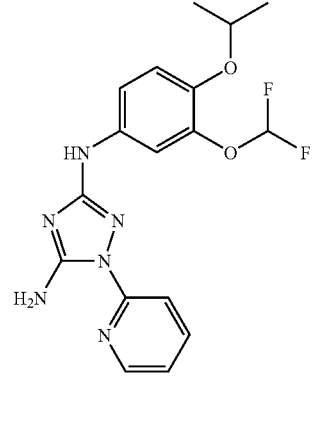
I-471
I-472
I-473
TABLE 1-continued
Examples of Compounds of Formula I:
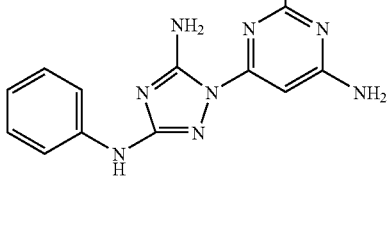
I-474
I-475
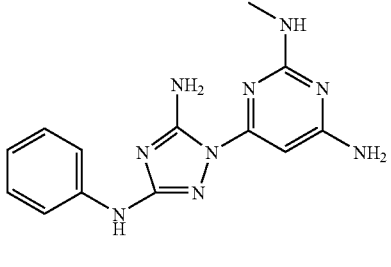
I-476

TABLE 1-continued
Examples of Compounds of Formula I:
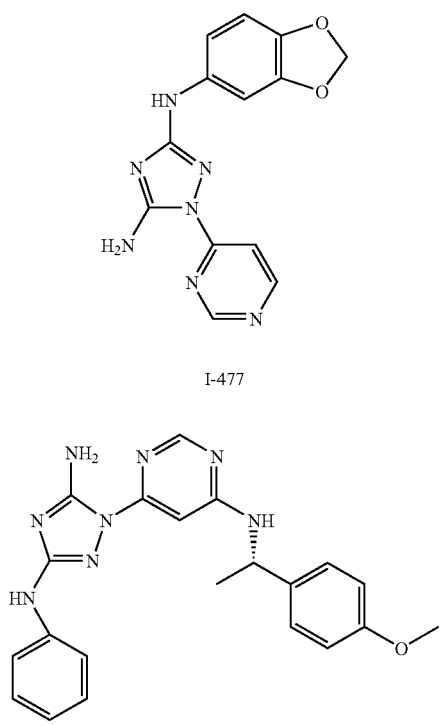
I-477
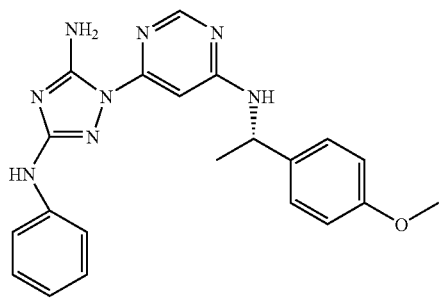
I-478
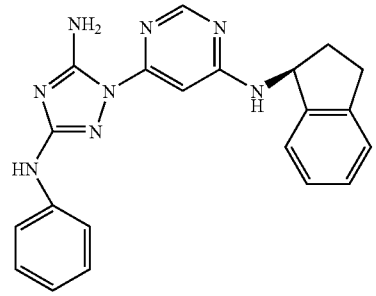
I-479
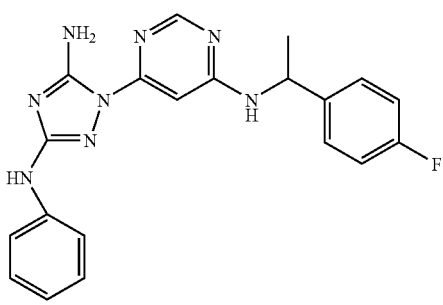
I-480
TABLE 1-continued
Examples of Compounds of Formula I:
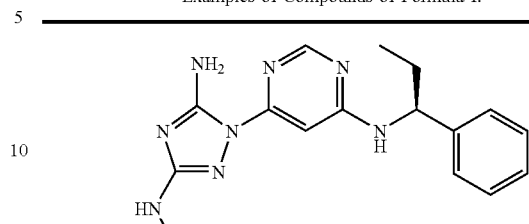
I-481
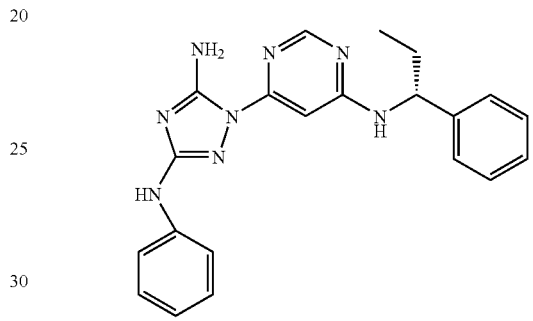
I-482
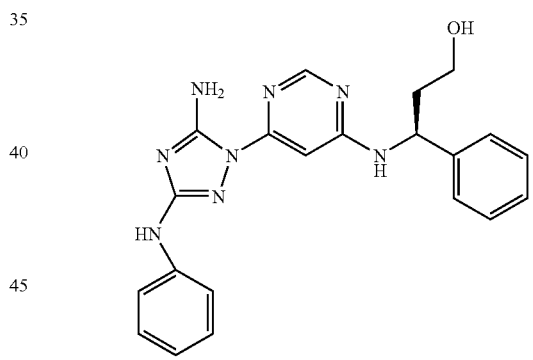
I-483
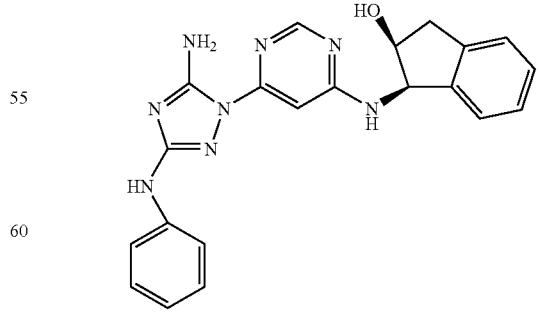
I-484

TABLE 1-continued
Examples of Compounds of Formula I:
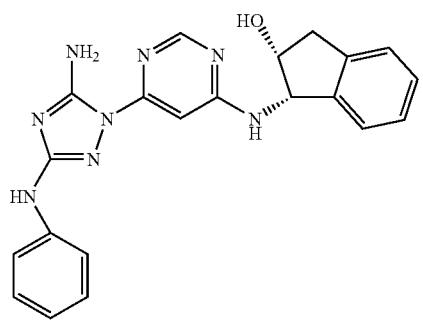
I-485
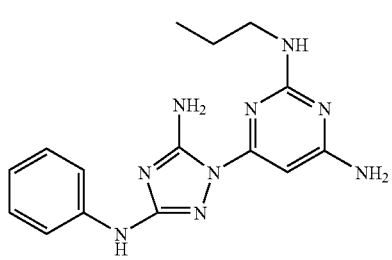
I-486
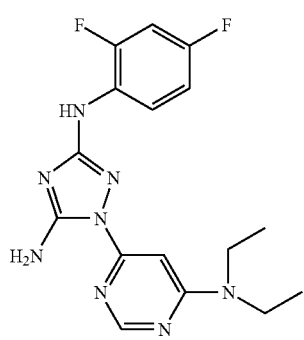
I-487
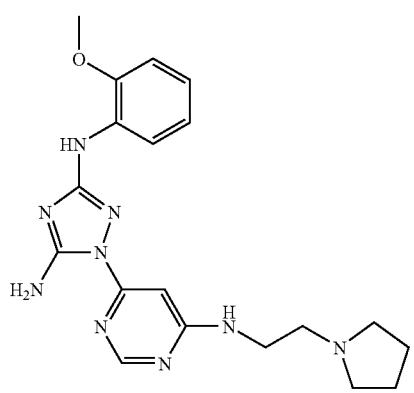
I-488
TABLE 1-continued
Examples of Compounds of Formula I:
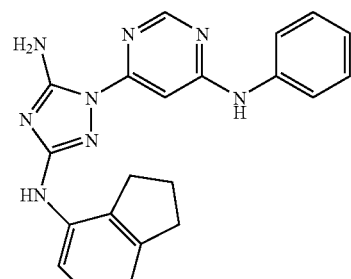
I-489
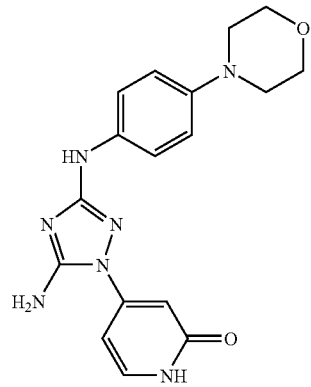
I-490
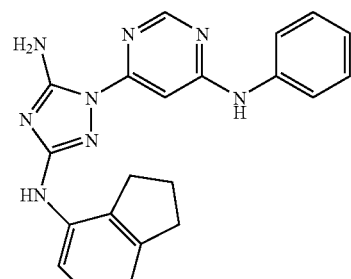
I-491
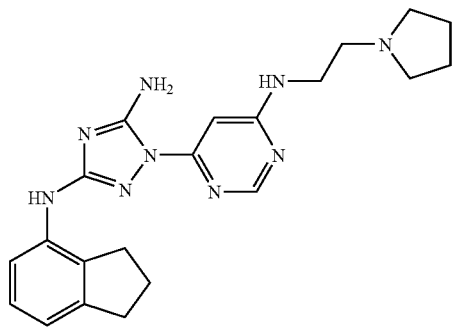
I-492

TABLE 1-continued
Examples of Compounds of Formula I:
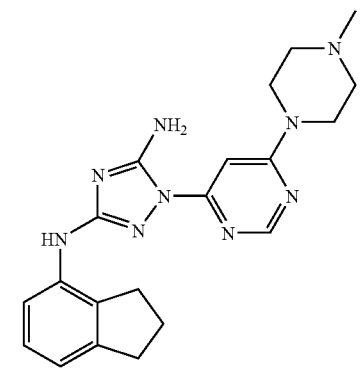
I-493
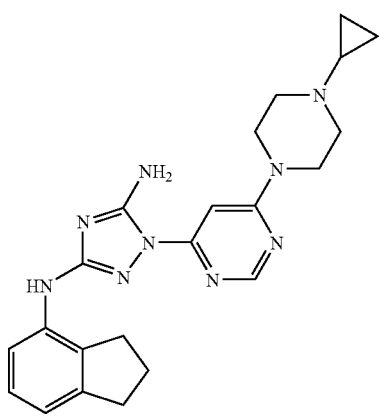
I-494
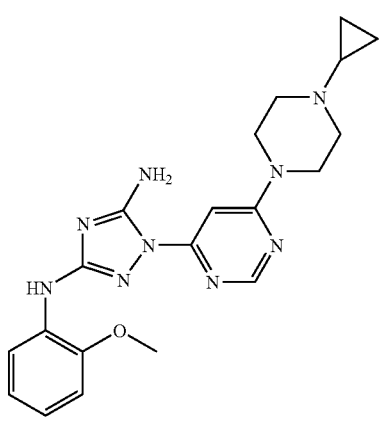
I-495
TABLE 1-continued
Examples of Compounds of Formula I:
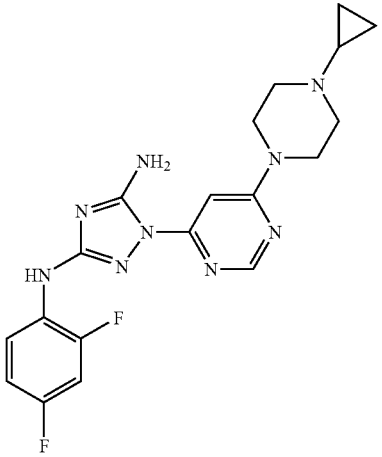
I-496
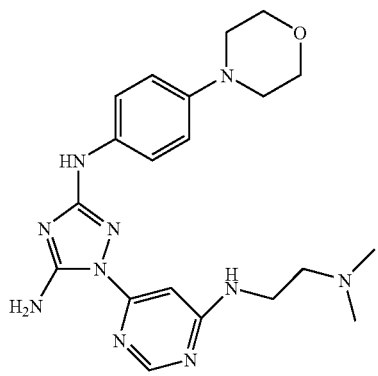
I-497
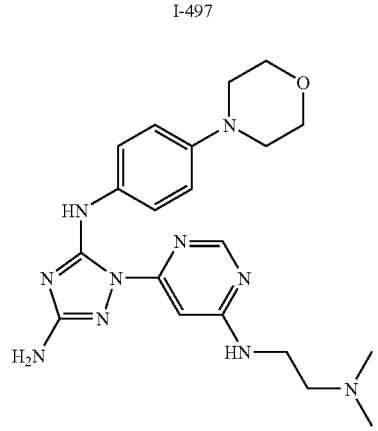
I-498

TABLE 1-continued
Examples of Compounds of Formula I:
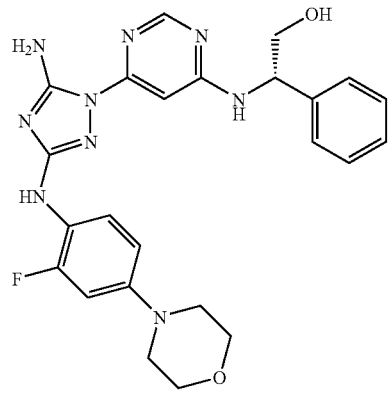
I-499
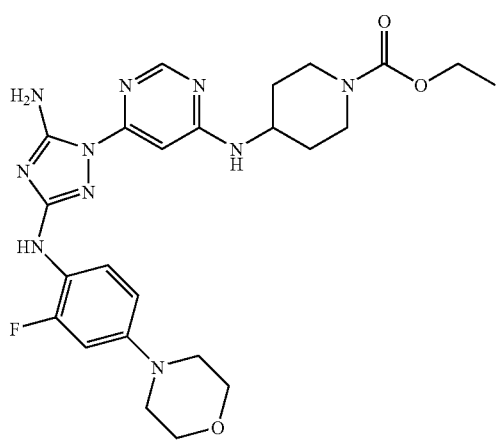
I-500
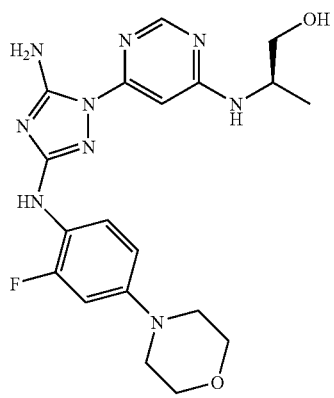
I-501
TABLE 1-continued
Examples of Compounds of Formula I:
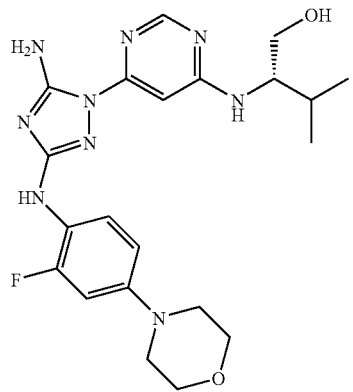
I-502
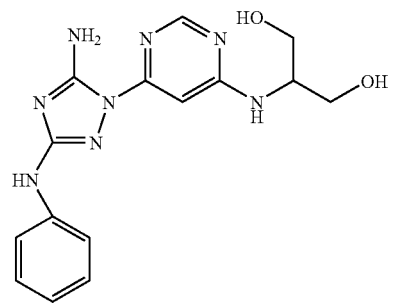
I-503
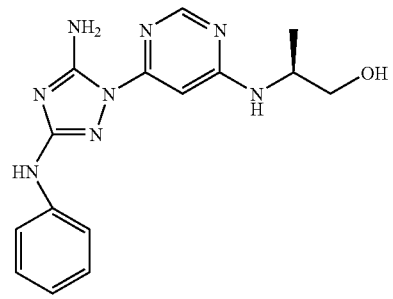
I-504
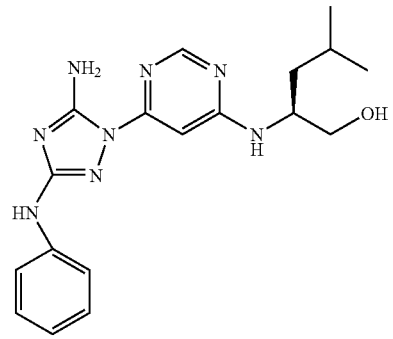
I-505

TABLE 1-continued
Examples of Compounds of Formula I:
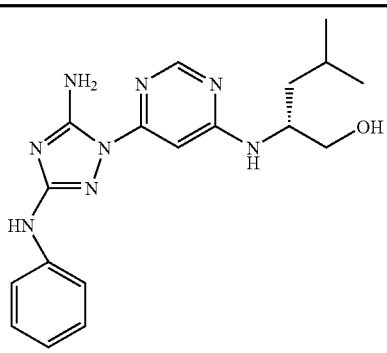
I-506
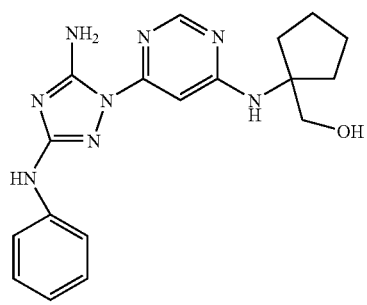
I-507
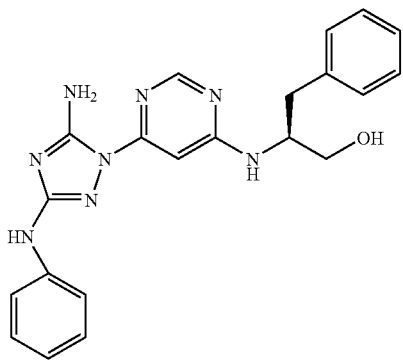
I-508
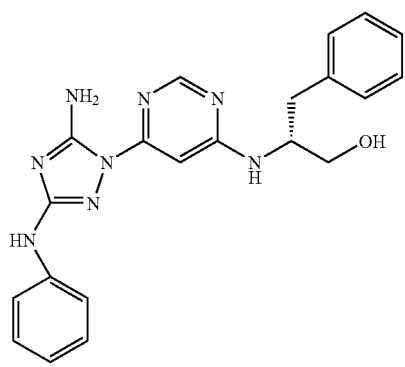
I-509
TABLE 1-continued
Examples of Compounds of Formula I:
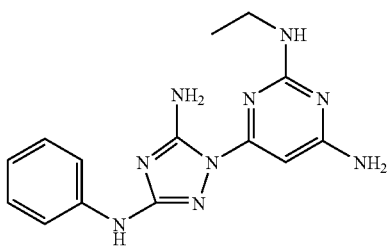
I-510
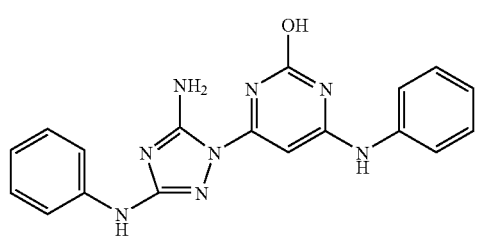
I-511
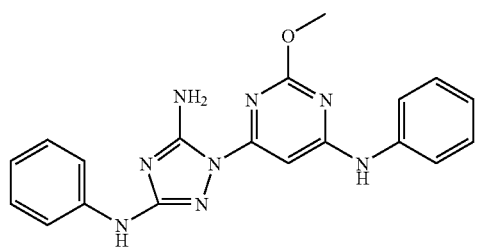
I-512
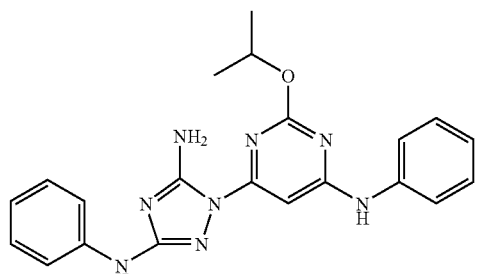
I-513

TABLE 1-continued
Examples of Compounds of Formula I:
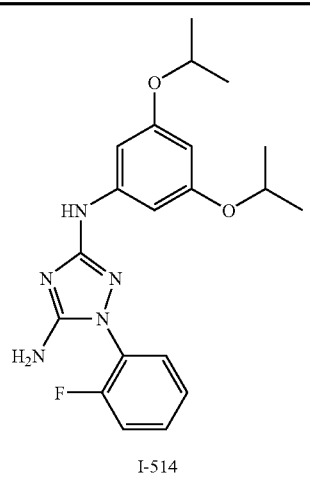
I-514
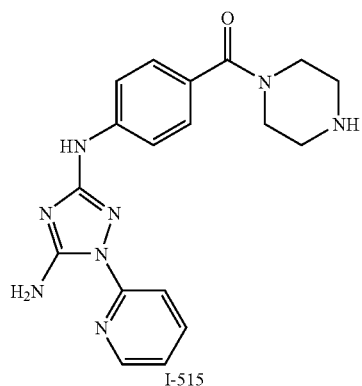
I-515
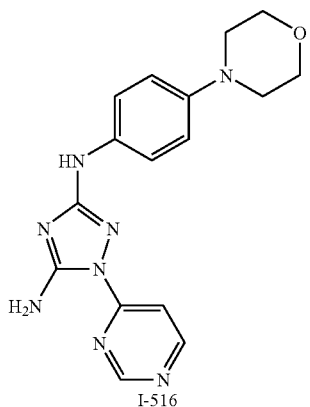
I-516
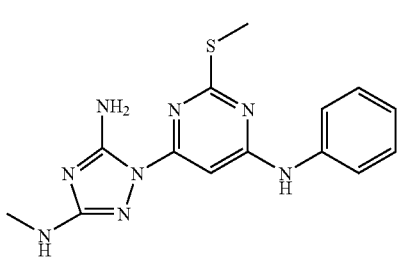
I-517
TABLE 1-continued
Examples of Compounds of Formula I:
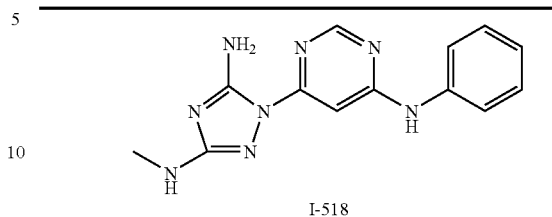
I-518
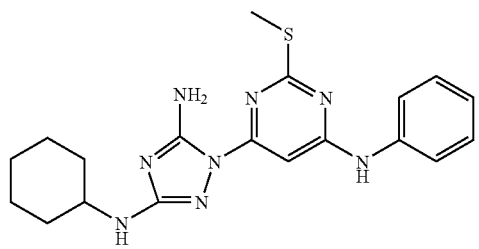
I-519
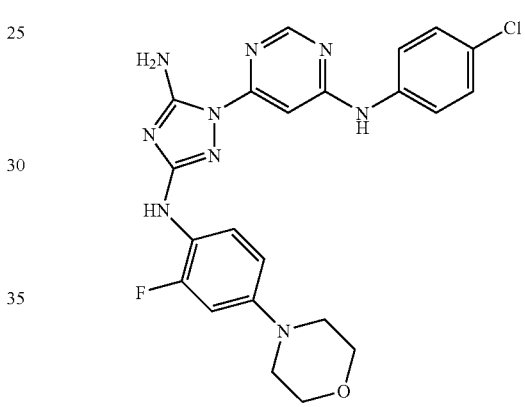
I-520
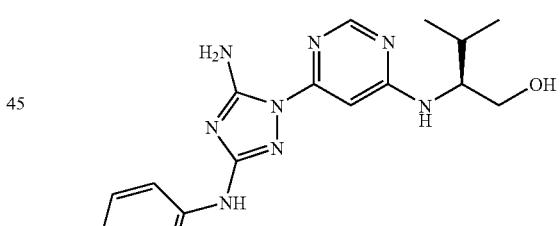
I-521
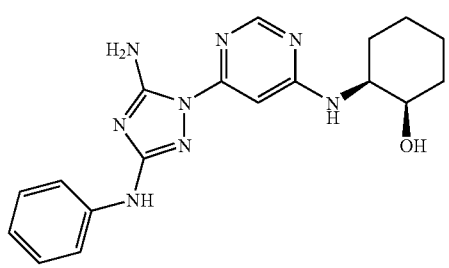
I-522

TABLE 1-continued
Examples of Compounds of Formula I:
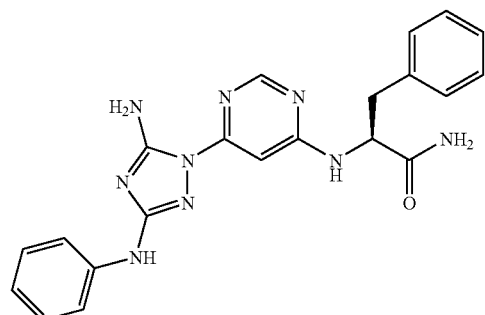
I-523
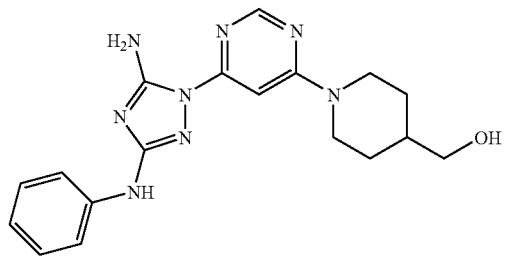
I-524
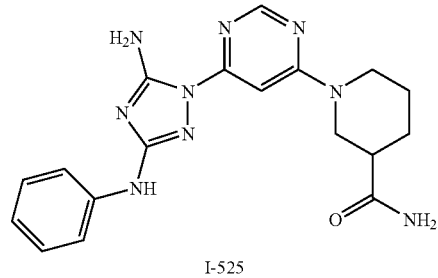
I-525
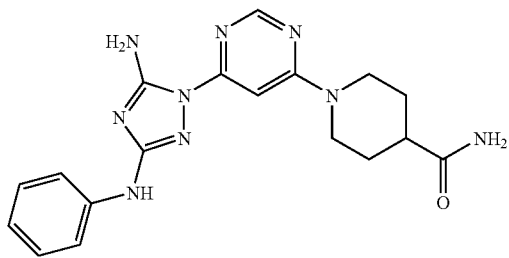
I-526
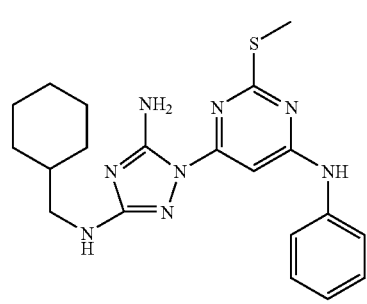
I-527
TABLE 1-continued
Examples of Compounds of Formula I:
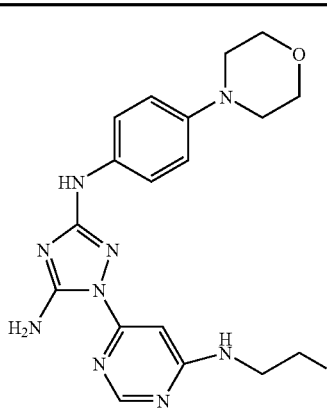
I-528
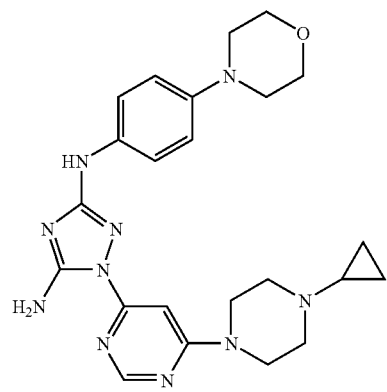
I-529
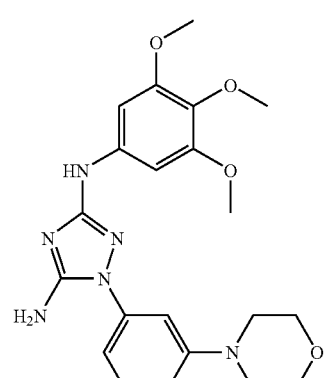
I-530

TABLE 1-continued
Examples of Compounds of Formula I:
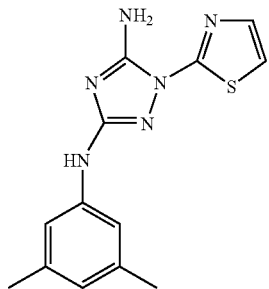
I-531
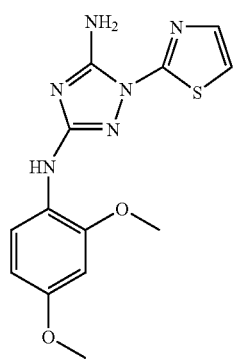
I-532
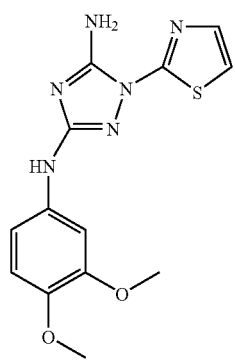
I-533
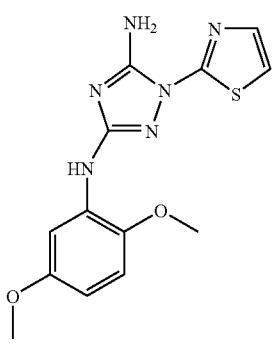
I-534
TABLE 1-continued
Examples of Compounds of Formula I:
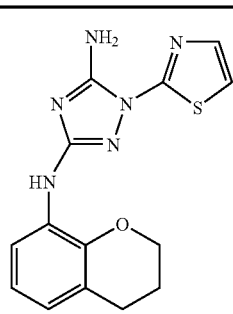
I-535
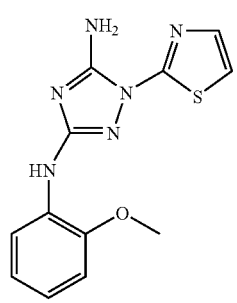
I-536
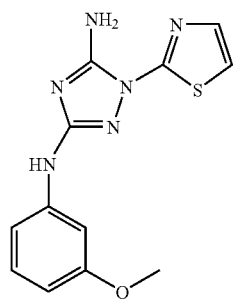
I-537
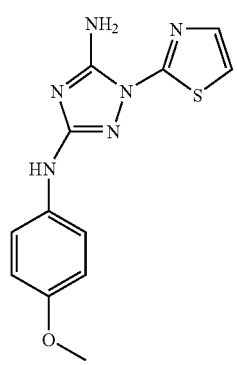
I-538

TABLE 1-continued
Examples of Compounds of Formula I:
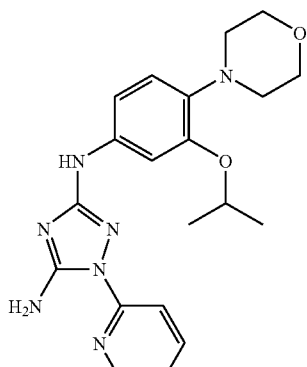
I-539
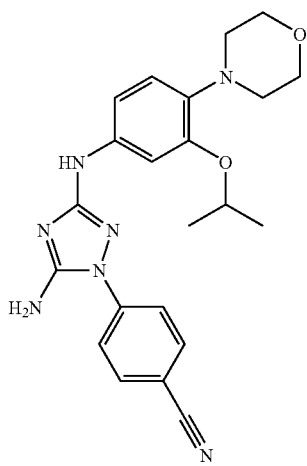
I-540
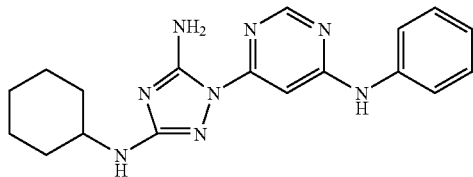
I-541
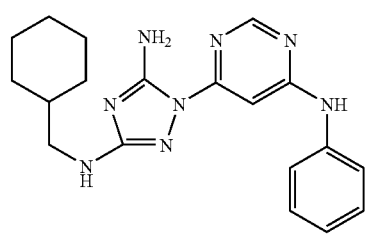
I-542
TABLE 1-continued
Examples of Compounds of Formula I:
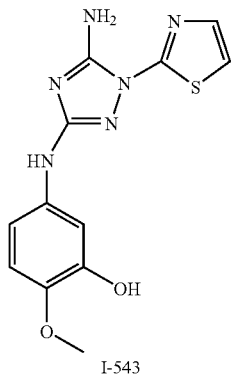
I-543
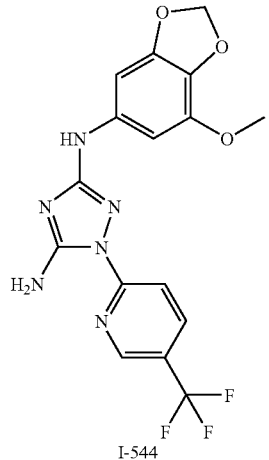
I-544
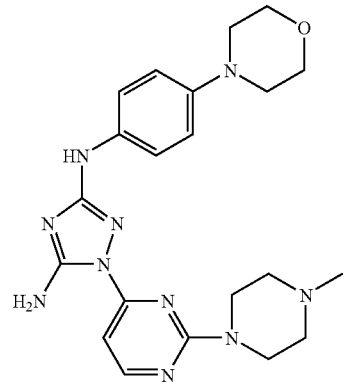
I-545
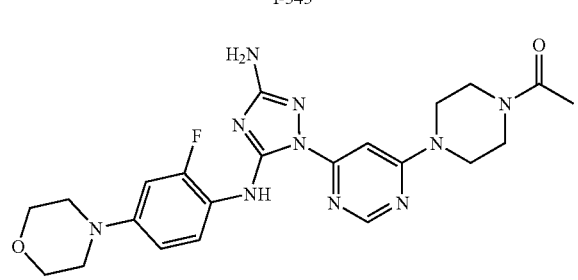
I-546

TABLE 1-continued
Examples of Compounds of Formula I:
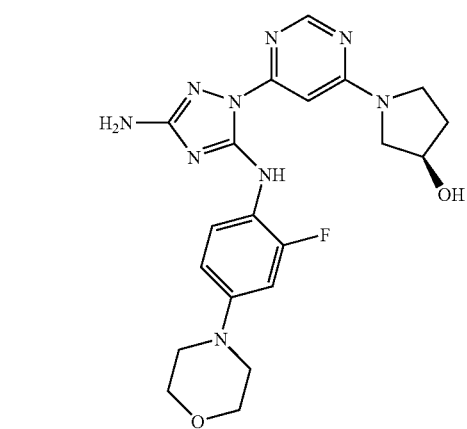
I-547
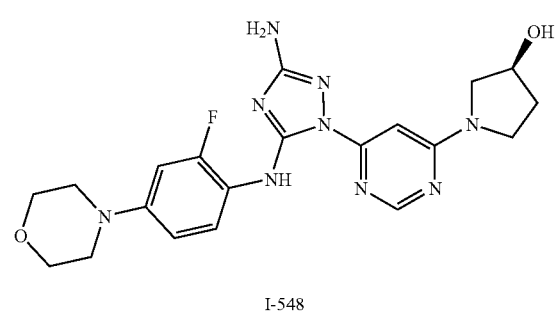
I-548
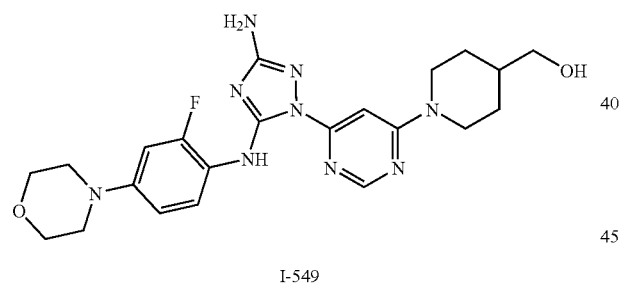
I-549
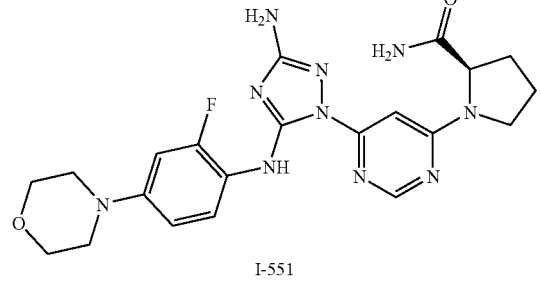
I-550
TABLE 1-continued
Examples of Compounds of Formula I:
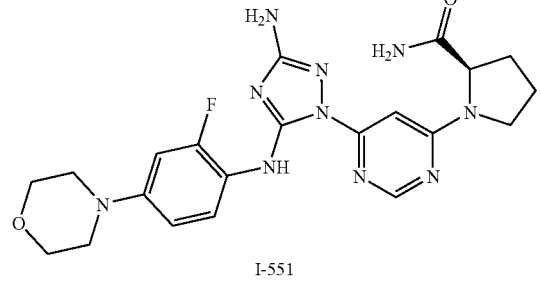
I-551
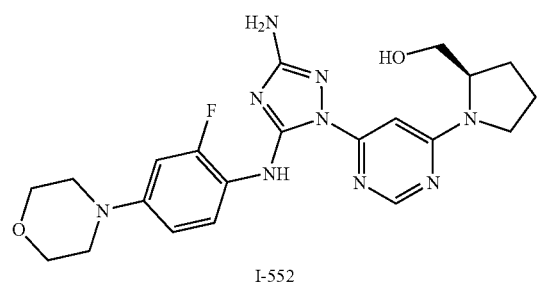
I-552
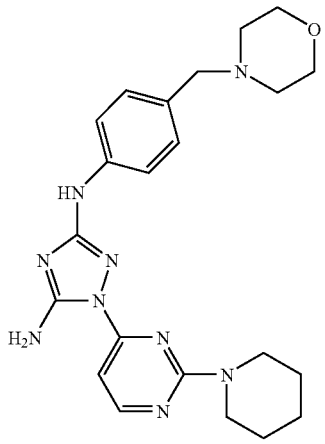
I-553
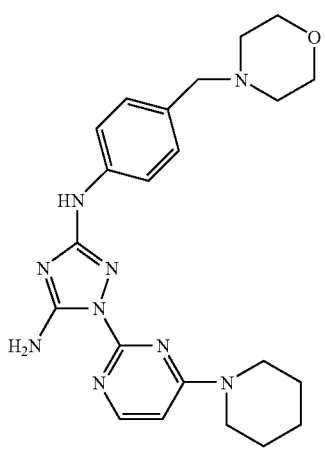
I-554

TABLE 1-continued
Examples of Compounds of Formula I:
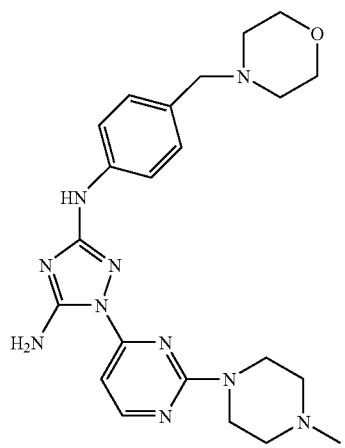
I-555
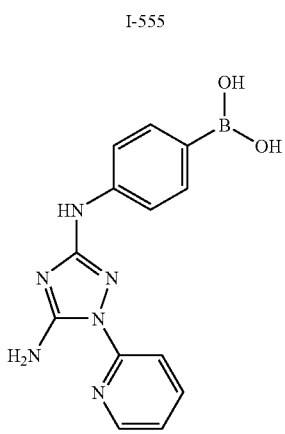
I-556
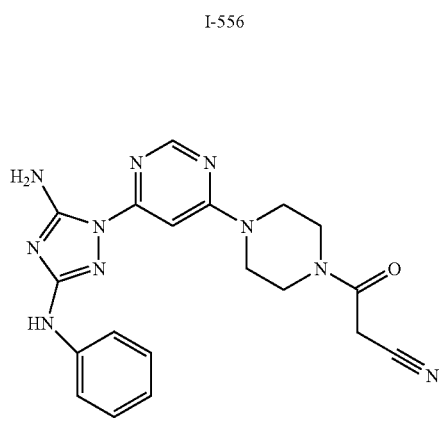
I-557
TABLE 1-continued
Examples of Compounds of Formula I:
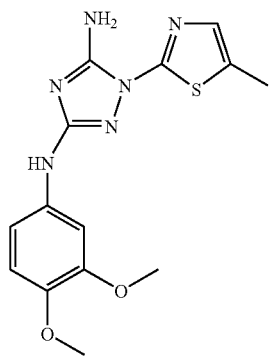
I-558
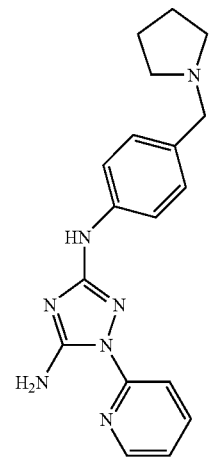
I-559
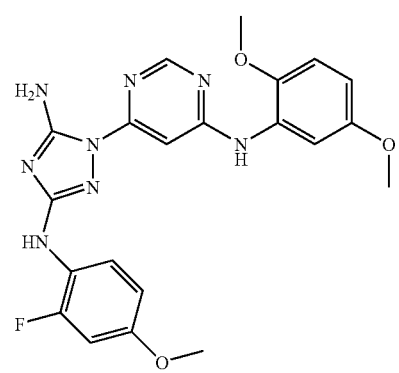
I-560

TABLE 1-continued
Examples of Compounds of Formula I:
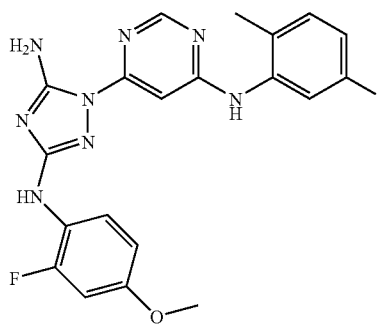
I-561
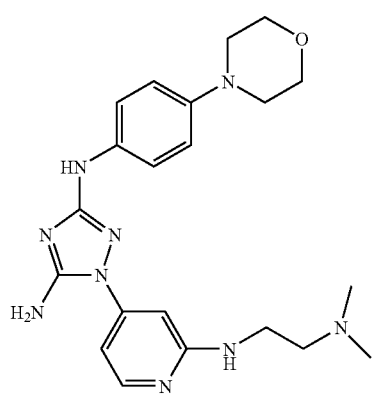
I-562
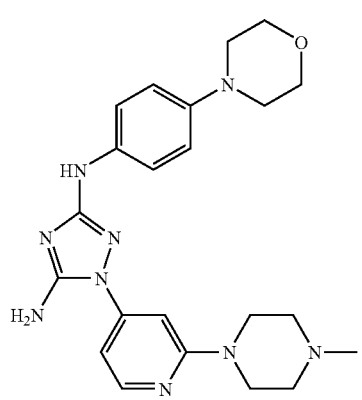
I-563
TABLE 1-continued
Examples of Compounds of Formula I:
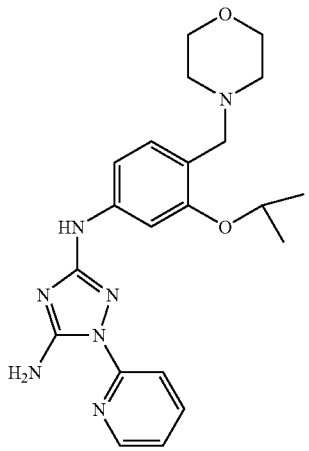
I-564
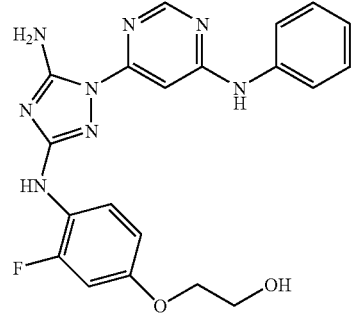
I-565
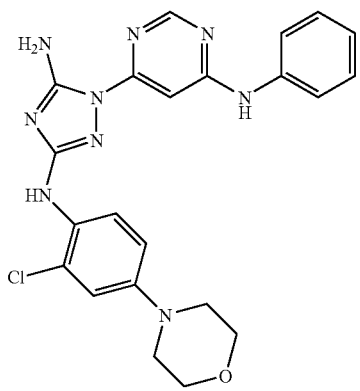
I-566

TABLE 1-continued
Examples of Compounds of Formula I:
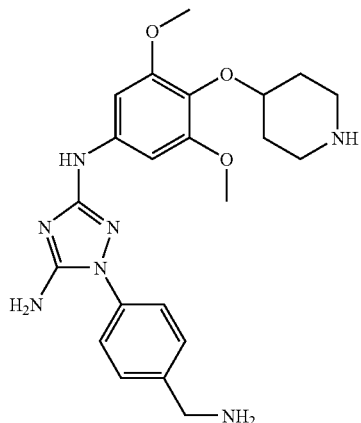
I-567
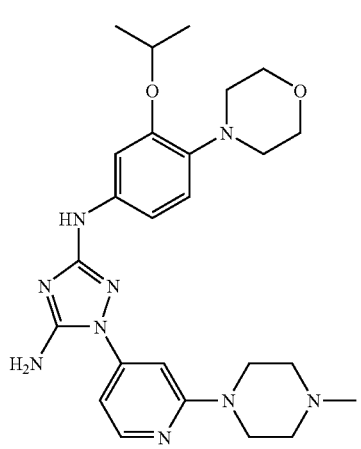
I-568
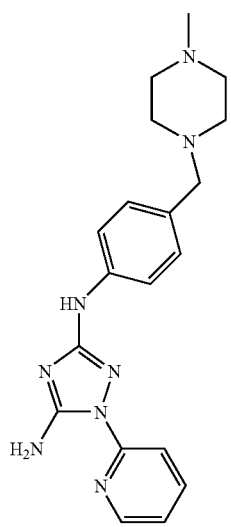
I-569
TABLE 1-continued
Examples of Compounds of Formula I:
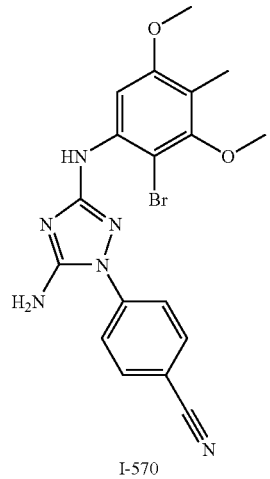
I-570
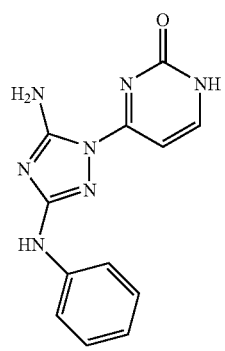
I-571
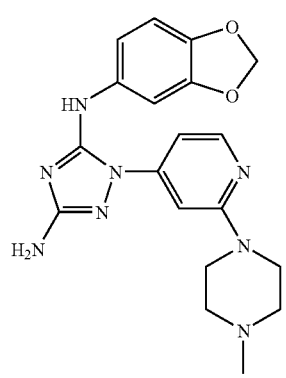
I-572
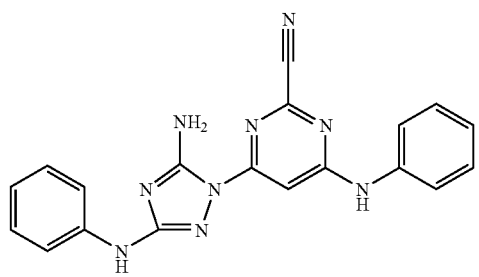
I-573

TABLE 1-continued
Examples of Compounds of Formula I:
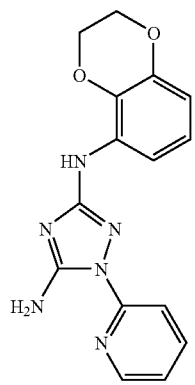
I-574
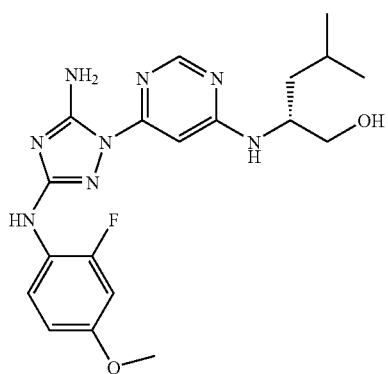
I-575
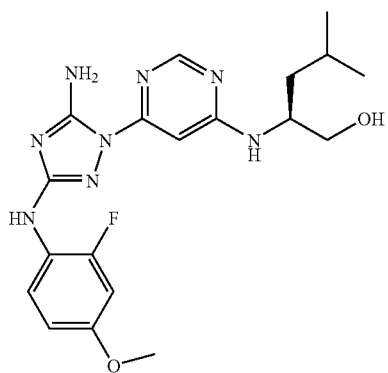
I-576
TABLE 1-continued
Examples of Compounds of Formula I:
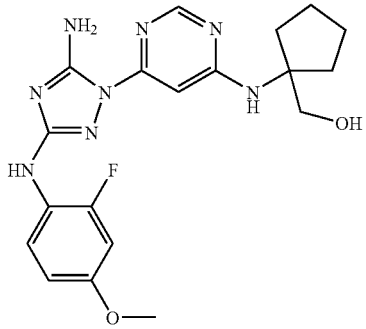
I-577
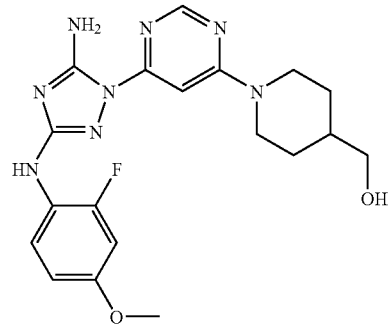
I-578
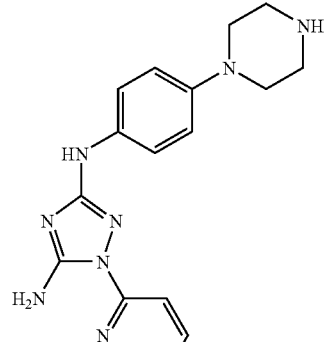
I-579
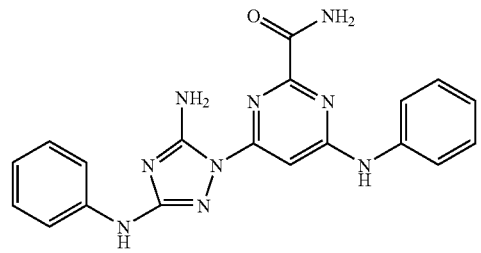
I-580

TABLE 1-continued
Examples of Compounds of Formula I:
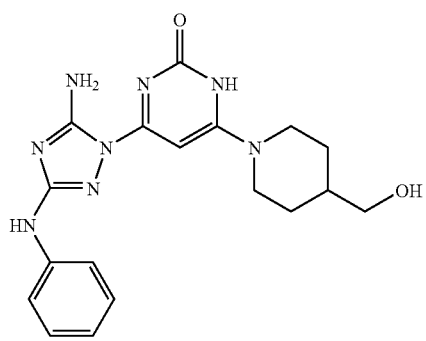
I-581
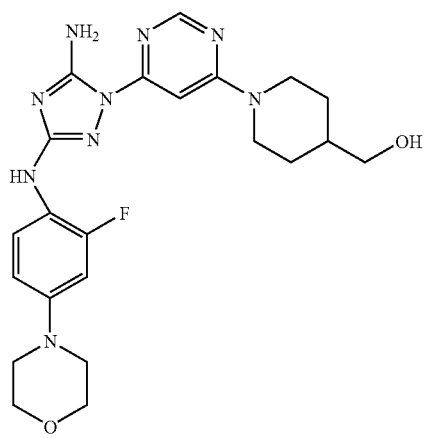
I-582
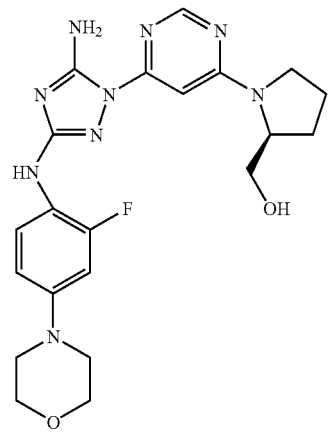
I-583
TABLE 1-continued
Examples of Compounds of Formula I:
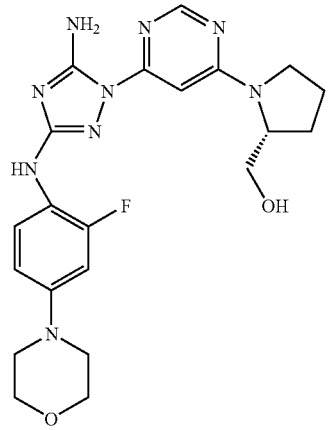
I-584
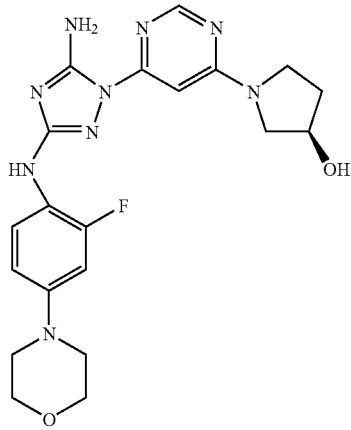
I-585
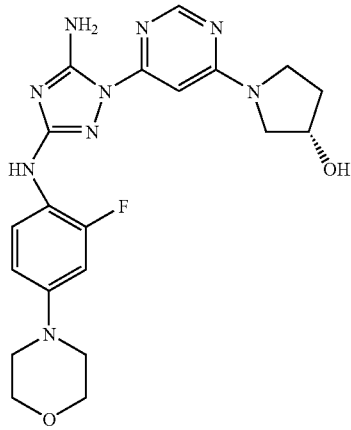
I-586

TABLE 1-continued
Examples of Compounds of Formula I:
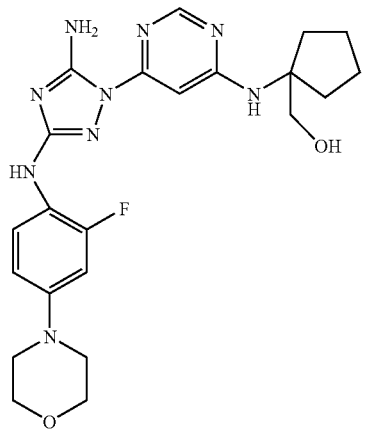
I-587
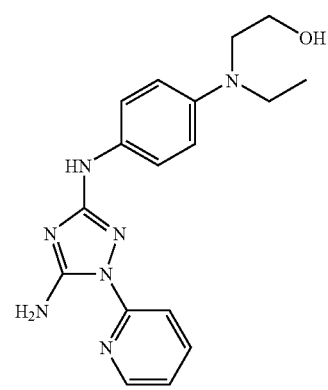
I-588
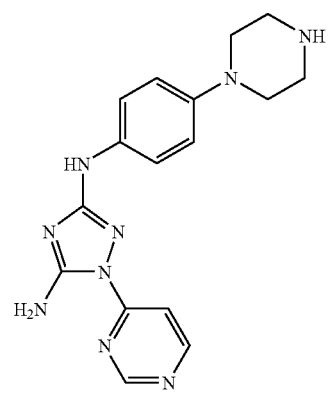
I-589
TABLE 1-continued
Examples of Compounds of Formula I:
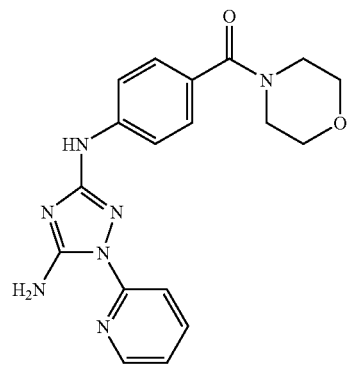
I-590
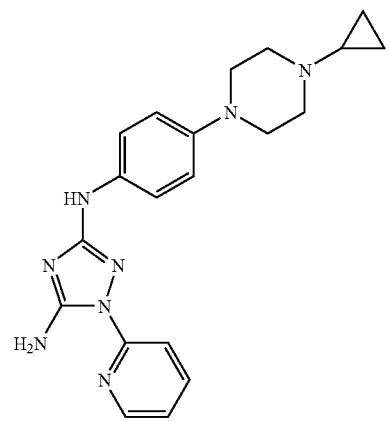
I-591
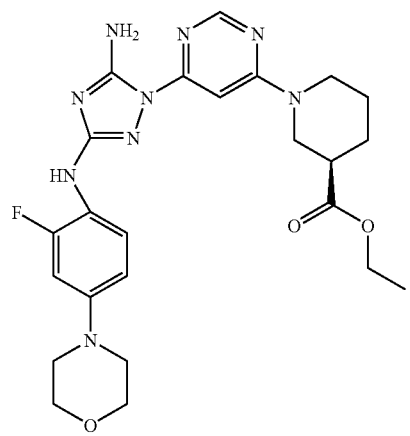
I-592

TABLE 1-continued
Examples of Compounds of Formula I:
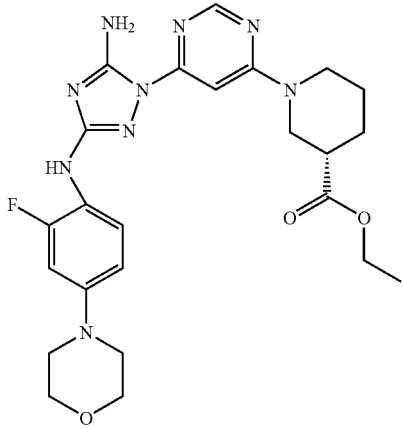
I-593
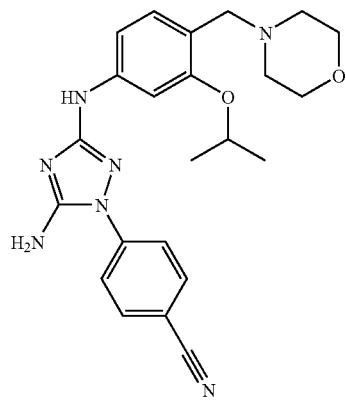
I-594
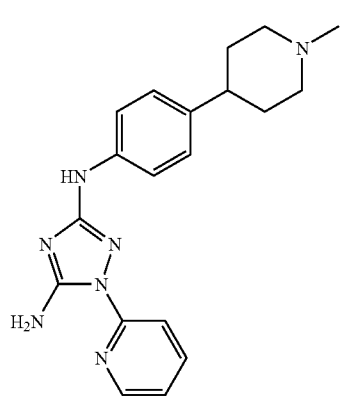
I-595
TABLE 1-continued
Examples of Compounds of Formula I:
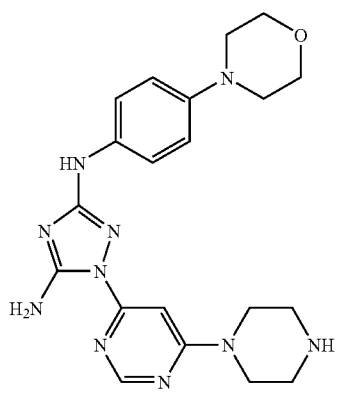
I-596
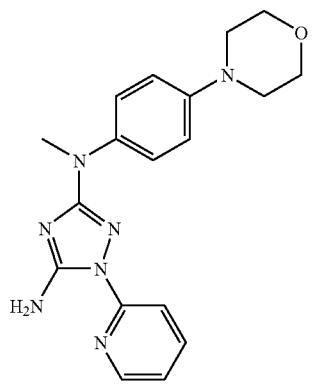
I-597
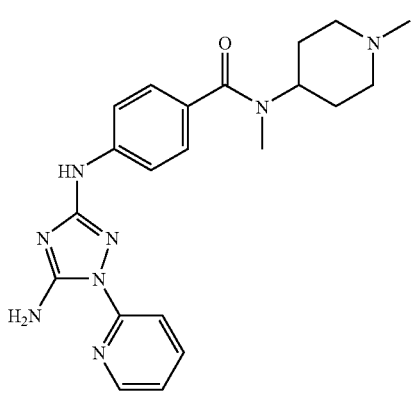
I-598

TABLE 1-continued
Examples of Compounds of Formula I:
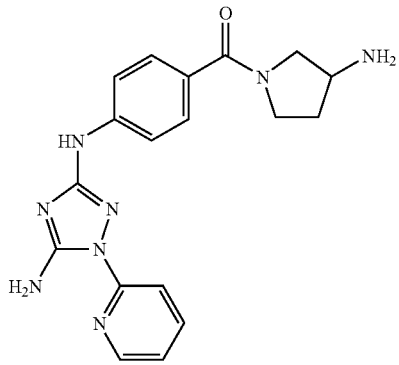
I-599
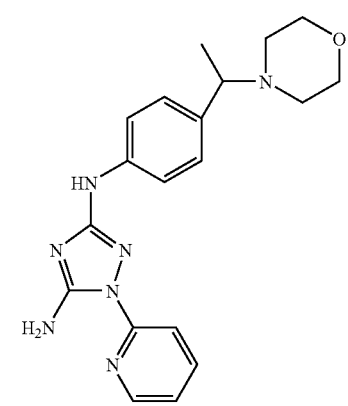
I-600
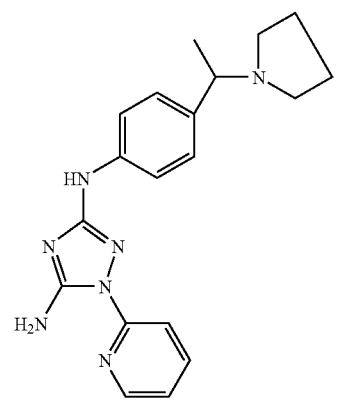
I-601
TABLE 1-continued
Examples of Compounds of Formula I:
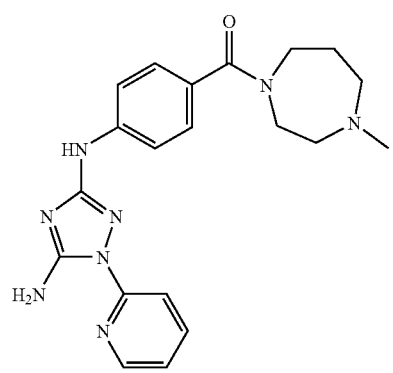
I-602
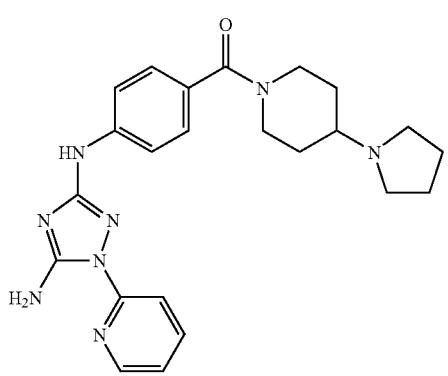
I-603
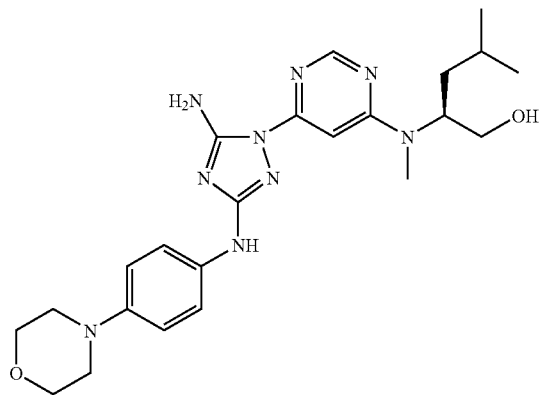
I-604

TABLE 1-continued
Examples of Compounds of Formula I:
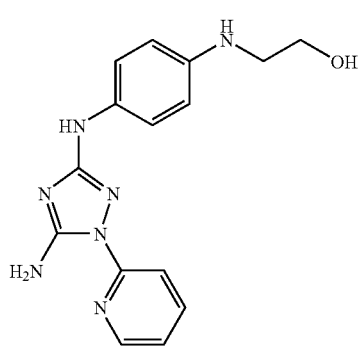
I-605
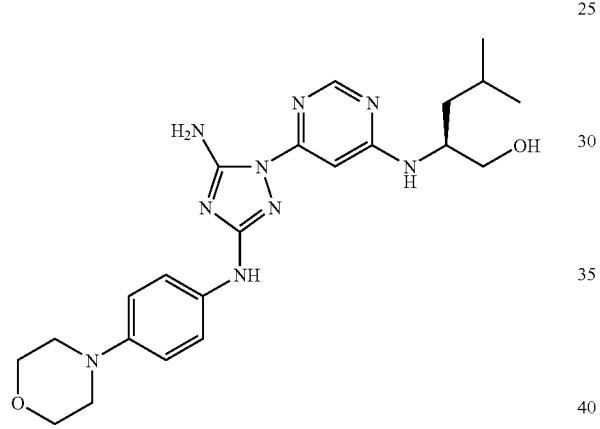
I-606
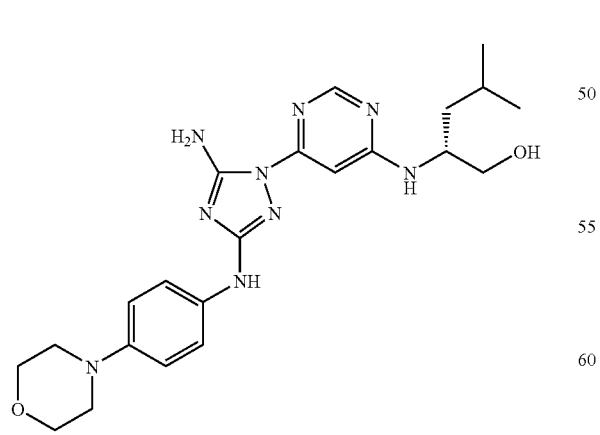
I-607
TABLE 1-continued
Examples of Compounds of Formula I:
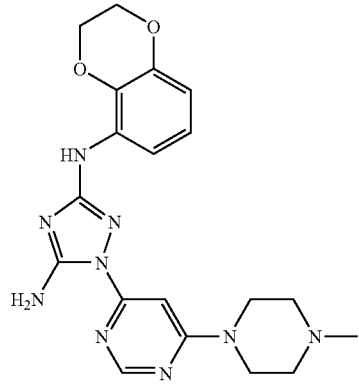
I-608
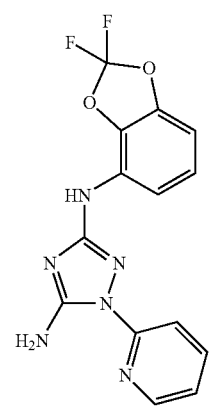
I-609
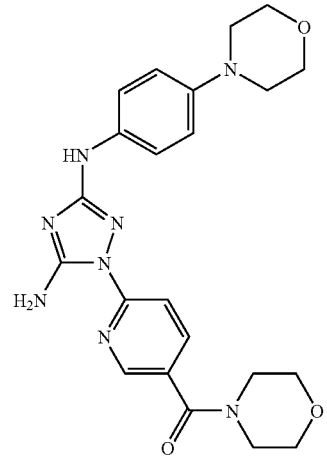
I-610

TABLE 1-continued
Examples of Compounds of Formula I:
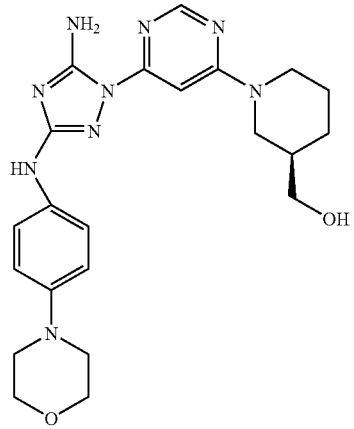
I-611
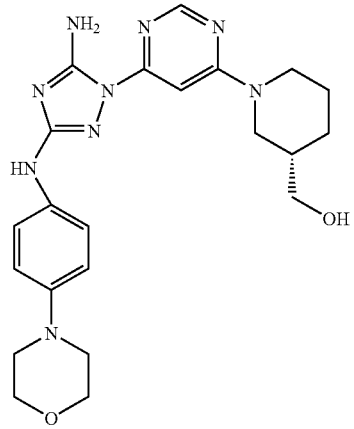
I-612
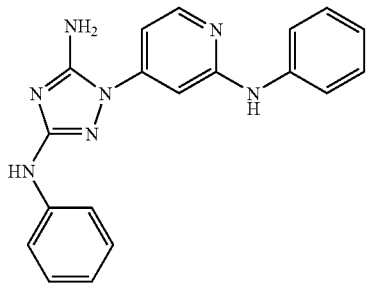
I-613
TABLE 1-continued
Examples of Compounds of Formula I:
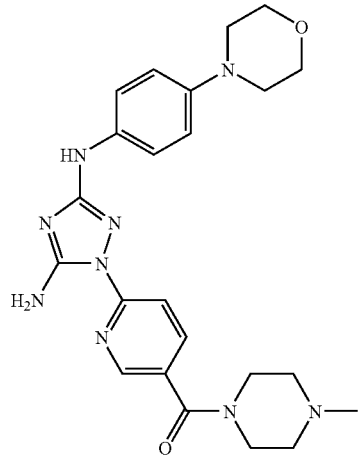
I-614
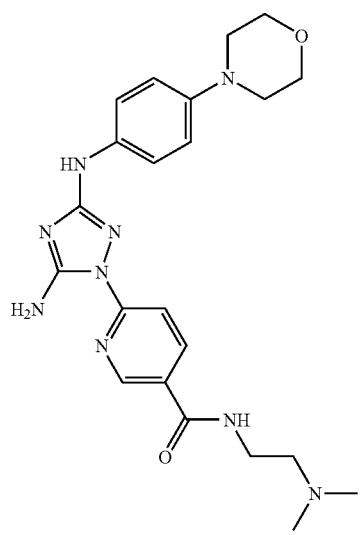
I-615
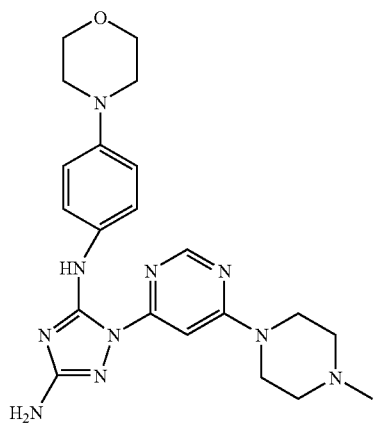
I-616

TABLE 1-continued
Examples of Compounds of Formula I:
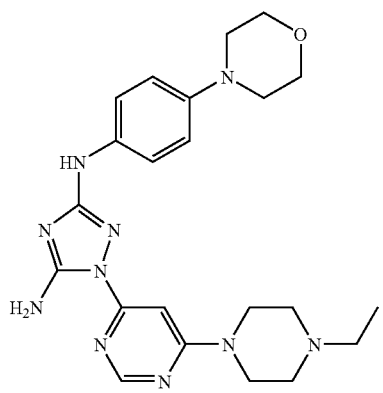
I-617
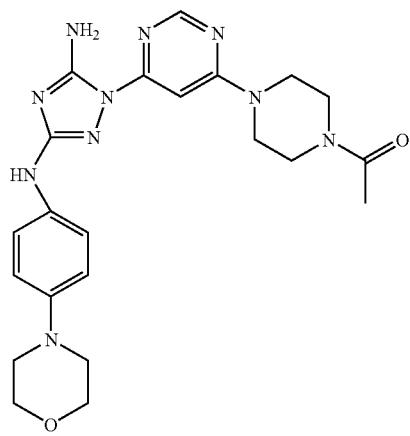
I-618
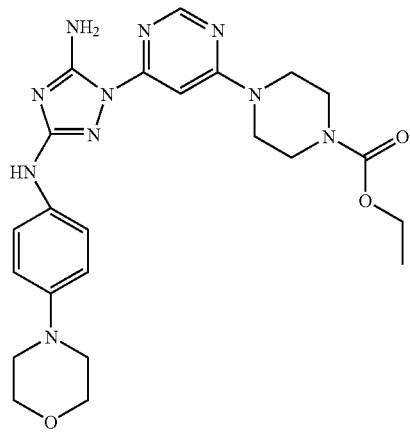
I-619
TABLE 1-continued
Examples of Compounds of Formula I:
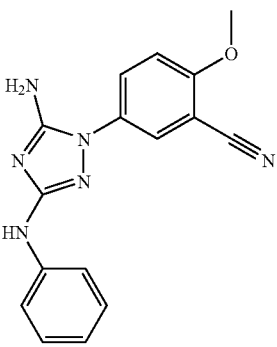
I-620
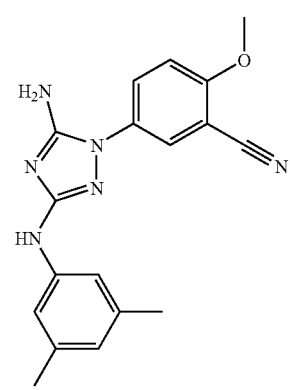
I-621
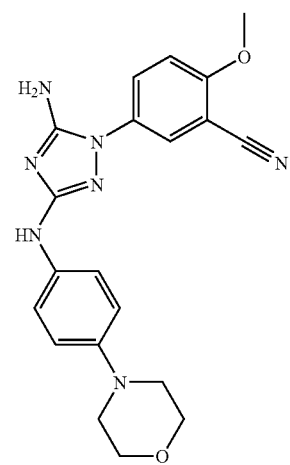
I-622

TABLE 1-continued
Examples of Compounds of Formula I:
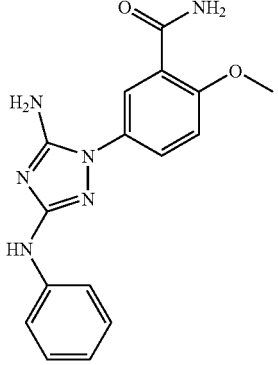
I-623
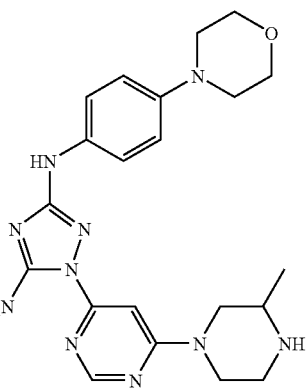
I-624
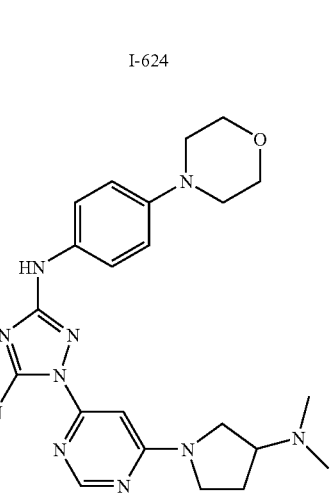
I-625
TABLE 1-continued
Examples of Compounds of Formula I:
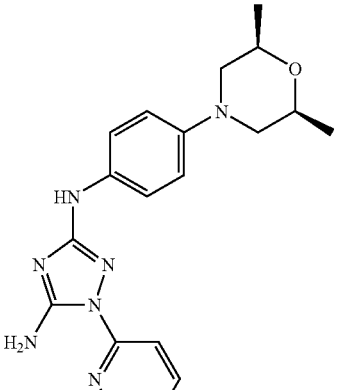
I-626
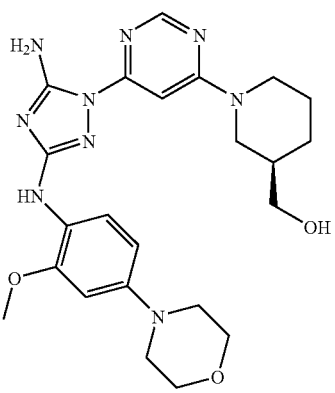
I-627
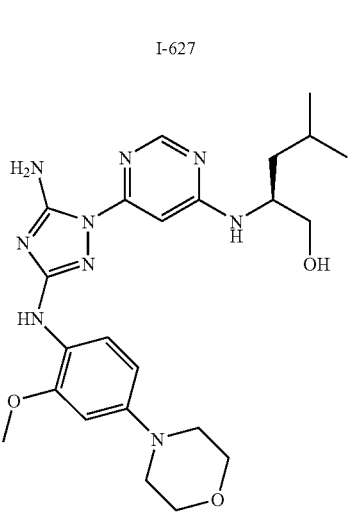
I-628

TABLE 1-continued
Examples of Compounds of Formula I:
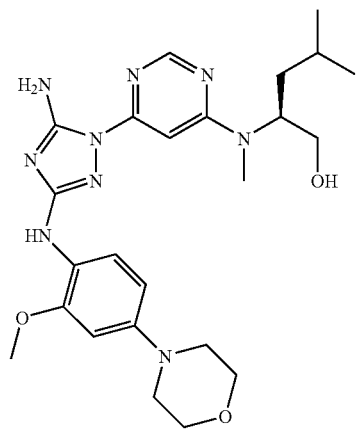
I-629
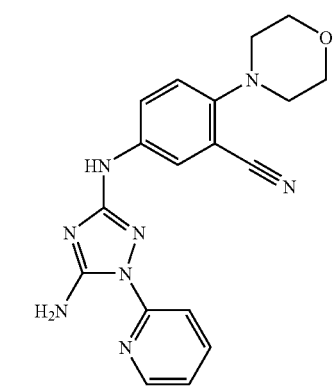
I-630
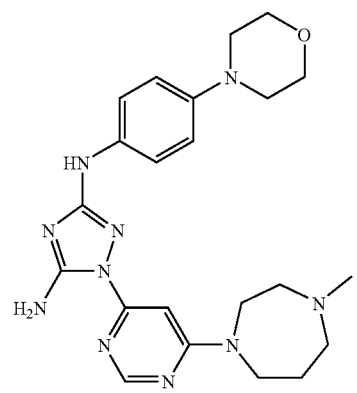
I-631
TABLE 1-continued
Examples of Compounds of Formula I:
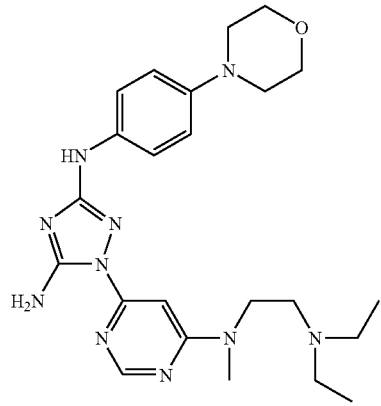
I-632
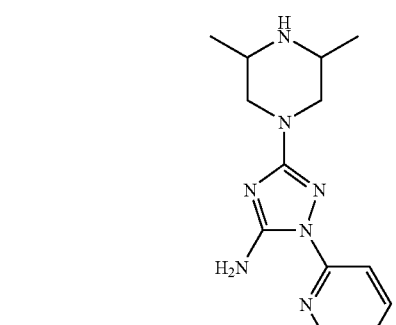
I-633
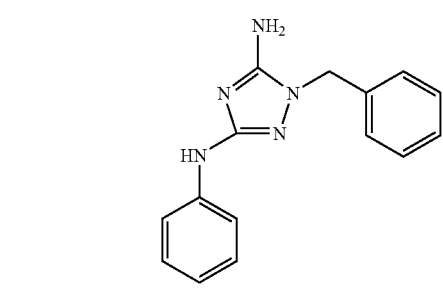
I-634
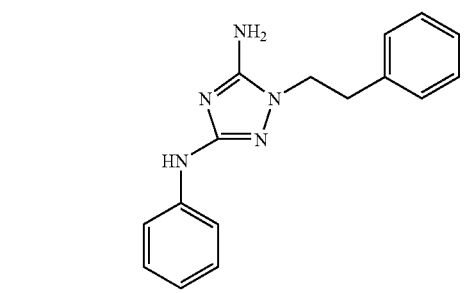
I-635

TABLE 1-continued
Examples of Compounds of Formula I:
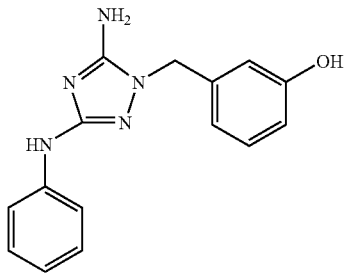
I-636
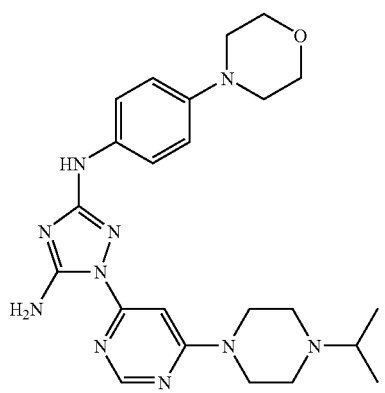
I-637
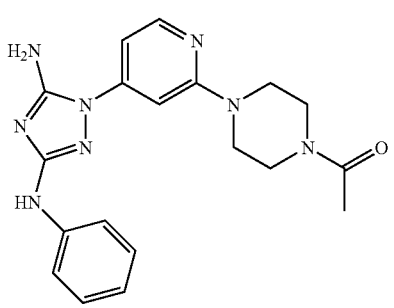
I-638
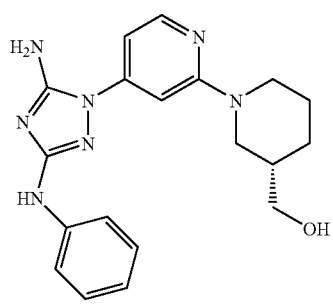
I-639
TABLE 1-continued
Examples of Compounds of Formula I:
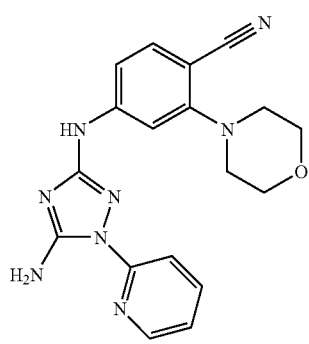
I-640
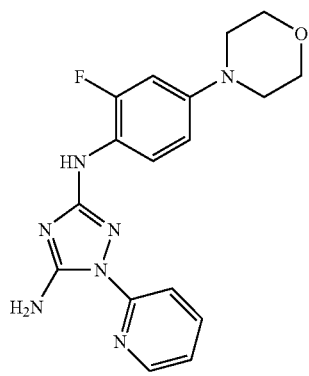
I-641
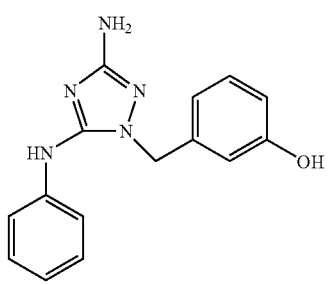
I-642
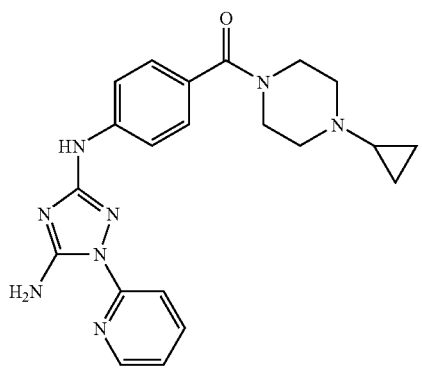
I-643

TABLE 1-continued
Examples of Compounds of Formula I:
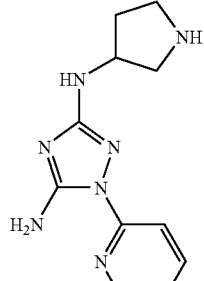
I-644
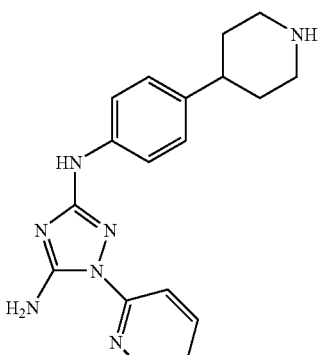
I-645
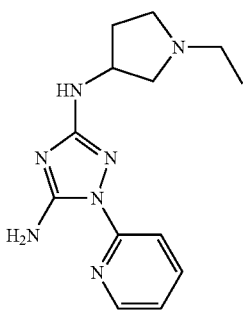
I-646
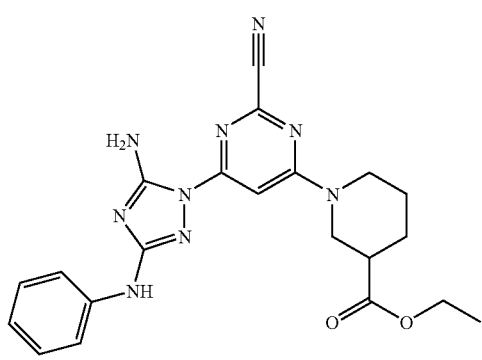
I-647
TABLE 1-continued
Examples of Compounds of Formula I:
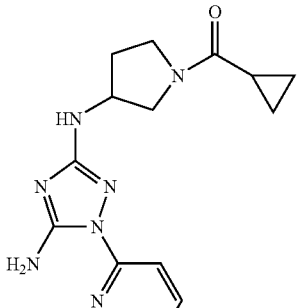
I-648
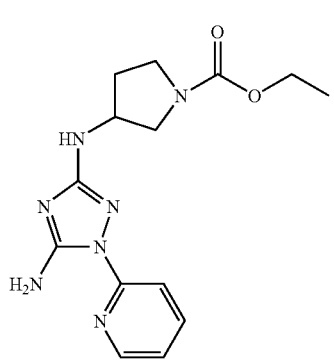
I-649
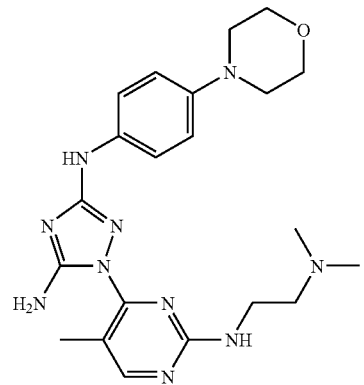
I-650
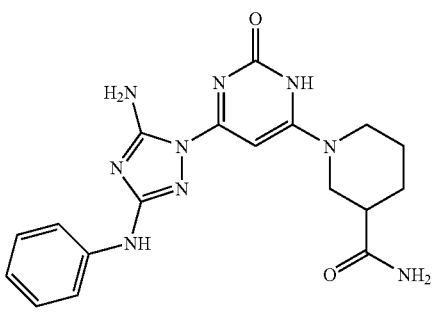
I-651

TABLE 1-continued
Examples of Compounds of Formula I:
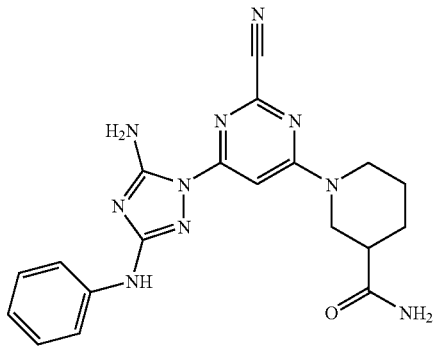
I-652
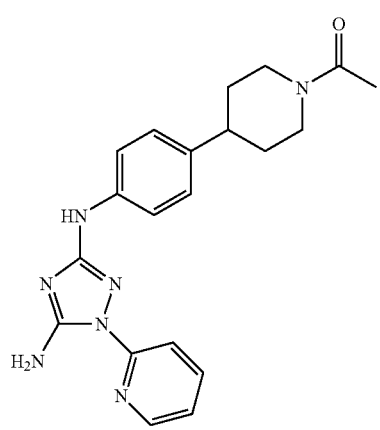
I-653
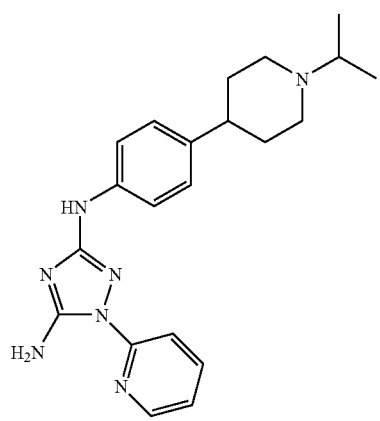
I-654
TABLE 1-continued
Examples of Compounds of Formula I:
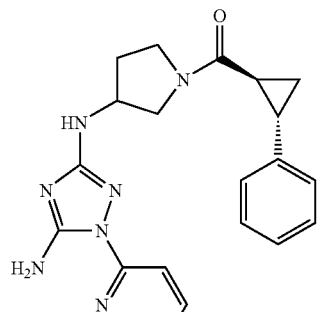
I-655
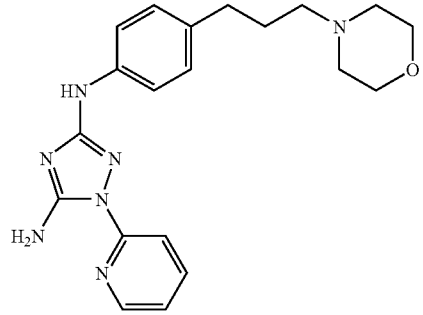
I-656
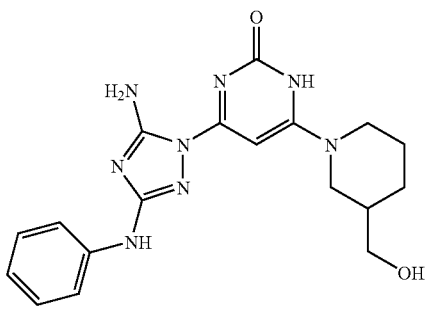
I-657
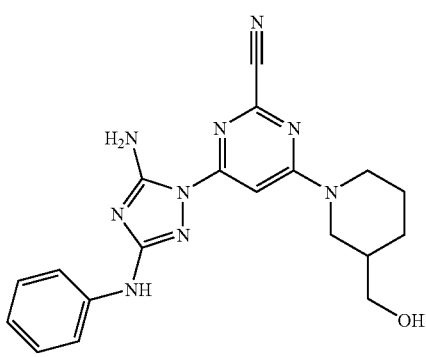
I-658

TABLE 1-continued
Examples of Compounds of Formula I:
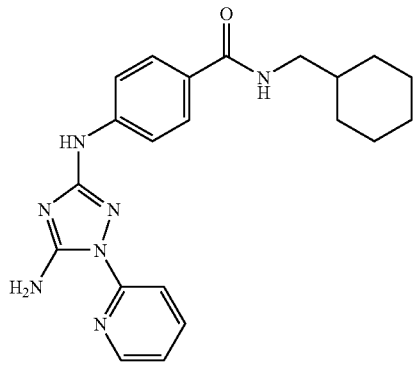
I-659
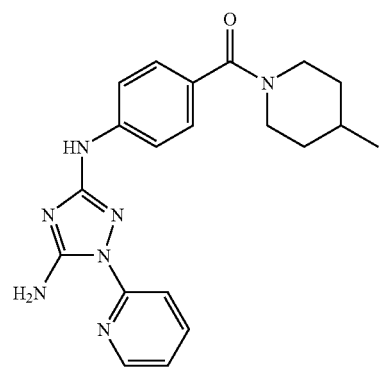
I-660
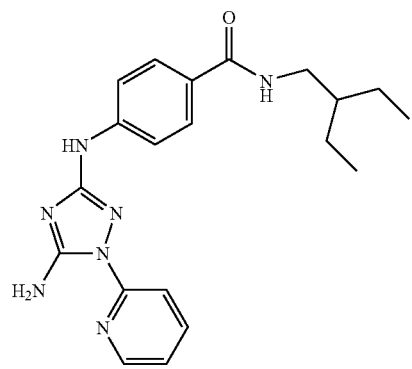
I-661
TABLE 1-continued
Examples of Compounds of Formula I:
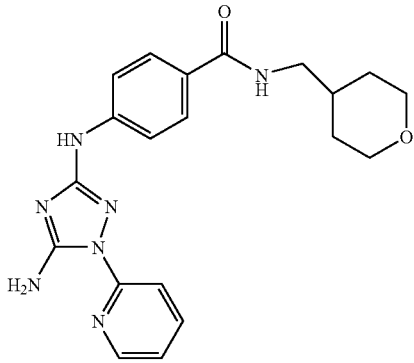
I-662
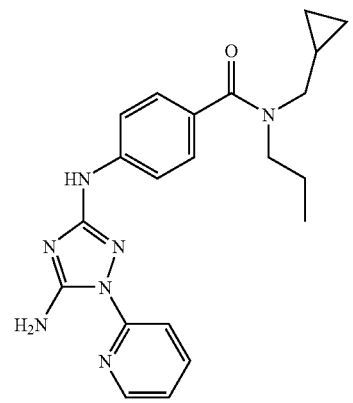
I-663
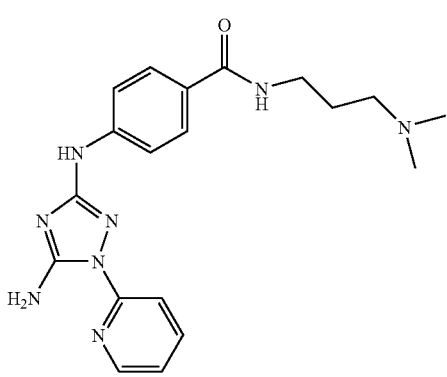
I-664

TABLE 1-continued
Examples of Compounds of Formula I:
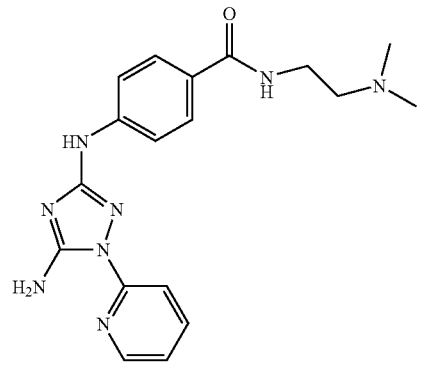
I-665
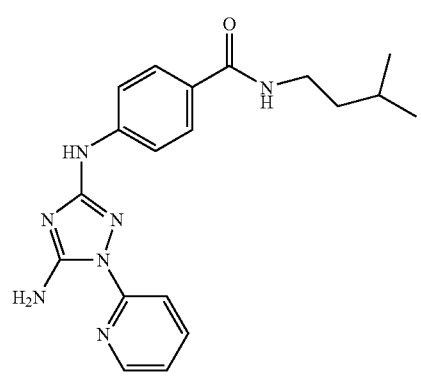
I-666
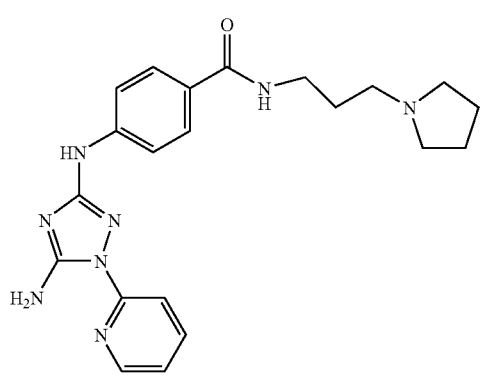
I-667
TABLE 1-continued
Examples of Compounds of Formula I:
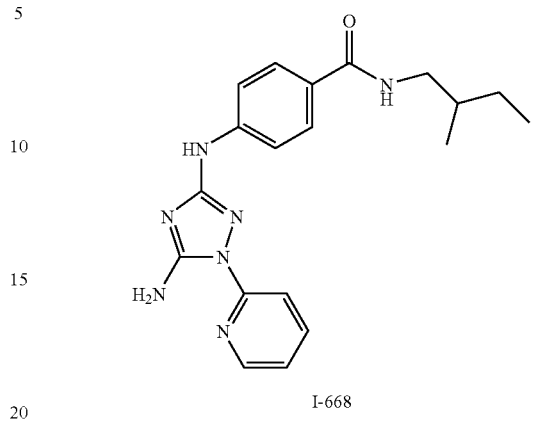
I-668
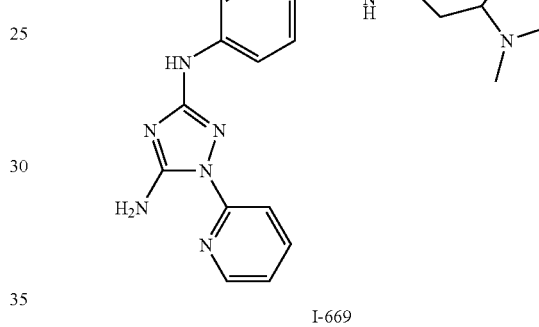
I-669
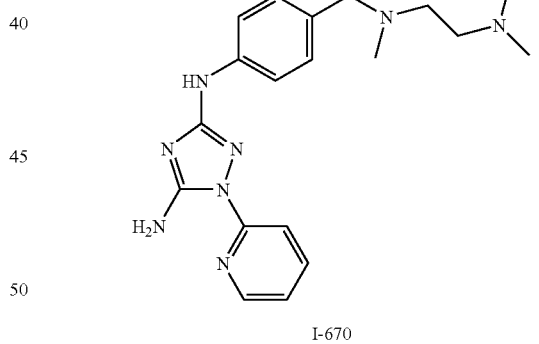
I-670
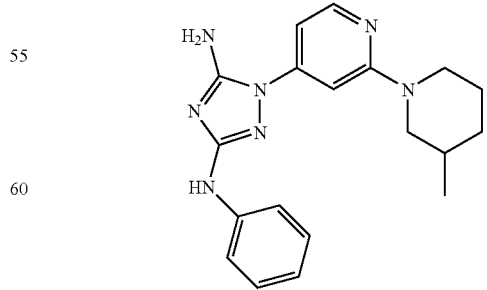
I-671

TABLE 1-continued
Examples of Compounds of Formula I:
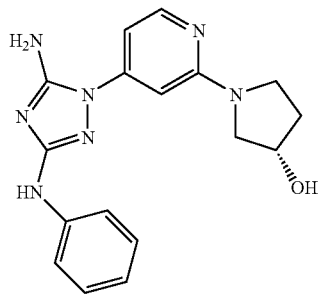
I-672
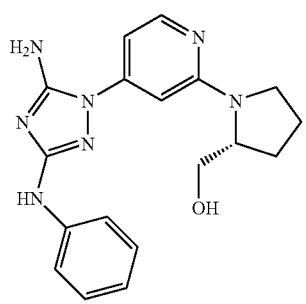
I-673
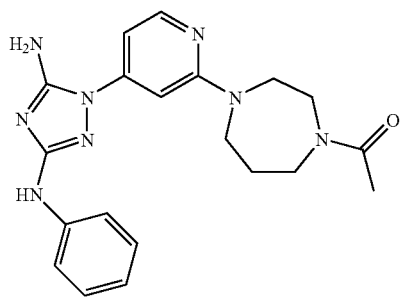
I-674
TABLE 1-continued
Examples of Compounds of Formula I:
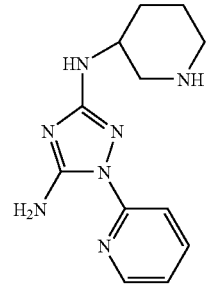
I-675
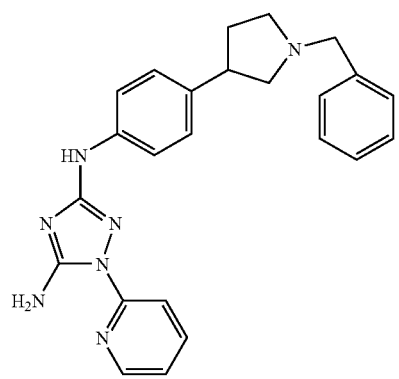
I-676
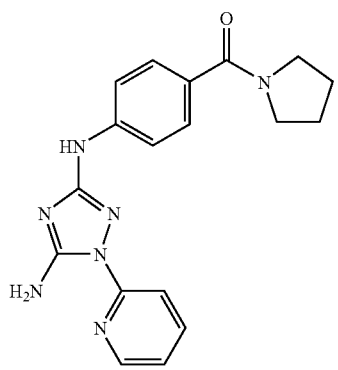
I-677
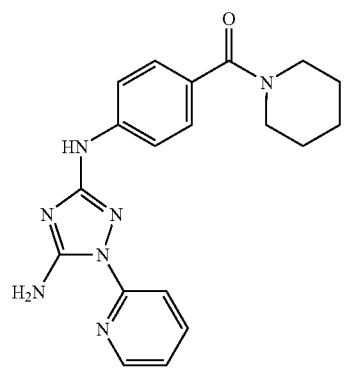
I-678

TABLE 1-continued
Examples of Compounds of Formula I:
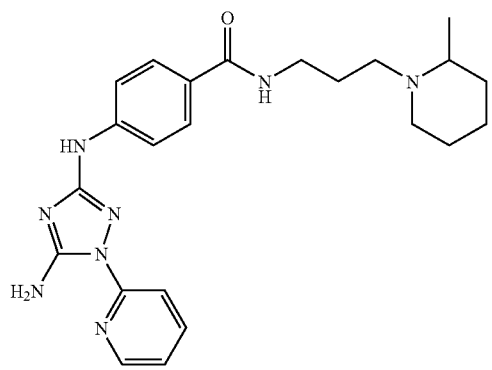
I-679
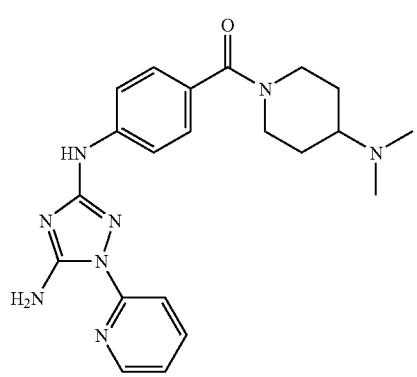
I-680
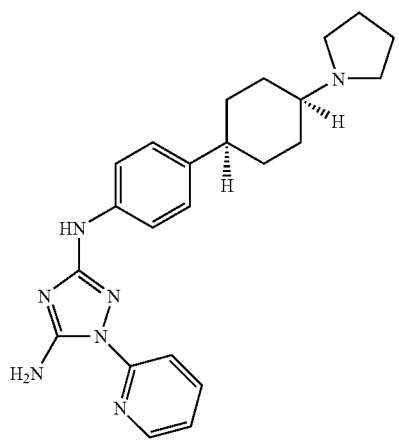
I-681
TABLE 1-continued
Examples of Compounds of Formula I:
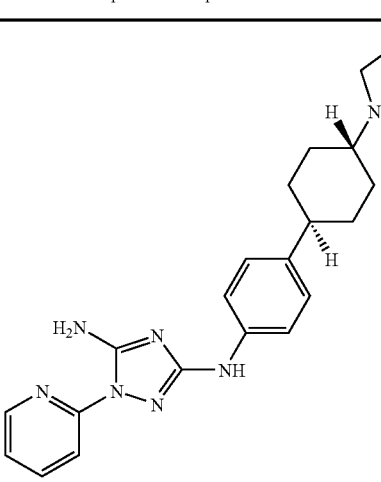
I-682
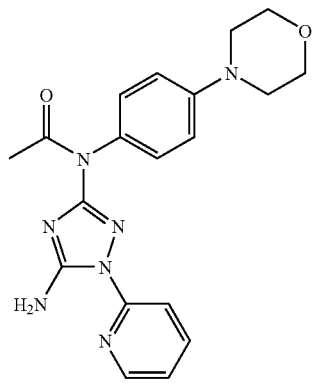
I-683
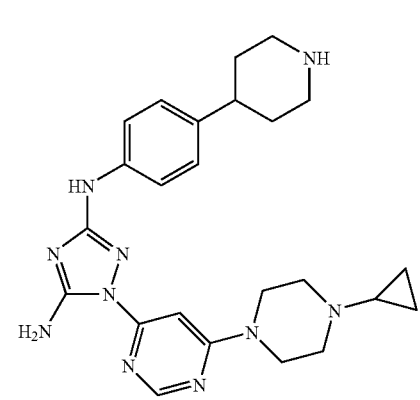
I-684

TABLE 1-continued
Examples of Compounds of Formula I:
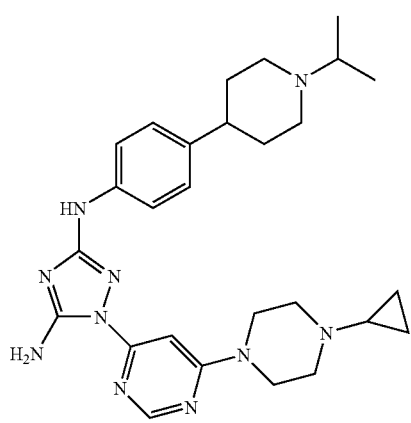
I-685
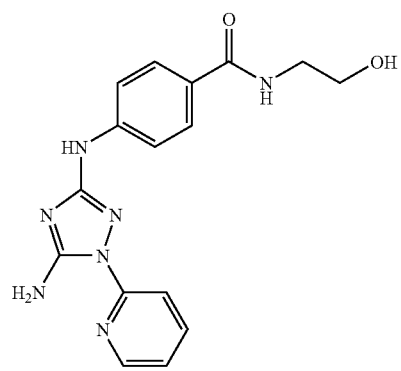
I-686
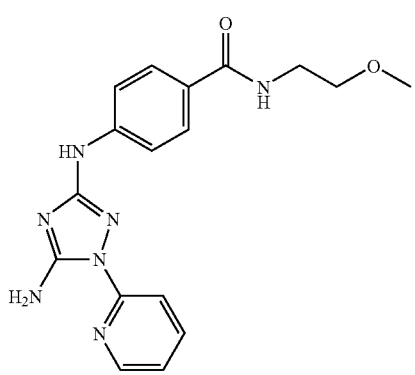
I-687
TABLE 1-continued
Examples of Compounds of Formula I:
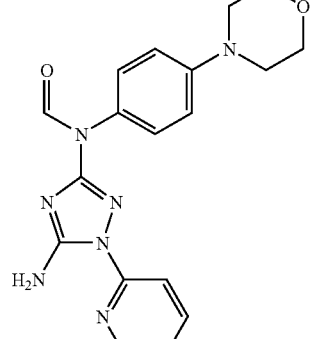
I-688
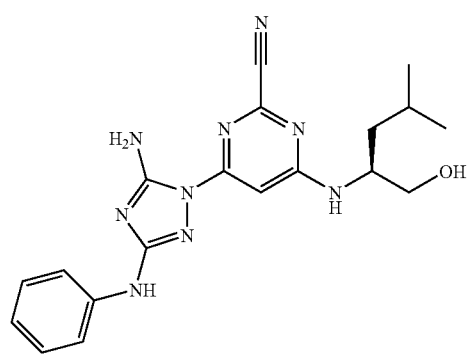
I-689
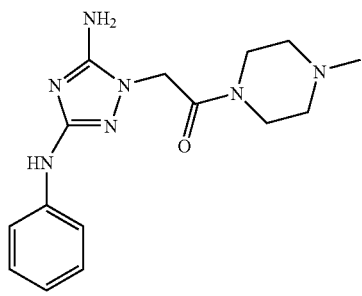
I-690
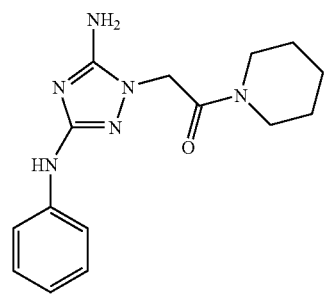
I-691

TABLE 1-continued

Examples of Compounds of Formula I:

I-692

I-693

I-694

I-695

I-696

I-697

I-698

TABLE 1-continued
Examples of Compounds of Formula I:
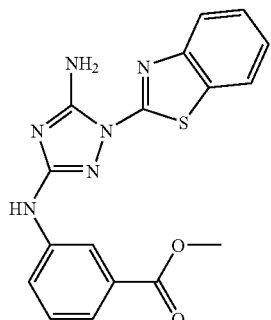
I-699
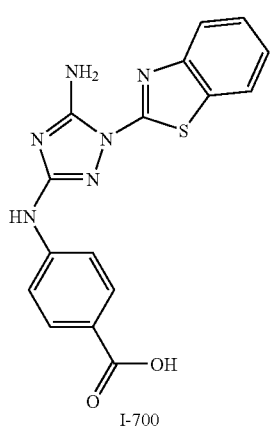
I-700
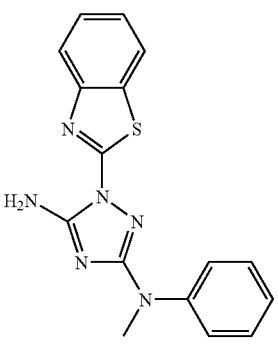
I-701
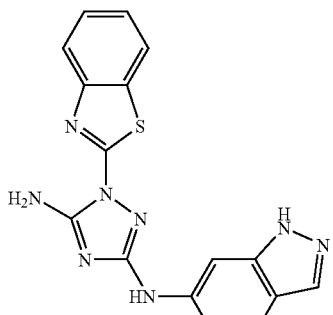
I-702
TABLE 1-continued
Examples of Compounds of Formula I:
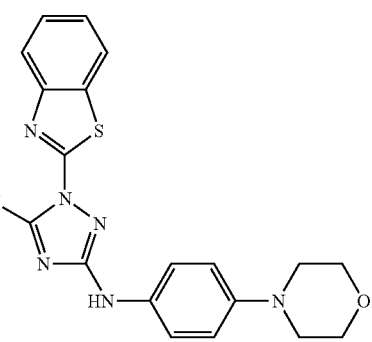
I-703
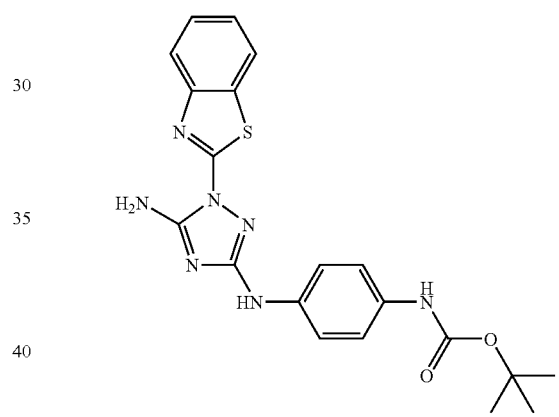
I-704
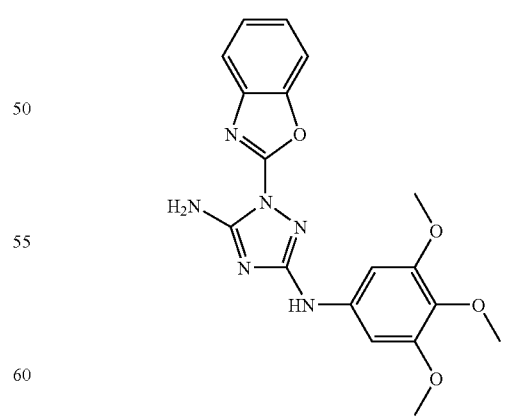
I-705

TABLE 1-continued
Examples of Compounds of Formula I:
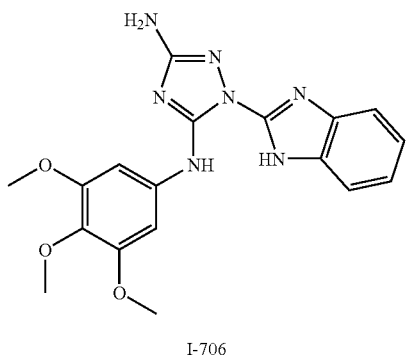
I-706
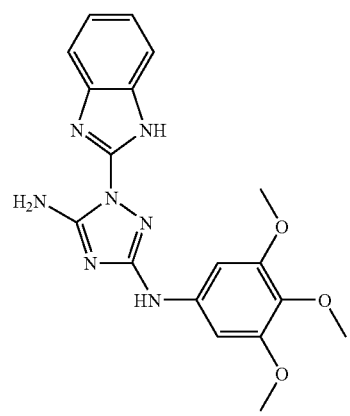
I-707
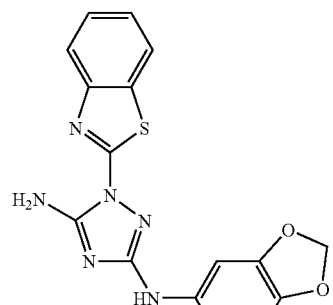
I-708
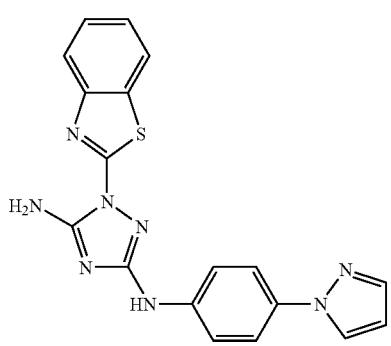
I-709
TABLE 1-continued
Examples of Compounds of Formula I:
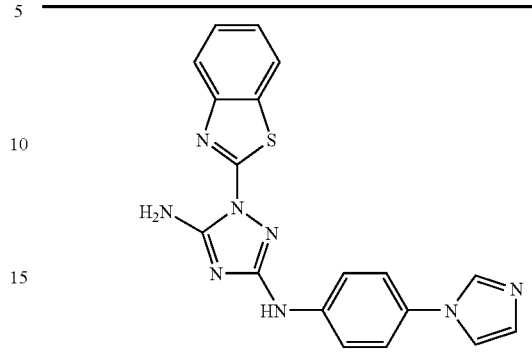
I-710
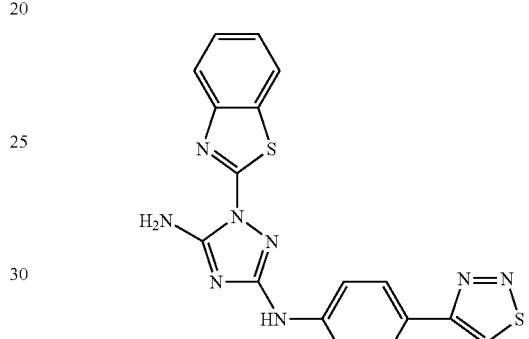
I-711
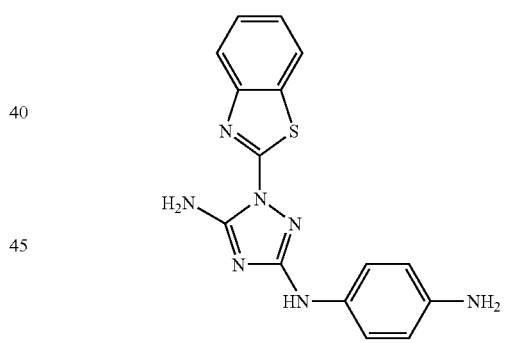
I-712
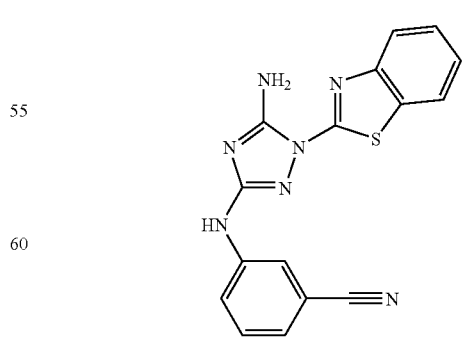
I-713

TABLE 1-continued
Examples of Compounds of Formula I:
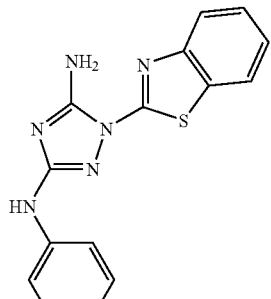
I-714
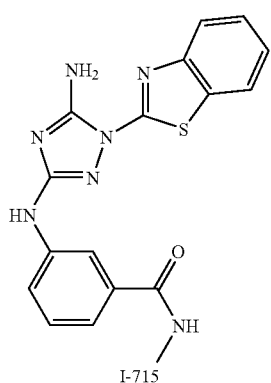
I-715
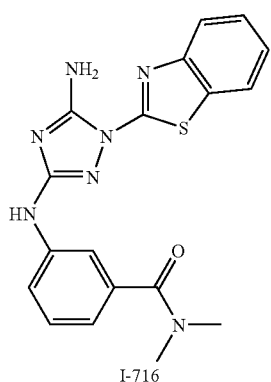
I-716
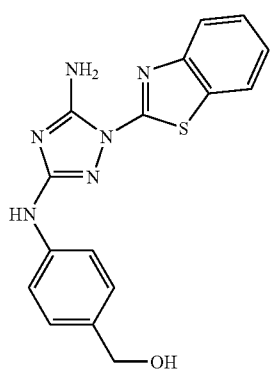
I-717
TABLE 1-continued
Examples of Compounds of Formula I:
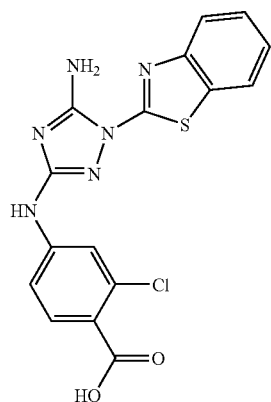
I-718
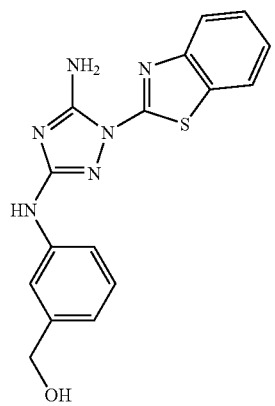
I-719
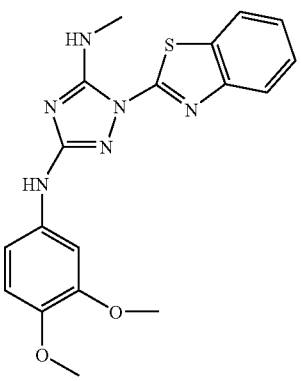
I-720

TABLE 1-continued
Examples of Compounds of Formula I:
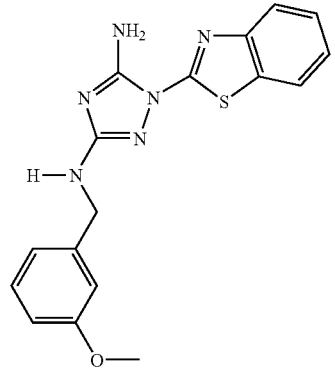
I-721
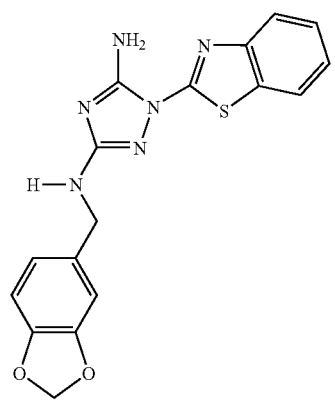
I-722
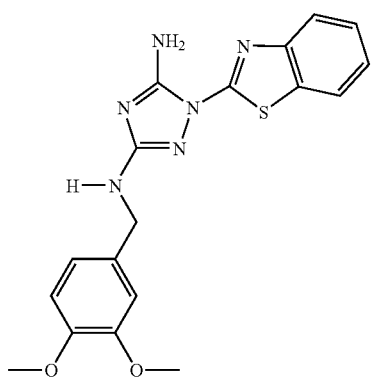
I-723
TABLE 1-continued
Examples of Compounds of Formula I:
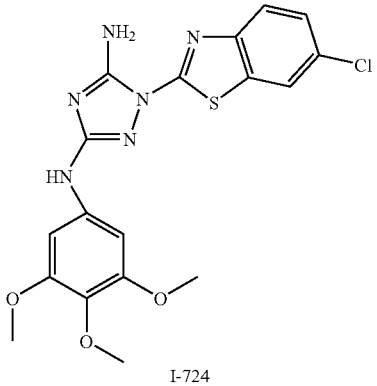
I-724
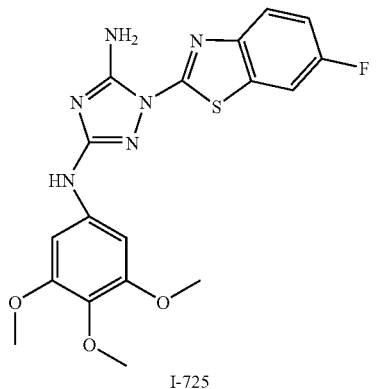
I-725
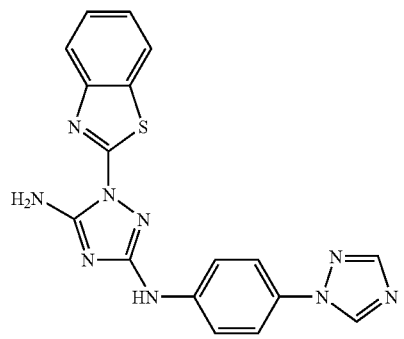
I-726
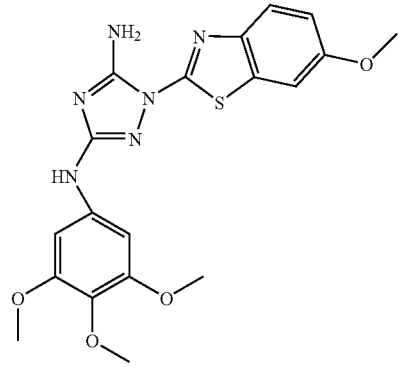
I-727

TABLE 1-continued
Examples of Compounds of Formula I:
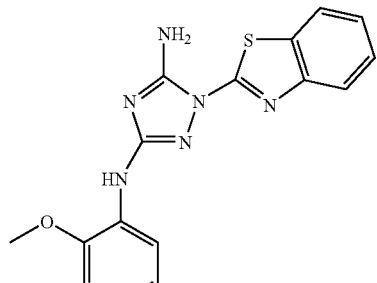
I-728
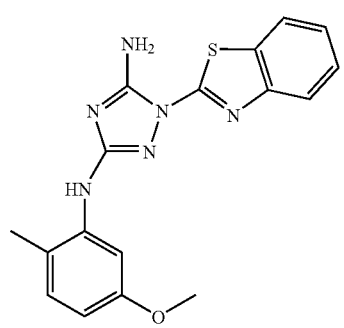
I-729
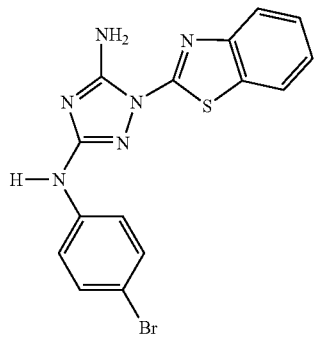
I-730
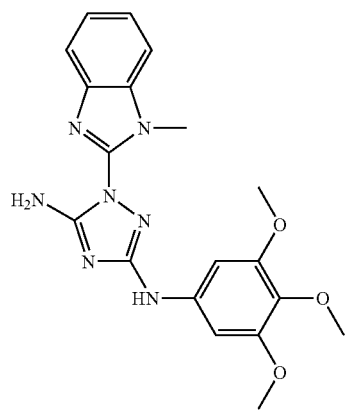
I-731
TABLE 1-continued
Examples of Compounds of Formula I:
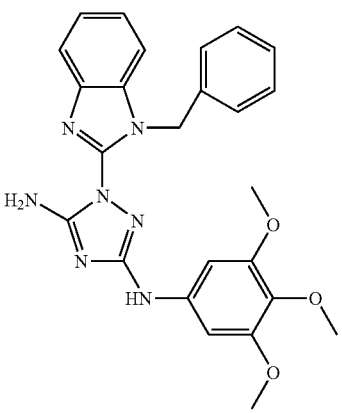
I-732
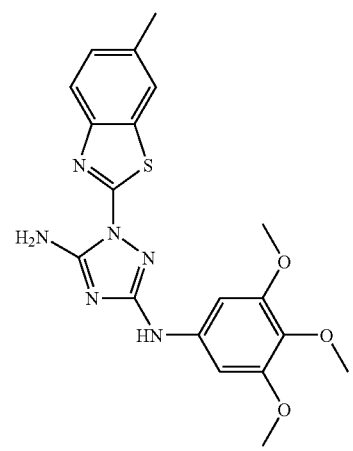
I-733
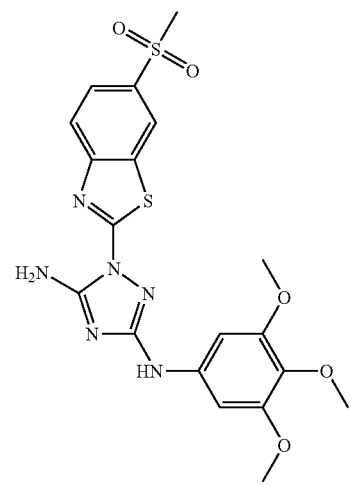
I-734

TABLE 1-continued
Examples of Compounds of Formula I:
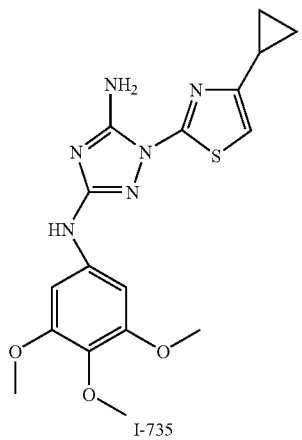
I-735
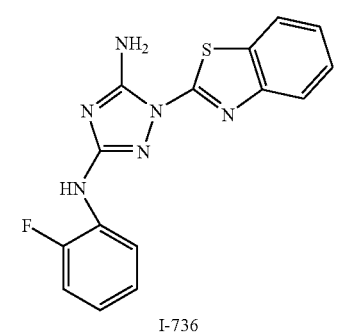
I-736
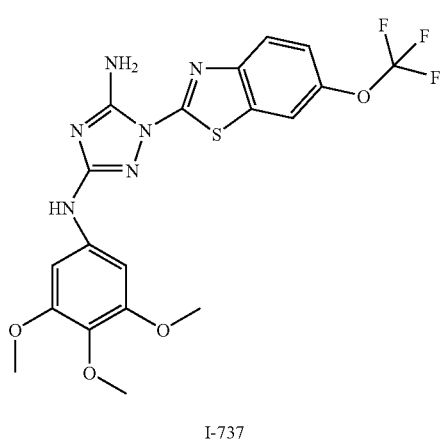
I-737
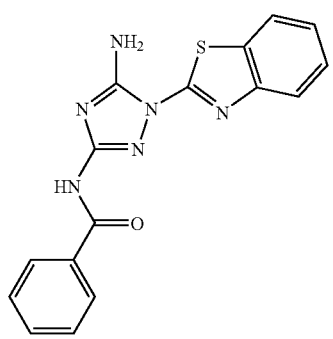
I-738
TABLE 1-continued
Examples of Compounds of Formula I:
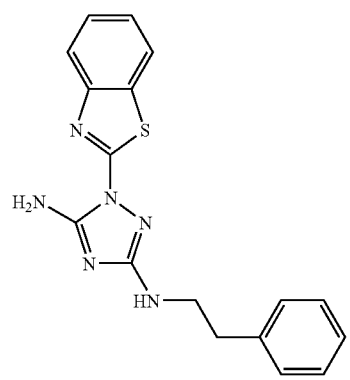
I-739
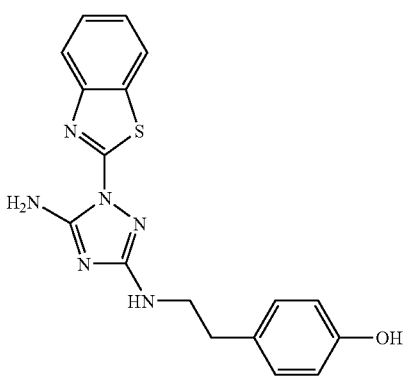
I-740
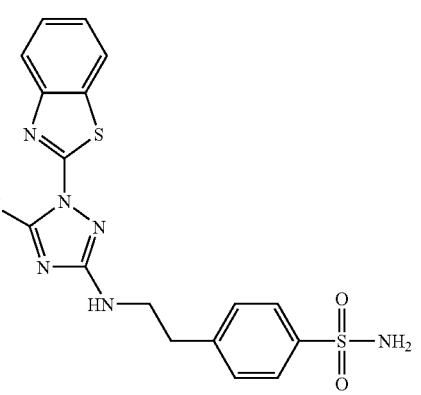
I-741

TABLE 1-continued
Examples of Compounds of Formula I:
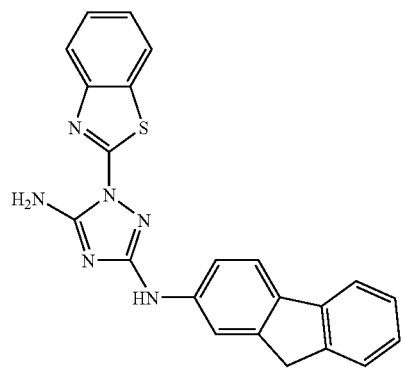
I-742
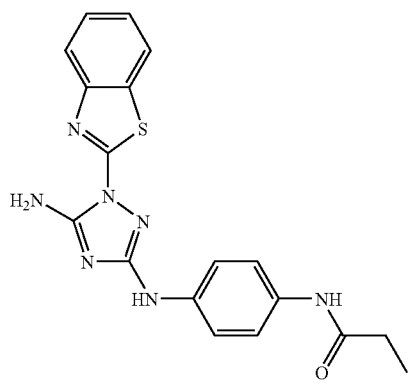
I-743
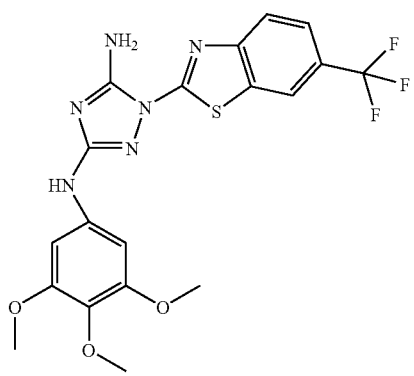
I-744
TABLE 1-continued
Examples of Compounds of Formula I:
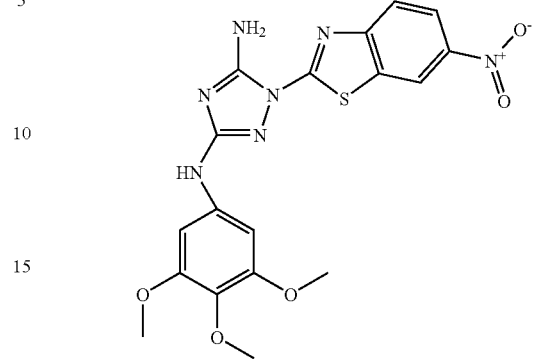
I-745
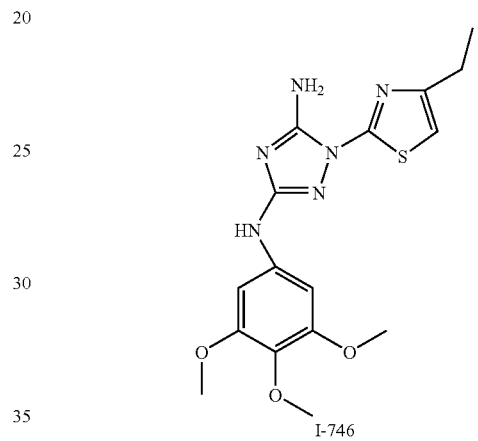
I-746
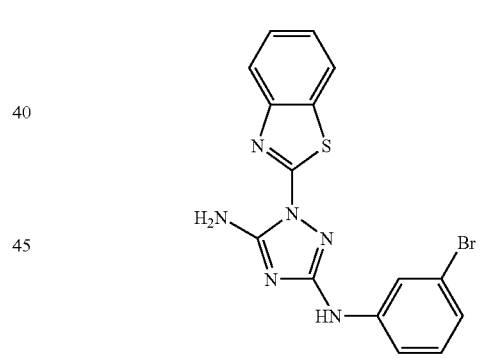
I-747
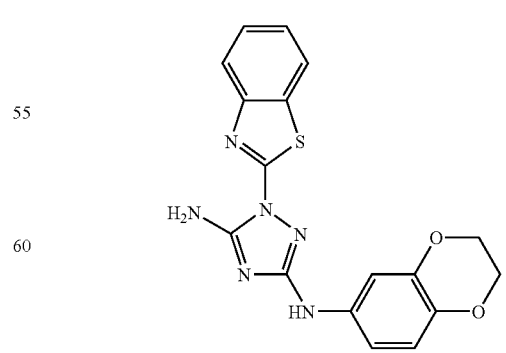
I-748

TABLE 1-continued
Examples of Compounds of Formula I:
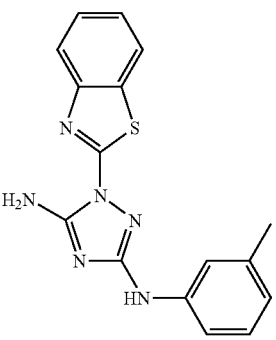
I-749
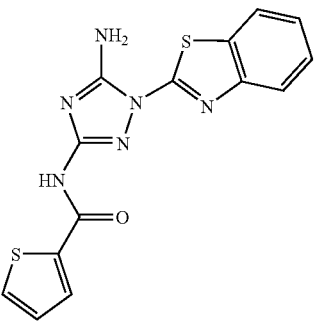
I-750
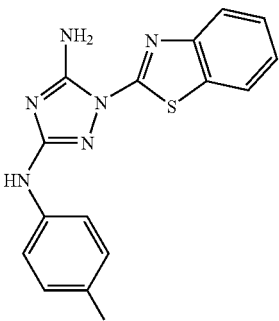
I-751
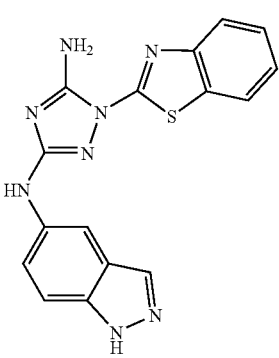
I-752
TABLE 1-continued
Examples of Compounds of Formula I:
I-753
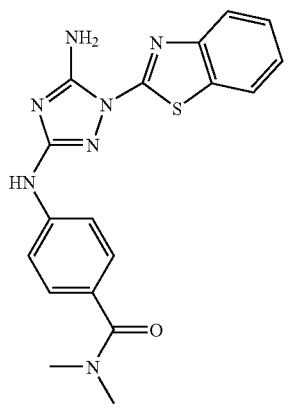
I-754
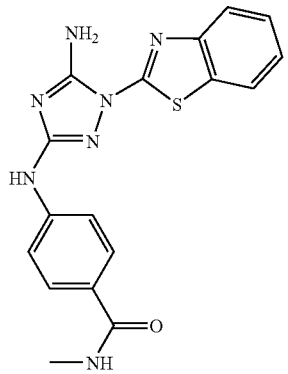
I-755

TABLE 1-continued
Examples of Compounds of Formula I:
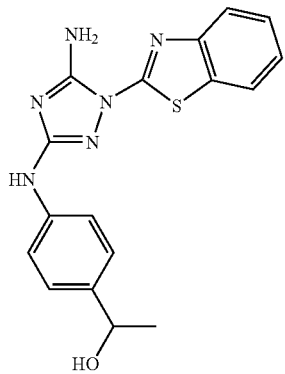
I-756
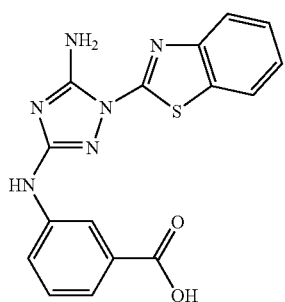
I-757
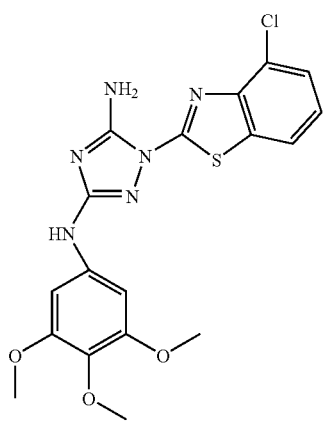
I-758
TABLE 1-continued
Examples of Compounds of Formula I:
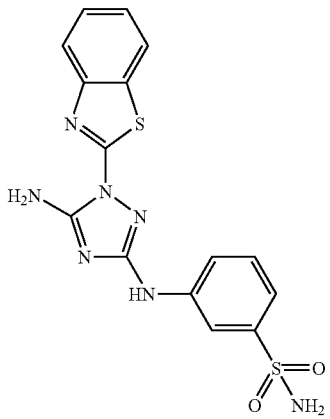
I-759
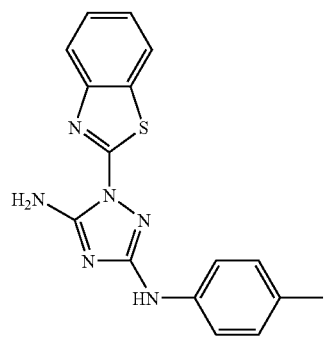
I-760
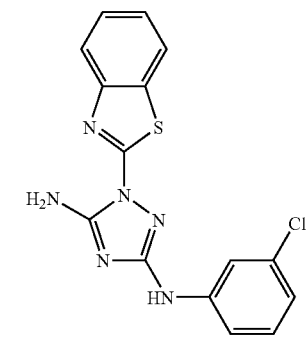
I-761
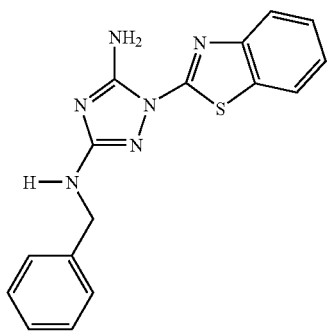
I-762

TABLE 1-continued
Examples of Compounds of Formula I:
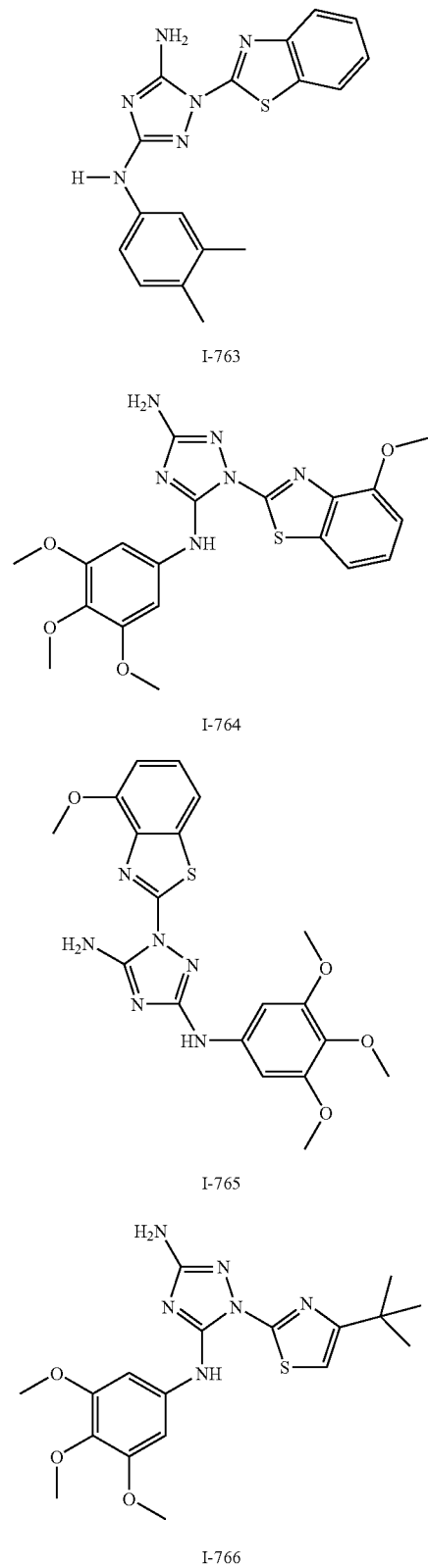
I-763
I-764
I-765
I-766
TABLE 1-continued
Examples of Compounds of Formula I:
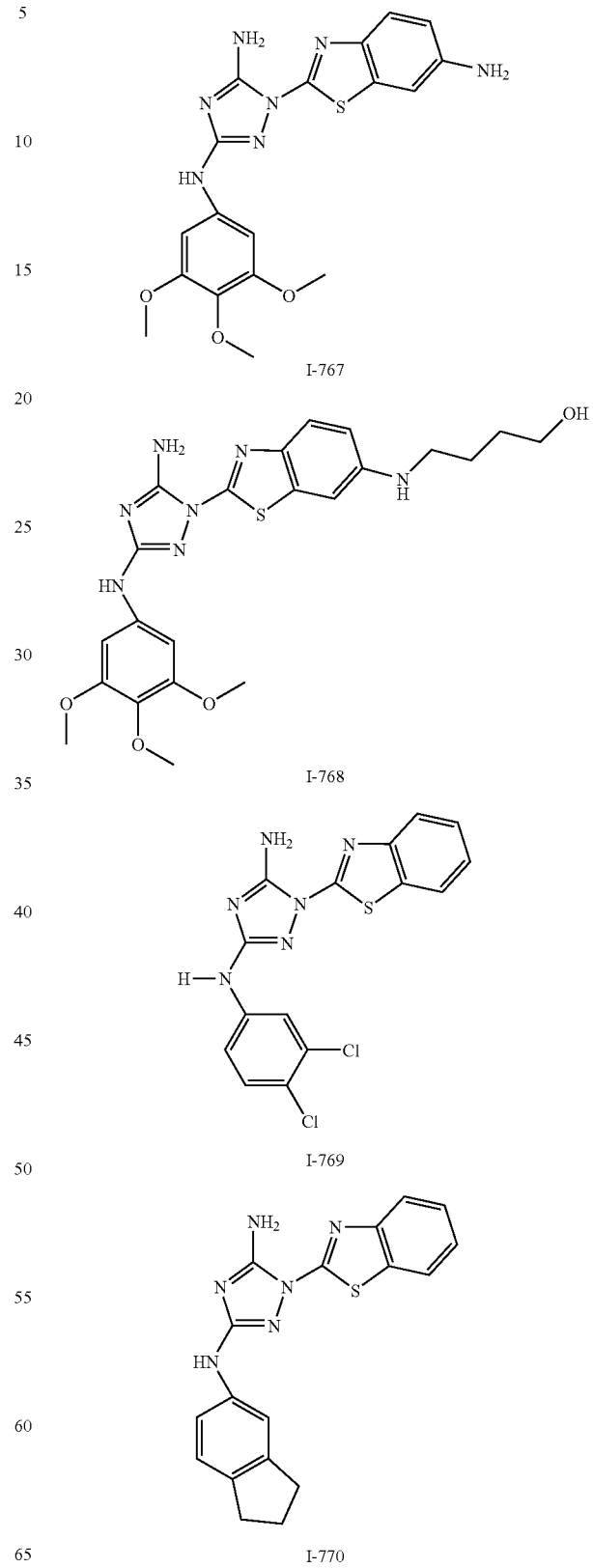
I-767
I-768
I-769
I-770

TABLE 1-continued
Examples of Compounds of Formula I:
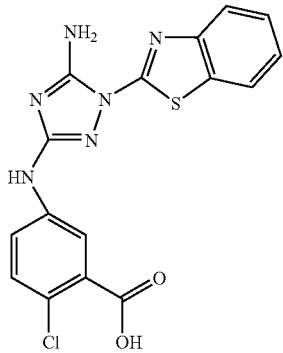
I-771
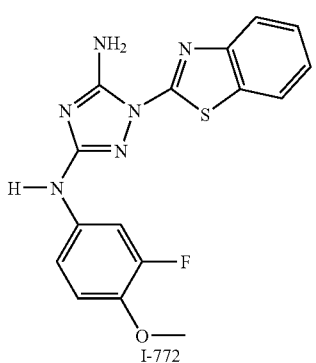
I-772
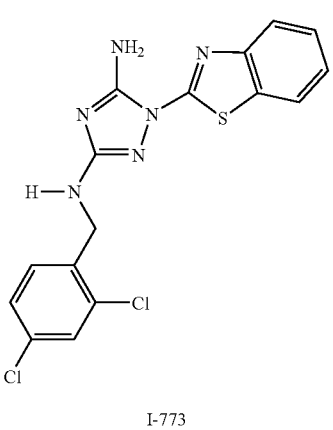
I-773
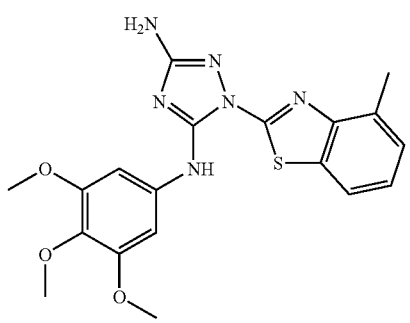
I-774
TABLE 1-continued
Examples of Compounds of Formula I:
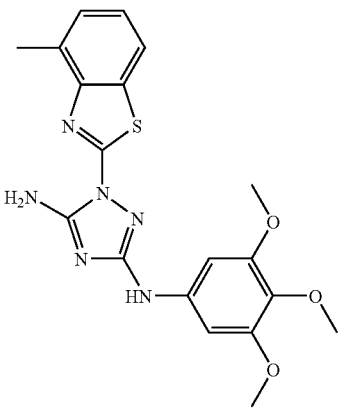
I-775
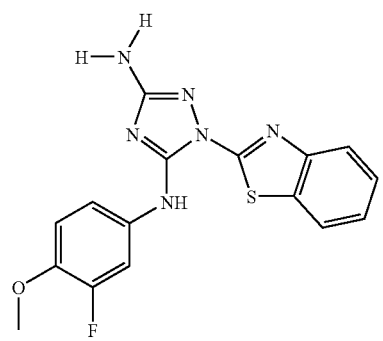
I-776
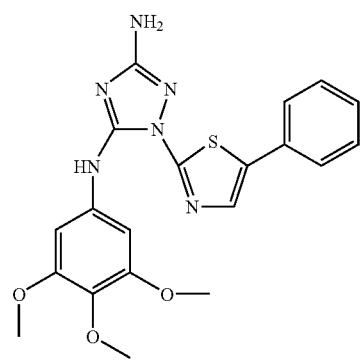
I-777

TABLE 1-continued
Examples of Compounds of Formula I:
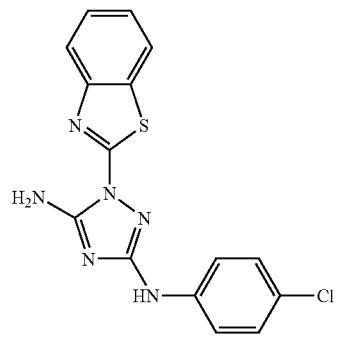
I-778
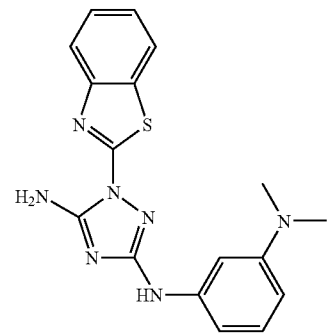
I-779
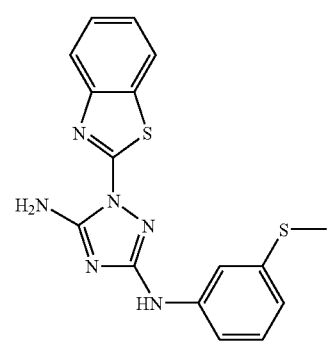
I-780
TABLE 1-continued
Examples of Compounds of Formula I:
I-781
I-782
I-783
I-784

TABLE 1-continued
Examples of Compounds of Formula I:
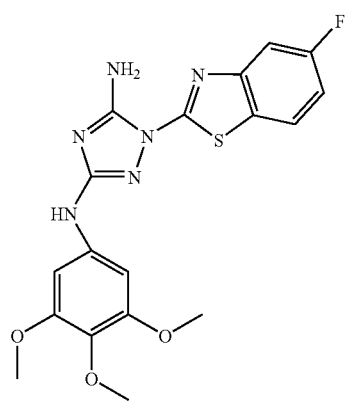
I-785
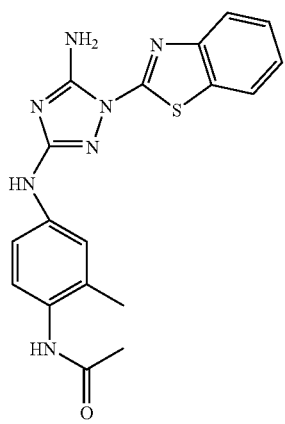
I-786
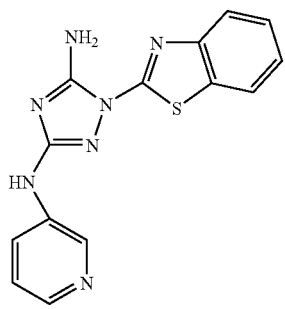
I-787
TABLE 1-continued
Examples of Compounds of Formula I:
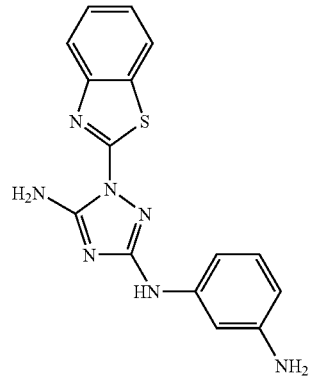
I-788
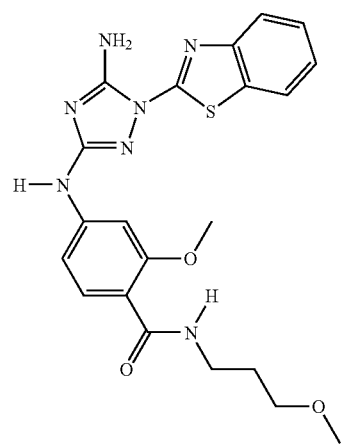
I-789
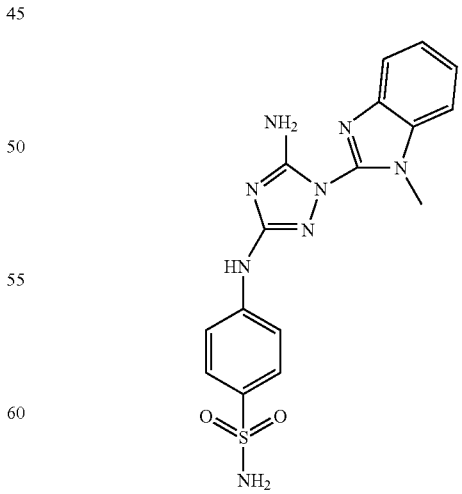
I-790

TABLE 1-continued
Examples of Compounds of Formula I:
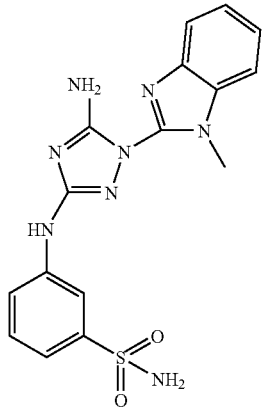
I-791
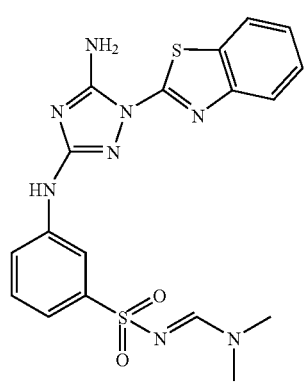
I-792
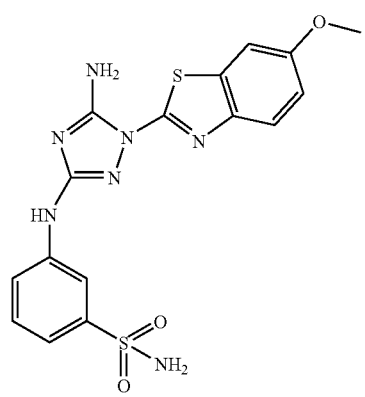
I-793
TABLE 1-continued
Examples of Compounds of Formula I:
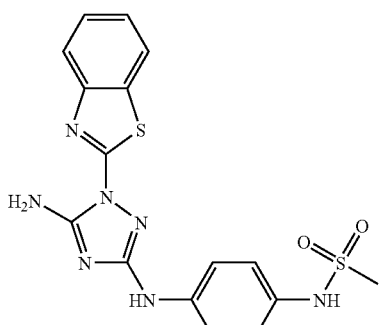
I-794
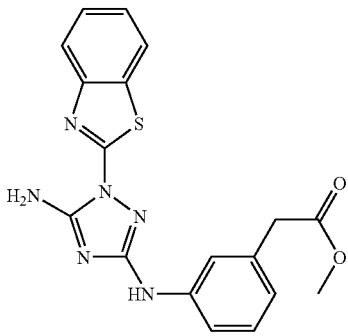
I-795
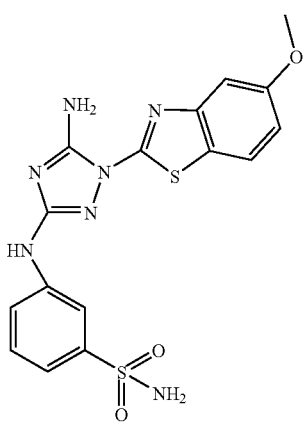
I-796

TABLE 1-continued
Examples of Compounds of Formula I:
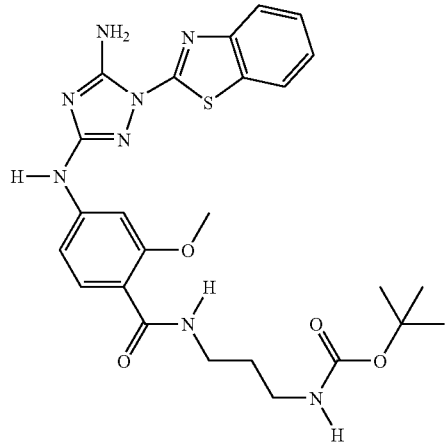
I-797
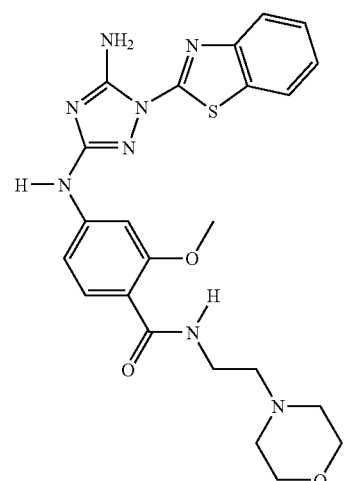
I-798
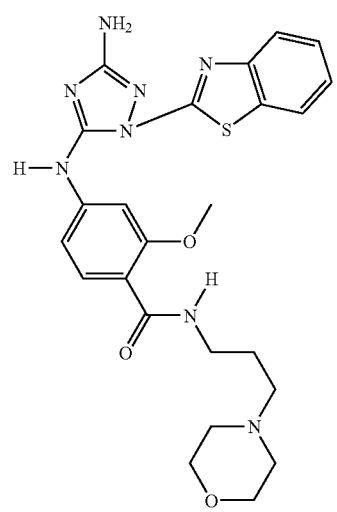
I-799
TABLE 1-continued
Examples of Compounds of Formula I:
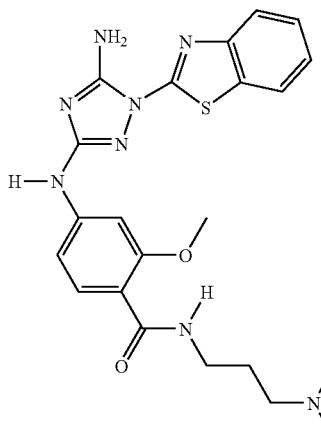
I-800
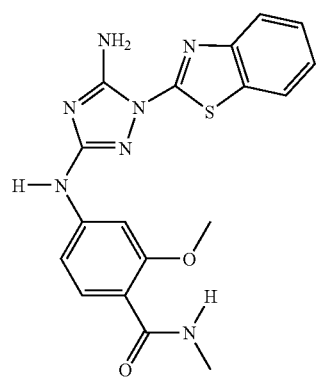
I-801
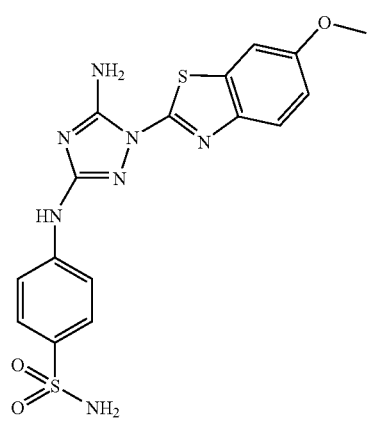
I-802

TABLE 1-continued
Examples of Compounds of Formula I:
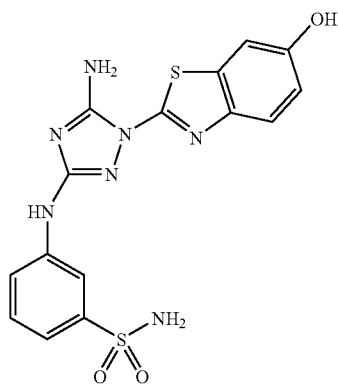
I-803
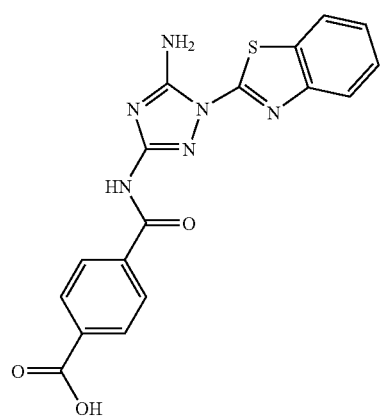
I-804
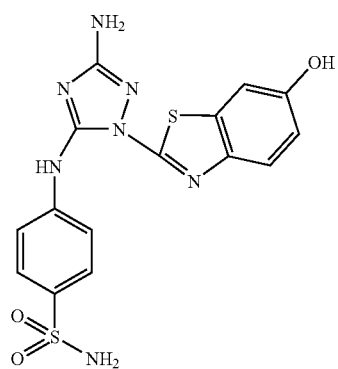
I-805
TABLE 1-continued
Examples of Compounds of Formula I:
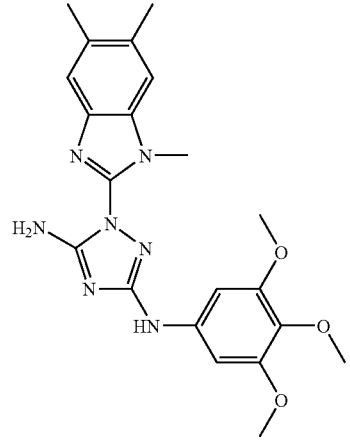
I-806
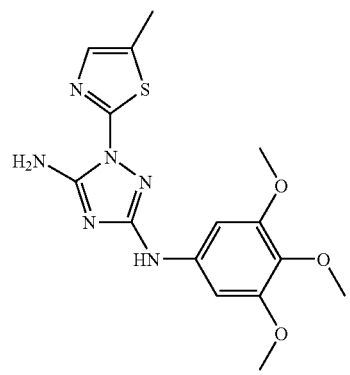
I-807
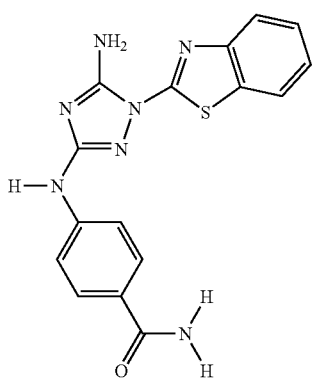
I-808

TABLE 1-continued

Examples of Compounds of Formula I:

I-809

I-810

I-811

I-812

I-813

I-814

I-815

I-816

TABLE 1-continued
Examples of Compounds of Formula I:
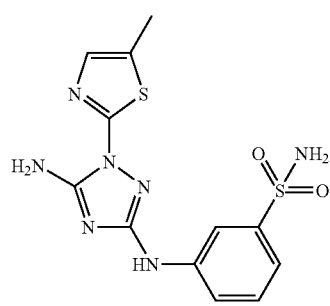
I-817
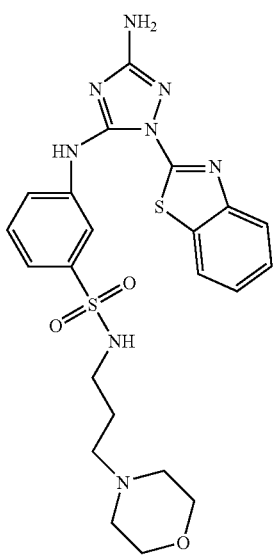
I-818
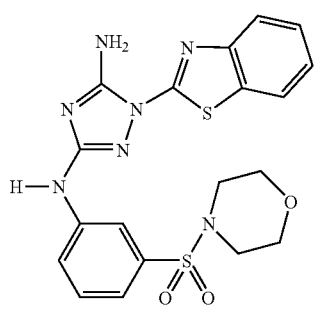
I-819
TABLE 1-continued
Examples of Compounds of Formula I:
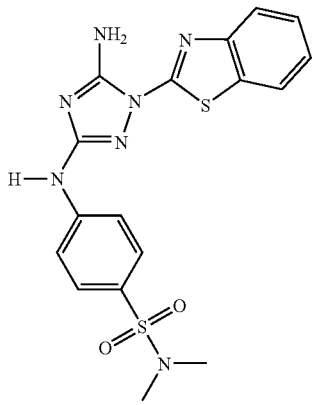
I-820
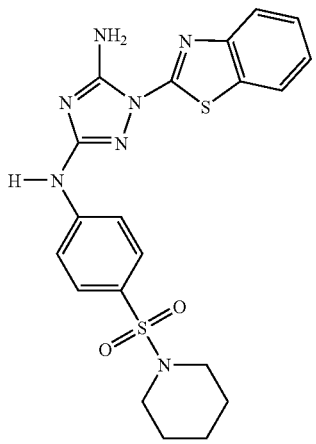
I-821
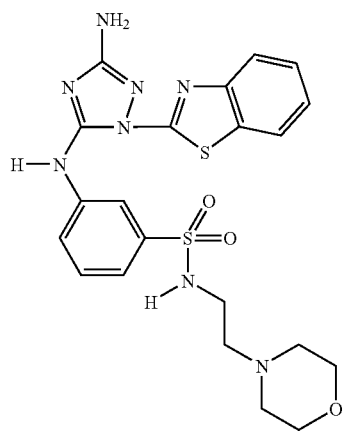
I-822

TABLE 1-continued
Examples of Compounds of Formula I:
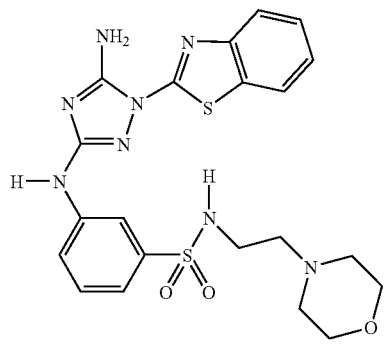
I-823
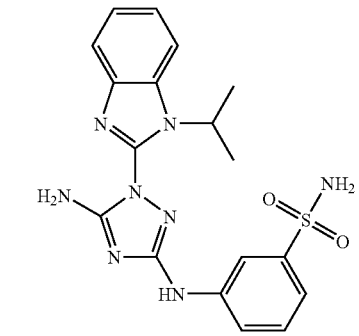
I-824
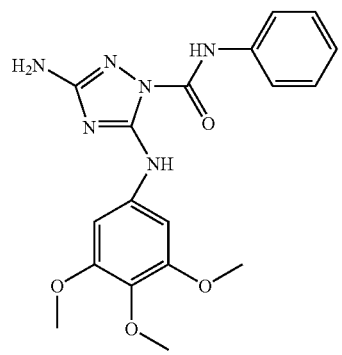
I-825
TABLE 1-continued
Examples of Compounds of Formula I:
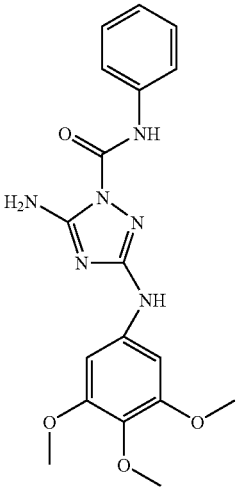
I-826
I-827
I-828

TABLE 1-continued
Examples of Compounds of Formula I:
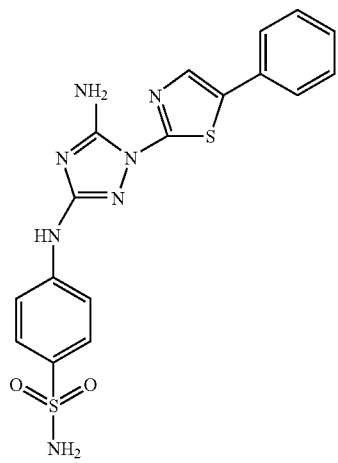
I-829
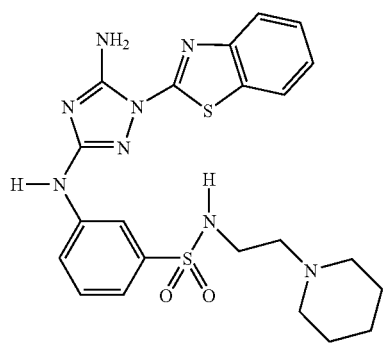
I-830
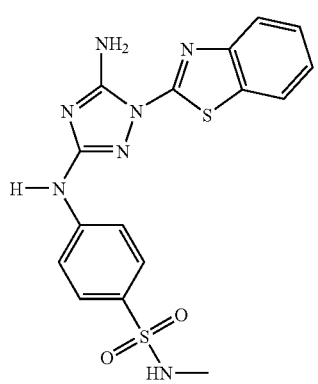
I-831
TABLE 1-continued
Examples of Compounds of Formula I:
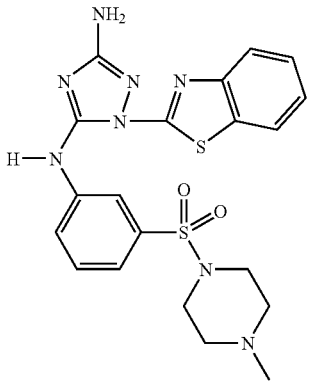
I-832
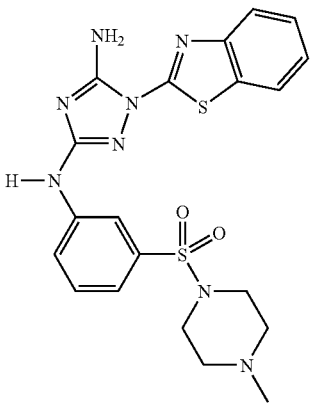
I-833
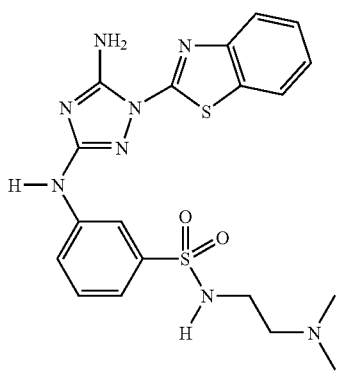
I-834

TABLE 1-continued
Examples of Compounds of Formula I:
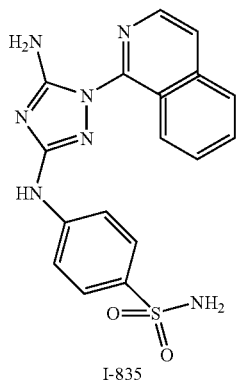
I-835
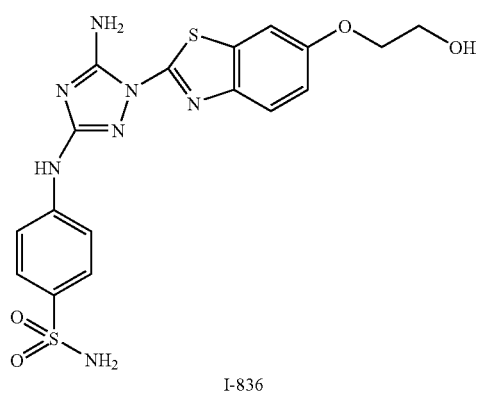
I-836
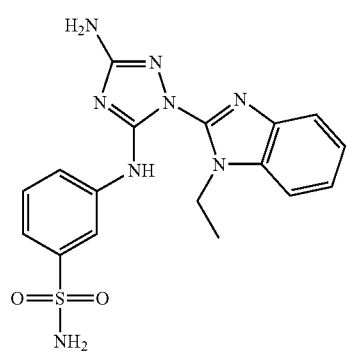
I-837
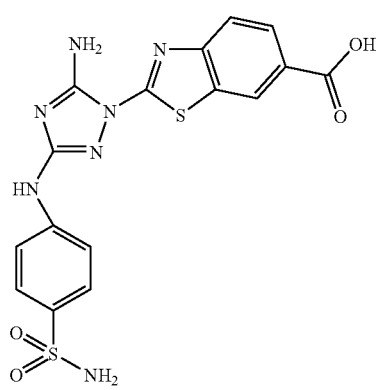
I-838
TABLE 1-continued
Examples of Compounds of Formula I:
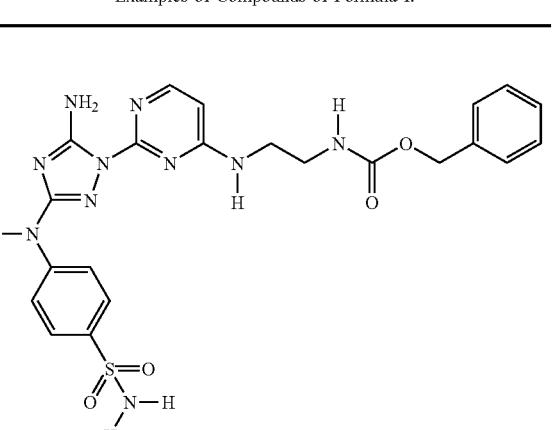
I-839
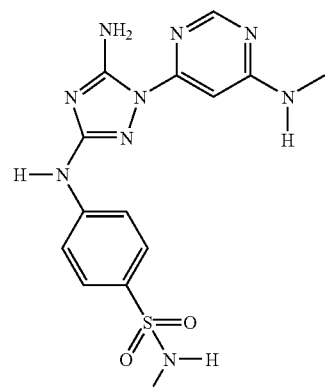
I-840
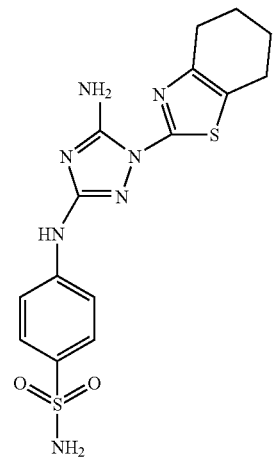
I-841

TABLE 1-continued
Examples of Compounds of Formula I:
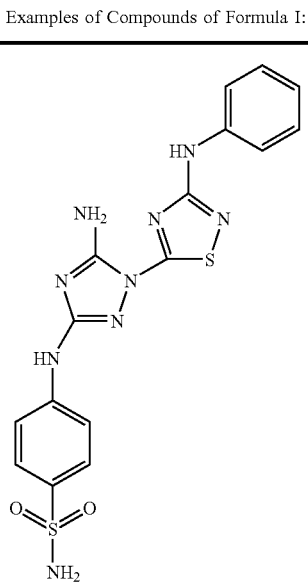
I-842
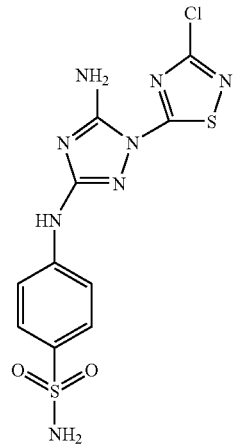
I-843
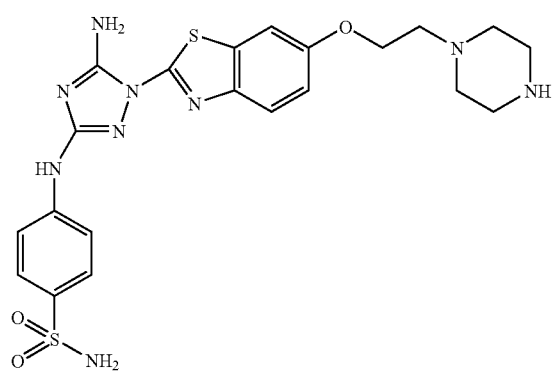
I-844
TABLE 1-continued
Examples of Compounds of Formula I:
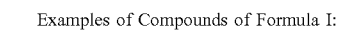
I-845
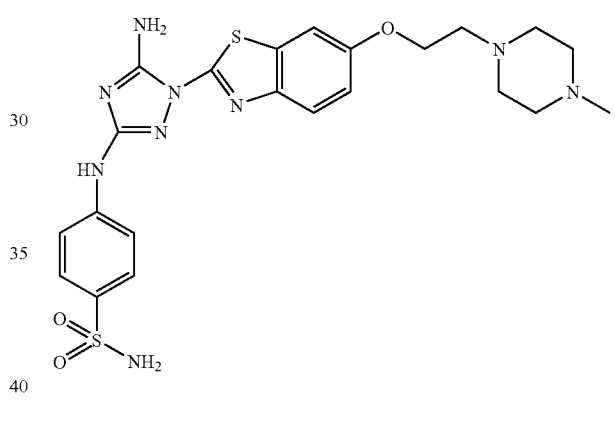
I-846
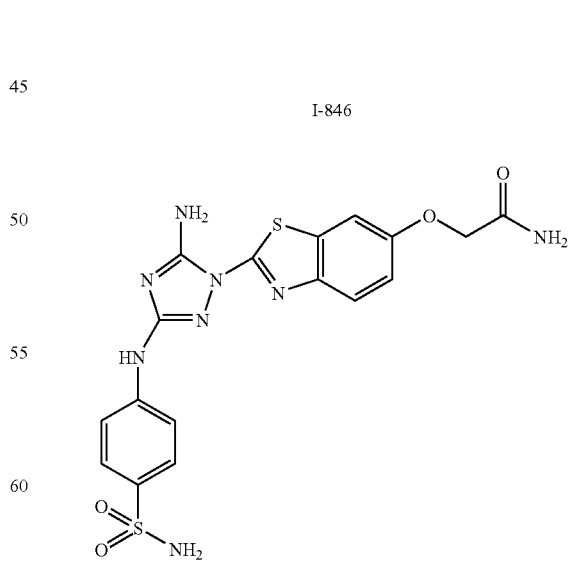
I-847

TABLE 1-continued
Examples of Compounds of Formula I:
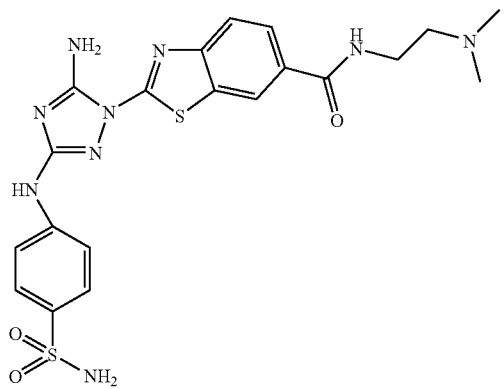
I-848
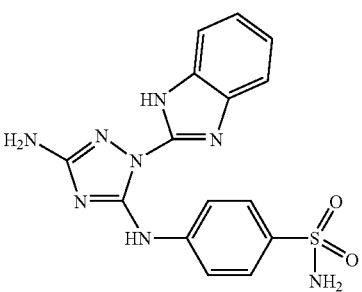
I-849
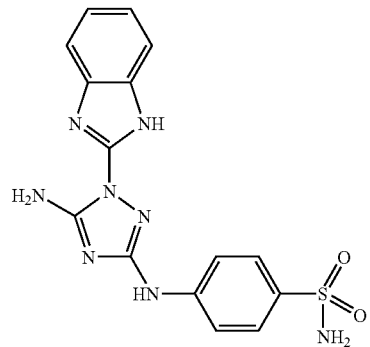
I-850
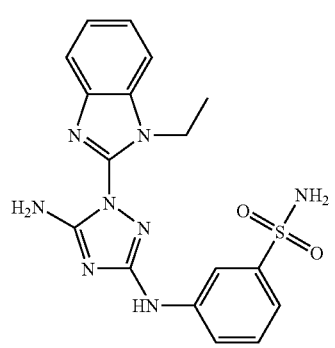
I-851
TABLE 1-continued
Examples of Compounds of Formula I:
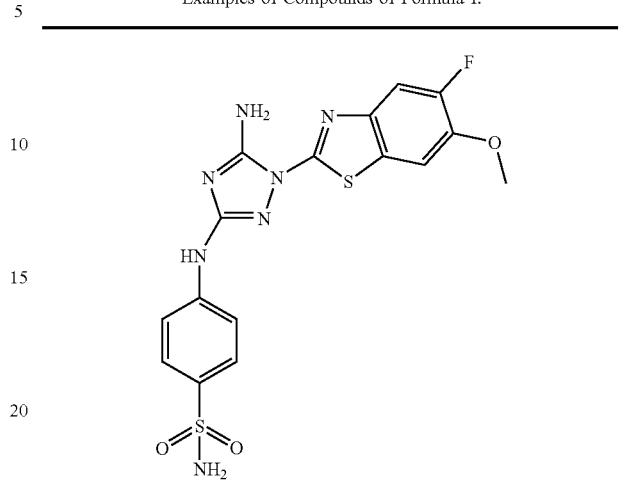
I-852
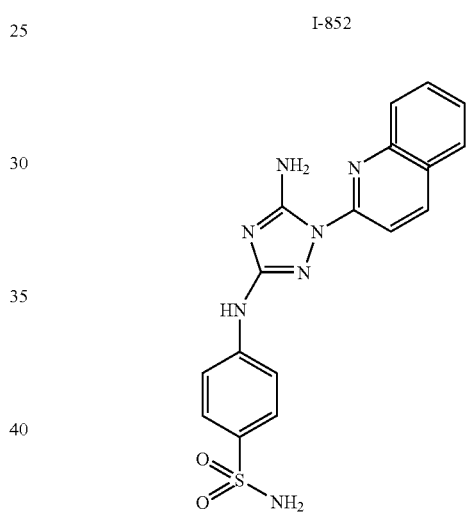
I-853
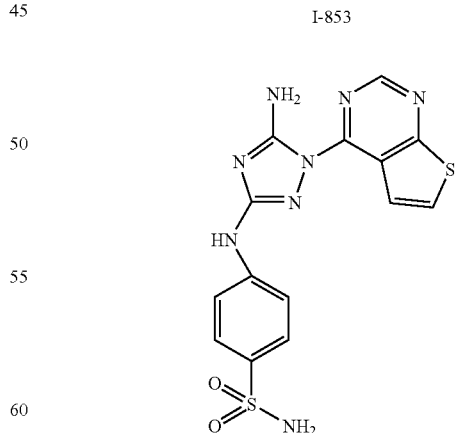
I-854

TABLE 1-continued
Examples of Compounds of Formula I:
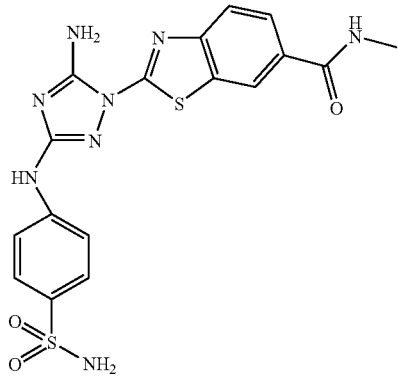
I-855
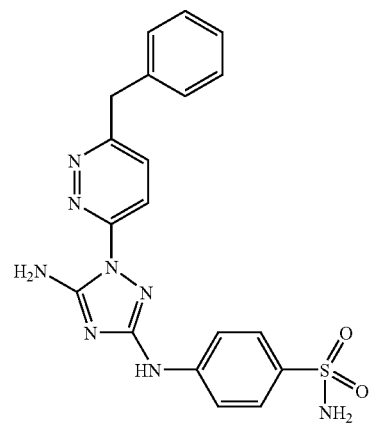
I-856
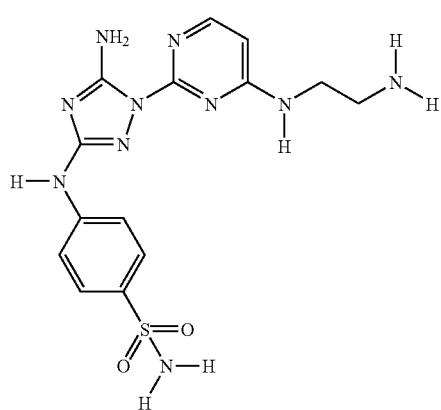
I-857
TABLE 1-continued
Examples of Compounds of Formula I:
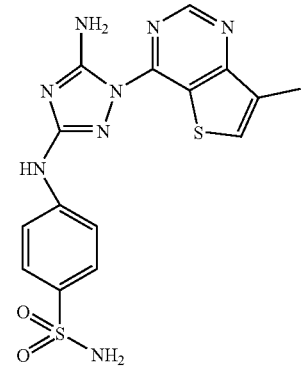
I-858
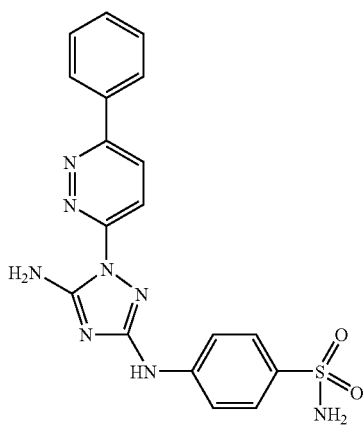
I-859
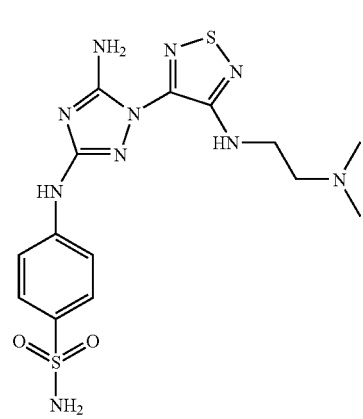
I-860

TABLE 1-continued
Examples of Compounds of Formula I:
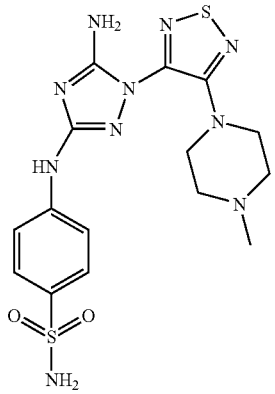
I-861
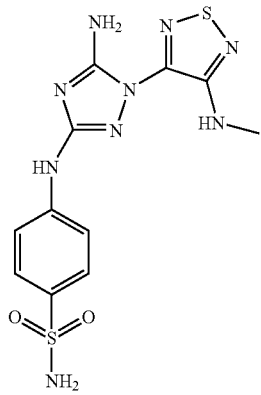
I-862
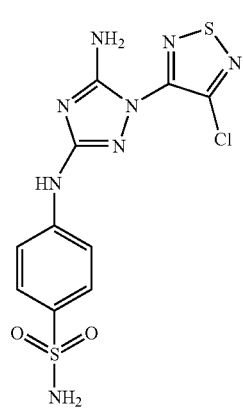
I-863
TABLE 1-continued
Examples of Compounds of Formula I:
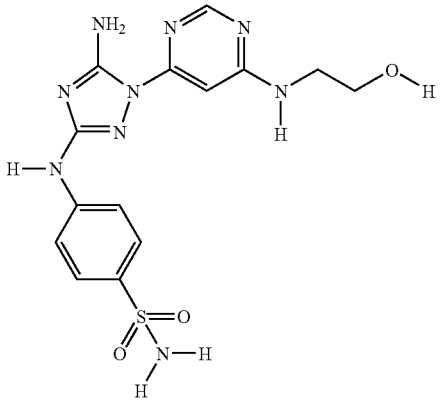
I-864
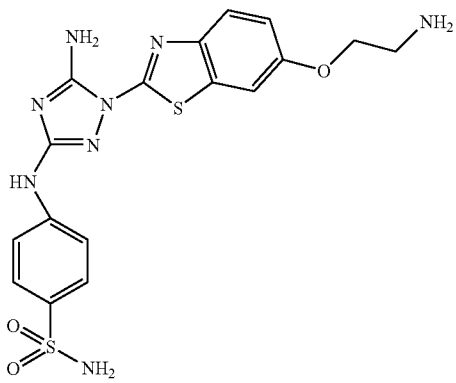
I-865
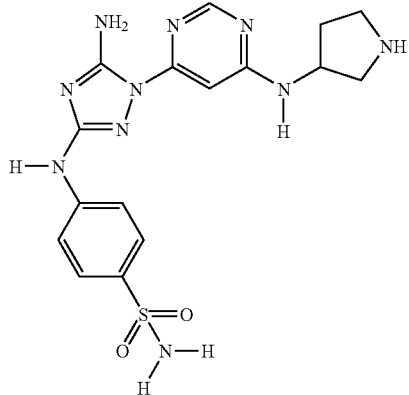
I-866

TABLE 1-continued
Examples of Compounds of Formula I:
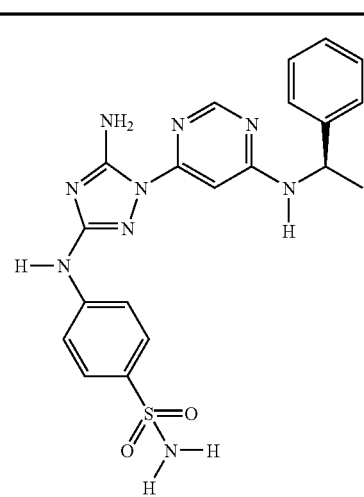
I-867
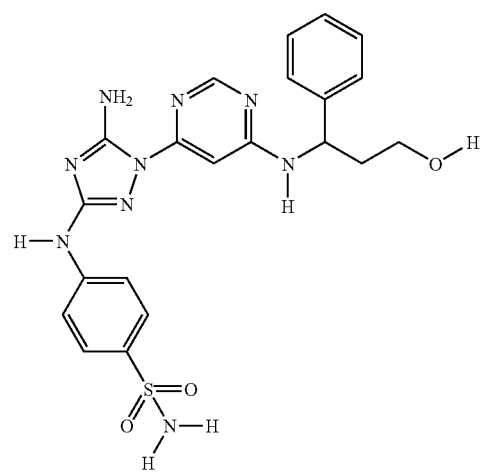
I-868
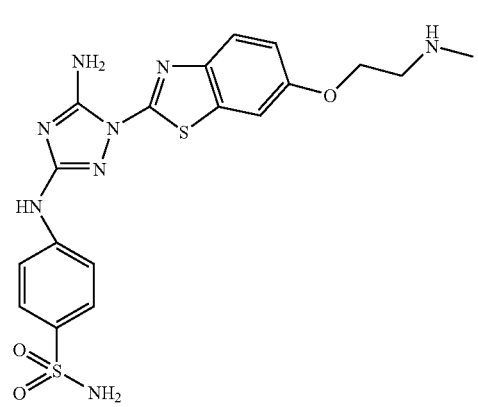
I-869
TABLE 1-continued
Examples of Compounds of Formula I:
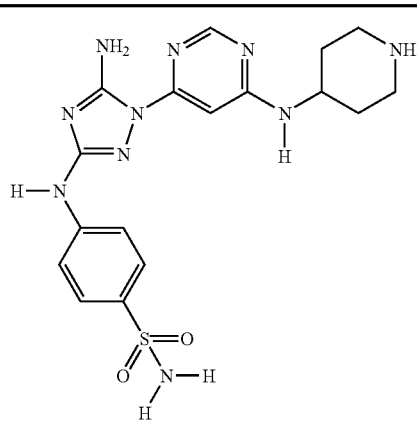
I-870
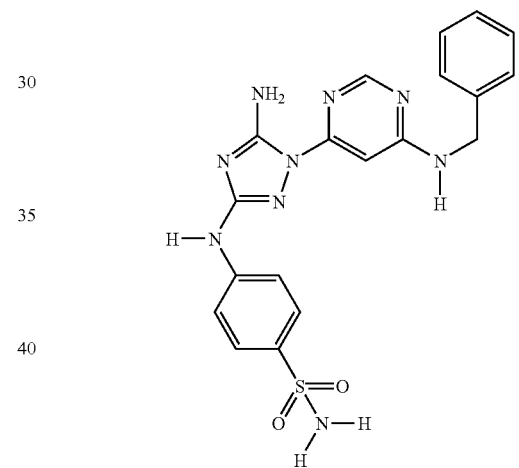
I-871
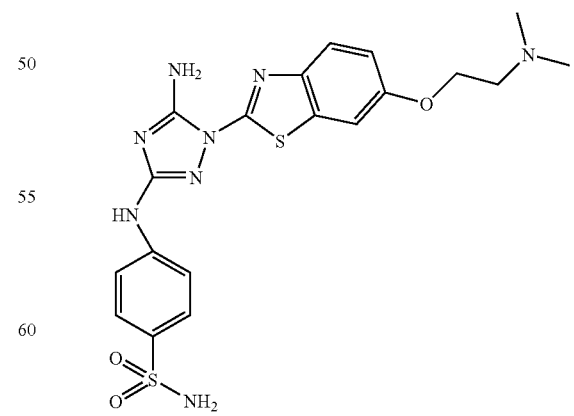
I-872

TABLE 1-continued
Examples of Compounds of Formula I:
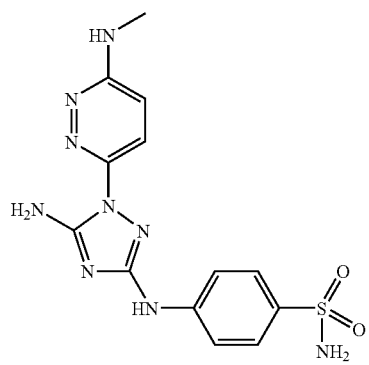
I-873
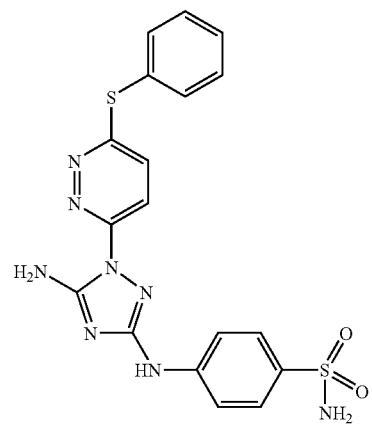
I-874
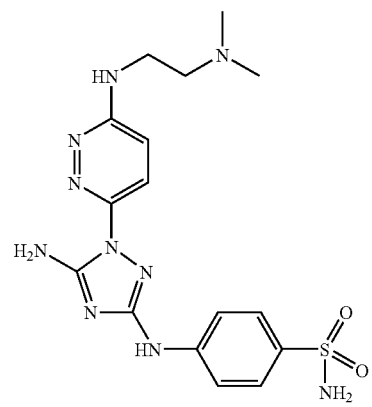
I-875
TABLE 1-continued
Examples of Compounds of Formula I:
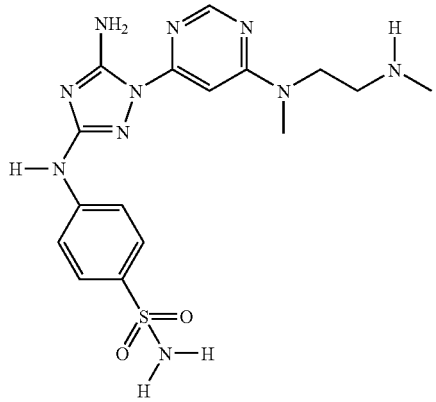
I-876
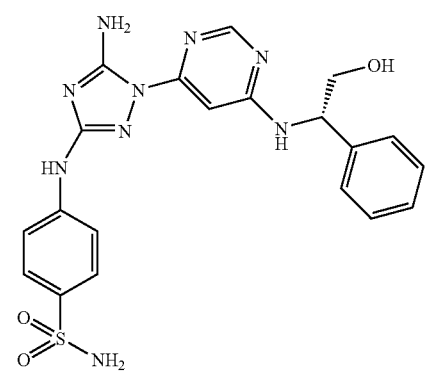
I-877
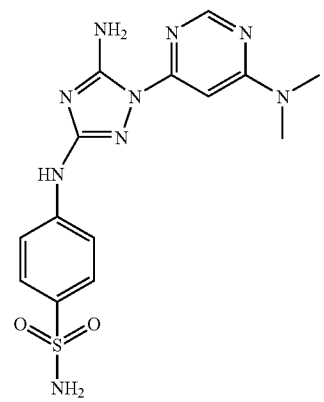
I-878

TABLE 1-continued
Examples of Compounds of Formula I:
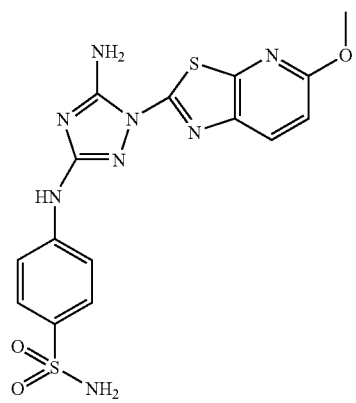
I-879
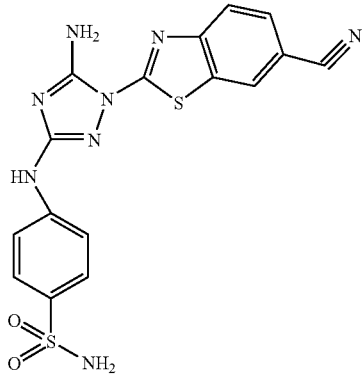
I-880
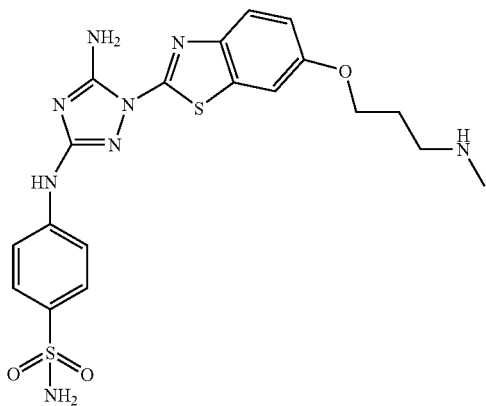
I-881
TABLE 1-continued
Examples of Compounds of Formula I:
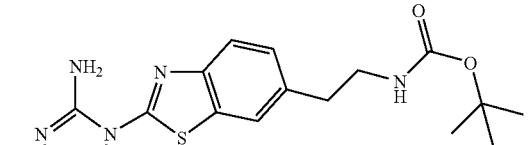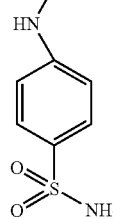
I-882
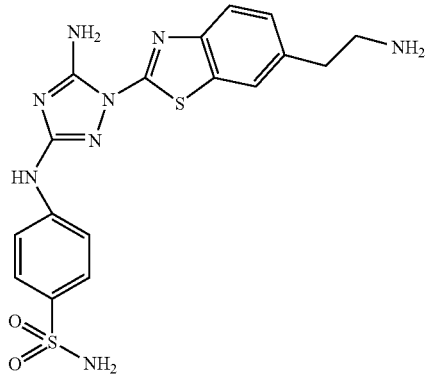
I-883
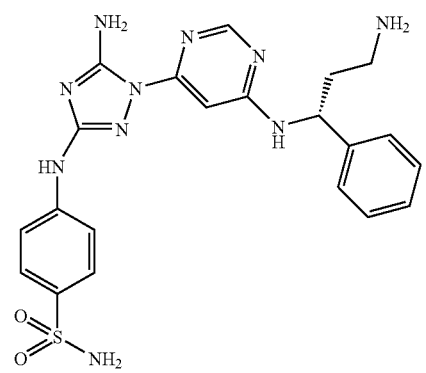
I-884

TABLE 1-continued
Examples of Compounds of Formula I:
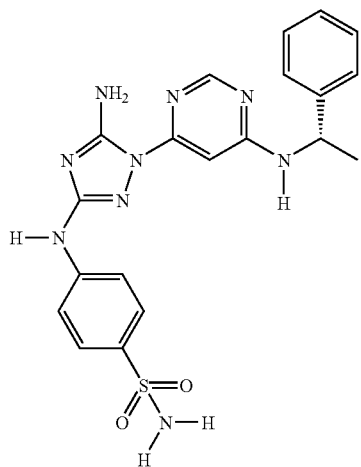
I-885
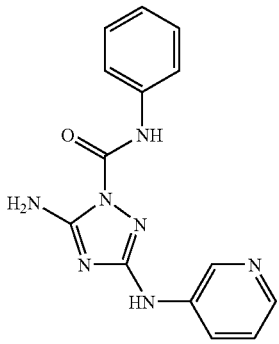
I-886
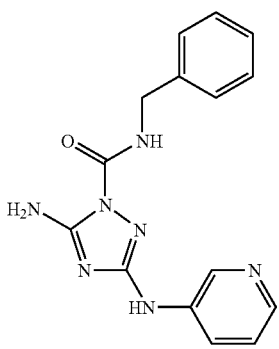
I-887
TABLE 1-continued
Examples of Compounds of Formula I:
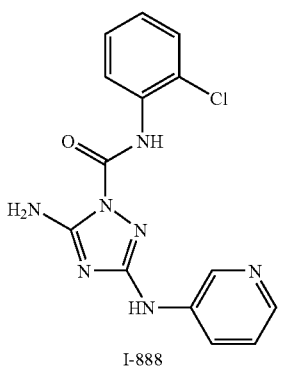
I-888
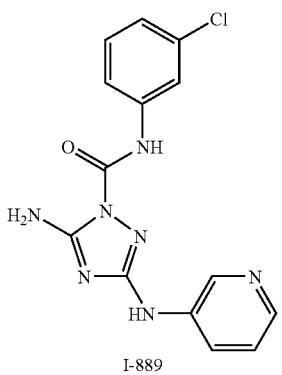
I-889
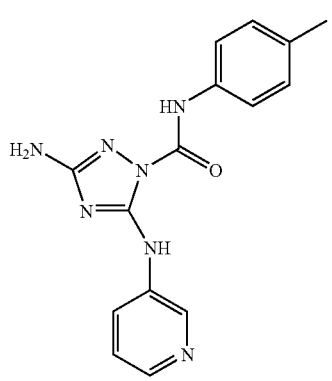
I-890
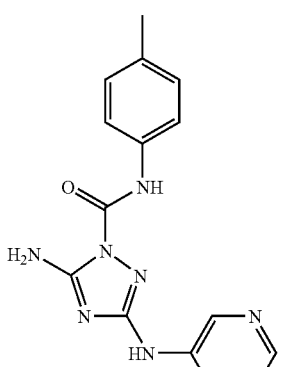
I-891

TABLE 1-continued
Examples of Compounds of Formula I:
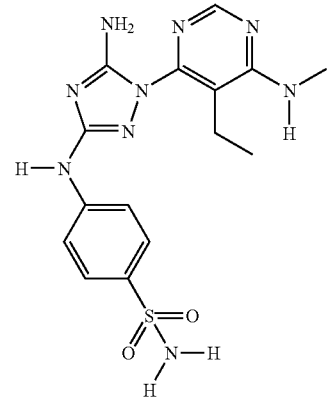
I-892
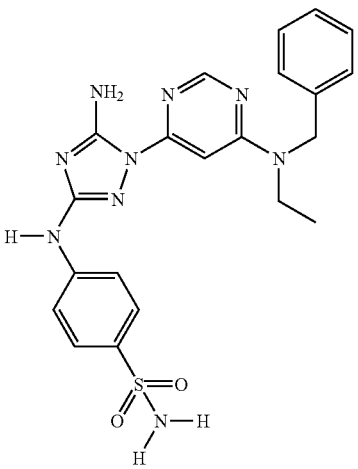
I-893
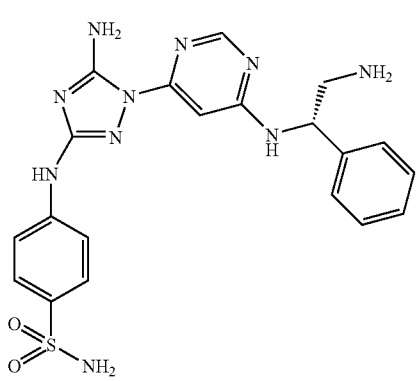
I-894
TABLE 1-continued
Examples of Compounds of Formula I:
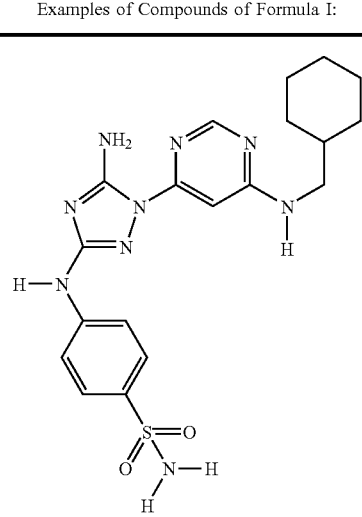
I-895
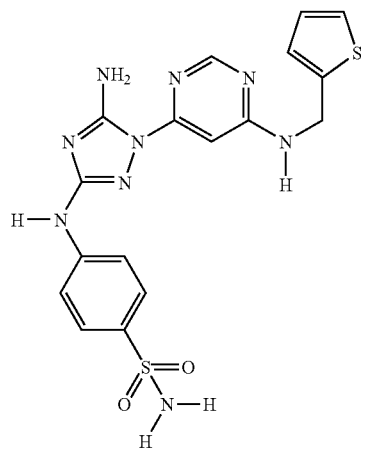
I-896
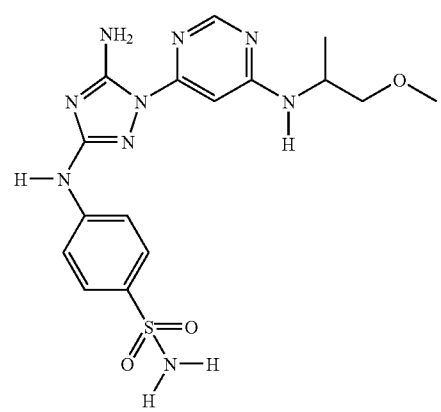
I-897

TABLE 1-continued
Examples of Compounds of Formula I:
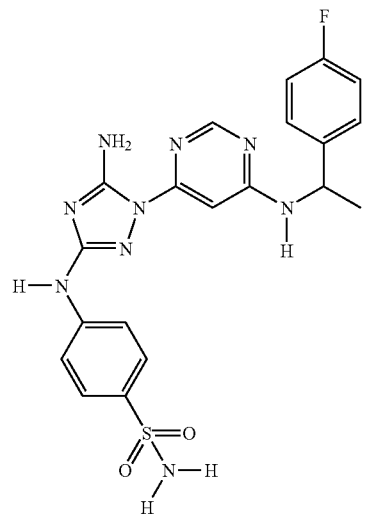
I-898
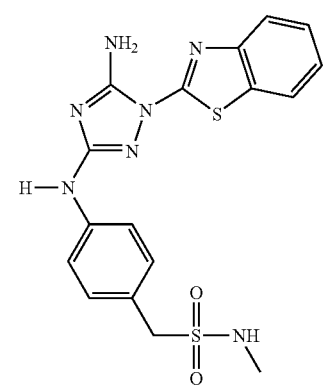
I-899
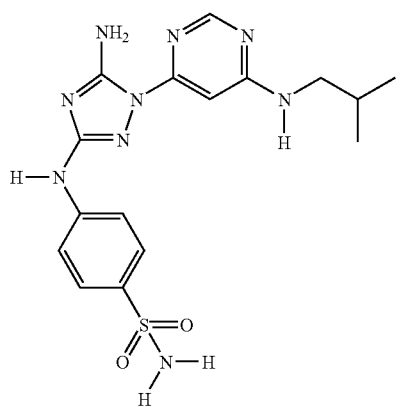
I-900
TABLE 1-continued
Examples of Compounds of Formula I:
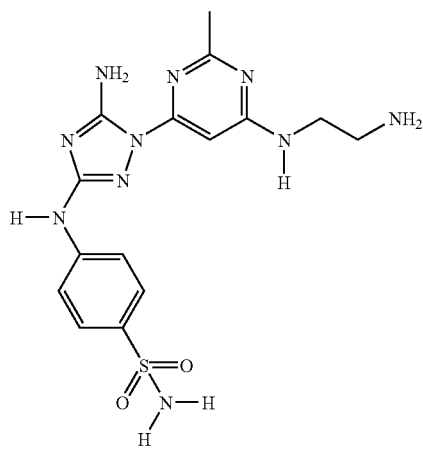
I-901
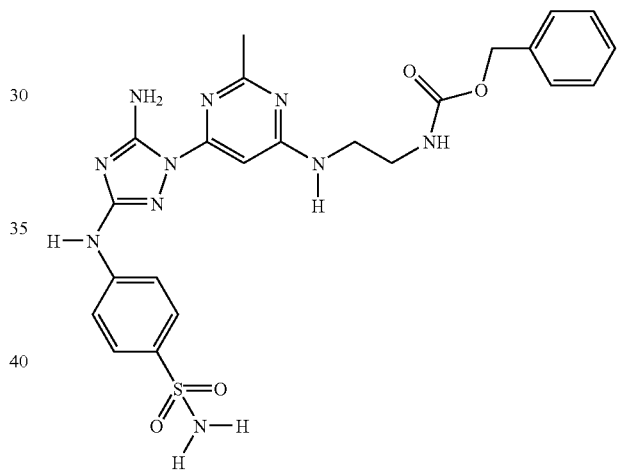
I-902
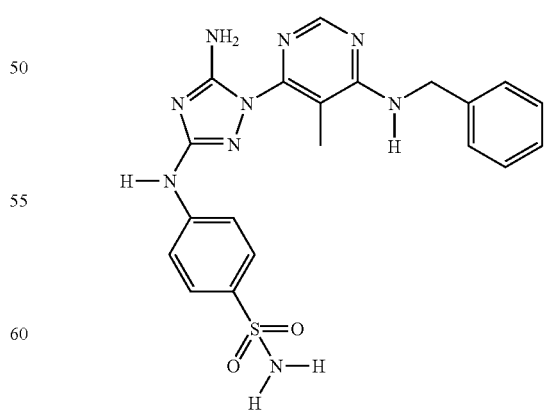
I-903

TABLE 1-continued

Examples of Compounds of Formula I:

I-904

I-905

I-906

I-907

I-908

I-909

TABLE 1-continued
Examples of Compounds of Formula I:
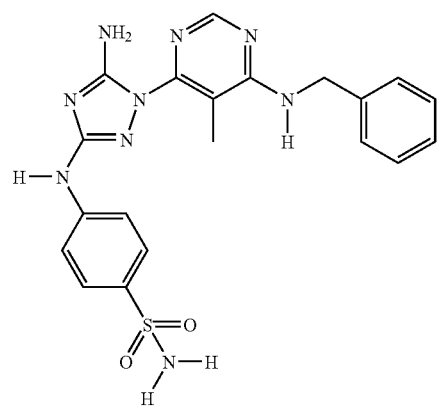
I-910
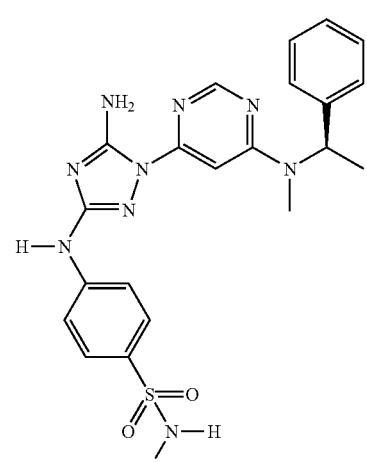
I-911
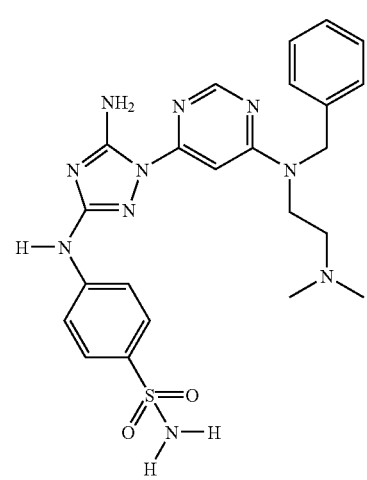
I-912
TABLE 1-continued
Examples of Compounds of Formula I:
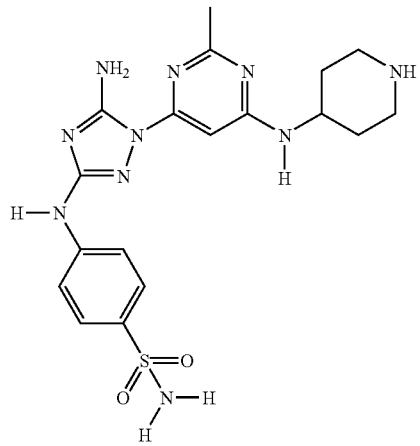
I-913
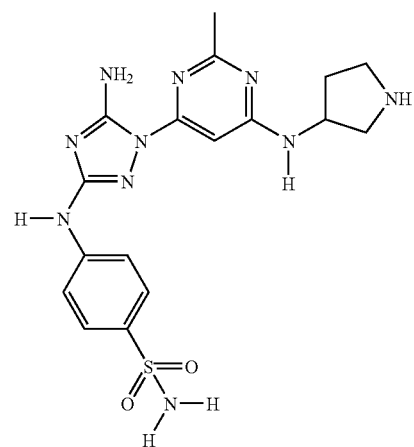
I-914
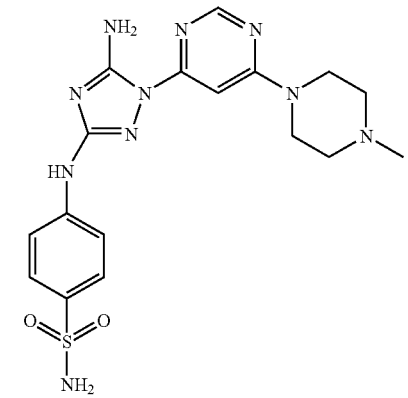
I-915

TABLE 1-continued
Examples of Compounds of Formula I:
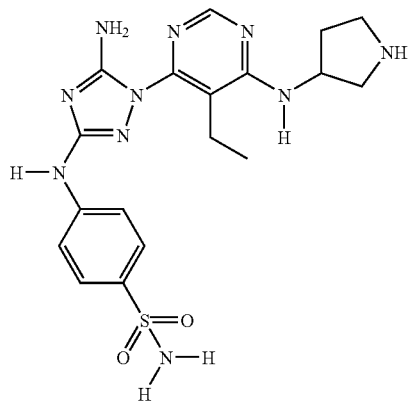
I-916
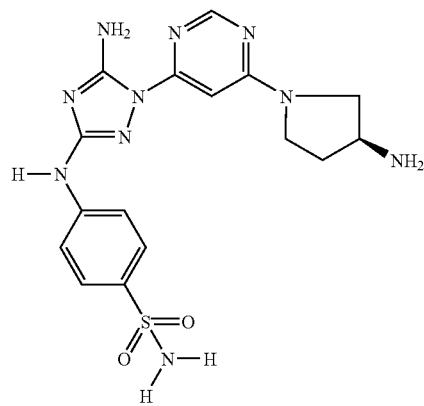
I-917
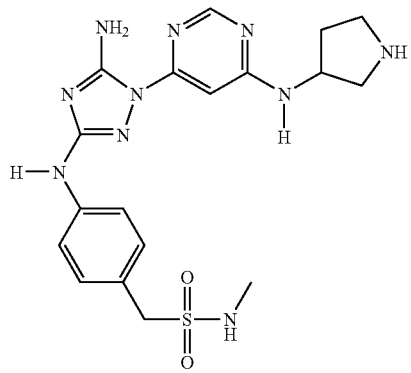
I-918
TABLE 1-continued
Examples of Compounds of Formula I:
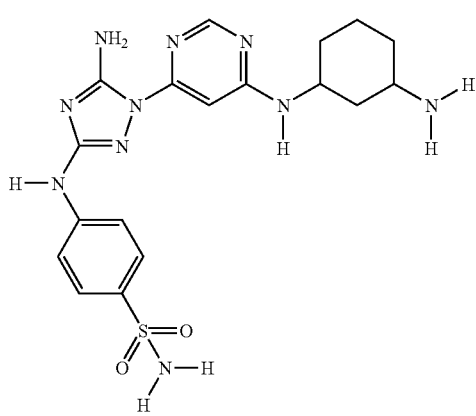
I-919
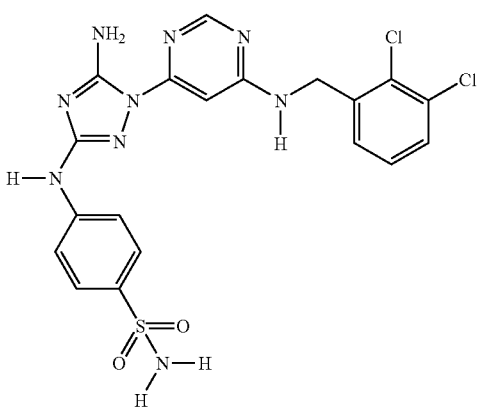
I-920
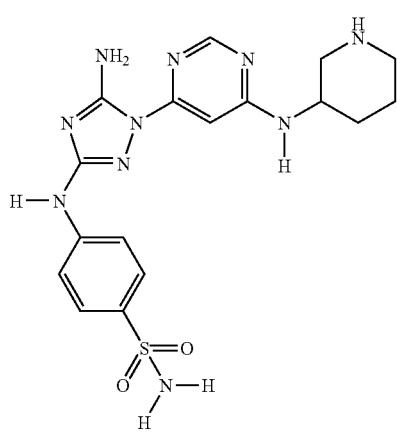
I-921

TABLE 1-continued
Examples of Compounds of Formula I:
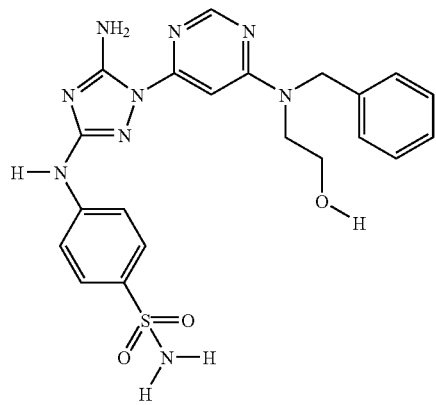
I-922
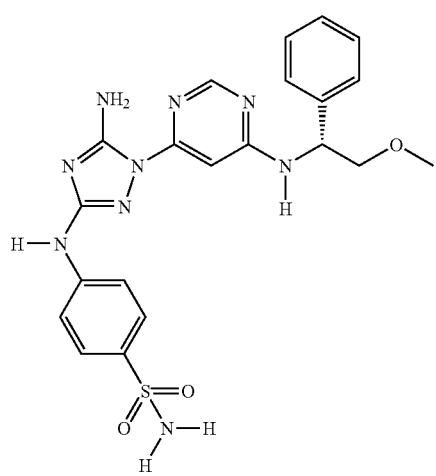
I-923
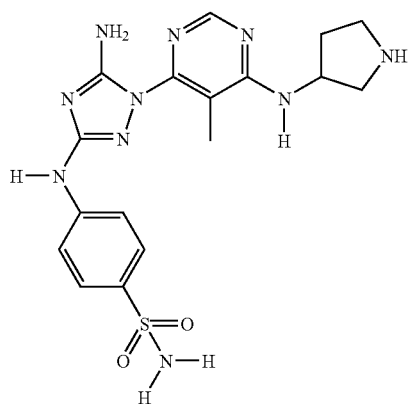
I-924
TABLE 1-continued
Examples of Compounds of Formula I:
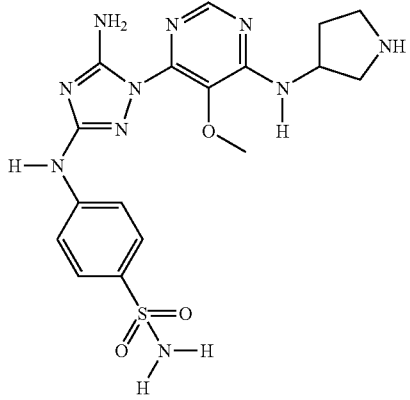
I-925
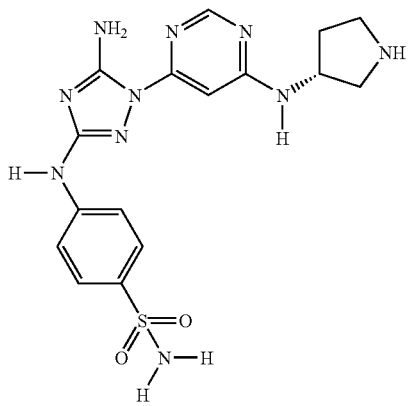
I-926
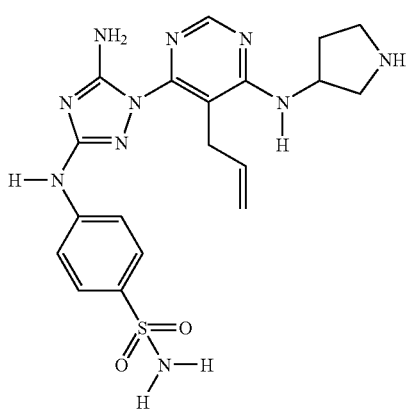
I-927

TABLE 1-continued
Examples of Compounds of Formula I:
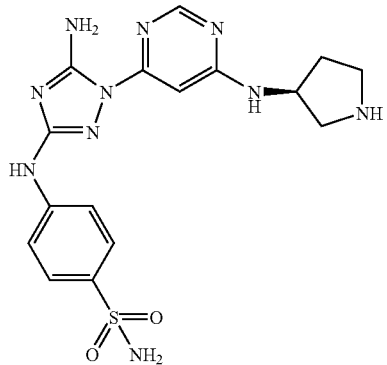
I-928
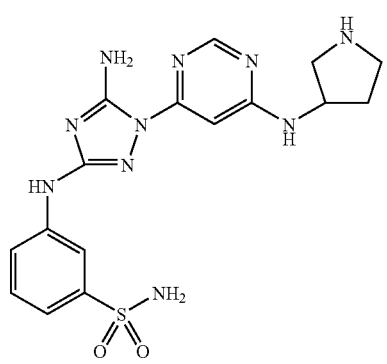
I-929
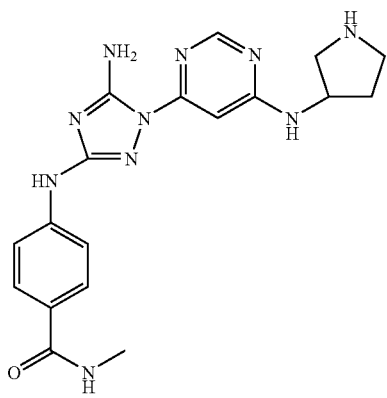
I-930
TABLE 1-continued
Examples of Compounds of Formula I:
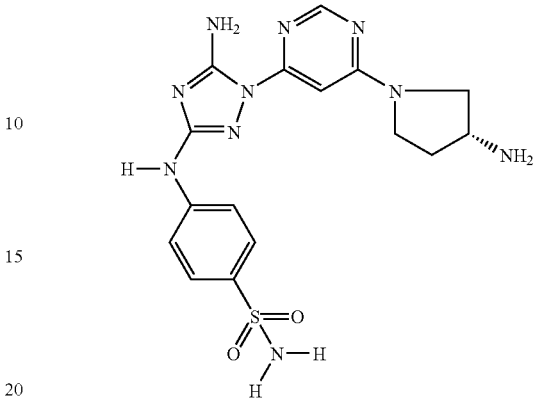
I-931
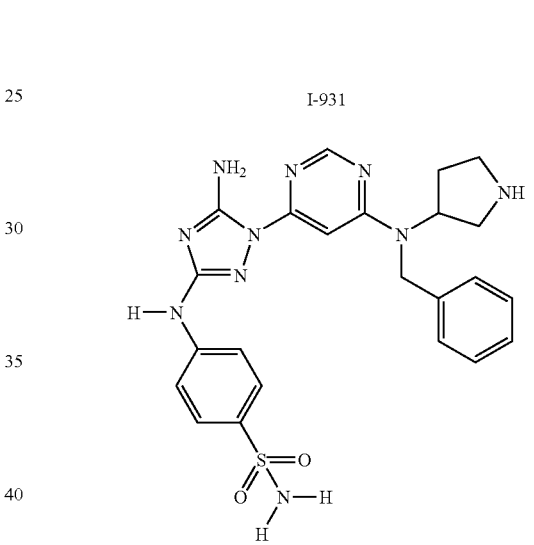
I-932
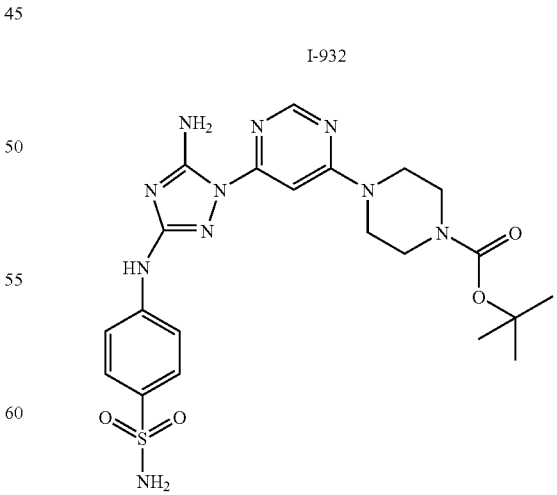
I-933

TABLE 1-continued
Examples of Compounds of Formula I:
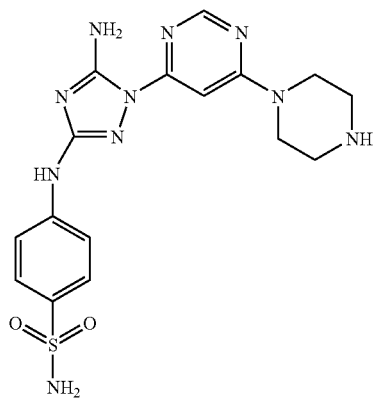
I-934
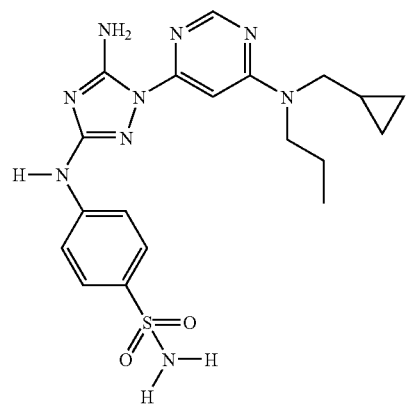
I-935
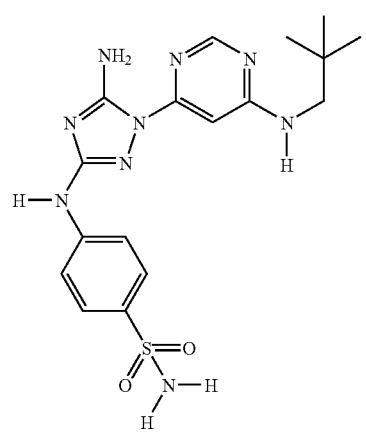
I-936
TABLE 1-continued
Examples of Compounds of Formula I:
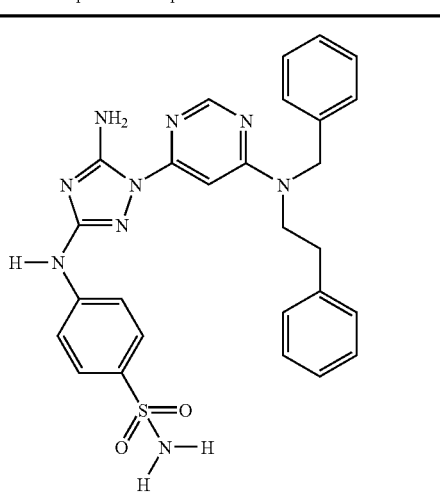
I-937
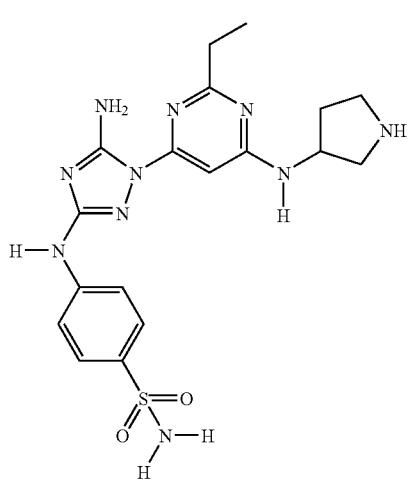
I-938
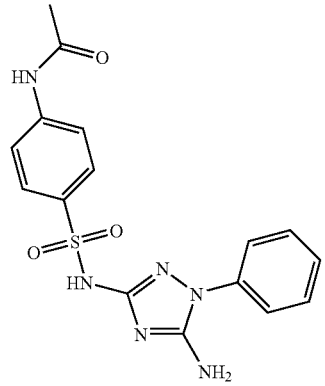
I-939

TABLE 1-continued
Examples of Compounds of Formula I:
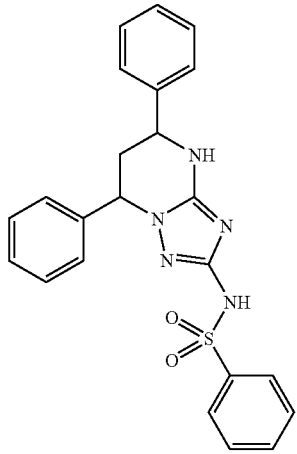
I-940
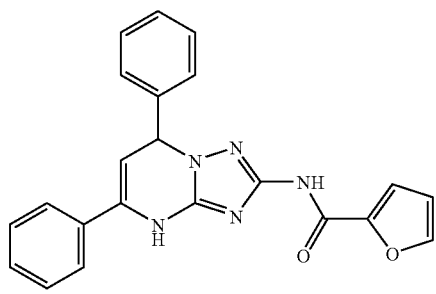
I-941
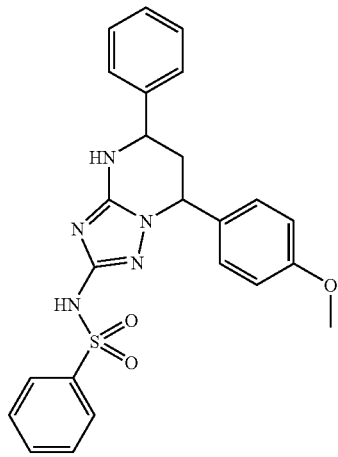
I-942
TABLE 1-continued
Examples of Compounds of Formula I:
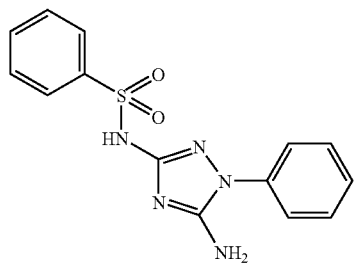
I-943
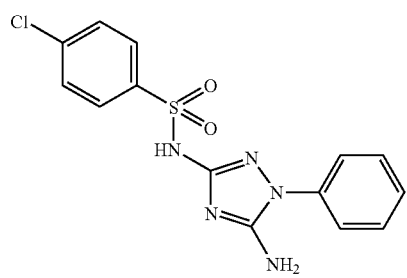
I-944
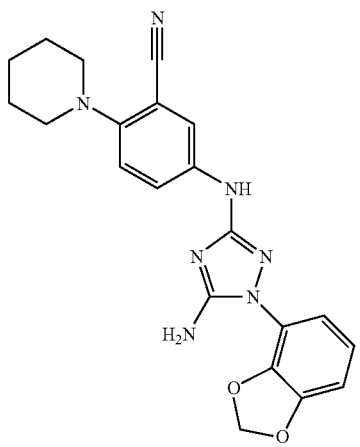
I-945
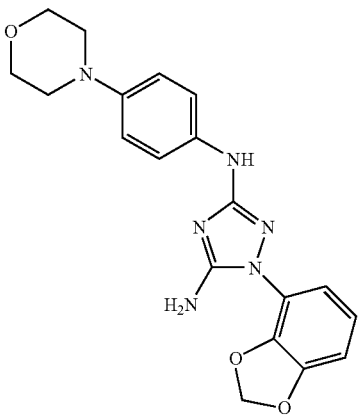
I-946

TABLE 1-continued
Examples of Compounds of Formula I:
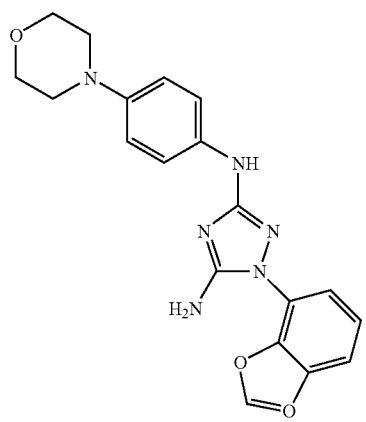
I-947
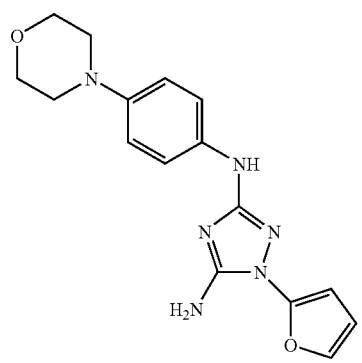
I-948
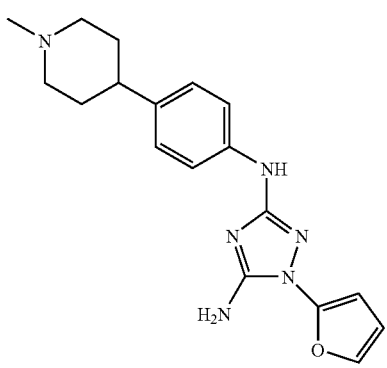
I-949
TABLE 1-continued
Examples of Compounds of Formula I:
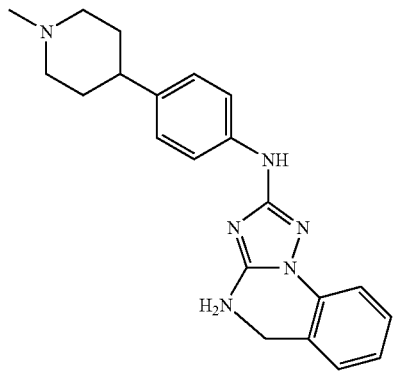
I-950
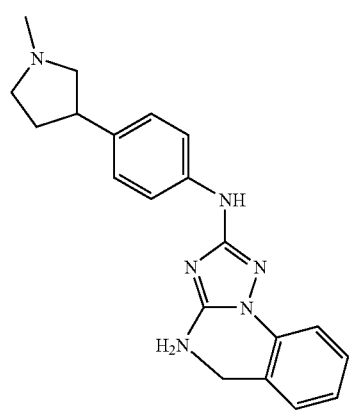
I-951
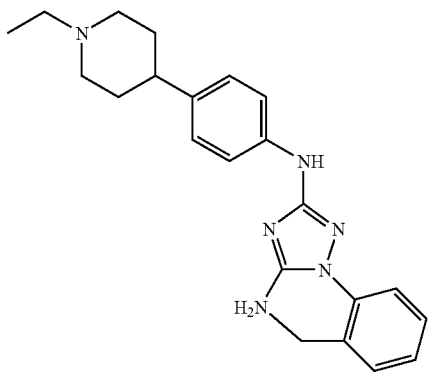
I-952

TABLE 1-continued
Examples of Compounds of Formula I:
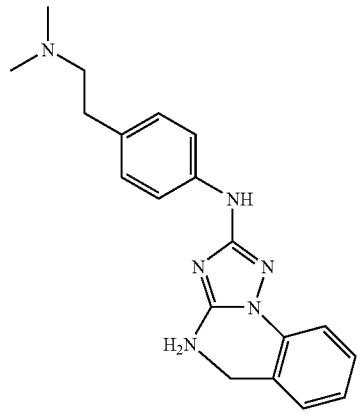
I-953
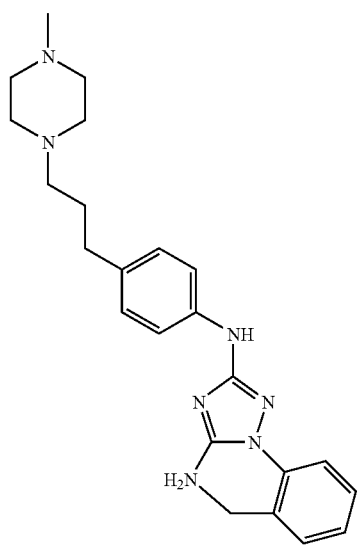
I-954
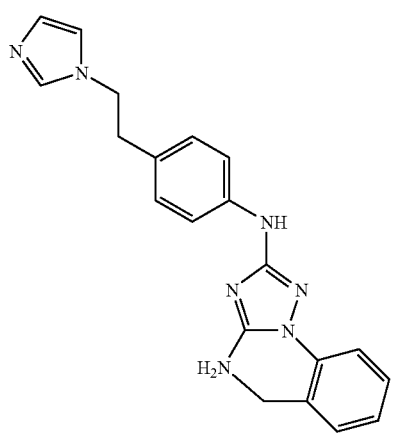
I-955
TABLE 1-continued
Examples of Compounds of Formula I:
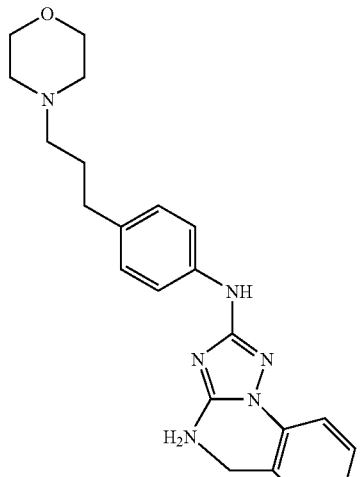
I-956
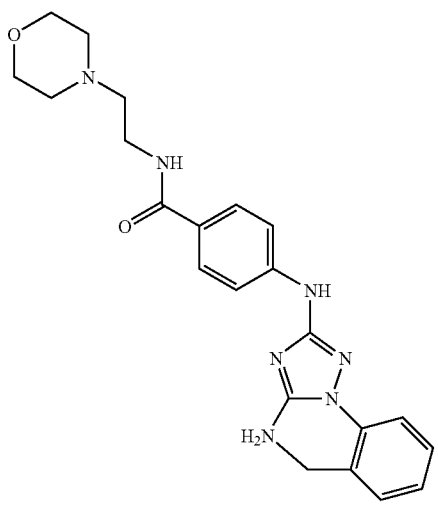
I-957
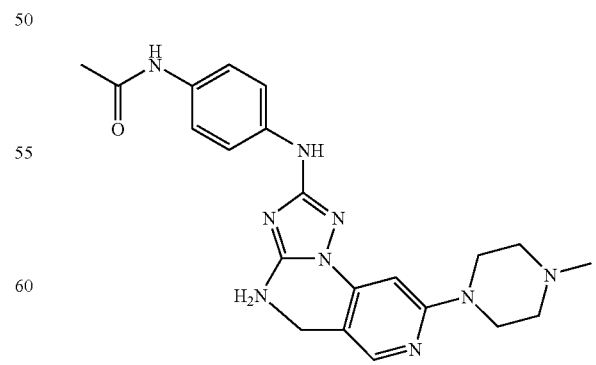
I-958

TABLE 1-continued
Examples of Compounds of Formula I:
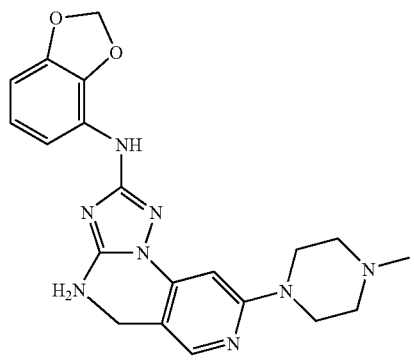
I-959
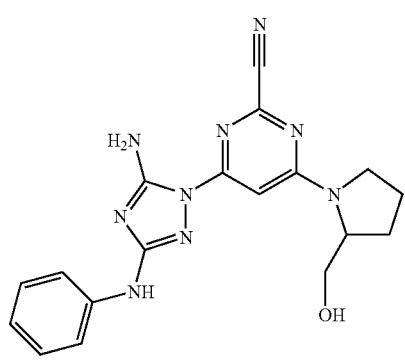
I-960
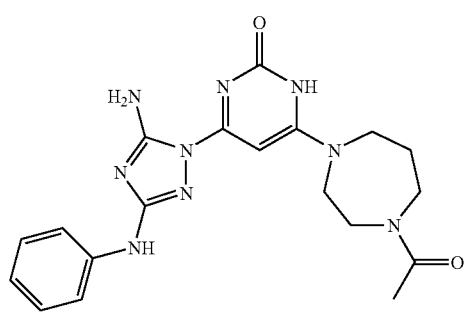
I-961
TABLE 1-continued
Examples of Compounds of Formula I:
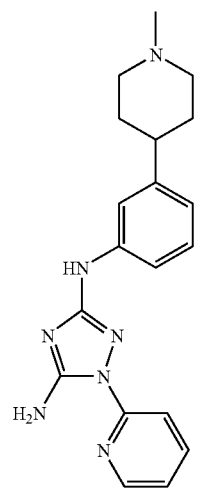
I-962
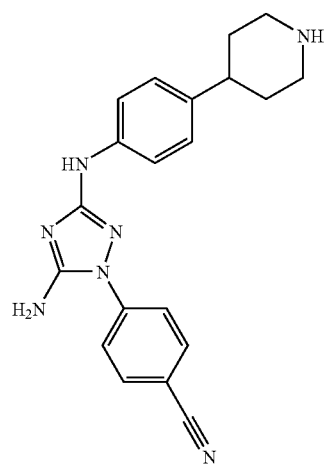
I-963
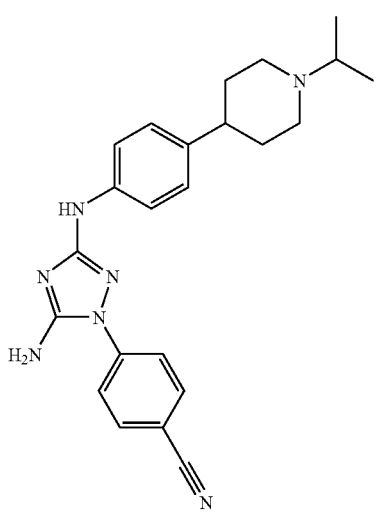
I-964

TABLE 1-continued
Examples of Compounds of Formula I:
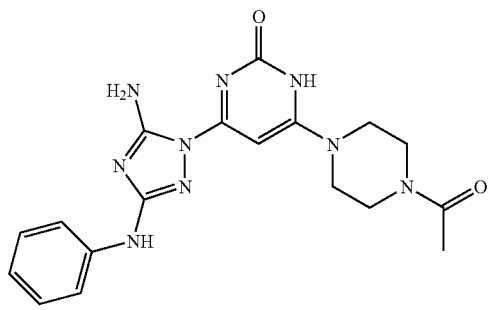
I-965
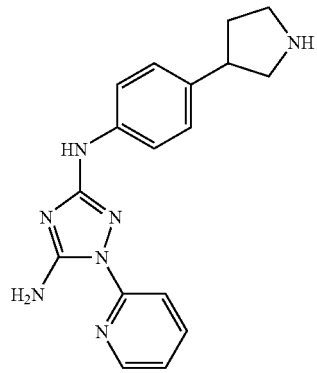
I-966
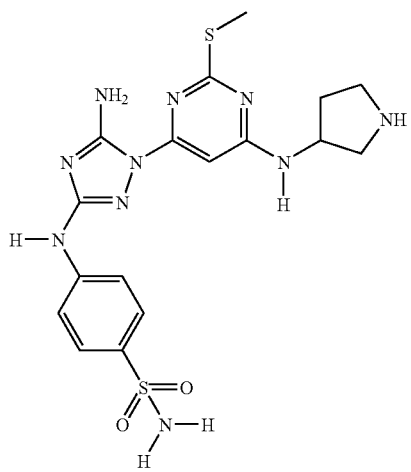
I-968
I-967
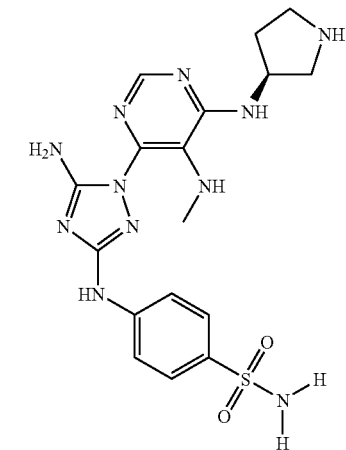
I-969
I-970

TABLE 1-continued
Examples of Compounds of Formula I:
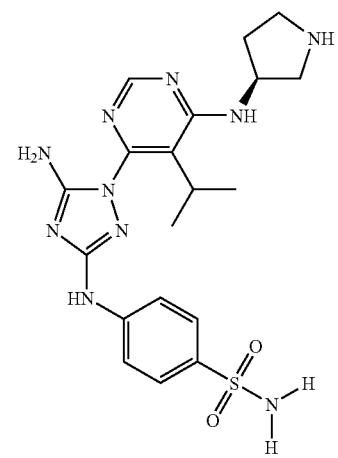
I-971
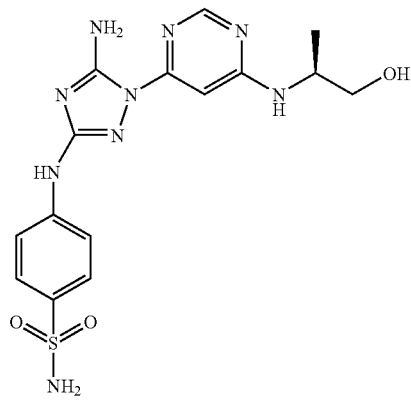
I-972
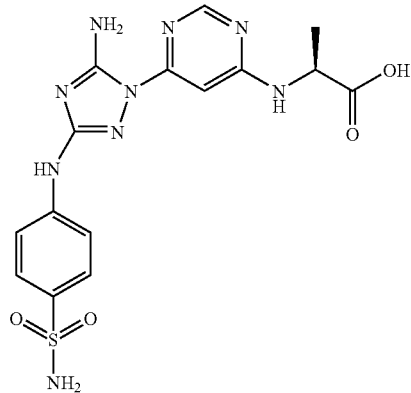
I-973
TABLE 1-continued
Examples of Compounds of Formula I:
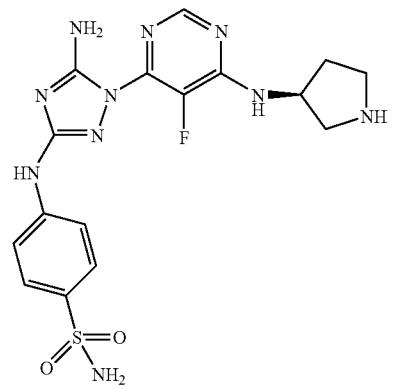
I-974
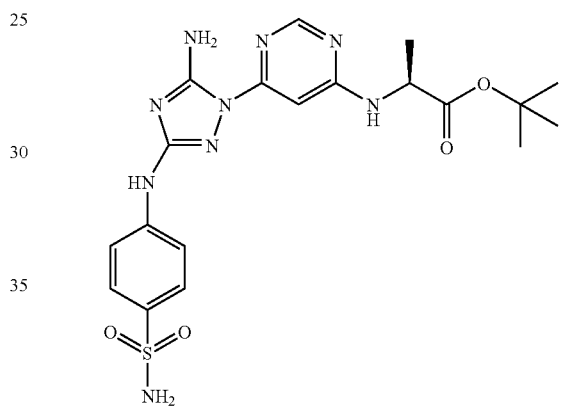
I-975
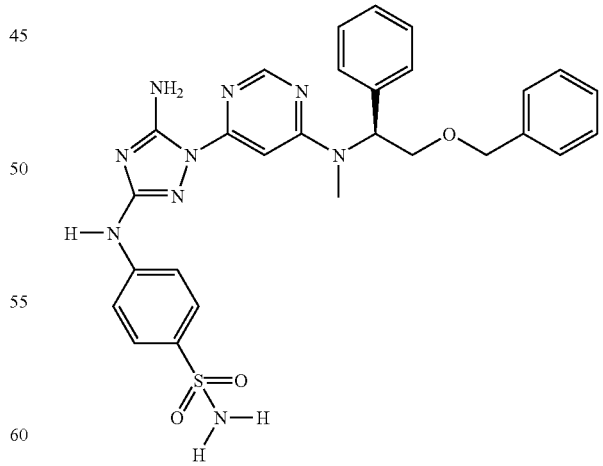
I-976

TABLE 1-continued

Examples of Compounds of Formula I:

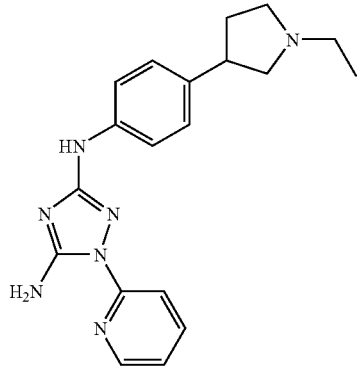

I-977

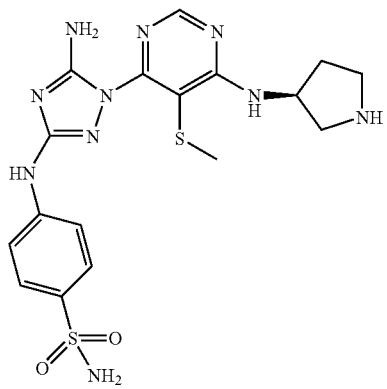

I-978

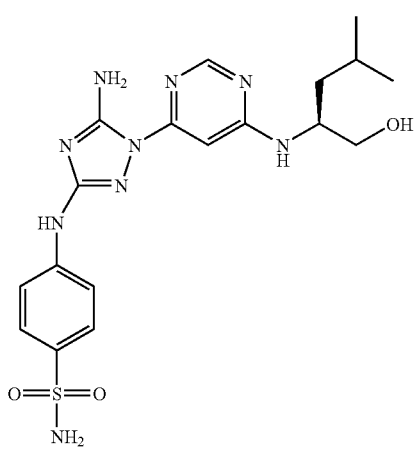

I-979

TABLE 1-continued

Examples of Compounds of Formula I:

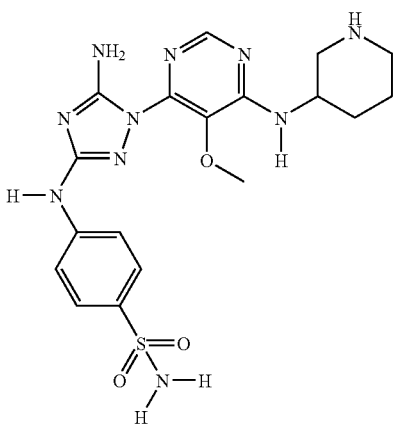

I-980

III. General Synthetic Methodology:

The compounds of this invention may be prepared in general by methods known to those skilled in the art for analogous compounds, as illustrated by the general scheme below, and the preparative examples that follow.

Scheme 1:

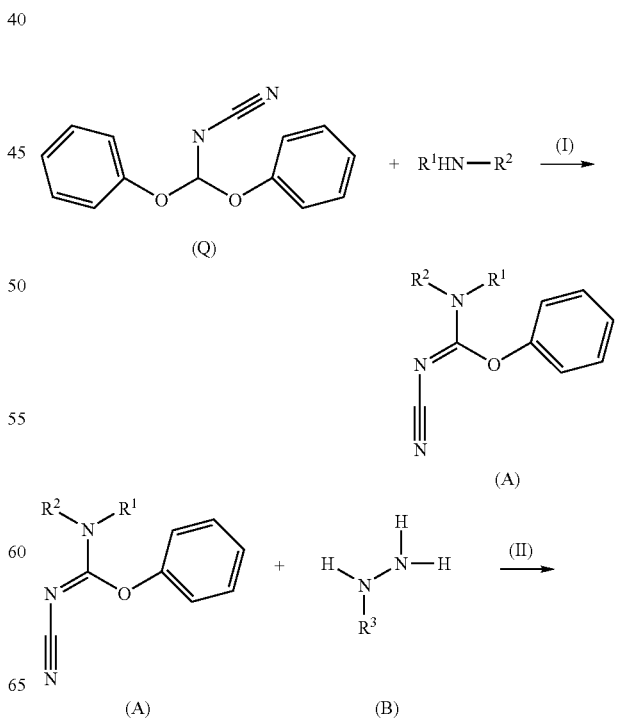

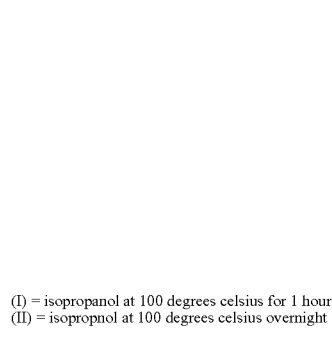

(I) = isopropanol at 100 degrees celsius for 1 hour
(II) = isopropnol at 100 degrees celsius overnight Scheme 1 above shows a general method for preparing compounds of formula I. For example, compounds of the invention can be prepared by reaction of starting material (Q) with an appropriate amine to generate intermediate (A). Subsequent reaction of (A) with an appropriate hydrazine yields desired compounds of general formula I.

Scheme 2 below depicts the synthesis of certain exemplary compounds where $R^3$ is $-(L)_m Ar^2$, which compounds are also prepared according to the general procedures described above.

Scheme 2:

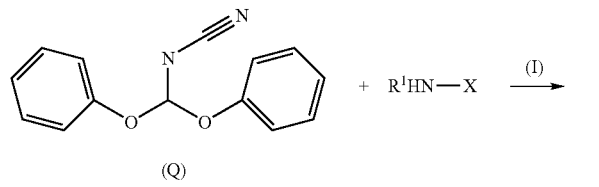

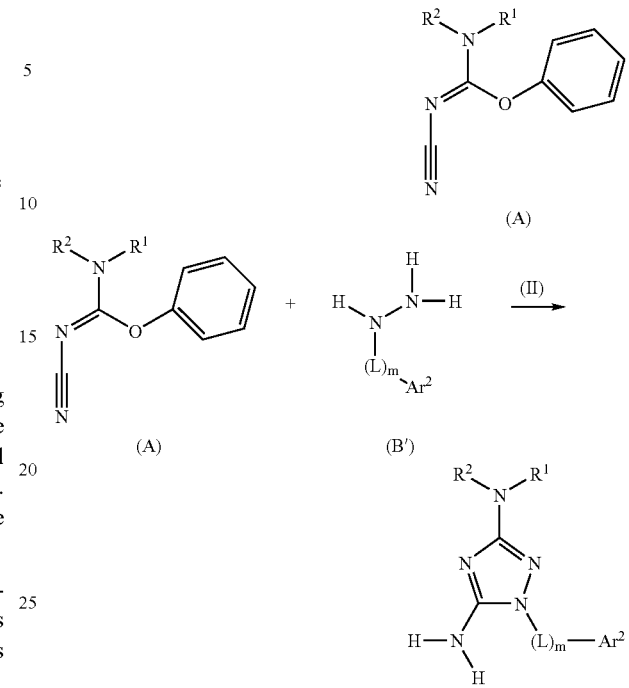

(I) = isopropanol at 100 degrees celsius for 1 hour
(II) = isopropnol at 100 degrees celsius overnight Scheme, 3, 4, and 5 below depicts the synthesis of certain exemplary compounds where $R^3$ and $R^5$, taken together form an optionally substituted ring as defined herein. Although the synthesis of certain compounds are depicted below, it will be appreciated that other bi- and tricyclic compounds as defined generally herein can also be prepared according to methods as described herein.

Scheme 3:

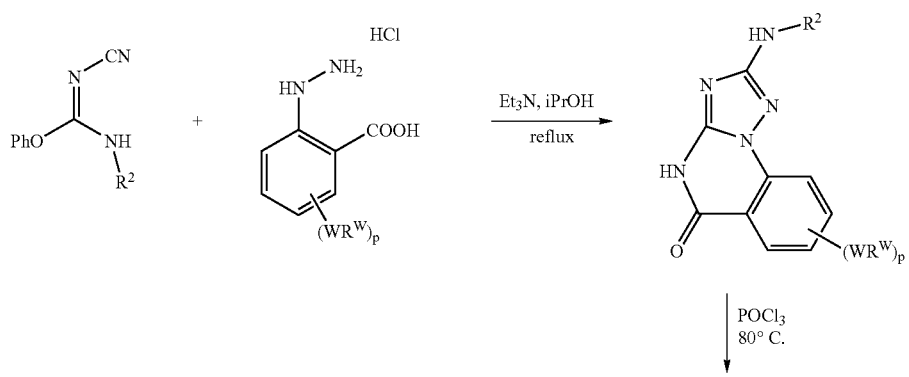

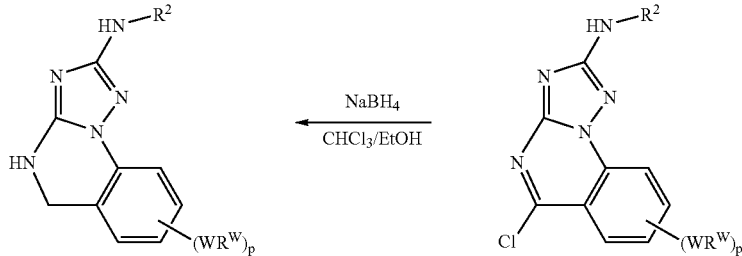

Schemes 4 and 5 depict general syntheses of compounds having the general formula:

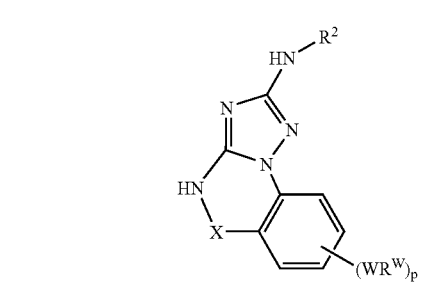

X = N, O

Scheme 4:

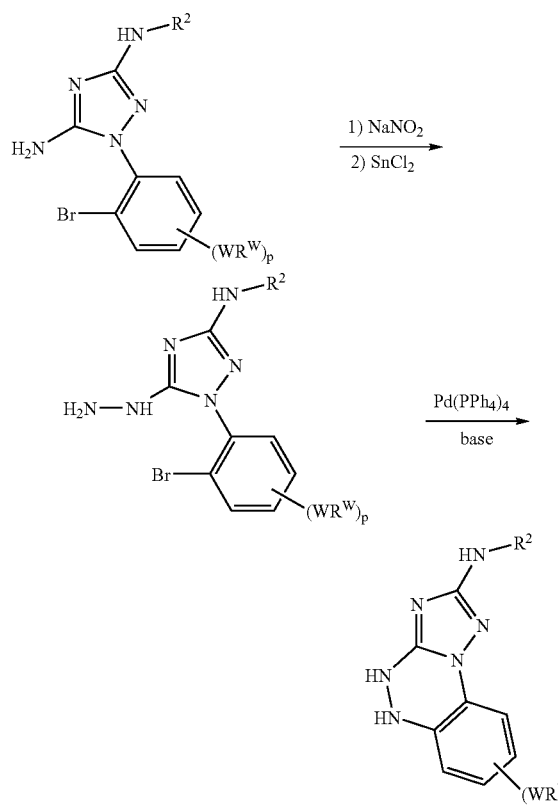

Scheme 5:

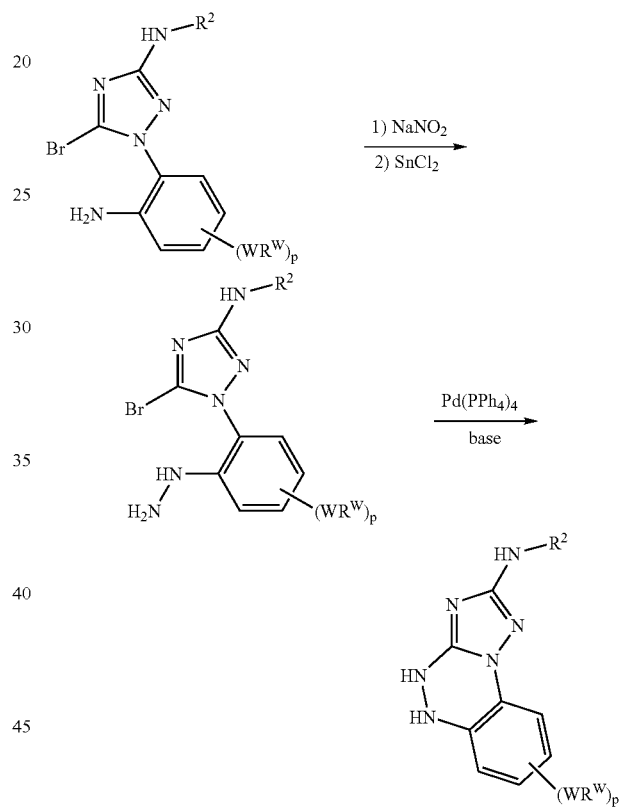

Although certain exemplary embodiments are depicted and described above and herein, it will be appreciated that a compounds of the invention can be prepared according to the methods described generally above using appropriate starting materials.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK, and thus, without wishing to be bound by any particular theory, the compounds and compositions are particularly useful for treating or lessening the severity of a disease, condition, or disorder where activation of one or more of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK is implicated in the disease, condition, or disorder. When activation of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK is implicated in a particular disease, condition, or disorder, the disease, condition, or disorder may also be referred to as "FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK-mediated disease" or disease symptom. Accordingly, in another aspect, the present invention provides a method for treating or lessening the severity of a disease, condition, or disorder where activation or one or more of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK is implicated in the disease state.

The activity of a compound utilized in this invention as an inhibitor of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK, may be assayed in vitro, in vivo or in a cell line. In vitro assays include assays that determine inhibition of either the phosphorylation activity or ATPase activity of activated FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK. Alternate in vitro assays quantitate the ability of the inhibitor to bind to FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK. Inhibitor binding may be measured by radiolabelling the inhibitor prior to binding, isolating the inhibitor/FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, or SYK complex and determining the amount of radiolabel bound. Alternatively, inhibitor binding may be determined by running a competition experiment where new inhibitors are incubated with FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK bound to known radioligands.

The term "measurably inhibit", as used herein means a measurable change in FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK activity between a sample comprising said composition and a FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK kinase and an equivalent sample comprising FLT-3, FMS, c-KIT, PDGFR, JAK, AGC sub-family of protein kinases (e.g., PKA, PDK, p70$^{S6K}$-1 and -2, and PKB), CDK, GSK, SRC, ROCK, and/or SYK kinase in the absence of said composition.

The term "FLT-3-mediated disease", as used herein means any disease or other deleterious condition in which a FLT-3 family kinase is known to play a role. Such conditions include, without limitation, hematopoietic disorders, in particular, acute-myelogenous leukemia (AML), acute-promyelocytic leukemia (APL), and acute lymphocytic leukemia (ALL).

According to another embodiment, the invention provides a method for treating or lessening the severity of a FMS-mediated disease or condition in a patient comprising the step of administering to said patient a composition according to the present invention.

The term "FMS-mediated disease", as used herein means any disease or other deleterious condition in which a FMS family kinase is known to play a role. Such conditions include, without limitation, cancer (including, but not limited to, ovarian, endometrial, and breast cancer), inflammatory disorders, and hypertension.

According to another embodiment, the invention provides a method for treating or lessening the severity of a c-KIT-mediated disease or condition in a patient comprising the step of administering to said patient a composition according to the present invention.

The term "c-KIT-mediated disease", as used herein means any disease or other deleterious condition in which a c-KIT family kinase is known to play a role. Such conditions include, without limitation, AML, chronic myelogenous leukemia (CML), mastocytosis, anaplastic large-cell lymphoma, ALL, gastrointestinal stromal tumor (GIST), T-cell lymphoma, adenoid cytsic carcinoma, angiosarcoma, endometrial carcinoma, small cell lung carcinoma, prostate cancer, ovarian cancer, breast carcinoma, thyroid carcinoma, malignant melanoma and colon carcinoma.

According to another embodiment, the invention provides a method for treating or lessening the severity of a CDK-2-mediated disease or condition in a patient comprising the step of administering to said patient a composition according to the present invention.

The term "CDK-2-mediated disease", as used herein means any disease or other deleterious condition in which CDK-2 is known to play a role. Accordingly, these compounds are useful for treating diseases or conditions that are known to be affected by the activity of CDK-2 kinase. Such diseases or conditions include cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, viral infections, neurodegenerative disorders, disorders associated with thymocyte apoptosis, or proliferative disorders resulting from the deregulation of the cell cycle, especially of the progression from $G_1$ to S phase.

According to another embodiment, the invention provides a method for treating or lessening the severity of a GSK-3-mediated disease or condition in a patient comprising the step of administering to said patient a composition according to the present invention.

According to another embodiment, the invention provides a method for treating or lessening the severity of a Src-mediated disease or condition in a patient comprising the step of administering to said patient a composition according to the present invention.

The term "Src-mediated disease" as used herein means any disease or other deleterious condition in which Src kinase plays a role. Such diseases or conditions include, without limitation, cancers such as colon, breast, hepatic and pancreatic cancer, autoimmune diseases such as transplant rejection, allergies, rheumatoid arthritis, leukemia, bone remodeling diseases such as osteoporosis and viral diseases such as hepatitus B infection.

According to another embodiment, the invention provides a method for treating or lessening the severity of a Syk-mediated disease or condition in a patient comprising the step of administering to said patient a composition according to the present invention.

The term "Syk-mediated disease" or "Syk-mediated condition", as used herein, means any disease or other deleterious condition in which Syk protein kinase is known to play a role. Such conditions include, without limitation, allergic disorders, especially asthma.

The term "JAK-mediated disease", as used herein means any disease or other deleterious condition in which a JAK family kinase is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer.

The term "p70$^{S6K}$-mediated condition" or "disease", as used herein, means any disease or other deleterious condition in which p70$^{S6K}$ is known to play a role. The term "p70$^{S6K}$-mediated condition" or "disease" also means those diseases or conditions that are alleviated by treatment with a p70$^{S6K}$ inhibitor. p70$^{S6K}$-mediated diseases or conditions include, but are not limited to, proliferative disorders, such as cancer and tuberous sclerosis.

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progessive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of FLT-3, FMS, c-KIT, PDGFR, JAK, AGC sub-family of protein kinases (e.g., PKA, PDK, $p70^{S6K}$-1 and -2, and PKB), CDK, GSK, SRC, ROCK, and/or SYK-kinase activity in a biological sample is useful for a variety of purposes that are known to one of skill in the art. Examples of such purposes include, but are not limited to, blood transfusion, organ-transplantation, biological specimen storage, and biological assays.

EXAMPLES

A) Synthesis of Exemplary Compounds of the Invention:

Compounds of general formula I were prepared according to the general procedure as follows (referring to Schemes 1 and 2):

The starting material (Q) was dissolved in 2-propanol to a 1M solution and heated to 100 degrees celsius. The amine was then added to the hot mixture and stirred for 1 hour in a sealed tube. The HPLC showed the reaction to be complete and was concentrated to dryness. The sample was then purified on the Combiflash normal phase system. Solvent system was Dichloromethane:Methanol. Starting at 0% Methanol and increasing over time to a maximum of 10% Methanol depending on the compound's properties.

The starting material (A) was dissolved in 2-propanol to a 1M solution. One equivalent of (B) was then added to this solution. The reaction was performed in a sealed tube at 100 degrees Celsius overnight. In the case where the hydrazine was a HCl salt, 1 equivalent of triethylamine was added.

The reactions were worked up as follows: The reaction was concentrated to dryness, LC/MS was performed to determine the reaction was complete. The product residue was dissolved in methanol and washed thru a pre-conditioned SCX column. The product was then eluted with methanol/ammonia solution. This was concentrated to dryness and further purified by Gilson reverse phase prep-chromatography.

The following examples exemplify the synthesis of various starting materials and compounds of the invention. Following each set of procedures is a list of certain exemplary compounds prepared by the inventive methods.

Example 1

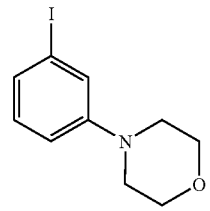

4-(3-Iodo-phenyl)-morpholine: To a solution of 1,3-diiodobenzene (5.05 g, 15.3 mmol) in isopropanol (16 mL) under nitrogen was added morpholine (1.33 g, 1.33 mL, 15.3 mmol), potassium phosphate (6.50 g, 30.6 mmol), ethylene glycol (1.90 g, 1.70 mL, 30.6 mmol) and copper (I) iodide (146 mg, 0.765 mmol). The mixture was heated at 80° C. for 15 h, and then cooled to room temperature. The solids were removed by filtration and the solution was concentrated. The residue was purified by silica gel column chromatograghy eluted with EtOAc:hexanes (5 to 25% EtOAc) to give 4-(3-iodo-phenyl)-morpholine (1.81 g, 41%) as a colorless oil. MS (ES+): m/z=290.0; $^1$H NMR (CDCl$_3$, 500 MHz): δ 3.15 (t, 4H), 3.85 (t, 4H), 6.87 (dd, 1H), 6.96-7.00 (m, 1H), 7.20 (d, 1H), 7.22-7.25 (m, 1H).

Example 2

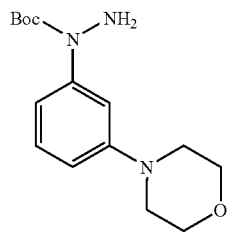

N-(3-Morpholin-4-yl-phenyl)-hydrazinecarboxylic acid tert-butyl ester: To a solution of 4-(3-iodo-phenyl)-morpholine (1.81 g, 6.26 mmol) in DMF (6.5 mL) under nitrogen was added tert-butylcarbazate (993 mg, 7.52 mmol), copper (I) iodide (59.5 mg, 0.313 mmol), 1,10-phenanthroline (113 mg, 0.626 mmol) and cesium carbonate (2.85 g, 8.77 mmol). The mixture was heated at 80° C. for 18 h and then cooled to room temperature. Water (100 mL) was added and the mixture was extracted with ethyl acetate. The organic layer was dried over MgSO$_4$, concentrated. The residue was purified by silica gel column chromatograghy eluted with EtOAc:hexanes (25 to 50% EtOAc) to give N-(3-morpholin-4-yl-phenyl)-hydrazinecarboxylic acid tert-butyl ester (1.14 g, 62%) as a yellowi oil. MS (ES+): m/z=294.2. $^1$H NMR (DMSO-d6, 500 MHz): δ 1.44 (s, 9H), 3.06 (t, 4H), 3.73 (t, 4H), 4.97 (s, 2H), 6.66 (dd, 1H), 6.91 (d, 1H), 7.01-7.05 (m, 1H), 7.09-7.14 (m, 1H).

Example 3

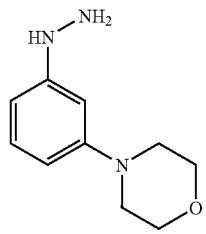

(3-morpholin-4-yl-phenyl)-hydrazine HCl salt: To a solution of N-(3-morpholin-4-yl-phenyl)-hydrazinecarboxylic acid tert-butyl ester (468 mg, 1.60 mmol) in methanol (20 mL) was added a solution of 4 N HCl in dioxane (10 mL). The mixture was stirred at room temperature overnight, then concentrated to give (3-morpholin-4-yl-phenyl)-hydrazine 3 HCl salt (484 mg, 100%) as a yellow solid. MS (ES+): m/z=194.1; $^1$H NMR (CD$_3$OD, 500 MHz): δ 3.60-3.71 (m, 4H), 4.06-4.15 (m, 4H), 7.06 (d, 1H), 7.26-7.35 (m, 2H), 7.50-7.58 (m, 1H).

Example 4

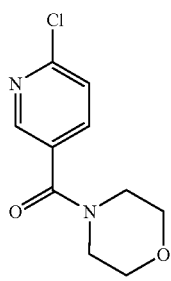

(6-Chloro-pyridin-3-yl)-morpholin-4-yl-methanone: To 6-chloro-nicotinoyl chloride (0.540 g, 3.07 mmoles) in dichloromethane (10 mL) was added of morpholine, (0.294 g, 1.1 equivalents) followed by triethylamine (940 uL, 2.2 equivalents). The reaction was stirred overnight at room temperature to give (6-chloro-pyridin-3-yl)-morpholin-4-yl-methanone. No starting material, 6-Chloro-nicotinoyl chloride, remained and mass spectrometry showed correct M+ion. An aqueous work-up was performed and the crude material was taken to the next step. The crude residue, (6-chloro-pyridin-3-yl)-morpholin-4-yl-methanone, weighed 0.610 g (88% yield) after aqueous work-up.

The following compounds were similarly prepared:

| Name | MS (M + H) | Retention time (HPLC method) | $^1$H-NMR 500 MHz (solvent) |
| --- | --- | --- | --- |
| (6-Chloro-pyridin-3-yl)-morpholin-4-yl-methanone | 226.99 | 3.15 | |
| (6-Chloro-pyridin-3-yl)-(4-methyl-piperazin-1-yl)-methanone | 239.95 | 1.0 | |
| 6-Chloro-N-(2-dimethylamino-ethyl)-nicotinamide | 227.97 | 1.26 | |

Example 5

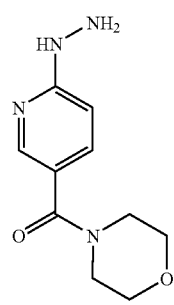

(6-Hydrazino-pyridin-3-yl)-morpholin-4-yl-methanone: To (6-chloro-pyridin-3-yl)-morpholin-4-yl-methanone (0.649 g, 2.86 mmoles) in ethanol (6 mL) was added 0.270 uL (3.0 equivalents) of hydrazine, followed by triethylamine 438.9 uL (1.1 equivalents). The reaction was stirred overnight at 100° C. to give (6-hydrazino-pyridin-3-yl)-morpholin-4-yl-methanone. The reaction was filtered and then concentrated to dryness. The crude residue, (6-hydrazino-pyridin-3-yl)-morpholin-4-yl-methanone, weighed 0.372 g (76% yield).

The following compounds were similarly prepared:

| Name | MS (M + H) |
| --- | --- |
| (6-Hydrazino-pyridin-3-yl)-morpholin-4-yl-methanone | 222.92 |
| (6-Hydrazino-pyridin-3-yl)-(4-methyl-piperazin-1-yl)-methanone | 236.00 |
| N-(2-Dimethylamino-ethyl)-6-hydrazino-nicotinamide | 224.01 |

Example 6

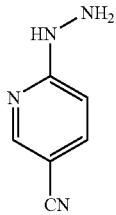

6-Hydrazino-nicotinonitrile (CF#H-1): A mixture of 6-chloro-nicotinonitrile (2.77 g, 20 mmol) and hydrazine hydrate (15 mL) was stirred at 100° C. for 3 h and evaporated. The residue was suspended in ether and filtered, then suspended in sodium bicarbonate solution and filtered, washing with water, and dried to provide 6-hydrazino-nicotinonitrile (1.25 g, 46% yield) as a tan solid. $^1$H-NMR (DMSO-d6, 500 MHz) 8.59 (s, 1H), 8.35 (s, 1H), 7.74 (d, 1H), 6.75(s, 1H), 4.44 (s, 2H) ppm; MS (FIA) 135.1 (M+H).

The following compounds were similarly prepared:

| Name | $^1$H-NMR |
| --- | --- |
| Benzothiazol-2-yl-hydrazine | (DMSO-d6, 500MHz)8.58(s, 1H), 7.79 (d, 2H), 7.36(t, 2H0, 7.25(t, 1H), 7.10(s, 1H), 4.86(s, 2H)ppm |
| (6-Trifluoromethyl-pyridin-2-yl)-hydrazine | (DMSO-d6, 500MHz): 8.04(s, 1H), 7.65 (t, 1H), 6.97(d, 1H), 6.92(d, 1H), 4.25(s, 2H) |

Example 7

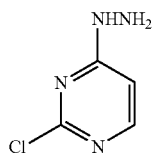

(2-Chloro-pyrimidin-4-yl)-hydrazine: To a solution of 2,4-dichloropyrimidine (1.49 g, 10.0 mmol) in ethanol (25 mL) was added triethylamine (2.02 g, 2.78 mL, 20.0 mmol) and hydrazine (321 mg, 0.321 mL, 10.0 mmol). The mixture was stirred at room temperature for 2 h. Water was added and the mixture was extracted with dichloromethane. The organic layer was dried over MgSO$_4$, concentrated. The residue was purified by silica gel column chromatograghy eluted with methanol:dichloromethane (2 to 5% methanol) to give (2-chloro-pyrimidin-4-yl)-hydrazine (330 mg, 23%) as a white solid. MS (ES+): m/z=144.9.

Example 8

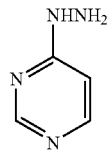

Pyrimidin-4-yl-hydrazine: To a solution of (2-chloro-pyrimidin-4-yl)-hydrazine in methanol was added ammonium formate and Pd/C (10%). The mixture was heated at 55° C. for 15 h. The mixture was cooled to room temperature and filtered, and the filtrate was concentrated. Water was added and the mixture was extracted with dichloromethane. The organic layer was dried over MgSO$_4$ and concentrated to give pyrimidin-4-yl-hydrazine (62.0 mg, 25%) as a yellow solid. MS (ES+): m/z=111.3; $^1$H NMR (CD$_3$OD, 500 MHz): δ 6.79 (s, br., 1H), 8.06 (d, 1H), 8.39 (s, 1H).

Scheme 6

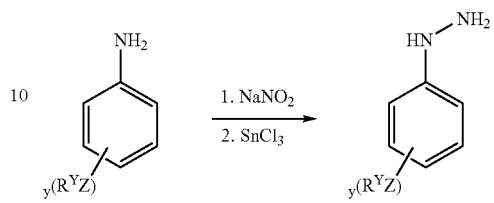

Example 9

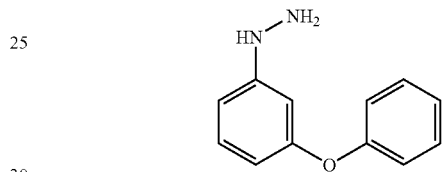

(3-Phenoxy-phenyl)-hydrazine: To a solution of 3-phenoxy-phenylaniline (2.32 g, 12.5 mmol) in methanol (5 mL), water (10 mL) and concentrated HCl (3 mL) at 0° C. was added in rapid drops a solution of sodium nitrite (0.87 g, 12.7 mmol) in water (2 mL). The reaction was stirred 10 min then treated in rapid drops with a 0° C. solution of tin chloride dihydrate (6.77 g, 30 mmol) in concentrated HCl (25 mL). The reaction was stirred for 1 h, then adjusted to ~pH 7 with 6N NaOH and sodium bicarbonate, then filtered through Celite, washing with 1:3 methanol: dichloromethane. The filtrate was separated, the aqueous phase was extracted with 1:3 methanol:dichloromethane (2×). The combined organic layer was dried over sodium sulfate, evaporated, then purified by flash chromatography (SiO$_2$) eluted with 35:65 ethyl acetate:hexanes to provide (3-phenoxy-phenyl)-hydrazine (1.78 g, 71% yield) as an orange oil. $^1$H-NMR (CDCl$_3$, 500 MHz) 7.30 (m, 2H), 7.14 (t, 1H), 7.08 (t, 1H), 7.00 (m, 2H), 6.52 (m, 1H), 6.47 (m, 1H), 6.45 (m, 1H) 5.2 (br 1H), 3.5 (br 2H) ppm; MS (FIA) 201.1 (M+H); HPLC (method A) 2.887 min.

The following compound was similarly prepared:

| Name | MS (M + H) | HPLC Method A | $^1$H-NMR |
| --- | --- | --- | --- |
| (2-Fluoro-4-iodo-phenyl)-hydrazine | 253.0 | 2.373 | (CDCl$_3$, 500MHz)7.28(d, 1H), 7.18(dd, 1H), 6.82(t, 1H), 5.38(s, 2H), 3.49(s, 2H)ppm |

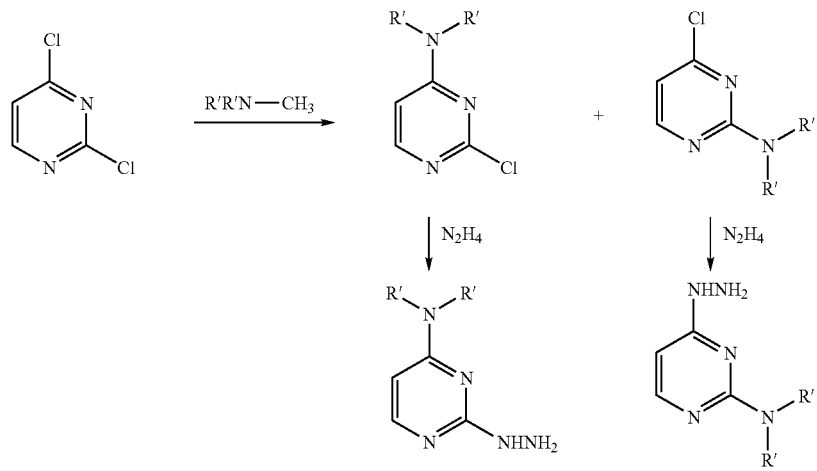

Example 10

4-Chloro-2-piperidin-1-yl-pyrimidine and 2-chloro-4-piperidin-1-yl-pyrimidine These intermediates were prepared following a procedure by K. Yoshida et al, J. Chem. Soc. Perkins Transactions I., (1992), 919-922. A solution of 2,4-dichloropyrimidine (4.00 g, 26.8 mmol) and 1-methylpiperidine (3.25 mL, 29.5 mmol) in 1,4-dioxane (60 mL) was stirred at 100° C. for 3d, then cooled and evaporated. Purification by flash chromatography ($SiO_2$) eluted with 15:85 ethyl acetate:hexanes provided 4-chloro-2-piperidin-1-yl-pyrimidine (0.58 g, 12% yield) as a pale yellow solid: $^1$H-NMR ($CDCl_3$, 500 MHz) 8.06 (d, 1H), 6.37 (d, 1H), 3.70 (m, 4H), 1.61 (m, 2H), 1.53 (m, 4H) ppm; MS (FIA) 198.1 (M+H); HPLC (method A) 3.550 min and 2-chloro-4-piperidin-1-yl-pyrimidine (1.87 g, 38% yield) as a white solid: $^1$H-NMR ($CDCl_3$, 500 MHz) 8.01 (d, 1H), 6.41 (d, 1H), 3.65 (m, 4H), 1.73 (m, 2H), 1.65 (m, 4H) ppm; MS (FIA) 198 (M+H); HPLC (method A) 2.583 min.

The following compounds were similarly prepared:

| Name | MS (M + H) | HPLC Method A | $^1$H-NMR |
|---|---|---|---|
| 4-Chloro-2-(4-methyl-piperazin-1-yl)-pyrimidine | 213.2 | 2.326 | (DMSO-d6, 500MHz)8.30(d, 1H), 6.71(d, 1H), 3.70(m, 4H), 2.35(m, 4H), 2.21(s, 3H)ppm |

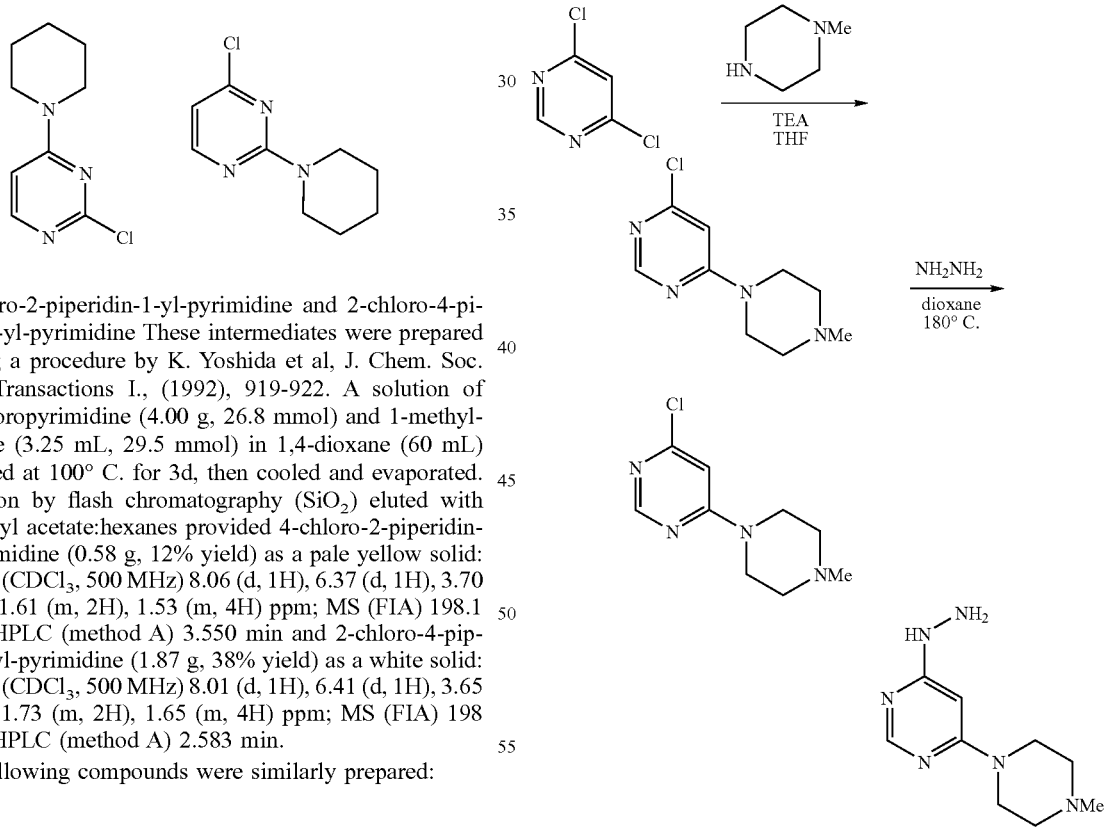

4-Chloro-6-(4-methyl-piperazin-1-yl)-pyrimidine 4,6-dichloropyrimidine, (2 g, 13.4 mmol), and N-methylpiperazine, (1.5 mL, 13.4 mmol), were dissolved in 20 mL THF along with TEA (1.9 mL, 13.4 mmol) and stirred for 18 h. The THF was evaporated and 10 mL water was added and then extracted with DCM. The DCM was dried with sodium sulfate, filtered and evaporated affording 2.4 g of 4-Chloro- 6-(4-methyl-piperazin-1-yl)-pyrimidine as a yellow waxy solid which was used without further purification.

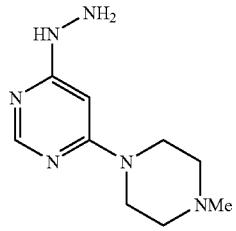

[6-(4-Methyl-piperazin-1-yl)-pyrimidin-4-yl]-hydrazine, 4-Chloro-6-(4-methyl-piperazin-1-yl)-pyrimidine, (200 mg, 0.94 mmol), and hydrazine hydrate, (200 µl, 4 mmol), were heated to 180° for 6 min in a Personal Chemistry Microwave. The solvent was evaporated affording [6-(4-Methyl-piperazin-1-yl)-pyrimidin-4-yl]-hydrazine as yellow brown crystals which were used without further purification.

The following compounds were made in a similar fashion:

| | |
|---|---|
| (6-Morpholin-4-yl-pyrimidin-4-yl)-hydrazine | MS ES+ 196.2 |
| N'-(6-Hydrazino-pyrimidin-4-yl)-N,N-dimethyl-ethane-1,2-diamine | MS ES+ 197.1 |
| [1-(6-Hydrazino-pyrimidin-4-yl)-pyrrolidin-3-yl]-dimethyl-amine | MS ES+ 223.2 |

Example 11

[6-(4-Ethyl-piperazin-1-yl)-pyrimidin-4-yl]-hydrazine.

Dissolve 4,6-dichloropyrimidine, (1.1 g, 7.4 mmol), in 20 mL isopropanol, add potassium carbonate, (2 g, 15 mmol), and N-ethylpiperazine, (843 mg, 7.4 mmol). Stir at rt for 18 h, then add hydrazine, (1.6 g, 50 mmol) and heat to reflux for 22 h. Cool and filter, then evaporate the solvent from the filtrate. Take up the residue in 20 mL boiling acetonitrile and filter. Upon cooling, a white precipitate forms. Filter to obtain approx 1 g [6-(4-Ethyl-piperazin-1-yl)-pyrimidin-4-yl]-hydrazine as a white solid. (60%). MS ES+ 223.2

Scheme 9

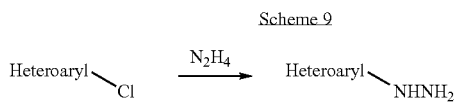

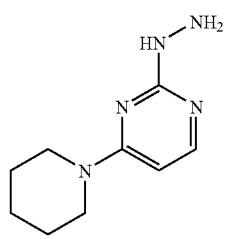

(4-Piperidin-1-yl-pyrimidin-2-yl)-hydrazine The title compound was prepared as described in Example 10: $^1$H-NMR (DMSO-d6, 500 MHz) 7.82 (br, 1H), 7.74 (br, 1H), 5.88 (s, 1H), 4.17 (s, 2H), 3.65 (m, 4H), 1.58 (m, 2H), 1.45 (m, 4H) ppm; MS (FIA) 194.2 (M+H); HPLC (method A) 0.648 min.

The following compounds were similarly prepared:

| Name | MS (M + H) | HPLC Method A | $^1$H-NMR |
|---|---|---|---|
| (2-Piperidin-1-yl-pyrimidin-4-yl)-hydrazine | 194.2 | 2.213 | (DMSO-d6, 500MHz)7.79(d, 1H), 7.42(s, 1H), 6.04(d, 1H), 3.98(s, 2H), 3.54(m, 4H), 1.61(m, 2H), 1.48(m, 4H)ppm |
| 4-Methyl-piperazin-1-yl)-pyrimidin-4-yl]-hydrazine | 209.2 | 2.335 | (DMSO-d6, 500MHz)7.8(m, 2H), 4.8(br, 2H), 4.2(br, 1H), 3.63(m, 4H), 2.29(m, 4H), 2.18(s, 3H)ppm |

Scheme 10

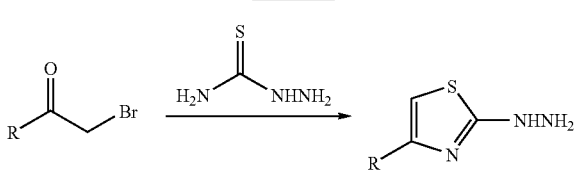

Example 12

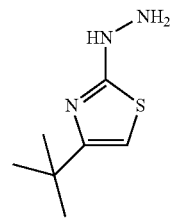

(4-tert-Butyl-thiazol-2-yl)-hydrazine: A mixture of 1-bromo-3,3-dimethyl-butan-2-one (1.35 mL, 10 mmol) and thio-semicarbazide (0.91 g, 10 mmol) in ethanol (35 mL) was refluxed for 1.5 h and evaporated. Purification by flash chromatography (SiO$_2$) provided (4-tert-butyl-thiazol-2-yl)-hydrazine (1.01 g, 59% yield) as an orange solid. $^1$H-NMR (DMSO-d6, 500 MHz) 9.0 (br, 1H), 7.3 (br, 2H), 6.37 (s, 1H), 1.22 (s, 9H) ppm; MS (LC-MS) 172.1 (M+H); HPLC (method A) 2.520 min.

The following compounds were similarly prepared:

| Name | MS ((M + H) | HPLC Method A | $^1$H-NMR |
|---|---|---|---|
| (4-Ethyl-thiazol-2-yl)-hydrazine | 144.0 | | (DMSO-d6, 500MHz)8.21(s, 1H), 6.18(s, 1H), 4.68(s, 2H), 2.44(q, 2H), 1.11(t, 3H)ppm |
| (4-Trifluoromethyl-thiazol-2-yl)-hydrazine | 184.1 | 2.194 | (DMSO-d6, 500MHz)8.92(s, 1H), 7.32(s, 1H), 5.04(s, 2H)ppm |
| (4-Phenyl-thiazol-2-yl)-hydrazine | 166.1 | 2.008 | (DMSO-d6, 500MHz)9.0(br, 1H), 7.67(d, 1H), 7.31(d, 1H), 7.20(t, 1H), 6.98(t, 1H), 5.03(s, 2H)ppm |

Example 13

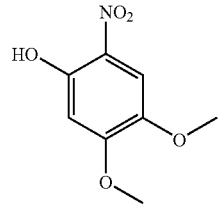

4,5-Dimethoxy-2-nitro-phenol: To a solution of 4,5-dimethoxy-2-nitro-benzaldehyde (3.75 g, 14.2 mmol) in dichloromethane (75 mL) at 0° C. under a nitrogen atmosphere was added meta-chloroperoxybenzoic acid (75% purity, 4.90 g, 28.4 mmol), then, trifluoroacetic acid (1.05 mL, 14.2 mmol). The reaction was stirred at room temperature for 18 h, then recooled to 0° C. Excess reagent was quenched with 5% sodium bisulfite solution and the precipitate was removed by filtration, washing with dichloromethane. The organic phase of the filtrate was washed with sodium bicarbonate and brine, was dried (sodium sulfate), and was evaporated to provide a yellow solid. This intermediate was suspended in methanol (50 mL), treated with 2N NaOH (16 mL, 32 mmol), and was stirred at room temperature for 1 h. The reaction was acidified with 1N HCl and was filtered, washing with methanol to provide 4,5-dimethoxy-2-nitro-phenol (2.00 g, 71% yield) as a bright yellow solid. $^1$H-NMR (CDCl$_3$, 500 MHz) 11.0 (s, 1H), 7.39 (s, 1H), 6.48 (s, 1H), 3.90 (s, 3H), 3.83 (s, 3H) ppm; MS (FIA) 197.9 (M–H); HPLC (Method A) 3.357 min.

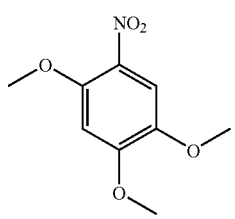

1,2,4-Trimethoxy-5-nitro-benzene: A mixture of 4,5-dimethoxy-2-nitro-phenol (2.00 g, 10 mmol), potassium carbonate (2.76 g, 20 mmol) and iodomethane (0.75 mL, 12 mmol) in DMF was placed in a sealed tube and heated at 75-80° C. for 20 h. The reaction was cooled and was filtered through Celite, washing with ethyl acetate. The filtrate was washed with water (the first wash was back-extracted with ethyl acetate), sodium bicarbonate and brine, was dried (sodium sulfate) and was evaporated. Purification by flash chromatography (SiO$_2$) eluted with 1:1 ethyl acetate:hexanes provided 1,2,4-trimethoxy-5-nitro-benzene (1.20 g, 57% yield) as a yellow solid. $^1$H-NMR (CDCl$_3$, 500 MHz) 7.53 (s, 1H), 6.50 (s, 1H), 3.92 (s, 3H), 3.91 (s, 3H), 3.84 (s, 3H) ppm; MS (FIA) 214.1 (M+H); HPLC (Method A) 3.253 min.

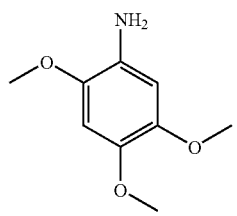

2,4,5-Trimethoxy-phenylamine: 1,2,4-Trimethoxy-5-nitro-benzene (1.20 g, 5.63 mmol) and tin chloride dihydrate (3.81 g, 16.9 mmol) in ethyl acetate (50 mL) was stirred at 65-70° C. for 20 h. The reaction was cooled, carefully neutralized with sodium bicarbonate and was filtered through Celite. The organic phase was washed with brine, dried (sodium sulfate) and was evaporated. Purification by flash chromatography (SiO$_2$) eluted with 3:7 ethyl acetate:hexanes provided 2,4,5-trimethoxy-phenylamine (0.56 g, 54% yield) as a tan solid. $^1$H-NMR (DMSO-d6, 500 MHz) 6.57 (s, 1H), 6.37 (s, 1H), 3.70 (s, 3H), 3.65 (s, 3H), 3.63 (s, 3H) ppm; HPLC (Method A) 2.163 min.

Scheme 11

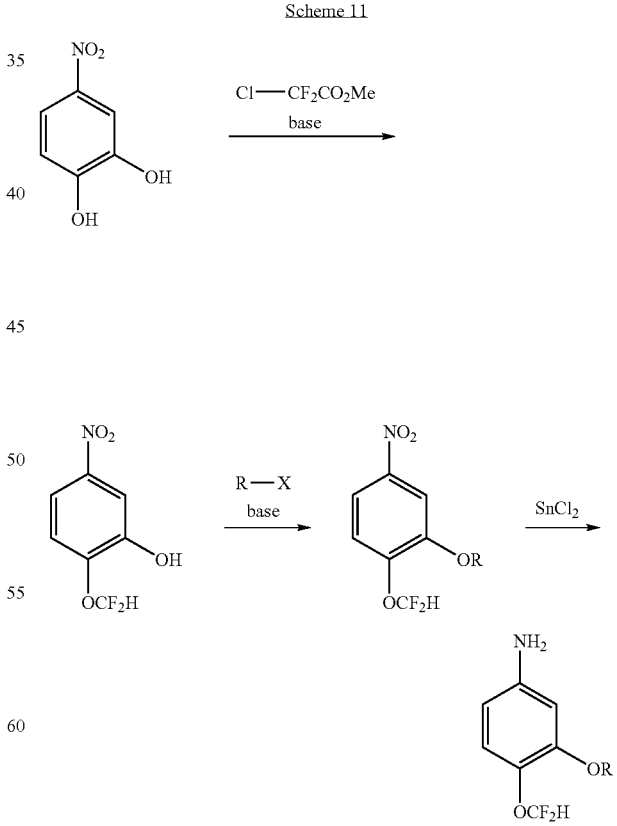

Example 14

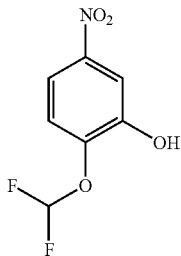

2-Difluoromethoxy-5-nitro-phenol: A solution of 4-nitrobenzene-1,2-diol (4.18 g, 27.1 mmol), methyl chlorodifluoroacetate (3.0 mL, 28.5 mmol) and cesium carbonate (11.05 g, 33.9 mmol) in DMF (75 mL) was heated at 90° C. for 24 h. The reaction was cooled, evaporated and diluted with ethyl acetate. Product was extracted twice into 1N NaOH, the combined aqueous phase was acidified, extracted with ethyl acetate (twice) and the organic layers were washed with water (twice) and brine, dried (sodium sulfate) and evaporated. Purification by flash chromatography ($SiO_2$) eluted with 2:8 ethyl acetate:hexanes provided 2-difluoromethoxy-5-nitro-phenol (1.50 g, 27% yield) as a bright yellow solid. $^1$H-NMR (DMSO-d6, 500 MHz) 10.9 (s, 1H), 7.76 (d, 1H), 7.73 (dd, 1H), 7.36 (d, 1H), 7.28 (t, 1H) ppm; MS (FIA) 204.1 (M–H); HPLC (Method A) 3.307 min.

The following compounds were similarly prepared:

| Name | Number | MS (M + H) | HPLC Method A | $^1$H-NMR |
|---|---|---|---|---|
| 2-Isopropoxy-5-nitro-phenol | CF#N-3 | 198.1 | 3.474 | (DMSO-d6, 500 MHz) 9.87 (s, 1H), 7.70 (dd, 1H), 7.62 (d, 1H), 7.12 (d, 1H), 4.76 (m, 1H), 1.31 (d, 6H) ppm |

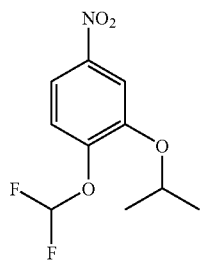

1-Difluoromethoxy-2-isopropoxy-4-nitro-benzene: 2-Difluoromethoxy-5-nitro-phenol (1.49 g, 7.26 mmol), iodo-iso-propane (0.87 mL, 8.72 mmol) and cesium carbonate (3.55 g, 10.9 mmol) in DMF (20 mL) in a sealed tube was heated at 90° C. for 20 h. The reaction was cooled and evaporated, was diluted with water and extracted (twice) with ethyl acetate. The combined organic phase was washed with water (three times) and brine, was dried (sodium sulfate) and was evaporated to provide 1-difluoromethoxy-2-isopropoxy-4-nitro-benzene (1.712 g, 95% yield) as an orange oil. $^1$H-NMR (CDCl$_3$, 500 MHz) 7.95 (m, 2H), 7.38 (d, 1H), 7.37 (t, 1H), 4.80 (m, 1H), 1.54 (d, 6H) ppm; MS (FIA) 216.1 (M–H); HPLC (Method A) 4.108 min.

The following compounds were similarly prepared:

| Name | Number | MS (M + H) | HPLC Method A | $^1$H-NMR |
|---|---|---|---|---|
| 2-Difluoromethoxy-1-isopropoxy-4-nitro-benzene | CF#N-4 | 218.2 | 4.084 | (CDCl$_3$, 500 MHz) 8.05 (dd, 1H), 8.00 (d, 1H), 6.95 (d, 1H), 6.52 (t, 1H), 4.65 (m, 1H), 1.36 (d, 6H) ppm |

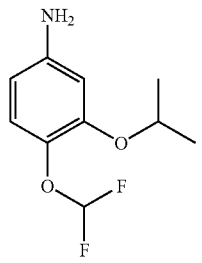

4-Difluoromethoxy-3-isopropoxy-phenylamine: To tin chloride dihydrate (5.46 g, 24.2 mmol) in concentrated HCl (7 mL) at 0° C. was added 1-difluoromethoxy-2-isopropoxy-4-nitro-benzene (1.712 g, 6.92 mmol) in ethyl acetate (7 mL) and the reaction was stirred for 1 h. The reaction was adjusted to ~pH7 with NaOH and was filtered through Celite, washing with ethyl acetate. The filtrate was separated and the aqueous phase was back extracted with ethyl acetate. The combined organic phase was washed with brine, dried (sodium sulfate) and evaporated. Purification by flash chromatography (SiO$_2$) eluted with 2:8 ethyl acetate:hexanes provided 4-difluoromethoxy-3-isopropoxy-phenylamine (0.55 g, 37% yield, 57% yield based on recovered starting material) as an orange oil. $^1$H-NMR (CDCl$_3$, 500 MHz) 6.94 (d, 1H), 6.41 (t, 1H), 6.31 (dd, 1H), 6.23 (d, 1H), 4.47 (m, 1H), 1.33 (d, 6H) ppm; MS (FIA) 218.2 (M+H); HPLC (Method A) 2.853 min.

The following compounds were similarly prepared:

| Name | Number | MS (M + H) | HPLC Method A | $^1$H-NMR |
|---|---|---|---|---|
| 3-Difluoromethoxy-4-isopropoxy-phenylamine | CF#A-3 | 218.2 | 2.827 | (CDCl$_3$, 500MHz)6.75(d, 1H), 6.50 (t, 1H), 6.45(dd, 1H), 4.26(m, 1H), 1.23(d, 6H)ppm |

Scheme 12

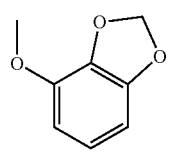

1. Cs$_2$CO$_3$
2. Bromo-chloro-methane, DMF

Example 15

4-Methoxy-benzo[1,3]dioxole: A mixture of 3-methoxy-benzene-1,2-diol (1.161 g, 8.28 mmol) in DMF (10 mL) was added to bromo-chloro-methane (611 ul, 1.1 equivalents) and stirred at 90 degrees Celsius for 4 hours. The mixture was poured into water and extracted with dichloromethane. The organic layer was poured thru a phase separator cartridge and concentrated to dryness. The crude product is a yellow liquid. The liquid was purified by column chromatography yielding 1.21 g, (96%). $^1$H-NMR (DMSO, 500 MHz) 6.7 (t, 1H), 6.63 (d, 1H), 6.58 (d, 1H), 5.97 (s, 2H), 3.83 (s, 3H)HPLC (method A) 2.86 min.

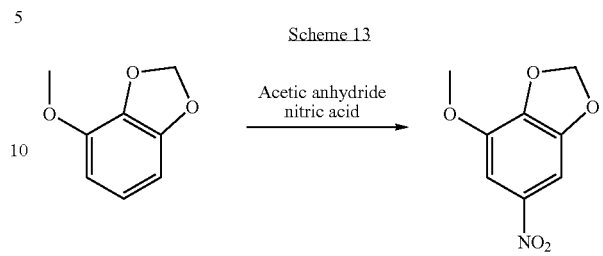

Scheme 13

Acetic anhydride nitric acid

Example 16

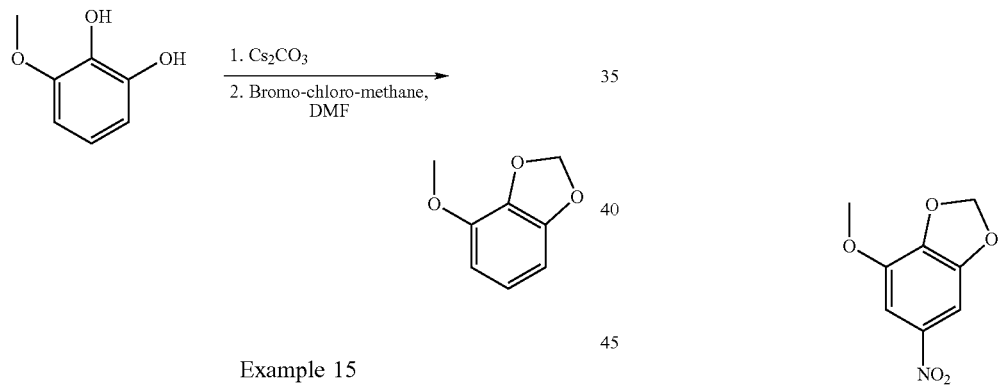

4-Methoxy-6-nitro-benzo[1,3]dioxole: 4-Methoxy-benzo[1,3]dioxole (2.03 g, 13.34 mmole) was dissolved in acetic anhydride (20 mL) and cooled in an ice bath while stirring. Nitric acid (1.5 mL) was added dropwise with an addition funnel over 30 minutes. The ice bath was removed and the mixture was stirred overnight allowing the reaction to heat up to room temperature. The mixture was poured into ice water and the product crashed out and was filtered and washed with water. The precipitate was dried under vacuum in a dessicator yielding (1.21 g, 46% yield) of 4-methoxy-6-nitro-benzo[1,3]dioxole. NMR-DMSO-d6: 7.63 (s, 1H), 7.52 (s, 1H), 6.25 (s, 2H), 3.95 (s, 3H)

Example 17

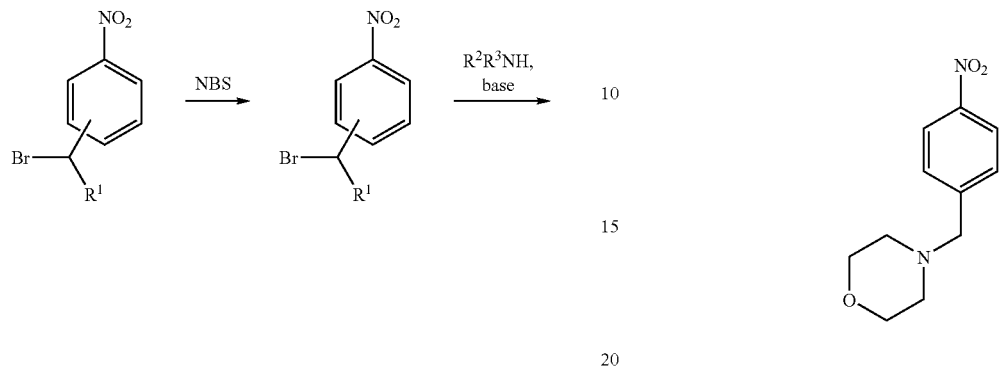

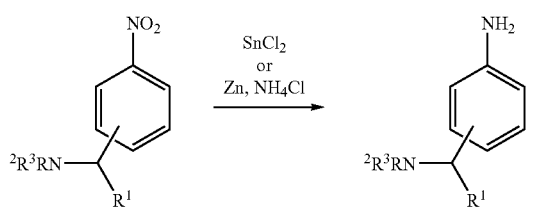

4-(4-Nitro-benzyl)-morpholine: To a mixture of 1-bromomethyl-4-nitro-benzene (5.0 g, 29.1 mmol) and potassium carbonate (12.0 g, 87 mmol) in THF (100 mL) was added morpholine (6.35 mL, 73 mmol) in a slow stream. The reaction was stirred 24 h at room temperature, was filtered through Celite and evaporated. Purification by flash chromatography (SiO$_2$) provided 4-(4-nitro-benzyl)-morpholine (5.27 g, 81% yield) as a pale yellow solid. $^1$H-NMR (DMSO-d6, 500 MHz) 8.20 (d, 2H), 7.60 (d, 2H), 3.61 (m, 6H), 2.38 (m, 4H) ppm; MS (FIA) 223.1 (M+H); HPLC (Method A) 1.577 min.

The following compounds were similarly prepared:

| Name | MS (M + H) | HPLC Method A | $^1$H-NMR |
|---|---|---|---|
| 1-methyl-4-(4-Nitro-benzyl)-piperazine | 236.3 | 2.202 | (DMSO-d6, 500 MHz) 8.19 (d, 2H), 7.58 (d, 2H), 3.59 (s, 2H), 2.35 (br m, 8H), 2.15 (s, 3H) ppm |
| 4-(4-Nitro-benzyl)-pyrrolidine | 207.2 | 2.262 | (DMSO-d6, 500 MHz) 8.18 (d, 2H), 7.59 (d, 2H), 3.71 (s, 2H), 2.45 (m, 4H), 1.71 (m, 4H) ppm |
| 4-(3-Nitro-benzyl)-morpholine | 223.1 | 1.260 | (DMSO-d6, 500 MHz) 8.17 (s, 1H), 8.13 (d, 1H), 7.78 (d, 1H), 7.64 (t, 1H), 3.61 (m, 6H), 2.38 (m, 4H) ppm |

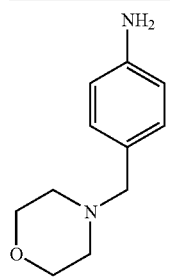

4-Morpholin-4-ylmethyl-phenylamine: Following the procedure described in Example 1. C. The title compound was obtained (1.70 g, 98% yield) as an orange solid. $^{1}$H-NMR (DMSO-d6, 500 MHz) 6.91 (d, 2H), 6.49 (d, 2H), 4.95 (s, 2H), 3.53 (m, 4H), 2.28 (m, 4H) ppm; MS (FIA) 193.2 (M+H); HPLC (Method A) 1.038 min.

The following compounds were similarly prepared:

| Name | MS (M + H) | HPLC Method A | $^{1}$H-NMR |
|---|---|---|---|
| 4-(1-Morpholin-4-yl-ethyl) phenylamine | 193.2 | 1.493 | (DMSO-d6, 500MHz)6.93(t, 1H), 6.53(s, 1H), 6.41(m, 2H), 5.00(s, 2H), 3.56(m, 4H), 2.31(m, 4H)ppm |

Example 18

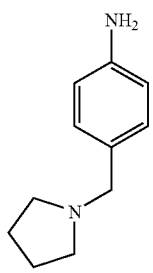

4-Pyrrolidin-1-ylmethyl-phenylamine: The title compound was prepared following procedures described above to provide (0.37 g, 20% yield) as a yellow oil. $^{1}$H-NMR (DMSO-d6, 500 MHz) 6.92 (d, 2H), 6.49 (d, 2H), 4.88 (s, 2H), 3.38 (s, 2H), 2.38 (m, 4H), 1.66 (m, 4H) ppm; MS (FIA) 177.2 (M+H); HPLC (Method A) 1.162 min.

Example 19

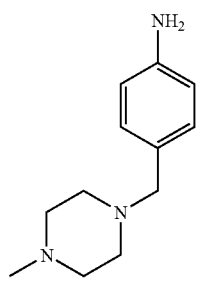

4-(4-Methyl-piperazin-1-ylmethyl)-phenylamine (CF#A-5): A mixture of 1-methyl-4-(4-nitro-benzyl)-piperazine (3.09 g, 13.1 mmol), zinc dust (4.29 g, 65.6 mmol) and ammonium chloride (2.81 g, 52.5 mmol) in methanol (100 mL) was refluxed 1 h, cooled, filtered through Celite (washing with methanol) and evaporated to provide 4-(4-methyl-piperazin-1-ylmethyl)-phenylamine (2.67 g, 99% yield) as a pale yellow, waxy solid. $^{1}$H-NMR (DMSO-d6, 500 MHz) 6.89 (d, 2H), 6.49 (d, 2H), 4.89 (s, 2H), 3.24 (s, 2H), 2.3 (br m, 8H) ppm; MS (FIA) 206.2 (M+H); HPLC (Method A) co-elutes with solvent front.

Example 20

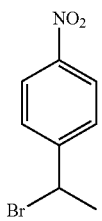

1-(1-Bromo-ethyl)-4-nitro-benzene: A mixture of 1-ethyl-4-nitro-benzene (3.4 mL, 25 mmol), N-bromosuccinimide (4.38 g, 24.6 mmol) and benzoylperoxide (0.04 g, 0.18 mmol) in carbon tetrachloride (30 mL) was refluxed 1 h, cooled and filtered, washing with 1:1 ethyl acetate:hexanes. The filtrate was evaporated and purified by flash chromatography (SiO$_2$) eluted with 2:98 ethyl acetate:hexanes to provide 1-(1-bromo-ethyl)-4-nitro-benzene (5.18 g, 90% yield) as a yellow oil. $^{1}$H-NM (CDCl$_3$, 500 MHz) 8.22 (d, 2H), 7.62 (d, 2H), 5.22 (q, 1H), 2.08 (d, 3H) ppm; HPLC (Method A) 3.837 min.

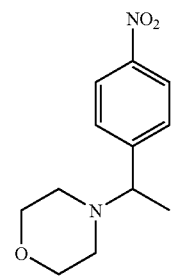

4-[1-(4-Nitro-phenyl)-ethyl]-morpholine: A mixture of 1-(1-bromo-ethyl)-4-nitro-benzene (1.24 g, 5.43 mmol), potassium carbonate (2.25 g, 16.3 mmol) and morpholine (1.2 mL, 13.6 mmol) in DMF (10 mL) was stirred at room temperature for 16 h, then evaporated. The residue was suspended in ethyl acetate, washed with water and brine, dried (sodium sulfate) and evaporated to provide 4-[1-(4-nitro-phenyl)-ethyl]-morpholine (1.225 g, 95% yield) as a yellow oil. $^{1}$H-NMR (DMSO-d6, 500 MHz) 8.19 (d, 2H), 7.16 (d, 2H), 3.56 (m, 5H), 2.41 (m, 2H), 2.26 (m, 2H), 1.29 (d, 3H) ppm; MS (FIA) 237.2 (M+H); HPLC (Method A) 2.248 min.

The following compounds were similarly prepared:

| Name | MS (M + H) | HPLC Method A | ¹H-NMR |
|---|---|---|---|
| 4-[1-(4-Nitro-phenyl)-ethyl]-pyrrolidine | 221.2 | 2.359 | (DMSO-d6, 500 MHz) 8.18 (d, 2H), 7.60 (d, 2H), 3.37 (q, 2H), 2.47 (m, 2H), 2.31 (m, 2H), 1.68 (m, 4H), 1.30 (d, 3H) ppm |

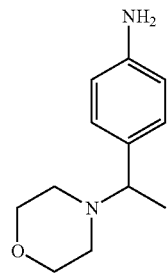

4-(1-Morpholin-4-yl-ethyl)-phenylamine: The title compound was prepared by methods described above. ¹H-NMR (DMSO-d6, 500 MHz) 6.90 (d, 2H), 6.49 (d, 2H), 4.87 (s, 2H), 3.51 (m, 4H), 3.14 (q, 1H), 2.30 (m, 2H), 2.25 (m, 2H), 1.21 (d, 3H) ppm; MS (FIA) 207.3 (M+H).

The following compounds were similarly prepared:

| Name | MS (M + H) | HPLC Method A | ¹H-NMR |
|---|---|---|---|
| 4-(1-pyrrolidinyl-ethyl)-phenylamine | 191.3 | | (DMSO-d6, 500MHz) 6.93(d, 2H), 6.48 (d, 2H), 4.86(s, 2H), 3.1(m, 1H), 2.45 (m, 2H), 2.29(m, 2H), 1.64(m, 2H), 1.21 (d, 3H)ppm |

Example 21

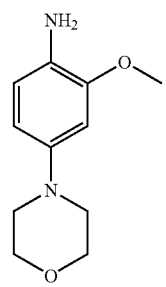

2-Methoxy-4-morpholino-4-yl-phenylamine: To a suspension of 5-morpholino-2-nitroanisole (0.76 g, 3.21 mmol) in MeOH (20 mL) under $N_2$ was added 5% Pd/C. The reaction was stirred under $H_2$ at RT for 4 h, filtered through celite which was washed with MeOH. The filtrate was concentrated in vacuo to give the product as a sticky purple solid (0.63 g, 95% yield)

| Name | MS (M + H) | HPLC Method A | ¹H-NMR |
|---|---|---|---|
| 2-Methoxy-4-morpholino-4-yl-phenylamine | 209.15 (method B) | | (DMSO-d6, 500MHz): 6.52(d, 1H)6.50 (d, 1H), 6.28(dd, 1H), 4.23(s, 2H), 3.80–3.65 (m, 7H), 2.95–2.90(m, m, 4H) |
| Indan-4-ylamine | | 2.72 (method A) | (CDCl3, 500MHz): 6.97(t, 1H), 6.68(d, 1H), 6.48(d, 1H), 3.54(br s, 2H), 2.90(t, 2H), 2.71(t, 2H), 2.20–1.97(m, 2H) |
| 7-Methoxy-benzo[1,3]dioxol-5-ylamine | 168.05 | | |

Scheme 15

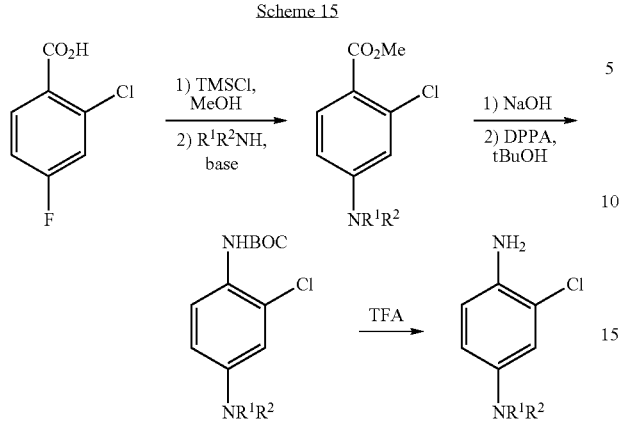

Example 22

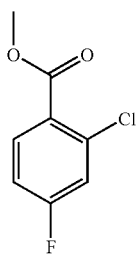

2-Chloro-4-fluoro-benzoic acid methyl ester: A mixture of 2-chloro-4-fluorobenzoic acid (6.5 g, 37 mmol) in methanol (100 mL) was treated with chlorotrimethylsilane (14.0 mL, 111 mmol), stirred 24 h at room temperature and evaporated. The residue was dissolved in dichloromethane, washed with sodium bicarbonate, dried (sodium sulfate) and evaporated to provide 2-chloro-4-fluoro-benzoic acid methyl ester (7.01 g, 99% yield) as a pale yellow oil. $^1$H-NMR (CDCl$_3$, 500 MHz) 7.93 (m, 1H), 7.22 (m, 1H), 7.06 (m, 1H), 3.95 (s, 3H) ppm; MS (FIA) 189.1 (M+H); HPLC (Method A) 3.37 min.

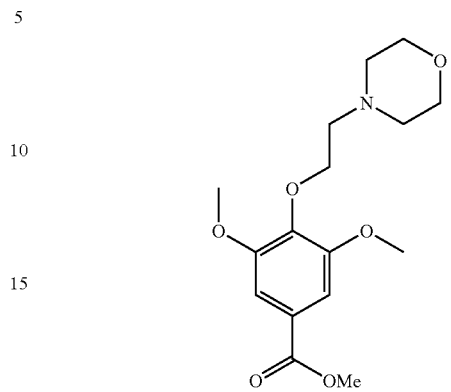

3,5-Dimethoxy-4-(2-morpholin-4-yl ethoxy)benzoic acid methyl ester: To a solution of methyl 3,5-dimethoxy-4-hydroxybenzoate (3.0 g, 14 mmol) in DMF (10 mL) was added 4-(2-chloroethyl)-morpholine hydrochloride (3.99 g, 21 mmol) and solid K$_2$CO$_3$ (8.4 g, 60 mmol). The mixture was heated at 60 C under N$_2$ for 30 h. Diluted with EtOAc (100 mL) and washed with H$_2$O (2×50 mL), back extracted the aqueous phase, and washed combined organics with brine. Dried over Na$_2$SO$_4$, filtered and evaporated to give the product as a brown solid (4.79 g, quantitative). $^1$H-NMR (CDCl$_3$, 500 MHz7.28 (s, 2H), 4.15 (t, 2H), 3.91 (s, 3H), 3.88 (s, 6H), 3.75-3.71 (m, 4H), 2.78 (t, 2H), 2.59 (br s, 4H) ppm; MS (FIA) 326.17 (M+H)

The following compound was similarly prepared:

| Name | MS (M + H) | RT (min) | $^1$H-NMR |
|---|---|---|---|
| 4-Isopropoxy-3,5-dimethoxy-benzoic acid methyl ester | 25.13 | 3.38 | (DMSO-d6, 500 MHz): 7.24 (s, 2H), 4.45–4.32 (m, 1H), 3.85 (s, 3H), 3.81 (s, 6H), 1.18 (d, 6H) |

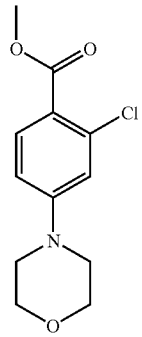

2-Chloro-4-morpholin-4-yl-benzoic acid methyl ester: A mixture of 2-chloro-4-fluoro-benzoic acid methyl ester (3.51 g, 18.6 mmol), morpholine (1.95 mL, 22.3 mmol) and potassium carbonate (5.12 g, 37.1 mmol) in N-methylpyrrolidinone (20 mL) was stirred at 120° C. for 5 h. The reaction was cooled, diluted with ethyl acetate and filtered through Celite. The filtrate was washed four times with water, once with brine, was dried (sodium sulfate) and evaporated. Purification by flash chromatography (SiO$_2$) eluted with 2:8 ethyl acetate:hexanes to provide 2-chloro-4-morpholin-4-yl-benzoic acid methyl ester (3.08 g, 65% yield) as a white solid. $^1$H-NMR (CDCl$_3$, 500 MHz) 7.79 (d, 1H), 6.81 (d, 1H), 6.67 (dd, 1H), 3.81 (s, 3H), 3.78 (m, 4H), 3.20 (m, 4H) ppm; MS (FIA) 256.1 (M+H); HPLC (Method A) 3.275 min.

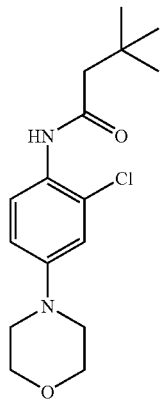

(2-Chloro-4-morpholin-4-yl-phenyl)-carbamic acid tert-butyl ester: A mixture of 2-chloro-4-morpholin-4-yl-benzoic acid methyl ester (3.08 g, 12.0 mmol) and 6N NaOH (2.5 mL, 15 mmol) in methanol (50 mL) and water (7.5 mL) was stirred 24 h at room temperature, then acidified with 2N HCl. The precipitate was filtered off, washed with water and dried to provide 2-chloro-4-morpholin-4-yl-benzoic acid (2.56 g, 88% yield) as a white solid. This intermediate (10.6 mmol) was suspended in tert-butanol (20 mL), treated with diphenylphosphoryl azide (2.30 mL, 10.6 mmol), then with triethylamine (1.45 mL, 10.6 mmol), was stirred at reflux for 20 h and evaporated. Purification by flash chromatography (SiO$_2$) eluted with 2:8 ethyl acetate:hexanes provided (2-chloro-4-morpholin-4-yl-phenyl)-carbamic acid tert-butyl ester (2.84 g) as a mixture (~1:1) with 2-chloro-4-morpholin-4-yl-benzoic acid tert-butyl ester. This mixture was carried on without further purification. $^1$H-NMR (CDCl$_3$, 500 MHz) 8.0 (br, 1H), 7.80 (d, 1H), 7.4 (d, 1H), 6.90 (d, 1H), 6.87 (d, 1H), 6.84 (dd, 1H), 6.75 (dd, 1H), 3.87 (m, 8H), 3.26 (m, 4H), 3.11 (m, 4H), 1.61 (s, 9H), 1.55 (s, 9H) ppm; MS (FIA) 313.1 (M+H); HPLC (Method A) 3.70 min.

The following compounds were prepared in a similar manner

| Name | MS (M + H) | HPLC RT (min) | $^1$H-NMR |
|---|---|---|---|
| [3,5-Dimethoxy-4-(2-morpholin-4-yl-ethoxy)-phenyl]-carbamic acid tert-butyl ester | 383.2 | 1.9 | (DMSO-d6, 500 MHz): 9.21 (s, 1H), 6.82 (s, 2H), 3.87 (t, 2H), 3.69 (s, 6H), 3.56 (t, 4H), 2.62–2.39 (m, 6H), 1.46 (s, 9H). |
| 4-(4-tert-Butoxycarbonylamino-2,6-dimethoxy-phenoxy)-piperidine-1-carboxylic acid benzyl ester | 487.3 | | |

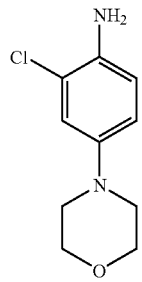

2-Chloro-4-morpholin-4-yl-phenylamine: A solution of impure (2-chloro-4-morpholin-4-yl-phenyl)-carbamic acid tert-butyl ester (2.84 g) in dichloromethane (30 mL) was treated with trifluoroacetic acid (3.5 mL), stirred at room temperature for 24 h and evaporated. The residue was dissolved in ethyl acetate, was washed with 1N NaOH, water, and brine, was dried (sodium sulfate) and evaporated. Purification by flash chromatography (SiO$_2$) eluted with 35:65 ethyl acetate:hexanes provided 2-chloro-4-morpholin-4-yl-phenylamine (0.77 g, 40% yield) as an off-white solid. $^1$H-NMR (CDCl$_3$, 500 MHz) 6.92 (br, 1H), 6.77 (br, 2H), 3.89 (m, 6H), 3.05 (m, 4H) ppm; MS (FIA) 213.1 (M+H); HPLC (Method A) 1.975 min.

Example 23

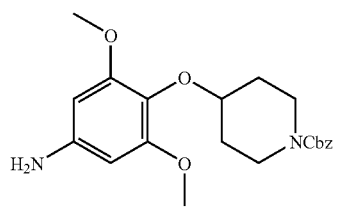

4-(4-Amino-2,6-dimethoxy-phenoxy)-piperidine-1-carboxylic acid benzyl ester: The title compound was prepared from 4-(4-tert-butoxycarbonylamino-2,6-dimethoxy-phenoxy)-piperidine-1-carboxylic acid benzyl ester following the procedure described in Example ST-3. MS (ES+): m/z=387.2.

Example 24

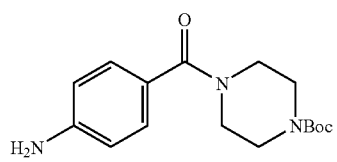

4-(4-Amino-phenyl)-piperazine-1-carboxylic acid tert-butyl ester: The title compound was prepared from 4-iodoaniline and tert-butyl piperazinecarboxylate following the procedure described in Example ST-1. MS (ES+): m/z=278.2.

Example 25

4-(4-Amino-benzoyl)-piperazine-1-carboxylic acid tert-butyl ester: To a solution of 4-aminobenzoic acid (411 mg, 3.00 mmol) in DMF (3.0 mL) at room temperature was added EDC (862 mg, 4.50 mmol), HOBt (608 mg, 4.50 mmol), triethylamine (606 mg, 0.835 mL, 6.00 mmol) and tert-butyl piperazinecarboxylate (671 mg, 3.60 mmol). The mixture was stirred for 22 h, and then 2 N aq. NaOH was added to adjust the PH>10. The mixture was extracted with ethyl acetate, and the organic layer was dried over MgSO$_4$, concentrated. The residue was purified by silica gel column chromatograghy eluted with EtOAc:hexanes (50 to 90% EtOAc) to give 4-(4-amino-benzoyl)-piperazine-1-carboxylic acid tert-butyl ester (796 mg, 87%) as a colorless oil. MS (ES+): m/z=306.2

Example 26

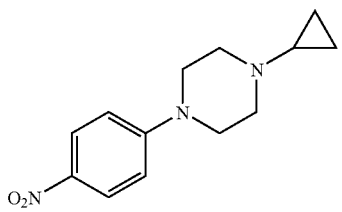

1-Cyclopropyl-4-(4-nitro-phenyl)-piperazine: To a solution of 1-(4-nitrophenyl)piperazine (1.04 g, 5.00 mmol) in methanol (25 mL) under nitrogen was added molecular sieves (1.0 g), acetic acid (3.00 g, 2.86 mL, 50.0 mmol), [(1-ethoxycyclopropyl)oxy]trimethylsilane (5.22 g, 5.99 mL, 30.0 mmol), sodium cyanoborohydride (1.41 g, 22.5 mmol). The mixture was stirred at room temperature for 2.5 d, filtered, and concentrated. To the residue was added water and 1N aq. NaOH to adjust the PH>11. The mixture was extracted ethyl acetate, and the organic layer was dried over Na$_2$SO$_4$, concentrated to give the title compound (1.24 g, 100%) as a yellow solid. MS (ES+): m/z=247.8.

Example 27

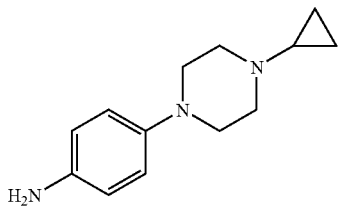

4-(4-Cyclopropyl-piperazin-1-yl)-phenylamine: To a solution of 1-cyclopropyl-4-(4-nitro-phenyl)-piperazine (1.24 g, 5.00 mmol) in methanol (25 mL) was added Pd/C (10%, 100 mg) and trifluoroacetic acid (1.0 mL). The mixture was stirred under 1 atm of hydrogen (balloon) overnight, filtered and concentrated. To the residue was added water and 1N aq. NaOH to adjust the PH>11. The mixture was extracted ethyl acetate, and the organic layer was dried over Na$_2$SO$_4$, concentrated to give the title compound (1.08 g, 100%) as a brown oil. MS (ES+): m/z=218.1.

Example 28

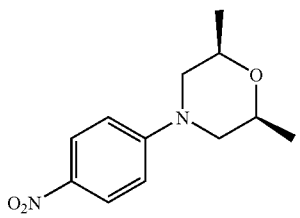

cis-2,6-Dimethyl-4-(4-nitro-phenyl)-morpholine: A mixture of 1-fluoro-4-nitrobenzene, 2,6-dimethylmorpholine (Purchased from Aldrich) and diisopropylamine was heated at 110° C. for 16 h. After being cooled to room temperature, the mixture was added water and extracted with EtOAc. The organic phase was dried over MgSO$_4$, concentrated. The residue was purified by silica gel column chromatograghy eluted with EtOAc: hexanes (5 to 35% EtOAc) to give trans-2,6-dimethyl-4-(4-nitro-phenyl)-morpholine (258 mg) and cis-2,6-dimethyl-4-(4-nitro-phenyl)-morpholine (838 mg) both as yellow solids. Trans-isomer: MS (ES+): m/z=237.2; $^1$H NMR (CDCl$_3$, 500 MHz): δ 1.30 (d, 6H), 3.17 (dd, 2H), 3.46 (dd, 2H), 4.15-4.22 (m, 2H), 6.77 (d, 2H), 8.14 (d, 2H). Cis-isomer: MS (ES+): m/z=237.2; $^1$H NMR (CDCl$_3$, 500 MHz): δ 1.29 (d, 6H), 2.62 (dd, 2H), 3.67 (dd, 2H), 3.73-3.81 (m, 2H), 6.84 (d, 2H), 8.14 (d, 2H).

Example 29

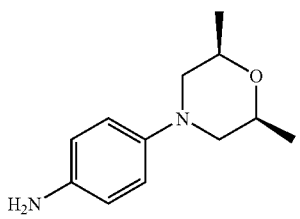

4-(2,6-Dimethyl-morpholin-4-yl)-phenylamine: The title compound was prepared from cis-2,6-dimethyl-4-(4-nitrophenyl)-morpholine following the procedure described above. MS (ES+): m/z=207.3.

Example 30

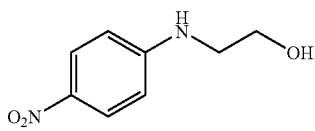

2-(4-Nitro-phenylamino)-ethanol: The title compound was prepared from 1-fluoro-4-nitrobenzene and 2-aminoethanol following the procedure described above. MS (ES+): m/z=183.0; $^1$H NMR (CDCl$_3$, 500 MHz): δ 3.41 (t, 2H), 3.92 (t, 2H), 6.59 (d, 2H), 8.11 (d, 2H).

Example 31

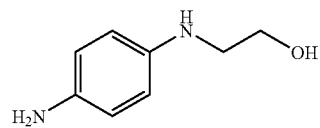

2-(4-Amino-phenylamino)-ethanol: The title compound was prepared from 2-(4-nitro-phenylamino)-ethanol following the procedure described above. MS (ES+): m/z=153.0.

Scheme 16

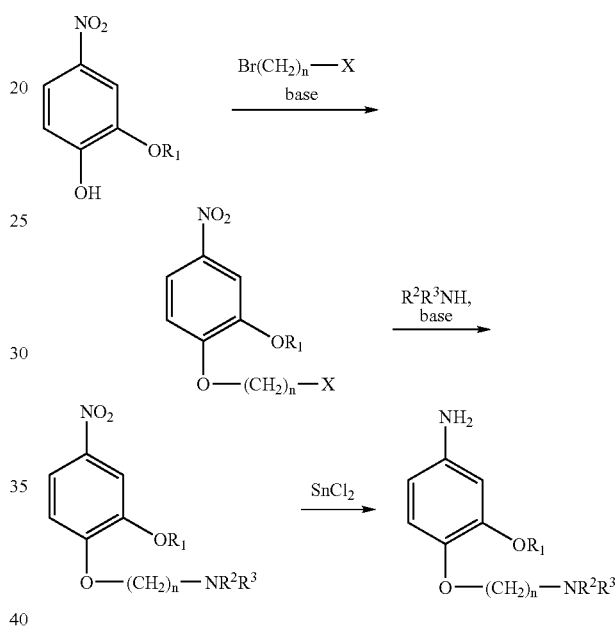

Example 32

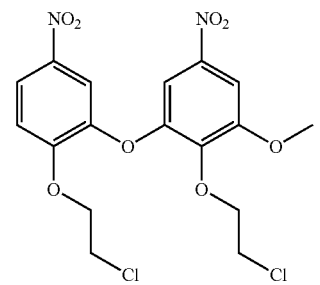

1-(2-Chloro-ethoxy)-2-methoxy-4-nitro-benzene: A mixture of 2-methoxy-4-nitro-phenol (2.50 g, 14.8 mmol), 1-bromo-2-chloro-ethane (1.35 mL, 16.3 mmol) and potassium carbonate (4.08 g, 29.6 mmol) in DMF (50 mL) in a sealed tube was heated at 90° C. for 18 h. The reaction was cooled and filtered, washing with ethyl acetate. The filtrate was washed with sodium bicarbonate, water (4 times) and brine, was dried (sodium sulfate) and evaporated. Purification by flash chromatography (SiO$_2$) eluted with 35:65 ethyl acetate:hexanes provided 1-(2-chloro-ethoxy)-2-methoxy-4- nitro-benzene (1.93 g, 56% yield) as an off-white solid. ¹H-NMR (DMSO-d6, 500 MHz) 7.89 (dd, 1H), 7.76 (d, 1H), 7.21 (d, 1H), 4.41 (t, 2H), 4.00 (t, 2H), 3.90 (s, 3H) ppm; HPLC (Method A) 3.781 min.

The following compounds were similarly prepared:

| Name | MS (M + H) | HPLC Method A | ¹H-NMR |
|---|---|---|---|
| 1-(4-Chloro-butoxy)-2-methoxy-4-nitro-benzene | | 4.204 | (DMSO-d6, 500 MHz) 7.9 (dd, 1H), 7.75 (d, 1H), 7.2 (d, 1H), 4.15 (t, 2H), 3.9 (s, 3H), 3.75 (t, 2H), 1.9 (m, 4H) ppm |
| 1-(3-Bromo-propoxy)-2-methoxy-4-nitro-benzene | | 4.121 | (DMSO-d6, 500 MHz) 7.90 (dd, 1H), 7.75 (d, 1H), 7.22 (d, 1H), 4.23 (t, 2H), 3.89 (s, 3H), 3.66 (t, 2H), 2.30 (m, 2H) ppm |
| 1-(3-Chloro-propoxy)-2-methoxy-4-nitro-benzene | | 3.843 | (DMSO-d6, 500 MHz) 7.89 (dd, 1H), 7.75 (d, 1H), 7.21 (d, 1H), 4.24 (t, 2H), 3.89 (s, 3H), 3.79 (t, 2H), 2.22 (m, 2H) ppm |
| 4-(2,6-Dimethoxy-4-methoxycarbonyl-phenoxy)-piperidine-1-carboxylic acid benzyl ester | 430.3 | | |

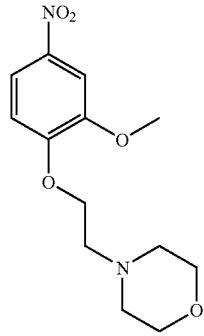

4-[2-(2-Methoxy-4-nitro-phenoxy)-ethyl]-morpholine: A mixture of 1-(2-chloro-ethoxy)-2-methoxy-4-nitro-benzene (0.60 g, 2.59 mmol), morpholine (0.28 mL, 3.11 mmol), sodium iodide (0.39 g, 2.59 mmol) and potassium carbonate (0.71 g, 5.18 mmol), in ethanol (5 mL) was heated in a sealed tube at 90° C. for 18 h, was cooled, filtered and evaporated. Purification by flash chromatography (SiO₂) eluted with 2:98 methanol:dichloromethane provided 4-[2-(2-methoxy-4-nitro-phenoxy)-ethyl]-morpholine (0.37 g, 51% yield) as a pale yellow solid. ¹H-NMR (DMSO-d6, 500 MHz) 7.89 (dd, 1H), 7.74 (d, 1H), 7.21 (d, 1H), 4.23 (t, 2H), 3.88 (s, 3H), 3.88 (m, 4H), 2.73 (t, 2H), 2.50 (m, 4H) ppm; MS (FIA) 283.2 (M+H); HPLC (Method A) 2.652 min.

The following compounds were similarly prepared:

| Name | MS (M + H) | HPLC Method A | ¹H-NMR |
|---|---|---|---|
| 4-[4-(2-Methoxy-4-nitro-phenoxy)-butyl]-morpholine | 311.1 | | (DMSO-d6, 500 MHz) 7.89 (dd, 1H), 7.73 (d, 1H), 7.18 (d, 1H), 4.13 (t, 2H), 3.88 (s, 3H), 3.55 (m, 4H), 2.32 (m, 6H), 1.78 (m, 2H), 1.57 (m, 2H) ppm |
| Diethyl-[2-(2-methoxy-4-nitro-phenoxythyl]-amine | 269.2 | 2.588 | (DMSO-d6, 500 MHz) 7.89 (dd, 1H), 7.73 (d, 1H), 7.20 (d, 1H), 4.15 (t, 2H), 3.88 (s, 3H), 2.81 (t, 2H), 2.55 (g, 4H), 0.97 (t, 6H) ppm |
| 1-[3-(2-Methoxy-4-nitro-phenoxy)-propyl]-1H-imidazole | 278.1 | 2.601 | (DMSO-d6, 500 MHz) 7.79 (dd, 1H), 7.76 (d, 1H), 7.76 (s, 1H), 7.20 (s, 1H), 7.15 (d, 1H), 6.89 (s, 1H), 4.13 (t, 2H), 4.05 (t, 2H), 3.91 (s, 3H), 2.23 (m, 2H) ppm |
| Diethyl-[3-(2-methoxy-4-nitro-phenoxy)-propyl]-amine | 283.2 | 2.811 | (DMSO-d6, 500 MHz) 7.88 (dd, 1H), 7.73 (d, 1H), 7.17 (d, 1H), 4.15 (t, 2H), 3.88 (s, 3H), 2.50 (m, 2H), 2.44 (q, 4H), 1.85 (m, 2H), 0.93 (t, 6H) ppm |
| 4-[3-(2-Methoxy-4-nitro-phenoxy)-propyl] | 325.1 | 2.962 | (DMSO-d6, 500 MHz) 7.89 (dd, 1H), 7.73 (d, 1H), 7.17 (d, 1H), 4.15 (t, 2H), 3.88 (s, 3H), 3.53 (m, 2H), 2.74 (d, 2H), 2.39 (t, 2H), 1.92 |

| Name | MS (M + H) | HPLC Method A | ¹H-NMR |
|---|---|---|---|
| -2,6-dimethyl-morpholine | | | (m, 2H), 1.57 (t, 2H), 1.04 (d, 6H) ppm |
| 4-[3-(2-Methoxy-4-nitro-phenoxy)-propyl]-morpholine | 297.1 | 2.574 | (DMSO-d6, 500 MHz) 7.89 (dd, 1H, 7.73 (d, 1H), 7.18 (d, 1H), 4.15 (t, 2H), 3.88 (s, 3H), 3.57 (m, 4H), 2.41 (t, 2H), 2.36 (m, 4H), 1.92 (m, 2H) ppm |

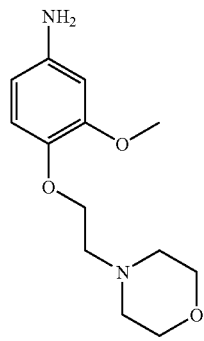

3-Methoxy-4-(2-morpholin-4-yl-ethoxy)-phenylamine: The title compound was prepared following the procedures described above to obtain (0.14 g, 43% yield) a red oil. 1H-NMR (DMSO-d6, 500 MHz) 6.65 (d, 1H), 6.24 (d, 1H), 6.03 (dd, 1H), 4.70 (s, 2H), 3.87 (t, 2H), 3.66 (s, 3H), 3.56 (m, 4H), 2.58 (t, 2H), 2.44 (m, 4H) ppm; MS (FIA) 253.2 (M+H); HPLC (Method A) co-elutes with solvent front.

The following compounds were similarly prepared:

| Name | MS (M + H) | HPLC Method A | ¹H-NMR |
|---|---|---|---|
| 3-Methoxy-4-(3-morpholin-4-yl-propoxy)-phenylamine | 267.2 | 2.746 | (DMSO-d6, 500MHz)6.62(d, 1H), 6.24(d, 1H), 6.03(dd, 1H), 4.68(s, 2H), 3.80(t, 2H), 3.66 (s, 3H), 3.56(m, 4H), 2.38(t, 2H), 2.34(m, 4H), 1.76 (m, 2H)ppm |
| 4-[3-(2,6-Dimethyl-morpholin-4-yl)-propoxy]-3-methoxy-phenylamine | 295.2 | 2.229 | (DMSO-d6, 500MHz)6.62(d, 1H), 6.24(d, 1H), 6.03(dd, 1H), 4.68(s, 2H), 3.79(t, 2H), 3.66 (s, 3H), 3.52(m, 4H), 2.72(d, 2H), 2.36(t, 2H), 1.76 (m, 2H), 1.56(t, 2H), 1.03(d, 6H)ppm |
| 4-(3-Diethylamino-propoxy)-3-methoxy-phenylamine | 253.2 | 2.075 | (DMSO-d6, 500MHz)6.63(d, 1H), 6.25(d, 1H), 6.04(dd, 1H), 4.70(s, 2H), 3.82(t, 2H), 3.66 (s, 3H), 2.6(br m, 6H), 1.8(br m, 2H), 1.00(br m, 6H)ppm |
| 4-(3-Imidazol-1-yl-propoxy)-3-methoxy-phenylamine | 248.2 | 1.681 | (DMSO-d6, 500MHz)7.61(s, 1H), 7.18(s, 1H), 6.88(s, 1H), 6.64(d, 1H), 6.26(d, 1H), 6.04(dd, 1H), 4.73(s, 2H), 4.11(t, 2H), 3.70(t, 2H), 3.68 (s, 3H), 2.04(m, 2H)ppm |
| 4-(2-Diethylamino-ethoxy)-3-methoxy-phenylamine | 239.2 | 2.190 | (DMSO-d6, 500MHz)6.64(d, 1H), 6.24(d, 1H), 6.03(dd, 1H), 4.68(s, 2H), 3.81(t, 2H), 3.66 (s, 3H), 2.67(m, 2H), 2.5(m, 4H), 0.95(t, 6H)ppm |
| 3-Methoxy-4-(4-morpholin-4-yl-butoxy)-phenylamine | 283.2 | | (DMSO-d6, 500MHz)6.62(d, 1H), 6.24(d, 1H), 6.03(dd, 1H), 4.67(s, 2H), 3.78(t, 2H), 3.66 (s, 3H), 3.55(m, 4H), 2.28(t, 2H), 2.32(m, 4H), 1.62 (m, 2H), 1.53(m, 2H)ppm |

Scheme 17:

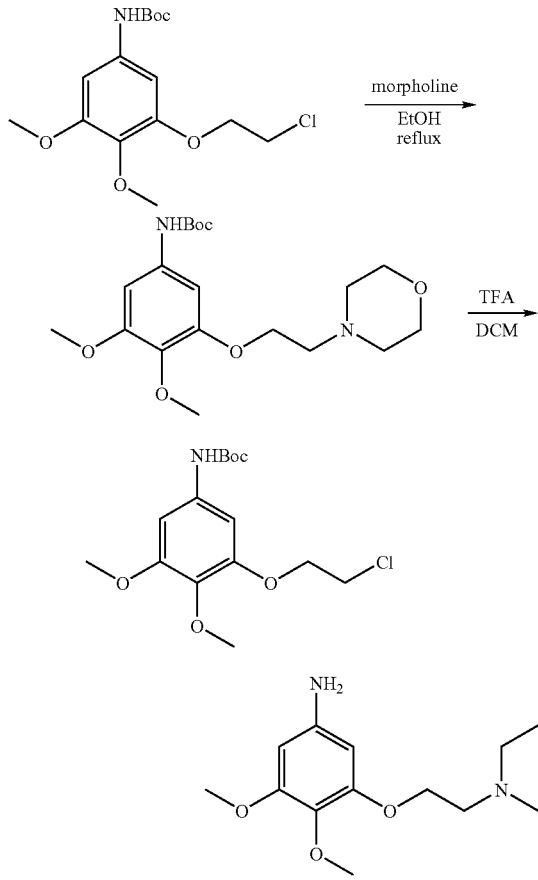

[3-(2-Chloro-ethoxy)-4,5-dimethoxy-phenyl]-carbamic acid tert-butyl ester 3-(2-Chloro-ethoxy)-4,5-dimethoxy-benzoic acid (500 mg, 1.9 mmol), DPPA, (550 mg, 2 mmol), and TEA, (2 mmol), were combined in 5 mL t-butanol and refluxed for 5 h. The t-butanol was removed under vacuum and the residue purified by silica gel chromatography (5% methanol/DCM, affording 90 mg [3-(2-Chloro-ethoxy)-4,5-dimethoxy-phenyl]-carbamic acid tert-butyl ester. NMR CDCl$_3$: 6.7(d, 2H), 6.4(bs, 1H), 4.3(t, 3H), 3.85(s, 3H), 3.80(s, 3H), 3.82(m, 2H), 1.5(s, 9H).

[3,4-Dimethoxy-5-(2-morpholin-4-yl-ethoxy)-phenyl]-carbamic acid tert-butyl ester

[3-(2-Chloro-ethoxy)-4,5-dimethoxy-phenyl]-carbamic acid tert-butyl ester. (90 mg, 0.27 mmol), in 1 mL ethanol was treated with 200 µL morpholine and refluxed for 18 h. The solvent and excess morpholine were evaporated and the residue purified by prep tlc, affording 79 mg [3,4-Dimethoxy-5-(2-morpholin-4-yl-ethoxy)-phenyl]-carbamic acid tert-butyl ester. MS ES+ 383.

3,4-Dimethoxy-5-(2-morpholin-4-yl-ethoxy)-phenylamine

[3,4-Dimethoxy-5-(2-morpholin-4-yl-ethoxy)-phenyl]-carbamic acid tert-butyl ester, (97 mg, 0.24 mmol, was stirred in 1 mL DCM and 1 mL TFA. After ~1 h, the TFA and DCM were evaporated and 2 mL sat. sodium bicarbonate solution was added. The aqueous layer was extracted with DCM which was evaporated affording 60 mg 3,4-Dimethoxy-5-(2-morpholin-4-yl-ethoxy)-phenylamine. MS ES+ 283.1

The following anilines were prepared using similar procedures:

| Name | MS (M + H) |
|---|---|
| 3-(2-Dimethylamino-ethoxy)-4,5-dimethoxy-phenylamine | 241.1 |
| 3-(2-Diethylamino-ethoxy)-4,5-dimethoxy-phenylamine | 269.2 |
| 3-[2-(2,6-Dimethyl-morpholin-4-yl)-ethoxy]-4,5-dimethoxy-phenylamine | 311.2 |
| 3,4-Dimethoxy-5-[2-(4-methyl-piperazin-1-yl)-ethoxy]-phenylamine | 296.2 |
| 3-(2-Imidazol-1-yl-ethoxy)-4,5-dimethoxy-phenylamine | 264.1 |
| 3,4-Dimethoxy-5-(3-morpholin-4-yl-propoxy)-phenylamine | 297.2 |
| 3-(3-Dimethylamino-propoxy)-4,5-dimethoxy-phenylamine | 255.2 |

Example 33

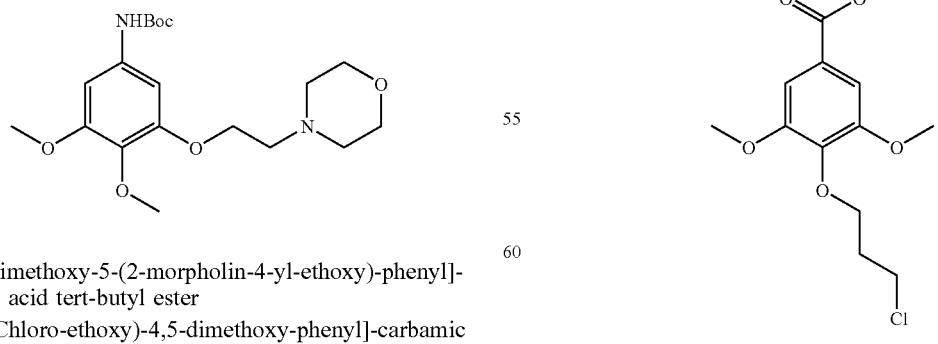

4-(3-Chloro-propoxy)-3,5-dimethoxy-benzoic acid methyl ester: The title compound was prepared following the procedures described above. $^1$H-NMR (CDCl$_3$, 500

MHz) 7.22 (s, 2H), 4.11 (t, 2H), 3.84 (s, 3H), 3.83 (s, 6H), 3.78 (t, 2H), 2.11 (m, 2H) ppm; HPLC (Method A) 4.060 min.

The following compounds were similarly prepared:

| Name | MS (M + H) | HPLC Method A | $^1$H-NMR |
| --- | --- | --- | --- |
| 4-(4-Chloro-butoxy)-3,5-dimethoxy-benzoic acid methyl ester | | 4.227 | (CDCl$_3$, 500 MHz) 7.32 (s, 2H), 4.09 (t, 2H), 3.94 (s, 3H), 3.92 (s, 6H), 3.68 (t, 2H), 2.7 (m, 2H), 1.92 (m, 2H) ppm |
| 3-(2-Chloro-ethoxy)-4,5-dimethoxy-benzoic acid methyl ester | | | NMR CDCl3: 7.35(s, 1H), 7.30 (s, 1H), 4.35(t, 3 .95 (s, 3H), 3.90 (s, 6H), 3.85 (t, 2H). |

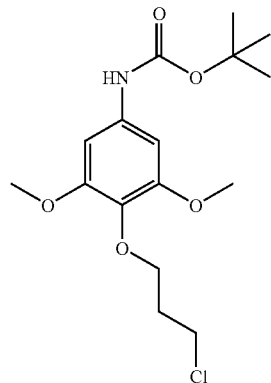

[4-(3-Chloro-propoxy)-3,5-dimethoxy-phenyl]-carbamic acid tert-butyl ester: The title compound was prepared following the procedure described in Example 7.C. $^1$H-NMR (CDCl$_3$, 500 MHz) 6.58 (s, 2H), 6.35 (s, 1H), 3.98 (t, 2H), 3.77 (t, 2H), 3.75 (s, 6H), 2.08 (m, 2H), 1.44 (s, 9H) ppm; MS (FHA) 246.1 (M+H−BOC); HPLC (Method A) 4.301 min.

The following compounds were similarly prepared:

| Name | MS (M + H − BOC) | HPLC Method A | $^1$H-NMR |
| --- | --- | --- | --- |
| [4-(4-Chloro-butoxy)-3,5-dimethoxy-phenyl]-carbamic acid tert-butyl ester | 260.2 | 4.394 | (CDCl$_3$, 500 MHz) 6.57 (s, 2H), 6.35 (s, 1H), 3.86 (t, 2H), 3.75 (s, 6H), 3.58 (t, 2H), 2.01 (m, 2H), 1.79 (m, 2H), 1.44 (s, 9H) ppm |
| [3-(2-Chloro-ethoxy)-4,5-dimethoxy-phenyl]-carbamic acid tert-butyl ester | | | NMR CDCl$_3$: 6.7 (d, 2H), 6.4 (bs, 1H), 4.3 (t, 3H), 3.85 (s, 3H), 3.80 (s, 3H), 3.82 (m, 2H), 1.5 (s, 9H). |

-continued

| Name | MS (M + H − BOC) | HPLC Method A | ¹H-NMR |
|---|---|---|---|
| 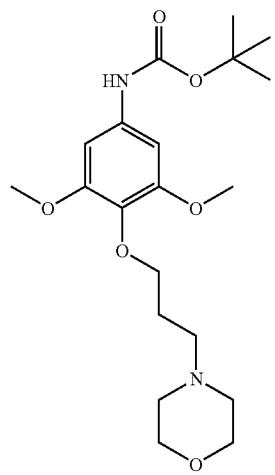 | | | |

[3,5-Dimethoxy-4-(3-morpholin-4-yl-propoxy)-phenyl]-carbamic acid tert-butyl ester: The title compound was prepared following the procedures described above. ¹H-NMR (DMSO-d6, 500 MHz) 9.2 (s, 1H), 6.82 (s, 2H), 3.80 (t, 2H), 3.69 (s, 6H), 3.56 (m, 4H), 2.42 (t, 2H), 2.33 (m, 4H), 1.72 (m, 2H), 1.46 (s, 9H) ppm; MS (FIA) 397.2 (M+H); HPLC (Method A) 3.049 min.

The following compounds were similarly prepared:

| Name | MS (M + H) | HPLC Method A | ¹H-NMR |
|---|---|---|---|
| {4-[3-(2,6-Dimethyl-morpholin-4-yl)-propoxy]-3,5-dimethoxy-phenyl}-carbamic acid tert-butyl ester | 425.3 | 3.346 | (DMSO-d6, 500 MHz) 9.20 (s, 1H), 6.82 (s, 2H), 3.79 (t, 2H), 3.69 (s, 6H), 3.51 (m, 2H), 2.70 (d, 2H), 2.39 (t, 2H), 1.71 (m, 2H), 1.56 (m, 2H), 1.46 (s, 9H), 1.03 (d, 6H) ppm |
| [4-(3-Diethylamino-propoxy)-3,5-dimethoxy-phenyl}-carbamic acid tert-butyl ester | 383.3 | 3.296 | (DMSO-d6, 500 MHz) 9.2 (s, 1H), 6.82 (s, 2H), 3.79 (t, 2H), 3.69 (s, 6H), 2.50 (m, 2H), 2.43 (q, 4H), 1.66 (m, 2H), 1.46 (s, 9H), 0.93 (t, 6H) ppm |
| {3,5-Dimethoxy-4-[3-(4-methyl-piperazin-1-yl)-propoxy]-phenyl}-carbamic acid tert-butyl ester | 410.3 | 2.916 | (DMSO-d6, 500 MHz) 9.2 (s, 1H), 6.82 (s, 2H), 3.78 (t, 2H), 3.69 (s, 6H), 2.40 (t, 2H), 2.3 (m, 8H), 2.13 (s, 3H), 1.70 (m, 2H), 1.46 (s, 9H) ppm |
| 3,5-Dimethoxy-4-(4-morpholin-4-yl-butoxy) phenyl}-carbamic acid tert-butyl ester | 411.3 | 3.183 | (DMSO-d6, 500 MHz) 9.2 (s, 1H), 6.82 (s, 2H), 3.76 (t, 2H), 3.69 (s, 6H), 3.56 (m, 4H), 2.32 (m, 4H), 2.28 (t, 2H), 1.57 (m, 4H), 1.46 (s, 9H) ppm |
| [4-(4-Diethylamino-butoxy)-3,5-dimethoxy-phenyl}-carbamic acid tert-butyl ester | 397.3 | 3.328 | SO-d6, 500 MHz) 9.2 (s, 1H), 6.82 (s, 2H), 3.76 (t, 2H), 3.69 (s, 6H), 2.42 (q, 4H), 2.36 (t, 2H), 1.55 (m, 2H), 1.50 (m, 2H), 1.46 (s, 9H), 0.93 (t, 6H) ppm |
| (2,3,4-Triethoxy-phenyl)-carbamic acid tert-butyl ester | 326.2 | 4.25 | |
| (3-Ethoxy-4-methoxy-phenyl)-carbamic acid tert-butyl ester | 268.1 | | |
| (2,3,4-Trimethoxy-phenyl)-carbamic acid tert-butyl ester | 284.1 | 3.75 | |
| [3-(3-Chloro-propoxy)-4,5-dimethoxy-phenyl]-carbamic acid tert-butyl ester | 346.0 | 4.07 | |
| [4-(3-Bromo-propoxy)- | 390.04 | 4.10 | |

-continued

| Name | MS (M + H) | HPLC Method A | $^1$H-NMR |
|---|---|---|---|
| 3,5-dimethoxy-phenyl]-carbamic acid tert-butyl ester | | | |
| (2,3,4-Triethoxy-phenyl)-carbamic acid terr-butyl ester | 326.2 | 4.25 | |
| (3-Ethoxy-4-methoxy-phenyl)-carbamic acid tert-butyl ester | 268.1 | | |
| (2,3,4-Trimethoxy-phenyl)-carbamic acid tert-butyl ester | 284.1 | 3.75 | |
| [3-(3-Chloro-propoxy)-4,5-dimethoxy-phenyl]-carbamic acid tert-butyl ester | 346.0 | 4.07 | |
| [4-(3-Bromo-propoxy)-3,5-dimethoxy-phenyl]-carbamic acid tert-butyl ester | 390.04 | 4.10 | |
| (2,3,4-Triethoxy-phenyl)-carbamic acid tert-butyl ester | 326.2 | 4.25 | |
| (3-Ethoxy-4-methoxy-phenyl)-carbamic acid tert-butyl ester | 268.1 | | |
| (2,3,4-Trimethoxy-phenyl)-carbamic acid tert-butyl ester | 284.1 | 3.75 | |
| [3-(3-Chloro-propoxy)-4,5-dimethoxy-phenyl]-carbamic acid tert-butyl ester | 346.0 | 4.07 | |
| [4-(3-Bromo-propoxy)-3,5-dimethoxy-phenyl]-carbamic acid tert-butyl ester | 390.04 | 4.10 | |
| (2,3,4-Triethoxy-phenyl)-carbamic acid tert-butyl ester | 326.2 | 4.25 | |

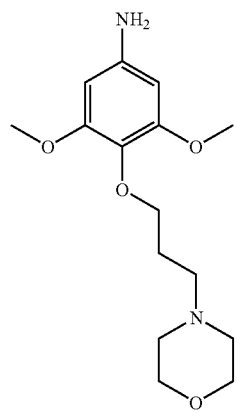

3,5-Dimethoxy-4-(3-morpholin-4-yl-propoxy)-phenylamine: The title compound was prepared following the procedure described above. The title compound was used in crude form and was not subjected to analysis.

The following compounds were similarly prepared:

| Name |
|---|
| 4-[3-(2,6-Dimethyl-morpholin-4-yl)-propoxy]-3,5-dimethoxy-phenylamine |
| 4-(3-Diethylamino-propoxy)-3,5-imethoxy-phenylamine |
| imethoxy-4-[3-(4-methyl-piperazin-propoxy]-phenylamine |
| 3,5-Dimethoxy-4-(4-morpholin-4-yl-butoxy)-phenylamine |
| 4-(4-Diethylamino-butoxy)-3,5-dimethoxy-phenylamine |

2-Fluoro-5-morpholin-4-yl-phenylamine

To a solution of 2-fluoro-5-nitro-phenylamine (4.68 g, 30 mmol), triethylamine (13.8 mL, 100 mmol) in dichloromethane (100 mL) was added trifluoroacetic anhydride (5.7 mL, 40 mmol) dropwise at 0° C. After 1 h, the reaction mixture was washed with water, diluted HCl (pH 2) and water, concentrated to give crude 2,2,2-trifluoro-N-(2-fluoro-5-nitro-phenyl)-acetamide (12.9 g).

The crude acetamide was dissolved in EtOAc (50 mL), shacked with 10% Pd/C (450 mg) under $H_2$ (50 psi) for 3 h. Filtration gave an N-(5-amino-2-fluoro-phenyl)-2,2,2-trifluoro-acetamide (8.42 g).

A mixture of the aniline (1.5 g, 6.7 mmol), bis(2-bromoethyl)ether (1.5 g, 6.7 mmol), diisopropylethylamine (4.7 mL, 31 mmol) in a mixture of toluene (100 mL) and dimethylactamide (DMA, 5 mL) was refluxed for 5 days. Concentration and column chromatography (hexane/EtOAc 7:3) gave 2,2,2-trifluoro-N-(2-fluoro-5-morpholin-4-yl-phenyl)-acetamide (1.45 g). LC-MS: m/e=291.1 (M–H), 293.2 (M+H). $^1$H-NMR (500 MHz, DMSO($d_6$)): 11.19 (s, 1H), 7.20 (t, 1H), 6.98 (dd, 1H), 6.94 (dt, 1H), 3.72 (t, 4H), 3.06 (t, 4H).

Scheme 18:

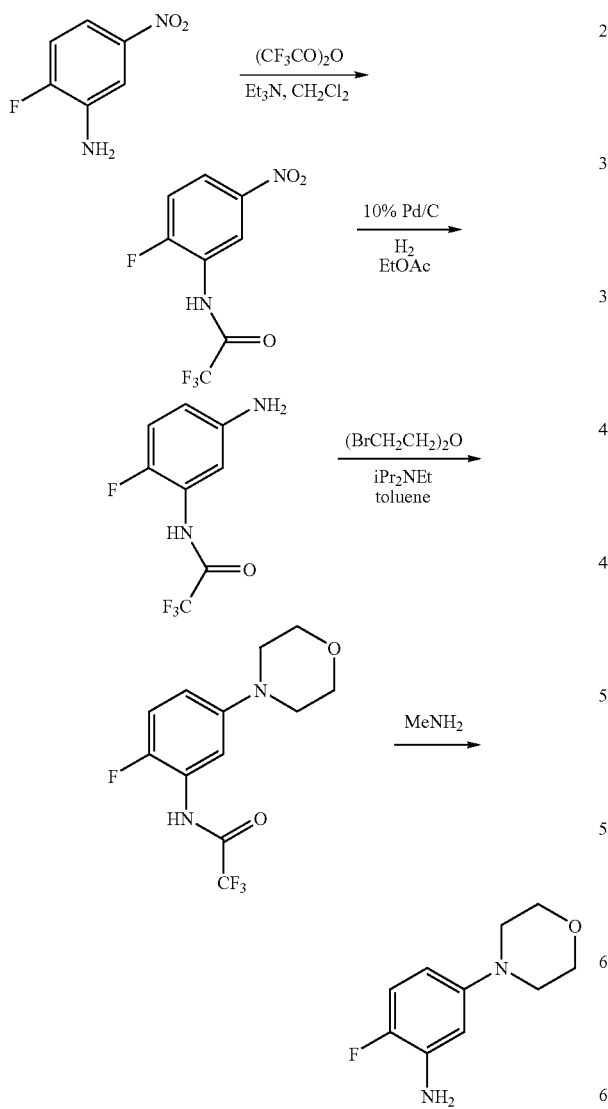

Scheme 19

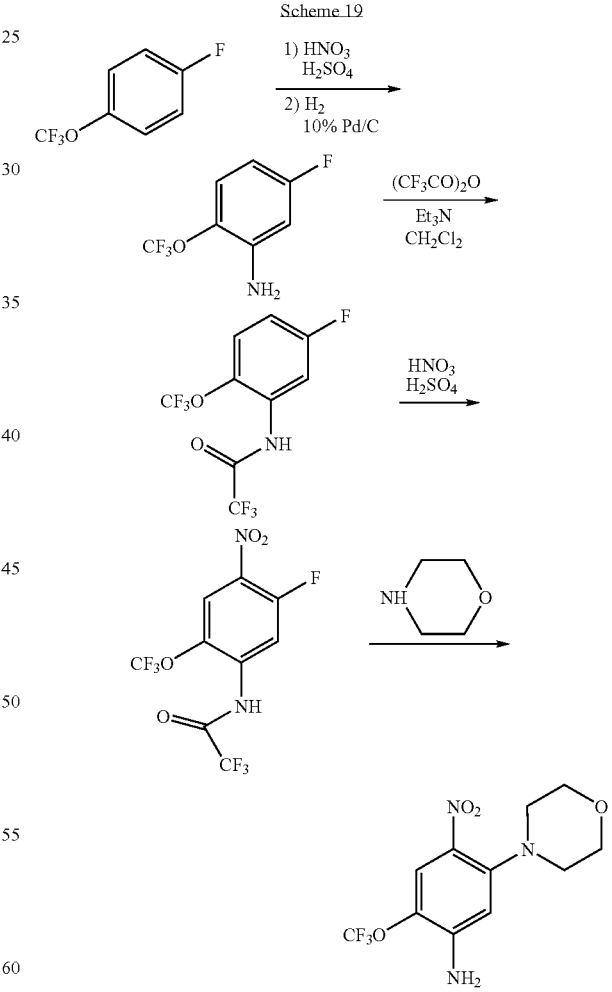

5-Morpholin-4-yl-4-nitro-2-trifluoromethoxy-phenylamine

At –10° C., 90% fuming nitric acid (25 mL) was added to concentrate sulfuric acid (50 mL) slowly to keep the temperature below 0° C. At –20° C. 1-fluoro-4-trifluoromethoxy-benzene (5 g, 27.7 mmol) was added portionwise to keep the temperature of the reaction mixture below 0° C. After addition, the reaction mixture was kept at 0° C. for 30 min, poured into ice-water, extracted with EtOAc. The extracts were concentrated to give a mixture (6.05 g) of 4-fluoro-2-nitro-1-trifluoromethoxy-benzene and 1-fluoro-2-nitro-4-trifluoromethoxy-benzene in a 3:1 ratio. The crude nitration product (6.05 g) was dissolved in ethanol (40 mL) and shacked with 10% Pd/C (310 mg) and concentrate HCl (2.8 mL) under $H_2$ (50 psi) for 3.5 h. Filtration and concentration gave a mixture (8.0 g) of 5-fluoro-2-trifluoromethoxy-phenylamine and its isomer 2-fluoro-5-trifluoromethoxy-phenylamine in 3:1 ratio. Without purification, the phenylamines (7 g, 35.8 mmol) were suspended in dichloromethane (100 mL), treated with trifluoroacetic anhydride (71 mmol) and triethylamine (20 mL) for 16 h. The reaction mixture was washed with saturated $NaHCO_3$ and brine. The organic phase was further purified by silica gel chromatography (hexane/EtOAc 9:1) to give a mixture (5.29 g) of 2,2,2-trifluoro-N-(5-fluoro-2-trifluoromethoxy-phenyl)-acetamide and its isomer in 1:4 ratio, which was nitrated in a same procedure as the first step. The nitrate (3 g) was heated under reflux with morpholine (10 mL) in 1,2-dichloroethane (30 mL) for 3 h. Evaporation to remove excess morpholine. The residue was diluted with dichloromethane, washed with HCl (0.5N, 100 mL). The organic phase was purified by FC (hexane/EtOAc 7:3 to 1:1) to give the title compound 5-morpholin-4-yl-4-nitro-2-trifluoromethoxy-phenylamine (2.48 g). LC-MS: m/e=306.1 (M–H), 308.2 (M+H). $^1$H-NMR (500 MHz, $CDCl_3$): 8.04 (s, 1H), 6.35 (s, 1H), 4.54 (br. s, 1H), 3.90 (t, 4H), 3.07 (t, 4H).

A solution of the acetamide (210 mg) in methanol (2 mL) was treated with 40% aqueous solution of methylamine (0.5 mL) for 16 h. Evaporation and the residue was suspended in water and filtration to give the title product (90 mg). FIA-MS: m/e=197.1 (M–H).

Example 34

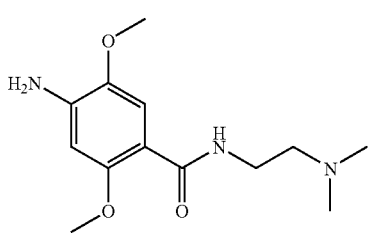

4-Amino-N-(2-dimethylaminoethyl)-2,5-dimethoxy-benzamide (DC-1787-162): To a solution of 4-amino-5-chloro-2-methoxybenzoic acid (300 mg, 1.49 mmol) in $CH_2Cl_2$ (8 mL) was added N,N-dimethylethylenediamine (263 mg, 2.98 mmol), EDCI (428 mg, 2.23 mmol), HOBT hydrate (201 mg, 1.49 mmol) and diisopropylethylenediamine (777 uL, 4.47 mmol). The reaction was stirred at RT for 48 h. The reaction was diluted with $CH_2Cl_2$, washed with saturated NaHCO3 and brine. Dried the organic phase over $MgSO_4$, filtered and evaporated to give an off white solid (423 mg, contains minor impurities). $^1$H-NMR (500 MHz, DMSO-d6) 8.08 (t, 1H), 7.70 (s, 1H), 6.47 (s, 1H), 5.96 (s, 2H), 3.82 (s, 1H), 3.34 (q, 2H), 2.45 (t, 2H), 2.25 (s, 6H) ppm; MS (FIA) 227.1 (M+H).

Example 35

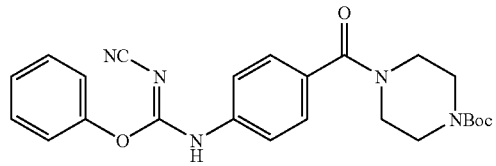

N-cyano-N'-((4-(4-tert-butoxycarbonyl)piperazinocarbonyl)-phenyl)-O-phenylisourea: A mixture of 4-(4-aminobenzoyl)-piperazine-1-carboxylic acid tert-butyl ester (520 mg, 1.70 mmol) and diphenyl cyanocarbonimide (406 mg, 1.70 mmol) in dimethylacetonitrile (3.0 mL) was heated at 150° C. for 30 min. The mixture was concentrated and purified by silica gel column chromatograghy eluted with EtOAc:hexanes (5 to 35% EtOAc) to give the title compound (177 mg, 23%) as a white solid. MS (ES+): m/z=450.1; $^1$H NMR ($CDCl_3$, 500 MHz): δ 1.48 (s, 9H), 3.26-3.83 (m, 8H), 7.16 (d, 2H), 7.34 (t, 1H), 7.42-7.49 (m, 6H).

Example 36

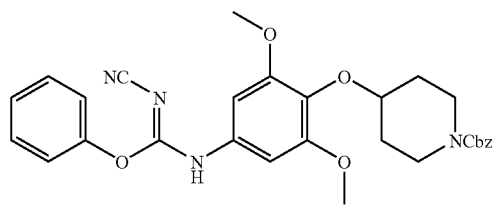

A mixture of 4-(4-amino-2,6-dimethoxy-phenoxy)-piperidine-1-carboxylic acid benzyl ester (57.8 mg, 0.180 mmol) and diphenyl cyanocarbonimide (42.8 mg, 0.180 mmol) in toluene (1.0 mL) was heated at 100° C. overnight. The mixture was concentrated and purified by silica gel column chromatograghy eluted with EtOAc:hexanes (40 to 60% EtOAc) to give the title compound (65.3 mg, 82%) as a colorless oil. MS (ES+): m/z=531.2.

Example 37

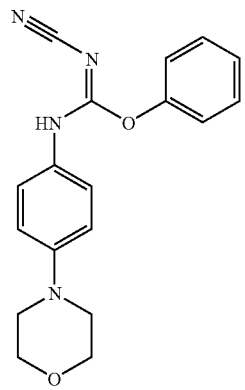

N-cyano-N'-(4-morpholino-phenyl)-O-phenylisourea: To 4-morpholino-aniline (196 g<1.10 mol) in isopropanol (2 L) was over 0.5 h diphenyl-cyanocarbon-imidate (250 g, 1.05 mol) and stirred 22 h. The solid was filtered, washing with iso-propanol until the wash was colorless, then slurrying in MTBE and filtering again. The compound was dried to provide N-cyano-N'-(4-morpholino-phenyl)-O-phenylisourea (319 g, 95% yield) as an off-white solid. $^1$H-NMR (500 MHz, DMSO-d6) 10.6 (s, 1H), 7.43 (t, 2H), 7.29 (m, 5H), 6.95 (d, 2H), 3.73 (m, 4H), 3.10 (m, 4H) ppm; MS (FIA) 323.2 (M+H); HPLC (method A) 3.126 min.

The following compounds were similarly prepared:

| Ar | MS (M + H) | Retention time (HPLC method) | $^1$H-NMR 500 MHz (solvent) |
|---|---|---|---|
| 3-chloro-4-morpholinophenyl | 357.1 | 3.360 (A) | (500 MHz, DMSO-d6) 10.6 (s, 1H), 7.43 (m, 2H), 7.35 (d, 1H), 7.29 (t, 2H), 7.18 (m, 1H), 7.08 (d, 1H), 6.95 (dd, 1H), 3.72 (m, 4H), 3.17 (m, 4H) ppm |
| 2,4,5-trimethoxyphenyl | 328.1 | 3.527 (A) | (500 MHz, DMSO-d6) 10.3 (s, 1H), 7.43 (m, 2H), 7.28 (t, 1H), 7.15 (m, 2H), 6.97 (s, 1H), 6.78 (s, 1H), 3.86 (s, 3H), 3.81 (s, 3H), 3.71 (s, 3H) ppm |
| 2-methoxyphenyl | 268.1 | 3.592 (A) | (500 MHz, DMSO-d6) 10.4 (s, 1H), 7.43 (t, 2H), 7.31 (m, 3H), 7.16 (d, 2H), 7.12 (dd, 1H), 6.98 (t, 1H), 3.88 (s, 3H), ppm |
| 3-isopropoxy-4-difluoromethoxyphenyl | 362.1 | 4.047 (A) | (500 MHz, DMSO-d6) 10.8 (s, 1H), 7.45 (t, 2H), 7.31 (m, 4H), 7.18 (d, 1H), 7.02 (d, 1H), 7.00 (t, 1H), 4.60 (m, 1H), 1.29 (d, 6H) ppm |

-continued
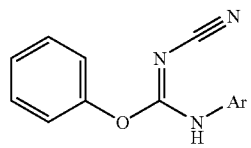
| Ar | MS (M + H) | Retention time (HPLC method) | $^1$H-NMR 500 MHz (solvent) |
|---|---|---|---|
| (3-difluoromethoxy-4-isopropoxyphenyl) | 362.2 | 4.039 (A) | (500 MHz, DMSO-d6) 10.8 (s, 1H), 7.45 (t, 2H), 7.31 (m, 4H), 7.17 (d, 1H), 7.03 (dd, 1H), 7.00 (t, 1H), 4.60 (m, 1H), 1.29 (d, 6H) ppm |
| (4-morpholinomethylphenyl) | 337.2 | 2.758 (A) | (500 MHz, DMSO-d6) 7.43 (m, 4H), 7.30 (m, 5H), 3.57 (m, 4H), 3.46 (s, 2H), 2.36 (m, 4H) ppm |
| (4-(4-methylpiperazinylmethyl)phenyl) | 350.2 | 2.622 (A) | (500 MHz, DMSO-d6) 7.2–7.5 (m, 5H), 6.95 (d, 2H), 6.5 (d, 2H), 2.7–2.4 (br m, 8H), 2.40 (s, 3H) ppm |
| (4-pyrrolidinylmethylphenyl) | 321.3 | 2.843 (A) | (500 MHz, DMSO-d6) 7.43 (m, 2H), 7.33 (m, 4H), 7.26 (m, 3H), 3.70 (m, 2H), 2.57 (s, 2H), 1.73 (m, 4H) ppm |

-continued
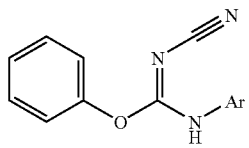
| Ar | MS (M + H) | Retention time (HPLC method) | $^1$H-NMR 500 MHz (solvent) |
|---|---|---|---|
| (4-(1-morpholinoethyl)phenyl) | 351.2 | 2.805 (A) | (500 MHz, DMSO-d6) 10.8 (s, 1H), 7.42 (m, 4H), 7.30 (m, 5H), 3.54 (m, 4H), 3.35 (m, 1H), 2.37 (m, 2H), 2.26 (m, 2H), 1.26 (d, 3H) ppm |
| (4-(1-pyrrolidinylethyl)phenyl) | 335.2 | 2.858 (A) | (500 MHz, DMSO-d6) 10.7 (s, 1H), 7.43 (t, 2H), 7.32 (m, 4H), 7.26, (m, 3H), 3.36 (m, 1H), 2.56 (m, 2H), 2.39 (m, 2H), 1.69 (m, 4H), 1.32 (d, 3H) ppm |
| (3-(morpholinomethyl)phenyl) | 337.1 | 2.630 (A) | (500 MHz, DMSO-d6) 10.9 (s, 1H), 7.45 (m, 3H), 7.35 (d, 2H), 7.30 (m, 3H), 7.16 (d, 1H), 3.54 (m, 4H), 3.47 (s, 2H), 2.35 (m, 4H) ppm |
| (3-methoxy-4-(3-morpholinopropoxy)phenyl) | 411.2 | 2.987 (A) | (500 MHz, DMSO-d6) 10.7 (s, 1H), 7.44 (t, 2H), 7.28 (m, 3H), 7.09 (s, 1H), 6.96 (s, 2H), 3.98 (t, 2H), 3.75 (s, 3H), 3.56 (m, 4H), 2.36 (m, 6H), 1.86 (m, 2H) ppm |

-continued
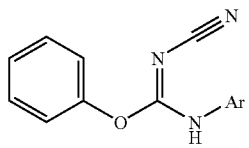
| Ar | MS (M + H) | Retention time (HPLC method) | ¹H-NMR 500 MHz (solvent) |
|---|---|---|---|
| (3,5-dimethylmorpholinopropoxy-methoxyphenyl) | 439.2 | 3.139 (A) | (500 MHz, DMSO-d6) 10.7 (s, 1H), 7.4 (m, 2H), 7.3 (m, 3H), 7.1 (s, 1H), 6.95 (s, 2H), 4.0 (m, 2H), 3.75 (s, 3H), 3.5 (m, 2H), 2.8 (m, 2H), 2.4 (m, 2H), 1.9 (m, 2H), 1.6 (m, 2H), 1.04 (d, 6H) ppm |
| (diethylaminopropoxy-methoxyphenyl) | 397.2 | 3.092 (A) | (500 MHz, DMSO-d6) 10.2 (s, 1H), 7.4 (m, 2H), 7.27 (m, 3H), 7.09 (s, 1H), 6.96 (s, 2H), 4.01 (t, 2H), 3.75 (s, 3H), 2.79 (m, 6H), 1.9 (m, 2H), 1.04 (t, 6H) ppm |
| (imidazolylpropoxy-methoxyphenyl) | 392.2 | 3.033 (A) | (500 MHz, DMSO-d6) 10.7 (s, 1H), 7.64)s, 1H), 7.4 (m, 2H), 7.3 (m, 3H), 7.15 (m, 3H), 6.96 (s, 2H), 4.13 (t, 2H), 3.88 (t, 2H), 3.78 (s, 3H), 2.51 (m, 2H) ppm |

-continued
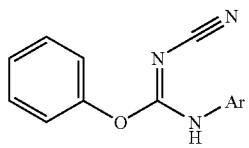
| Ar | MS (M + H) | Retention time (HPLC method) | $^1$H-NMR 500 MHz (solvent) |
|---|---|---|---|
| 4-(2-morpholinoethoxy)-3-methoxyphenyl | 397.2 | 2.769 (A) | (500 MHz, DMSO-d6) 10.7 (s, 1H), 7.44 (t, 2H), 7.28 (m, 3H), 7.10 (d, 1H), 6.98 (m, 2H), 4.06 (t, 2H), 3.75 (s, 3H), 3.57 (m, 4H), 2.68 (t, 2H), 2.47 (m, 4H) ppm |
| 4-(2-diethylaminoethoxy)-3-methoxyphenyl | 383.2 | 2.867 (A) | (500 MHz, DMSO-d6) 10.6 (s, 1H), 7.4 (m, 2H), 7.3 (m, 3H), 7.1 (s, 1H), 6.95 (m, 2H), 4.03 (t, 2H), 3.78 (m, 2H), 3.76 (s, 3H), 3.85 (m, 2H), 3.65 (m, 2H), 0.99 (t, 6H) ppm |
| 4-(4-morpholinobutoxy)-3-methoxyphenyl | 425.2 | 2.845 (A) | (500 MHz, DMSO-d6) 10.7 (s, 1H), 7.44 (t, 2H), 7.27 (m, 3H), 7.08 (s, 1H), 6.95 (s, 2H), 3.96 (t, 2H), 3.75 (s, 3H), 3.55 (m, 4H), 2.31 (m, 6H), 1.71 (m, 2H), 1.56 (m, 2H) ppm |

-continued
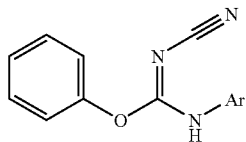
| Ar | MS (M + H) | Retention time (HPLC method) | ¹H-NMR 500 MHz (solvent) |
|---|---|---|---|
| benzo[1,3]dioxol-5-yl | 282.1 | 3.488 (A) | NMR (500 Ml4z, DMSO-d6) 10.7 (s, 1H), 7.44 (t, 2H), 7.27 (m, 3H), 7.09 (d, 1H), 6.90 (m, 2H), 6.04 (s, 2H) ppm |
| 4-(4-Boc-piperazin-1-yl)phenyl | 422.4 | | (CDCl$_3$): δ 1.49 (s, 9H), 3.13–3.19 (m, 4H), 3.56–3.64 (m, 4H), 6.94 (d, 2H), 7.13 (d, 2H), 7.24–7.33 (m, 3H), 7.39–7.44 (m, 2H) |
| 4-(4-cyclopropyl-piperazin-1-yl)phenyl | 362.2 | | (CDCl$_3$): δ 0.39–0.54 (m, 4H), 1.61–1.72 (m, 1H), 2.71–2.83 (m, 4H), 3.13–3.22 (m, 4H), 6.90 (d, 2H), 7.12 (d, 2H), 7.20–7.33 (m, 3H), 7.37–7.44 (m, 2H) |
| 4-(2,6-dimethylmorpholin-4-yl)phenyl | 351.3 | | (CDCl$_3$): δ 1.28 (d, 6H), 2.42–2.50 (m, 2H), 3.43–3.49 (m, 2H), 3.77–3.87 (m, 2H), 6.93 (d, 2H), 7.14 (d, 2H), 7.24–7.34 (m, 3H), 7.39–7.46 (m, 2H) |
| 4-(2-hydroxyethylamino)phenyl | 297.2 | | (CD$_3$SOCD$_3$): δ 3.01–3.13 (m, 2H), 3.48–3.60 (m, 2H), 4.59–4.70 (m, 1H), 5.54–5.67 (m, 1H), 6.57 (d, 2H), 7.05–7.54 (m, 7H), 10.4 (s, 1H) |

-continued

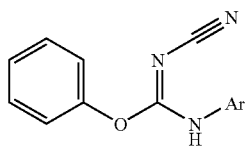

| Ar | MS (M + H) | Retention time (HPLC method) | ¹H-NMR 500 MHz (solvent) |
|---|---|---|---|
| 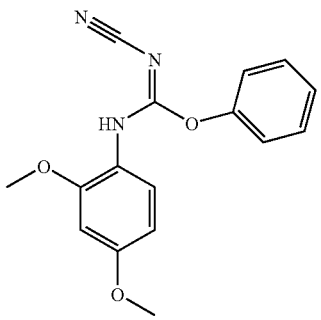 | 380.2 | 1.77 | |

Example 38

N-cyano-N'-(2,4-dimethoxy-phenyl)-O-phenylisourea:

To a suspension of diphenyl-cyanocarbon-imidate (3.0 g, 12.59 mmol) in isopropanol (15 mL) was added 2,4-dimethoxyaniline (2.02 g, 13.22 mmol). The reaction was stirred at RT for 24-48 h. The solid was filtered, washed with iso-propanol and dried under high vacuum to give the title compound as a brown solid (3.55 g, 95% yield). ¹H-NMR (500 MHz, DMSO-d6) 10.60 (br s, 1H), 7.52-7.40 (m, 3H), 7.35-7.07 (m, 3H), 7.00 (d,d, 1H), 6.85 (dd, 1H)3.81 (s, 3H) ppm; LC-MS 289.12 (M+H); HPLC (method A) 3.32 min.

The following compounds were similarly prepared

| Ar | MS (M + H) | Retention time (HPLC method) | ¹H-NMR 500 MHz (solvent) |
|---|---|---|---|
| 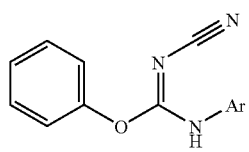 | 286.13 | 3.36 | DMSO d6: 10.60 (br s, 1H), 7.52–7.40 (m, 3H), 7.35–7.07 (m, 3H), 7.00 (d, d, 1H), 6.85 (dd, 1H) 3.81 (s, 3H) |

-continued

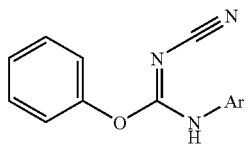

| Ar | MS (M + H) | Retention time (HPLC method) | ¹H-NMR 500 MHz (solvent) |
|---|---|---|---|
| 2,4-dimethoxyphenyl | 289.12 | 3.32 | DMSO d6: 10.28 (s, 1H), 7.51–7.38 (m, 2H), 7.35–7.05 (m, 4H), 6.69 (s, 1H), 6.52 (d, 1H), 3.88 (s, 3H) 3.80 (s, 3H) |
| 4-methoxy-2-methylphenyl | 282.13 | 3.34 | DMSO d6: 10.35 (br s, 1H), 7.55–7.04 (m, 6H), 6,86 (s, 1H), 6.85–6.75 (m, 1H) |
| 2,3-dimethoxyphenyl | 298.1 | 3.3 | DMSO d6: 10.47 (s, 1H), 7.43 (t, 2H), 7.28 (t, 2H), 7.19 (d, 2H), 7.15–7.03 (m, 2H), 6.97 (d, d, 1H) 3.83 (s, 3H), 3.80 (s, 3H) |
| 4-(diethylamino)-2-methylphenyl | 323.2 | 1.94 | DMSO d6: 10.21–9.95 (m, 1H), 7.55–6.95 (m, 6H), 6.57–6.43 (m, 2H), 3.39–3.22 (m, 4H), 2.31–2.09 (m, 3H), 1.12–0.97 (m, 6H) |
| 2-methylphenyl | 252.15 | 3.33 | DMSO d6: 10.49 (s, 1H), 7.57–7.07 (m, 8H), 2.32 (s, 3H) |
| 5,6,7,8-tetrahydronaphthalen-1-yl | 292.16 | 3.88 | DMSO d6: 10.35 (s, 1H), 7.58–7.45 (m, 2H), 7.32–7.01 (m, 6H), 2.81–2.64 (m, 4H), 1.85–1.62 (m, 4H) |
| 2-methoxy-4-morpholinophenyl | 353.1 | 3.06 | DMSO d6: 10.16 (s, 1H), 7.51–7.45 (m, 2H), 7.27 (t, 1H), 7.19–7.01 (m, 3H), 7.63 (d, 1H), 6.5 (d, 1H) 3.88 (s, 3H), 3.79–3.61 (m, 4H) |

-continued
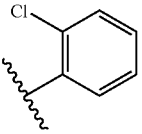
| Ar | MS (M + H) | Retention time (HPLC method) | ¹H-NMR 500 MHz (solvent) |
|---|---|---|---|
| 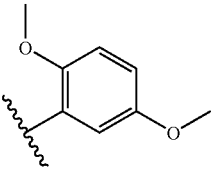 | 271.98 | 3.42 | DMSO d6: 10.89 (s, 1H), 7.65–7.51 (m, 2H), 7.49–7.36 (m, 4H), 7.35–7.16 (m, 3H) |
| 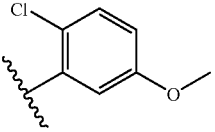 | 298.12 | 3.32 | DMSO d6: 10.45 (s, 1H), 7.43 (t, 2H), 7.18 (t, 1H), 7.03 (d, 2H), 7.04 (d, 1H), 6.95 (d, 1H), 6.89 (dd, 1H), 3.82 (s, 3H), 3.72 (s, 3H) |
| 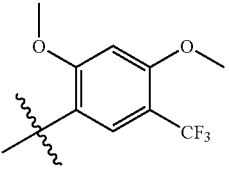 | 302.06 | 3.49 | DMSO d6: 10.88 (s, 1H), 7.48 (d, 1H), 7.44 (t, 1H), 7.30 (t, 1H) 7.30–7.17 (m, 3H), 6.98 (dd, 1H), 3.78 (s, 3H), |
| 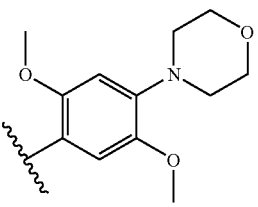 | 364.0 (M − H) | 3.8 | DMSO d6: 10.35 (s, 1H), 7.59 (s, 1H), 7.52–7.40 (m, 2H), 7.35–7.06 (m, 3H), 6.93 (s, 1H), 4.02 (s, 3H), 3.95 (s, 3H) |
| 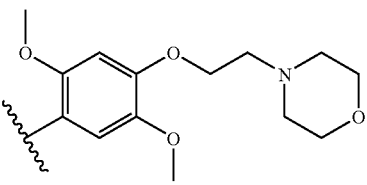 | 383.2 | 3.0 | DMSO d6: 10.39 (s, 1H), 7.42 (t, 2H), 7.27 (t, 1H), 7.15 (br s, 2H), 6.96 (s, 1H), 6.63 (s, 1H), 3.85 (s, 3H), 3.87–3.63 (m, 7H), 3.09–2.90 (m, 4H) |
| 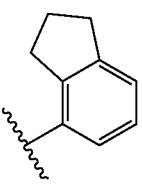 | 427.25 | 1.85 | DMSO d6: 10.29 (s, 1H), 7.46–7.40 (m, 2H), 7.27 (t, 1H), 7.15 (br s, 2H), 6.97 (s, 1H), 6.80 (s, 1H), 4.13 (t, 2H), 3.85 (s, 3H), 3.71 (s, 3H), 3.57 (t, 4H), 2.69 (t, 2H), 2.53–2.42 (m, 4H) |
|  | 278.2 | 3.73 | DMSO d6: 10.55 (s, 1H), 7.49–7.35 (m, 2H), 7.33–7.02 (m, 6H), 2.99–2.82 (m, 4H) |

-continued

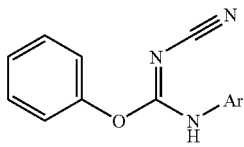

| Ar | MS (M + H) | Retention time (HPLC method) | $^1$H-NMR 500 MHz (solvent) |
|---|---|---|---|
| 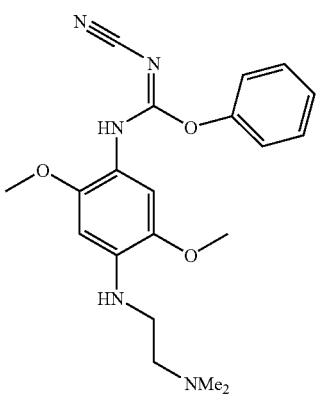 | 318.1 | 3.78 | DMSO d6: 11.23 (s, 1H), 7.51–7.13 (m, 8H) |

Example 39

N-cyano-1-[4-(2-dimethylamino-ethylamino)-2,5-dimethoxyphenyl]-2-phenylisourea: To a solution of N-(2-dimethylaminoethyl)-2,5-dimethoxybenzene 1,4-diamine hydrochloride (0.05 g, 0.143 mmol) in distilled water (1 mL) was added K$_2$CO$_3$ (0.065 g, 0.47 mmol). This was diluted with EtOAc (1 mL) and diphenylcyano-carbonimidate (0.032 g, 0.136 mmol) was added. The reaction was stirred at RT for 18 h. The precipitate was filtered and washed with minimal EtOAc to give the title compound as a light purple solid (0.015 g, 29% yield). $^1$H-NMR (500 MHz, DMSO-d6) 10.11 (s, 1H), 7.51-7.33 (m, 2H), 7.31-6.98 (m, 3H), 6.81-6.64 (m, 1H), 6.28 (br s, 1H), 4.87 (br s, 1H), 3.85-3.62 (m, 5H), 3.12 (s, 3H), 2.17 (s, 6H) ppm; LC-MS 384.3 (M+H); HPLC 1.9 min(method A).

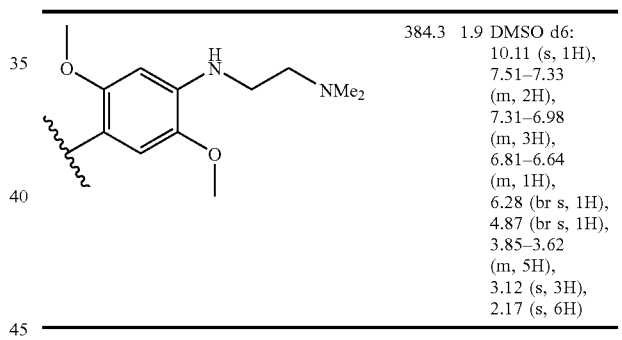

384.3 1.9 DMSO d6: 10.11 (s, 1H), 7.51–7.33 (m, 2H), 7.31–6.98 (m, 3H), 6.81–6.64 (m, 1H), 6.28 (br s, 1H), 4.87 (br s, 1H), 3.85–3.62 (m, 5H), 3.12 (s, 3H), 2.17 (s, 6H)

Example 40

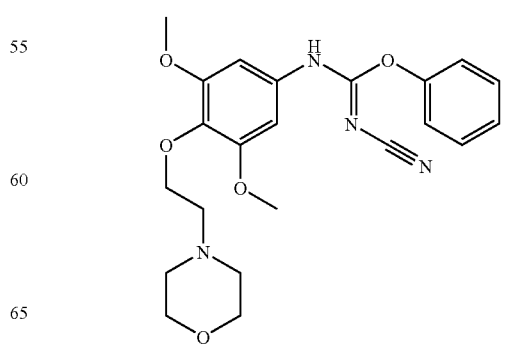

N-cyano-1-[3,5-dimethoxy-4-(2-morpholino4-yl-ethoxy)phenyl]-2-phenylisourea: A solution of 3,5-dimethoxy-4-(2-morpholin-4-yl-ethoxy-phenylamine (0.62 mmol) in isopropanol (5 mL) and triethylamine (0.25 mL, 1.79 mmol) was stirred at RT for 10 min. A solution of diphenylcyanocarbonimidate (163 mg, 0.68 mmol) in isopropanol (1 mL) was added and the reaction heated at 60° C. for 3 h. Evaporated solvent and purified by column chromatography, eluting with 2% to 5% MeOH in $CH_2Cl_2$ Isolated the title compound as a yellow solid (0.275 g, quantitative). $^1$H-NMR (500 MHz, DMSO-d6) 10.9-10.49 (br, 1H), 7.45 (t, 2H), 7.35-7.25 (m, 3H), 5.76(s, 2H), 4.0-3.94 (m, 2H), 3.76 (s, 6H), 3.68-3.50 (br s, 4H), 2.80-2.35 (m, 6H) ppm; LC-MS 427.18 (M+H); HPLC 1.78 min.

| Ar | MS (M + H) | Retention time (HPLC method) | $^1$H-NMR 500 MHz (solvent) |
|---|---|---|---|
| 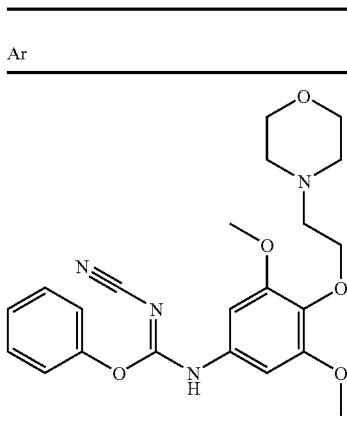 | 427.18 | 1.78 | DMSO d6: 10.9–10.49 (br, 1H), 7.45 (t, 2H), 7.35–7.25 (m, 3H), 5.76 (s, 2H), 4.0–3.94 (m, 2H), 3.76 (s, 6H), 3.68–3.50 (br s, 4H), 2.80–2.35 (m, 6H) |

Example 41

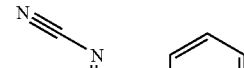

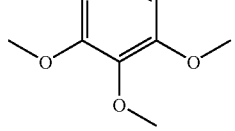

N-cyano-N'-(3,4,5-trimethoxyphenyl)-O-phenylisourea:
A mixture of 3,4,5-trimethoxyaniline (1.83 g, 10 mmol) and diphenyl-cyanocarbon-imidate (2.62 g, 11 mmol) in isopropanol (30 mL) was stirred at 100-110° C. for 1 h. The reaction was cooled and filtered, washing with ether to provide the title compound (2.79 g, 85% yield) as a white solid. $^1$H-NMR (500 MHz, DMSO-d6) 10.8 (s, 1H), 7.45 (t, 2H), 7.31 (m, 3H), 6.83 (s, 2H), 3.76 (s, 6H), 3.65 (s, 3H) ppm; MS (FIA) 328.1 (M+H); HPLC (method A) 3.211 min.

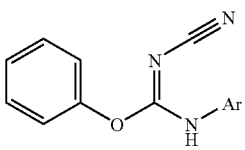

The following compounds were similarly prepared

| Ar | MS | Retention time (HPLC method) | ¹H-NMR 500 MHz (solvent) |
|---|---|---|---|
| 3,4-dimethoxyphenyl | 298.1 | 3.185 (A) | NMR (500 MHz, DMSO-d6) 10.7 (s, 1H), 7.44 (t, 2H), 7.28 (m, 3H), 7.10 (s, 1H), 6.97 (m, 2H), 3.75 (s, 6H) ppm |
| 2,4-difluorophenyl | 274.1 | 3.638 (A) | NMR (500 MHz, DMSO-d6) 10.7 (s, 1H), 7.6 (m, 1H), 7.4 (m, 3H), 7.31 (t, 1H), 7.15 (m, 3H) ppm |
| 4-(diethylamino)phenyl | 309.1 | 2.654 (A) | NMR (500 MHz, DMSO-d6) 10.5 (s, 1H), 7.43 (m, 2H), 7.28 (t, 1H), 7.21 (m, 4H), 6.64 d, 2H), 3.32 (q, 4H), 1.07 (t, 6H) ppm |
| 4-acetylphenyl | 280.1 | 3.268 (A) | NMR (500 MHz, DMSO-d6) 11.2 (s, 1H), 7.99 (dd, 2H), 7.62 (d, 2H), 7.46 (t, 2H), 7.35 (m, 3H), 2.57 (s, 3H) ppm |
| 4-benzoylphenyl | 342.1 | 3.629 (A) | NMR (500 MHz, DMSO-d6) 11.2 (s, 1H), 7.80 (d, 2H), 7.73 (m, 2H), 7.67 (m, 3H), 7.57 (t, 2H), 7.47 (t, 2H), 7.35 (m, 3H) ppm |

-continued

| Ar | MS | Retention time (HPLC method) | ¹H-NMR 500 MHz (solvent) |
|---|---|---|---|
| *3-acetylphenyl* | 280.1 | 3.184 (A) | NMR (500 MHz, DMSO-d6) 11.0 (s, 1H), 8.04 (d, 2H), 7.84 (d, 1H), 7.76 (dd, 2H), 7.57 (t, 1H), 7.46 (t, 2H), 7.31 (m, 3H), 2.59 (s, 3H) ppm |
| *3,5-dimethoxy-4-(3-morpholinopropoxy)phenyl* | 441.2 | 3.017 (A) | NMR (500 MHz, DMSO-d6) 10.8 (s, 1H), 7.46 (m, 2H), 7.36 (d, 1H), 7.30 (d, 1H), 7.15 (m, 3H), 6.85 (s, 1H), 4.0 (m, 2H), 3.91 (m, 2H), 3.76 (s, 6H), 3.66 (t, 2H), 3.48 (m, 2H), 3.35 (m, 2H), 3.1 (m, 2H), 2.01 (m, 2H) ppm |
| *3,5-dimethoxy-4-(3-(2,6-dimethylmorpholino)propoxy)phenyl* | 469.2 | 3.194 (A) | NMR (500 MHz, DMSO-d6) 10.8 (s, 1H), 7.46 (m, 2H), 7.36 (d, 1H), 7.30 (d, 1H), 7.15 (t, 3H), 6.85 (s, 1H), 3.91 (m, 2H), 3.83 (m, 2H), 3.78 (s, 6H), 3.50 (d, 2H), 3.31 (m, 2H), 2.67 (m, 2H), 2.01 (m, 2H), 1.15 (d, 6H) ppm |
| *3,5-dimethoxy-4-(3-(diethylamino)propoxy)phenyl* | 397.3 | 3.037 (A) | NMR (500 MHz, DMSO-d6) 7.44 (t, 2H), 7.28 (m, 3H), 7.10 (s, 1H), 6.95 (s, 2H), 4.0 (t, 2H), 3.75 (s, 6H), 3.18 (s, 2H), 2.85 (m, 4H), 1.95 (m, 2H), 1.10 (t, 6H) ppm |

| Ar | MS | Retention time (HPLC method) | $^1$H-NMR 500 MHz (solvent) |
|---|---|---|---|
| 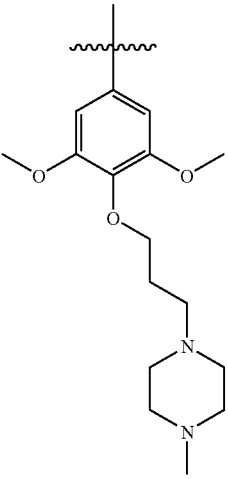 | 454.2 | 2.885 (A) | NMR (500 MHz, DMSO-d6) 10.8 (s, 1H), 7.4 (m, 2H), 7.3 (m, 2H), 7.30 (d, 1H), 7.15 (m, 3H), 6.7 (s, 2H), 3.9 (m, 2H), 3.77 (s, 6H), 3.75 (m, 2H), 3.3 (m, 4H), 2.85 (s, 3H), 1.97 (m, 2H) ppm |
| 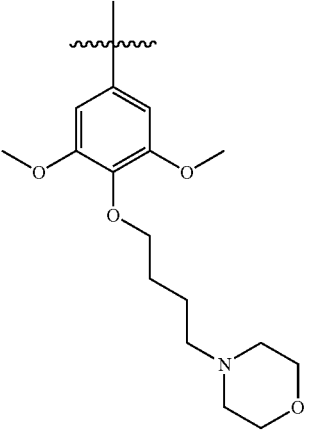 | 455.2 | 3.095 (A) | NMR (500 MHz, DMSO-d6) 10.8 (s, 1H), 7.46 (m, 2H), 7.36 (d, 1H), 7.30 (d, 1H), 7.15 (m, 3H), 6.85 (s, 1H), 4.0 (m, 2H), 3.9 (m, 2H), 3.77 (s, 6H), 3.6 (t, 2H), 3.45 (d, 2H), 3.15 (m, 2H), 3.05 (m, 2H), 1.85 (m, 2H), 1.65 (m, 2H) ppm |
| 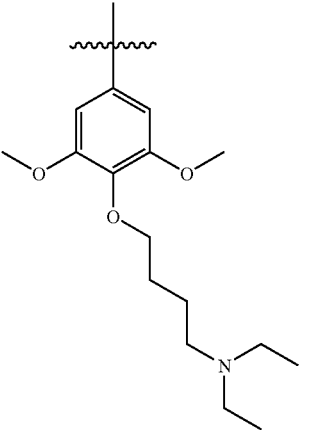 | 441.2 | 3.205 (A) | NMR (500 MHz, DMSO-d6) 10.8 (s, 1H), 7.46 (m, 2H), 7.36 (d, 1H), 7.30 (d, 1H), 7.15 (m, 3H), 6.85 (s, 1H), 3.9 (m, 2H), 3.74 (s, 6H), 3.1 (m, 10H), 1.8 (m, 2H), 1.65 (m, 2H), 1.2 (t, 6H) ppm |
| 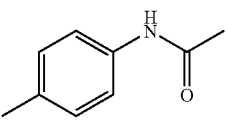 | 295.1 | 2.54 | DMSO d6: 10.76 (s, 1H), 10.03 (s, 1H), 7.58 (d, 2H), 7.46–7.40 (m, 4H), 7.31–7.25 (m, 3H), 2.04 (s, 3H) |

-continued
| Ar | MS | Retention time (HPLC method) | ¹H-NMR 500 MHz (solvent) |
|---|---|---|---|
| 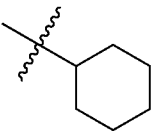 | 244.2 | | |
| 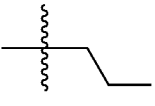 | 204.2 | | |
| 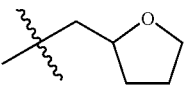 | 246.2 | | |
| 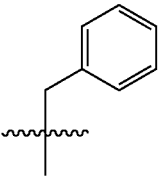 | 252.2 | | |
| 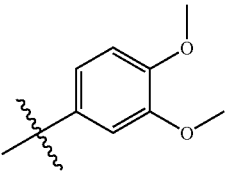 | 298.2 | | |
| 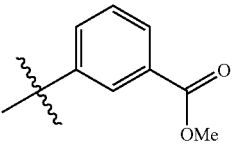 | 296.1 | | |
| 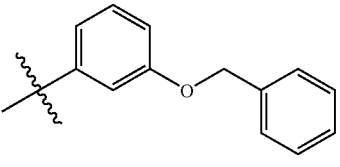 | 344.2 | | |
| 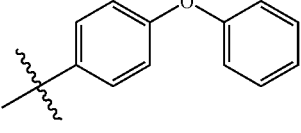 | 330.2 | | |
| 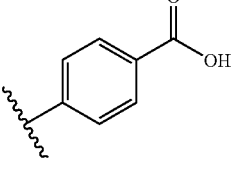 | 282.0 | | |

-continued
| Ar | MS | Retention time (HPLC method) | ¹H-NMR 500 MHz (solvent) |
|---|---|---|---|
| 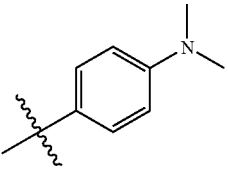 | 281.2 | | |
| 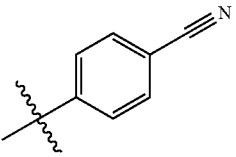 | 263.2 | | |
| 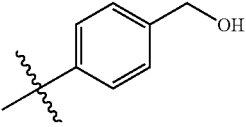 | 268.2 | | |
| 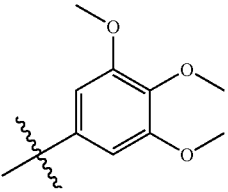 | 328.0 | 2.01 | |
| 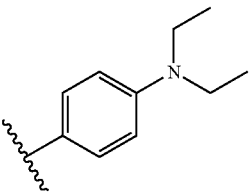 | 309.1 | 1.9 | |
| 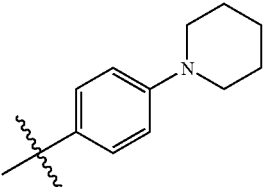 | 321.1 | 2.1 | |
| 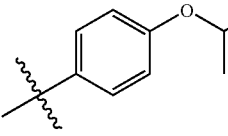 | 296.0 | 3.7 | |
| 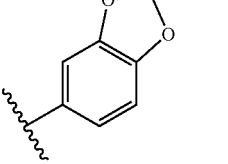 | 282.0 | 3.2 | |

-continued
| Ar | MS | Retention time (HPLC method) | ¹H-NMR 500 MHz (solvent) |
|---|---|---|---|
| 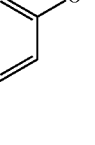 | 296.0 | 3.2 | |
| 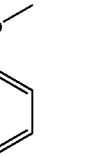 | 282.0 | 3.6 | |
| 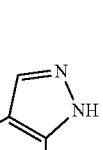 | 278.0 | 2.6 | |
|  | 321.0 | 2.9 | |
| 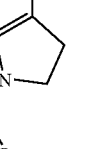 | 282.0 | 3.5 | |
| 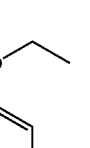 | 323.0 | 3.0 | |
|  | 272.1 | 3.38 | |

-continued
| Ar | MS | Retention time (HPLC method) | ¹H-NMR 500 MHz (solvent) |
|---|---|---|---|
| 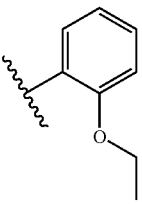 | 282.1 | 3.60 | |
| 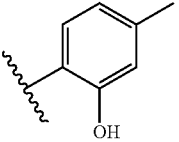 | 268.1 | 4.03 | |
| 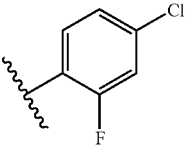 | 290.1 | 3.64 | |
| 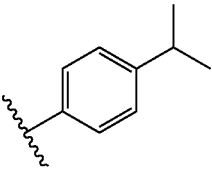 | 280.1 | 4.03 | |
| 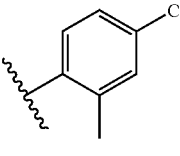 | 286.1 | 3.73 | |
| 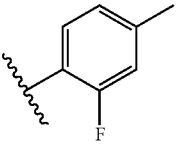 | 270.1 | 3.51 | |
| 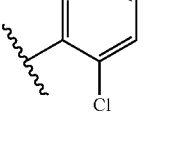 | 286.1 | 3.68 | |
| 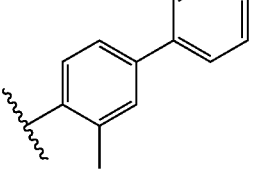 | 328.1 | 4.16 | |

-continued
| Ar | MS | Retention time (HPLC method) | $^1$H-NMR 500 MHz (solvent) |
|---|---|---|---|
| 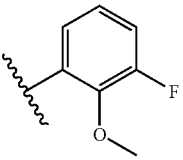 | 286.1 | 3.42 | |
| 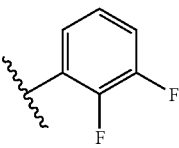 | 274.1 | 3.34 | |
| 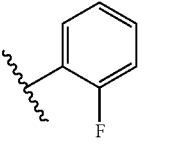 | 256.1 | 3.25 | |
| 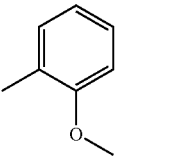 | 268.2 | | |
| 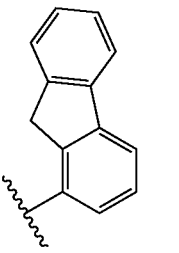 | 326.2 | | |
| 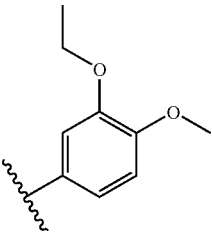 | 312.2 | | |
| 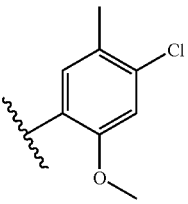 | 316.1 | | |

-continued
| Ar | MS | Retention time (HPLC method) | ¹H-NMR 500 MHz (solvent) |
|---|---|---|---|
| 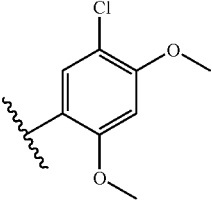 | 332.1 | | |
| 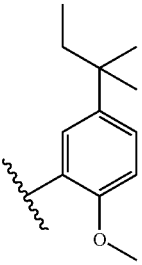 | 338.2 | 4.63 | |
| 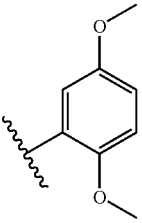 | 298.0 | 3.39 | |
| 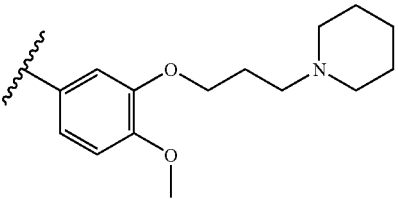 | 409.2 | 2.07 | |
| 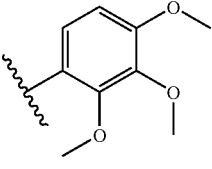 | 327.8 | 3.28 | |
| 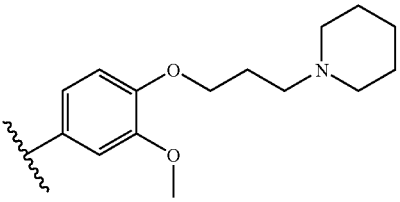 | 409.2 | 2.03 | |
| 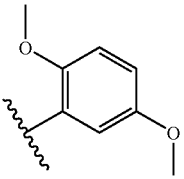 | 326.1 | 3.94 | |

-continued
| Ar | MS | Retention time (HPLC method) | ¹H-NMR 500 MHz (solvent) |
|---|---|---|---|
| 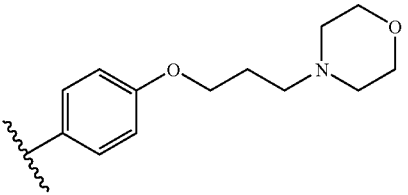 | 381.17 | 1.88 | |
| 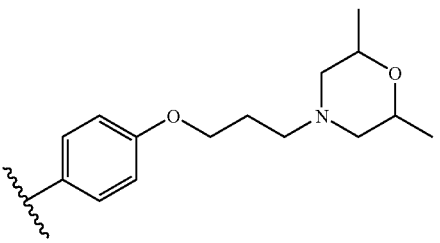 | 409.22 | 2.10 | |
| 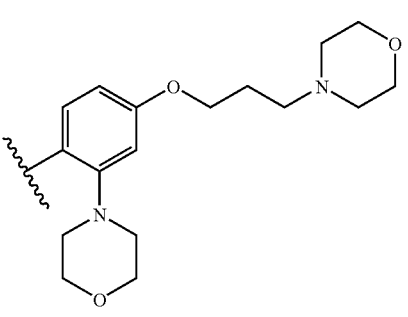 | 466.34 | | |
| 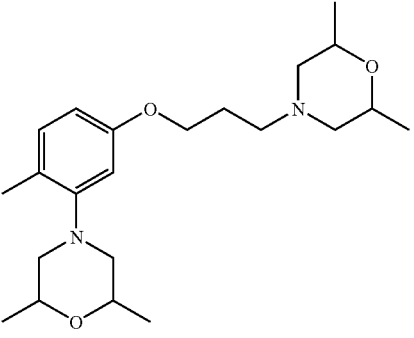 | 522.3 | 2.47 | |
| 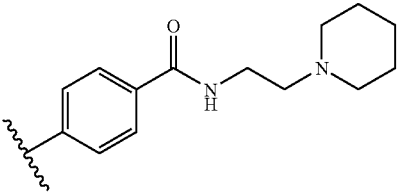 | 392.32 | 1.90 | |
| 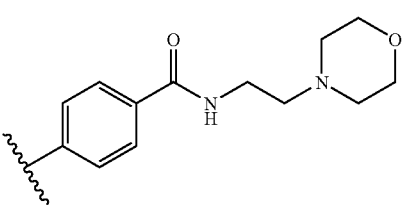 | 394.21 | 1.76 | |

-continued
| Ar | MS | Retention time (HPLC method) | $^1$H-NMR 500 MHz (solvent) |
|---|---|---|---|
| 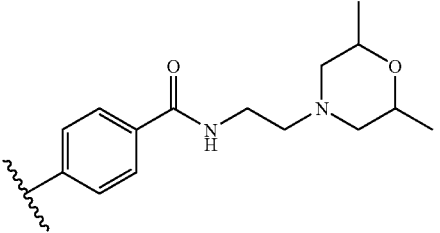 | 422.35 | 2.06 | |
| 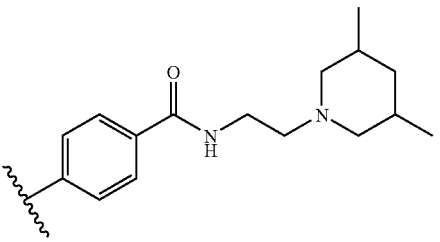 | 420.26 | | |
| 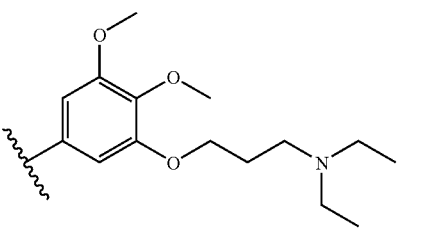 | 427.21 | 2.11 | |
| 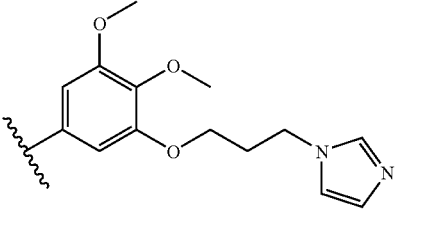 | 422.22 | 2.04 | |
| 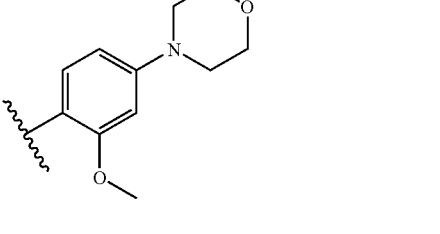 | 353.23 | 3.19 | |
| 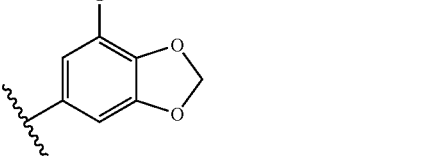 | 312.04 | 3.33 | |

-continued

| Ar | MS | Retention time (HPLC method) | ¹H-NMR 500 MHz (solvent) |
|---|---|---|---|
| [3,5-dimethoxy-4-(3-(diethylamino)propoxy)phenyl] | 427.26 | 2.09 | |
| [3-(methoxycarbonyl)phenyl] | 296.1 | | |
| [4-carboxyphenyl] | 282.0 | | |
| [3-methoxyphenyl-methyl] | 268.1 | 3.45 (A) | DMSO (d6): 10.84 (s, 1H), 7.45 (t, 2H), 7.30 (m, 4H), 7.06 (m, 2H), 6.82 (dd, 1H). |
| [4-methoxyphenyl-methyl] | 268.1 | 3.38 (A) | DMSO (d6): 10.67 (s, 1H), 7.43 (t, 2H), 7.37 (d, 2H), 7.26 (d, 2H), 7.28 (t, 1H), 6.96 (d, 2H). |
| [4-(methoxycarbonyl)phenyl-methyl] | 296.1 | 3.40 (A) | DMSO (d6): 11.17 (s, 1H), 7.98 (d, 2H), 7.64 (d, 2H), 7.46 (t, 2H), 7.34 (d, 2H), 7.31 (t, 1H), 3.84 (s, 3H). |
| [3-carbamoylphenyl-methyl] | 281.1 | 2.77 (A) | DMSO (d6): 10.95 (s, 1H), 8.03 (s, 1H), 7.95 (s, 1H), 7.74 (d, 1H), 7.62 (d, 1H), 7.46 (m, 4H), 7.30 (m, 3H), |
| [4-sulfamoylphenyl-methyl] | 317.0 | 2.80 (A) | DMSO (d6): 11.04 (s, 1H), 7.95 (s, 1H), 7.69 (td, 2H), 7.60 (t, 1H), 7.45 (m, 4H), 7.31 (m,3H), |
| [3-sulfamoylphenyl-methyl] | 317.0 | 2.83 (A) | DMSO (d6): 11.08 (s, 1H), 7.82 (d, 2H), 7.63 (d, 2H), 7.45 (t, 2H), 7.33 (d, 2H), 3.31 (d, 2H), 7.30 (t, 1H). |

-continued
| Ar | MS | Retention time (HPLC method) | 1H-NMR 500 MHz (solvent) |
|---|---|---|---|
| 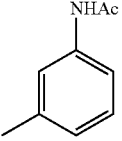 | 295.1 | 2.94 (A) | DMSO (d6): 10.85 (s, 1H), 10.01 (s, 1H), 7.80 (s, 1H), 7.45 (t, 2H), 7.38 (d, 1H), 7.27 (m, 4H), 7.13 (d, 1H), 2.04 (s, 3H). |
| 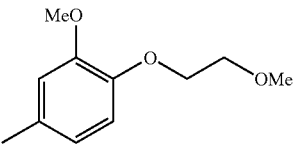 | 342.1 | 3.19 (A) | DMSO (d6): 10.63 (s, 1H), 7.44 (t, 2H), 7.29 (d, 1H), 7.26 (d, 2H), 7.10 (s, 1H), 6.95 (s, 2H), 4.06 (m, 2H), 3.75 (s, 3H), 3.64 (m, 2H), 3.30 (s, 3H). |
| 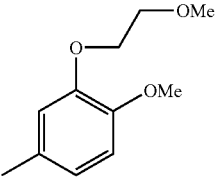 | 342.1 | 3.20 (A) | DMSO (d6): 10.62 (s, 1H), 7.43 (t, 2H), 7.29 (d, 1H), 7.25 (d, 2H), 7.10 (d, 1H), 6.97 (m, 2H), 4.06 (dd, 2H), 3.75 (s, 3H), 3.66 (dd, 2H), 3.29 (s, 3H). |
| 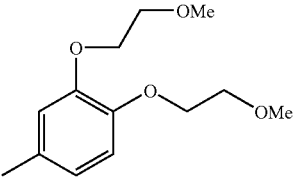 | 386.2 | 3.21 (A) | DMSO (d6): 10.60 (s, 1H), 7.44 (t, 2H), 7.29 (d, 1H), 7.26 (d, 2H), 7.11 (d, 1H), 6.97 (m, 2H), 4.08 (m, 4H), 3.64 (dd, 4H), 3.29 (s, 3H), 3.31 (s, 3H), 3.30 (s, 3H). |
| 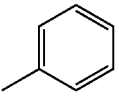 | 238.2 | 3.27 (A) | DMSO (d6): 10.82 (s, 1H), 7.45 (m, 6H), 7.23 (m, 4H). |
| 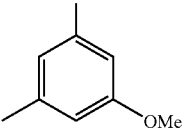 | 298.1 | 3.39 (A) | DMSO (d6): 10.77 (s, 1H), 7.44 (t, 2H), 7.29 (d, 2H), 6.68 (d, 2H), 6.39 (t, 1H), 3.73 (s, 6H). |
| 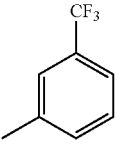 | 306.1 | 3.61 (A) | DMSO (d6): 11.01 (s, 1H), 7.86 (s, 1H), 7.79 (d, 1H), 7.65 (t, 1H), 7.60 (d, 1H), 7.46 (m, 2H), 7.35 (m, 3H). |
| 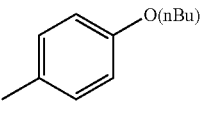 | 310.1 | 3.86 (A) | DMSO (d6): 10.62 (s, 1H), 7.43 (t, 2H), 7.33 (d, 2H), 7.27 (t, 1H), 7.24 (d, 2H), 6.93 (d, 2H), 3.95 (t, 2H), 1.68 (m, 2H), 1.42 (m, 2H), 0.92 (t, 3H). |
| 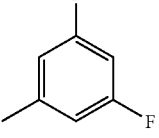 | 274.1 | 3.59 (A) | DMSO (d6): 10.91 (s, 1H), 7.62 (ddd, 1H), 7.49 (t, 1H), 7.45 (t, 2H), 7.31 (m, 4H). |

-continued

| Ar | MS | Retention time (HPLC method) | ¹H-NMR 500 MHz (solvent) |
|---|---|---|---|
| 2-chloro-3,6-dimethoxy-4-methylphenyl | 332.0 | 3.63 (A) | DMSO (d6): 10.50 (s, 1H), 7.43 (t, 2H), 7.28 (t, 1H), 7.22 (d, 2H), 7.17 (d, 2H), 3.84 (s, 3H), 3.81 (s, 3H). |
| 4-chloro-2-methyl-methoxyphenyl | 302.1 | 3.60 (A) | |
| methyl 4-methoxy-3-methylbenzoate | 326.1 | 3.32 (A) | |
| 4-methoxy-3-methyl-(trifluoromethyl)phenyl | 336.1 | 3.71 (A) | |
| 2,3,5-trimethoxy-6-methylphenyl | 328.1 | 3.55 (A) | DMSO (d6): 8.70 (s, 1H), 7.55 (t, 1H), 7.45 (m, 1H), 7.40 (t, 1H), 6.92 (s, 2H), 6.34 (s, 2H), 3.69 (s, 6H), 3.56 (s, 3H). |
| 2,5-difluoro-methylphenyl | 274.1 | 3.52 (A) | DMSO (d6): 10.92 (s, 1H), 7.45 (m, 4H), 7.30 (t, 1H), 7.23 (m, 3H). |
| 4-methoxy-3-methyl-(trifluoromethoxy)phenyl | 352.1 | 4.11 (A) | |
| 2-(trifluoromethoxy)-methylphenyl | 322.1 | 3.75 (A) | |
| 2-isopropoxy-5-methoxy-methylphenyl | 326.2 | 4.00 (A) | |
| 4-(trifluoromethoxy)-2-methyl-5-nitro-morpholinophenyl | 452.2 | 4.08 (A) | DMSO (d6): 11.30 (s, 1H), 8.07 (s, 1H), 7.55 (s, 1H), 7.46 (t, 2H), 7.30 (t, 1H), 7.18 (d, 2H), 3.70 (t, 4H), 3.02 (t, 4H). |

-continued
| Ar | MS | Retention time (HPLC method) | $^1$H-NMR 500 MHz (solvent) |
|---|---|---|---|
| 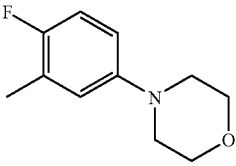 | 341.2 | 3.50 (A) | |
| 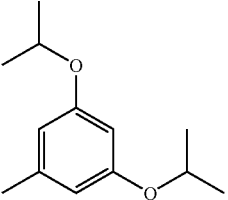 | 354.2 | 4.30 (A) | DMSO (d6): 10.69 (s, 1H), 7.44 (t, 2H), 7.29 (d, 1H), 7.28 (d, 2H), 6.61 (s, 2H), 6.30 (t, 1H), 4.55 (m, 2H), 1.24 (d, 12H). |
| 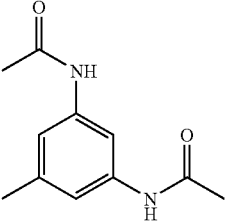 | 352.2 | 2.35 | |
| 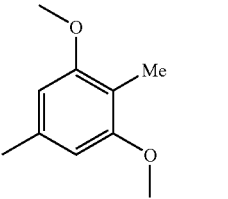 | 312.2 | 3.88 (A) | |
| 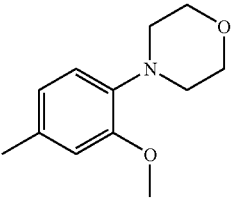 | 353.3 | 3.02 (A) | DMSO (d6): 10.66 (s, 1H), 7.44 (t, 2H), 7.29 (d, 1H), 7.26 (d, 2H), 7.08 (d, 1H), 6.98 (dd, 1H), 6.88 (d, 1H), 3.77 (s, 3H), 3.70 (t, 4H), 2.94 (t, 4H). |
| 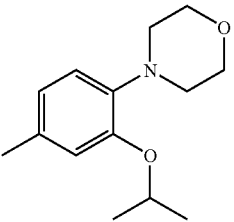 | 381.3 | 3.09 | |

| Ar | MS | Retention time (HPLC method) | $^1$H-NMR 500 MHz (solvent) |
|---|---|---|---|
| 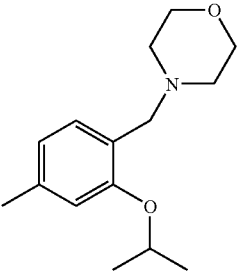 | 395.3 | 1.96 | DMSO (d6): 10.73 (s, 1H), 7.44 (t, 2H), 7.28 (m, 4H), 7.11 (s, 1H), 6.98 (d, 1H), 4.55 (m, 1H), 3.55 (m, 4H), 3.41 (s, 2H), 2.37 (m, 4H), 1.27 (d, 6H). |
| 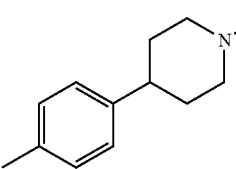 | 335.3 | 1.82 | |
| 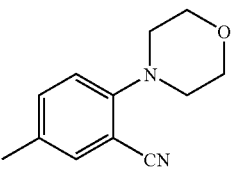 | 348.3 | 3.27 | DMSO (d6): 10.81 (s, 1H), 7.82 (s, 1H), 7.68 (dd, 1H), 7.44 (t, 2H), 7.30 (m, 3H), 7.21 (d, 1H), 3.75 (t, 4H), 3.14 (t, 4H). |

The following exemplify the methods used in preparation of the diaminotriazoles. The examples also serve to describe the several purification methods. The data for these compounds is contained in the table following.

Example 42

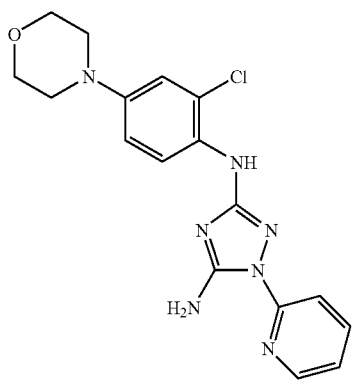

Method A

N3-(2-Chloro-4-morpholin-4-yl-phenyl)-1-pyridin-2-yl-1H-[1,2,4]triazole-3,5-diamine: A mixture of N-cyano-N'-(2-chloro-4-morpholino-phenyl)-O-phenylisourea (0.10 g, 0.28 mmol) and 2-hydrazinopyridine (0.046 g, 0.42 mmol) in iso-propanol (3 mL) was heated at 115° C. for 20 h. The precipitate was filtered, washed with iso-propanol and purified by flash chromatography (SiO$_2$) eluted with 2:98 methanol: dichloromethane to provide the title compound (0.080 g, 79% yield) as a white solid.

Example 43

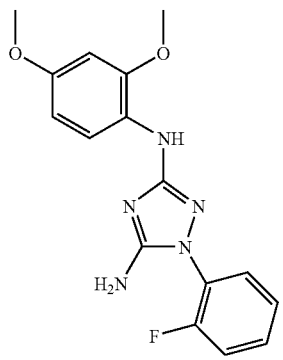

Method A*

N3-(2,4-Dimethoxy-phenyl)-1-(2-fluoro-phenyl)-1H-[1,2,4]triazole-3,5-diamine: A mixture of N-cyano-N'-(2,4-dimethoxyphenyl)-O-phenylisourea (0.10 g, 0.34 mmol), 2-fluoro-phenylhydrazine hydrochloride (0.08 g, 0.50 mmol) and triethylamine (0.01 mL, 0.68 mmol) in isopropanol (3 mL) was heated at 100° C. for 18 h and evaporated. Purification by flash chromatography (SiO$_2$) eluted with 1:1 ethyl acetate:hexanes provided the title compound (0.10 g, 85% yield).

Example 44

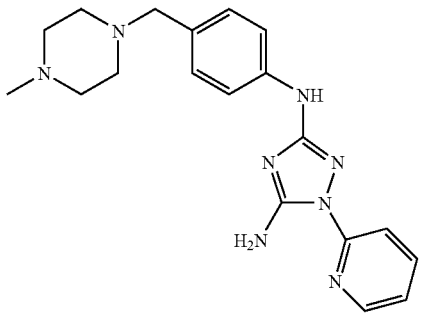

Method A**

4-[5-Amino-3-(3,4-dimethoxy-phenylamino)-[1,2,4]triazol-1-yl]-benzonitrile: To N-cyano-N'-(3,4-dimethoxy-phenyl)-O-phenylisourea (0.215 g, 0.723 mmoles) in isopropanol (3 mL) was added 0.184 g (1.5 equivalents) of 4-Hydrazino-benzonitrile hydrochloride, followed by triethylamine 152 uL (1.5 equivalents) and catalytic (0.2 equivalents) 4-dimethylaminopyridine. The reaction was stirred overnight at 100 degrees Celsius. The reaction mixture was concentrated to dryness and purified by reverse phase column chromatography. The pure fractions were dried to provide 4-[5-amino-3-(3,4-dimethoxy-phenylamino)-[1,2,4]triazol-1-yl]-benzonitrile as tan solid (18.3 mg, 7.5% yield).

Method B

N3-[4-(4-Methyl-piperazin-1-ylmethyl)-phenyl]-1-pyridin-2-yl-1H-[1,2,4]triazole-3,5-diamine: A mixture of N-cyano-N'-(4-(4-methyl)piperazinylmethyl-phenyl)-O-phenylisourea (0.60 g, 1.72 mmol) and 2-hydrazinopyridine (0.23 g, 2.06 mmol) in iso-propanol (8 mL) was heated by microwave (Emrys instrument) at 180° C. for 10 min, then evaporated. Purification by flash chromatography (SiO$_2$) eluted with 0.2:2:98 NH$_4$OH: methanol dichloromethane provided the title compound (0.54 g, 87% yield) as a pale tan solid.

Example 45

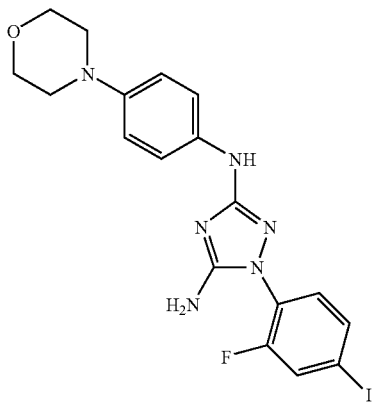

Method C 1-(2-Fluoro-4-iodo-phenyl)-N-3-(4-morpholin-4-yl-phenyl)-1H-[1,2,4]triazole-3,5-diamine: A mixture of N-cyano-N'-(4-morpholino-phenyl)-O-phenylisourea (0.69 g, 2.14 mmol) and 2-fluoro-4-iodo-phenylhydrazine (0.65 g, 2.57 mmol) in dimetheyl acetamide (4 mL) was heated at 120° C. for 24 h. The reaction is diluted with ethyl acetate, washed with water (3 times) and brine, dried (sodium sulfate) and evaporated. Purification by flash chromatography (SiO$_2$) eluted with 4:96 methanol:dichloromethane, followed by semi-preparative HPLC provided the title compound (0.03 g, 5% yield) as a white lyophilate.

Example 46

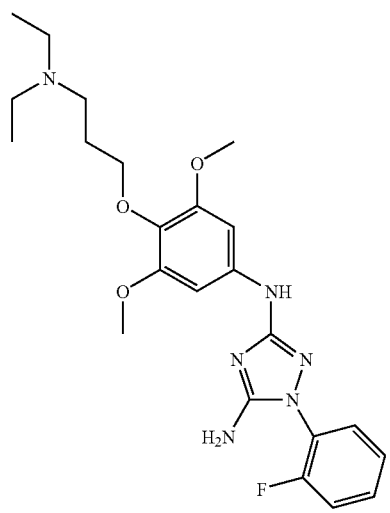

Method C*

N3-[4-(3-Diethylamino-propoxy)-3,5-dimethoxy-phenyl]-1-(2-fluorophenyl)-1H-[1,2,4]triazole-3,5-diamine: A solution of 2-fluoro-phenylhydrazine hydrochloride (0.15 g, 0.91 mmol) and triethylamine (0.13 mL, 0.91 mmol) in dimethylacetaimde (1 mL) was stirred 0.5 h at room temperature. N-cyano-N'-(4-(3-diethylamino-propoxy)-3,5-dimethoxy-phenyl)-O-phenylisourea (0.30 g as a mixture with triethylamine-trifluoroacetic acid salt, 0.45 mmol) in dimethylacetamide (1 mL) was added and the reaction was stirred at 120° C. for 20 h. The precipitate was removed and the filtrate was washed with ether. The remaining aqueous phase was evaporated and was purified by semi-preparative HPLC to provide the title compound (0.01 g, 4% yield) as a yellow lyophilate.

Example 47

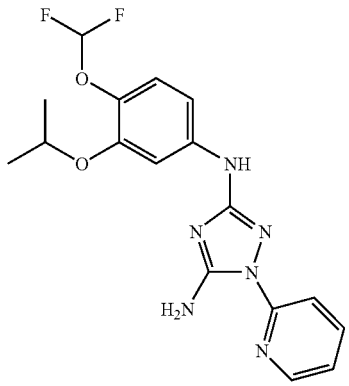

Method D

N3-(4-Difluoromethoxy-3-isopropoxy-phenyl)-1-pyridin-2-yl-1H-[1,2,4]triazole-3,5-diamine: A mixture of N-cyano-N'-(4-difluoromethoxy-3-iso-propyloxyphenyl)-O-phenylisourea (0.10 g, 0.28 mmol) and 2-hydrazino-pyridine (0.06 g, 0.56 mmol) in dimethylacetamide (3 mL) was heated in the microwave apparatus at 220° C. for 15 min. The reaction was cooled, poured into ice-water and stirred for 0.5 h. The precipitate was filtered off, washed with cold water and dried to provide the title compound (0.10 g, 97% yield) as a pale pink solid.

Example 48

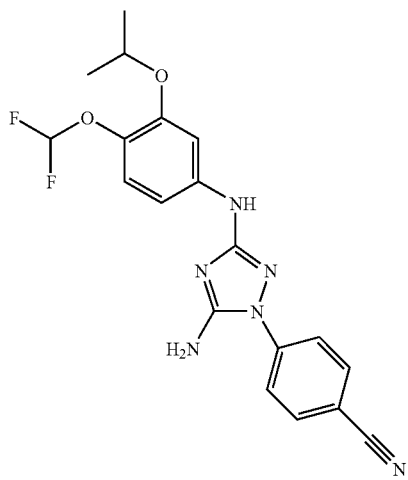

Method D*:

4-[5-Amino-3-(4-difluoromethoxy-3-isopropoxy-phenylamino)-[1,2,4]triazol-1-yl]-benzonitrile: A mixture of N-cyano-N'-(3-difluoromethoxy-4-iso-propyloxyphenyl)-O-phenylisourea (0.10 g, 0.28 mmol), 4-cyano-phenyl-hydrazine (0.09 g, 0.55 mmol) and triethylamine (0.08 mL, 0.55 mmol) in dimethylacetamide (3 mL) was heated in the microwave apparatus at 220° C. for 5 min. The cooled reaction was poured into ice-water and the crude product was obtained by filtration. Purification by semi-preparative HPLC provided the title compound (0.07 g, 51% yield) as a light orange solid.

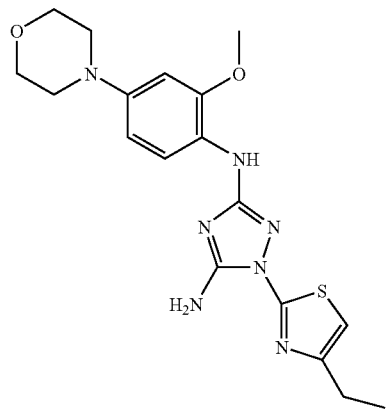

Example 49

Method E 1-(4-Ethyl-thiazol-2-yl)-N-3-(2-methoxy-4-morpholin-4-yl-phenyl)-1H-[1,2,4]triazole-3,5-diamine: A mixture of N-cyano-N'-(2-methoxyphenyl)-O-phenylisourea (0.10 g, 0.28 mmol), (4-ethyl-thiazol-2-yl)-hydrazine (0.060 g, 0.56 mmol) and DMAP (several crystals) in dimethylacetamide (3 mL) was heated in the microwave apparatus at 220° C. for 7 min. Purification by semi-preparative HPLC provided the title compound (0.01 g, 8% yield).

Example 50

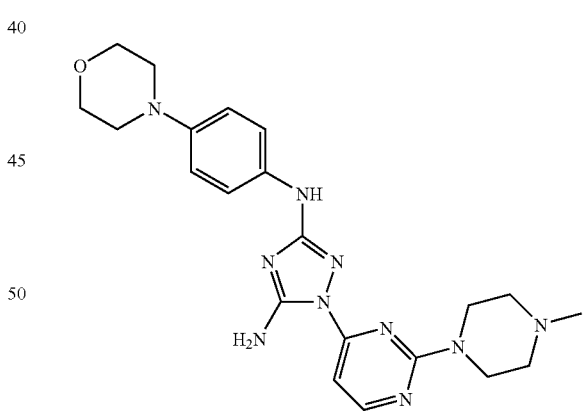

Method G

1-[2-(4-Methyl-piperazin-1-yl)-pyrimidin-4-yl]-N-3-(4-morpholin-4-yl-phenyl)-1H-[1,2,4]triazole-3,5-diamine: A mixture of N-cyano-N'-(4-morpholinopheny)-O-phenylisourea (0.10 g, 0.31 mmol) and [2-(4-Methyl-piperazin-1-yl)-pyrimidin-4-yl]-hydrazine (0.08 g, 0.34 mmol) in N-methylpyrrolidinone (3 mL) was heated in the microwave apparatus at 220° C. for 5 min. Purification by semi-preparative HPLC provided the title compound (0.09 g, 2% yield).

Example 51

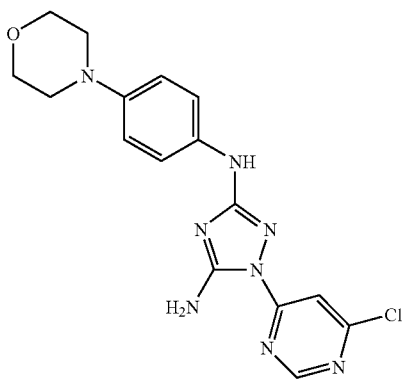

Method G*

1-(6-Chloro-pyrimidin-4-yl)-N-3-(4-morpholin-4-yl-phenyl)-1H-[1,2,4]triazole-3,5-diamine: A mixture of N-cyano-N'-(4-morpholinopheny)-O-phenylisourea (8.76 g, 27.2 mmol, 4-cgloro-6-hydrazino-pyrimidine (4.12 g, 28.5 mmol) and di-iso-propylethylamine (18.9 mL, 109 mmol) in N-methyl-pyrrolidinone (50 mL) was heated in the microwave apparatus at 220° C. for 5 min, cooled, poured into ice-water, stirred 0.5 h and filtered to obtain crude product (9.30 g). Purification by flash chromatography (SiO₂) eluted with 2:98 methanol dichloromethane provided the title compound (3.91 g, 39% yield) as a yellow powder.

Example 52

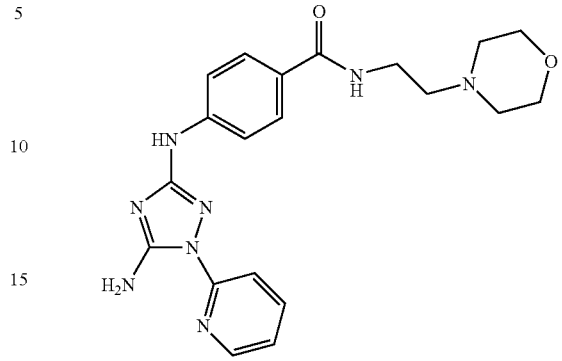

Method H 4-(5-Amino-1-pyridin-2-yl-1H-[1,2,4]triazol-3-ylamino)-N-(2-morpholin-4-yl-ethyl)-benzamide: To 4-(5-amino-1-pyridin-2-yl-1H-[1,2,4]triazol-3-ylamino)-benzoic acid (4.635 g, 15.643 mmole) in tetrahydrofuran (50 mL) was added (7.12 g, 1.2 equivalents) of HBTU, followed by 2-morpholin-4-yl-ethylamine (2.24 g, 1.1 equivalents) and triethylamine (5.45 mL, 2.5 equivalents). The reaction was stirred overnight at room temperature. The solid was filtered, washing with tetrahydrofuran, cold ethanol, water, ethanol, and finally ether. The compound was dried to provide 4-(5-amino-1-pyridin-2-yl-1H-[1,2,4]triazol-3-ylamino)-N-(2-morpholin-4-yl-ethyl)-benzamide (1.17 g, 18% yield) as a white solid. The organic phases contained product also but was not further islolated.

Purification procedures:
1. Precipitation from solvent
2. Silica gel
3. Semi-preparative HPLC Retention time from LC-MS unless otherwise indicated.

| Name | cyclisation procedure | Purification procedure | MS (M + H) | Retention time (min) | NMR |
|---|---|---|---|---|---|
| N3-(3,4-Dimethoxy-phenyl)-1-(2-piperidin-1-yl-pyrimidin-4-yl)-1H-[1,2,4]triazole-3,5-diamine | A | 3 | 397.20 | 2.90 | (500 MHz, DMSO-d6) 8.98 (s, 1H), 8.35 (d, 1H),,7.63 (s, 2H), 7.36 (d, 1H), 7.10 (dd, 1H), 6.86 (d, 1H),, 6.80 (d, 1H), 3.76 (s, 3H), 3.69 (s, 5H), 1.64 (,2H),,1.57 (m, 4H) ppm |
| N3-Benzo[1,3]dioxol-5-yl-1-(2-piperidin-1-yl-pyrimidin-4-yl)-1H-[1,2,4]triazole-3,5-diamine | A | 3 | 381.10 | 3.20 | (500 MHz, DMSO-d6) 9.07 (s, 1H), 8.36 (d, 1H),,7.63 (s, 2H), 7.29 (d, 1H), 7.04 (M, 1H), 6.80 (M, 2H),, 5.94 (s, 2H), 3.69 (br m, 4H), 1.65, (m, 2H),,1.57 (m, 4H) ppm |
| N3-Benzol[1,3]dioxol-5-yl-1-(4-piperidin-1-yl-pyrimidin-2-yl)-1H-[1,2,4]triazole-3,5-diamine | A | 3 | 381.10 | 2.30 | (500 MHz, DMSO-d6) 9.19 (s, 1H), 8.10 (d, 1H), 7.67 (br s, 2H), 7.47 (d, 1H), 7.03 (m, 1H),,6.80 (m, 2H), 5.95 (s, 2H), 3.76 (br m, 4H),,1.68 (m, 2H), 1.62 (m, 4H) ppm. |
| N3-(4-Diethylamino-phenyl)-1-(2-piperidin-1-yl-pyrimidin-4-yl)-1H-[1,2,4]triazole-3,5-diamine | A | 3 | 408.20 | 2.00 | (500 MHz, DMSO-d6) 10.9 (br s, 1H), 9.63 (br s, 1H),,8.39 (d, 1H), 7.77 d, 2H), 7.68 (s, 1H), 7.51 (d, 2H),,6.86 (d, 2H), 3.70 (m, 4H), 3.62 (m, 2H), 3.51 (m, 2H),,1.65 (m, 2H), 1.57 (m, 4H), 1.00 (t, 6H) ppm |

| Name | cyclisation procedure | Purification procedure | MS (M + H) | Retention time (min) | NMR |
|---|---|---|---|---|---|
| N3-(3,4-Dimethoxy-phenyl)-1-(4-piperidin-1-yl-pyrimidin-2-yl)-1H-[1,2,4]triazole-3,5-diamine | A | 3 | 397.20 | 2.20 | (500 MHz, DMSO-d6) 9.00 (s, 1H), 8.09 (d, 1H), 7.70 (s, 2H), 7.50 (s, 1H), 7.09 (s, 1H), 6.83 (d, 1H),,6.75 (d, 1H), 3.76 (s, 7H), 3.69 (s, 3H), 1.67 (m, 2H),,1.60 (m, 4H) ppm |
| 1-Benzothiazol-2-yl-N3-(4-diethylamino-phenyl)-1H-[1,2,4]triazole-3,5-diamine | A* | 3 | 380.10 | 2.50 | (500 MHz, DMSO-d6) 11.0 (br s. 1H), 9.88 (s, 1H),,8.07 (d, 1H), 7.88 (d, 2H), 7.76 (d, 2H), 7.52 (m, 3H),, 7.38 (t, 1H), 3.64 (m, 2H), 3.53 (m, 2H), 1.01 (t, 6H) ppm |
| N3-Benzo[1,3]dioxol-5-yl-1-(4-phenyl-thiazol-2-yl)-1H-[1,2,4]triazole-3,5-diamine | A | 2.3 | 379.10 | 4.20 | (500 MHz, DMSO-d6) 9.22 (s, 1H), 8.02 (d, 2H), 7.80 (s, 1H), 7.63 (s, 2H), 7.46 (t, 2H), 7.37 (t, 1H),, 7.30 (d, 1H), 6.98 (dd, 1H), 8.84 (d, 1H),, 5.95 (s, 2H) ppm |
| N3-(4-Diethylamino-phenyl)-1-(4-phenyl-thiazol-2-yl)-1H-[1,2,4]triazole-3,5-diamine | A | 3 | 406.10 | 2.70 | (500 MHz, DMSO-d6) 11.2 (br s, 1H), 10.2 (br s, 1H), 7.8–8.0 (m, 5H), 7.65 (br m, 1H), 7.52 (m, 2H), 7.41 (m, 1H), 6.10 (m, 2H), 3.55 (br m, 4H),,1.03 (m, 6H) ppm. |
| N3-(4-Diethylamino-phenyl)-1-(4-piperidin-1-yl-pyrimidin-2-yl)-1H-[1,2,4]triazole-3,5-diamine | A | 3 | 408.20 | 1.60 | (500 MHz, DMSO-d6) 11.1 (br s, 1H), 9.63 (br s, 1H),,8.14 (d, 1H), 7.82 (d, 2H), 7.73 (s, 1H), 7.48 (s, 2H),,6.77 (d, 1H, 3,73 (M, 4H), 3.62 (m, 2H),,3.51 (m, 2H), 1.68 (m, 2H), 1.60 (m, 4H), 1.00 (t, 6H) ppm |
| 6-[5-Amino-3-(4-diethylamino-phenylamino)-[1,2,4]triazol-1-yl]-nicotinonitrile | A | 2.3 | 349.20 | 1.90 | (500 MHz, DMSO-d6) 11.0 (hr s, 1H), 9.73 (br s, 1H),, 8.86 (s, 1H), 8.42 (d, 1H), 7.91 (s, 1H), 7.82 (m, 3H),,7.52 (d, 2H), 3.63 (br m, 2H), 3.52 (br m, 2H), 1.00 (t, 6H) ppm |
| N3-(3,4-Dimethoxy-phenyl)-1-(4-phenyl-thiazol-2-yl)-1H-[1,2,4]triazole-3,5-diamine | A | 2.3 | 395.20 | 4.00 | (DMSO-d6, 500 MHz) 9.97 (s, 1H), 8.00 (d, 2H),,7.82 (s, 1H), 7.51 (t, 2H), 7.39 (m, 2H), 7.21 (dd, 1H),, 6.99 (d, 1H), 3.83 (s, 3H), 3.76 (s, 3H) ppm |
| N3-(3,4-Dimethoxy-phenyl)-1H-[1,2,4]triazole-3,5-diamine | A | 3 | | | (DMSO-d6, 500 MHz) 12.5 (br s, 1H), 9.3 (br s, 1H), 7.5 (br s, 2H), 7.08 (d, 1H), 6.94 (dd, 1H), 6.89 (d, 1H),, 3.73 (s, 3H), 3.70 (s, 3h) ppm |
| 1-(2-Fluoro-phenyl)-N3-(4-morpholin-4-yl-phenyl)-1H-[1,2,4]triazole-3,5-diamine | A* | 2 | 355.00 | 1.60 | (DMSO-d6, 500 MHz) 8.56 (s, 1H), 7.4–7.55 (m, 2H), 7.38 (d, 2H), 7.33 (t, 1H), 6.81 (d, 2H), 6.28 (s, 2H),, 3.71 (m, 4H), 2.95 (m, 4H) ppm |
| 1-[4-(5-Amino-1-pyridin-2-yl-1H-[1,2,4]triazol-3-ylamino)-phenyl]-ethanone | A | 2 | 295.20 | 2.90 | (DMSO-d6, 500 MHz) 9.73 (s, 1H), 8.43 (m, 1H), ,8.01 (m, 1H), 7.89 (d, 2H), 7.75 (m, 2H), 7.71 (d, 2H),, 7.24 (m, 1H), 2.50 (S, 3H) ppm |
| N3-(2,4-Dimethoxy-phenyl)-1-(2-fluoro-phenyl)-1H-[1,2,4]triazole-3,5-diamine | A* | 2 | 330.10 | 2.70 | (DMSO-d6, 500 MHz) 7.83 (d, 1H), 7.53 (m, 1H), ,7.48 (m, 1H), 7.41 (m, 1H), 7.33 (m, 1H), 6.86 (s, 1H),, 6.58 (d, 1H), 6.44 (dd, 1H), 6.34 (s, 2H), 3.84 (s, 3H), ,3.70 (s, 1H) ppm |
| [4-(5-Amino-1-pyridin-2-yl-1H-[1,2,4]triazol-3-ylamino)-phenyl]-phenyl-methanone | A | 3 | 357.10 | 3.70 | (DMSO-d6, 500 MHz) 9.82 (s, 1H), 8.43 (m, 1H), 7.98 (m, 1H), 7.77 (m, 7H), 7.69 (d, 1H), 7.64 (t, 1H), ,7.55 (t, 2H), 7.24 (m, 1H) ppm |
| 1-(2-Fluoro-phenyl)-N3-(4-morpholin-4-ylmethyl-phenyl)-1H-[1,2,4]triazole-3,5-diamine | A* | 3 | | | (DMSO-d6, 500 MHz) 9.60 (br s, 1H), 9.19, (s, 1H), 7.55 (d, 2H), 7.50 (m, 1H), 7.43 (m,1H), 7.35(m, 1H),, 7.30 (d, 2H), 6.40 (s, 2H), 4.22 (m, 2H), 3.95 (m, 2H), ,3.59 (m, 2H), 3.24 (m, 2H), 3.08 (m, 2H) ppm |
| N3-(3-Morpholin-4-ylmethyl-phenyl)-1-pyridin-2-yl-1H-[1,2,4]triazole-3,5-diamine | A | 3 | | | (DMSO-d6, 500 MHz) 9.91 (br s, 1H), 9.38, (s, 1H), 8.43 (m, 1H), 7.99 (m, 1H), 7.72 (m, 3H), 7.67 (s, 1H), 7.37 (t, 1H), ,7.24 (m, 1H), 6.98 (d, 1H), 4.33 (m, 2H), 3.98 (m, 2H),, 3.64 (m, 2H), 3.32 (m, 2H), 3.17 (m, 2H) ppm |
| 1-(2-Fluoro-phenyl)- | A* | 3 | | | (DMSO-d6, 500 MHz) 9.79 (br s, |

-continued

| Name | cyclisation procedure | Purification procedure | MS (M + H) | Retention time (min) | NMR |
|---|---|---|---|---|---|
| N3-(3-morpholin-4-ylmethyl-phenyl)-1H-[1,2,4]triazole-3,5-diamine | | | | | 1H), 9.14, (s, 1H), 7.61 (d, 1H), 7.55 (m, 3H), 7.43 (m, 1H), 7.35 (m, 1H),, 7.30 (t, 1H), 6.90 (d, 1H), 6.40 (s, 2H), 4.25 (m, 2H), 3.93 (m, 2H),, 3.60 (m, 2H), 3.27 (m, 2H), 3.13 (m, 2H) ppm |
| N3-(2,4-Dimethoxy-phenyl)-1-(2-piperidin-1-yl-pyrimidin-4-yl)-1H-[1,2,4]triazole-3,5-diamine | A | 2 | 397.10 | 3.30 | (DMSO-d6, 500 MHz) 8.36 (d, 1H), 7.95 (d, 1H), 7.62 (s, 2H), 7.24 (s, 1H), 6.78 (d, 1H), 6.61 (d, 1H), ,6.52 (dd, 1H), 3.84 (s, 3H), 3.73 (s, 3H), 3.69 (m, 4H), ,1.63 (m, 2H), 1.56 (m, 4H) ppm |
| N3-(4-Morpholin-4-yl-phenyl)-1-(2-piperidin-1-yl-pyrimidin-4-yl)-1H-[1,2,4]triazole-3,5-diamine | A | 3 | 422.30 | 2.20 | (500 MHz, DMSO-d6) 9.20 (br s, 1H), 8.37 (d, 1H), 7.65 (s, 2H), 7.57 (br s, 2H), 7.10 (br s, 2H), ,6.83 (d, 1H), 3.81 (s, 4H), 3.70 (s, 4H), 3.18 (br s, 4H),, 1.64 (m, 2H), 1.57 (m, 4H) ppm |
| N3-(2-Chloro-4-morpholin-4-yl-phenyl)-1-pyridin-2-yl-1H-[1,2,4]triazole-3,5-diamine | A | 2 | 372.20 | 3.10 | (500 MHz, DMSO-d6) 8.40 (m 1H), 7.94 (m, 2H), 7.69 (s, 2H), 7.62 (m, 2H), 7.20 (m, 1H), 7.00 (d, 1H),, 6.95 (dd, 1H), 3.73 (t, 4H), 3.06 (t 4H) ppm |
| N3-[3-Methoxy-4-(3-morpholin-4-yl-propoxy)-phenyl]-1-pyridin-2-yl-1H-[1,2,4]triazole-3,5 diamine | A | 3 | 426.20 | 1.70 | (500 MHZ, DMSO-d6) 9.6 (s, 1H), 8.97 (s, 1H), 8.41 (m, 1H), 7.97 (m, 1H), 7.67 (m, 2H), 7.43 (m, 1H),, 7.43 (d, 1H), 7.20 (m, 1H), 7.12 (dd, 1H), 6.91 (d, 1H),, 4.00 (m, 2H), 3.98 (m, 2H), 3.80 (s, 3H), 3.65 (t, 2H), ,3.51 (d, 1H), 3.31 (m, 2H), 3.13 (m, |
| 1-Pyridin-2-yl-N3-(2,4,5-trimethoxy-phenyl)-1H-[1,2,4]triazole-3,5-diamine | A | 3 | 343.10 | 2.80 | (500 MHz, DMSO-d6) 8.42 (m, 1H), 8.01 (m, 1H), 7.93 (s, 3H), 7.66 (d, 1H), 7.44 (s, 1H), 7.24 (m, 1H),, 6.78 (s, 1H), 3.84 (s, 3H), 3.79 (s, 3H), 3.76 (s, 3H) ppm |
| N3-{4-[3-(2,6-Dimethyl-morpholin-4-yl)-propoxy]-3-methoxy-phenyl}-1-pyridin-2-yl-1H-[1,2,4]tri azole-3,5-diamine | A | 3 | 454.20 | 2.00 | (500 MHz, DMSO-d6) 9.70 (s, 1H), 8.96 (s, 1H), 8.40 (m, 1H), 7.97 (m, 1H), 7.69 (s, 1H),, 7.66 (d, 1H), 7.43 (d, 1H), 7.21 (m, 1H), 7.12 (dd, 1H),, 6.90, 3.98 (t, 2H), 3.80 (s, 5H), 3.54 (d, 2H), 3.27 (m, 2H), 2.68 (m, 2H), 2.11 (m, 2H), 1.26 (d, 6H) |
| 1-(2-Fluoro-4-iodo-phenyl)-N3-(4-morpholin-4-yl-phenyl)-1H-[1,2,4]triazole-3,5-diamine | C | 3 | 481.00 | 2.30 | (500 MHz, DMSO-d6) 8.9 (br s, 1H), 7.88 (dd, 1H), ,7.71 (d, 1H), 7.45 (m, 2H), 7.33 (t, 1H), 7.07 (br, 2H), ,6.56 (br s, 2H), 3.80 (m, 4H), 3.20 (m, 4H) |
| N3-[3-Methoxy-4-(4-morpholin-4-yl-butoxy)-phenyl]-1-pyridin-2-yl-1H-[1,2,4]triazole-3,5-diamine | A | 3 | 440.20 | 1.80 | (500 MHz, DMSO-d6) 9.60 (s, 1H), 8.93 (s, 1H), ,8.41 (dd, 1H), 7.98 (m, 1H), 7.66 (m, 2H), 7.41 (d, 1H),, 7.19 (m, 1H), 7.11 (dd, 1H), 6.88 (d, 1H), 3.99 (d, 2H), 3.93 (t, 2H), 3.79 (s, 3H), 3.64 (t, 2H), 3.45 (d, 2H),, 3.19 (m, 2H), 3.06 (m, 2H), 1.82 ( |
| N3-[3-Methoxy-4-(2-morpholin-4-yl-ethoxy)-phenyl]-1-pyridin-2-yl-1H-[1,2,4]triazole-3,5-diamine | A | 3 | 412.20 | | (500 MHz, DMSO-d6) 9.99 (s, 1H), 9.05 (s, 1H) ,8.41 (dd, 1H), 7.97 (m, 1H), 7.67 (m, 2H), 7.47 (d, 1H),, 7.21 (m, 1H), 7.13 (dd, 1H), 7.00 (d, 1H), 4.21 (d, 2H), 4.00 (m, 2H), 3.82 (s, 3H), 3.73 (t, 2H), 3.53 (m, 4H), ,3.22 (m, 2H), ppm |
| N3-[4-(2-Diethylamino-ethoxy)-3-methoxy-phenyl]-1-pyridin-2-yl-1H-[1,2,4]triazole-3,5-diamine | A | 3 | 398.30 | 1.80 | (500 MHz, DMSO-d6) 9.34 (s, 1H), 9.03 (s, 1H), 8.41 (dd, 1H), 7.97 (m, 1H), 7.67 (m, 2H), 7.47 (d, 1H),, 7.21 (m, 1H), 7.13 (dd, 1H), 6.97 (d, 1H), 4.20 (d, 2H), 3.82 (s, 3H), 3.48 (m, 2H), 3.29 (m, 4H), 1.25 (t, 6H) ppm |
| N3-[4-(3-Imidazol-1-yl-propoxy)-3-methoxy-phenyl]-1-pyridin-2-yl-1H-[1,2,4]triazole-3,5-diamine | A | 3 | 407.20 | 1.90 | (500 MHZ, DMSO-d6) 9.16 (s, 1H), 8.96 (s, 1H), ,8.40 (dd, 1H), 7.97 (t, 1H), 7.83 (s, 1H), 7.7 (m, 3H), ,7.41 (d, 1H), 7.21 (m, 1H), 7.10 (dd, 1H), 6.88 (d, 1H), ,4.39 (t, 2H), 3.92 (t, 2H), 3.79 (s, 3H), 2.26 (m, 2H) ppm |

| Name | cyclisation procedure | Purification procedure | MS (M + H) | Retention time (min) | NMR |
|---|---|---|---|---|---|
| N3-[4-(3-Diethylamino-propoxy)-3,5-dimethoxy-phenyl[-1-(2-fluoro-phenyl)-1H-[1,2,4]triazole-3,5-diamine | C* | 3 | 459.20 | 1.80 | (500 MHz, DMSO-d6) 9.05 (s, 1H), 8.79 (s, 1H), 7.56 (t, 1H), 7.43 (m, 2H), 7.33 (t, 1H), 6.94 (s, 2H), ,6.42 (s, 2H), 3.85 (t, 2H), 3.70 (s, 6H), 3.28 (m, 2H), ,3.16 (m, 4H), 1.92 (m, 2H), 1.21 (t, 6H) ppm |
| 4-{-Amino-3-[3,5-dimethoxy-4-(3-morpholin-4-yl-propoxy)-phenylamino]-[1,2,4]triazol-1-yl}benzonitrile | C* | 3 | 480.20 | 1.90 | (500 MHz, DMSO-d6) 9.65 (s, 1H), 9.00 (s, 1H), ,7.94 (d, 2H), 7.80 (d, 2H), 7.01 (s, 2H), 6.82 (s, 2H), ,4.00 (d, 2H), 3.85 (t, 2H), 3.76 (s, 6H), 3.65 (t, 2H), ,3.48 (d, 2H), 3.35 (m, 2H), 3.13 (m, 2H), 1.98 (m, 2H) ppm |
| 4-(5-Amino-3-{3,5-dimethoxy-4-[3-(4-methyl-piperazin-1-yl)-propoxy]-phenylamino)-[1,2,4]triazol-1-yl)-benzonitrile | C* | 3 | 493.20 | 1.50 | (500 MHz, DMSO-d6) 9.00 (s, 1H), ,7.94 (d, 2H), 7.80 (d, 2H), 7.01 (s, 2H), 6.82 (s, 2H), , 3.84 (t, 2H), 3.76 (s, 6H), 2.7 –3.7 (br, 13H), 1.92 (m, 2H) ppm |
| 4-(5-Amino-3-{4-[3-(2,6-dimethyl-morpholin-4-yl)-propoxy]-3,5-dimethoxy-phenylamino{-[1,2,4]triazol-1-yl-benzonitrile | C* | 3 | 508.20 | 2.10 | (500 MHz, DMSO-d6) 9.77 (s, 1H), 9.01 (s, 1H), ,7.95 (d, 2H), 7.80 (d, 2H), 7.01 (s, 2H), 6.82 (s, 2H), , 3.80 (m, 4H), 3.76 (s, 6H), 3.51 (d, 2H), 3.31 (m, 2H), 2.69 (m, 2H),, 2.01 (m, 2H), 1.15 (d, 6H) ppm |
| N3-{4-[3-(2,6-Dimethyl-morpholin-4-yl)-propoxy]-3,5-dimethoxy-phenyl}-1-(2-fluoro-phenyl)-1H-[1,2,4]triazole-3,5-diamine | C* | 3 | 501.20 | 1.90 | (500 MHz, DMSO-d6) 9.75 (s, 1H), 8.80 (s, 1H), ,7.56 (dt, 1H), 7.45 (m, 2H), 7.34 (dt, 1H), 6.94 (s, 2H), 6.42 (s, 2H), , 3.81 (m, 4H), 3.70 (s, 6H), 3.50 (d, 2H), 3.32 (m, 2H), 2.67 (m, 2H), ,1.99 (m, 2H), 1.15 (d, 6H) ppm |
| N3-[4-(4-Diethylamino-butoxy)-3,5-dimethoxy-phenyl]-1-(2-fluoro-phenyl)-1H-[1,2,4]triazole-3,5-diamine | C* | 3 | 473.20 | 1.90 | (500 MHz, DMSO-d6) 9.00 (s, 1H), 8.76 (s, 1H), 7.55 (dt, 1H), 7.44 (m, 2H), 7.33 (dt, 1H), 6.93 (s, 2H), 6.41 (s, 2H), , 3.78 (t, 2H), 3.69 (s, 6H), 3.13 (m, 6H), 1.78 (m, 2H), 1.65 (m, 2H) ppm |
| 4-{5-Amino-3-[4-(4-diethylamino-butoxy)-3,5-dimethoxy-phenylamino]-[1,2,4]triazol-1-yl}-benzonitrile | C* | 3 | 480.20 | 2.10 | (500 MHz, DMSO-d6) 9.05 (s, 1H), 8.98 (s, 1H), 7.94 (d, 2H), 7.80 (d, 2H), 7.00 (s, 2H), 6.81 (s, 2H), , 3.80 (t, 2H), 3.75 (s, 6H), 3.13 (m, 6H), 1.80 (m, 2H), ,1.64 (m, 2H), 1.21 (t, 6H) |
| N3-[3,5-Dimethoxy-4-(3-morpholin-4-yl-propoxy)-phenyl]-1-pyridin-2-yl-1H-[1,2,4]triazole-3,5-diamine | A | 3 | 456.20 | 1.90 | (500 MHz, DMSO-d6) 9.66 (s, 1H), 9.05 (s, 1H), 8.41 (dd, 1H), 7.97 (m, 1H), 7.71 (s, 2H), 7.65 (d, 1H), ,7.21 (m 1H), 6.81 (s, 2H), 4.00 (d, 2H), 3.86 (t, 2H), ,3.80 (s, 6H), 3.65 (t, 2H), 3.49 (d, 2H), 3.36 (m, 2H),, 3.14 (m, 2H),, 2.00 (m, 2H) |
| N3-[4-(3-Diethylamino-propoxy)-3,5-dimethoxy-phenyl]-1-pyridin-2-yl-1H-[1,2,4]triazole-3,5-diamine | A | 3 | 442.20 | 2.00 | (500 MHz, DMSO-d6) 9.10 (s, 1H), 9.05 (s, 1H), ,8.41 (dd, 1H), 7.97 (dt, 1H), 7.71 (s, 2H), 7.65 (d, 1H), ,7.21 (m 1H), 7.06 (s, 2H), 3.88 (t, 2H),, 3.80 (s, 6H), 3.30 (m, 2H), 3.18 (m, 4H),, 1.94 (m, 2H),, 1.22 (t, 6H) |
| N3-{3,5-Dimethoxy-4-[3-(4-inethyl-piperazin-1-yl)-propoxyl-phenyl}-1-pyridin-2-yl-1H-[1,2,4]tri-azole-3,5-diamine | A | 3 | 469.20 | 1.50 | (500 MHz, DMSO-d6) 9.05 (s, 1H), 8.41 (dd, 1H), ,7.97 (dt, 1H), 7.70 (s, 2H), 7.64 (d, 1H), ,7.21 (m 1H), 7.06 (s, 2H), 3.85 (t, 2H), 3.79 (s, 6H), ,2.8–3.7 (br, 8H), 2.81 (s, 2H), 1.94 (m, 2H) |
| N3-[3,5-Dimethoxy-4-(4-morpholin-4-yl-butoxy)-phenyl]-1-pyridin-2-yl-1H- | A | 3 | 470.30 | 2.00 | (500 MHz, DMSO-d6) 9.70 (s, 1H), 9.08 (s, 1H), ,8.41 (dd, 1H), 7.97 (dt, 1H), 7.70 (s, 2H), 7.65 (d, 1H),, 7.21 (m, 1H), 7.05 (s, 2H), 3.99 (d, 2H), |

| Name | cyclisation procedure | Purification procedure | MS (M + H) | Retention time (min) | NMR |
|---|---|---|---|---|---|
| [1,2,4]triazole-3,5-diamine | | | | | 3.81 (m, 2H),,3.79 (s, 6H), 3.66 (t, 2H), 3.45 (d, 2H), 3.18 (m, 2H),, 3.07 (m, 2H), 1.85 (m, 2H), 1.65 (m |
| 1-Benzothiazol-2-yl-N3-(2-inethoxy-4-morpholin-4-yl-phenyl)-1H-[1,2,4]triazole-3,5-diamine | B, G | 3 | 424.20 | 3.43 | (DMSO-d6, 500 MHz) 8.04 (d, 1H), 7.86 (m, 2H), 7.79 (s, 2H), 7.50 (m, 2H), 7.36 (t, 1H), 6.74 (s, 1H), ,6.59 (d, 1H), 3.86 (s, 3H), 3.77 (m, 4H), 3.14 (m, 4H) |
| N3-(4-Morpholin-4-yl-phenyl)-1-(3-phenoxy-phenyl)-1H-[1,2,4]triazole-3,5-diamine | D, G | 3 | 429.20 | 2.81 | (500 MHz, DMSO-d6) 8.80 (br s, 1H), 7.46 (m, 5H),,7.35 (d, 1H), 7.21 (m, 2H), 7.12 (d, 2H), 7.02 (br s, 2H), ,6.90 (dd, 1H), 6.5 (br s, 2H), 3.79 (m, 4H), 3.13 (m, 4H) ppm |
| N3-(2-Methoxy-4-morpholin-4-yl-phenyl)-1-(4-trifluoromethyl-thiazol-2-yl)-1H-[1,2,4]triazole-3,5-diamine | D* | 3 | 442.00 | 3.23 | (DMSO-d6, 500 MHz) 8.11 (s, 1H), 7.78 (d, 1H), 7.51 (s, 1H), 7.47 (s, 2H), 6.70 (s, 1H), 6.55 (d, 1H),, 3.84 (s, 3H), 3.76 (m, 4H), 3.11 (m, 4H) |
| 1-(6-Methoxy-benzothiazol-2-yl)-N3-(2-methoxy-4-morpholin-4-yl-phenyl)-1H-[1,2,4]triazole-3,5-diamine | F | 3 | 454.10 | 3.35 | (500 MHz, DMSO-d6) 7.86 (d, 1H), 7.75 (d, 1H), ,7.70 (s, 2H), 7.64 (d, 1H), 7.46 (s, 1H), 7.09 (dd, 1H),, 6.73 (s, 1H), 6.58 (d, 1H), 3.86 (s, 3H), 3.83 (s, 3H), ,3.77 (m, 4H), 3.13 (m, 4H) |
| 1-(4-Ethyl-thiazol-2-yl)-N3-(2-methoxy-4-morpholin-4-yl-phenyl)-1H-[1,2,4]triazole-3,5-diamine | D* | 3 | 402.30 | 3.11 | (500 MHz, DMSO-d6) 7.79 (d, 1H), 7.50 (s, 2H), ,7.27 (s, 1H), 6.92 (s, 1H), 6.64 (d, 1H), 6.50 (dd, 1H),, 3.84 (s, 3H), 3.74 (m, 4H), 3.06 (m, 4H), 2.68 (q, 2H), ,1.23 (t, 3H) |
| 1-(4-tert-Butyl-thiazol-2-yl)-N5-(2-methoxy-4-morpholin-4-yl-phenyl)-1H-[1,2,4]triazole-3,5-diamine | B, G | 3 | 430.20 | 3.95 | (500 MHz, DMSO-d6) 10.3 (s, 1H), 8.26 (d, 1H),, 6.91 (s, 1H), 6.72 (d, 1H), 6.54 (dd, 1H), 5.94 (s, 2H),, 3.93 (s, 3H), 3.75 (m, 4H), 3.10 (m, 4H), 1.37 (s, 9H) |
| 4-[5-Amino-3-(4-difluoromethoxy-3-isopropoxy-phenylamino)-[1,2,4]triazol-1-yl]-benzonitrile | E | 3 | 401.30 | 3.86 | (500 MHz, DMSO-d6) 9.09 (s, 1H), 7.95 (d, 2H), ,7.79 (d, 2H), 7.54 (s, 1H), 7.02 (m, 2H), 6.84 (t, 1H), ,6.79 (br s, 2H), 4.51 (m, 1H), 1.33 (d, 6H) |
| N3-(4-Difluoromethoxy-3-isopropoxy-phenyl)-1-pyridin-2-yl-1H-[1,2,4]triazole-3,5-diamine | D | 1 | 377.30 | 4.00 | (500 MHz, DMSO-d6) 9.13 (s, 1H), 8.41 (dd, 1H), ,7.99 (m, 1H), 7.66 (m, 3H), 7.21 (m, 1H), 7.10 (dd, 1H),, 7.03 (d, 1H), 6.85 (t, 1H), 4,55 (m, 1H), 1.36 (d, 6H) |
| N3-(3-Difluoromethoxy-4-isopropoxy-phenyl)-1-pyridin-2-yl-1H-[1,2,4]triazole-3,5-diamine | D | 3 | 377.30 | 3.95 | (500 MHz, DMSO-d6) 9.09 (s, 1H), 8.41 (dd, 1H), 7.98 (dt, 1H), 7.65 (d, 1H), 7.64 (hr s, 2H), 7.60 (d, 1H),, 7.38 (dd, 1H), 7.20 (dt, 1H), 7.05, (d, 1H), 7.00 (t, 1H),, 4.43 (m, 1H), 1.25 (d, 6H) |
| N3-(4-Morpholin-4-yl-phenyl)-1-(4-piperidin-1-yl-pyrimidin-2-yl)-1H-[1,2,4]triazole-3,5-diamine | D | 3 | 422.30 | 1.67 | (500 MHz, DMSO-d6) 9.08 (s, 1H), 8.09 (d, 1H), ,7.64 (s, 2H), 7.58 (d, 2H), 6.94 (s, 2H), 6.82 (d, 1H), ,3.75 (s, 8H), 3.07 (s, 4H), 1.68 (m, 2H), 1.62 (m, 4H) |
| 4-[5-Amino-3-(3-difiuoromethoxy-4-isopropoxy-phenylamino)-[1,2,4]triazol-1-yl]-benzonitrile | E | 3 | 401.30 | 3.82 | (500 MHz, DMSO-d6) 9.03 (s, 1H), 7.94 (d, 2H), 7.79 (d, 2H), 7.50 (d, 1H), 7.36 (dd, 1H), 7.04 (d, 1H),, 6.97 (t, 1H), 6.78 (s, 2H), 4.42 (m, 1H), 1.24 (d, 6H) |
| 1-[2-(4-Methyl-piperazin-1-yl)-pyrimidin-4-yl]-N3-(4-morpholin-4-yl-phenyl)-1H- | G | 3 | 437.30 | 1.50 | (500 MHz, DMSO-d6) 8.85 (s, 1H), 8.37 (d, 1H), 7.53 (s, 2H), 7.48 (d, 2H), 6.87 (d, 2H), 6.83 (d, 1H), ,3.72 (m, 4H), 3.68 (m, 4H), 2.99 (m, 4H), 2.39 (m, 4H),, 2.22 (s, 3H) |

| Name | cyclisation procedure | Purification procedure | MS (M + H) | Retention time (min) | NMR |
|---|---|---|---|---|---|
| [1,2,4]triazole-3,5-diamine | | | | | |
| N3-(4-Morpholin-4-ylmethyl-phenyl)-1-(2-piperidin-1-yl-pyrimidin-4-yl)-1H-[1,2,4]triazole-3,5-diamine | D | 3 | 436.30 | 1.68 | (500 MHz, DMSO-d6) 9.42 (s, 1H), 8.38 (d, 1H), 7.67 (d, 2H), 7.63 (s, 2H), 7.38 (d, 2H), 6.83 (d, 1H), ,4.26 (m, 2H), 3.96 (d, 2H), 3.70 (m, 4H), 3.62 (t, 2H), ,3.27 (d, 2H), 3.08 (m, 2H), 1.64 (m, 2H), ,1.57 (m, 4H) |
| N3-(4-Morpholin-4-ylmethyl-phenyl)-1-(4-piperidin-1-yl-pyrimidin-2-yl)-1H-[1,2,4]triazole-3,5-diamine | D | 3 | 436.30 | 1.01 | (500 Mhz, DMSO-d6) 9.34 (s, 1H), 8.13 (d, 1H), 7.72 (d, 2H), 7.67 (s, 2H), 7.35 (d, 2H), 6.71 (d, 1H), ,4.25 (m, 2H), 3.97 (d, 2H), 3.71 (m, 4H), 3.62 (t, 2H), ,3.26 (d, 2H), 3.07 (m, 2H), 1.68 (m, 2H), ,1.59 (m, 4H) |
| 1-[2-(4-Methyl-piperazin-1-yl)-pyrimidin-4-yl]-N3-(4-morpholin-4-ylmethyl-phenyl)-1H-[1,2,4]triazole-3,5-diamine | D | 3 | | | (500 MHz, DMSO-d6) 9.42 (s, 1H), 8.46 (d, 1H), 7.67 (d, 2H), 7.53 (s, 2H), 7.37 (d, 2H), 7.00 (d, 1H), ,4.6 (m, 2H), 4.25 (m, 2H), 3.97 (d, 2H), 3.62 (t, 2H), ,3.53 (d, 2H), 3.25 (m, 4H), 3.09 (m, 4H), 2.86 (s, 3H) |
| 1-Pyridin-2-yl-N3-(4-pyrrolidin-1-ylmethyl-phenyl)-1H-[1,2,4]triazole-3,5-diamine | B | 3 | 336.20 | 1.65 | (500 MHz, DMSO-d6) 9.32 (s, 1H), 8.42 (m, 1H), 7.97 (m, 1H), 7.68 (m, 5H), 7.38 (d, 2H), 7.23 (m, 1H),, 4,25 (d, 2H), 3.35 (m, 2H), 3.08 (m, 2H), 2.03 (m, 2H),, 1.85 (m, 2H) |
| N3-[4-(1-Morpholin-4-yl-ethyl)-phenyl]-1-pyridin-2-yl-1H-[1,2,4]triazole-3,5-diamine | B | 3 | | 2.72 | (500 MHz, DMSO-d6) 9.36 (s, 1H), 8.42 (m, 1H), ,7.99 (dt, 1H), 7.69 (m, 5H), 7.39 (d, 2H), 7.22 (m, 1H),, 4.43 (m, 1H), 4.00 (d, 1H), 3.91 (d, 1H), 3.69 (t, 1H), ,3.60 (t, 3H), 3.00 (m, 2H), 2.84 (m, 1H), 1.65 (d, 3H) |
| 1-Pyridin-2-yl-N3-[4-(1-pyrrolidin-1-yl-ethyl)-phenyl]-1H-[1,2,4]triazole-3,5-diamine | B | 3 | 350.20 | 2.81 | (500 MHz, DMSO-d6) 9.31 (s, 1H), 8.42 (dd, 1H) ,7.98 (dt, 1H), 7.68 (m, 5H), 7.38 (d, 2H), 7.22 (m, 1H),, 4.34 (m, 1H), 3.62 (m, 1H), 2.94 (m, 2H), 2.01 (m, 1H), ,1.90 (m, 2H), 1.78 (m, 1H) 1.61 (d, 3H) |
| N3-[4-(3-Diethylamino-propoxy)-3-methoxy-phenyl]-1-pyridin-2-yl-1H-[1,2,4]triazole-3,5-diamine | D | 3 | 412.30, 412.20 | 1.90, 1.78 | (500 MHz, DMSO-d6) 9.15 (s, 1H), 8.97 (s, 1H), 8.41 (m, 1H), 7.97 (m, 1H), 7.67 (m, 2H), 7.43 (s, 1H), ,7.21 (m, 1H), 7.11 (m, 1H), 6.91 (m, 1H), 3.99 (t, 2H), ,3.80 S, 3H), 3.1–3.3 (m, 6H), 2.03 (m. 2H), 1.21 (t, 6H) |
| N3-[4-(4-Methyl-piperazin-1-ylmethyl)-phenyl]-1-pyridin-2-yl-1H-[1,2,4]triazole-3,5-diamine | B | 2 | 365.30, 365.20 | 0.17, 2.04 | (500 MHz, DMSO-d6) 9.27 (s, 1H), 8.42 (m, 1H), 7.98 (m, 1H), 7.67 (m, 5H), 7.30 (d, 2H), 7.22 (m, 1H),, 3.98 (br, 2H), 3.3 (br, 8H), 2.79 (s, 3H) |
| N3-(4-Morpholin-4-ylmethyl-phenyl)-1-pyridin-2-yl-1H-[1,2,4]triazole-3,5-diamine | B | 1 | 352.20 | 0.24 | (DMSO-d6, 500 MHz) 9.80 (br s, 1H), 9.42, (s, 1H), 8.42 (d, 1H), ,7.99 (m, 1H), 7.72 (m, 2H), 7.69 (d, 2H), 7.37 (d, 2H), ,7.23 (m, 2H), 7.24 (m, 1H), 4.26 (m, 2H), 3.97 (m, 2H),, 3.61 (m, 2H), 3.27 (m, 2H), 3.09 (m, 2H) |
| 1-Benzothiazol-2-yl-N3-(3,4-dimethoxy-phenyl)-1H-[1,2,4]triazole-3,5-diamine | A* | 2 | 369.10, | 3.70, 3.70, 3.70 | (500 MHz, DMSO-d6) 9.22 (s, 1H), 8.06 (s, 1H), ,7.85 (d, 1H), 7.79 (s, 2H), 7.51 (t, 1H), 7.48 (dd, 1H),, 7.36 (m, 1H), 7.05 (dd, 1H),, 6.88 (d, 1H), 3.81 (s, 3H), 3.71 (s, 3H) |
| 4-{5-Amino-3-[4-(3-diethylamino-propoxy)-3,5-dimethoxy-phenylamino]-[1,2,4]triazol-1-yl}-benzonitrile | C* | 3 | 466.20 | 1.90, 2.00 | (500 MHz, DMSO-d6) 9.05 (s, 1H), 9.00 (s, 1H),7.94 (d, 2H), 7.80 (d, 2H), 7.01 (s, 2H), ,6.82 (s, 2H), 3.87 (t, 2H), 3.76 (s, 6H), 3.31 (m, 2H),, 3.18 (m, 4H), 1.94 (m, 2H), 1.22 (t, 6H) ppm, |
| N3-(3,4-Dimethoxy-phenyl)-1-(2-piperidin-1-yl-pyrimidin-4-yl)-1H-[1,2,4]triazole-3,5-diamine | A | 3 | 397.20 | 2.90 | (500 MHz, DMSO-d6) 8.98 (s, 1H), 8.35 (d, 1H), 7.63 (s, 2H), 7.36 (d, 1H), 7.10 (dd, 1H), 6.86 (d, 1H),, 6.80 (d, 1H), 3.76 (s, 3H), 3.69 (s, 5H), 1.64 (,2H),,1.57 (m, 4H) ppm |

-continued

| Name | cyclisation procedure | Purification procedure | MS (M + H) | Retention time (min) | NMR |
|---|---|---|---|---|---|
| N3-Benzo[1,3]dioxol-5-yl-1-(2-piperidin-1-yl-pyrimidin-4-yl)-1H-[1,2,4]triazole-3,5-diamine | A | 3 | 381.10 | 3.20 | (500 MHz, DMSO-d6) 9.07 (s, 1H), 8.36 (d, 1H), ,7.63 (s, 2H), 7.29 (d, 1H), 7.04 (m, 1H), 6.80 (m, 2H),, 5.94 (s, 2H), 3.69 (br m, 4H), 1.65, (m, 2H), ,1.57 (m, 4H) ppm |
| N3-Benzo[1,3]dioxol-5-yl-1-(4-piperidin-1-yl-pyrimidin-2-yl)-1H-[1,2,4]triazole-3,5-diamine | A | 3 | 381.10 | 2.30 | (500 MHz, DMSO-d6) 9.19 (s, 1H), 8.10 (d, 1H), ,7.67 (br s, 2H), 7.47 (d, 1H), 7.03 (m, 1H), ,6.80 (m, 2H), 5.95 (s, 2H), 3.76 (br m, 4H), ,1.68 (m, 2H), 1.62 (m, 4H) ppm. |
| N3-(4-Diethylamino-phenyl)- 1 -(2-piperidin- l-yl-pyrimidin-4-yl)- 1H-[1,2,4]triazole-3,5-diamine | A | 3 | 408.20 | 2.00 | (500 MHz, DMSO-d6) 10.9 (br s, 1H), 9.63 (br s, 1H),, 8.39 (d, 1H), 7.77 d, 2W, 7.68 (s, 1H), 7.51 (d, 2H), ,6.86 (d, 2H), 3,70 (m, 4H), 3.62 (m, 2H), 3.51 (m, 2H), ,1.65 (m, 2H), 1.57 (m, 4H), 1.00 (t, 6H) ppm |
| N3-(3,4-Dimethoxy-phenyl)-1-(4-piperidin-1-yl-pyrimidin-2-yl)-1H-[1,2,4]triazole-3,5-diamine | A | 3 | 397.20 | 2.20 | (500 MHz, DMSO-d6) 9.00 (s, 1H), 8.09 (d, 1H), 7.70 (s, 2H), 7.50 (s, 1H), 7.09 (s, 1H), 6.83 (d, 1H), ,6.75 (d, 1H), 3.76 (s, 7H), 3.69 (s, 3H), 1.67 (m, 2H), ,1.60 (m, 4H) ppm |
| 1-Benzothiazol-2-yl-N3-(4-diethylamino-phenyl)-1H-[1,2,4]triazole-3,5-diamine | A* | 3 | 380.10 | 2.50 | (500 MHz, DMSO-d6) 11.0(brs, 1H), 9.88 (s, 1H), 8.07 (d, 1H), 7.88 (d, 2H), 7.76 (d, 2H), 7.52 (m, 3H),, 7.38 (t, 1H), 3.64 (m, 2H), 3.53 (m, 2H), ,1.01 (t, 6H) ppm |
| N3-Benzo[1,3]dioxol-5-yl-1-(4-phenyl-thiazol-2-yl)-1H-[1,2,4]triazole-3,5-diamine | A | 2,3 | 379.10 | 4.20 | (500 MHz, DMSO-d6) 9.22 (s, 1H), 8.02 (d, 2H), ,7.80 (s, 1H), 7.63 (s, 2H), 7.46 (t, 2H), 7.37 (t, 1H),, 7.30 (d, 1H), 6.98 (dd, 1H), 8.84 (d, 1H),, 5.95 (s, 2H) ppm |
| N3-(4-Diethylamino-phenyl)-1-(4-phenyl-thiazol-2-yl)-1H-[1,2,4]triazole-3,5-diamine | A | 3 | 406.10 | 2.70 | (500 MHz, DMSO-d6) 11.2 (br s, 1H), 10.2 (br s, 1H), ,7.8–8.0 (m,. 5H), 7.65 (br m, 1H), 7.52 (m, 2H),, 7.41 (m, 1H), 6.10 (m, 2H), 3.55 (br m, 4H), ,1.03 (m, 6H) ppm. |
| N3-(4-Diethylamino-phenyl)-1-(4-piperidin-1-yl-pyrimidin-2-yl)-1H-[1,2,4]triazole-3,5-diamine | A | 3 | 408.20 | 1.60 | (500 MHz, DMSO-d6) 11.1 (br s, 1H), 9.63 (br s, 1H), 8.14 (d, 1H), 7.82 (d, 2H), 7.73 (s, 1H), 7.48 (s, 2H), ,6.77 (d, 1H), 3,73 (m, 4H), 3.62 (m, 2H), ,3.51 (m, 2H), 1.68 (m, 2H), 1.60 (m, 4H), 1.00 (t, 6H) ppm |
| 6-[5-Amino-3-(4-diethylamino-phenylamino)-[1,2,4]triazol-1-yl]-nicotinonitrile | A | 2,3 | 349.20 | 1.90 | (500 MHz, DMSO-d6) 11.0 (br s, 1H), 9.73 (br s, 1H),, 8.86 (s, 1H), 8.42 (d, 1H), 7.91 (s, 1H), 7.82 (m, 3H), ,7.52 (d, 2H), 3.63 (br m, 2H), 3.52 (br m, 2H), 1.00 (t, 6H) ppm |
| N3-(3,4-Dimethoxy-phenyl)-1-(4-phenyl-thiazol-2-yl)-1H-[1,2,4]triazole-3,5-diamine | A | 2,3 | 395.20 | 4.00 | (DMSO-d6, 500 MHz) 9.97 (s, 1H), 8.00 (d, 2H), 7.82 (s, 1H), 7.51 (t, 2H), 7.39 (m, 2H), 7.21 (dd, 1H),, 6.99 (d, 1H), 3.83 (s, 3H), 3.76 (s, 3H) ppm |
| N3-(3,4-Dimethoxy-phenyl)-1H-[1,2,4]triazole-3,5-diamine | A | 3 | | | (DMSO-d6, 500 MHz) 12.5 (br s, 1H), 9.3 (br s, 1H), 7.5 (br s, 2H), 7.08 (d, 1H), 6.94 (dd, 1H), 6.89 (d, 1H),, 3.73 (s, 3H), 3.70 (s, 3H) ppm |
| 1-(2-Fluoro-phenyl)-N3-(4-morpholin-4-yl-phenyl)-1H-[1,2,4]triazole-3,5-diamine | A* | 2 | 355.00 | 1.60 | (DMSO-d6, 500 MHz) 8.56 (s, 1H), 7.4–7.55 (m, 2H), 7.38 (d, 2H), 7.33 (t, 1H), 6.81 (d, 2H), 6.28 (s, 2H),, 3.71 (m, 4H), 2,95 (m, 4H) ppm |
| 1-[4-(5-Amino-1-pyridin-2-yl-1H-[1,2,4]triazol-3-ylamino)-phenyl]-ethanone | A | 2 | 295.20 | 2.90 | (DMSO-d6, 500 MHz) 9.73 (s, 1H), 8.43 (m, 1H), 8.01 (m, 1H), 7.89 (d, 2H), 7.75 (m, 2H), 7.71 (d, 2H),, 7.24 (m, 1H), 2.50 (S, 3H) ppm |
| N3-(2,4-Dimethoxy-phenyl)-1-(2-fluoro-phenyl)-1H-[1,2,4]triazole-3,5-diamine | A* | 2 | 330.10 | 2.70 | (DMSO-d6, 500 MHz) 7.83 (d, 1H), 7.53 (m, 1H), ,7.48 (m, 1H), 7.41 (m, 1H), 7.33 (m, 1H), 6.86 (s, 1H),, 6.58 (d, 1H), 6.44 (dd, 1H), 6.34 (s, 2H), 3.84 (s, 3H), ,3.70 (s, 1H) ppm |
| [4-(5-Amino-1- | A | 3 | 357.10 | 3.70 | (DMSO-d6, 500 MHz) 9.82 (s, 1H), |

-continued

| Name | cyclisation procedure | Purification procedure | MS (M + H) | Retention time (min) | NMR |
|---|---|---|---|---|---|
| pyridin-2-yl-1H-[1,2,4]triazol-3-ylamino)-phenyl]-phenyl-methanone | | | | | 8.43 (m, 1H), 7.98 (m, 1H), 7.77 (m, 7H), 7.69 (d, 1H), 7.64 (t, 1H), 7.55 (t, 2H), 7.24 (m, 1H) ppm |
| 1-(2-Fluoro-phenyl)-N3-(4-morpholin-4-ylmethyl-phenyl)-1H-[1,2,4]triazole-3,5-diamine | A* | 3 | | | (DMSO-d6, 500 MHz) 9.60 (br s, 1H), 9.19, (s, 1H), 7.55 (d, 2H), 7.50 (m, 1H), 7.43 (m,1H), 7.35(m, 1H), 7.30 (d, 2H), 6.40 (s, 2H), 4.22 (m, 2H), 3.95 (m, 2H), 3.59 (m, 2H), 3.24 (m, 2H), 3.08 (m, 2H) ppm |
| N3-(3-Morpholin-4-ylmethyl-phenyl)-1-pyridin-2-yl-1H-[1,2,4]triazole-3,5-diamine | A | 3 | | | (DMSO-d6, 500 MHz) 9.91 (br s, 1H), 9.38, (s, 1H), 8.43 (m, 1H), 7.99 (m, 1H), 7.72 (m, 3H), 7.67 (s, 1H), 7.37 (t, 1H), 7.24 (m, 1H), 6.98 (d, 1H), 4.33 (m, 2H), 3.98 (m, 2H), 3.64 (m, 2H), 3.32 (m, 2H), 3.17 (m, 2H) ppm |
| 1-(2-Fluoro-phenyl)-N3-(3-morpholin-4-ylmethyl-phenyl)-1H-[1,2,4]triazole-3,5-diamine | A* | 3 | | | (DMSO-d6, 500 MHz) 9.79 (br s, 1H), 9.14, (s, 1H), 7.61 (d, 1H), 7.55 (m, 3H), 7.43 (m,1H), 7.35 (m, 1H), 7.30 (t, 1H), 6.90 (d, 1H), 6.40 (s, 2H) ppm |
| N3-(2,4-Dimethoxy-phenyl)-1-(2-piperidin-1-yl-pyrimidin-4-yl)-1H-[1,2,4]triazole-3,5-diamine | A | 2 | 397.10 | 3.30 | (DMSO-d6, 500 MHz) 8.36 (d, 1H), 7.95 (d, 1H), 7.62 (s, 2H), 7.24 (s, 1H), 6.78 (d, 1H), 6.61 (d, 1H), 6.52 (dd, 1H), 3.84 (s, 3H), 3.73 (s, 3H), 3.69 (m, 4H), 1.63 (m, 2H), 1.56 (m, 4H) ppm |
| N3-(3,4-Dimethoxy-phenyl)-1-quinolin-2-yl-1H-[1,2,4]triazole-3,5-diamine | A | 1 | 363.10 | 3.60 | (DMSO-d6, 500 MHz) 3.71 (s, 3H), 3.80 (s, 3H), 6.89 (d, 1H), 7.19–7.21 (dd, 1H), 7.39 (d, 1H), 7.52–7.55 (m, 1H), 7.94 (d, 1H), 7.96 (d, 1H), 8.03 (s, 2H), 8.08 (d, 1H), 8.52 (d, 1H), 8.93 (s, 1H) |
| N3-(4-Diethylamino-phenyl)-1-quinolin-2-yl-1H-[1,2,4]triazole-3,5-diamine | A | 1 | 374.20 | 2.40 | (DMSO-d6, 500 MHz) 1.06 (t, 6H), 3.26 (q, 4H), 6.68 (d, 2H), 7.49 (d, 2H), 7.53 (d, 1H), 7.74–7.77 (m, 1H), 7.94–7.98 (m, 4H), 8.05 (d, 1H), 8.49 (d, 1H), 8.69 (s, 1H) |
| N3-(3,4-Dimethoxy-phenyl)-1-(6-methyl-pyridin-2-yl)-1H-[1,2,4]triazole-3,5-diamine | A | 1 | 327.20 | 3.10 | (DMSO-d6, 500 MHz) 2.51 (s, 3H), 3.69 (s, 3H), 3.77 (s, 3H), 6.85 (d, 1H), 7.05 (d, 1H), 7.12–7.14 (dd, 1H), 7.38 (d, 1H), 7.47 (d, 1H), 7.67 (s, 2H), 7.84 (t, 1H), 8.85 (s, 1H) |
| N3-(4-Diethylamino-phenyl)-1-(6-methyl-pyridin-2-yl)-1H-[1,2,4]triazole-3,5-diamine | A | 1 | 338.30 | 2.10 | (DMSO-d6, 500 MHz) 1.04 (s, 6H), 2.50 (s, 3H), 3.24 (q, 4H), 6.65 (d, 2H), 7.03 (d, 1H), 7.45 (d, 1H), 7.47 (d, 2H), 7.62 (s, 2H), 7.83 (t, 1H), 8.60 (s, 1H) |
| N3-(4-Isopropoxy-phenyl)-1-quinolin-2-yl-1H-[1,2,4]triazole-3,5-diamine | A | 2 | 361.2 | | (DMSO-d6, 500 MHz); 8.94 (s, 1H), 8.51 (d, 1H), 8.1–7.9 (m, 5H), 7.76 (t, 1H), 7.60–7.52 (m, 3H), 6.90–6.82 (m, 2H), 4.55–4.45 (m, 1H), 1.89 (d, 6H) |
| N3-(4-Diethylamino-phenyl)-1-(6-ethoxy-pyridin-2-yl)-1H-[1,2,4]triazole-3,5-diamine | Method A | 2 | 368.25 | | |
| N3-(3,4-Dimethoxy-phenyl)-1-(6-phenyl-pyrimidin-4-yl)-1H-[1,2,4]triazole-3,5-diamine | Method A | 1 | 390.15 | 3.60 | d6-DMSO 3.71 (s, 3H), 3.86 (s, 3H), 6.90 (d, 1H), 7.07–7.09 (dd, 1H), 7.59–7.61 (m, 4H), 7.91 (s, 2H), 8.02 (s, 1H), 8.15–8.16 (m, 2H), 9.02 (s, 1H), 9.14 (s, 1H) |
| N3-(3,4-Dimethoxy-phenyl)-1-(6-ethoxy-pyridin-2-yl)-1H-[1,2,4]triazole-3,5-diamine | Method A | 3 | 357.20 | 3.43 | d6-DMSO 1.37 (t, 3H), 3.69 (s, 3H), 3.76 (s, 3H), 4.29 (q, 2H), 6.60 (d, 1H), 6.86 (d, 1H), 7.11–7.13 (dd, 1H), 7.21 (d, 1H), 7.37 (d, 1H), 7.45 (br s, 2H),7.86 (t, 1H), 8.87 (s, 1H) |
| 1-(3-Chloro-4-fluoro-phenyl)-N3-(3,4-dimethoxy-phenyl)-1H-[1,2,4]triazole-3,5-diamine | Method A* | 2 | 364.09 | 3.13 | d6-DMSO 3.67 (s, 3H), 3.72 (s, 3H), 6.68 (br s, 2H), 6.83 (d, 1H), 7.07–7.09 (dd, 1H), 7.25 (d, 1H), 7.55 (t, 1H), 7.58–7.61 (m, 1H), 7.75–7.77 (dd, 1H), 8.77 (s, 1H) |
| N3-(3,4-Dimethoxy- | Method | 2 | 390.06 | 2.10 | d6-DMSO 3.25 (s, 3H), 3.71 (s, |

| Name | cyclisation procedure | Purification procedure | MS (M + H) | Retention time (min) | NMR |
|---|---|---|---|---|---|
| phenyl)-1-(4-methanesulfonyl-phenyl)-1H-[1,2,4]triazole-3,5-diamine | A | | | | 3H), 3.72 (s, 3H), 6.88 (d, 1H), 7.04–7.06 (dd, 1H), 7.12 (d, 1H), 7.82 (d, 2H), 8.02 (d, 2H), 8.97 (s, 1H) |
| 4-[5-Amino-3-(4-diethylamino-phenylamino)-[1,2,4]triazol-1-yl]-benzenesulfonamide | Method A* | 2 | 402.13 | 2.15 | d6-DMSO 1.03 (t, 6H), 3.23 (q, 4H), 6.6 1-6.62 (m, 4H), 7.39–7.41 (m, 4H), 7.76 (d, 2H), 7.88 (d, 2H), 8.52 (s, 1H) |
| N3-(4-Diethylamino-phenyl)-1-(4-methanesulfonyl-phenyl)-1H-[1,2,4]triazole-3,5-diamine | Method A | 2 | 401.10 | 2.10 | d6-DMSO 1.00 (t, 6H), 3.26 (s, 3H), 3.51 (br s, 2H), 3.63 (br s, 2H), 5.50 (br s, 1H), 7.53 (br s, 2H), 7.64 (hr s, 2H), 7.83 (d, 2H), 8.02 (d, 2H), 9.48 (brs, 1H), 11.10(br s, 1H) |
| 1-(3-Chloro-4-fluoro-phenyl)-N3-(4-diethylamino-phenyl)-1H-[1,2,4]triazole-3,5-diamine | Method A* | 3 | 375.12 | 2.10 | d6-DMSO 0.991 Ct, 6H), 3.46–3.51 (m, 2H), 3.59–3.60 (m, 2H), 6.66 (s, 1H), 7.47 (d, 2H), 7.54–7.61 (m, 2H), 7.70 (d, 2H), 7.76–7.78 (dd, 1H), 9.44 (s, 1H), 10.90 (s, 1H) |
| 3-[5-Amino-3-(3,4-dimethoxy-phenylamino)-[1,2,4]triazol-1-yl]-benzonitrile | Method A* | 2 | 337.10 | 2.70 | d6-DMSO 3.68 (s, 3H), 3.76 (s, 3H), 6.70 (s, 2H), 6.84 (d, 1H), 7.10–7.12 (dd, 1H), 7.28 (d, 1H), 7.66–7.72 (m, 2H), 7.92–7.94 (m, 1H), 7.97 (s, 1H), 8.77 (s, 1H) |
| N-{4-[5-Amino-1-(6-methyl-pyridin-2-yl)-1H-[1,2,4]triazol-3-ylamino]-phenyl}-acetamide | Method A | 1 | 324.14 | 2.54 | d6-DMSO 2.00 (s, 3H), 2.50 (s, 3H), 7.06 (d, 1H), 7.43 (d, 2H), 7.51–7.54 (m, 3H), 7.67 (s, 2H), 7.84 (t, 1H), 8.99 (s, 1H), 9.73 (s, 1H) |
| N3-(2-Fluoro-4-methoxy-phenyl)-1-pyridin-2-yl-1H-[1,2,4]triazole-3,5-diamine | Method A | 1 | 301.15 | 3.21 | d6-DMSO 3.74 (s, 3H), 6.74–6.77 (dd, 1H), 6.84-6.87 (dd, 1H), 7.18–7.21 (m, 1H), 7.63 (s, 1H), 7.67 (s, 2H), 7.93–7.98 (m, 2H), 8.29 (s, 1H), 8.39–8.40 (m, 1H) |
| N3-(2,4-Dimethoxy-phenyl)-1-(6-methyl-pyridin-2-yl)-1H-[1,2,4]triazole-3,5-diamine | Method A | 1 | 327.16 | 3.47 | d6-DMSO 2.50 (s, 3H), 3.73 (s, 3H), 3.85 (s, 3H), 6.52–6.54 (dd, 1H), 6.62 (d, 2H), 7.06 (d, 1H), 7.10 (s, 1H), 7.48 (d, 1H), 7.69 (s, 2H), 7.84 (t, 1H), 8.01 (d, 1H) |
| N3-(3,4-Dimethoxy-phenyl)-1-pyridin-2-yl-1H-[1,2,4ltriazole-3,5-diamine | Method A | 2 | 313.15 | 3.28 | d6-DMSO 3.77 (s, 3H), 3.81 (s, 3H), 6.62 (d, 1H), 7.02 (t, 1H), 7.21–7.24 (m, 1H), 7.59 (s, 1H), 7.70–7.71 (m, 3H), 7.86 (d, 1H), 7.96–8.00 (m, 1H), 8.41–8.42 (m, 1H), |
| 6-[5-Amino-3-(2,4-dimethoxy-phenylamino)-[1,2,4]triazol-1-yl]-nicotinonitrile | Method A | 1 | 338.10 | 3.40 | d6DMSO 3.74 (s, 3H), 3.84 (s, 3H), 6.00 (d, 1H), 6.62 (s, 1H), 7.35 (S, 1H), 7.75 (d, 1H), 7.84 (s, 2H), 7.98 (d, H), 8.37 (d, 1H), 8.83 (s, 1H) |
| N3-(4-Methoxy-2-methyl-phenyl)-1-pyridin-2-yl-1H-[1,2,4]triazole-3,5-diamine | Method A | 1 | 297.10 | 2.90 | d6-DMSO 2.24 (s, 314), 3.71 (s, 3H), 6.72–6.74 (m, 2H), 7.16–7.18 (m, 1H), 7.56 (d, 1H), 7.61 (s, 2H), 7.66 (d, 1H), 7.70 (s, 1H), 7.91–7.94 (m, 1H), 8.38–8.39 (m, 1H) |
| N3-(4-Diethylamino-2-methyl-phenyl)-1-pyridin-2-yl-1H-[1,2,4]triazole-3,5-diamine | Method A | 1 | 338.20 | 1.75 | d6-DMSO 1.06 (t, 6H), 2.20 (s, 314), 3.27 (q, 414), 6.48–6.50 (m, 2H), 7.15 (t, 1H), 7.44 (d, 1H), 7.50 (s, 1H), 7.53 (d, 1H), 7.56 (s, 2H), 7.88–7.91 (m, 1H), 8.36 (d, 1H) |
| 1-Pyridin-2-yl-N3-o-tolyl-1H-[1,2,4]triazole-3,5-diamine | Method A | 2 | 267.20 | 3.27 | d6-DMSO 2.27 (s, 3H), 6.86 (t, 1H), 7.11–7.16 (m, 2H), 7.19–7.21 (m, 1H), 7.64 (d, 1H), 7.66 (s, 2H), 7.83 (s, 1H), 7.94–7.97 (m, 2H),8.40–8.41 (m, 1H) |
| 1-Pyridin-2-yl-N3-(5,6,7,8-tetrahydro-naphthalen-1-yl)-1H-[1,2,4]triazole-3,5 | Method A | 1 | 307.10 | 3.90 | d6-DMSO 1.67–1.69 (m, 2H), 1.75–1.77 (m, 2H), 2.63–2.66 (m, 2H), 2.70–2.72 (m, 2H), 6.68 (d, 1H), 7.04 1H), 8.39–8.40 (m, 1H) |
| N3-(2,4-Dimethoxy-phenyl)-1-(6-methyl-4-trifluoromethyl-pyridin-2-yl)-1H-[1,2,4]triazole-3,5- | Method A | 1 | 395.10 | 4.30 | d6-DMSO 2.62 (s, 314), 3.74 (s, 3H), 3.84 (s, 314), 6.55–6.57 (m, 1H) 6.6 1–6.62 (m, 1H), 7.25 (s, 1H), (s, 1H), 7.62 (s, 1H), 7.75 (s, 2H), 7.93 (d, 1H) |

| Name | cyclisation procedure | Purification procedure | MS (M + H) | Retention time (min) | NMR |
|---|---|---|---|---|---|
| diamine | | | | | |
| N3-(2-Methoxy-4-morpholin-4-yl-phenyl)-1-pyridin-2-yl-1H-[1,2,4]triazole-3,5-diamine | Method A | 1 | 368.20 | 2.30 | d6-DMSO 3.05 (t, 4H), 3.74 (t, 4H), 3.85 (s, 3H), 6.50–6.52 (dd, 1H), 6.61 (d, 1H), 7.09 (s, 1H), 7.19–7.21 (m, 1H), 7.67–7.68 (m, 3H), 7.95–7.98 (m, 2H), 8.39–8.40 (m, 1H) |
| N3-(2-Methoxy-4-morpholin-4-yl-phenyl)-1-(6-methyl-pyridin-2-yl)-1H-[1,2,4]triazole-3,5-diamine | Method A | 1 | 436.10 | 3.10 | d6-DMSO 3.05–3.07 (m, 4H), 3.74–3.76 (m, 4H), 3.85 (s, 3H), 6.50–6.52 (m, 1H), 6.66 (d, 1H), 7.25 (s, 1H), 7.60 (s, 2H), 7.71 (d, 1H), 7.95 (d, 2H), 8.24 (t, 1H) |
| 1-(6-Methyl-pyridin-2-yl)-N3-(4-morpholin-4-yl-phenyl)-1H-[1,2,4]triazole-3,5-diamine | Method A | 1 | 406.10 | 2.83 | d6-DMSO 3.00 (t, 4H), 3.74 (t, 4H), 6.89 (d, 2H), 7.52 (d, 2H), 7.58 (s, 2H), 7.70 (d, 1H), 7.95 (d, 1H), 8.25 (t, 1H), 8.96 (s, 1H) |
| N3-(2-Chloro-phenyl)-1-(6-methyl-pyridin-2-yl)-1H-[1,2,4]triazole-3,5-diamine | Method F | 2 | 355.10 | 4.35 | d6-DMSO 6.96–6.99 (m, 1H), 7.32–7.36 (m, 1H), 7.44–7.45 (m, 1H), 7.68 (s, 2H), 7.65 (d, 1H), 7.98–7.99 (m, 2H), 8.23–8.28 (m, 2H) |
| 6-[5-Amino-3-(4-morpholin-4-yl-phenylamino)-[1,2,4]triazol-1-yl]-nicotinonitrile | Method F | 3 | 363.20 | 2.16 | d6-DMSO 3.17 (br s, 4H), 3.80 (br s, 4H), 7.10 (br s, 2H), 7.58 (d, 2H), 7.76 (d, 1H), 7.85 (br s, 2H), 8.38–8.41 (m, 1H), 8.84 (d, 1H), 9.21 (br s, 1H) |
| 6-[5-Amino-3-(2-chloro-phenylamino)-[1,2,4]triazol-1-yl]-nicotinonitrile | Method F | 3 | 312.11 | 3.72 | d6-DMSO 6.97–7.00 (m, (1H), 7.32–7.36 (m, 1H), 7.43–7.45 (m, 1H), 7.78 (d, 1H), 7.92 (s, 2H), 8.21–8.23 (m, 1H), 8.38–8.41 (m, 1H), 8.85 (d, 1H) |
| N3-(2,5-Dimethoxy-phenyl)-1-(6-trifluoromethyl-pyridin-2-yl)-1H-[1,2,4]triazole-3,5-diamine | Method F | 2 | 381.11 | 4.03 | d6-DMSO 3.75 (s, 3H), 3.82 (s, 3H), 6.43-6.46 (m, 1H), 6.91 (d, 1H), 7.50 (s, 1H), 7.67 (s, 2H), 7.74 (d, 1H), 7.85 (d, 1H), 7.93 (d, 1H), 8.30 (t, 1H) |
| 6-[5-Amino-3-(4-morpholin-4-yl-phenylamino)-[1,2,4[triazol-1-yl]-nicotinamide | Method A | 3 | 381.20 | 1.50 | d6-DMSO 3.16 (br s, 4H), 3.80 (br s, 4H), 7.09 (br s, 2H), 7.57–7.59 (m, 3H), 7.71 (d, 1H), 7.79 (br s, 2H), 8.14 (br s, 1H), 8.37–8.39 (m, 1H), 8.86–8.87 (m, 1H), 9.10 (br s, 1H) |
| N3-(2-Chloro-5-methoxy-phenyl)-1-pyridin-2-yl-1H-[1,2,4]triazole-3,5-diamine | Method A | 1 | 317.10 | 3.80 | d6-DMSO 3.80 (s, 3H), 6.53–6.55 (m, 1H), 7.23–7.26 (m, 1H), 7.32 (d, 1H), 7.65 (d, 1H), 7.71 (s, 1H), 7.78 (s, 2H), 7.98–8.02 (m, 2H), 8.42–8.44 (m, 1H) |
| 6-[5-Amino-3-(2,5-dimethoxy-phenylamino)-[1,2,4]triazol-1-yl]-nicotinonitrile | Method F | 3 | 338.14 | 3.43 | d6-DMSO 3.74 (s, 3H), 3.81 (s, 3H), 6.43–6.46 (dd, 1H), 6.91 (d, 1H), 7.54 (s, 1H), 7.71 (d, 1H), 7.83 (d, 1H), 7.90 (s, 2H), 8.41–8.44 (dd, 1H), 8.69 (d, 1H) |
| N3-(2,4-Dimethoxy-5-trifluoromethyl-phenyl)-1-pyridin-2-yl-1H-[1,2,4]triazole-3,5-diamine | Method A | 1 | 381.10 | 3.90 | d6-DMSO 3.90 (s, 3H), 3.97 (s, 3H), 6.91 (s, 1H), 7.21–7.23 (m, 1H), 7.53 (s, 1H), 7.58 (d, 1H), 7.74 (s, 2H), 7.99–8.03 (m, 1H), 8.41–8.42 (m, 1H), 8.44 (s, 1H) |
| N3-(2,5-Dimethoxy-4-morpholin-4-yl-phenyl)-1-pyridin-2-yl-1H-[1,2,4]triazole-3,5-diamine | Method A | 1 | 398.20 | 2.14 | d6-DMSO 2.93–2.95 (m, 4H), 3.71–3.73 (m, 4H), 3.82 (s, 3H), 3.83 (s, 3H), 6.63 (s, 1H), 7.20–7.23 (m, 2H), 7.65 (d, 1H), 7.72 (s, 2H), 7.97–8.00 (m, 2H), 8.40–8.41 (m, 1H) |
| 4-{5-Amino-3-[3,5-dimethoxy-4-(2-morpholin-4-yl-ethoxy)-phenylamino]-[1,2,4]triazol-1-yl}-benzonitrile | Method C | 1 | 466.30 | 1.80 | d6-DMSO 2.46 (br s, 4H), 2.58 (t, 2H), 3.56–3.58 (m, 4H), 3.74 (s, 6H), 3.86 (t, 2H), 6.80 (s, 2H), 6.99 (s, 2H), 7.80 (d, 2H), 7.94 (d, 2H), 8.95 (s, 1H) |
| N3-[2,5-Dimethoxy-4-(2-morpholin-4-yl-ethoxy)-phenyl]-1-pyridin-2-yl-1H-[1,2,4]triazole-3,5-diamine | Method A | 1 | 442.20 | 1.90 | d6-DMSO 2.49–2.50 (m, 4H), 2.66 (t, 2H), 3.58–3.60 (m, 4H), 3.80 (s, 3H), 3.82 (s, 3H), 4.06 (t, 2H), 6.78 (s, 1H), 7.19–7.22 (m, 2H), 7.65 (d, 1H), 7.71 (s, 2H), 7.96–8.0 (m, 2H), |

| Name | cyclisation procedure | Purification procedure | MS (M + H) | Retention time (min) | NMR |
|---|---|---|---|---|---|
| diamine | | | | | 8.40–8.41 (m, 1H) |
| 4-{5-Amino-3-[2,5-dimethoxy-4-(2-morpholin-4-yl-ethoxy)-phenylamino]-[1,2,4]triazol-1-yl}-benzonitrile | Method C* | 3 | 466.21 | 1.93 | d6-DMSO 3.22–3.24 (m, 2H), 3.53–3.60 (m, 4H), 3.72–3.74 (m, 2H), 3.77 (s, 3H), 3.82 (s, 3H), 4.02–4.04 (m, 2H), 4.26–4.28 (m, 2H), 6.86 (s, 3H), 7.34 (s, 1H), 7.78–7.79 (m, 2H), 7.94–7.97 (m, 2H), 7.98 (s, 1H), 10.0 (s, 1H) |
| 6-[5-Amino-3-(2-methoxy-4-morpholin-4-yl-phenylamino)-[1,2,4]triazol-1-yl]-nicotinamide | Method C | 3 | 411.06 | | d6-DMSO 3.13 (br s, 4H), 3.78 (br s, 4H), 3.87 (s, 3H), 6.62 (br s, 1H), 6.75 (br s, 1H), 7.37 (s, 1H), 7.57 (s, 1H), 7.71 (d, 1H), 7.91 (s, 2H), 8.00 (d, 1H), 8.16 (s, 1H), 8.37–8.39 (m, 1H), 8.86–8.87 (m, 1H) |
| 6-[5-Amino-3-(2-methoxy-4-morpholin-4-yl-phenylamino)-[1,2,4]triazol-1-yl]-nicotinonitrile | Method C | 2 | 393.10 | 2.58 | d6-DMSO 3.06 (s, 4H), 3.74 (s, 4H), 3.85 (s, 3H), 6.50–6.52 (m, 1H), 6.66 (s, 1H), 7.30 (s, 1H), 7.73–7.74 (m, 1H), 7.83 (s, 2H), 7.92–7.94 (m, 1H), 8.37–8.38 (m, 1H), 8.82 (s, 1H) |
| 1-(6-Methyl-pyridin-2-yl)-N3-(4-morpholin-4-yl-phenyl)-1H-[1,2,4]triazole-3,5-diamine | Method | | 352.25 | 2.31 | d6-DMSO 2.50 (s, 3H), 2.99 (t, 4H), 3.73 (t, 4H), 6.88 (d, 2H), 7.05 (d, 1H), 7.47 (d, 1H), 7.51 (d, 2H), 7.65 (s, 2H), 7.84 (t, 1H), 8.80 (s, 1H), |
| N3-(4-Methoxy-phenyl)-1-pyridin-2-yl-1H-[1,2,4]triazole-3,5-diamine | A | 3 | 283.1 | 3.12 | DMSO(d6): 8.95 (br.s, 1H), 8.41 (dd, 1H), 7.99 (td, 1H), 7.8 (m, 2H), 7.69 (d, 1H), 7.55 (m, 2H), 7.21 (dd, 1H), 6.86 (m, 2H), 3.70 (s, 3H) |
| N3-(3-Methoxy-phenyl)-1-pyridin-2-yl-1H-[1,2,4]triazole-3,5-diamine | A | 3 | 283.10 | 3.19 | DMSO(d6): 9.18 (br.s, 1H), 8.42 (dd, 1H), 8.00 (td, 1H), 7.8 (m, 2H), 7.68 (d, 1H), 7.37 (m, 1H), 7.24 (dd, 1H), 7.15 (m, 2H), 6.43 (m, 1H), 3.75 (s, 3H) |
| 4-(5-Amino-1-pyridin-2-yl-1H-[1,2,4]triazol-3-ylamino)-benzoic acid methyl ester | A | 3 | 311.1 | 3.26 (A) | DMSO(d6): 9.74 (s, 1H), 8.42 (dd, 1H), 8.00 (td, 1H), 7.87 (d, 2H), 7.77 (br. s, 2H), 7.75 (d, 1H), 7.72 (d, 2H), 7.24 (dd, 1H), 3.80 (s, 3H) |
| 3-(5-Amino-1-pyridin-2-yl-1H-[1,2,4]triazol-3-ylamino)-benzamide | A | 3 | 296.1 | 2.23 | DMSO(d6): 9.30 (s, 1H), 8.42 (dd, 1H), 8.03 (m, 1H), 8.01 (td, 1H), 7.86 (br.s, 1H), 7.84 (dt, 1H), 7.77 (br. s, 2H), 7.73 (d, 1H), 7.31 (m, 2H), 7.27 (br.s, 1H), 7.23 (dd, 1H). |
| 4-(5-Amino-1-pyridin-2-yl-1H-[1,2,4]triazol-3-ylamino) benzenesulfonamide | A | 3 | 332.1 | 2.36 | DMSO(d6): 9.66 (s, 1H), 8.43 (dd, 1H), 8.00 (td, 1H), 7.73 (m, 7H), 7.23 (dd, 1H), 7.12 (br.s, 2H). |
| 3-(5-Amino-1-pyridin-2-yl-1H-[1,2,4]triazol-3-ylamino)-benzenesulfonamide | A | 3 | 332.1 | 2.47 | DMSO(d6): 9.54 (s, 1H), 8.43 (dd, 1H), 8.19 (t, 1H), 8.00 (td, 1H), 7.80 (dd, 1H), 7.7S (m, 2H), 7.73 (d, 1H), 7.44 (t, 1H), 7.32 (s, 2H), 7.30 (d, 1H), 7.23 (dd, 1H). |
| N3-(2,4-Dimethoxy-phenyl)-1-pyridin-2-yl-1H-[1,2,4]triazole-3,5-diamine | A | 3 | 313.2 | 3.16 | DMSO(d6): 8.44 (dd, 1H), 8.17 (br.s, 2H), 8.01 (td, 1H), 7.99 (d, 1H), 7.72 (d, 1H), 7.63 (br.s, 1H), 7.28 (dd, 1H), 6.65 (d, 1H), 6.55 (dd, 1H), 3.86 (s, 3H), 3.73 (s, 3H).. |
| N3-C3,4-Dimethoxy-phenyl)-1-C2-fluoro-phenyl)-1H-[1,2,4]triazole-3,5-diamine | A* | 3 | 330.2 | 2.90 (A) | DMSO(d6): 8.60 (s, 1H), 7.54 (td, 1H), 7.46 (m, 1H), 7.40 (t, 1H), 7.22 (t, 1H), 7.38 (d, 1H), 7.06 (dd, 1H), 6.79 (d, 1H), 6.31 (s, 2H), 3.68 (s, 3H), 3.63 (s, 3H). |
| N-[4-(5-Amino-1-pyridin-2-yl-1H-[1,2,4]triazol-3-ylamino)-phenyl]-acetamide | A | 3 | 338.1 | 3.09 | DMSO(d6): 9.74 (s, 1H), 9.05 (s, 1H), 8.40 (dd, 1H), 7.97 (td, 1H), 7.73 (d, 1H, m, 2H), 7.53 (d, 2H), 7.45 (d, 2H), 7.20 (dd, 1H), 2.03 (s, 3H). |
| N-[3-(5-Amino-1-pyridin-2-yl-1H-[1,2,4]triazol-3-ylamino)-phenyl]-acetamide | A | 3 | 310.2 | 2.77 (A) | DMSO(d6): 9.86 (s, 1H, NH), 9.13 (s, 1H, NH), 8.41 (dd, 1H), 7.99 (m, 2H), 7.84 (d, 1H), 7.75 (m, 2H, NH2), 7.24 (d, 1H), 7.22 (dd, 1H), 7.13 (t, 1H), 7.09 (d, 1H), 2.07 (s, 3H, CH3) |

-continued

| Name | cyclisation procedure | Purification procedure | MS (M + H) | Retention time (min) | NMR |
|---|---|---|---|---|---|
| 1-(2-Chloro-phenyl)-N3-(3,4-dimethoxy-phenyl)-1H-[1,2,4]triazole-3,5-diamine | A* | 3 | 346.2 | 2.90 (A) | DMSO(d6): 8.55 (s, 1H), 7.65 (m, 1H), 7.53 (m, 1H), 7.49 (m, 2H), 7.17 (d, 1H), 7.07 (dd, 1H), 6.78 (d, 1H), 6.20 (s, 2H), 3.68 (s, 3H), 3.65 (s, 3H)., CDCl3: 7.5 (m, 2H), 7.4 (m, 2H), 7.1 (d, 1H), 6.9 (dd, 1H), ,6.7 (d, 1H), 6.6 (bs ,1H), 3.8 (s, 3H), 3.7 (s, 3H). |
| N3-[4-Methoxy-3-(2-methoxy-ethoxy)-phenyl]-1-pyridin-2-yl-1H-[1,2,4]triazole-3,5-diamine | A | 3 | 357.2 | 2.96 | DMSO(d6): 8.88 (s, 1H), 8.41 (dd, 1H), 7.97 (td, 1H), 7.68 (m, 3H), 7.36 (d, 1H), 7.21 (dd, 1H), 7.18 (dd, 1H), 6.89 (d, 1H), 4.08 (t, 2H), 3.71 (s, 3H), 3.70 (t, 2H), 3.33 (s, 3H). |
| N3-[3-Methoxy-4-(2-methoxy-ethoxy)-phenyl]-1-pyridin-2-yl-1H-[1,2,4]triazole-3,5-diamine | A | 3 | 357.2 | 2.83 | DMSO(d6): 8.90 (s, 1H), 8.41 (dd, 1H), 7.97 (td, 1H), 7.68 (m, 3H), 7.40 (d, 1H), 7.21 (dd, 1H), 7.12 (dd, 1H), 6.86 (d, 1H), 3.99 (t, 2H), 3.78 (s, 3H), 3.63 (t, 2H), 3.32 (s, 3H). |
| N3-[3,4-Bis-(2-methoxy-ethoxy)-phenyl]-1-pyridin-2-yl-1H-[1,2,4]triazole-3,5-diamine | A | 3 | 401.2 | 2.90 | DMSO(d6): 8.91 (s, 1H), 8.41 (dd, 1H), 7.98 (td, 1H), 7.68 (m, 3H), 7.39 (d, 1H), 7.21 (dd, 1H), 7.14 (dd, 1H), 6.89 (d, 1H), 4.11 (t, 2H), 4.03 (t, 2H), 3.70 (t, 2H), 3.62 (t, 2H), 3.35 (s, 3H), 3.32 (s, 3H). |
| N3-Phenyl-1-pyridin-2-yl-1H-[1,2,4]triazole-3,5-diamine | A | 3 | 253.1 | 3.21 | DMSO(d6): 9.12 (s, 1H), 8.41 (dd, 1H), 7.98 (td, 1H), 7.70 (d, 1H), 7.68 (br. s, 2H), 7.63 (d, 2H), 7.25 (t, 2H), 7.21 (dd, 1H), 6.82 (t, 1H). |
| N3-(3,5-Dimethoxy-phenyl)-1-pyridin-2-yl-1H-[1,2,4]triazole-3,5-diamine | A | 3 | 313.1 | 3.19 (A) | DMSO(d6): 9.08 (s, 1H), 8.41 (dd, 1H), 8.00 (td, 1H), 7.70 (s, 2H), 7.64 (d, 1H), 7.23 (dd, 1H), 6.90 (d, 2H), 6.03 (t, 1H), 6.73 (s, 6H). |
| 1-Pyridin-2-yl-N3-(3-trifluoromethyl-phenyl)-1H-[1,2,4]triazole-3,5-diamine | A | 3 | 321.1 | 3.86 | DMSO(d6): 9.58 (s, 1H), 8.42 (dd, 1H), 8.03 (s, 1H), 8.01 (td, 1H), 7.87(dd, 1H), 7.70 (s, 2H), 7.66 (d, 1H), 7.48 (t, 1H), 7.23 (dd, 1H), 7.15 (d, 1H). |
| N3-(4-Butoxy-phenyl)-1-pyridin-2-yl-1H[1,2,4]triazole-3,5-diamine | A | 3 | 325.2 | 3.55 (A) | DMSO(d6): 8.88 (s, 1H), 8.40 (dd, 1H), 7.97 (td, 1H), 7.67 (m, 3H), 7.52(d, 2H), 7.17 (dd, 1H), 6.81 (d, 2H), 3.90 (t, 2H), 1.67 (m, 2H), 1:42 (m, 2H), 0.93 (t, 3H). |
| N3-(3,5-Difluoro-phenyl)-1-pyridin-2-yl-1H-[1,2,4]triazole-3,5-diamine | A | 3 | 289.1 | 3.37 (A) | DMSO(d6): 9.41 (s, 1H), 8.42 (dd, 1H), 8.00 (td, 1H), 7.75 (m, 3H), 7.68(d, 1H), 7.30 (m, 2H), 7.23 (dd, 1H) |
| 1-(2-Fluoro-phenyl)-N3-(3,4,5-trimethoxy-phenyl)-1H-[1,2,4]triazole-3,5-diamine | C* | 3 | 360.1 | 2.97 (A) | 1H-DMSO(d6): 8.71 (s, 1H), 7.56 (td, 1H), 7.46 (m, 1H), 7.41 (td, 1H), 7.32 (td, 1H), 6.92 (s, 2H), 6.34 (s, 2H), 3.68 (s, 6H), 3.55 (s, 3H)., |
| 4-[5-Amino-3-(3,4,5-trimethoxy-phenylamino)-[1,2,4]triazol-1-yl]-benzonitrile | C* | 3 | 367.2 | 3.08 (A) | 1H-DMSO(d6): 8.95 (s, 1H), 7.94 (d, 2H), 7.80 (d, 2H), 7.00 (s, 2H), 6.80 (s, 2H), 3.82 (s, 6H), 3.56 (s, 3H).,,8.93(1H), 7.93 (J=8.7, 2H), 7.79 (J=8.7, 2H), 6.98 (2H), 6.79 (2H), 3.73 (6H), 3.57 (3H),(500 MHz, DMSO-d6) 8.99 (s, 1H), 7.95 (d, 2H), ,7.80 ( |
| 4-[3-Amino-5-(3,4,5-trimethoxy-phenylamino)-[1,2,4]triazol-1-yl]-benzonitrile | C* | 3 | 367.2 | 2.83 (A) | 1H-DMSO(d6): 8.95 (s, 1H), 7.94 (d, 2H), 7.73 (d, 2H), 6.85 (s, 2H), 5.60 (s, 2H), 3.73 (s, 6H), 3.60 (s, 3H)., |
| N3-(4-Chloro-2,5-dimethoxy-phenyl)-1-pyridin-2-yl-1H-[1,2,4]triazole-3,5-diamine | A | 3 | 347.1 | 3.57 (A) | DMSO(d6): 8.44 (ddd, 1H), 8.17 (s, 1H), 8.01 (td, 1H), 7.88 (br. s, 2H, NH2), 7.70 (s, 1H), 7.68 (d, 1H), 7.25 (ddd, 1H), 7.08 (s, 1H), 3.90 (s, 3H), 3.83 (s, 3H). |
| N3-(5-Chloro-2-methoxy-phenyl)-1-pyridin-2-yl-1H-[1,2,4]triazole-3,5-diamine | A | 3 | 313.1 | 3.34 | DMSO(d6): 8.45 (dd, 1H), 8.22 (d, 1H), 8.05 (td, 1H), 7.97 (m, 2H), 7.81 (s, 1H), 7.66 (d, 1H), 7.28 (dd, 1H), 7.00 (d, 1H), 6.92 (dd, 1H), 3.89 (s, 3H) |
| 2-(5-Amino-1-pyridin-2-yl-1H- | A | 3 | 325.2 | 3.53 | DMSO(d6): 11.17 (s, 1H), 9.85 (s, 1H), 8.49 (d, 1H), 8.42 (d, 1H), 7.98 |

| Name | cyclisation procedure | Purification procedure | MS (M + H) | Retention time (min) | NMR |
|---|---|---|---|---|---|
| [1,2,4]triazol-3-ylamino)-4-tert-butyl-phenol | | | | | (t, 1H), 7.59 (d, 1H), 7.20 (t, 1H), 6.83 (d, 1H), 6.78 (d, 1H), 5.70 (br.s, 2H), 1.28 (s, 9H) |
| N3-(2-Methoxy-5-nitro-phenyl)-1-pyridin-2-yl-1H-[1,2,4]triazole-3,5-diamine | A | 3 | 328.1 | 3.51 | DMSO(d6): 9.20 (d, 1H), 8.45 (d, 1H), 8.10 (s, 1H), 8.06 (t, 1H), 7.87 (dd, 1H), 7.81 (s, 2H), 7.69 (d, 1H), 7.26 (t, 1H), 7.20 (d, 1H), 4.00 (s, 3H). |
| 3-(5-Amino-1-pyridin-2-yl-1H-[1,2,4]triazol-3-ylamino)-4-methoxy-benzoic acid methyl ester | A | 3 | 341.1 | 3.29 | DMSO(d6): 8.90 (d, 1H), 8.43 (d, 1H), 8.05 (td, 1H), 7.78 (s, 2H), 7.69 (d, 1H), 7.64 (s, 1H), 7.55 (dd, 1H), 7.25 (dd, 1H), 7.11 (d, 1H), 3.92 (s, 3H), 3.84 (s, 3H). |
| N3-(2-Methoxy-5-trifluoromethyl-phenyl)-1-pyridin-2-yl-1H-[1,2,4]triazole-3,5-diamine | A | 3 | 351.2 | 4.00 | DMSO(d6): 8.56 (d, 1H), 8.44 (d, 1H), 8.05 (td, 1H), 7.86 (s, 1H), 7.84 (m, 2H), 7.61 (d, 1H), 7.25 (d, 1H), 7.24 (d, 1H), 7.17 (dd, 1H), 3.97 (s, 3H) |
| 3-(5-Amino-1-pyridin-2-yl-1H-[1,2,4]triazol-3-ylamino)-biphenyl-4-ol | A | 3 | 345.1 | 3.47 | DMSO(d6): 11.30 (s, 1H), 10.32 (br.s, 1H), 8.66 (d, 1H), 8.45 (dd, 1H), 8.00 (td, 1H), 7.61 (d, 1H), 7.57 (m, 2H), 7.45 (t, 2H), 7.30 (t, 1H), 7.23 (td, 1H), 7.13 (dd, 1H), 6.98 (d, 1H), 5.80 (m, 2H). |
| 1-Pyridin-2-yl-N3-(2,3,5-trimethoxy-phenyl)-1H-[1,2,4]triazole-3,5-diamine | A | 3 | 343.1 | 3.21 | DMSO(d6): 8.46 (dd, 1H), 8.10 (m, 2H), 8.04 (td, 1H), 7.95 (br.s, 1H), 7.69 (d, 1H), 7.53 (d, 1H), 7.28 (dd, 1H), 6.25 (d, 1H), 3.82 (s, 3H), 3.79 (s, 3H), 3.72 (s, 3H) |
| N3-(2,5-Difluoro-phenyl)-1-pyridin-2-yl-1H-[1,2,4]triazole-3,5-diamine | C | 3 | 289.1 | 3.70 | DMSO(d6): 9.03 (s, 1H), 8.43 (dd, 1H), 8.12 (ddd, 1H), 8.01 (td, 1H), 7.80 (br.s, 2H), 7.68 (d, 1H), 7.25 (dd, 1H), 7.20 (ddd, 1H), 6.69 (m, 1H) |
| N3-(2-Methoxy-5-trifluoromethoxy-phenyl)-1-pyridin-2-yl-1H-[1,2,4]triazole-3,5-diamine | A | 3 | 367.2 | 3.90 (A) | DMSO(d6): 8.43 (dd, 1H), 8.25 (d, 1H), 8.02 (td, 1H), 7.85 (br. s, 2H, NH2), 7.81 (s, 1H, NH), 7.62 (d, 1H), 7.26 (dd, 1H), 7.06 (d, 1H), 6.85 (dd, 1H), 3.90 (s, 3H) |
| 1-Pyridin-2-yl-N3-(2-trifluoromethoxy-phenyl)-1H-[1,2,4]triazole-3,5-diamine | A | 3 | 337.10 | 3.90 | DMSO(d6): 8.63 (s, 1H), 8.42 (dd, 1H), 8.35 (dd, 1H), 8.00 (td, 1H), 7.74 (br.s, 2H), 7.71 (d, 1H), 7.34 (td, 1H), 7.31 (dd, 1H), 7.23 (dd, 1H), 6.98 (td, 1H). |
| N3-(2-Isopropoxy-5-methoxy-phenyl)-1-pyridin-2-yl-1H-[1,2,4]triazole-3,5-diamine | C | 3 | 341.1 | 3.82 | DMSO(d6): 8.43 (dd, 1H), 8.02 (td, 1H), 7.86 (m, 2H, NH2), 7.85 (d, 1H), 7.67 (d, 1H), 7.33 (s, 1H), 7.25 (dd, 1H), 6.94 (d, 1H), 6.42 (dd, 1H), 4.55 (m, 1H), 3.74 (s, 3H), 1.28 (s, 3H), 1.26 (s, 3H). |
| N3-(2-Fluoro-5-morpholin-4-yl-phenyl)-1-pyridin-2-yl-1H-[1,2,4]triazole-3,5-diamine | C | 3 | 356.2 | 3.24 | 8.49 (m, 1H), 8.40 (d, 1H), 8.00 (td, 1H), 7.90 (dd, 1H), 7.76 (br.s, 2H), 7.61 (d, 1H), 7.22 (dd, 1H), 7.05 (dd, 1H), 6.50 (dd, 1H), 3.78 (m, 4H), 3.09 (m, 4H). |
| 4-[5-Amino-3-(3,5-diisopropoxy-phenylamino)-[1,2,4]triazol-1-yl]-benzonitrile | D* | 3 | 393.2 | 4.00 (A) | DMSO(d6): 8.92 (s, 1H), 7.95 (d, 2H), 7.80 (d, 2H), 6.77 (s, 2H), 6.76 (m, 2H), 5.95 (s, 1H), 4.47 (m, 2H), 1.21 (s, 6H), 1.22 (s, 6H). |
| 4-[5-Amino-3-(3,5-dimethoxy-phenylamino)-[1,2,4]triazol-1-yl]-benzonitrile | D* | 3 | 335.2 (M-1) | 3.11 | DMSO(d6): 9.00 (s, 1H), 7.94 (d, 2H), 7.79 (d, 2H), 6.83 (d, 2H), 6.77 (m, 2H), 6.00 (t, 1H), 3.70 (s, 6H). |
| 3-[5-Amino-3-(3,4,5-trimethoxy-phenylamino)-[1,2,4]triazol-1-yl]-benzonitrile | D* | 3 | 365.2 (M-1) | 2.74 | DMSO(d6): 8.86 (s, 1H), 7.98 (m, 1H), 7.94 (dt, 1H), 7.72 (dt, 1H), 7.68 (t, 1H), 6.97 (s, 2H), 6.75 (m, 2H), 3.75 (s, 6H), 3.58 (s, 3H). |
| N-{3-Acetylamino-5-[5-amino-1-(4-cyano-phenyl)-1H-[1,2,4]triazol-3-ylaminol]-phenyl}- | C* | 3 | 391.2 | 2.05 | DMSO(d6): 9.76 (s, 2H), 8.97 (s, 1H), 7.93 (d, 2H), 7.90 (d, 2H), 7.54 (s, 2H), 7.40 (s, 1H), 6.71 (s, 2H), 2.02 (s, 6H). |

-continued

| Name | cyclisation procedure | Purification procedure | MS (M + H) | Retention time (min) | NMR |
|---|---|---|---|---|---|
| acetamide | | | | | |
| 4-[5-Amino-3-(3,5-dimethoxy-4-methyl-phenylamino)-[1,2,4]triazol-1-yl]-benzonitrile | D* | 3 | 351.3 | 3.50 | DMSO(d6): 8.92 (s, 1H), 7.93 (d, 2H), 7.80 (d, 2H), 6.97 (s, 2H), 6.8 (br, s, 2H), 3.74 (s, 6H), 1.91 (s, 3H). |
| N3-(3-Methoxy-4-morpholin-4-yl-phenyl)-1-pyridin-2-yl-1H-[1,2,4]triazole-3,5-diamine | D | 3 | 368.3 | 1.79 | DMSO(d6): 9.35 (br.s, 1H), 8.42 (dd, 1H), 8.00 (td, 1H), 7.77 (m, 2H), 7.70 (d, 1H), 7.61 (s, 1H), 7.32 (m, 1H), 7.22 (m, 2H), 3.94 (s, 3H), 3.90 (m, 4H), 3.38 (m, 4H). |
| 4-[5-Amino-3-(3-methoxy-4-morpholin-4-yl-phenylamino)-[1,2,4]triazol-1-yl]-benzonitrile | D* | 3 | 392.2 | 1.79 | DMSO(d6): 9.18 (br.s, 1H), 7.94 (d, 2H), 7.80 (d, 2H), 7.47 (s, 1H), 7.18 (br.s, 2H), 6.81 (m, 2H), 3.78 (m, 7H), 3.90 (m, 4H), 3.20 (m, 4H). |
| N3-(3,5-Dimethoxy-phenyl)-1-(2-fluoro-phenyl)-1H-[1,2,4]triazole-3,5-diamine | D* | 3 | 386.3 | 3.90 | DMSO(d6): 8.73 (s, 1H), 7.54 (td, 1H), 7.48 (m, 1H), 7.40 (t, 1H), 7.32 (t, 1H), 6.68 (d, 2H), 6.4 (m, 2H), 5.59 (m, 1H), 4.46 (m, 2H), 1.23 (s, 6H), 1.21 (s, 6H) |
| N3-(3-Isopropoxy-4-morpholin-4-yl-phenyl)-1-pyridin-2-yl-1H-[1,2,4]triazole-3,5-diamine | D | 3 | 396.3 | 2.42 | DMSO(d6): 9.27 (s, 1H, NH), 8.42 (dd, 1H), 8.00 (td, 1H), 7.73 (m, 2H, NH2), 7.65 (d, 1H), 7.60 (s, 1H), 7.22 (m, 2H), 7.14 (d, 1H), 4.69 (m, 1H), 3.90 (m, 4H), 3.38 (m, 4H), 1.42 (d, 6H) |
| 4-[5-Amino-3-(3-isopropoxy-4-morpholin-4-yl-phenylamino)-[1,2,4]triazol-1-yl]-benzonitrile | D* | 3 | 420.3 | 2.31 | DMSO(d6): 9.20 (s, 1H, NH), 7.96 (d, 2H), 7.80 (d, 2H), 7.54 (s, 1H), 7.20(m, 1H), 7.11 (dd, 1H), 6.82 (m, 2H), 4.64 (m, 1H), 3.88 (m, 4H), 3.34 (m, 4H), 1.38 (d, 6H) |
| N3-(3-Isopropoxy-4-morpholin-4-ylmethyl-phenyl)-1-pyridin-2-yl-1H-[1,2,4]triazole-3,5-diamine | D | 3 | 410.3 | 3.00 (A) | DMSO(d6):9.36 (s, 1H, NH), 8.42 (dd, 1H), 8.00 (td, 1H), 7.70 (m, 2H, NH2), 7.65 (d, 1H), 7.62 (d, 1H), 7.30 (d, 1H), 7.23 (dd, 1H), 7.12 (dd, 1H), 4.63 (m, 1H), 4.20 (s, 2H), 3.97 (d, 2H), 3.65 (t, 2H), 3.31 (d, 2H), 3.10 (m, 2H), 1.41 (s, 3H), 1.40 (s, |
| 4-[5-Amino-3-(3-isopropoxy-4-morpholin-4-ylmethyl-phenylamino)-[1,2,4]triazol-1-yl]-benzonitrile | D* | 3 | 434.3 | 3.02 | DMSO(6): 9.30 (s, 1H), 7.95 (d, 2H), 7.79 (d, 2H), 7.58 (d, 1H), 7.28 (d, 1H), 7.08 (dd, 1H), 6.80 (br. s, 2H, NH2), 4.60 (m, 1H), 4.18 (d, 2H), 3.96 (d, 2H), 3.64 (t, 2H), 7.30 (d, 2H), 3.10 (q, 2H), 1.38 (d, 6H). |
| N3-[4-(1-Methyl-piperidin-4-yl)-phenyl]-1-pyridin-2-yl-1H-[1,2,4]triazole-3,5-diamine | D | 3 | 350.3 | 2.74 (A) | DMSO(d6): 9.06 (s, 1H), 8.41 (dd, 1H), 7.98 (td, 1H), 7.70 (d, 1H), 7.69 (m, 2H), 7.58 (d, 2H), 7.20 (dd, 1H), 7.10 (d, 2H), 3.50 (d, 2H), 3.06 (m, 2H), 2.81 (d, 3H), 2.70 (tt, 1H), 2.00 (d, 2H), 1.80 (m, 2H). |
| 5-(5-Amino-1-pyridin-2-yl-1H-[1,2,4]triazol-3-ylamino)-2-morpholin-4-yl-benzonitrile | D | 3 | 363.3 | 3.20 | DMSO(d6):9.32 (s, 1H), 8.41 (d, 1H), 8.00 (td, 1H), 7.95 (d, 1H), 7.80 (dd, 1H), 7.74 (m, 2H), 7.65 (d, 1H), 7.21 (dd, 1H), 7.18 (d, 1H), 3.76 (m, 4H), 3.02 (m, 4H). |
| N3-(4-Methoxy-phenyl)-1-pyridin-2-yl-1H-[1,2,4]triazole-3,5-diamine | A | 3 | 283.1 | 3.12 | DMSO(d6): 8.95 (br.s, 1H), 8.41 (dd, 1H), 7.99 (td, 1H), 7.8 (m, 2H), 7.69 (d, 1H), 7.55 (m, 2H), 7.21 (dd, 1H), 6.86 (m, 2H), 3.70 (s, 3H) |
| N3-(3-Methoxy-phenyl)-1-pyridin-2-yl-1H-[1,2,4]triazole-3,5-diamine | A | 3 | 283.10 | 3.19 | DMSO(d6): 9.18 (br.s, 1H), 8.42 (dd, 1H), 8.00 (td, 1H), 7.8 (m, 2H), 7.68 (d, 1H), 7.37 (m, 1H), 7.24 (dd, 1H), 7.15 (m, 2H), 6.43 (m, 1H), 3.75 (s, 3H) |
| 4-(5-Amino-1-pyridin-2-yl-1H-[1,2,4]triazol-3-ylamino)-benzoic acid methyl ester | A | 3 | 311.1 | 3.26 (A) | DMSO(d6): 9.74 (s, 1H), 8.42 (dd, 1H), 8.00 (td, 1H), 7.87 (d, 2H), 7.77 (br. s, 2H), 7.75 (d, 1H), 7.72 (d, 2H), 7.24 (dd, 1H), 3.80 (s, 3H) |
| 3-(5-Amino-1-pyridin-2-yl-1H- | A | 3 | 296.1 | 2.23 | DMSO(d6): 9.30 (s, 1H), 8.42 (dd, 1H), 8.03 (m, 1H), 8.01 (td, 1H), |

-continued

| Name | cyclisation procedure | Purification procedure | MS (M + H) | Retention time (min) | NMR |
|---|---|---|---|---|---|
| [1,2,4]triazol-3-ylamino)-benzamide | | | | | 7.86 (br.s, 1H), 7.84 (dt, 1H), 7.77 (br. s, 2H), 7.73 (d, 1H), 7.31 (m, 2H), 7.27 (br.s, 1H), 7.23 (dd, 1H). |
| 4-(5-Amino-1-pyridin-2-yl-1H-[1,2,4]triazol-3-ylamino)-benzenesulfonamide | A | 3 | 332.1 | 2.36 | DMSO(d6): 9.66 (s, 1H), 8.43 (dd, 1H), 8.00 (td, 1H), 7.73 (m, 7H), 7.23 (dd, 1H), 7.12 (br.s, 2H). |
| 3-(5-Amino-1-pyridin-2-yl-1H-[1,2,4]triazol-3-ylamino)-benzenesulfonamide | A | 3 | 332.1 | 2.47 | DMSO(d6): 9.54 (s, 1H), 8.43 (dd, 1H), 8.19 (t, 1H), 8.00 (td, 1H), 7.80 (dd, 1H), 7.75 (m, 2H), 7.73 (d, 1H), 7.44 (t, 1H), 7.32 (s, 2H), 7.30 (d, 1H), 7.23 (dd, 1H). |
| N3-(2,4-Dimethoxy-phenyl)-1-pyridin-2-yl-1H-[1,2,4]triazole-3,5-diamine | A | 3 | 313.2 | 3.16 | DMSO(d6): 8.44 (dd, 1H), 8.17 (br.s, 2H), 8.01 (td, 1H), 7.99 (d, 1H), 7.72 (d, 1H), 7.63 (br.s, 1H), 7.28 (dd, 1H), 6.65 (d, 1H), 6.55 (dd, 1H), 3.86 (s, 3H), 3.73 (s, 3H).. |
| N3-(3,4-Dimethoxy-phenyl)-1-(2-fluoro-phenyl)-1H-[1,2,4]triazole-3,5-diamine | A* | 3 | 330.2 | 2.90 (A) | DMSO(d6): 8.60 (s, 1H), 7.54 (td, 1H), 7.46 (m, 1H), 7.40 (t, 1H), 7.22 (t, 1H), 7.38 (d, 1H), 7.06 (dd, 1H), 6.79 (d, 1H), 6.31 (s, 2H), 3.68 (s, 3H), 3.63 (s, 3H). |
| N-[4-(5-Amino-1-pyridin-2-yl-1H-[1,2,4]triazol-3-ylamino)-phenyl]-acetamide | A | 3 | 338.1 | 3.09 | DMSO(d6): 9.74 (s, 1H), 9.05 (s, 1H), 8.40 (dd, 1H), 7.97 (td, 1H), 7.73 (d, 1H, m, 2H), 7.53 (d, 2H), 7.45 (d, 2H), 7.20 (dd, 1H), 2.03 (s, 3H). |
| N-[3-(5-Amino-1-pyridin-2-yl-1H-[1,2,4]triazol-3-ylamino)-phenyl]-acetamide | A | 3 | 310.2 | 2.77 (A) | DMSO(d6): 9.86 (s, 1H, NH), 9.13 (s, 1H, NH), 8.41 (dd, 1H), 7.99 (m, 2H), 7.84 (d, 1H), 7.75 (m, 2H, NH2), 7.24 (d, 1H), 7.22 (dd; 1H), 7.13 (t, 1H), 7.09 (d, 1H), 2.07 (s, 3H, CH3) |
| 1-(2-Chloro-phenyl)-N3-(3,4-dimethoxy-phenyl)-1H-[1,2,4]triazole-3,5-diamine | A* | 3 | 346.2 | 2.90 (A) | DMSO(d6): 8.55 (s, 1H), 7.65 (m, 1H), 7.53 (m, 1H), 7.49 (m, 2H), 7.17 (d, 1H), 7.07 (dd, 1H), 6.78 (d, 1H), 6.20 (s, 2H), 3.68 (s, 3H), 3.65 (s, 3H).,CDCl3: 7.5(m, 2H), 7.4(m, 2H), 7.1(d, 1H), 6.9(dd, 1H),, 6.7(d, 1H), 6.6(bs, 1H), 3.8(s, 3H), 3.7(s, 3H). |
| N3-[4-Methoxy-3-(2-methoxy-ethoxy)-phenyl]-1-pyridin-2-yl-1H-[1,2,4]triazole-3,5-diamine | A | 3 | 357.2 | 2.96 | DMSO(d6): 8.88 (s, 1H), 8.41 (dd, 1H), 7.97 (td, 1H), 7.68 (m, 3H), 7.36 (d, 1H), 7.21 (dd, 1H), 7.18 (dd, 1H), 6.89 (d, 1H), 4.08 (t, 2H), 3.71 (s, 3H), 3.70 (t, 2H), 3.33 (s, 3H). |
| N3-[3-Methoxy-4-(2-methoxy-ethoxy)-phenyl]-1-pyridin-2-yl-1H-[1,2,4]triazole-3,5-diamine | A | 3 | 357.2 | 2.83 | DMSO(d6): 8.90 (s, 1H), 8.41 (dd, 1H), 7.97 (td, 1H), 7.68 (m, 3H), 7.40 (d, 1H), 7.21 (dd, 1H), 7.12 (dd, 1H), 6.86 (d, 1H), 3.99 (t, 2H), 3.78 (s, 3H), 3.63 (t, 2H), 3.32 (s, 3H). |
| N3-[3,4-Bis-(2-methoxy-ethoxy)-phenyl]-1-pyridin-2-yl-1H-[1,2,4]triazole-3,5-diamine | A | 3 | 401.2 | 2.90 | DMSO(d6): 8.91 (s, 1H), 8.41 (dd, 1H), 7.98 (td, 1H), 7.68 (m, 3H), 7.39 (d, 1H), 7.21 (dd, 1H), 7.14 (dd, 1H), 6.89 (d, 1H), 4.11 (t, 2H), 4.03 (t, 2H), 3.70 (t, 2H), 3.62 (t, 2H), 3.35 (s, 3H), 3.32 (s, 3H). |
| N3-Phenyl-1-pyridin-2-yl-1H-[1,2,4]triazole-3,5-diamine | A | 3 | 253.1 | 3.21 | DMSO(d6): 9.12 (s, 1H), 8.41 (dd, 1H), 7.98 (td, 1H), 7.70 (d, 1H), 7.68 (br. s, 2H), 7.63 (d, 2H), 7.25 (t, 2H), 7.21 (dd, 1H),6.82 (t, 1H). |
| N3-(3,5-Dimethoxy-phenyl)-1-pyridin-2-yl-1H-[1,2,4]triazole-3,5-diamine | A | 3 | 313.1 | 3.19 (A) | DMSO(d6): 9.08 (s, 1H), 8.41 (dd, 1H), 8.00 (td, 1H), 7.70 (s, 2H), 7.64 (d, 1H), 7.23 (dd, 1H), 6.90 (d, 2H), 6.03 (t, 1H), 6.73 (s, 6H). |
| 1-Pyridin-2-yl-N3-(3-trifluoromethyl-phenyl)-1H-[1,2,4]triazole-3,5-diamine | A | 3 | 321.1 | 3.86 | DMSO(d6): 9.58 (s, 1H), 8.42 (dd, 1H), 8.03 (s, 1H), 8.01 (td, 1H), 7.87(dd, 1H), 7.70 (s, 2H), 7.66 (d, 1H), 7.48 (t, 1H), 7.23 (dd, 1H), 7.15 (d, 1H). |
| N3-(4-Butoxy-phenyl)-1-pyridin-2-yl-1H-[1,2,4]triazole-3,5-diamine | A | 3 | 325.2 | 3.55 (A) | DMSO(d6): 8.88 (s, 1H), 8.40 (dd, 1H), 7.97 (td, 1H), 7.67 (m, 3H), 7.52(d, 2H), 7.17 (dd, 1H), 6.81 (d, 2H), 3.90 (t, 2H), 1.67 (m, 2H), 1.42 (m, 2H), 0.93 (t, 3H). |

| Name | cyclisation procedure | Purification procedure | MS (M + H) | Retention time (min) | NMR |
|---|---|---|---|---|---|
| N3-(3,5-Difluoro-phenyl)-1-pyridin-2-yl-1H-[1,2,4]triazole-3,5-diamine | A | 3 | 289.1 | 3.37 (A) | DMSO(d6): 9.41 (s, 1H), 8.42 (dd, 1H), 8.00 (td, 1H), 7.75 (m, 3H), 7.68(d, 1H), 7.30 (m, 2H), 7.23 (dd, 1H) |
| 1-(2-Fluoro-phenyl)-N3-(3,4,5-trimethoxy-phenyl)-1H-[1,2,4]triazole-3,5-diamine | C* | 3 | 360.1 | 2.97 (A) | 1H-DMSO(d6): 8.71 (s, 1H), 7.56 (td, 1H), 7.46 (m, 1H), 7.41 (td, 1H), 7.32 (td, 1H), 6.92 (s, 2H), 6.34 (s, 2H), 3.68 (s, 6H), 3.55 (s, 3H)., |
| 4-[5-Amino-3-(3,4,5-trimethoxy-phenylamino)-[1,2,4]triazol-1-yl]-benzonitrile | C* | 3 | 367.2 | 3.08 (A) | 1H-DMSO(d6): 8.95 (s, 1H), 7.94 (d, 2H), 7.80 (d, 2H), 7.00 (s, 2H), 6.80 (s, 2H), 3.82 (s, 6H), 3.56 (s, 3H) |
| 4-[3-Amino-5-(3,4,5-trimethoxy-phenylamino)-[1,2,4]triazol-1-yl]-benzonitrile | C* | 3 | 367.2 | 2.83 (A) | 1H-DMSO(d6): 8.95 (s, 1H), 7.94 (d, 2H), 7.73 (d, 2H), 6.85 (s, 2H), 5.60 (s, 2H), 3.73 (s, 6H), 3.60 (s, 3H)., |
| N3-(4-Chloro-2,5-dimethoxy-phenyl)-1-pyridin-2-yl-1H-[1,2,4]triazole-3,5-diamine | A | 3 | 347.1 | 3.57 (A) | DMSO(d6): 8.44 (ddd, 1H), 8.17 (s, 1H), 8.01 (td, 1H), 7.88 (br. s, 2H, NH2), 7.70 (s, 1H), 7.68 (d, 1H), 7.25 (ddd, 1H), 7.08 (s, 1H), 3.90 (s, 3H), 3.83 (s, 3H). |
| N3-(5-Chloro-2-methoxy-phenyl)-1-pyridin-2-yl-1H-[1,2,4]triazole-3,5-diamine | A | 3 | 313.1 | 3.34 | DMSO(d6): 8.45 (dd, 1H), 8.22 (d, 1H), 8.05 (td, 1H), 7.97 (m, 2H), 7.81 (s, 1H), 7.66 (d, 1H), 7.28 (dd, 1H), 7.00 (d, 1H), 6.92 (dd, 1H), 3.89 (s, 3H) |
| 2-(5-Amino-1-pyridin-2-yl-1H-[1,2,4]triazol-3-ylamino)-4-tert-butyl-phenol | A | 3 | 325.2 | 3.53 | DMSO(d6): 11.17 (s, 1H), 9.85 (s, 1H), 8.49 (d, 1H), 8.42 (d, 1H), 7.98 (t, 1H), 7.59 (d, 1H), 7.20 (t, 1H), 6.83 (d, 1H), 6.78 (d, 1H), 5.70 (br.s, 2H), 1.28 (s, 9H) |
| N3-(2-Methoxy-5-nitro-phenyl)-1-pyridin-2-yl-1H-[1,2,4]triazole-3,5-diamine | A | 3 | 328.1 | 3.51 | DMSO(d6): 9.20 (d, 1H), 8.45 (d, 1H), 8.10 (s, 1H), 8.06 (t, 1H), 7.87 (dd, 1H), 7.81 (s, 2H), 7.69 (d, 1H), 7.26 (t, 1H), 7.20 (d, 1H), 4.00 (s, 3H). |
| 3-(5-Amino-1-pyridin-2-yl-1H-[1,2,4]triazol-3-ylamino)-4-methoxy-benzoic acid methyl ester | A | 3 | 341.1 | 3.29 | DMSO(d6): 8.90 (d, 1H), 8.43 (d, 1H), 8.05 (td, 1H), 7.78 (s, 2H), 7.69 (d, 1H), 7.64 (s, 1H), 7.55 (dd, 1H), 7.25 (dd, 1H), 7.11 (d, 1H), 3.92 (s, 3H), 3.84 (s, 3H). |
| N3-(2-Methoxy-5-trifluoromethyl-phenyl)-1-pyridin-2-yl-1H-[1,2,4]triazole-3,5-diamine | A | 3 | 351.2 | 4.00 | DMSO(d6): 8.56 (d, 1H), 8.44 (d, 1H), 8.05 (td, 1H), 7.86 (s, 1H), 7.84 (m, 2H), 7.61 (d, 1H), 7.25 (d, 1H), 7.24 (d, 1H), 7.17 (dd, 1H), 3.97 (s, 3H) |
| 3-(5-Amino-1-pyridin-2-yl-1H-[1,2,4]triazol-3-ylamino)-biphenyl-4-ol | A | 3 | 345.1 | 3.47 | DMSO(d6): 11.30 (s, 1H), 10.32 (br.s, 1H), 8.66 (d, 1H), 8.45 (dd, 1H), 8.00 (td, 1H), 7.61 (d, 1H), 7.57 (m, 2H), 7.45 (t, 2H), 7.30 (t, 1H), 7.23 (td, 1H), 7.13 (dd, 1H), 6.98 (d, 1H), 5.80 (m, 2H). |
| 1-Pyridin-2-yl-N3-(2,3,5-trimethoxy-phenyl)-1H-[1,2,4]triazole-3,5-diamine | A | 3 | 343.1 | 3.21 | DMSO(d6): 8.46 (dd, 1H), 8.10 (m, 2H), 8.04 (td, 1H), 7.95 (br.s, 1H), 7.69 (d, 1H), 7.53 (d, 1H), 7.28 (dd, 1H), 6.25 (d, 1H), 3.82 (s, 3H), 3.79 (s, 3H), 3.72 (s, 3H) |
| N3-(2,5-Difluoro-phenyl)-1-pyridin-2-yl-1H-[1,2,4]triazole-3,5-diamine | C | 3 | 289.1 | 3.70 | DMSO(d6): 9.03 (s, 1H), 8.43 (dd, 1H), 8.12 (ddd, 1H), 8.01 (td, 1H), 7.80 (br.s, 2H), 7.68 (d, 1H), 7.25 (dd, 1H), 7.20 (ddd, 1H), 6.69 (m, 1H) |
| N3-(2-Methoxy-5-trifluoromethoxy-phenyl)-1-pyridin-2-yl-1H-[1,2,4]triazole-3,5-diamine | A | 3 | 367.2 | 3.90 (A) | DMSO(d6): 8.43 (dd, 1H), 8.25 (d, 1H), 8.02 (td, 1H), 7.85 (br. s, 2H, NH2), 7.81 (s, 1H, NH), 7.62 (d, 1H), 7.26 (dd, 1H), 7.06 (d, 1H), 6.85 (dd, 1H), 3.90 (s, 3H) |
| 1-Pyridin-2-yl-N3-(2-trifluoromethoxy-phenyl)-1H-[1,2,4]triazole-3,5-diamine | A | 3 | 337.10 | 3.90 | DMSO(d6): 8.63 (s, 1H), 8.42 (dd, 1H), 8.35 (dd, 1H), 8.00 (td, 1H), 7.74 (br.s, 2H), 7.71 (d, 1H), 7.34 (td, 1H), 7.31 (dd, 1H), 7.23 (dd, 1H), 6.98 (td, 1H). |

-continued

| Name | cyclisation procedure | Purification procedure | MS (M + H) | Retention time (min) | NMR |
|---|---|---|---|---|---|
| N3-(2-Isopropoxy-5-methoxy-phenyl)-1-pyridin-2-yl-1H-[1,2,4]triazole-3,5-diamine | C | 3 | 341.1 | 3.82 | DMSO(d6): 8.43 (dd, 1H), 8.02 (td, 1H), 7.86 (m, 2H, NH2), 7.85 (d, 1H), 7.67 (d, 1H), 7.33 (s, 1H), 7.25 (dd, 1H), 6.94 (d, 1H), 6.42 (dd, 1H), 4.55 (m, 1H), 3.74 (s, 3H), 1.28 (s, 3H), 1.26 (s, 3H). |
| N3-(2-Fluoro-5-morpholin-4-yl-phenyl)-1-pyridin-2-yl-1H-[1,2,4]triazole-3,5-diamine | C | 3 | 356.2 | 3.24 | 8.49 (m, 1H), 8.40 (d, 1H), 8.00 (td, 1H), 7.90 (dd, 1H), 7.76 (br.s, 2H), 7.61 (d, 1H), 7.22 (dd, 1H), 7.05 (dd, 1H), 6.50 (m, 1H), 3.78 (m, 4H), 3.09 (m, 4H). |
| 4-[5-Amino-3-(3,5-diisopropoxy-phenylamino)-[1,2,4]triazol-1-yl]-benzonitrile | D* | 3 | 393.2 | 4.00 (A) | DMSO(d6): 8.92 (s, 1H), 7.95 (d, 2H), 7.80 (d, 2H), 6.77 (s, 2H), 6.76 (m, 2H), 5.95 (s, 1H), 4.47 (m, 2H), 1.21 (s, 6H), 1.22 (s, 6H). |
| 4-[5-Amino-3-(3,5-dimethoxy-phenylamino)-[1,2,4]triazol-1-yl]-benzonitrile | D* | 3 | 335.2 (M-1) | 3.11 | DMSO(d6): 9.00 (s, 1H), 7.94 (d, 2H), 7.79 (d, 2H), 6.83 (d, 2H), 6.77 (m, 2H), 6.00 (t, 1H), 3.70 (s, 6H). |
| 3-[5-Amino-3-(3,4,5-trimethoxy-phenylamino)-[1,2,4]triazol-1-yl]-benzonitrile | D* | 3 | 365.2 (M-1) | 2.74 | DMSO(d6): 8.86 (s, 1H), 7.98 (m, 1H), 7.94 (dt, 1H), 7.72 (dt, 1H), 7.68 (t, 1H), 6.97 (s, 2H), 6.75 (m, 2H), 3.75 (S. 6H), 3.58 (s, 3H). |
| N-{3-Acetylamino-5-[5-amino-1-(4-cyano-phenyl)-1H-[1,2,4]triazol-3-ylaminol-phenyl)-acetamide | C* | 3 | 391.2 | 2.05 | DMSO(d6): 9.76 (s, 2H), 8.97 (s, 1H), 7.93 (d, 2H), 7.90 (d, 2H), 7.54 (s, 2H), 7.40 (s, 1H), 6.71 (s, 2H), 2.02 (s, 6H). |
| 4-[5-Amino-3-(3,5-dimethoxy-4-methyl-phenylamino)-[1,2,4]triazol-1-yl]-benzonitrile | D* | 3 | 351.3 | 3.50 | DMSO(d6): 8.92 (s, 1H), 7.93 (d, 2H), 7.80 (d, 2H), 6.97 (s, 2H), 6.8 (br, s, 2H), 3.74 (s, 6H), 1.91 (s, 3H). |
| N3-(3-Methoxy-4-morpholin-4-yl-phenyl)-1-pyridin-2-yl-1H-[1,2,4]triazole-3,5-diamine | D | 3 | 368.3 | 1.79 | DMSO(d6): 9.35 (br.s, 1H), 8.42 (dd, 1H), 8.00 (td, 1H), 7.77 (m, 2H), 7.70 (d, 1H), 7.61 (s, 1H), 7.32 (m, 1H), 7.22 (m, 2H), 3.94 (s, 3H), 3.90 (m, 4H), 3.38 (m, 4H). |
| 4-[5-Amino-3-(3-methoxy-4-morpholin-4-yl-phenylamino)-[1,2,4]triazol-1-yl]-benzonitrile | D* | 3 | 392.2 | 1.79 | DMSO(d6): 9.18 (br.s, 1H), 7.94 (d, 2H), 7.80 (d, 2H), 7.47 (s, 1H), 7.18 (br.s, 2H), 6.81 (m, 2H), 3.78 (m, 7H), 3.90 (m, 4H), 3.20 (m, 4H). |
| N3-(3,5-Dimethoxy-phenyl)-1-(2-fluoro-phenyl)-1H-[1,2,4]triazole-3,5-diamine | D* | 3 | 386.3 | 3.90 | DMSO(d6): 8.73 (s, 1H), 7.54 (td, 1H), 7.48 (m, 1H), 7.40 (t, 1H), 7.32 (t, 1H), 6.68 (d, 2H), 6.4 (m, 2H), 5.59 (m, 1H), 4.46 (m, 2H), 1.23 (s, 6H), 1.21 (s, 6H) |
| N3-(3-Isopropoxy-4-morpholin-4-yl-phenyl)-1-pyridin-2-yl-1H-[1,2,4]triazole-3,5-diamine | D | 3 | 396.3 | 2.42 | DMSO(d6): 9.27 (s, 1H, NH), 8.42 (dd, 1H), 8.00 (td, 1H), 7.73 (m, 2H, NH2), 7.65 (d, 1H), 7.60 (s, 1H), 7.22 (m, 2H), 7.14 (d, 1H), 4.69 (m, 1H), 3.90 (m, 4H), 3.38 (m, 4H), 1.42 (d, 6H) |
| 4-[5-Amino-3-(3-isopropoxy-4-morpholin-4-yl-phenylamino)-[1,2,4]triazol-1-yl]-benzonitrile | D* | 3 | 420.3 | 2.31 | DMSO(d6): 9.20 (s, 1H, NH), 7.96 (d, 2H), 7.80 (d, 2H), 7.54 (s, 1H), 7.20 (m, 1H), 7.11 (dd, 1H), 6.82 (m, 2H), 4.64 (m, 1H), 3.88 (m, 4H), 3.34 (m, 4H), 1.38 (d, 6H) |
| N3-(3-Isopropoxy-4-morpholin-4-ylmethyl-phenyl)-1-pyridin-2-yl-1H-[1,2,4]triazole-3,5-diamine | D | 3 | 410.3 | 3.00 (A) | DMSO(d6):9.36 (s, 1H, NH), 8.42 (dd, 1H), 8.00 (td, 1H), 7.70 (m, 2H, NH2), 7.65 (d, 1H), 7.62 (d, 1H), 7.30 (d, 1H), 7.23 (dd, 1H), 7.12 (dd, 1H), 4.63 (m, 1H), 4.20 (s, 2H), 3.97 (d, 2H), 3.65 (t, 2H), 3.31 (d, 2H), 3.10 (m, 3H), 1.41 (d, 3H), 1.40 (s, |
| 4-[5-Amino-3-(3-isopropoxy-4-morpholin-4-ylmethyl- | D* | 3 | 434.3 | 3.02 | DMSO(6): 9.30 (s, 1H), 7.95 (d, 2H), 7.79 (d, 2H), 7.58 (d, 1H), 7.28 (d, 1H), 7.08 (dd, 1H), 6.80 (br. s, 2H, NH2), 4.60 (m, 1H), 4.18 (d, 2H), |

| Name | cyclisation procedure | Purification procedure | MS (M + H) | Retention time (min) | NMR |
|---|---|---|---|---|---|
| phenylamino)-[1,2,4]triazol-1-yl]-benzonitrile | | | | | 3.96 (d, 2H), 3.64 (t, 2H), 7.30 (d, 2H), 3.10 (q, 2H), 1.38 (d, 6H). |
| 4-[5-Amino-3-(2,4-dimethoxy-phenylamino)-[1,2,4]triazol-1-yl]-benzonitrile | A* | 1 | 337.00 | 3.18 | DMSO: 7.9(m, 3H), 7.8(d, 2H), 7.1(s, 1H), 6.8(s, 2H),,6.6(s, 1H), 6.5(d, 1H), 3.9(s, 3H), 3.7(s, 3H) |
| 4-[3-Amino-5-(2-chloro-phenylamino)-[1,2,4]triazol-1-yl]-benzonitrile | A* | 1 | 311.00 | 3.04 | DMSO: 8.7(s, 1H), 8.0(d, 2H), 7.8(d, 2H), 7.6(d, 1H), 7.4(d, 1H),,7.3(t, 1H), 7.1(t, 1H), 5.7(bs, 2H), |
| 4-[3-Amino-5-(4-morpholin-4-yl-phenylamino)-[1,2,4]triazol-1-yl]-benzonitrile | A* | 2 | 362.20 | 2.01 | DMSO: 8.8(s, 1H), 7.9(d, 2H), 7.8(d, 2H), 7.3(d, 2H), 6.9(d, 2H),,5.6(s, 2H), 3.7(m, 4H), 3.0(m, 4H). |
| 4-{5-Amino-3-[3-methoxy-4-(3-piperidin-1-yl-propoxy)-phenylamino]-[1,2,4]triazol-1-yl}-benzonitrile | A* | 3 | 448.30 | 1.88 | acetone-d6: 10.1(bs, 1H), 9.1(bs, 1H), 7.9(bs, 4H), 7.4(m, 3H), 7.1 (d, 1H), 6.9(d, 1H), 4.2(m, 2H), 3.9(s, 3H), 3.8(m, 2H), 3.1(m, 2H),2.3(m, 2H), 2.0–1.8(m, 5H), 1.6(m, 1H) |
| N3-(2,4-Dimethoxy-phenyl)-1-[4-(1H-tetrazol-5-yl)-phenyl]-1H-[1,2,4]triazole-3,5-diamine | | 3 | 380.20 | 2.61 | acetone-d6: 8.3(d, 2H), 8.1(d, 1H), 7.9(d, 2H),,7.3(bs, 1H), 6.7(bs, 2H), 6.6(m, 1H), 6.5(dd, 1H),,3.9(s, 3H), 3.8(s, 3H). |
| 4-[5-Amino-3-(2,5-dimethoxy-phenylamino)-[1,2,4]triazol-1-yl]-benzonitrile | A* | 3 | 337.00 | 3.35 | DMSO-d6: 8.0(d, 2H), 7.8(m, 3H), 7.3(s, 1H), 6.90(d, 1H),,6.85(s, 2H), 6.4(dd, 1H), 3.8(s, 3H), 3.7(s, 3H). |
| 4-[3-Amino-5-(2,5-dimethoxy-phenylamino)-[1,2,4]triazol-1-yl]-benzonitrile | C | 2 | 337.00 | 3.06 | DMSO-d6: 8.1(s, 1H), 8.0(d, 2H), 7.8(d, 2H), 7.5(s, 1H), 6.9(d, 1H),,6.5(dd, 1H), 5.6(bs, 2H), 3.8(s, 3H), 3.7(s, 3H). |
| N3-(2,5-Dimethoxy-4-pyridin-4-yl-phenyl)-1-pyridin-2-yl-1H-[1,2,4]triazole-3,5-diamine | A* | 2 | 390.30 | 2.13 | DMSO-d6: 8.55(d, 2H), 8.45(m, 1H), 8.20(s, 1H), 8.0(t, 1H),, 7.8(bs, 2H), 7.75(d, 1H), 7.70(s, 1H), 7.60(m, 2H), 7.25(m, 1H),,7.07(bs, 1H), 3.90(s, 3H), 3.85(3, 3H). |
| N3-[3,4-Dimethoxy-5-(3-morpholin-4-yl-propoxy)-phenyl]-1-pyridin-2-yl-1H-[1,2,4]triazole-3,5-diamine | A* | 2 | 456.30 | 1.89 | CDC13: 8.30(m, 1H), 7.8(m, 1H), 7.7(d, 1H), 7.05(m, 1H),,6.8(d, 1H), 6.75(s, 1H), 6.70(bs, 2H), 6.6(s, 1H), 4.1(t, 2H),,3.85(s, 3H), 3.75(s, 3H), 3.70(m, 4H), 2.6(m, 2H), 2.5(m, 4H),,2.05(m, 2H). |
| N3-[3-(3-Dimethylamino-propoxy)-4,5-dimethoxy-phenyl]-1-pyridin-2-yl-1H-[1,2,4]triazole-3,5-diamine | A* | 2 | 414.20 | 1.93 | CDC13: 8.3(m, 1H), 7.75(m, 1H), 7.65(d, 1H), 7.0(m, 1H),,6.80(m, 1H), 6.75(bs, 2H), 6.75(m, 1H), 4.0(t, 2H), 3.8(s, 3H),,3.7(s, 3H), 2.55(t, 2H), 2.25(s, 6H), 2.0(m, 2H). |
| 4-{5-Amino-3-[3-(2-dimethylamino-ethoxy)-4,5-dimethoxy-phenylamino]-[1,2,4]triazol-1-yl}-benzonitrile | C* | 2 | 424.20 | 1.84 | DMSO-d6: 9.0(s, 1H), 8.0 (d, 2H), 7.8(d, 2H), 7.05(m, 1H).,7.0(m, 1H), 6.8(bs, 2H), 4.3(t, 2H), 3.75(s, 3H), 3.65(s, 3H), ,3.5(m, 2H), 2.9(bs, 6H). |
| 1-Pyridin-4-yl-N3-(3,4,5-trimethoxy-phenyl)-1H-[1,2,4]triazole-3,5-diamine | B | 2 | 343.20 | 1.61 | DMSO-d6: 9.0(s, 1H), 8.6(d, 2H), 7.6(d, 2H), 7.0(s, 2H), 6.85(bs, 2H). 3.75(s, 6H), 3.6(s, 3H). |
| 1-Pyridin-4-yl-N5-(3,4,5-trimethoxy-phenyl)-1H-[1,2,4]triazole-3,5- | B | 2 | 343.20 | 1.61 | DMSO-d6: 9.0(s, 1H), 8.6(d, 2H), 7.6(d, 2H), 6.8(s, 2H), 5.6(bs, 2H), 3.7(s, 6H), 3.6(s, 3H)., |

-continued

| Name | cyclisation procedure | Purification procedure | MS (M + H) | Retention time (min) | NMR |
|---|---|---|---|---|---|
| diamine | | | | | |
| 4-(5-Amino-3-[3,4-dimethoxy-5-(2-morpholin-4-yl-ethoxy)-phenylamino]-[1,2,4]triazol-1-yl)-benzonitrile | C* | 2 | 466.10 | 1.96 | |
| 4-(5-Amino-3-{3-[2-(2,6-dimethyl-morpholin-4-yl)-ethoxy]-4,5-dimethoxy-phenylamino}-[1,2,4]triazol-1-yl)-benzonitrile | A | 2 | 494.30 | 2.10 | DMSO-d6: 8.95(s, 1H), 7.95(d, 2H), 7.80(d, 2H), 7.0(d, 1H), ,6.9(d, 1H), 6.75(bs, 2H),4.05(t, 1H), 3.75(s, 3H), 3.6(s, 3H),,3.55(m, 2H), 2.85(d, 2H), 3.75(t, 2H), 1.75(t, 2H), 1.05(d, 6H). |
| 4-(5-Amino-3-{3,4-dimethoxy-5-[2-(4-methyl-piperazin-1-yl)-ethoxy]-phenylamino}-[1,2,4]triazol-1-yl)-benzonitrile | A* | 2 | 479.30 | 1.75 | DMSO-d6: 9.0(s, 1H), 7.95(d, 2H), 7.80(d, 2H), 7.0(s, 2H),, 6.8(bs, 2H), 4.15(m, 2H), 4.05(m, 2H), 3.75(s, 3H), 3.65(s, 3H),,3.15(s, 3H), 2.8(m, 4H), 2.65(m, 4H). |
| 4-[5-Amino-3-(2-methoxy-4-morpholin-4-ylmethyl-phenylamino)-[1,2,4]triazol-1-yl]-benzonitrile | A* | 3 | 406.20 | 1.77 | DMSO-d6: 8.0(d, 1H), 7.95(d, 2H), 7.8(d, 2H), 7.25(s, 1H), ,6.9(s, 1H), 6.8(m, 3H), 3.9(s, 3H), 3.6(m, 4H), 3.4(s, 2H),,2.35(m, 4H). |
| 4-{5-Amino-3-[2-methoxy-4-(4-methyl-piperazin-1-ylmethyl)-phenylamino]-[1,2,4]triazol-1-yl}-benzonitrile | A* | 3 | 419.30 | 1.34 | DMSO-d6: 8.1(d, 1H), 7.95(d, 2H), 7.8(d, 2H), 7.55(bs, 1H),, 7.05(bs, 1H), 6.95(d, 1H), 6.85(bs, 2H), 3.9(s, 3H), 2.8(bs, 3H), |
| 4-{5-Amino-3-[3-(2-imidazol-1-yl-ethoxy)-4,5-dimethoxy-phenylamino]-[1,2,4]triazol-1-yl}-benzonitrile | A* | 2 | | | |
| 4-{3-Amino-5-[3-(2-diethylamino-ethoxy)-4,5-dimethoxy-phenylamino]-[1,2,4]triazol-1-yl}-benzonitrile | A* | 3 | | | |
| N3-(2-Methoxy-4-morpholin-4-ylmethyl-phenyl)-1-pyridin-2-yl-1H-[1,2,4]triazole-3,5-diamine | B* | 3 | 382.20 | 1.70 | DMSO-d6: 8.4(d, 1H), 8.1(d, 1H), 7.95(m, 1H), 7.7(m, 3H),,7.3(s, 1H), 7.2(m, 1H), 6.9(s, 1H), 6.85(d, 1H), 3.85(s, 3H),,3.6(m, 4H), 3.4(s, 2H), 2.4(bs, 4H). |
| N3-[2-Methoxy-4-(4-methyl-piperazin-1-ylmethyl)-phenyl]-1-pyridin-2-yl-1H-[1,2,4]triazole-3,5-diamine | B | 3 | 395.20 | 1.30 | DMSO-d6:8.45(d, 1 H), 8.25(d, 1H), 8.0(m, 1H), 7.8(bs, 2H), ,7.7(d, 1H), 7.6(s, 1H), 7.25(m, 1H), 7.1(s, 1H), 7.0(d, 1H),,4.2(bs, 2H), 3.9(s, 3H), 3.8-3.0(vbs, 8H), 2.85(bs, 3H). |
| 1-[6-(2-Dimethylamino-ethylamino)-pyrimidin-4-yl]-N3-(2-methoxy-phenyl)-1H-[1,2,4]triazole-3,5-diamine. | B | 2 | 370.30 | 1.59 | CD3CN: 8.4(s, 1H), 8.2(bs, 1H), 8.0(m, 1H), 7.8(m, 1H), 6.9(m, 4H),, 6.75(s, 1H), 3.85(s, 3H), 3.7(m, 2H), 3.25(m, 2H), 2.8(s, 6H). |
| 2-[5-Amino-3-(2-fluoro-phenylamino)-[1,2,4]triazol-1-yl]-pyrimidine-5-carbonitrile | B | 1 | | | DMSO-d6: 9.2(s, 2H), 8.75(s, 1H), 8.2(m, 1H), 7.9(bs, 2H),7.15(m, 2H), 6.9(m, 1H). |
| 2-[5-Amino-3-(2- | B | 1 | 309.10 | 2.78 | DMSO-d6: 9.2(s, 2H), 8.2(m, 1H), |

| Name | cyclisation procedure | Purification procedure | MS (M + H) | Retention time (min) | NMR |
|---|---|---|---|---|---|
| methoxy-phenylamino)-[1,2,4]triazol-1-yl]-pyrimidine-5-carbonitrile | | | | | 7.9(bs, 2H), 7.5(s, 1H), 7.0(m, 3H),, 3.85(s, 3H). |
| N3-(2-Methoxy-phenyl)-1-(6-morpholin-4-yl-pyrimidin-4-yl)-1H-[1,2,4]triazole-3,5-diamine | G | 3 | 369.20 | 3.30 | DMSO-d6: 8.5(s, 1H), 8.1(d, 1H), 7.9(bs, 2H), 7.4(bs, 1H), ,7.0-6.8(m, 3H), 6.8(s, 1H), 3.9(s, 3H), 3.7(m, 4H), 3.6(m, 4H). |
| N3-(2-Methoxy-phenyl)-1-[6-(4-methyl-piperazin-1-yl)-pyrimidin-4-yl]-1H-[1,2,4]triazole-3,5-diamine | B | 3 | 382.20 | 1.70 | CDCl3: 8.3(s, 1H), 8.1(d, 1H), 7.05(bs, 1H), 6.95(t, 1H), 6.8(m, 2H),,6.75(s, 1H), 6.65(bs, 2H), 3.85(s, 3H), 3.70(m, 4H),,2.45(m, 4H), 2.3(s, 3H). |
| N3-(2-Methoxy-4-morpholin-4-yl-phenyl)-1-[6-(4-methyl-piperazin-1-yl)-pyrimidin-4-yl]-1H-[1,2,4]triazole-3,5-diamine | B | 2 | 467.20 | 1.50 | CDCl3: 8.3(s, 1H), 8.0(d, 1H), 6.85(s, 1H), 6.75(s, 1H),6.65(bs, 2H),, 6.5(dd, 1H),6.45(m, 1H), 3.8(m, 7H), 3.7(m, 4H), 3.05(m, 4H),,2.45(m, 4H), 2.3(s, 3H), 1.5(bs, 2H). |
| N3-(2-Methoxy-4-morpholin-4-yl-phenyl)-1H-[1,2,4]triazole-3,5-diamine | B | 2 | 291.10 | 0.30 | DMSO-d6: 11.1(bs, 1H), 7.9(d, 1H), 6.6(d, 1H), 6.4(dd, 1H), 5.8(bs, 2H),,3.85(s, 3H), 3.75(m, 4H), 3.0(m, 4H). |
| 1-{6-[(2-Dimethylamino-ethyl)-methyl-amino]-pyrimidin-4-yl}-N3-(2-methoxy-phenyl)-1H-[1,2,4]triazole-3,5-diamine | B | 3 | 384.20 | 1.90 | CD3CN: 8.45(s, 1H), 8.3(bs, 2H), 8.15(m, 1H), 7.9(bs, 1H), 7.05(m, 3H),,6.80(m, 1H), 4.0(m, 2H), 3.9(s, 3H), 3.35(m, 2H), 3. 15(s, 3H),,2.9(bs, 6H). |
| 1-{6-[(2-Dimethylamino-ethyl)-methyl-amino]-pyrimidin-4-yl}-N3-(2-methoxy-4-morpholin-4-yl-phenyl)-1H-[1,2,4]triazole-3,5-diamine | B | 2 | 469.20 | 1.67 | |
| 1-[6-(3-Dimethylamino-pyrrolidin-1-yl)-pyrimidin-4-yl]-N3-(2-methoxy-phenyl)-1H-[1,2,4]triazole-3,5-diamine | B | 2 | 396.30 | 1.80 | DMSO: 8.4(s, 1H), 8.1(s, 1H), 7.8(bs, 2H), 7.4(s, 1H), 6.9(m, 3H), 6.5(s, 1H), 3.9(s, 3H), 3.7(m, 1H), 3.4(m, 1H), 3.2(m, 2H),, 2.8(m, 1H), 2.2(bs, 6H), 1.9(m, 1H)., |
| 1-[6-(2-Dimethylamino-ethylamino)-pyrimidin-4-yl]-N3-phenyl-1H-[1,2,4]triazole-3,5-diamine | G | 3 | 340.20 | 1.80 | MeOH-d4: 8.4(s, 1H), 7.5(d, 2H) 7.2(m, 2H), 6.9(m, 1H), 6.8(s, 1H),,3 .8(m, 2H), 3.4(m, 2H), 3.0(s, 6H). |
| 1-[6-(2-Dimethylamino-ethylamino)-pyrimidin-4-yl]-N3-(2-methoxy-4-morpholin-4-yl-phenyl)-1H-[1,2,4]triazole-3,5-diamine | 100 THF 6h | 2 | 455.30 | 1.80 | CD3CN: 11.1(s, 1H), 8.3(s, 1H), 8.1(d, 1H), 6.6(s, 1H), 6.4(m, 2H),, 5.9(bs, 1H), 4.4(m, 1H), 3.8(s, 3H), 3.7(m, 4H), 3.2(m, 8H),,3.0(m, 4H), 2.4(m, 2H). |
| N3-(4-Morpholin-4-yl-phenyl)-1-(6-morpholin-4-yl-pyrimidin-4-yl)-1H-[1,2,4]triazole-3,5-diamine | G | 3 | 424.20 | 2.70 | DMSO-d6: 8.8(s, 1H), 8.4(s, 1H), 7.7(bs, 2H), 7.5(d, 2H), 6.9(d, @H),, 6.7(s, 1H), 3.7(m, 8H), 3.6(m, 4H), 3.0(m, 4H). |
| N3- | G | 3 | 383.20 | 3.05 | DMSO-d6: 9.0(s, 1H), 8.4(s, 1H), |

| Name | cyclisation procedure | Purification procedure | MS (M + H) | Retention time (min) | NMR |
|---|---|---|---|---|---|
| Benzo[1,3]dioxol-5-yl-1-(6-morpholin-4-yl-pyrimidin-4-yl)-1H-[1,2,4]triazole-3,5-diamine | | | | | 7.7(bs, 2H), 7.2(s, 1H), 7.0(m, 1H),,6.8(d, 1H), 6.7(s, 1H), 5.9(s, 2H), 3.7(m, 4H), 3.6(m, 4H)., |
| 1-[6-(4-Methyl-piperazin-1-yl)-pyrimidin-4-yl]-N3-(4-morpholin-4-yl-phenyl)-1H-[1,2,4]triazole-3,5-diamine | | | 298.10 | 2.50 | acetone-d6: 8.9(s, 1H), 8.8(d, 1H), 8.1(bs, 1H), 7.4(m, 3H),,7.1(d, 1H), 6.8(d, 1H), 5.9(s, 2H). |
| N3-Benzo[1,3]dioxol-5-yl-1-pyrimidin-4-yl-1H-[1,2,4]triazole-3,5-diamine | G | 1 | 354.20 | 1.39 | DMSO-d6: 11.4(bs, 1H), 8.75(s, 1H), 7.45(m, 3H), 6.85(d, 2H),,6.7(bs, 2H), 6.6(d, 1H), 6.4(s, 1H) 3.75(m, 4H), 2.95(m, 4H). |
| 1-[6-(2-Dimethylamino-ethylamino)-pyrimidin-4-yl[-N3-(4-morpholin-4-yl-phenyl)-1H-[1,2,4]triazole-3,5-diamine | | 2 | 425.20 | 0.30 | DMSO-d6: 8.8(s, 1H), 8.3(s, 1H), 7.65(bs, 2H), 7.5(d, 2H), 6.85(d, 2H),, 6.65(bs, 1H), 3.7(m, 4H), 3.4(bs, 2H), 3.0(m, 4H), 2.4(m, 2H),,2.2(bs, 6H). |
| 1-[6-(2-Dimethylamino-ethylamino)-pyrimidin-4-yl]-N5-(4-morpholin-4-yl-phenyl)-1H-[1,2,4]triazole-3,5-diamine | | 2 | 425.20 | 0.30 | DMSO-d6: 8.4(bs, 1H), 7.55(m, 3H), 6.95(d, 2H),,6.5(bs, 1H), 5.7(bs, 2H), 3.75(m, 4H), 3.5(bs, 2H), 3.05(m, 4H),,2.4(m, 2H), 2.2(s, 6H). |
| N3-(4-Morpholin-4-yl-phenyl)-1-pyrimidin-4-yl-1H-[1,2,4]triazole-3,5-diamine | | 2 | 339.40 | 1.60 | DMSO-d6: 8.95(s, 1H), 8.90(s, 1H), 7.8(bs, 2H), 7.6(s, 1H), ,7.5(d, 2H), 6.9(d, 2H), 3.75(m, 4H), 3.0(m, 4H). |
| N3-(4-phenylboronic acid)-1-pyridin-2-yl-1H-[1,2,4]triazole-3,5-diamine | | 1 | 297.00 | 2.30 | DMSO-d6: 9.3(bs, 1H), 8.4(m, 1H), 8.0(m, 1H), 7.7(m, 3H), 7.55(m, 2H),,7.2(m, 1H). |
| 1-[6-(2-Dimethylamino-ethylamino)-pyridin-4-yl]-N3-(4-morpholin-4-yl-phenyl)-1H-[1,2,4]triazole-3,5-diamine | | 2 | 424.30 | 0.88 | CD3CN: 7.9(d, 1H), 7.5(d, 2H), 7.1 (m, 3H), 3.9(m, 4H), ,3.75(m, 2H), 3.25(m, 2H), 3.2(m, 4H), 2.8(s, 6H). |
| 1-[2-(4-Methyl-piperazin-1-yl)-pyridin-4-yl]-N3-(4-morpholin-4-yl-phenyl)-1H-[1,2,4]triazole-3,5-diamine | | 2 | 436.20 | 0.50 | DMSO-d6: 9.8(bs, 1H), 8.85(bs, 1H), 8.2(d, 1H), 7.5(d, 2H),,7.0(d, 1H), 6.95(s, 1H), 6.90(m, 2H), 6.7(bs, 2H), 4.45(m, 2H), ,3.75(m, 4H), 3.5(m, 2H), 3.2-3.0(m, 8H), 2.85(s, 3H). |
| N3-(3-Isopropoxy-4-morpholin-4-yl-phenyl)-1-[2-(4-methyl-piperazin-1-yl)-pyridin-4-yl]-1H-[1,2,4]triazole-3,5-diamine | | 2 | 494.40 | 2.68 | DMSO-d6: 8.75(s, 1H), 8.10(d, 1H), 7.40(s, 1H), 6.95(d, 1H), ,6.90(d, 1H), 6.85(s, 1H), 6.75(d, 1H), 6.60(bs, 2H), 4.50(m, 1H),,3.70(m, 4H), 3.50(m, 4H), 2.90(m, 4H), 2.40(m, 4H),,2.22(s, 3H), 1.32(d, 6H). |
| N5-Benzo[1,3]dioxol-5-yl-1-[2-(4-methyl-piperazin-1-yl)-pyridin-4-yl]-1H-[1,2,4]triazole-3,5-diamine | | 2 | 395.20 | 1.50 | CD3CN: 8.1(d, 1H), 7.2(s, 1H), 7.0(s, 1H), 6.8(d, 1H), ,6.7(m, 1H), 6.65(d, 1H), 5.7(s, 2H), 5.2(bs, 2H), 3.5(m, 4H), 3.2(s, 3H),,2.4(m, 4H). |
| 2-{[4-(5-Amino-1-pyridin-2-yl-1H-[1,2,4]triazol-3-ylamino)-phenyl]- | | 2 | 340.10 | 2.10 | DMSO-d6: 8.55(bs, 1H), 8.38(m, 1H), 7.95(m, 1H), 7.65(m, 1H),, 7.56(m, 2H), 7.43(m, 2H), 7.17(m, 1H), 6.65(m, 2H),,4.57(t, 1H), |

-continued

| Name | cyclisation procedure | Purification procedure | MS (M + H) | Retention time (min) | NMR |
|---|---|---|---|---|---|
| ethyl-amino}-ethanol |  |  |  |  | 3.51 (m, 2H), 3.30(m, 4H), 1.04(t, 3H). |
| N3-Methyl-N3-(4-morpholin-4-yl-phenyl)-1-pyridin-2-yl-1H-[1,2,4]triazole-3,5-diamine |  | 2 | 352.20 | 2.50 | DMSO-d6:8.37(m, 1H), 7.91(m, 1H), 7.58(m, 3H), 7.30(d, 2H),, 7.16(m, 1H), 6.91(d, 2H), 3.75(m, 4H), 3.35(s, 3H), 3.05(m, 4H). |
| -[6-(4-Ethyl-piperazin-1-yl)-pyrimidin-4-yl]-N3-(4-morpholin-4-yl-phenyl)-1H-[1,2,4]triazole-3,5-diamine | G | 1 | 451.40 | 1.64 | DMSO-d6: 8.84(s, 1H), 8.37(s, 1H), 7.72(bs, 2H), 7.48(d, 2H),, 6.88(d, 2H), 6.70(s, 1H), 3.73(m, 4H), 3.64(m, 4H), 3.00(m, 4H),,2.45(t, 4H), 2.37(q, 2H), 1.04(t, 3H). |
| 1-[6-(3-Methyl-piperazin-1-yl)-pyrimidin-4-yl]-N3-(4-morpholin-4-yl-phenyl)-1H-[1,2,4]triazole-3,5-diamine |  | 2 | 437.33 | 0.31 | DMSO-d6: 8.82(s, 1H), 8.35(s, 1H), 7.71 (bs, 2H), 7 .47(d, 2H),,6.87(d, 2H), 6.68(s, 1H), 4.25(m, 1H), 4. 15(m, 1H), 3.72(m, 4H),,2.97(m, 5H), 2.89(t, 1H), 2.67(m, 2H), 2.53(m, 1H), 2.34(m, 1H),, 1 .04(d, 3H). |
| 1-[6-(3-Dimethylamino-pyrrolidin-1-yl)-pyrimidin-4-yl]-N3-(4-morpholin-4-yl-phenyl)-1H-[1,2,4] triazole-3,5-diamine |  | 2 | 451.40 | 0.80 | DMSO-d6: 8.82(s, 1H), 8.34(s, 1H), 7.70(s, 2H), 7.49(d, 2H), 6.87(d, 2H),,6.39(s, 1H), 3.71(m, 4H), 2.99(m, 4H), 2.49(s, 7H), 1.86(bs, 1H), 3.9-2.6( 5H). |
| 1-[6-(4-Methyl-[1,4]diazepan-1-yl)-pyrimidin-4-yl]-N3-(4-morpholin-4-yl-phenyl)-1H-[1,2,4]triazole-3,5-diamine |  | 2 | 451.40 | 0.91 | CD3CN: 8.41(s, 1H), 7.94(bs.(2H), 7.62(d, 2H) 7.36(d, 2H),,6.79(s, 1H), 3.94(m, 4H), 3.8-3.4(m, 6H), 3.36(m, 4H), 3.17(m, 2H),,2.82(s, 3H), 2.37(m, 1H), 2.26(m, 1H). |
| 1-{6-[(2-Diethylamino-ethyl)-methyl-amino]-pyrimidin-4-yl}-N3-(4-morpholin-4-yl-phenyl)-1H-[1,2,4] triazole-3,5-diamine |  | 2 | 467.20 | 1.46 | CD3CN: 8.25(s, 1H),7.43(d, 2H), 6.83(m, 3H), 6.64(bs, 1H),,3.66(m, 4H), 3.57(m.2H), 3.08(s, 3H), 2.98(m, 4H), 2.6-2.4,(m, 6H), 0.95(t, 6H). |
| 1-[6-(4-Isopropyl-piperazin-1-yl)-pyrimidin-4-yl]-N3-(4-morpholin-4-yl-phenyl)-1H-[1,2,4]triazole-3,5-diamine |  | 1 | 465.20 | 0.30 | DMSO-d6: 8.85(s, 1H), 8.36(s, 1H), 7.72(bs, 2H), 7.45(d, 2H),, 6.85(d, 2H), 6.72(s, 1H), 3.75(m, 4H), 3.65(m, 4H), 3.05(m, 4H),,2.72(m, 1H), 2.50(m, 4H), 1.00(d, 6H). |
| 1-[6-(4-Methyl-piperazin-1-yl)-pyrimidin-4-yl]-N3-(4-morpholin-4-yl-phenyl)-1H-[1,2,4]triazole-3,5-diamine | G | 2 | 437.20 | 1.50 | DMSO-d6: 9.9(bs, 1H), 8.9(s, 1H), 8.4(s, 1H), 7.75(bs, 2H),,7.5(d, 2H), 6.9(d, 2H), 6.8(s, 1H), 4.5(m, 2H), 3.75(4H), 3.5(m, 2H),,3.3(m, 2H), 3.1(m, 6H), 2.8(s, 3H) |
| 1-[6-(2 Dimethylamino-ethylamino)-pyrimidin-4-yl]-N3-(2-fluoro-phenyl)-1H-[1 ,2,4]triazole-3,5-diamine | G | 3 | 357.20 | 3.26 | DMSO-d6:8.6(s, 1H), 8.45(s, 1H), 8.15(m, 1H), 7.8(bs, 2H), 7.15(m, 2H), 6.9(m, 1H), 6.75(s, 1H),,3.75(m, 4H), 3.65(m, 4H) |
| 4-[5-Amino-3-(4-morpholin-4-yl-phenylamino)-[1,2,4]triazol-1-yl]-benzonitrile | 125° 20h NMP | 1 | 362.30 | 2.04 | DMSO: 8.8(s, 1H), 8.0(d, 2H). 7.8(d, 2H), 7.5(d, 2H), 6.9(d, 2H),,6.8(bs, 2H), 3.8(m, 4H), 3.0(m, 4H)., |
| N3-[3,5-Dimethoxy-4-(2-morpholin-4-yl-ethoxy)-phenyl]-1-(2-fluoro-phenyl)-1H-[1,2,4]triazole-3,5-diamine | C | 2 | 459.17 | 1.53 | 1HNMR DMSO; 104-10.29 (br S, 1H), 8.83 (s, 1H), 7.6-7.3 ,(m, 4H), 6.97 (s, 2H), 4.1-3.95 (m, 2H), 3.85-3.74 (m, 2H), ,3.71 (s, 6H), 3.59-3.56 (m, 2H), 3.45 (br s, 2H), 3.27-3.09 (m, 2H) |
| 4-[5-Amino-3-(4-isopropoxy-3,5-dimethoxy- | Method C* | 3 | 395.30 | 3.35 | DMSO: 8.87 (s, 1H), 7.93 (d, 2H), 7.80 (d, 2H), 6.98 (s, 2H), ,6.87-6.63 (br s, 2H), 4.24-3.98 (m, 1H), 3.72 |

-continued

| Name | cyclisation procedure | Purification procedure | MS (M + H) | Retention time (min) | NMR |
|---|---|---|---|---|---|
| phenylamino)-[1,2,4]triazol-1-yl]-benzonitrile | | | | | (s, 6H), 1.15 (d, 6H) |
| N3-Indan-4-yl-1-pyridin-2-yl-1H-[1,2,4]triazole-3,5-diamine | Method A | 1 | 293.10 | 3.75 | DMSO: 8.48-8.3 1 (m, 1H), 8.08-7.90 (m, 2H), 7.85 (d, 1H), ,7.73-7.50 (m, 3H), 7.28-7.14 (m, 1H), 7.07 (t, 1H), 6.78 (d, 1H), ,2.96-2.72 (m, 4H), 2.11-1.86 (m, 2H) |
| N3-(2,3-Dihydro-benzo[1,4]dioxin-5-yl)-1-pyridin-2-yl-1H-[1,2,4]triazole-3,5-diamine | Method B* | 1 | 311.10 | 3.60 | 1HNMR: DMSO-d6: 8.83 (s, 1H), 8.40-8.38 (m, 1H), 8.0-7.95, (m, 1H), 7.65-7.60 (m, 3H), 7.27 (d, 1H), 7.20-7.15 (m, 1H), ,6.99 (d,d, 1H), 6.72 (d, 1H), 4.22-4.15 (m, 4H) |
| 1-(6-Chloro-pyrimidin-4-yl)-N3-(2,2-difluoro-benzo[1,3]dioxol-4-yl)-1H-[1,2,4]triazole-3,5-diamine | Method | 1 | 368.1 | 4.04 | DMSO-d6: 9.43 (s, 1H), 8.83 (s, 1H), 7.96 (s, 2H), 7.80 (d, 1H), 7.59 (s, 1H), 7.18 (t, 1H), 6.97 (d, 1H) |
| N3-(2,2-Difluoro-benzo[1,3]dioxol-4-yl)-1-pyridin-2-yl-1H-[1,2,4]triazole-3,5-diamine | Method B | 3 | 333.20 | 3.95 | DMSO-d6: 9.18 (s, 1H), 8.43-8.35 (m, 1H), 7.97-7.94 (m, 1H),7.87-7.83 (m, 1H), 7.71-7.65 (m, 3H), 7.3-7.22 (m, 1H), ,7.20-7.10 (m, 1H), 6.95-6.9 (m, 1H) |
| 1-Cyclohexyl-N3-(3,4,5-trimethoxy-phenyl)-1H-[1,2,4]triazole-3,5-diamine | A* | 3 | 348.20 | 2.45 | NMR performed in Methanol-d4: 6.83 (s, 2H), 4.05 (m, 1H),,3.85 (s, 6H), 3.71 (s, 3H), 1.98-1.71 (m, 5H), 1.47 (m, 2H),,1.27 (m, 1H) |
| 1-(6-Methyl-4-trifluoromethyl-pyridin-2-yl)-N3-(3,4,5-trimethoxy-phenyl)-1H-[1,2,4ltriazole-3,5-diamine | A | 1 | 424.90 | 3.91 | NMR performed in DMSO-d6: 9.12 (s, 1H), 7.76 (s, 2H),,7.68 (s, 1H), 7.46 (s, 1H), 7.08 (s, 2H), 3.80 (s, 6H), ,3.60 (s, 3H), 2.62 (s, 3H) |
| 1-(4,6-Dimethyl-pyridin-2-yl)-N3-(3,4,5-trimethoxy-phenyl)-1H-[1,2,4]triazole-3,5-diamine | A | 1 | 373.10 | 2.27 | NMR performed in DMSO-d6: 9.12 (s, 1H), 7.87 (s, 2H),,7.27 (s, 1H), 7.05 (s, 2H), 3.80 (s, 6H), ,3.60 (s, 3H), 2.60 (s, 3H), 2.45 (s, 3H) |
| 1-(4-Methyl-thiazol-2-yl)-N3-(3,4,5-trimethoxy-phenyl)-1H-[1,2,4]triazole-3,5-diamine | A | 1 | 363.10 | 3.09 | NMR performed in DMSO-d6: 9.20 (s, 1H), 7.55 (s, 2H),,7.03 (s, 2H), 6.95 (s, 1H), 3.78 (s, 6H), ,3.61 (s, 3H), 2.34 (s, 3H) |
| N3-(4-Dimethylamino-phenyl)-1-(2,6-dimethyl-pyrimidin-4-yl)-1H-[1,2,4]triazole-3,5-diamine | A | 3 | 325.0 | 2.673 | DMSO-d6: 8.80 (s, 1H), 7.80 (s, 2H), 7.48 (d, 2H), ,7.29 (s, 1H), 6.71 (d, 2H), 2.80 (s, 6H), 2.57 (s, 3H), 2.45 (s, 3H) |
| N3-(4-Piperidin-1-yl-phenyl)-1-pyridin-2-yl-1H-[1,2,4]triazole-3,5-diamine | A | 3 | 336.10 | 1.59 | DMSO-d6: 8.80 (s, 1H), 8.40 (d, 1H), 7.98 (t, 1H), 7.67 (m, 3H), 7.48 (m, 2H),7.19 (t, 1H), 6.85 (m, 2H), 3.00 (m, 4H),1.61 (m, 4H), 1.49 (m, 2H) |
| N3-(4-Isopropoxy-phenyl)-1-pyridin-2-yl-1H-[1,2,4]triazole-3,5-diamine | A | 1 | 311.10 | 3.24 | DMSO-d6: 8.89 (s, 1H), 8.41 (d, 1H), 7.97 (t, 1H), 7.77 (m, 3H), 7.52 (m, 2H),7.20 (t, 1H), 6.85 (m, 2H), 4.49 (m, 1H), 1.25 (d, 6H) |
| N3-(2,3-Dihydro-benzo[1,4]dioxin-6-yl)-1-pyridin-2-yl-1H-[1,2,4]triazole-3,5-diamine | A | 1 | 311.10 | 2.73 | DMSO-d6: 8.90 (s, 1H), 8.40(d, 1H), 8.00 (t, 1H), 7.65 (m, 3H), 7.30 (d, 1H), 7.20 (t, 1H), 7.00 (m, 1H), 6.75 (d, 1H),4.20 (m, 4H) |
| N3-(3-Ethoxy-phenyl)-1-pyridin-2-yl-1H-[1,2,4]triazole-3,5-diamine | A | 1 | 297.10 | 3.18 | DMSO-d6: 9.10 (s, 1H), 8.42 (d, 1H), 8.00 (t, 1H), 7.66 (m, 3H), 7.30 (t, 1H),7.20 (t, 1H), 7.13 (m, 2H), 6.40 (d, 1H), 4.00 (m, 2H), 1.35 (m, 3H) |
| N3-(4-Diethylamino-phenyl)-1-pyridin-2- | A | 3 | 324.20 | 1.45 | DMSO-d6: 8.63 (s, 1H), 8.38 (d, 1H), 7.95 (t, 1H), ,7.67 (d, 1H), 7.62 |

| Name | cyclisation procedure | Purification procedure | MS (M + H) | Retention time (min) | NMR |
|---|---|---|---|---|---|
| yl-1H-[1,2,4]triazole-3,5-diamine | | | | | (s, 2H), 7.45 (m, 2H), 7.18 (t, 1H),,6.65 (m, 2H), 3.25 (m, 4H), 1.05 (m, 6H) |
| 4-(5-Amino-1-pyridin-2-yl-1H-[1,2,4]triazol-3-ylamino)-benzonitrile | A | 3 | 278.10 | 2.95 | DMSO-d6: 9.86 (s, 1H), 8.44 (d, 1H)), 8.01 (t, 1H), ,7.82-7.69 (m, 7H), 7.25 (t, 1H) |
| N3-[4-(4-Methyl-piperazin-1-yl)-phenyl]-1-pyridin-2-yl-1H-[1,2,4]triazole-3,5-diamine | A | 1 | 351.40 | 1.27 | DMSO-d6: 8.80 (s, 1H), 8.40 (d, 1H), 7.98 (t, 1H), ,7.65 (m, 3H), 7.50 (d, 2H), 7.19 (t, 1H), 6.85 (d, 2H),, 3.01 (m, 4H), 2.45 (m, 4H), 2.21 (s, 3H)) |
| N3-(1H-Indazol-5-yl)-1-pyridin-2-yl-1H-[1,2,4]triazole-3,5-diamine | A | 1 | 293.10 | 2.12 | DMSO-d6: 12.82 (s, 1H), 9.07 (s, 1H)), 8.41 (d, 1H), ,8.15 (s, 1H)) 7.99 (m, 2H), 7.78 (d, 1H), 7.70 (s, 2H),, 7.45 (m, 2H)), 7.23 (t, 1H) |
| 1-[7-(5-Amino-1-pyridin-2-yl-1H-[1,2,4]triazol-3-ylamino)-2,3-dihydro-indol-1-yl]-ethanone | A | 1 | 336.10 | 2.55 | DMSO-d6: 9.05 (s, 1H)), 8.57 (s, 1H), 8.41 (d, 1H), ,7.98 (t, 1H)), 7.80 (d, 1H), 7.65 (s, 2H), 7.25 (d, 1H)),, 7.21 (t, 1H), 7.07 (d, 1H)), 4.09 (t, 2H), 3.05 (t, 2H), ,2.18 (s, 3H) |
| N3-(4-Ethoxy-phenyl)-1-pyridin-2-yl-1H-[1,2,4]triazole-3,5-diamine | A | 1 | 297.10 | 3.09 | DMSO-d6: 8.90 (s, 1H)), 8.40 (d, 1H)), 7.98 (t, 1H)), ,7.67 (m, 3H), 7.55 (m, 2H), 7.20 (t, 1H), 6.85 (m, 2H)),, 3.96 (q, 2H), 1.31 (t, 3H) |
| N3-(4-Chloro-3-methyl-phenyl)-1-pyridin-2-yl-1H-[1,2,4]triazole-3,5-diamine | A | 1 | 301.10 | 3.96 | DMSO-d6: 9.23 (s, 1H), 8.41 (d, 1H), 7.99 (t, 1H), ,7.71 (m, 3H), 7.55 (s, 1H), 7.50 (d, 1H)), 7.25 (d, 1H),, 7.20 (t, 1H), 2.31 (s, 3H)) |
| N3-(4-Ethyl-phenyl)-1-pyridin-2-yl-1H-[1,2,4]triazole-3,5-diamine | A | 1 | 281.30 | 3.51 | MeOH-d4: 8.38 (d, 1H), 7.90 (t, 1H), 7.75 (d, 1H), ,7.48 (d, 2H), 7.15 (t, 1H), 7.10 (d, 2H), 2.59 (q, 2H),, 1.20 (t, 3H) |
| 5-(5-Amino-1-pyridin-2-yl-1H-[1,2,4]triazol-3-ylamino)-2-methoxy-phenol | A | 3 | 299.10 | 2.21 | MEOH-d4: 8.40 (d, 1H), 7.98 (t, 1H), 7.85 (d, 1H), ,7.25 (m, 2H), 6.90 (m, 2H), 3.82 (s, 3H) |
| N3-(3-Chloro-4-morpholin-4-yl-phenyl)-1-pyridin-2-yl-1H-[1,2,4]triazole-3,5-diamine | A | 1 | 372.10 | 3.47 | DMSO-d6: 9.21 (s, 1H), 8.42 (d, 1H), 8.00 (t, 1H), ,7.75 (m, 3H), 7.67 (d, 1H), 7.53 (d, 1H), 7.24 (t, 1H),, 7.13 (d, 1H), 3.72 (m, 4H), 2.90 (m, 4H) |
| 1-Pyridin-2-yl-N3-(3,4,5-triethoxy-phenyl)-1H-[1,2,4]triazole-3,5-diamine | A | 1 | 385.20 | 3.74 | DMSO-d6: 8.91 (s, 1H), 8.41 (d, 1H), 7.99 (t, 1H), ,7.69 (s, 2H), 7.62 (d, 1H), 7.21 (t, 1H), 7.05 (s, 2H),, 4.05 (m, 4H), 3.86 (m, 2H), 1.35 (m, 6H), 1.22 (t, 3H) |
| N3-C3,4-Diethoxy-phenyl)-1-pyridin-2-yl-1H-[1,2,4]triazole-3,5-diamine | A | 1 | 341.10 | 3.37 | DMSO-d6: 8.86 (s, 1H), 8.40 (d, 1H), 7.99 (t, 1H), ,7.65 (m, 3H), 7.35 (s, 1H), 7.20 (t, 1H), 7.12 (d, 1H),, 6.85 (d, 1H), 4.04 (q, 2H), 3.95 (q, 2H), 1.38 (t, 3H), ,1.29 (t, 3H) |
| N3-C3-Chloro-4-diethylamino-phenyl)-1-pyridin-2-yl-1H-[1,2,4]triazole-3,5-diamine | A | 3 | 358.10 | 1.70 | Methanol-d4: 8.44 (d, 1H), 8.07 (s, 1H), 7.95 (t, 1H), ,7.75 (m, 2H), 7.65 (m, 1H), 7.23 (t, 1H), 3.70 (m, 4H),, 1.15 (m, 6H), |
| N3-[3-Methoxy-4-(3-piperidin-1-yl-propoxy)-phenyl]-1-pyridin-2-yl-1H-[1,2,4]triazole-3,5-diamine | A | 3 | 424.20 | 1.76 | Methanol-d4: 8.45 (d, 1H), 7.99 (t, 1H), 7.78 (d, 1H), ,7.35 (s, 1H), 7.28 (t, 1H), 7.10 (m, 1H), 6.95 (d, 1H),, 4.12 (m, 2H), 3.91 (s, 3H), 3.67 (d, 2H), 3.38 (t, 2H), ,2.99 (t, 2H), 2.25 (m, 2H), 2.00 (m, 2H), 1.85 (m, 3H),, 1.55 (m, 1H) |
| N3-(2-Ethoxy-phenyl)-1-pyridin-2-yl-1H-[1,2,4]triazole-3,5-diamine | A | 1 | 297.10 | 3.70 | DMSO-d6: 8.42 (d, 1H), 8.19 (d, 1H), 7.99 (t, 1H), ,7.72 (m, 3H), 7.25 (m, 2H), 6.95 (m, 2H), 6.85 (t, 1H),, 4.13 (q, 2H), 1.43 (t, 3H) |
| N3-(2-Fluoro-4-methyl-phenyl)-1-pyridin-2-yl-1H-[1,2,4]triazole-3,5-diamine | A | 1 | 285.10 | 3.70 | DMSO-d6: 8.43 (m, 2H), 8.05 (t, 1H), 7.98 (t, 1H), ,7.70 (m, 3H), 7.23 (t, 1H), 7.01 (d, 1H), 6.95 (d, 1H),, 2.28 (s, 3H) |

| Name | cyclisation procedure | Purification procedure | MS (M + H) | Retention time (min) | NMR |
|---|---|---|---|---|---|
| diamine | | | | | |
| N3-(2-Chloro-4-methyl-phenyl)-1-pyridin-2-yl-1H-[1,2,4]triazole-3,5-diamine | A | 1 | 301.10 | 4.01 | DMSO-d6: 8.42 (d, 1H), 8.10 (d, 1H), 7.98 (t, 1H), ,7.73 (s, 2H), 7.68 (m, 2H), 7.25 (s, 1H), 7.22 (t, 1H),,7.15 (d, 1H), 2.27 (s, 3H) |
| N3-(3-Methyl-biphenyl-4-yl)-1-pyridin-2-yl-1H-[1,2,4]triazole-3,5-diamine | A | 1 | 343.10 | 4.30 | DMSO-d6: 8.42 (d, 1H), 8.10 (d, 1H), 7.99 (m, 2H), ,7.66 (m, 5H), 7.45 (m, 4H), 7.30 (t, 1H), 7.22 (t, 1H), ,2.38 (s, 3H) |
| N3-(9H-Fluoren-1-yl)-1-pyridin-2-yl-1H-[1,2,4]triazole-3,5-diamine | A | 1 | 341.10 | 4.26 | DMSO-d6: 8.61 (s, 1H), 8.45 (d, 1H), 8.10 (d, 1H),,7.99 (t, 1H), 7.86 (d, 1H), 7.71 (m, 3H), 7.60 (d, 1H),, 7.50 (d, 1H), 7.38 (m, 2H), 7.33 (t, 1H), 7.23 (t, 1H), ,3.97 (s, 2H) |
| N3-(4-Chloro-2-fluoro-phenyl)-1-pyridin-2-yl-1H-[1,2,4]triazole-3,5-diamine | A | 1 | 305.00 | 3.90 | DMSO-d6: 8.89 (s, 1H), 8.43 (d, 1H), 8.28 (t, 1H), ,8.00 (t, 1H), 7.80 (s, 2H), 7.70 (d, 1H), 7.39 (d, 1H),, 7.24 (m, 2H) |
| N3-(4-Chloro-2-methyl-phenyl)-1-pyridin-2-yl-1H-[1,2,4]triazole-3,5-diamine | A | 1 | 301.00 | 3.92 | DMSO-d6: 8.42 (d, 1H), 8.05 (s, 1H), 7.99 (m, 2H), ,7.78 (s, 2H), 7.65 (d, 1H), 7.21 (m, 3H), 2.28 (s, 3H) |
| N3-(2,4-Difluoro-phenyl)-1-pyridin-2-yl-1H-[1,2,4]triazole-3,5-diamine | A | 1 | 289.00 | 3.50 | DMSO-d6: 8.68 (s, 1H), 8.41 (d, 1H), 8.18 (m, 1H), ,7.97 (t, 1H), 7.77 (s, 2H), 7.67 (d, 1H), 7.25 (m, 2H),, 7.05 (t, 1H) |
| N3-(2-Chloro-phenyl)-1-pyridin-2-yl-1H-[1,2,4]triazole-3,5-diamine | A | 3 | 287.10 | 3.72 | DMSO-d6: 8.43 (d, 1H), 8.27 (d, 1H), 7.99 (t, 1H), ,7.81 (m, 3H), 7.71 (d, 1H), 7.45 (d, 1H), 7.35 (t, 1H),, 7.25 (t, 1H), 6.95 (t, 1H) |
| N3-(4-Isopropyl-phenyl)-1-pyridin-2-yl-1H-[1,2,4]triazole-3,5-diamine | A | 3 | 295.20 | 3.98 | DMSO-d6: 9.05 (s, 1H), 8.43 (d, 1H), 7.99 (t, 1H), ,7.80 (s, 2H), 7.70 (d, 1H), 7.53 (d, 2H), 7.22 (t, 1H),, 7.13 (d, 2H), 2.82 (m, 1H), 1.20 (d, 6H) |
| N3-(3-Fluoro-2-methoxy-phenyl)-1-pyridin-2-yl-1H-[1,2,4]triazole-3,5-diamine | A | 3 | 301.10 | 3.60 | DMSO-d6: 8.43 (d, 1H), 8.07 (d, 1H), 8.00 (m, 2H), ,7.74 (m, 3H), 7.25 (t, 1H), 7.08 (m, 1H), 6.77 (t, 1H), ,3.89 (s, 3H) |
| N3-(2-Ethyl-phenyl)-1-pyridin-2-yl-1H-[1,2,4]triazole-3,5-diamine | A | 3 | 281.20 | 3.55 | DMSO-d6: 8.41 (d, 1H), 7.95 (m, 2H), 7.85 (s, 1H), ,7.65 (m, 3H), 7.19 (m, 3H), 6.92 (t, 1H), 2.71 (q, 2H),, 1.15 (t, 3H) |
| N3-(2-Fluoro-phenyl)-1-pyridin-2-yl-1H-[1,2,4]triazole-3,5-diamine | A | 3 | 271.20 | 3.35 | DMSO-d6: 8.60 (s, 1H), 8.42 (d, 1H), 8.25 (t, 1H), ,7.99 (t, 1H), 7.73 (m, 3H), 7.24 (t, 1H), 7.15 (m, 2H),, 6.90 (m, 1H) |
| N3-(2-Methoxy-phenyl)-1-pyridin-2-yl-1H-[1,2,4]triazole-3,5-diamine | A | 3 | 283.20 | 3.35 | DMSO-d6: 8.42 (d, 1H), 8.21 (d, 1H), 7.99 (t, 1H), ,7.74 (m, 3H), 7.35 (s, 1H), 7.23 (t, 1H), 6.97 (m, 2H),, 6.89 (t, 1H), 3.88 (s, 3H) |
| N3-(3-Ethoxy-4-methoxy-phenyl)-1-pyridin-2-yl-1H-[1,2,4]triazole-3,5-diamine | A | 1 | 327.10 | 3.00 | DMSO-d6: 8.85 (s, 1H), 8.41 (d, 1H), 7.99 (t, 1H), ,7.65 (m, 3H), 7.35 (s, 1H), 7.20 (t, 1H), 7.14 (d, 1H),,6.85 (d, 1H), 4.02 (q, 2H), 3.70 (s, 3H), 1.38 (t, 3H) |
| N3-(4-Chloro-2-methoxy-5-methyl-phenyl)-1-pyridin-2-yl-1H-[1,2,4]triazole-3,5-diamine | A | 1 | 331.00 | 4.20 | DMSO-d6: 8.43 (d, 1H), 8.11 (s, 1H), 8.01 (t, 1H), 7.94 (s, 2H), 7.75 (d, 1H), 7.60 (s, 1H), 7.25 (t, 1H),, 7.05 (s, 1H), 3.87 (s, 3H), 2.32 (s, 3H) |
| N3-(5-Chloro-2,4-dimethoxy-phenyl)-1-pyridin-2-yl-1H-[1,2,4]triazole-3,5-diamine | A | 1 | 346.90 | 3.70 | DMSO-d6: 8.43 (d, 1H), 8.15 (s, 1H), 8.02 (t, 1H), ,7.85 (s, 2H), 7.64 (d, 1H), 7.51 (s, 1H), 7.25 (t, 1H),, 6.88 (s, 1H), 3.93 (s, 3H), 3.85 (s, 3H) |
| 4-(5-Amino-1-pyridin-2-yl-1H-[1,2,4]triazol-3-ylamino)-N-(2-diethylamino-ethyl)- | A | 1 | 395.30 | 1.80 | MeOH-d4: 8.43 (d, 1H), 7.99 (t, 1H), 7.85 (m, 3H), ,7.70 (d, 2H), 7.25 (t, 1H), 3.75 (m, 2H), 3.39 (m, 2H),, 3.32 (m, 4H), 1.35 (m, 6H) |

-continued

| Name | cyclisation procedure | Purification procedure | MS (M + H) | Retention time (min) | NMR |
|---|---|---|---|---|---|
| benzamide | | | | | |
| N3-[5-(1,1-Dimethyl-propyl)-2-methoxy-phenyl]-1-pyridin-2-yl-1H-[1,2,4]triazole-3,5-diamine | A | 1 | 353.20 | 4.70 | DMSO-d6: 8.44 (d, 1H), 8.25 (s, 1H), 8.05 (t, 1H), ,7.95 (s, 2H), 7.65 (d, 1H), 7.50 (s, 1H), 7.25 (t, 1H),, 6.92 (d, 1H), 6.83 (d, 1H), 3.85 (s, 3H), 1.65 (q, 2H), ,1.29 (s, 6H), 0.69 (t, 3H) |
| 1-Pyridin-2-yl-N3-(2,3,4-trimethoxy-phenyl)-1H-[1,2,4]triazole-3,5-diamine | A | 3 | 343.10 | 3.10 | DMSO-d6: 8.42 (d, 1H), 7.98 (t, 1H), 7.84 (d, 1H), ,7.79 (s, 2H), 7.69 (d, 1H), 7.58 (s, 1H), 7.22 (t, 1H),, 6.78 (d, 1H), 3.85 (s, 3H), 3.78 (s, 3H), 3.76 (s, 3H) |
| 1-(2,4-Difluoro-phenyl)-N3-(3,4,5-trimethoxy-phenyl)-1H-[1,2,4]triazole-3,5-diamine | A | 3 | 378.20 | 2.70 | DMSO-d6: 8.78 (s, 1H), 7.64 (m, 1H), 7.51 (m, 1H), ,7.24 (m, 1H), 6.90 (s, 2H), 6.55 (s, 2H), 3.68 (s, 6H), ,3.55 (s, 3H) |
| N3-(4-Morpholin-4-yl-phenyl)-1-phenyl-1H-[1,2,4]triazole-3,5-diamine | A | 1 | 337.30 | 1.80 | DMSO-d6: 8.61 (s, 1H), 7.57 (d, 2H), 7.45 (m, 4H), 7.28 (t, 1H), 6.84 (d, 2H), 6.38 (s, 2H), 3.71 (m, 4H),, 2.98 (m, 4H) |
| 1-(2-Fluoro-phenyl)-N3-[3-methoxy-4-(3-piperidin-1-yl-propoxy)-phenyl]-1H-[1,2,4]triazole- | A* | 3 | 441.20 | 1.70 | Methanol-d4: 7.63 (t, 1H), 7.59 (m, 1H), 7.39 (m, 2H), ,7.21 (s, 1H), 6.99 (d, 1H), 6.90 (d, 1H), 4.09 (t, 2H),, 3.83 (s, 3H), 3.65 (d, 2H), 3.35 (t, 2H), 2.96 (t, 2H),,2.21 (m, 2H), 1.99 (m, 2H), 1.86 (m, 1H), 1.79 (m, 2H),,1.55 (m, 1H) |
| N3-(2,5-Diethoxy-phenyl)-1-pyridin-2-yl-1H-[1,2,4]triazole-3,5-diamine | A | 3 | 341.20 | 4.00 | Methanol-d4: 8.45 (d, 1H), 8.01 (t, 1H), 7.82 (m, 2H), ,7.28 (m, 1H), 6.86 (d, 1H), 6.47 (d, 1H), 4.05 (m, 4H), ,1.43 (m, 6H) |
| N3-[3-Methoxy-4-(3-piperidin-1-yl-propoxy)-phenyl]-1-phenyl-1H-[1,2,4]triazole-3,5-diamine | A | 3 | 423.30 | 1.90 | Methanol-d4: 7.59 (m, 4H), 7.47 (t, 1H), 7.27 (s, 1H), ,7.03 (d, 1H), 6.92 (d, 1H), 4.1 (m, 2H), 3.84 (s, 3H),, 3.65 (m, 2H), 3.35 (m, 2H), 2.96 (m, 2H), 2.22 (m, 2H), ,1.98 (m, 2H), 1.89-1.50 (m, 4H) |
| N3-{4-[3-(2,6-Dimethyl-morpholin-4-yl)-propoxy]-phenyl}-1-pyridin-2-yl-1H-[1,2,4]triazole-3,5-diamine | A | 3 | 424.30 | 2.00 | MeOH-d4: 8.42 (d, 1H), 7.95 (t, 1H), 7.78 (d, 1H), ,7.50 (d, 2H), 7.24 (t, 1H), 6.92 (d, 2H), 4.1 (m,2H),, 3.85 (m, 2H), 3.55 (m, 2H), 3.37 (m, 2H), 2.74 (t, 2H),,2.24 (m, 2H), 1.25 (d, 6H) |
| N3-[2-Morpholin-4-yl-4-(3-morpholin-4-yl-propoxy)-phenyl]-1-pyridin-2-yl-1H-[1,2,4]triazole-3,5-diamine | A | 3 | 481.20 | 2.00 | DMSO-d6: 8.4 (d, 1H), 8.05 (d, 1H), 7.96 (t, 1H), 7.70 (m, 3H), 7.37 (s, 1H), 7.21 (t, 1H), 6.79 (m, 1H), ,6.75 (d, 1H), 3.98 (t, 2H), 3.79 (m, 4H), 3.59 (m, 4H), 2.82 (m, 4H), 2.4 (m, 6H), 1.87 (m, 2H) |
| N3-[4-(3-Morphohn-4-yl-propoxy)-phenyl]-1-pyridin-2-yl-1H-[1,2,4]triazole-3,5-diamine | A | 3 | 396.20 | 1.80 | Methanol-d4: 8.42 (d, 1H), 7.95 (t, 1H), 7.75 (d, 1H),,7.52 (d, 2H), 7.23 (t, 1H), 6.92 (d, 2H), 4.11 (m, 4H),, 3.76 (t, 2H), 3.57 (m, 2H), 3.40 (m, 2H), 3.23 (m, 2H), ,2.25 (m, 2H) |
| 4-(5-Amino-1-pyridin-2-yl-1H-[1,2,4]triazol-3-ylamino)-N-[2-(3,5-dimethyl-piperidin-1-yl)-ethyl]-benzamide | A | 3 | 435.20 | 2.20 | Methanol-d4: 8.43 (d, 1H), 7.96 (t, 1H), 7.84 (m, 3H), 7.70 (d, 2H), 7.25 (t, 1H), 3.77 (m, 2H), 3.64 (m, 2H), 3.34 (m, 2H), 2.56 (m, 2H), 1.95 (m, 3H) 1.03 (d, 6H), ,0.93 (m, 1H) |
| N3-(4-Diethylamino-phenyl)-1-phenyl-1H-[1,2,4]triazole-3,5-diamine | A | 1 | 323.00 | 1.40 | DMSO-d6: 8.41 (s, 1H), 7.57 (d, 2H), 7.49 (t, 2H), 7.40 (d, 2H), 7.26 (t, 1H), 6.64 (d, 2H), 6.35 (s, 2H),, 3.24 (m, 4H), 1.02 (t, 6H) |
| 1-Phenyl-N3-(4-piperidin-1-yl-phenyl)-1H-[1,2,4]triazole-3,5-diamine | A | 1 | 335.00 | 1.60 | DMSO-d6: 8.56 (s, 1H), 7.58 (d, 2H), 7.49 (t, 2H), ,7.43 (d, 2H), 7.28 (t, 1H), 6.82 (d, 2H), 6.38 (s, 2H),, 2.96 (m, 4H), 1.62 (m, 4H), 1.49 (m, 2H) |
| N3-(4-Isopropoxy-phenyl)-1-phenyl-1H-[1,2,4]triazole-3,5-diamine | A | 1 | 310.10 | 3.20 | DMSO-d6: 8.67 (s, 1H), 7.57 (d, 2H), 7.48 (m, 4H), ,7.29 (t, 1H), 6.80 (d, 2H), 6.40 (s, 2H), ,4.46 (m, 1H), 1.23 (d, 6H) |
| N3-(2,3-Dihydro-benzo[1,4]dioxin-6- | A | 1 | 310.10 | 2.70 | DMSO-d6: 8.68 (s, 1H), 7.57 (d, 2H), 7.49 (t, 2H), ,7.29 (t, 1H), 7.24 |

-continued

| Name | cyclisation procedure | Purification procedure | MS (M + H) | Retention time (min) | NMR |
|---|---|---|---|---|---|
| yl)-1-phenyl-1H-[1,2,4]triazole-3,5-diamine | | | | | (s, 1H), 6.92 (d, 1H), 6.80 (d, 1H),, 6.41 (s, 2H), 4.15 (m, 4H) |
| N3-(3-Ethoxy-phenyl)-1-phenyl-1H-[1,2,4]triazole-3,5-diamine | A | 1 | 296.10 | 3.20 | DMSO-d6: 8.90 (s, 1H), 7.58 (d, 2H), 7.50 (t, 2H), ,7.30 (t, 1H), 7.25 (s,1H), 7.07 (m, 2H), 6.45 (s, 2H),, 6.35 (m, 1H), 3.90 (q, 2H), 1.32 (t, 3H) |
| N3-[4-(4-Methyl-piperazin-1-yl)-phenyl]-1-phenyl-1H-[1,2,4]triazole-3,5-diamine | A | 3 | 350.1 | 0.67 | DMSO-d6: 9.71 (bs, 1H), 8.85 (s, 1H), 7.58 (d, 2H), ,7.52 (d, 2H), 7.48 (m, 2H), 7.32 (t, 1H), 6.92 (d, 2H),, 6.68 (bs, 2H), 3.66 (m, 2H), 3.52 (m, 2H), 3.18 (m, 2H), ,2.86 (m, 5H) |
| N3-(4-Ethoxy-phenyl)-1-phenyl-1H-[1,2,4]triazole-3,5-diamine | A | 1 | 296.10 | 2.90 | DMSO-d6: 8.65 (s, 1H), 7.58 (d, 2H), 7.48 (m, 4H), ,7.29 (t, 1H), 6.80 (d, 2H), 6.40 (s, 2H), 3.95 (q, 2H),, 1.30 (t, 3H) |
| 4-[5-Amino-3-(benzo[1,3]dioxol-5-ylamino)-[1,2,4]triazol-1-yl]-benzonitrile | A** | 3 | 320.90 | 3.10 | DMSO-d6: 8.96 (s, 1H), 7.95 (d, 2H), 7.80 (d, 2H), ,7.29 (s, 1H), 7.01 (d, 1H), 6.80 (m, 3H), 5.92 (s, 2H) |
| 4-[5-Amino-3-(2,3-dihydro-benzo[1,4]dioxin-6-ylamino)-[1,2,4]triazol-1-yl]-benzonitrile | A** | 3 | 335.00 | 3.00 | DMSO-d6: 8.84 (s, 1H), 7.95 (d, 2H), 7.80 (d, 2H), ,7.25 (s, 1H), 6.94 (d, 1H), 6.75 (s, 2H), 6.70 (d, 1H),, 4.19 (dd, 4H) |
| 4-[5-Amino-3-(3,4-dimethoxy-phenylamino)-[1,2,4]triazol-1-yl]-benzonitrile | A** | 3 | 337.00 | 2.80 | DMSO-d6: 8.87 (s, 1H), 7.94 (d, 2H), 7.80 (d, 2H), ,7.30 (s, 1H), 7.11 (d, 1H), 6.85 (m, 3H), 3.75 (s, 3H),, 3.69 (s, 3H) |
| 4-(5-Amino-1-pyridin-2-yl-1H-[1,2,4]triazol-3-ylamino)-N-(3-morpholin-4-yl-propyl)-benzamide | A | 3 | 423.20 | 1.77 | Methanol-d4: 8.42 (d, 1H), 7.95 (t, 1H), 7.82 (m, 3H), ,7.69 (d, 2H), 7.24 (t, 1H), 4.09 (m, 2H), 3.8 (m, 2H), ,3.52 (m, 4H), 3.23 (m, 2H), 3.15 (m, 2H), 2.07 (m, 2H) |
| 4-(5-Amino-3-{3,4-dimethoxy-5-[3-(4-methyl-piperazin-1-yl)-propoxy]-phenylamino}-[1,2,4]triazol-1-yl)-benzonitrile | A** | 3 | 493.20 | 1.70 | Methanol-d4: 7.89 (d, 2H), 7.82 (d, 2H), 6.94 (d, 2H), ,4.15 (t, 2H), 3.85 (s, 3H), 3.73 (s, 3H), 3.49 (m, 7H),, 3.35 (m, 1H), 3.30 (m, 2H), 2.94 (s, 3H), 2.24 (m, 2H) |
| 4-{5-Amino-3-[3-(3-diethylamino-propoxy)-4,5-dimethoxy-phenylamino]-[1,2,4]triazol-1-yl}-benzonitrile | A** | 3 | 466.30 | 2.10 | Methanol-d4: 7.90 (d, 2H), 7.82 (d, 2H), 6.95 (s, 2H), ,4.15 (t, 2H), 3.85 (s, 3H), 3.75 (s, 3H), 3.40 (t, 2H),, 3.29 (m, 4H), 2.21 (m, 2H), 1.35 (t, 6H) |
| 6-[5-Amino-3-(4-isopropoxy-phenylamino)-[1,2,4]triazol-1-yl]-nicotinonitrile | B* | 3 | 336.10 | 3.70 | DMSO-d6: 9.02 (s, 1H), 8.81 (s, 1H), 8.36 (d, 1H), ,7.77 (m, 3H), 7.52 (d, 2H), 6.83 (d, 2H), 4.48 (m, 1H), ,1.26 (d, 6H) |
| 4-[5-Amino-3-(7-methoxy-benzo[1,3]dioxol-5-ylamino)-[1,2,4]triazol-1-yl]-benzonitrile | G* | 1 | 351.20 | 3.10 | DMSO-d6: 8.91 (s, 1H), 7.93 (d, 2H), 7.78 (d, 2H), ,6.95 (s, 1H), 6.90 (s, 1H), 6.74 (s, 2H), 5.89 (s, 2H),, 3.81 (s, 3H) |
| 6-[5-Amino-3-(2-methoxy-phenylamino)-[1,2,4]triazol-1-yl]-nicotinonitrile | B* | 1 | 308.10 | 3.50 | DMSO-d6: 8.85 (s, 1H), 8.38 (d, 1H), 8.17 (d, 1H), ,7.85 (s, 2H), 7.80 (d, 1H), 7.47 (s, 1H), 7.03-6.88 (m, 3H),,3.88 (s, 3H) |
| {4-[5-Amino-3-(2-methoxy-phenylamino)-[1,2,4]triazol-1-yl]-phenyl}-morpholin-4-yl-methanone | H | 3 | 395.30 | 2.65 | Methanol-d4: 8.05 (d, 1H), 7.73 (d, 2H), 7.62 (d, 2H), ,7.01-6.89 (m, 3H), 3.95 (s, 3H), 3.82-3.45 (m, 8H) |
| {4-[5-Amino-3-(2- | H | 3 | 408.30 | 1.66 | Methanol-d4: 8.05 (d, 1H), 7.78 (d, |

| Name | cyclisation procedure | Purification procedure | MS (M + H) | Retention time (min) | NMR |
|---|---|---|---|---|---|
| methoxy-phenylamino)-[1,2,4]triazol-1-yl]-phenyl}-(4-methyl-piperazin-1-yl)-methanone | | | | | 2H), 7.67 (d, 2H), ,7.01-6.89 (m, 3H), 3.95 (s, 3H), 3.65-3.25 (m, 8H),,2.95 (s, 3H) |
| 4-[5-Amino-3-(2-methoxy-phenylamino)-[1,2,4]triazol-1-yl] N-methyl-benzamide | H | 3 | 339.10 | 2.50 | Methanol-d4: 8.05 (m, 3H), 7.73 (d, 2H), ,7.05-6.93 (m, 3H), 3.95 (s, 3H), 2.95 (s, 3H), |
| 4-[5-Amino-3-(2-methoxy-phenylamino)-[1,2,4]triazol-1-yl]-N-(2-dimethylamino-ethyl)-benzamide | H | 3 | 396.20 | 1.80 | Methanol-d4: 8.05 (m, 3H), 7.75 (d, 2H), ,7.0-6.89 (m, 3H), 3.93 (s, 3H), 3.78 (t, 2H), 3.4 (t, 2H), ,3.0 (s, 6H), |
| {4-[5-Amino-3-(2-methoxy-phenylamino)-[1,2,4]triazol-1-yl]-phenyl}-piperidin-1-yl-methanone | H | 3 | 393.20 | 3.20 | Methanol-d4: 8.0 (d, 1H), 7.72 (d, 2H), ,7.58(d, 2H), 7.02-6.89 (m, 3H), 3.93 (s, 3H), ,3.75 (m, 2H), 3.43 (m, 2H), 1.78-1.55 (m, 6H) |
| 6-[5-Amino-3-(2-fluoro-phenylamino)-[1,2,4]triazol-1-yl]-nicotinonitrile | B* | 1 | 296.10 | 3.40 | DMSO-d6: 8.85 (s, 1H), 8.73 (s, 1H), 8.40 (d, 1H), ,8.20 (t, 1H), 7.85 (s, 2H), 7.78 (d, 1H), 7.15 (m, 2H),,6.95 (m, 1H) |
| {4-[5-Amino-3-(2-methoxy-4-morpholin-4-yl-phenylamino)-[1,2,4]triazol-1-yl]-phenyl}-(4-methyl-piperazin-1-yl)-methanone | H | 3 | 493.40 | 2.10 | Methanol-d4: 8.07 (d, 1H), 7.75 (d, 2H), 7.68 (d, 2H), ,6.97 (m, 2H), 3.95 (m, 7H), 3.45 (m, 6H), ,3.44-3.25 (m, 6H), 2.95 (s, 3H), |
| {4-[5-Amino-3-(2-methoxy-4-morpholin-4-yl-phenylamino)-[1,2,4]triazol-1-yl]-phenyl}-morpholin-4-yl-methanone | H | 3 | 480.40 | 2.00 | Methanol-d4: 8.05 (d, 1H), 7.73 (d, 2H), 7.62 (d, 2H), ,6.95 (m, 2H), 3.95 (m, 7H), 3.72 (m, 6H), ,3.57-3.3 (m, 6H), |
| {4-[5-Amino-3-(2-methoxy-4-morpholin-4-yl-phenylamino)-[1,2,4]triazol-1-yl)-phenyl}-piperidin-1-yl-methanone | H | 3 | 478.30 | 2.40 | Methanol-d4: 8.05 (d, 1H), 7.71 (d, 2H), 7.57 (d, 2H), ,6.98 (m, 2H), 3.98 (m, 7H), 3.74 (m, 2H), ,3.55-3.3 (m, 6H), 1.75-1.5 (m, 6H), |
| 4-[5-Amino-3-(2-methoxy-4-morpholin-4-yl-phenylamino)-[1,2,4]triazol-1-yl]-N-(2-dimethylamino-ethyl)-benzamide | H | 3 | 481.30 | 1.10 | Methanol-d4: 8.05 (m, 3H), 7.75 (d, 2H), 6.92 (m, 2H), 3.95 (m, 7H), 3.80 (t, 2H), 3.48-3.3 (m, 6H), ,2.98 (s, 6H), |
| 4-[5-Amino-3-(2-methoxy-4-morpholin-4-yl-phenylamino)-[1,2,4]triazol-1-yl]-N,N-dimethyl-benzamide | H | 3 | 438.30 | 3.10 | Methanol-d4: 8.08 (d, 1H), 7.71 (d, 2H), 7.60 (d, 2H),,7.06 (s, 1H), 6.97 (d, 1H), 3.98 (m, 7H), 3.48 (m, 4H),, 3.13 (s, 3H), 3.04 (s, 3H) |
| 6-[5-Amino-3-(benzo[1,3]dioxol-5-ylamino)-[1,2,4]triazol-1-yl]-nicotinonitrile | D* | 1 | 322.00 | 3.40 | DMSO-d6: 9.1 (s, 1H), 8.8 (s, 1H), 8.35 (d, 1H), ,7.8 (s, 2H), 7.72 (d, 1H), 7.3 (s, 1H), 7.05 (d, 1H), ,6.8 (d, 1H), 5.92 (s, 2H) |
| N3-(7-Methoxy-benzo[1,3]dioxol-5-yl)-1-pyridin-2-yl-1H-[1,2,4]triazole-3,5-diamine | B* | 3 | 327.00 | 3.30 | DMSO-d6: 8.86 (s, 1H), 8.4 (d, 1H), 7.98 (t, 1H), ,7.65 (m, 3H), 7.2 (t, 1H), 7.0 (s, 1H), 6.95 (s, 1H), ,5.9 (s, 2H), 3.84 (s, 3H) |
| 1-(5-Methyl-pyridin-2-yl)-N3-(4-morpholin-4-yl-phenyl)-1H- | B | 1 | 352.30 | 2.30 | DMSO-d6: 8.74 (s, 1H), 8.22 (s, 1H), 7.78 (d, 1H), ,7.6 (d, 1H), 7.5 (m, 4H), 6.87 (d, 2H), 3.74 (m, 4H),, 2.98 (m, 4H), 2.3 (s, 3H) |

-continued

| Name | cyclisation procedure | Purification procedure | MS (M + H) | Retention time (min) | NMR |
|---|---|---|---|---|---|
| [1,2,4]triazole-3,5-diamine | | | | | |
| N3-Benzo[1,3]dioxol-5-yl-1-(5-methyl-pyridin-2-yl)-1H-[1,2,4]triazole-3,5-diamine | B | 1 | 311.20 | 3.30 | DMSO-d6: 8.9 (s, 1H), 8.23 (s, 1H), 7.8 (d, 1H), ,7.57 (m, 3H), 7.33 (s, 1H), 7.05 (d, 1H), 6.82 (d, 1H), ,5.93 (s, 2H), 2.3 (s, 3H) |
| N3-(7-Methoxy-benzo[1,3]dioxol-5-yl)-1-(5-methyl-pyridin-2-yl)-1H-[1,2,4]triazole-3,5-diamine | B | 1 | 341.20 | 3.38 | DMSO-d6: 8.91 (s, 1H), 8.23 (s, 1H), 7.8 (d, 1H), ,7.57 (m, 3H), 6.96 (s, 2H), 5.9 (s, 2H), 3.84 (s, 3H), ,2.3 (s, 3H) |
| N3-(4-Morpholin-4-yl-phenyl)-1-(5-trifluoromethyl-pyridin-2-yl)-1H-[1,2,4]triazole-3,5-diamine | B | 1 | 406.30 | 2.85 | DMSO-d6: 8.93 (s, 1H), 8.75 (s, 1H), 8.31 (d, 1H), ,7.8 (m, 3H), 7.51 (d, 2H), 6.9 (d, 2H), 3.72 (m, 4H),, 3.0 (m, 4H) |
| N3-Benzo[1,3]dioxol-5-yl-1-(5-trifluoromethyl-pyridin-2-yl)-1H-[1,2,4]triazole-3,5-diamine | B | 1 | 365.20 | 3.86 | DMSO-d6: 9.07 (s, 1H), 8.78 (s, 1H), 8.33 (d, 1H), ,7.8 (m, 3H), 7.34 (s, 1H), 7.05 (d, 1H), 6.82 (d, 1H),, 5.93 (s, 2H), |
| N3-Benzo[1,3]dioxol-5-yl-1-(6-methyl-pyridin-2-yl)-1H-[1,2,4]triazole-3,5-diamine | B | 1 | 311.20 | 3.35 | DMSO-d6: 8.9 (s, 1H), 7.85 (t, 1H), 7.65 (s, 2H), ,7.47 (d, 1H), 7.35 (s, 1H), 7.05 (d, 2H), 6.8 (d, 1H), ,5.9 (s, 2H), 2.5 (s, 3H) |
| N3-(7-Methoxy-benzo[1,3]dioxol-5-yl)-1-(6-methyl-pyridin-2-yl)-1H-[1,2,4]triazole-3,5-diamine | B | 1 | 341.20 | 3.40 | DMSO-d6: 8.91 (s, 1H), 7.86 (t, 1H), 7.65 (s, 2H), ,7.45 (d, 1H), 7.05 (d, 1H), 6.95 (d, 2H), 5.9 (s, 2H), ,3.82 (s, 3H), 2.5 (s, 3H) |
| N3-(7-Methoxy-benzo[1,3]dioxol-5-yl)-1-(5-trifluoromethyl-pyridin-2-yl)1H-[1,2,4]triazole-3,5-diamine | B | 3 | 395.14 | 3.84 | DMSO-d6: 9.08 (s, 1H), 8.77 (s, 1H), 8.34 (d, 1H), ,7.80 (m, 3H), 6.99 (s, 2H), 5.90 (s, 2H), 3.85 (s, 3H) |
| [4-(5-Amino-1-pyridin-2-yl-1H-[1,2,4]triazol-3-ylamino)-phenyl]-morpholin-4-yl-methanone | H | 3 | 366.20 | 3.30 | Methanol-d4: 8.45 (m, 1H), 7.97 (t, 1H), 7.82 (d, 1H), ,7.67 (d, 2H), 7.45 (d, 2H), 7.25 (t, 1H), 3.85-3.6 (m, 8H) |
| 4-(5-Amino-1-pyridin-2-yl-1H-[1,2,4]triazol-3-ylamino)-N-methyl-N-(1-methyl-piperidin-4-yl)-benzamide | H | 3 | 407.30 | 1.40 | Methanol-d4: 8.42 (d, 1H), 7.95 (t, 1H), 7.82 (d, 1H), ,7.68 (d, 2H), 7.43 (d, 2H), 7.24 (t, 1H), 4.4 (m, 1H), 3.60 (m, 2H), 3.15 (m, 2H), 2.96 (s, 3H), 2.87 (s, 3H), ,2.17 (m, 2H), 2.05 (m, 2H) |
| [4-(5-Amino-1-pyridin-2-yl-1H-[1,2,4]triazol-3-ylamino)-phenyl]-(3-amino-pyrrolidin-1-yl)-methanone | H | 3 | 365.20 | 1.00 | Methanol-d4: 8.42 (m, 1H), 7.95 (t, 1H), 7.80 (d, 1H), 7.69 (d, 2H), 7.55 (d, 2H), 7.22 (t, 1H), 3.99 (m, 2H),, 3.88-3.62 (m, 3H), 2.43 (m, 1H), 2.1 (m, 1H) |
| [4-(5-Amino-1-pyridin-2-yl-1H-[1,2,4]triazol-3-ylamino)-phenyl]-(4-methyl-[1,4]diazepan-1-yl)-methanone | H | 3 | 393.30 | 1.00 | Methanol-d4: 8.42 (d, 1H), 7.95 (t, 1H), 7.80 (d, 1H), ,7.69 (d, 2H), 7.47 (d, 2H), 7.25 (t, 1H), 4.35-3.35 (m, 8H),,2.95 (s, 3H), 2.2 (m, 2H) |
| [4-(5-Amino-1-pyridin-2-yl-1H-[1,2,4]triazol-3-ylamino)-phenyl]-(4- | H | 3 | 433.30 | 1.50 | Methanol-d4: 8.42 (d, 1H), 7.95 (t, 1H), 7.80 (d, 1H), ,7.69 (d, 2H), 7.42 (d, 2H), 7.22 (t, 1H), 4.4 (m, 2H),, 3.67 (m, 2H), 3.45 (m, 1H), 3.25-3.0 |

| Name | cyclisation procedure | Purification procedure | MS (M + H) | Retention time (min) | NMR |
|---|---|---|---|---|---|
| pyrrolidin-1-yl-piperidin-1-yl)-methanone | | | | | (m, 4H), ,2.28-1.97 (m, 6H), 1.66 (m, 2H) |
| {6-[5-Amino-3-(4-morpholin-4-yl-phenylamino)-[1,2,4]triazol-1-yl]-pyridin-3-yl)-morpholin-4-yl-methanone | D | 3 | 451.20 | 1.80 | Methanol-d4: 8.5 (s, 1H), 8.01 (d, 1H), 7.84 (d, 1H), ,7.73 (d, 2H), 7.45 (d, 2H), 4.02 (m, 4H), ,3.87-3.47 (m, 12H) |
| {6-[5-Amino-3-(4-morpholin-4-yl-phenylamino)-[1,2,4]triazol-1-yl]-pyridin-3-yl}-(4-methyl-piperazin-1-yl)-methanone | D | 3 | 463.90 | 1.80 | Methanol-d4: 8.56 (s, 1H), 8.07 (d, 1H), 7.88 (d, 1H), ,7.71 (d, 2H), 7.38 (d, 2H), 4.0 (m, 4H), 3.47 m, 4H),, 3.46-3.2 (m, 8H), 2.96 (s, 3H) |
| 6-[5-Amino-3-(4-morpholin-4-yl-phenylamino)-[1,2,4]triazol-1-yl]-N-(2-dimethylamino-ethyl)-nicotinamide | D | 3 | 452.30 | 2.00 | Methanol-d4: 8.9 (s, 1H), 8.37 (d, 1H), 7.85 (d, 1H), ,7.72 (d, 2H), 7.38 (d, 2H), 4.01 (t, 4H), 3.8 (t, 2H), ,3.5 (m, 4H), 3.41 (t, 2H), 3.01 (s, 6H) |
| N3-(2,5-Dimethoxy-phenyl)-1-pyridin-2-yl-1H-[1,2,4]triazole-3,5-diamine | A | 1 | 313.10, 313.10 | 3.40, 3.40 | DMSO-d6: 8.45 (d, 1H), 8.05 (t, 1H), 7.95 (s, 2H), ,7.86 (d, 1H), 7.67 (d, 1H), 7.55 (s, 1H), 7.27 (t, 1H), 6.91 (d, 1H), 6.45 (d, 1H), 3.84 (s, 3H), 3.75 (s, 3H),DMSO(d6): 8.43 (dd, 1H), 8.02 (td, 1H), 7.93 (br. s, 2H), 7.86 (d, 1H), 7.65 (d, 1H), 7.54 |
| N3-Benzo[1,3]dioxol-5-yl-1-pyridin-2-yl-1H-[1,2,4]triazole-3,5-diamine | A | 3 | 297.10, 297.20 | 2.82, 3.06 | DMSO-d6: 9.02 (s, 1H), 8.40 (d, 1H), 7.99 (t, 1H), ,7.80-7.65 (m, 3H), 7.32 (d, 1H), 7.21 (t, 1H), 7.05 (d, 1H),,6.83 (d, 1H), 5.95 (s, 2H), DMSO: 8.9 (s, 1H), 8.46-8.26 (d,d, 1H), 8.06-7.88 (m, 1H), ,7.72-7.52 (m, 3H), 7.41-7.24 (d, 1H), 7.24-7.10 (d,d, |
| 1-Pyridin-2-yl-N3-(3,4,5-trimethoxy-phenyl)-1H-[1,2,4]triazole-3,5-diamine | A | 1 | 343.20, 343.10 | 2.90, 2.90 | (DMSO-d6): 9.0 (s, 1H), 8.42 (d, 1H), 7.98 (t, 1H), ,7.70 (s, 2H), 7.66 (d, 1H), 7.21 (t, 1H), 7.05 (s, 2H),, 3.79 (s, 6H), 3.60 (s, 3H),(DMSO-d6): 9.0 (s,1H), 8.42 (d, 1H), 7.98 (t, 1H),,7.70 (s, 2H), 7.66 (d, 1H), 7.21 (t, 1H), 7.05 (s, 2H), ,3.79 (s, |
| N3-(4-Morpholin-4-yl-phenyl)-1-pyridin-2-yl-1H-[1,2,4]triazole-3,5-diamine | A | 1 | 338.50, | 2.00 | DMSO-d6: 9.85 (s, 1H), 8.40 (d, 1H), 7.95 (t, 1H), 7.65 (m, 3H), 7.51 (m, 2H),7.20 (t, 1H), 6.90 (m, 2H), 3.75 (m, 4H),3.00 (m, 4H), |
| 4-(5-Amino-1-pyridin-2-yl-1H-[1,2,4]triazol-3-ylamino)-N-(2-morpholin-4-yl-ethyl)-benzamide | A | 3 | 409.30, | 1.70, 2. | Methanol-d4: 8.42 (d, 1H), 7.95 (t, 1H), 7.85 (d, 2H), ,7.81 (d, 1H), 7.69 (d, 2H), 7.24 (t, 1H), 4.11 (m, 2H),, 3.85-3.65 (m, 6H), 3.39 (m, 2H), 3.2 (m, 2H) |
| 1-(3-Morpholin-4-yl-phenyl)-N3-(3,4,5-trimethoxy-phenyl)-1H-[1,2,4]triazole-3,5-diamine | D* | | 427.30 | 2.70 | 1H NMR (CD3SOCD3, 500 MHz):☐ 3.13–3.19 (m, 4H), 3.59 (s, 3H), 3.72–3.78 (m, 4H), 3.74 (s, 6H), 6.88–6.93 (m, 1H), 6.97 (s, 2H), 7.00–7.04 (m, LH), 7.10–7.13 (m, 1H), 7.30–7.35 (m, 1H), 8.86 (s, br., 1H). |
| 4-[4-(5-Amino-1-pyridin-2-yl-1H-[1,2,4]triazol-3-ylamino)-benzoyl]-piperazine-1-carboxylic acid tert-butyl ester | D | | 465.2 | | |
| 4-[4-(5-Amino-1-pyridin-2-yl-1H-[1,2,4]triazol-3-ylamino)-phenyl]-piperazine-1-carboxylic acid tert- | D | | 465.2 | | |

| Name | cyclisation procedure | Purification procedure | MS (M + H) | Retention time (min) | NMR |
|---|---|---|---|---|---|
| butyl ester 4-{4-[5-Amino-1-(4-cyano-phenyl)-1H-[1,2,4]triazol-3-ylamino]-2,6-dimethoxy-phenoxy}-piperidine 1-carboxylic acid benzyl ester | D | | 570.2 | | |
| N3-(4-Piperazin-1-yl-phenyl)-1-pyrimidin-4-yl-1H-[1,2,4]triazole-3,5-diamine | | | 338.00 | 2.50 | 1H NMR (CD$_3$OD, 500 MHz):☐ 3.30–3.41 (m, 8H), 7.02 (d, 2H), 7.54 (d, 2H), 7.75 (d, 1H), 8.73 (d, 1H), 8.96 (s, 1H). |
| N$^3$-[4-(4-Cyclopropyl-piperazin-1-yl)-phenyl]-1-pyridin-2-yl-1H-[1,2,4]triazole-3,5-diamine | D | HPLC 95-5 | 377.30 | 2.40 | 1H NMR (CD$_3$OD, 500 MHz):☐ 0.97–1.10 (m, 4H), 2.89–2.96 (m, 1H), 3.18–3.73 (m, br., 8H), 6.84–7.20 (m, br., 2H), 7.24–7.36 (m, 1H), 7.41–7.68 (m, br., 2H), 7.81 (d, 1H), 7.96–8.03 (m, 1H), 8.46 (d, 1H). |
| 2-[4-(5-Amino-1-pyridin-2-yl-1H-[1,2,4]triazol-3-ylamino)-phenylamino]-ethanol | D | HPLC 90-10 | 312.10 | 2.00 | 1HNMR (CD$_3$OD, 500 MHz):☐ 3.42–3.49 (m, 2H), 3.73–3.80 (m, 2H), 7.20–7.26 (m, 1H), 7.38–7.45 (m, 2H), 7.44–7.83 (m, 3H), 7.91–7.99 (m, 1H), 8.39–8.45 (m, 1H). |
| N3-[4-(2,6-Dimethyl-morpholin-4-yl)-phenyl]-1-pyridin-2-yl-1H-[1,2,4]triazole-3,5-diamine | D | HPLC 90-10 | 366.30 | 2.50 | 1H NMR (CD$_3$OD, 500 MHz):☐ 1.30 (d, 6H), 2.07 (s, 1H), 2.92 (s, 1H), 3.05 (s, 1H), 3.10–3.20 (m, 2H), 3.58 (d, 2H), 3.97–4.06 (m, 2H), 7.20–7.25 (m, 1H), 7.42–7.51 (m, 2H), 7.71–7.77 (m, 2H), 7.80 (d, 1H), 7.92–7.98 (m, 1H), 8.43 (d, 1H). |
| 1-Phenyl-N3-(3,4,5-trimethoxy-phenyl)-1H-[1,2,4]triazole-3,5-diamine | A | 1 | 342.10, 342.20 | 2.62, 2.60 | DMSO-d6: 8.80 (s, 1H), 7.55 (s, 2H),,7.63 (d, 2H), 7.50 (t, 2H), 7.28 (t, 1H), 7.01 (s, 2H), ,6.47 (s, 2H), 3.74 (s, 6H), 3.59 (s, 3H),(500 MHz, DMSO-d6) 8.87 (s, 1H), 7.61 (dd, 2H), ,7.50 (t, 2H), 7.30 (t, 1H), 6.97 (s, 2H), 6.65 (br s, |
| 1,N3-Diphenyl-1H-[1,2,4]triazole-3,5-diamine | A | 3 | 252.2 | | DMSO-d6: 8.92 (s, 1H), 7.58 (m, 4H), 7.5 (t, 2H), 7.3 (t, 1h), 7.2 (t, 2H), 6.77 (t, 1H), 6.44 (s, 2H) |
| 3-(5-Amino-1-pyridin-2-yl-1H-[1,2,4]triazol-3-ylamino)-benzoic acid methyl ester | A | 1 | 311.2 | | DMSO-d6: 9.43 (s, 1H), 8.43 (d, 1H), 8.30 (m, 1H), 8.02 (t, 1H), 7.91 (d, 1H), 7.75 (s, 2H), 7.71 (d, 1H), 7.43, (m, 2H), 7.33 (t, 1H), 3.86 (s, 3H) |
| 3-[5-Amino-1-(3-methoxy-phenyl)-1H-[1,2,4]triazol-3-ylamino]-benzoic acid methyl ester | A | 3 | 340.2 | | DMSO-d6: 9.33 (s, 1H), 8.23 (m, 1H), 7.84 (d, 1H), 7.39 (m, 3H), 7.17 (d, 1H), 7.15 (t, 1H), 6.88 (d, 1H), 6.52 (s, 2H), 3.83 (s, 6H) |
| 3-[5-Amino-1-(4-methoxy-phenyl)-1H-[1,2,4]triazol-3-ylamino]-benzoic acid methyl ester | A | 3 | 340.2 | | DMSO-d6: 9.33 (s, 1H), 8.13 (t, 1H), 7.86 (d, 1H), 7.5 (m, 2H), 7.38 (m, 2H), 7.09 (m, 2H), 6.65 (bs, 2H), 3.81 (s, 6H) |
| 3-(5-Amino-1-phenyl-1H-[1,2,4]triazol-3-ylamino)-benzoic acid methyl ester | A | 3 | 310.2 | | DMSO-d6: 9.3 (s, 1H), 8.15 (m, 1H), 7.85 (d, 1H), 7.6 (m, 2H), 7.48 (m, 2H), 7.34 (m, 3H), 6.69 (bs, 2H), 3.82 (s, 3H) |
| N3-(3-Benzyloxy-phenyl)-1-(3-methoxy-phenyl)-1H-[1,2,4]triazole-3,5-diamine | A* | 3 | 388.3 | | DMSO-d6: 9.0 (s, 1H), 7.4 (m, 7H), 7.1 (m, 4H), 6.85 (d, 1H), 6.65 (bs, 2H), 6.45 (d, 1H), 5.05 (s, 2H), 3.8 (s, 3H) |
| N3-(3-Benzyloxy-phenyl)-1-(4-methoxy-phenyl)-1H-[1,2,4]triazole-3,5-diamine | A* | 3 | 388.3 | | DMSO-d6: 9.1 (s, 1H), 7.3–7.5 (m, 8H), 7.05 (m, 4H), 6.7 (bs, 2H), 6.45 (d, 1H), 5.05 (s, 2H), 3.85 (s, 3H) |
| N3-(3-Benzyloxy-phenyl)- 1-phenyl- | A | 3 | 358.3 | | DMSO-d6: 9.0 (s, 1H), 7.6 (m, 2H), 7.5 (m, 2H), 7.4 (m, 2H), 7.35 (m, |

| Name | cyclisation procedure | Purification procedure | MS (M + H) | Retention time (min) | NMR |
|---|---|---|---|---|---|
| 1H-[1,2,4]triazole-3,5-diamine | | | | | 5H), 7.1 (m, 2H), 6.65 (bs, 2H), 6.45 (d, 1H), 5.05 (s, 2H) |
| 1-(3-Methoxy-phenyl)-N3-(4-phenoxy-phenyl)-1H-[1,2,4]triazole-3,5-diamine | A* | 3 | 374.3 | | DMSO-d6: 9.15 (s, 1H), 7.6 (m, 2H), 7.43 (m, 1H), 7.32 (m, 2H), 7.18 (m, 2H), 7.05 (m, 1H), 7.0-6.6 (m, 7H), 3.8 (s, 3H) |
| 1-(4-Methoxy-phenyl)-N3-(4-phenoxy-phenyl)-1H-[1,2,4]triazole-3,5-diamine | A* | 3 | 374.3 | | DMSO-d6: 9.1 (s, 1H), 7.6 (d, 2H), 7.5 (d, 2H), 7.35 (d, 2H), 7.05 (m, 3H), 6.95-6.90 (m, 4H), 6.65 (bs, 2H), 3.8 (s, 3H) |
| N3-(4-Phenoxy-phenyl)-1-phenyl-1H-[1,2,4]triazole-3,5-diamine | A | 3 | 344.2 | | DMSO-d6: 9.1 (s, 1H), 7.59 (m, 4H), 7.5 (m, 2H), 7.31 (m, 3H), 7.05 (m, 1H), 6.95-6.90 (m, 4H), 6.75 (bs, 2H) |
| 4-(5-Amino-1-pyridin-2-yl- 1H-[1,2,4]triazol-3-ylamino)-benzoic acid | A | 3 | 297.2 | | DMSO-d6: 9.7 (s, 1H), 8.45 (m, 1H), 8.1-7.7 (m, 7H), 7.25 (m, 1H) |
| 4-[5-Amino-1-(3-methoxy-phenyl)-1H-[1,2,4]triazol-3-ylamino]-benzoic acid | A* | 3 | 326.2 | | DMSO-d6: 9.53 (s, 1H), 7.8 (m, 2H), 7.6 (m, 2H), 7.4 (m, 1H), 7.2-7.1 (m, 2H), 6.9 (m, 1H), 6.6 (bs, 2H), 3.85 (s, 3H) |
| 4-[5-Amino-1-(4-methoxy-phenyl)-1H-[1,2,4]triazol-3-ylamino]-benzoic acid | A* | 3 | 326.2 | | DMSO-d6: 9.45 (s, 1H), 7.8 (d, 2H), 7.6 (d, 2H), 7.5 (d, 2H), 7.05 (m, 2H), 6.35 (s, 2H), 3.81 (s, 3H) |
| 4-(5-Amino-1-phenyl-1H-[1,2,4]triazol-3-ylamino)-benzoic acid | A | 3 | 296.2 | | DMSO-d6: 9.5 (s, 1H), 7.8 (m, 2H), 7.65-7.45 (m, 6H), 7.33 (m, 1H), 6.55 (s, 2H) |
| 1-(3-Methoxy-phenyl)-N3-phenyl-1H-[1,2,4]triazole-3,5-diamine | A* | 3 | 282.2 | | DMSO-d6: 8.95 (s, 1H), 8.18 (s, 1H), 7.55 (d, 2H), 7.39 (t, 1H), 7.25-7.1 (m, 3H), 6.85 (d, 1H), 6.75 (t, 1H), 6.45 (s, 2H), 3.8 (s, 3H) |
| 1-(4-Methoxy-phenyl)-N3-phenyl-1H-[1,2,4]triazole-3,5-diamine | A* | 3 | 282.2 | | DMSO-d6: 8.85 (s, 1H), 7.55 (d, 2H), 7.45 (d, 2H), 7.2 (t, 2H), 7.05 (d, 2H), 6.75 (t, 1H), 6.25 (s, 2H), 3.8 (s, 3H) |
| N3-(3,4-Dimethoxy-phenyl)-1-(3-methoxy-phenyl)-1H-[1,2,4]triazole-3,5-diamine | A* | 3 | 342.2 | | DMSO-d6: 8.7 (s, 1H), 8.15 (s, 1H), 7.35 (m, 2H), 7.15 (m, 2H), 7.05 (d, 1H), 6.85 (m, 2H), 6.45 (s, 2H), 3.82 (s, 3H), 3.75 (s, 3H), 3.68 (s, 3H) |
| N3-(3,4-Dimethoxy-phenyl)-1-(4-methoxy-phenyl)-1H-[1,2,4]triazole-3,5-diamine | A* | 3 | 342.2 | | DMSO-d6: 8.6 (s, 1H), 8.15 (s, 1H), 7.45 (m, 2H), 7.27 (d, 1H), 7.1 (d, 1H), 7.05 (d, 2H), 6.8 (d, 1H), 6.25 (s, 2H), 3.8 (s, 3H), 3.7 (s, 3H), 3.68 (s, 3H) |
| N3-(3,4-Dimethoxy-phenyl)-1-phenyl-1H-[1,2,4]triazole-3,5-diamine | A | 3 | 312.2 | | DMSO-d6: 8.7 (s, 1H), 7.61 (d, 2H), 7.5 (t, 2H), 7.27 (m, 2H), 7.11 (d, 1H), 6.82 (d, 1H), 6.41 (s, 2H), 3.75 (s, 3H), 3.68 (s, 3H) |
| N3-(4-Phenoxy-phenyl)-1-pyridin-2-yl-1H-[1,2,4]triazole-3,5-diamine | A | 3 | 345.2 | | DMSO-d6: 9.17 (s, 1H), 8.4 (d, 1H), 7.99 (t, 1H), 7.7 (m, 5H), 7.35 (m, 2H), 7.2 (t, 1H), 7.05 (t, 1H), 7.0 (d, 2H), 6.92 (m, 2H) |
| [4-(5-Amino-1-pyridin-2-yl-1H-[1,2,4]triazol-3-ylamino)-phenyl]-methanol | A | 3 | 283.2 | | DMSO-d6: 9.08 (s, 1H), 8.4 (m, 1H), 7.98 (t, 1H), 7.7 (m, 3H), 7.59 (d, 2H), 7.2 (m, 3H), 5.0 (m, 1H), 4.4 (m, 2H) |
| N3-Benzyl-1-pyridin-2-yl-1H-[1,2,4]triazole-3,5-diamine | A | 3 | 267.2 | | DMSO-d6: 8.32 (d, 1H), 7.88 (t, 1H), 7.52 (m, 3H), 7.37 (d, 2H), 7.3 (m, 2H), 7.21 (t, 1H), 7.11 (m, 1H), 6.56 (t, 1H), 4.32 (d, 2H) |
| N3-Benzyl-1-(4-methoxy-phenyl)-1H-[1,2,4]triazole-3,5-diamine | A | 3 | 296.2 | | DMSO-d6: 7.4-7.27 (m, 6H), 7.2 (t, 1H), 6.98 (m, 2H), 6.15 (t, 1H), 6.05 (s, 2H), 4.25 (d, 2H), 3.76 (s, 3H) |
| N3-Benzyl-1-phenyl- | A | 3 | 266.2 | | DMSO-d6: 7.5–7.18 (m, 10H), 6.25 |

| Name | cyclisation procedure | Purification procedure | MS (M + H) | Retention time (min) | NMR |
|---|---|---|---|---|---|
| 1H-[1,2,4]triazole-3,5-diamine | | | | | (m, 3H), 4.35 (d, 2H) |
| N3-(3,4-Dimethoxy-phenyl)-1-pyridin-2-yl-1H-[1,2,4]triazole-3,5-diamine | A | 3 | 313.2 | | DMSO-d6: 8.88 (s, 1H), 8.38 (m, 1H), 7.95 (m, 1H), 7.65 (m, 3H), 7.35 (m, 1H), 7.15 (m, 2H), 6.83 (m, 1H), 3.8 (s, 3H), 3.68 (s, 3H) |
| N3-(3-Benzyloxy-phenyl)-1-pyridin-2-yl-1H-[1,2,4]triazole-3,5-diamine | A | 3 | 359.3 | | DMSO-d6: 9.15 (s, 1H), 8.41 (d, 1H), 7.97 (m, 1H), 7.7 (s, 2H), 7.61 d, 1H), 7.45 (d, 2H), 7.38 (m, 3H), 7.3 (m, 1H), 7.15 (m, 3H), 6.5 (d, 1H),5.1 (s, 2H) |
| N3-Biphenyl-3-yl-1-pyridin-2-yl-1H-[1,2,4]triazole-3,5-diamine | A | 3 | 329.2 | | DMSO-d6: 9.25 (s, 1H), 8.42 (m, 1H), 8.0 (m, 1H), 7.9 (s, 1H), 7.72 (m, 4H), 7.65 (d, 2H), 7.47 (m, 2H), 7.35 (m, 2H), 7.2 (m, 1H), 7.11 (m, 1H) |
| 1-(3-Methoxy-phenyl)-N3-(tetrahydro-furan-2-ylmethyl)-1H-[1,2,4]triazole-3,5-diamine | A* | 3 | 290.2 | | DMSO-d6: 7.65 (bs, 2H), 7.46 (t, 1H), 7.1 (m, 2H), 6.98 (d, 1H), 6.68 (bs, 1H), 4.0 (m, 1H), 3.83 (s, 3H), 3.78 (m, 1H), 3.65 (m, 1H), 3.15 (m, 2H), 1.92 (m, 1H), 1.85 (m, 2H), 1.55 (m, 1H) |
| 1-(2-Fluoro-4-iodo-phenyl)-N3-(3,4,5-trimethoxy-phenyl)-1H-[1,2,4]triazole-3,5-diamine | A | 2 | 486.0 | 3.2 | (500 MHz, DMSO-d6) 8.74 (s, 1H), 7.86 (dd, 1H), 7.68 (dd, 1H), 7.34 (t, 1H), 6.91 (s, 2H), 6.42 (s, 2H), 3.69 (s, 6H), 3.57 (s, 3H) ppm. |
| 4-[5-Amino-3-(benzo[1,3]dioxol-5-ylamino)-[1,2,4]triazol-1-yl]-benzoic acid | G | 1 | 340.1 | 2.49 | (500 MHz, DMSO-d6) 8.83 (s, 1H), 8.03 (d, 2H), 7.71 (m, 3H), 7.29 (d, 1H), 6.99 (d, 1H), 6.61 (s, 1H), 5.91 (s, 2H) ppm. |
| 1-(6-Chloro-pyrimidin-4-yl)-N3-(4-morpholin-4-yl-phenyl)-1H-[1,2,4]triazole-3,5-diamine | G* | 2 | 373.2 | 2.751 | (500 MHz, DMSO-d6) 9.04 (s, 1H), 8.80 (s, 1H), 7.87 (s, 2H), 7.58 (s, 1H), 7.50 (d, 2H), 6.91 (d, 2H), 3.73 (m, 4H), 3.01 (m, 4H) ppm. |
| 1-(6-Chloro-pyrimidin-4-yl)-N3-(2,4-difluoro-phenyl)-1H-[1,2,4]triazole-3,5-diamine | G* | 1 | 324.1 | 3.58 | (500 MHz, DMSO-d6) 8.84 (s, 1H), 8.81 (s, 1H), 8.13 (m, 1H), 7.93 (s, 2H), 7.59 (s, 1H), 7.24 (m, 1H), 7.07 (m, 1H)) ppm |
| 1-(6-Chloro-pyrimidin-4-yl)-N3-(2-methoxy-phenyl)-1H-[1,2,4]triazole-3,5-diamine | G* | 1 | 318.1 | 3.58 | (500 MHz, DMSO-d6) 8.82 (s, 1H), 8.13 (d, 1H), 7.94 (s, 2H), 7.66 (s, 1H), 7.55 (s, 1H), 6.99 (m, 2H), 6.91 (d, 1H), 3.87 (s, 3H) ppm |
| 1-(6-Chloro-pyrimidin-4-yl)-N3-indan-4-yl-1H-[1,2,4]triazole-3,5-diamine | G* | 1 | 328.2 | 4.02 | (500 MHz, DMSO-d6) 8.81 (s, 1H), 8.30 (s, 1H), 7.88 (s, 2H), 7.79 (d, 1H), 7.55 (d, 1H), 7.12 (t, 1H), 6.83 (d, 1H), 2.88 (m, 4H), 2.01 (m, 2H) ppm |
| 4-[5-Amino-3-(3,4,5-trimethoxy-phenylamino)-[1,2,4]triazol-1-yl]-benzoic acid | C | 2 | 386.1 | | |
| N5-(3,5-Dimethyl-phenyl)-1-thiazol-2-yl-1H-[1,2,4]triazole-3,5-diamine | A | 2 | 287.10 | 3.8 | DMSO: 9.96, s, 1H; 7.64, d, 1H: 7.43, d, 1H; 7.28, s, 2H; 6.68, s, 1H; 6.08, bs, 2H; 2.22, s, 6H |
| N3-(3,5-Dimethyl-phenyl)-1-(4-methyl-thiazol-2-yl)-1H-[1,2,4]triazole-3,5-diamine | A | 2 | 301.10 | 4.2 | Acetone-d6: 7,32,s, 2H; 6.87, s, 1H; 6.71, s, 1H; 2.38, s,3H; 2.26, s, 6H |
| 1-Benzothiazol-2-yl-N3-(3,5-dimethyl-phenyl)-1H-[1,2,4]triazole-3,5-diamine | A | 1 | 337.10 | 4.6 | DMSO-d6: 9.25 (s, 1H); 8.08 (d, 1H); 7.86 (d, 1H); 7.78 (bs, 2H); 7.51 (dd, 1H); 7.34 (dd, 1H); 7.21 (s, 2H); 6.50 (s, 1H); 2.22 (s, 6H) |
| 1-Benzothiazol-2-yl-N3-(3,5-dimethoxy-phenyl)-1H- | A | 1 | 369.2 | 4.1 | DMSO-d6: 9.41 (s, 1H); 8.06 (d, 1H); 7.86 (d, 1H); 7.76 (bs, 2H); 7.48 (dd, 1H); 7.39 (dd, 1H); 6.88 (s, |

| Name | cyclisation procedure | Purification procedure | MS (M + H) | Retention time (min) | NMR |
|---|---|---|---|---|---|
| [1,2,4]triazole-3,5-diamine | | | | | 2H); 6.03 (s, 1H); 3.76 (s, 6H), 1H NMR (DMSO-d6): 3.74 (6H, s), 6.06 (1H, t), 6.89 (2H, d), 7.37 (1H, t), 7.50 (1H, t), 7.81 (2H, s), 7.87 (1H, d), 8. |
| 1-Benzothiazol-2-yl-N3-(3-methoxy-5-trifluoromethyl-phenyl)-1H-[1,2,4]triazole-3,5-diamine | A | 1 | 407.10 | 4.7 | DMSO-d6: 9.82 (s, 1H); 8.10 (d, 1H); 7.91 (bs, 2H); 7.86 (d, 1H); 7.58 (s, 1H); 7.52 (s, 1H); 7.50 (dd, 1H); 7.34 (dd, 1H); 6.74 (s, 1H); 3.86 (s, 3H) |
| 3-(5-Amino-1-benzothiazol-2-yl-1H-[1,2,4]triazol-3-ylamino)-5-trifluoromethyl phenol | A | 1 | 393.10 | 4 | DMSO-d6: 10.00 (bs, 1H); 9.69 (s, 1H); 8.08 (d, 1H); 7.80–7.95 (m, 3H); 7.45–7.53 (m, 2H); 7.35 (dd, 1H); 7.30 (s, 1H); 6.55 (s, 1H) |
| 3-[3-(5-Amino-1-benzothiazol-2-yl-1H-[1,2,4]triazol-3-ylamino)-5-trifluoromethyl-phenoxy]-propan-1-ol | A | 1 | 451.20 | 4.1 | DMSO-d6: 9.85 (s, 1H); 8.08 (d, 1H); 7.88 (bs, 2H); 7.86 (d, 1H); 7.56 (s, 1H); 7.48–7.52 (m, 2H); 7.39 (dd, 1H); 6.73 (s, 1H); 4.11 (t, 2H); 3.57 (t, 2H); 1.91 (m, 2H) |
| N3-(3,5-Dimethyl-phenyl)-1-(5-methyl-thiazol-2-yl)-1H-[1,2,4]triazole-3,5-diamine | A | 2 | 301.10 | 4.14 | DMSO-d6: 9.03 (s, 1H); 7.42 (bs, 2H); 7.24 (s, 1H); 7.18 (s, 2H); 6.47 (s, 1H); 2.41 (s, 3H); 2.24 (s, 6H) |
| N5-(3,5-Dimethyl-phenyl)-1-(5-methyl-thiazol-2-yl)-1H-[1,2,4]triazole-3,5-diamine | A | 2 | 301.10 | 4.22 | DMSO-d6: 9.85 (s, 1H); 7.33 (s, 1H); 7.27 (s, 2H); 6.68 (s, 1H); 5.99 (bs, 2H); 2.36 (s, 3H); 2.26 (s, 6H) |
| N3-(3,5-Dimethoxy-phenyl)-1-(5-methyl-thiazol-2-yl)-1H-[1,2,4]triazole-3,5-diamine | A | 2 | 333.1 | 3.61 | DMSO-d6: 9.18 (s, 1H); 7.43 (bs, 2H); 7.22 (s, 1H); 6.82 (s, 2H); 6.01 (s, 1H); 3.72 (s, 6H); 2.42 (s, 3H),DMSO-d6: 9.19 (s, 1H); 7.42 3H) |
| N5-(3,5-Dimethoxy-phenyl)-1-(5-methyl-thiazol-2-yl)-1H-[1,2,4]triazole-3,5-diamine | A | 2 | 333.10 | 3.61 | DMSO-d6: 9.88 (s, 1H); 7.31 (s, 1H); 6.92 (s, 2H); 6.18 (s, 1H); 5.98 (bs, 2H); 3.76 (s, 6H); 2.39 (s, 3H) |
| N3-(3-Methoxy-5-trifluoromethyl-phenyl)-1-(5-methyl-thiazol-2-yl)-1H-[1,2,4]triazole-3,5-diamine | A | 2 | 371.10 | 4.3 | DMSO-d6: 9.66 (s, 1H); 7.51 (s, 1H); 7.48 (bs, 2H); 7.46 (s, 1H); 7.28 (s, 1H); 6.66 (s, 1H); 3.78 (s, 3H); 2.37 (s, 3H) |
| N5-(3-Methoxy-5-trifluoromethyl-phenyl)-1-(5-methyl-thiazol-2-yl)-1H-[1,2,4]triazole-3,5-diamine | A | 2 | 371.10 | 4.37 | DMSO-d6: 10.05 (s, 1H); 7.72 (s, 1H); 7.65 (s, 1H); 7.32 (s, 1H); 6.89 (s, 1H); 6.02 (BS 2H); 3.86 (s, 3H); 2.38 (s, 3H) |
| N3-(3,5-Dimethoxy-phenyl)-1-thiazol-2-yl-1H-[1,2,4]triazole-3,5-diamine | A | 2 | 319.10 | 3.31 | DMSO-d6: 9.22 (s, 1H); 7.61 (d, 1H); 7.48 (bs, 2H); 7.40 (d, 1H); 6.86 (s, 2H); 6.00 (s, 1H); 3.72 (s, 6H) |
| N5-(3,5-Dimethoxy-phenyl)-1-thiazol-2-yl-1H-[1,2,4]triazole-3,5-diamine | A | 2 | 319.10 | 3.36 | DMSO-d6; 9.96 (s, 1H); 7.59 (d, 1H); 7.41 (d, 1H); 6.92 (s, 2H); 6.20 (s, 1H); 5.97 (bs, 2H); 3.78 (s, 6H) |
| N3-(3-Methoxy-5-trifluoromethyl-phenyl)-1-thiazol-2-yl-1H-[1,2,4]triazole-3,5-diamine | A | 2 | 357.10 | | DMSO-d6: 9.68 (s, 1H); 7.59 (d, 1H); 7.56 (bs, 2H); 7.53 (s, 1H); 7.48 (s, 1H); 7.42 (d, 1H); 6.69 (s, 1H); 3.82 (s, 1H) |
| N5-(3-Methoxy-5-trifluoromethyl-phenyl)-1-thiazol-2-yl-1H-[1,2,4]triazole-3,5-diamine | A | 2 | 357.10 | 4.06 | DMSO-d6: 10.19 (s, 1H); 7.77 (s, 1H); 7.68 (d, 1H); 7.66 (s, 1H); 7.42 (d, 1H); 6.89 (s, 1H); 6.06 (bs, 2H); 3.84 (s, 3H) |
| N3-(3-Benzyloxy-phenyl)-1-thiazol-2- | A | 2 | 365.20 | 4.11 | DMSO-d6: 7.60 (bs, 1H); 7.52 (d, 1H); 7.48 (s, 1H); 7.46 (s, 1H); 7.30– |

| Name | cyclisation procedure | Purification procedure | MS (M + H) | Retention time (min) | NMR |
|---|---|---|---|---|---|
| yl-1H-[1,2,4]triazole-3,5-diamine | | | | | 7.40 (m, 6H); 7.22 (dd, 1H); 7.08 (d, 1H); 7.02 (d, 1H); 6.64 (d, 1H); 5.10 (s, 2H) |
| N3-(2-Methoxy-phenyl)-1-(5-methyl-thiazol-2-yl)-1H-[1,2,4]triazole-3,5-diamine | A | 2 | 303.10 | 3.85 | DMSO-d6: 8.02 (d, 1H); 7.52 (s, 1H); 7.48 (bs, 2H); 7.22 (s, 1H); 6.99 (d, 1H); 6.87-6.93 (m, 2H); 3.86 (s, 3H); 2.38 (s, 3H) |
| N3-(3-Methoxy-phenyl)-1-(5-methyl-thiazol-2-yl)-1H-[1,2,4]triazole-3,5-diamine | A | 2 | 303.2 | 3.59 | DMSO-d6: 9.23 (s, 1H); 7.43 (bs, 2H); 7.34 (s, 1H); 7.23 (s, 1H); 7.12 (dd, 1H); 7.03 (d, 1H); 6.41 (d, 1H); 3.78 (s, 3H); 2.39 (s, 3H),DMSO-d6: 9.21 (s, 1H); 7.42 (bs, 2H); 7.31 (s, 1H); 7.22 (s, 1H); 7.11 (dd, 1H); 7.03 (d, 1H); 6.42 (d, 1H); 3.74 (s, 3 |
| N3-(4-Methoxy-phenyl)-1-(5-methyl-thiazol-2-yl)-1H-[1,2,4]triazole-3,5-diamine | A | 2 | 303.20 | 3.47 | DMSO-d6: 8.99 (s, 1H); 7.45 (d, 2H); 7.38 (bs, 2H); 7.24 (s, 1H); 6.86 (d, 2H); 3.68 (s, 3H); 2.38 (s, 3H) |
| N3-(3,5-Dimethyl-phenyl)-1-thiazol-2-yl-1H-[1,2,4]triazole-3,5-diamine | A | 2 | 287.20 | 4.69 | DMSO-d6: 9.05 (s, 1H); 7.54 (d, 1H); 7.50 (bs, 2H); 7.37 (d, 1H); 7.18 (s, 2H); 6.48 (s, 1H); 2.22 (s, 6H) |
| N3-(2,4-Dimethoxy-phenyl)-1-thiazol-2-yl-1H-[1,2,4]triazole-3,5-diamine | A | 2 | 319.20 | 4.07 | DMSO-d6: 7.85(d, 1H); 7.55 (d, 1H); 7.49 (bs, 2H); 7.36 (d, 1H); 7.32 (s, 1H); 6.60 (d, 1H); 6.50 (m, 1H); 3.82 (s, 3H); 3.72 (s, 3H); |
| N3-(3,4-Dimethoxy-phenyl)-1-thiazol-2-yl-1H-[1,2,4]triazole-3,5-diamine | A | 2 | 319.20 | 3.49 | DMSO-d6: 9.02 (s, 1H); 7.58 (d, 1H); 7.49 (bs, 2H); 7.42 (s, 1H); 7.39 (d, 1H); 7.02 (d, 1H); 6.88 (d, 1H); 3.77 (s, 3H); 3.70 (s, 3H) |
| N3-(2,5-Dimethoxy-phenyl)-1-thiazol-2-yl-1H-[1,2,4]triazole-3,5-diamine | A | 2 | 319.20 | 4.2 | DMSO-d6: 7.80 (d, 1H); 7.58 (d, 1H); 7.56 (m, 3H); 7.42 (d, 1H); 6.88 (d, 1H); 6.43 (d, 1H); 3.80 (s, 3H); 3.75 (s, 3H) |
| N3-(2,3-Dihydro-benzo[1,4]dioxin-5-yl)-1-thiazol-2-yl-1H-[1,2,4]triazole-3,5-diamine | A | 2 | 317.10 | 3.77 | DMSO-d6: 9.02 (s, 1H); 7.58 (d, 1H); 7.51 (bs, 2H); 7.39 (d, 1H); 7.21 (s, 1H); 6.92 (dd, 1H); 6.76 (d, 1H); 4.18-4.14(m, 4H) |
| N3-(2-Methoxy-phenyl)-1-thiazol-2-yl-1H-[1,2,4]triazole-3,5-diamine | A | 2 | 289.20 | 4.29 | DMSO-d6: 8.02 (d, 1H); 7.60 (d, 1H); 7.57 (bs, 2H); 7.51 (s, 1H); 7.41 (d, 1H); 7.00 (d, 1H); 6.95-6.88 (m, 2H); 3.86 (s, 3H) |
| N3-(3-Methoxy-phenyl)-1-thiazol-2-yl-1H-[1,2,4]triazole-3,5-diamine | A | 2 | 289.20 | 3.99 | DMSO-d6: 9.22 (s, 1H); 7.59 (d, 1H); 7.50 (bs, 2H); 7.40 (d, 1H); 7.37 (s, 1H); 7.13 (dd, 1H); 7.08 (d, 1H); 6.42 (d, 1H); 3.72 (s, 3H) |
| N3-(4-Methoxy-phenyl)-1-thiazol-2-yl-1H-[1,2,4]triazole-3,5-diamine | A | 2 | 289.20 | 3.81 | DMSO-d6: 9.02 (s, 1H); 7.52 (d, 1H); 7.49 (m, 4H); 7.32 (d, 1H); 6.82 (d, 2H); 3.70 (s, 3H) |
| 5-(5-Amino-1-thiazol-2-yl-1H-[1,2,4]triazol-3-ylamino)-2-methoxy-phenol | A | 2 | 305.20 | 3.01 | DMSO-d6: 8.92 (s, 1H): 7.56 (d, 1H); 7.50 (bs, 2H); 7.42 (d, 1H); 7.02 (d, 1H); 6.98 (dd, 1H); 6.86 (d, 1H); 3.69 (s, 3H) |
| N3-(3,4-Dimethoxy-phenyl)-1-thiazol-2-yl-1H-[1,2,4]triazole-3,5-diamine | A | 2 | 333.20 | 3.18 | DMSO-d6: 8.98 (bs, 1H); 7.37 (bs, 3H); 7,23 (s, 1H); 7.01 (d, 1H); 6.82 (d, 1H); 3.72 (s, 3H); 3.62 (s, 3H); 2.32 (s, 3H) |
| N5-(3,5-Dimethyl-phenyl)-1-thiazol-2-yl-1H-[1,2,4]triazole-3,5-diamine | A | 2 | 287.10 | 3.8 | DMSO: 9.96, s, 1H; 7.64, d, 1H: 7.43, d, 1H; 7.28, s, 2H; 6.68, s, 1H; 6.08, bs, 2H; 2.22, s, 6H |
| N3-(3,5-Dimethyl-phenyl)-1-(4-methyl-thiazol-2-yl)-1H-[1,2,4]triazole-3,5-diamine | A | 2 | 301.10 | 4.2 | Acetone-d6: 7,32, s, 2H; 6.87, s, 1H; 6.71, s, 1H; 2.38, s, 3H; 2.26, s, 6H |
| 1-Benzothiazol-2-yl-N3-(3,5-dimethyl-phenyl)-1H-[1,2,4]triazole-3,5-diamine | A | 1 | 337.10 | 4.6 | DMSO-d6: 9.25 (s, 1H); 8.08 (d, 1H); 7.86 (d, 1H); 7.78 (bs, 2H); 7.51 (dd, 1H); 7.34 (dd, 1H); 7.21 (s, 2H); 6.50 (s, 1H); 2.22 (s, 6H) |

| Name | cyclisation procedure | Purification procedure | MS (M + H) | Retention time (min) | NMR |
|---|---|---|---|---|---|
| 1-Benzothiazol-2-yl-N3-(3,5-dimethoxy-phenyl)-1H-[1,2,4]triazole-3,5-diamine | A | 1 | 369.2 | 4.1 | DMSO-d6: 9.41 (s, 1H); 8.06 (d, 1H); 7.86 (d, 1H); 7.76 (bs, 2H); 7.48 (dd, 1H); 7.39 (dd, 1H); 6.88 (s, 2H); 6.03 (s, 1H); 3.76 (s, 6H),1H NMIR (DMSO-d6): 3.74 (6H, s), 6.06 (1H, t), 6.89 (2H, d), 7.37 (1H, t), 7.50 (1H, t), 7.81 (2H, s), 7.87 (1H, d), 8. |

Example 53

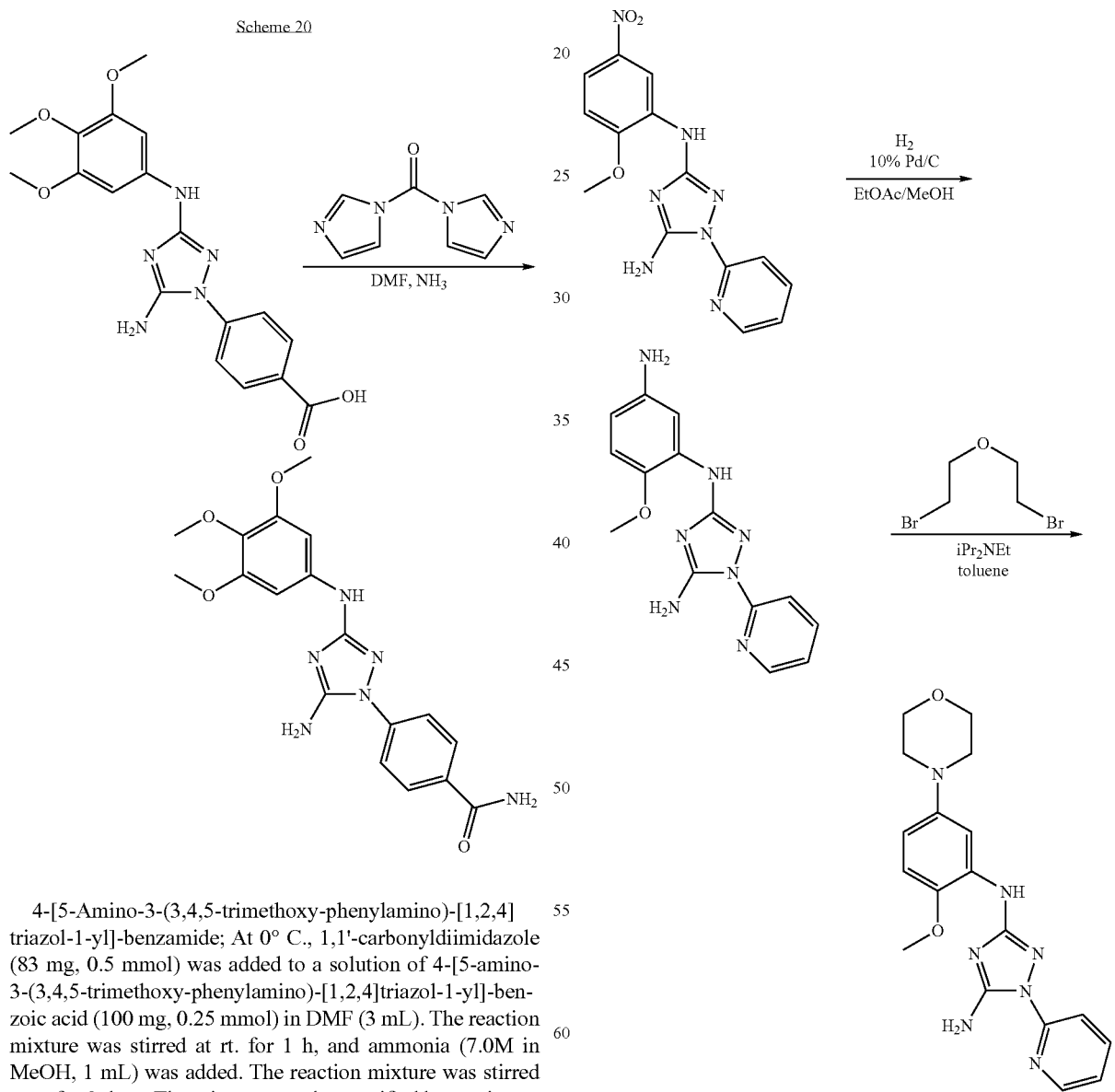

4-[5-Amino-3-(3,4,5-trimethoxy-phenylamino)-[1,2,4]triazol-1-yl]-benzamide; At 0° C., 1,1'-carbonyldiimidazole (83 mg, 0.5 mmol) was added to a solution of 4-[5-amino-3-(3,4,5-trimethoxy-phenylamino)-[1,2,4]triazol-1-yl]-benzoic acid (100 mg, 0.25 mmol) in DMF (3 mL). The reaction mixture was stirred at rt. for 1 h, and ammonia (7.0M in MeOH, 1 mL) was added. The reaction mixture was stirred at rt. for 2 days. The mixture was then purified by semi-prep HPLC. FIA-MS: m/e=385.1 (M+H), 383.1 (ES−). $R^t$=3.60 min (method A). $^1$H-NMR (500 MHz, DMSO(d6)):8.87 (s, 1H), 8.02 (br.s, 1H), 7.99 (d, 2H), 7.67 (d, 2H), 7.39 (br.s, 1H), 7.00 (s, 2H), 6.62 (s, 2H), 3.78 (s, 6H), 3.65 (s, 3H).

N3-(5-Amino-2-methoxy-phenyl)-1-pyridin-2-yl-1H-[1,2,4]triazole-3,5-diamine and N3-(2-Methoxy-5-morpholin-4-yl-phenyl)-1-pyridin-2-yl-1H-[1,2,4]triazole-3,5-diamine Hydrogenation of N3-(5-nitro-2-methoxy-phenyl)-1-pyridin-2-yl-1H-[1,2,4]triazole-3,5-diamine with 10% Pd/C in a mixed solvent of EtOAc/MeOH (1:1) gave N3-(5-Amino-2-methoxy-phenyl)-1-pyridin-2-yl-1H-[1,2,4]triazole-3,5-diamine. FIA-MS: m/e=298.2 (M+H). R$^t$=2.40 min (method A). $^1$H-NMR (500 MHz, DMSO(d6)): 9.93 (br.s, 2H), 8.45 (dd, 1H), 8.33 (d, 1H), 8.00 (td, 1H), 7.88 (d, 1H), 7.82 (br.s, 2H), 7.99 (s, 1H), 7.26 (dd, 1H), 7.08 (d, 1H), 6.87 (dd, 1H), 3.90 (s, 3H).

A solution of N3-(5-Amino-2-methoxy-phenyl)-1-pyridin-2-yl-1H-[1,2,4]triazole-3,5-diamine (160 mg, 0.5 mmol) and bis(2-bromoethyl)ether (140 mg, 0.6 mmol) and isopropylethylamine (258 mg, 2 mmol) in a mixture of toluene (30 mL) and DMAC (3 mL) was heated at 110° C. for 70 h. Concentration. The residue was purified by HPLC to give the title compound (26 mg). FIA-MS: m/e=368.2 (M+H). R$^t$=2.13. $^1$H-NMR (500 MHz, DMSO(d6)): 8.43 (dd, 1H), 8.03 (m, 2H), 7.90 (m, 1H), 7.68 (d, 1H), 7.56 (br.s, 1H), 7.26 (dd, 1H), 6.94 (d, 1H), 6.64 (dd, 1H), 3.80 (s, 3H), 3.28 (br.s, 4H).

reaction mixture was cooled to room temperature, neutralized with 6N HCl. Precipitate came out and collected by filtration to give the title compound (1.20 g) in 95% yield. Small amount was further purified by HPLC. FIA-MS: m/e=327.1 (M+H), 325.0 (M–H). R$^t$=3.09 min (Method A). $^1$H-NMR (500 MHz, DMSO(d6)): 12.53 (s, 1H), 8.81 (d, 1H), 8.43 (dd, 1H), 8.01 (td, 1H), 7.78 (s, 2H), 7.65 (d, 1H), 7.56 (s, 1H), 7.353 (dd, 1H), 7.23 (dd, 1H), 7.07 (dd, 1H), 3.92 (s, 3H).

Scheme 22

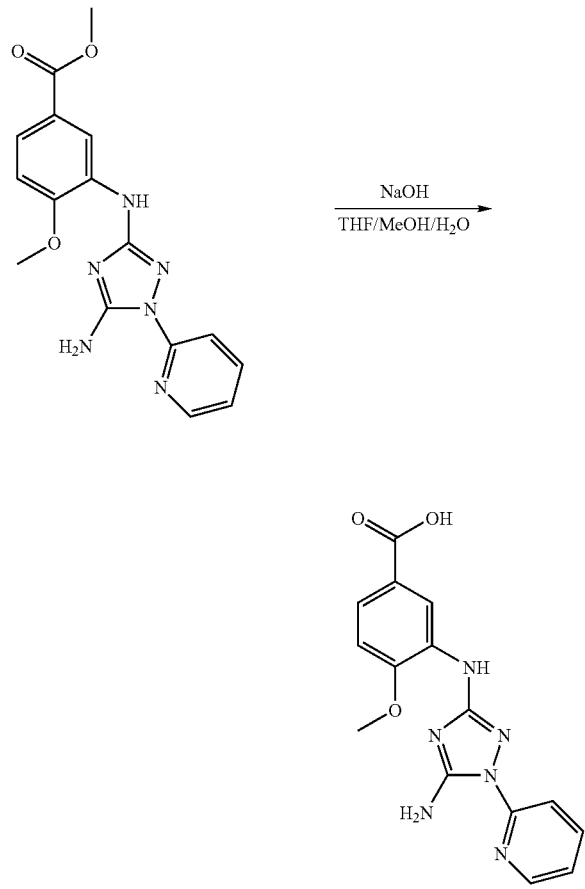

Scheme 23

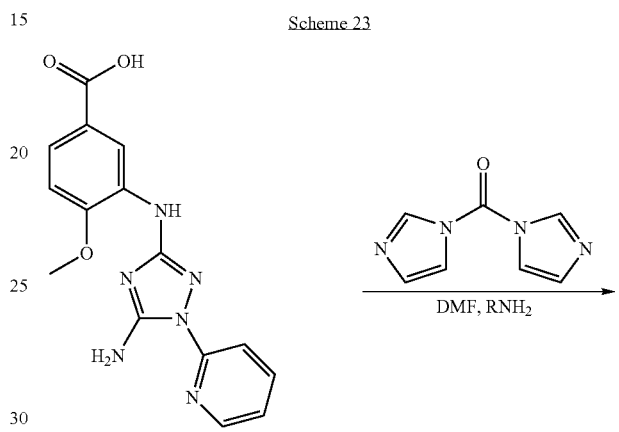

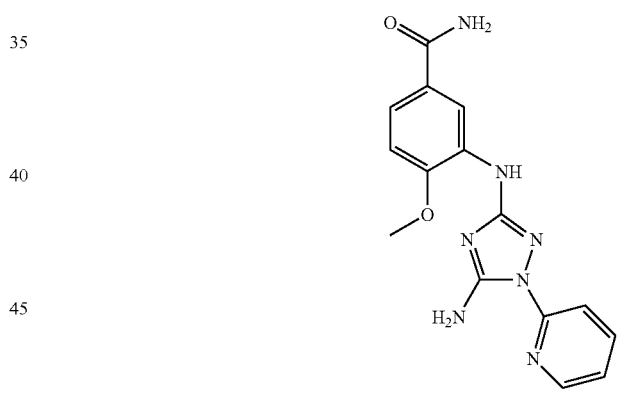

3-(5-Amino-1-pyridin-2-yl-1H-[1,2,4]triazol-3-ylamino)-4-methoxy-benzoic acid. A suspension of 3-(5-Amino-1-pyridin-2-yl-1H-[1,2,4]triazol-3-ylamino)-4-methoxy-benzoic acid methyl ester (1.31 g, 3.85 mmol) in a mixed solvent of THF (40 mL), MeOH (5 mL) and water (10 mL) was treated with 2N NaOH (8 mL) at 50° C. for 1 h. The 3-(5-Amino-1-pyridin-2-yl-1H-[1,2,4]triazol-3-ylamino)-4-methoxy-benzamide. A suspension of 3-(5-Amino-1-pyridin-2-yl-1H-[1,2,4]triazol-3-ylamino)-4-methoxy-benzoic acid (108 mg, 0.8 mmol) in a mixed solvent of THF (50 mL) and DMF (15 mL) was treated with 1,1'-carbonyldiimidazole (194 mg, 1.2 mmol) at room temperature. After 1 h, ammonia in MeOH (7.0M, 1 mL) was added. The reaction mixture was stirred at 50 C for 16 h, poured into water. Precipitate was collected by filtration and further purified by HPLC to give 3-(5-Amino-1-pyridin-2-yl-1H-[1,2,4]triazol-3-ylamino)-4-methoxy-benzamide (112 mg). FIA-MS: m/e=326.1 (M+1). R$^t$=2.65 min (Method A). $^1$H-NMR(500 MHz, DMSO(d6)): 8.65 (d, 1H), 8.43 (dd, 1H), 8.02 (td, 1H), 7.98 (m, 1H), 7.83 (m, 1H), 7.73 (d, 1H), 7.70 (m, 1H), 7.47 (dd, 1H), 7.27 (ff, 1H), 7.14 (m, 1H), 7.04 (d, 1H), 3.90 (s, 1H).

The following compounds were similarly prepared

| Name | MS (M + H) | Retention time (min) | NMR |
|---|---|---|---|
| [3-(5-Amino-1-pyridin-2-yl-1H-[1,2,4]triazol-3-ylamino)-4-methoxy-phenyl]-morpholin-4-yl-methanone | 396.1 | 3.06 (method A) | DMSO-d6: 8.44(d, 1H), 8.26(d, 1H), 8.06(m, 2H), 8.02(t, 1H), 7.88(s, 1H), 7.67(d, 1H), 7.30(td, 1H), 7.08(d, 1H), 7.02(d, 1H), 3.90(s, 1H), 3.60(m, 4H), 3.55(m, 4H). |
| 3-(5-Amino-1-pyridin-2-yl-1H-[1,2,4]triazol-3-ylamino)-N-(2-dimethylamino-ethyl)-4-methoxy-benzamide | 397.2 | 2.79 min Method A | DMSO-d6: 9.52(d, 1H), 8.73(d, 1H), 8.54(t, 1H), 8.45(d, 1H), 8.02(td, 1H), 7.86(m, 1H), 7.72(d, 1H), 7.62(s, 1H), 7.45(dd, 1H), 7.25(dd, 1H), 7.08(d, 1H), 3.93(s, 1H), 3.60(q, 2H), 3.29(q, 2H), 2.88(s, 3H), 2.86(s, 3H). |

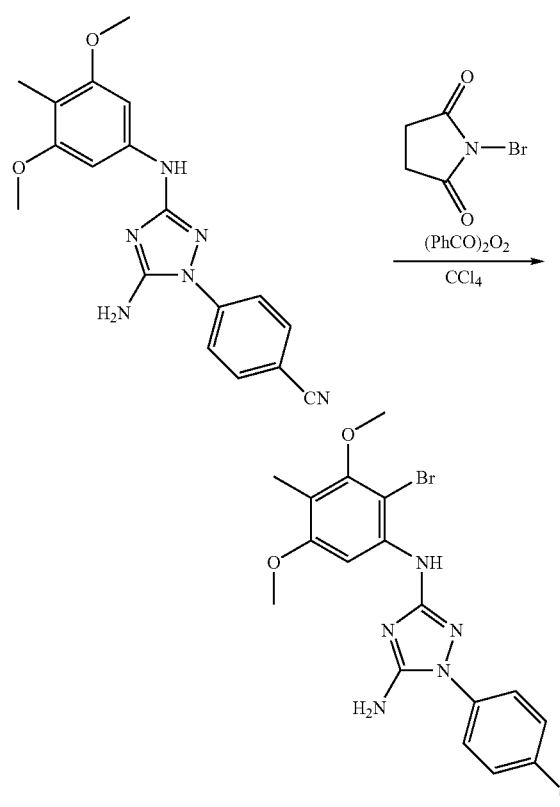

Scheme 24

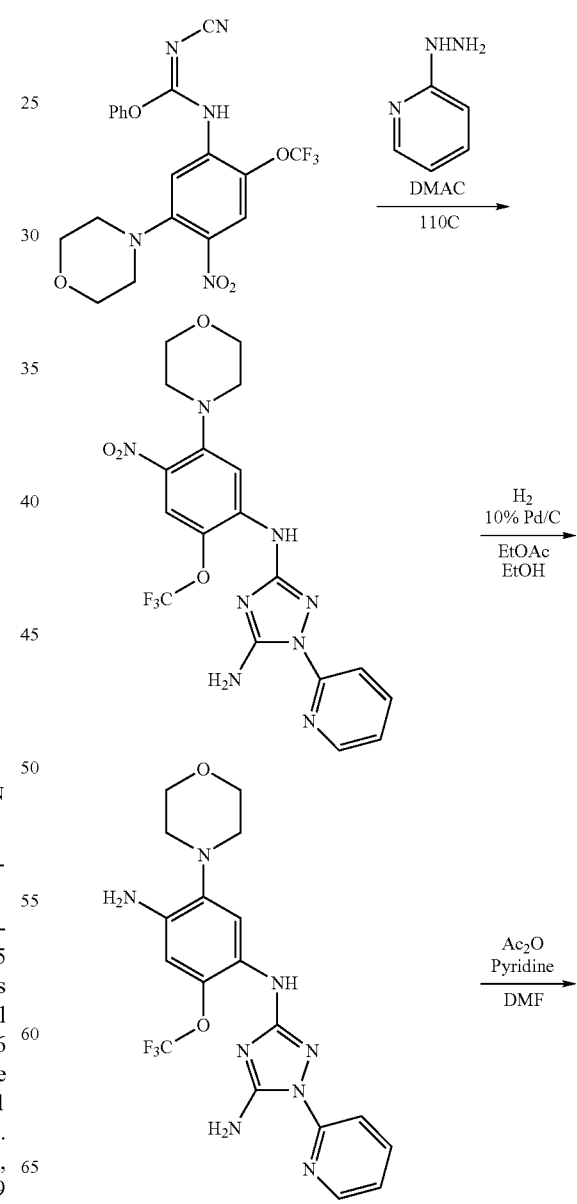

Scheme 25

4-[5-Amino-3-(2-bromo-3,5-dimethoxy-4-methyl-phenylamino)-[1,2,4]triazol-1-yl]-benzonitrile.

To a suspension of 4-[5-Amino-3-(3,5-dimethoxy-4-methyl-phenylamino)-[1,2,4]triazol-1-yl]-benzonitrile (155 mg, 0.44 mmol) in CCl₄ (10 mL) and benzene (10 mL) was added N-bromosuccimide (100 mg, 0.56 mmol) and benzoyl peroxide (10 mg). The reaction mixture was refluxed for 16 h. Concentration. The residue was purified by HPLC to give the title compound (80 mg). FIA-MS: m/e=429.1 and 431.1 (M+H), 427.1 and 429.1 (M−H). $R_f$=3.89 min (Method A). ¹H-NMR (500 MHz, DMSO(d6)): 7.95 (d, 2H), 7.82 (s, 1H), 7.80 (d, 2H), 7.37 (s, 1H), 6.88 (br. s, 2H), 3.80 (s, 3H), 3.69 (s, 3H), 2.08 (s, 3H).

-continued

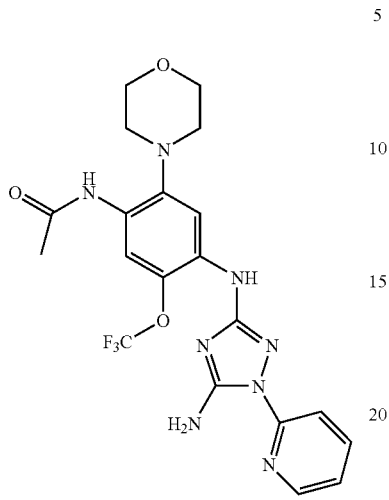

[1,2,4]triazole-3,5-Diamine and N-[4-(5-Amino-1-pyridin-2-yl-1H-[1,2,4]triazol-3-ylamino)-2-morpholin-4-yl-5-trifluoromethoxy-phenyl]-acetamide.

A solution of 1-cyano-3-(5-morpholin-4-yl-4-nitro-2-trifluoromethoxy-phenyl)-2-phenyl-isourea (3.60 g, 8 mmol), 2-hydrazinopyridine (2.0 g, 18.3 mmol) in DMA (50 mL) was stirred at 110° C. for 18 h. Evaporation under high vacuum and the residue was suspended in water (200 mL) and filtered. The solid was suspended in a mixture of EtOH (50 mL) and EtOAc (30 mL), shacked with 10% Pd/C (835 mg) and 6N HCl (2 mL) under $H_2$ (50 psi) for 18 h. The reaction mixture was filtered through Celite and the Celite was washed with DMF. The filtrate and the washings were combined and distilled under high vacuum then lyophilized to give the title compound (2.35 g). A small amount was further purified by HPLC for the biological assay. FIA-MS: m/e=437.2 (M+H). $R^t$=3.14 (Method A). $^1$H-NMR (500 MHz, DMSO(d6)): 8.41 (d, 1H), 8.31 (m, 1H), 8.0 (t, 1H), 7.96 (m, 1H), 7.75 (br.s, 2H), 7.61 (d, 1H), 7.22 (dd, 1H), 6.93 (m, 1H), 5.0 (br.s, 2H), 3.79 (m, 4H), 2.86 (m, 4H).

A solution of N3-(4-Amino-5-morpholin-4-yl-2-trifluoromethoxy-phenyl)-1-pyridin-2-yl-1H-[1,2,4]triazole-3,5-Diamine (150 mg, 0.34 mmol) in DMF (6 mL) was treated with pyridine (0.1 mL) and acetic anhydride (0.040 mL) at 23° C. for 4 h. Concentration and the residue was purified by HPLC to give the title compound (43 mg). FIA-MS: m/e=479.2 (M+H). $R^t$=3.30 min (Method A). $^1$H-NMR (500 MHz, DMSO(d6)): DMSO(d6): 8.89 (s, 1H), 8.56 (s, 1H), 8.43 (dd, 1H), 8.19 (s, 1H), 8.02 (td, 1H), 7.88 (s, 1H), 7.75 (m, 2H), 7.65 (d, 1H), 7.23 (dd, 1H), 3.82 (m, 4H), 2.88 (m, 4H), 2.11 (s, 3H).

Example 54

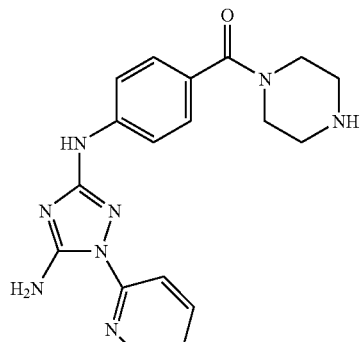

[4-(5-Amino-1-pyridin-2-yl-1H-[1,2,4]triazol-3-ylamino)-phenyl]-piperazin-1-yl-methanone: A mixture of 4-[4-(5-amino-1-pyridin-2-yl-1H-[1,2,4]triazol-3-ylamino)-benzoyl]-piperazine-1-carboxylic acid tert-butyl ester (22.1 mg) and trifluoroacetic acid (0.50 mL) was stirred at room temperature for 1 h. The reaction mixture was concentrated to give the title compound (13.6 mg) as a white solid. MS (ES+): m/z=365.1; $^1$H NMR (CD$_3$SOCD$_3$, 500 MHz): δ 3.09-3.23 (m, 4H), 3.63-3.76 (m, 4H), 7.20-7.25 (m, 1H), 7.41 (d, 2H), 7.64-7.74 (m, 4H), 7.95-8.02 (m, 1H), 8.39-8.44 (m, 1H), 8.66-8.95 (m, 2H), 9.44-9.48 (m, 1H).

Example 55

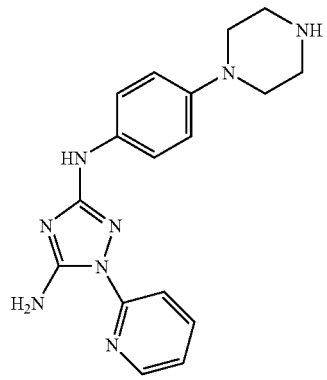

N$^3$-(4-piperazin-1-yl-phenyl)-1-pyridin-2-yl-1H-[1,2,4]triazole-3,5-diamine: The title compound was prepared from 4-[4-(5-amino-1-pyridin-2-yl-1H-[1,2,4]triazol-3-ylamino)-phenyl]-piperazine-1-carboxylic acid tert-butyl ester following the procedures described above. MS (ES+): m/z=337.20; $^1$H NMR (CD$_3$OD, 500 MHz): δ 3.34-3.41 (m, 8H), 7.06 (d, 2H), 7.30 (dd, 1H), 7.53 (d, 2H), 7.82 (d, 1H), 7.97-8.02 (m, 1H), 8.45-8.48 (m, 1H).

Example 56

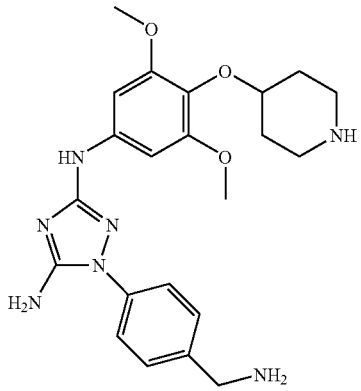

1-(4-Aminomethyl-phenyl)-N³-[3,5-dimethoxy-4-(piperidin-4-yloxy)-phenyl]-1H-[1,2,4]triazole-3,5-diamine: The title compound was prepared from 4-{4-[5-amino-1-(4-cyano-phenyl)-1H-[1,2,4]triazol-3-ylamino]-2,6-dimethoxy-phenoxy}-piperidine-1-carboxylic acid benzyl ester following the procedures described above. MS (ES+): m/z=440.20; ¹H NMR (CD₃OD, 500 MHz): δ 1.90-2.09 (m, 4H), 3.13-3.21 (m, 2H), 3.50-3.59 (m, 2H), 3.82 (s, 6H), 4.19 (s, 2H), 4.29-4.35 (m, 1H), 6.93 (s, 2H), 7.61 (d, 2H), 7.70 (d, 2H).

Scheme 26

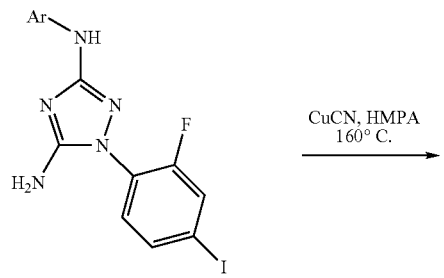

Example 57

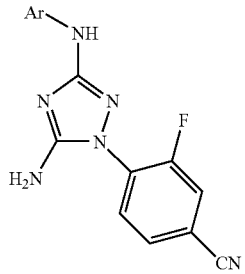

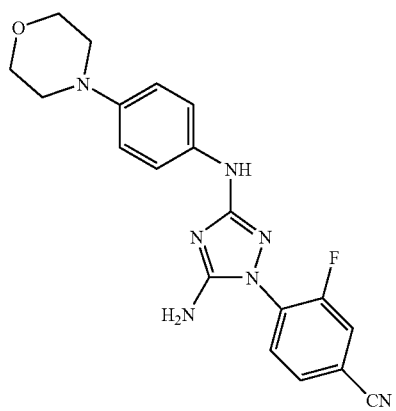

4-[5-Amino-3-(4-morpholin-4-yl-phenylamino)-[1,2,4]triazol-1-yl]-3-fluoro-benzonitrile: A mixture of 1-(2-fluoro-4-iodo-phenyl)-N-3-(4-morpholino-phenyl)-1H-[1,2,4]triazole-3,5-diamine (0.48 g, 0.99 mmol) and copper (I) cyanide (0.09 g, 0.99 mmol) in HMPA (3 mL) was heated at 55° C. for 2 h, then poured into water (75 mL) and filtered, washing with water. The filter cake was suspended in chloroform (100 mL) and methanol (5 mL), was refluxed for 2 h, cooled, filtered and evaporated. Purification by semi-preparative HPLC provided the title compound (0.04 g, 9% yield) as a pale tan lyophilate.

The following compounds were prepared using a similar method:

| Name | MS (M + H) | Retention time (min) | NMR |
|---|---|---|---|
| 4-[5-Amino-3-(3,4,5-trimethoxy-phenylamino)-[1,2,4]triazol-1-yl]-3-fluoro-benzonitrile | 385.20 | 2.80 | (500MHz, DMSO-d6)8.88(s, 1H), 8.11 (dd, 1H), , 7.82(m, 2H), 6.93(s, 2H), 6.70 (br s, 2H), , 3.70(s, 6H), 3.57(s, 3H)ppm. |
| 4-[5-Amino-3-(4-morpholin-4-yl-phenylamino)-[1,2,4]triazol-1-yl]-3-fluoro-benzonitrile | 380.10 | 1.80 | (500MHz, DMSO-d6)8.85(br s, 1H), 8.12 (dd, 1H), , 7.84(dd, 1H), 7.77(t, 1H), 7.44 (d, 2H), 6.96(m, 2H), , 6.66(br s 2H), 3.73 (m, 4H), 3.09(m, 4H)ppm |

Example 58

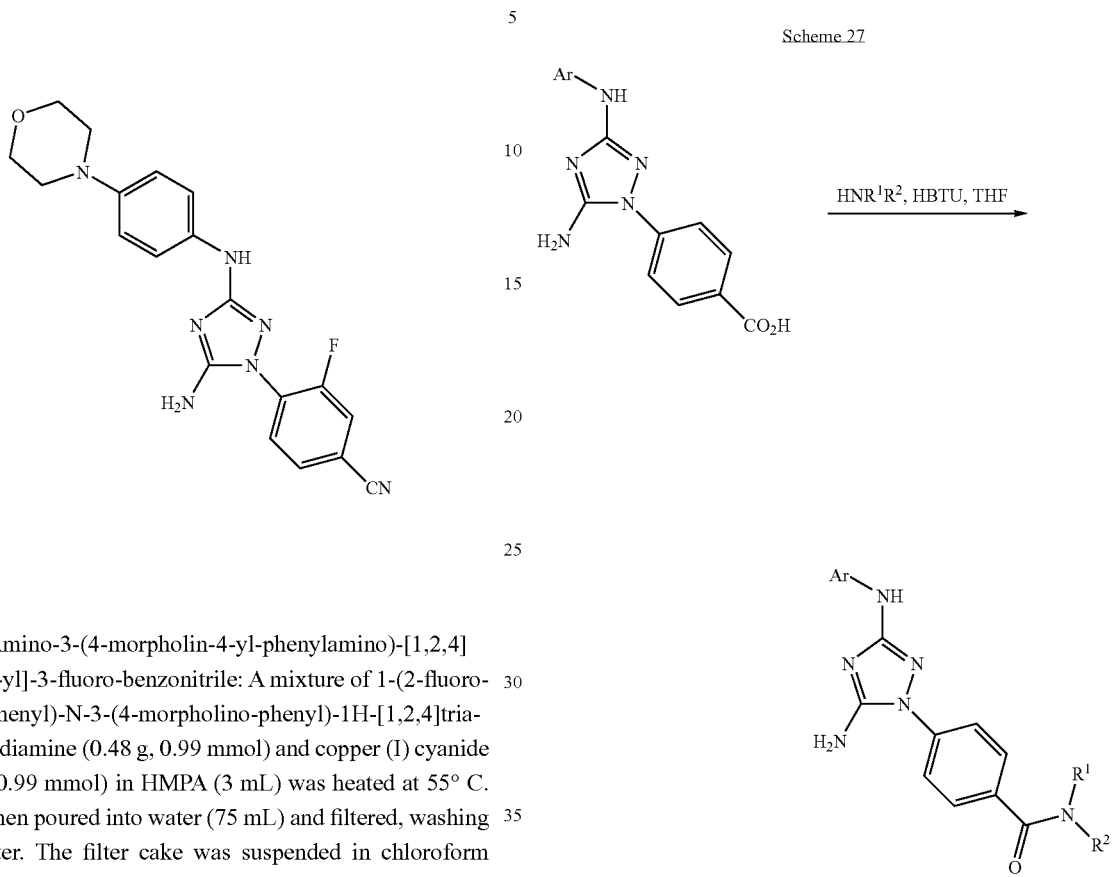

4-[5-Amino-3-(4-morpholin-4-yl-phenylamino)-[1,2,4]triazol-1-yl]-3-fluoro-benzonitrile: A mixture of 1-(2-fluoro-4-iodo-phenyl)-N-3-(4-morpholino-phenyl)-1H-[1,2,4]triazole-3,5-diamine (0.48 g, 0.99 mmol) and copper (I) cyanide (0.09 g, 0.99 mmol) in HMPA (3 mL) was heated at 55° C. for 2 h, then poured into water (75 mL) and filtered, washing with water. The filter cake was suspended in chloroform (100 mL) and methanol (5 mL), was refluxed for 2 h, cooled, filtered and evaporated. Purification by semi-preparative HPLC provided the title compound (0.04 g, 9% yield) as a pale tan lyophilate.

| Name | MS (M + H) | Retention time (min) | NMR |
|---|---|---|---|
| 4-[5-Amino-3-(3,4,5-trimethoxy-phenylamino)-[1,2,4]triazol-1-yl]-3-fluoro-benzonitrile | 385.20 | 2.80 | (500MHz, DMSO-d6)8.88(s, 1H), 8.11 (dd, 1H), , 7.82(m, 2H), 6.93(s, 2H), 6.70(br s, 2H), 3.70(s, 6H), 3.57(s, 3H)ppm. |
| 4-[5-Amino-3-(4-morpholin-4-yl-phenylamino)-[1,2,4]triazol-1-yl]-3-fluoro-benzonitrile | 380.10 | 1.80 | (500MHz, DMSO-d6)8.85(br s, 1H), 8.12 (dd, 1H), , 7.84(dd, 1H), 7.77(t, 1H), 7.44(d, 2H), 6.96(m, 2H), , 6.66(br s 2H), 3.73(m, 4H), 3.09 (m, 4H)ppm |

Example 59

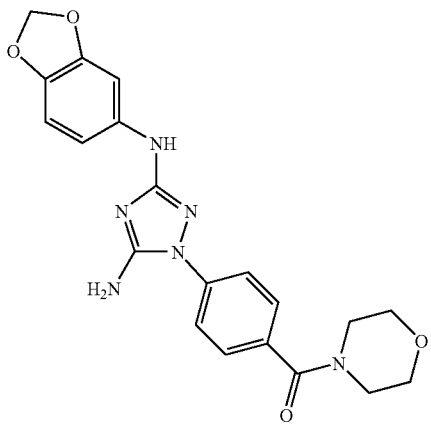

{4-[5-Amino-3-(benzo[1,3]dioxol-5-ylamino)-[1,2,4]triazol-1-yl]-phenyl}-morpholin-4-yl-methanone: A mixture of 4-[5-amino-3-(benzo[1,3]dioxol-5-ylamino)-[1,2,4]triazol-1-yl]-benzoic acid (0.15 g, 0.44 mmol), morpholine (0.05 mL, 0.55 mmol) and HBTU (0.21 g, 0.55 mmol) in THF (5 mL) was stirred at room temperature for 4 h. The reaction was diluted with water, extracted with methanol/dichloromethane, dried (sodium sulfate) and evaporated. Purification by 2 successive semi-preparative HPLC's provided the title compound (0.008 g, 5% yield) as a pale pink lyophilate.

The following compounds were prepared using a similar method:

Example 60

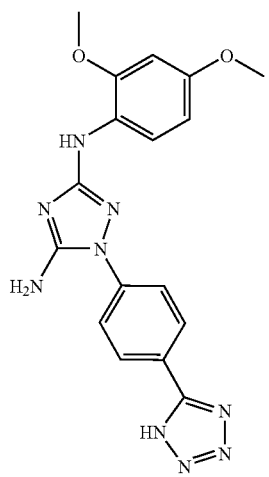

N3-(2,4-Dimethoxy-phenyl)-1-[4-(1H-tetrazol-5-yl)-phenyl]-1H-[1,2,4]triazole-3,5-diamine 4-[5-Amino-3-(2,4-dimethoxy-phenylamino)-[1,2,4]triazol-1-yl]-benzonitrile (52 mg, 0.15 mmol) and trimethylsilyl azide (20 mg, 0.165 mol) were suspended in 1 mL toluene with a catalytic amount of di-butyltin oxide and heated to 110° C. for 18 hours. The toluene was evaporated and the residue purified by preparative HPLC affording 13 mg product as the TFA salt.

| Name | MS (M + H) | Retention time(min) | NMR |
|---|---|---|---|
| {4-[5-Amino-3-(benzo[1,3]dioxol-5-ylamino)-[1,2,4]triazol-1-yl]-phenyl}-morpholin-4-yl-methanone | 409.20 | 2.38 | (500MHz, DMSO-d6)8.79(s, 1H), 7.63 (d, 2H), , 7.53(d, 2H), 7.29(d, 1H), 6.97(dd, 1H), 6.77(d, 1H), , 6.50(s, 2H), 5.90(s, 2H), 3.4–3.6(br m, 8H)ppm |
| {4-[5-Amino-3-(benzo[1,3]dioxol-5-ylamino)-[1,2,4]triazol-1-yl]-phenyl}-(4-methyl-piperazin-1-yl)methanone | 422.20 | 1.27 | (500MHz, DMSO-d6)8.79(s, 1H), 7.62 (d, 2H), , 7.49(d, 2H), 7.29(d, 1H), 6.97 (dd, 1H), 6.77(d, 1H), , 6.50(s, 2H), 5.90(s, 2H), 3.5(br m, 4H), 2.3(br m, 4H), , 2.21(s, 3H) ppm |
| 4-[5-Amino-3-(benzo[1,3]dioxol-5-ylamino)-[1,2,4]triazol-1-yl]-N-methyl-benzamide | 353.20 | 2.22 | (500MHz, DMSO-d6)8.80(s, 1H), 8.44 (q, 1H), , 7.94(d, 2H), 7.65(d, 2H), 7.28(d, 1H), 6.98(dd, 1H), , 6.78(d, 1H), 6.54(s, 2H), 5.91 (s, 2H), 2.80(d, 3H)ppm |
| 4-[5-Amino-3-(benzo[1,3]dioxol-5-ylamino)-[1,2,4]triazol-1-yl]-benzamide | 339.10 | 2.09 | (500MHz, DMSO-d6)8.80(s, 1H), , 7.98 (m, 3H), 7.64(d, 2H), 7.35(s, 1H), 7.28(d, 1H), 6.98(dd, 1H), , 6.78(d, 1H), 6.54(s, 2H), 5.91 (s, 2H), ppm |
| 4-[5-Amino-3-(benzo[1,3]dioxol-5-ylamino)-[1,2,4]triazol-1-yl]-N,N-dimethyl-benzamide | 367.20 | 2.36 | (500MHz, DMSO-d6)8.79(s, 1H), 7.62 (d, 2H), , 7.51(d, 2H), 7.29(d, 1H), 6.98(dd, 1H), 6.77(d, 1H), , 6.49(s, 2H), 5.90(s, 2H), 2.98(s, 6H)ppm |

| Name | Purification procedure | MS (M + H) | Retention time(min) | NMR |
|---|---|---|---|---|
| N3-(2,4-Dimethoxy-phenyl)-1-[4-(1H-tetrazol-5-yl)-phenyl]-1H-[1,2,4]triazole-3,5-diamine | 3 | 380.20 | 2.61 | acetone-d6: 8.3(d, 2H), 8.1(d, 1H), 7.9(d, 2H), 7.3(bs, 1H), 6.7(bs, 2H), 6.6(m, 1H), 6.5(dd, 1H), 3.9(s, 3H), 3.8(s, 3H). |

Scheme 28:

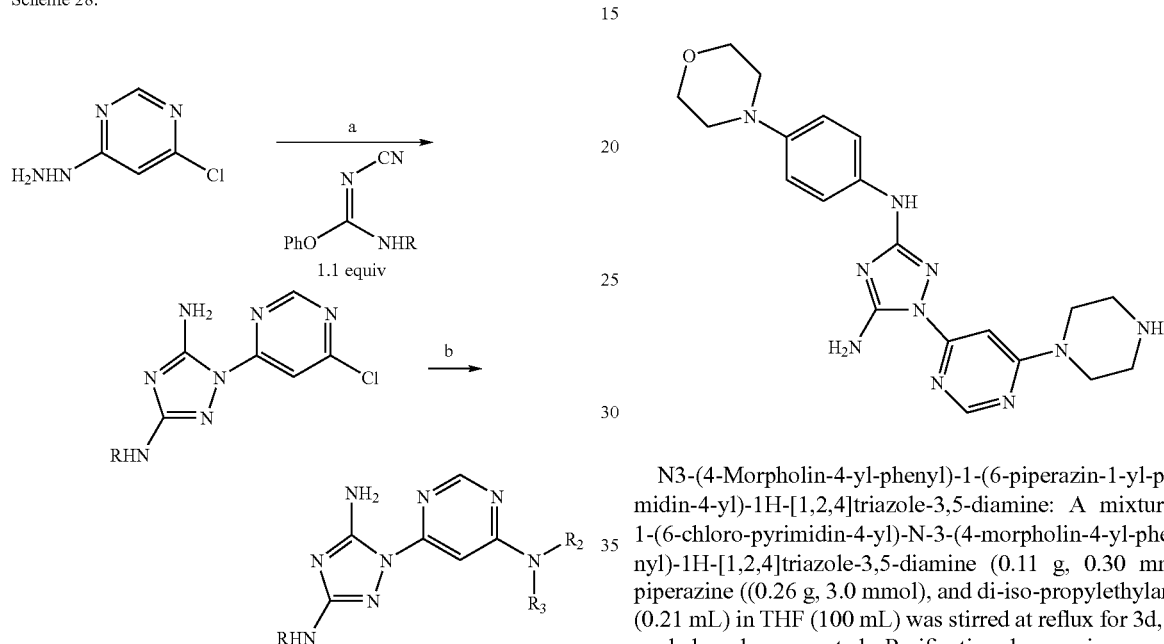

(a) NMP, 220 C, microwave (b) Substitution Method A: amine, THF, DIEA, reflux; Substitution Method B: amine, NMP, 220 C, microwave Example 61

N3-(4-Morpholin-4-yl-phenyl)-1-(6-piperazin-1-yl-pyrimidin-4-yl)-1H-[1,2,4]triazole-3,5-diamine: A mixture of 1-(6-chloro-pyrimidin-4-yl)-N-3-(4-morpholin-4-yl-phenyl)-1H-[1,2,4]triazole-3,5-diamine (0.11 g, 0.30 mmol), piperazine ((0.26 g, 3.0 mmol), and di-iso-propylethylamine (0.21 mL) in THF (100 mL) was stirred at reflux for 3d, then cooled and evaporated. Purification by semi-preparative HPLC provided the title compound (0.13 g, 64% yield) as a pale yellow solid.

The following compounds were prepared using similar methods as indicated (scheme 28)

| Name | Substitution Method | MS (M + H) | Retention time(min) | 1H NMR |
|---|---|---|---|---|
| N3-(2,4-Difluoro-phenyl)-1-[6-(4-methyl-piperazin-1-yl)-pyrimidin-4-yl]-1H-[1,2,4]triazole-3,5-diamine | A | 388.30 | 1.63 | (500MHz, DMSO-d6)8.62(s, 1H), 8.47 (d, 1H), 8.13(m, 1H), 7.82(s, 2H), 7.23 (m, 1H), 7.02(m, 1H), 6.86(s, 1H), 4.55 (d, 2H), 3.54(d, 2H), 3.29(t, 2H), 3.11(m, 2H), 2.86(s, 3H)ppm |
| 1-(6-Diethylamino-pyrimidin-4-yl)-N3-(2,4-difluoro-phenyl)-1H-[1,2,4]triazole-3,5-diamine | A | 361.20 | 3.91 | (500MHz, DMSO-d6)8.66 9s, 1H), 8.36 (s, 1H), 8.04(m, 1H), 7.77(s, 2H), 7.21 (m, 1H), 7.01(m, 1H), 6.56(s, 1H), 3.54 (m, 4H), 1.15(t, 6H)ppm |
| N3-(2-Methoxy-phenyl)-1-[6-(2-pyrrolidin-1-yl-ethylamino)-pyrimidin-4-yl]-1H-[1,2,4]triazole-3,5-diamine | A | 396.30 | 1.81 | (500MHz, DMSO-d6)9.48(s, 1H), 8.39(s, 1H), 8.12(dd, 1H), 7.87(sd, 1H), 7.77(s, 2H), &.38(s, 1H), 7.01(dd, 1H), 6.91(m, 2H), 6.70(s, 1H), 3.87(s, 3H), 3.70(m, 2H), 3.62(m, 2H), 3.34(m, 2H), 3.08(m, 2H), 2.02(m, 2H), 1.87(m, 2H)ppm |
| N3-(2,4-Difluoro-phenyl)-1-[6-(2- | A | 402.30 | 1.85 | (500MHz, DMSO-d6)8.62(s, 1H), 8.39(s, 3H), 8.06(m, 1H), 7.84(s, 1H), 7.75(s, |

-continued

| Name | Substitution Method | MS (M + H) | Retention time(min) | 1H NMR |
|---|---|---|---|---|
| pyrrolidin-1-yl-ethylamino)-pyrimidin-4-yl]-1H-[1,2,4]triazole-3,5-diamine | | | | 2H), 7.24(m, 1H), 6.99(m, 1H), 6.62(s, 1H), 3.68(m, 2H), 3.61(m, 2H), 3.34(m, 2H), 3.07(m, 2H), 2.02(m, 2H), 1.86(m, 2H)ppm |
| N3-Indan-4-yl-1-[6-(2-pyrrolidin-1-yl-ethylamino)-pyrimidin-4-yl]-1H[1,2,4]triazole-3,5-diamine | A | 406.30 | 2.70 | (500MHz, DMSO-d6)8.39(s, 1H), 8.08(s, 3H), 7.85(s, 1H), 7.80(d, 1H), 7.71(s, 2H), 7.05(t, 1H), 6.81(d, 1H), 6.65(s, 1H), 3.69(m, 2H), 3.61(m, 2H), 3.35(m, 2H), 3.07(m, 2H), 2.86(, m, 4H), 2.01(m, 4H), 1.86(m, 2H)ppm |
| N3-Indan-4-yl-1-[6-(4-methyl-piperazin-1-yl)-pyrimidin-4-yl]-1H-[1,2,4]triazole-3,5-diamine | A | 392.30 | 2.61 | (500MHz, DMSO-d6)8.48(s, 1H), 8.08(s, 1H), 7.80(d, 1H), 7.77(s, 2H), 7.08(t, 1H), 6.84(s, 1H), 6.80(d, 1H), 4.52(m, 2H), 3.54(m, 2H), 3.30(m, 2H), 3.11(m, 2H), 2.85(m, 7H), 1.99(m, 4H), ppm |
| 1-[6-(4-Cyclopropyl-piperazin-1-yl)-pyrimidin-4-yl]-N3-indan-4-yl-1H-[1,2,4]triazole-3,5diamine | A | 418.30 | 2.15 | (500MHz, DMSO-d6)8.48(s, 1H), 8.10(s, 1H), 7.80(d, 1H), 7.77(s, 2H), 7.07(t, 1H), 6.84(s, 1H), 6.81(d, 1H), 4.53(br m, 2H), 3.59(br m, 2H), 3.30(br m, 4H), 2.86 (m, 5H), 1.99(m, 2H), 0.97(br m, 2H), 0.84(br m, 2H)ppm |
| 1-[6-(4-Cyclopropyl-piperazin-1-yl)-pyrimidin-4-yl]-N3-(2-methoxy-phenyl)-1H-[1,2,4]triazole-3,5-diamine | A | 408.30 | 1.88 | (500MHz, DMSO-d6)8.48(s, 1H), 8.16 (dd, 1H), 7.84(s, 2H), 7.38(s, 1H), 7.00 (dd, 1H), 6.99(m, 3H), 4.6(br m, 2H), 3.87(s, 3H), 3.6(br m, 2H), 3.30(br m, 4H), 2.9(br m, 1H), 0.98(br m, 2H), 0.85 (br m, 2H)ppm |
| 1-[6-(4-Cyclopropyl-piperazin-1-yl)-pyrimidin-4-yl]-N3-(2,4-difluoro-phenyl)-1H-[1,2,4]triazole-3,5-diamine | A | 414.30 | 2.45 | (500MHz, DMSO-d6)8.64(s, 1H), 8.47(s, 1H), 8.12(m, 1H), 7.82(s, 2H), 7.23(m, 1H), 7.01(m, 1H), 6.83(s, 1H), 4.5(br m, 2H), 3.6(br m, 2H), 3.30(br m, 4H), 2.85 (br m, 1H), 0.95(br m, 2H), 0.83(br m, 2H)ppm |
| N3-(4-Morpholin-4-yl-phenyl)-1-[6-(2-pyrrolidin-1-yl-ethylamino)-pyrimidin-4-yl]-1H-[1,2,4]triazole-3,5-diamine | A | 451.30 | 0.24 | (500MHz, DMSO-d6)8.91(s, 1H), 8.38(s, 1H), 7.84(s, 1H), 7.70(s, 2H), 7.50(d, 2H), 6.90(d, 2H), 6.66(s, 1H), 3.76(m, 4H), 3.69(m, 2H), 3.62(br m, 2H), 3.35 (m, 2H), 3.04(m, 6H), 2.02(m, 2H), 1.86 (m, 2H)ppm |
| N3-(4-Morpholin-4-yl-phenyl)-1-(6-piperazin-1-yl-pyrimidin-4-yl)-1H-[1,2,4]triazole-3,5diamine | A | 423.30 | 1.98 | (500MHz, DMSO-d6)8.93(s, 1H), 8.88(s, 1H), 8.45(s, 1H), 7.76(s, 2H), 7.53(d, 2H), 6.94(d, 2H), 6.82,(s, 1H), 3.89(m, 4H), 3.76(m, 4H), 3.24(m, 4H), 3.05(m, 4H)ppm |
| 1-[6-(4-Methyl-piperazin-1-yl)-pyrimidin-4-yl]-N5-(4-morpholin-4-yl-phenyl)-1H-[1,2,4]triazole-3,5-diamine | A | 437.30 | 2.30 | (DMSO-d6, 500MHz)10.85(s, 1H), 8.54 (d, 1H), 7.58(dd, 2H), 6.96(d, 2H), 6.76 (s, 1H), 5.80(br, 2H), 4.5(br m, 2H), 3.75 (m, 4H), 3.53(m, 2H), 3.29(m, 2H), 3.10 (m, 2H), 3.07(m, 4H), 2.85(s, 3H)ppm |
| 1-[6-(4-Cyclopropyl-piperazin-1-yl)-pyrimidin-4-yl]-N3-(4-morpholin-4-yl-phenyl)-1H-[1,2,4]triazole-3,5-diamine | A | 463.40 | 2.07 | (500MHz, DMSO-d6)8.92(s, 1H), 8.47(s, 1H), 7.76(s, 2H), 7.53(d, 2H), 6.92(d, 2H), 6.86(s, 1H), 4.5(br m, 2H), 3.75(m, 4H), 3.6(br m, 2H), 3.3(br m, 4H), 3.04 (m, 4H), 2.9(br m, 1H), 0.98(m, 2H), 0.86(m, 2H)ppm |
| 1-[6-(1-Benzyl-pyrrolidin-3-ylamino)-pyrimidin-4-yl]-N3-phenyl-1H-[1,2,4]triazole-3,5-diamine | B | 428 | | 1H NMR(500MHz, CDCl3)d 8.32(1H, s), 7.50(2H, d), 7.31(7H, m), 6.95(1H, t), 6.65(1H, s), 6.63(1H, s), 3.75(2H, dd), 2.90(1H, m), 2.75(1H, m), 2.70(1H, m), 2.40(2H, m)ppm. |
| 2-[6-(5-Amino-3-phenylamino-[1,2,4]triazol-1-yl)-pyrimidin-4-ylamino]-2-phenyl-ethanol | B | 389 | | 1H NMR(500MHz, DMSO-d6)d 9.10(1H, s), 8.28(1H, s), 8.10(1H, br s), 7.65(5H, m), 7.43–7.20(7H, m), 6.85(1H, t), 5.21(1H, br s), 4.95(1H, br s), 3.65(2H, br s)ppm |
| 2-[6-(5-Amino-3-phenylamino-[1,2,4]triazol-1-yl)-pyrimidin-4-ylamino]-2-phenyl-ethanol | B | 389 | | 1H NMR(500MHz, DMSO-d6)d 9.10(1H, s), 8.28(1H, s), 8.10(1H, br s), 7.65(5H, m), 7.43–7.20(7H, m), 6.85(1H, t), 5.21(1H, br s), 4.95(1H, br s), 3.65(2H, br s)ppm |
| 1-{6-[1-(4-Methoxy- | B | 403.3 | 3.5 | 1H NMR(500MHz, DMSO-d6)d 9.08(1H, |

| Name | Substitution Method | MS (M + H) | Retention time(min) | 1H NMR |
|---|---|---|---|---|
| phenyl)-ethylamino]-pyrimidin-4-yl}-N3-phenyl-1H-[1,2,4]triazole-3,5-diamine | | | | s), 8.26(1H, s), 8.04(1H, d), 7.66(2H, s), 7.59(2H, m), 7.34–7.20(4H, m), 6.89 (3H, m), 3.70(3H, s), 1.44(3H, d)ppm. |
| 1-[6-(Indan-1-ylamino)-pyrimidin-4-yl]-N3-phenyl-1H-[1,2,4]triazole-3,5-diamine | B | 385.2 | 3.83 | 1H NMR(500MHz, DMSO-d6)d 9.10(1H, s), 8.39(1H, s), 8.01(1H, d), 7.70(2H, s), 7.61(2H, d), 7.30–7.10(8H, m), 6.80(1H, m), 6.70(1H, s), 3.30(2H, m), 3.10–2.80 (3H, m)ppm |
| 1-{6-[1-(4-Fluoro-phenyl)-ethylamino]-pyrimidin-4-yl}-N3-phenyl-1H-[1,2,4]triazole-3,5-diamine | B | 391.3 | 3.61 | 1H NMR(500MHz, DMSO-d6)d 9.09(1H, s), 8.26(1H, s), 8.11(1H, d), 7.66(2H, s), 7.59(2H, m), 7.42(2H, m), 7.25(2H, m), 7.15(2H, t), 6.89(1H, m), 5.30(1H, br s), 1.45(3H, d)ppm. |
| N3-Phenyl-1-[6-(1-phenyl-propylamino)-pyrimidin-4-yl]-1H-[1,2,4]triazole-3,5-diamine | B | 387.3 | 3.76 | 1H NMR(500MHz, DMSO-d6)d 9.09(1H, s), 8.26(1H, s), 8.05(1H, d), 7.62(2H, s), 7.59(2H, m), 7.45–7.18(8H, m), 6.89 (1H, m), 5.30(1H, br s), 1.80(2H, m), 0.9 (3H, m)ppm. |
| N3-Phenyl-1-[6-(1-phenyl-propylamino)-pyrimidin-4-yl]-1H-[1,2,4]triazole-3,5-diamine | B | 387.3 | 3.76 | 1H NMR(500MHz, DMSO-d6)d 9.09(1H, s), 8.26(1H, s), 8.05(1H, d), 7.62(2H, s), 7.59(2H, m), 7.45–7.18(8H, m), 6.89 (1H, m), 5.30(1H, br s), 1.80(2H, m), 0.9 (3H, m)ppm. |
| 3-[6-(5-Amino-3-phenylamino-[1 2,4]triazol-1-yl)-pyrimidin-4-ylamino]-3-phenyl-propan-1-ol | B | 403.2 | 2.87 | 1H NMR(500MHz, DMSO-d6)d 9.09(1H, s), 8.26(1H, s), 8.12(1H, d), 7.62(2H, s), 7.59(2H, m), 7.45–7.18(8H, m), 6.89 (1H, m), 5.30(1H, br s), 4.55(1H, m), 3.50(2H, m), 1.90(2H, m)ppm. |
| 1-[6-(5-Amino-3-phenylamino-[1,2,4]triazol-1-yl)-pyrimidin-4-ylamino]-indan-2-ol | B | 401.3 | 3.27 | 1H NMR(500MHz, DMSO-d6)d 9.09(1H, s), 8.32(1H, s), 7.70(3H, s), 7.60(3H, m), 7.32–7.10(6H, m), 6.89(1H, m), 5.60 (1H, br s), 5.08(1H, br s), 4.50(1H, br s), 3.05(1H, dd), 2.85(1H, dd)ppm. |
| 1-{6-[1-(4-Fluoro-phenyl)-ethylamino]-pyrimidin-4-yl}-N3-phenyl-1H-[1,2,4]triazole-3,5-diamine | B | 391.3 | 3.61 | 1H NMR(500MHz, DMSO-d6)d 9.09(1H, s), 8.26(1H, s), 8.11(1H, d), 7.66(2H, s), 7.59(2H, m), 7.42(2H, m), 7.25(2H, m), 7.15(2H, t), 6.89(1H, m), 5.30(1H, br s), 1.45(3H, d)ppm. |
| 1-[6-(5-Amino-3-phenylamino-[1,2,4]triazol-1-yl)-pyrimidin-4-ylamino]-indan-2-ol | B | 401.3 | 3.27 | 1H NMR(500MHz, DMSO-d6)d 9.09(1H, s), 8.32(1H, s), 7.70(3H, s), 7.60(3H, m), 7.32–7.10(6H, m), 6.89(1H, m), 5.60 (1H, br s), 5.08(1H, br s), 4.50(1H, br s), 3.05(1H, dd), 2.85(1H, dd)ppm. |
| 2-[6-(5-Amino-3-phenylamino-[1,2,4]triazol-1-yl)-pyrimidin-4-ylamino]-propane-1,3-diol | B | 343.2 | 1.9 | 1H NMR(500MHz, MeOD-d4)d 8.30(1H, s), 7.56(2H, d), 7.23(2H, t), 6.89(1H, t), 6.81(1H, s), 3.71(5H, m)ppm. |
| 2-[6-(5-Amino-3-phenylamino-[1,2,4]triazol-1-yl)-pyrimidin-4-ylamino]-propan-1-ol | B | 327.2 | 2.39 | 1H NMR(500MHz, MeOD-d4)d 8.30(1H, s), 7.56(2H, d), 7.23(2H, t), 6.89(1H, t), 6.77(1H, s), 4.10(1H, m), 3.55(2H, m), 1.23(3H, d)ppm. |
| 2-[6-(5-Amino-3-phenylamino-[1,2,4]triazol-1-yl)-pyrimidin-4-ylamino]-4-methyl-pentan-1-ol | B | 369.3 | 3.26 | 1H NMR(500MHz, MeOD-d4)d 8.29(1H, s), 7.53(2H, d), 7.23(2H, t), 6.89(1H, t), 6.74(1H, s), 3.55(2H, m), 1.71(1H, m), 1.50(2H, t), 0.95(7H, m)ppm. |
| 2-[6-(5-Amino-3-phenylamino-[1,2,4]triazol-1-yl)-pyrimidin-4-ylamino]-4-methyl-pentan-1-ol | B | 369.3 | 3.26 | 1H NMR(500MHz, MeOD-d4)d 8.29(1H, s), 7.53(2H, d), 7.23(2H, t), 6.89(1H, t), 6.74(1H, s), 3.55(2H, m), 1.71(1H, m), 1.50(2H, t), 0.95(7H, m)ppm. |
| {1-[6-(5-Amino-3-phenylamino-[1,2,4]triazol-1-yl)-pyrimidin-4-ylamino]-cyclopentyl}-methanol | B | 367.3 | 3.13 | 1H NMR(500MHz, MeOD-d4)d 8.70(1H, s), 7.57(2H, d), 7.34(2H, t), 7.30(1H, t), 7.05(1H, s), 3.81(2H, s), 2.03(4H, m), 1.85(4H, m)ppm. |
| 2-[6-(5-Amino-3-phenylamino-[1,2,4]triazol-1-yl)-pyrimidin-4-ylamino]- | B | 403.28 | 3.31 | 1H NMR(500MHz, MeOD-d4)d 8.20(1H, s), 7.57(2H, d), 7.30–7.20(6H, m), 7.15(1H, t), 6.89(1H, t), 6.69(1H, s), 3.61(2H, m), 3.40(1H, t), 3.00(1H, dd), |

-continued

| Name | Substitution Method | MS (M + H) | Retention time(min) | 1H NMR |
|---|---|---|---|---|
| 3-phenyl-propan-1-ol | | | | 2.85(1H, dd)2.31(1H, t), 2.0(1H, m) ppm. |
| 2-[6-(5-Amino-3-phenylamino-[1,2,4]triazol-1-yl)-pyrimidin-4-ylamino]-3-phenyl-propan-1-ol | B | 403.28 | 3.31 | 1H NMR(500MHz, MeOD-d4)d 8.20(1H, s), 7.57(2H, d), 7.30–7.20(6H, m), 7.15(1H, t), 6.89(1H, t), 6.69(1H, s), 3.61(2H, m), 3.40(1H, t), 3.00(1H, dd), 2.85(1H, dd), 2.31(1H, t), 2.0(1H, m) ppm. |
| 2-[6-(5-Amino-3-phenylamino-[1,2,4]triazol-1-yl)-pyrimidin-4-ylamino]-3-methyl-butan-1-ol | B | 355.3 | 2.87 | 1H NMR(500MHz, CDCl3)d 8.11(1H, s), 7.40(2H, d), 7.38(1H, m), 7.21(3H, m), 7.0(2H, br s), 6.81(1H, t), 6.55(1H, s), 3.76(1H, dd), 3.65(1H, dd), 0.90(7H, m)ppm. |
| 2-[6-(5-Amino-3-phenylamino-[1,2,4]triazol-1-yl)-pyrimidin-4-ylamino]-cyclohexanol | B | 367.3 | 3.22 | 1H NMR(500MHz, MeOD-d4)d 8.27(1H, s), 7.57(2H, d), 7.25(2H, t), 6.89(1H, t), 6.79(1H, br s), 4.01(1H, m), 1.90–1.40 (9H, m)ppm. |
| 2-[6-(5-Amino-3-phenylamino-[1,2,4]triazol-1-yl)-pyrimidin-4-ylamino]-3-phenyl-propionamide | B | 416.3 | 3.42 | 1H NMR(500MHz, MeOD-d4)d 8.24(1H, s), 7.31–7.20(6H, m), 7.17(1H, t), 6.89 (1H, t), 6.82(1H, br s), 3.30(1H, dd), 3.23(1H, dd), 2.99 ppm. |
| {1-[6-(5-Amino-3-phenylamino-[1,2,4]triazol-1-yl)-pyrimidin-4-yl]-piperidin-4-yl}-methanol | B | 367.3 | 2.79 | 1H NMR(500MHz, MeOD-d4)d 8.30(1H, s), 7.50(2H, d), 7.25(2H, t), 6.89(1H, t), 6.80(1H, br s), 3.40(2H, dd), 2.99(2H, t), 1.82(4H, m), 1.22(4H, m)ppm. |
| 1-[6-(5-Amino-3-phenylamino-[1,2,4]triazol-1-yl)-pyrimidin-4-yl]-piperidine-3-carboxylic acid amide | B | 380.3 | 2.87 | 1H NMR(500MHz, DMSO-d6)d 9.12(1H, s), 8.39(1H, s), 7.75(2H, s), 7.59(2H, d), 7.38(1H, br s), 7.20(2H, t), 6.90(1H, s), 6.80(1H, t), 6.75(1H, s), 3.05(2H, m), 2.31(1H, m), 1.95(1H, m), 1.78(1H, m), 1.67(1H, m), 1.41(1H, m)ppm. |
| 1-[6-(5-Amino-3-phenylamino-[1,2,4]triazol-1-yl)-pyrimidin-4-yl]-piperidine-4-carboxylic acid amide | B | 380.3 | 2.65 | 1H NMR(500MHz, DMSO-d6)d 9.10(1H, s), 8.37(1H, s), 7.75(2H, s), 7.58(2H, d), 7.30(1H, br s), 7.24(2H, t), 6.81(1H, s), 6.80(1H, t), 6.73(1H, s), 4.35(2H, m), 3.05(2H, m), 2.41(1H, m), 1.81(2H, m), 1.55(2H, m)ppm. |
| 3-{4-[6-(5-Amino-3-phenylamino-[1,2,4]triazol-1-yl)-pyrimidin-4-yl]-piperazin-1-yl}-3-oxo-propionitrile | B | 405.2 | 2.72 | 1H NMR(500MHz, CDCl3)d 8.31(1H, s), 7.40(2H, d), 7.25(2H, t), 6.89(1H, t), 6.77(1H, s), 6.65(2H, br s), 6.45(1H, s), 3.82(2H, m), 3.70(4H, m), 3.52(2H, m), 3.40(2H, s)ppm. |
| (1-{6-[5-Amino-3-(2-fluoro-4-morpholin-4-yl-phenylamino)-[1,2,4]triazol-1-yl]-pyrimidin-4-yl}-piperidin-4-yl)-methanol | B | 470.3 | 2.53 | 1H NMR(500MHz, CDCl3)d 8.28(1H, s), 8.00(1H, t), 6.80(2H, br s), 6.71(1H, s), 6.70–6.55(3H, m), 4.42(2H, m), 3.87 (4H, m), 3.50(2H, m), 3.40(3H, m), 3.00 (4H, m), 2.86(2H, m), 1.80(2H, m)ppm. |
| (1-{6-[5-Amino-3-(2-fluoro-4-morpholin-4-yl-phenylamino)-[1,2,4]triazol-1-yl]-pyrimidin-4-yl}-pyrrolidin-2-yl)-methanol | B | 456.3 | 2.42 | 1H NMR(500MHz, CDCl3)d 8.20(1H, s), 7.99(1H, t), 6.77(2H, br s), 6.62(2H, m), 6.53(2H, d), 3.77(4H, m), 3.69(1H, dd), 3.60(1H, t), 3.50(1H, m), 3.00(4H, m), 2.05(2H, m). 1.70(4H, m)ppm. |
| (1-{6-[5-Amino-3-(2-fluoro-4-morpholin-4-yl-phenylamino)-[1,2,4]triazol-1-yl]-pyrimidin-4-yl-1}-pyrrolidin-2-yl)-methanol | B | 456.3 | 2.42 | 1H NMR(500MHz, CDCl3)d 8.20(1H, s), 7.99(1H, t), 6.77(2H, br s), 6.62(2H, m), 6.53(2H, d), 3.77(4H, m), 3.69(1H, dd), 3.60(1H, t), 3.50(1H, m), 3.00(4H, m), 2.05(2H, m). 1.70(4H, m)ppm. |
| 1-{6-[5-Amino-3-(2-fluoro-4-morpholin-4-yl-phenylamino)-[1,2,4]triazol-1-yl]-pyrimidin-4-yl}-pyrrolidin-3-ol | B | 442.3 | 2.13 | 1H NMR(500MHz, CDCl3)d 8.40(1H, s), 7.93(1H, t), 6.90(2H, br s), 6.63(1H, s), 4.48(1H, s), 3.85(4H, m), 3.65(2H, br s), 3.42(4H, m), 3.20(1H, m), 2.40(2H, m), 2.15(2H, m), 2.0(2H, m)ppm. |
| 1-{6-[5-Amino-3-(2-fluoro-4-morpholin-4- | B | 442.3 | 2.13 | 1H NMR(500MHz, CDCl3)d 8.40(1H, s), 7.93(1H, t), 6.90(2H, br s), 6.63(1H, |

| Name | Substitution Method | MS (M + H) | Retention time(min) | 1H NMR |
|---|---|---|---|---|
| yl-phenylamino)-[1,2,4]triazol-1-yl]-pyrimidin-4-yl}-pyrrolidin-3-ol | | | | s), 4.48(1H, s), 3.85(4H, m), 3.65(2H, br s), 3.42(4H, m), 3.20(1H, m), 2.40(2H, m), 2.15(2H, m), 2.0(2H, m)ppm. |
| (1-{6-[5-Amino-3-(2-fluoro-4-morpholin-4-yl-phenylamino)-[1,2,4]triazol-1-yl]-pyrimidin-4-ylamino}-cyclopentyl)-methanol | B | 470.3 | 2.76 | 1H NMR(500MHz, CDCl3)d 8.29(1H, s), 8.02(1H, t), 6.82–6.70(3H, m), 3.82(4H, m), 3.77(2H, s), 3.09(4H, m), 2.00(2H, m), 1.90(2H, m), 1.8(2H, m), 1.70(2H, m)ppm. |
| 1-{6-[5-Amino-3-(2-fluoro-4-morpholin-4-yl-phenylamino)-[1,2,4]triazol-1-yl]-pyrimidin-4-yl}-piperidine-3-carboxylic acid ethyl ester | B | 512.3 | 3.57 | 1H NMR(500MHz, CDCl3)d 8.28(1H, s), 7.96(1H, t), 6.88(1H, br s), 6.73(1H, s), 6.70–6.62(2H, m), 4.05(2H, q), 3.80(4H, m), 3.28(1H, dd)3.15(1H, t), 3.02(4H, m), 2.49(1H, m), 2.05(1H, m), 1.76(2H, m), 1.52(1H, m), 1.20(3H, t)ppm |
| 1-{6-[5-Amino-3-(2-fluoro-4-morpholin-4-yl-phenylamino)-[1,2,4]triazol-1-yl]-pyrimidin-4-yl}-piperidine-3-carboxylic acid ethyl ester | B | 512.3 | 3.57 | 1H NMR(500MHz, CDCl3)d 8.28(1H, s), 7.96(1H, t), 6.88(1H, br s), 6.73(1H, s), 6.70–6.62(2H, m), 4.05(2H, q), 3.80(4H, m), 3.28(1H, dd)3.15(1H, t), 3.02(4H, m), 2.49(1H, m), 2.05(1H, m), 1.76(2H, m), 1.52(1H, m), 1.20(3H, t)ppm |
| 2-({6-[5-Amino-3-(4-morpholin-4-yl-phenylamino)-[1,2,4]triazol-1-yl]-pyrimidin-4-yl}-methyl-amino)-4-methyl-pentan-1-ol | B | 468.3 | 2.65 | 1H NMR(500MHz, CDCl3)d 8.21(1H, s), 7.33(2H, d), 6.84(2H, d), 6.70(2H, br s), 6.66(1H, s), 6.40(1H, s), 3.80(4H, m), 3.62(2H, m), 3.02(4H, m), 2.89(3H, s), 1.50(2H, m), 1.42(1H, m), 1.21(1H, m), 0.85(6H, m)ppm. |
| 2-{6-[5-Amino-3-(4-morpholin-4-yl-phenylamino)-[1,2,4]triazol-1-yl]-pyrimidin-4-ylamino}-4-methyl-pentan-1-ol | B | 454.3 | 2.31 | 1H NMR(500MHz, CDCl3)d 8.13(1H, s), 7.33(2H, d), 7.12(1H, br s), 6.97(2H, br s), 6.80(2H, d), 6.57(1H, s), 3.80(2H, m), 3.53(1H, m), 3.00(4H, m), 1.60(1H, m), 1.34(2H, m), 0.90(3H, m), 0.85(4H m)ppm. |
| 2-{6-[5-Amino-3-(4-morpholin-4-yl-phenylamino)-[1,2,4]triazol-1-yl]-pyrimidin-4-ylamino}-4-methyl-pentan-1-ol | B | 454.3 | 2.31 | 1H NMR(500MHz, CDCl3)d 8.13(1H, s), 7.33(2H, d), 7.12(1H, br s), 6.97(2H, br s), 6.80(2H, d), 6.57(1H, s), 3.80(2H, m), 3.53(1H, m), 3.00(4H, m), 1.60(1H, m), 1.34(2H, m), 0.90(3H, m), 0.85(4H, m)ppm. |
| (1-{6-[5-Amino-3-(4-morpholin-4-yl-phenylamino)-[1,2,4]triazol-1-yl]-pyrimidin-4-yl}-piperidin-3-yl)-methanol | B | 452.3 | 2.05 | 1H NMR(500MHz, CDCl3)d 8.24(1H, s), 7.35(2H, d), 6.84(4H, m), 6.72(1H, s), 3.92(1H, dd), 3.78(4H, m), 3.48(1H, m), 3.41(1H, m), 3.29(1H, m), 3.00(4H, m), 1.80(2H, m), 1.67(1H, m), 1.50(1H, m), 1.36(1H, m)ppm. |
| (1-{6-[5-Amino-3-(4-morpholin-4-yl-phenylamino)-[1,2,4]triazol-1-yl]-pyrimidin-4-yl}-piperidin-3-yl)-methanol | B | 452.3 | 2.16 | 1H NMR(500MHz, CDCl3)d 8.24(1H, s), 7.35(2H, d), 6.84(4H, m), 6.72(1H, s), 3.92(1H, dd), 3.78(4H, m), 3.48(1H, m), 3.41(1H, m), 3.29(1H, m), 3.00(4H, m), 1.80(2H, m), 1.67(1H, m), 1.50(1H, m), 1.36(1H, m)ppm. |
| 1-(4-{6-[5-Amino-3-(4-morpholin-4-yl-phenylamino)-[1,2,4]triazol-1-yl]-pyrimidin-4-yl}-piperazin-1-yl)-ethanone | B | 465.4 | 2.02 | 1H NMR(500MHz, MeOD-d4)d 8.38(1H, s), 7.47(2H, d), 6.95(2H, d), 6.82(1H, s), 3.81(6H, m), 3.78–3.62(6H, m), 3.08(4H, m), 2.12(3H, s)ppm. |
| 4-{6-[5-Amino-3-(4-morpholin-4-yl-phenylamino)-[1,2,4]triazol-1-yl]-pyrimidin-4-yl}-piperazine-1-carboxylic acid ethyl ester | B | 495.4 | 2.61 | 1H NMR(500MHz, MeOD-d4)d 8.38(1H, s), 7.47(2H, d), 6.95(2H, d), 6.82(1H, s), 4.15(2H, q), 3.81(4H, m), 3.74(4H, m), 3.59(4H, m), 3.08(4H, m), 1.25(3H, t)ppm. |
| (1-{6-[5-Amino-3-(2-methoxy-4-morpholin-4-yl-phenylamino)-[1,2,4]triazol-1-yl]-pyrimidin-4-yl}- | B | 482.4 | 2.39 | 1H NMR(500MHz, CDCl3)d 8.24(1H, s), 7.97(1H, d), 6.82(1H, s), 6.75(1H, s), 6.63(2H, s), 6.50(1H, dd), 6.46(1H, s), 3.90(1H, dd), 3.80(7H, m), 3.48(3H, m), 3.35(1H, m), 3.0(4H, m), 1.82(2H, |

| Name | Substitution Method | MS (M + H) | Retention time(min) | 1H NMR |
|---|---|---|---|---|
| piperidin-3-yl)-methanol | | | | m), 1.68(1H, m), 1.50(1H, m), 1.40(1H, m)ppm. |
| 2-{6-[5-Amino-3-(2-methoxy-4-morpholin-4-yl-phenylamino)-[1,2,4]triazol-1-yl]-pyrimidin-4-ylamino}-4-methyl-pentan-1-ol | B | 484.4 | 2.57 | 1H NMR(500MHz, CDCl3)d 8.20(1H, s), 7.99(1H, d), 6.89(1H, s), 6.70(2H, s), 6.60(1H, s), 6.43(2H, s), 3.80(7H, m), 3.72(1H, dd), 3.53(1H, dd), 3.0(4H, m), 1.64(1H, m), 1.40(2H, m), 0.93(3H, d), 0.87(3H, d)ppm. |
| 2-({6-[5-Amino-3-(2-methoxy-4-morpholin-4-yl-phenylamino)-[1,2,4]triazol-1-yl]-pyrimidin-4-yl}-methyl-amino)-4-methyl-pentan-1-ol | B | 498.4 | 2.9 | 1H NMR(500MHz, CDCl3)d 8.29(1H, s), 8.04(1H, d), 6.90(1H, s), 6.80(2H, s), 6.70(1H, s), 6.43(2H, m), 3.89(7H, m), 3.70(2H, m), 3.10(4H, m), 2.92(3H, s), 1.61(2H, m), 1.30(1H, m), 0.90(6H, t) ppm. |
| 1-{4-[4-(5-Amino-3-phenylamino-[1,2,4]triazol-1-yl)-pyridin-2-yl]-piperazin-1-yl}-ethanone | B | 379.2 | 1.88 | 1H NMR(500MHz, CDCl3)d 8.20(1H, d), 7.93(1H, s), 7.41(2H, d), 7.21(2H, t), 6.89(1H, t), 6.81(1H, s), 6.80(1H, d), 6.39(1H, s), 3.70(2H, m), 3.63(2H, m), 3.51(4H, m), 2.10(3H, s)ppm. |
| [4'-(5-Amino-3-phenylamino-[1,2,4]triazol-1-yl)-3,4,5,6-tetrahydro-2H-[1,2']bipyridinyl-3-yl]-methanol | B | 366.3 | 1.84 | 1H NMR(500MHz, CDCl3)d 8.05(1H, d), 7.35(2H, d), 7.20(2H, t), 7.01(1H, m), 6.83(1H, t), 6.75(1H, s), 6.61(1H, d), 3.75(1H, dd), 3.70(1H, dd), 3.50–3.20 (4H, m), 1.79(2H, m), 1.60(1H, m), 1.45 (1H, m), 1.25(1H, m)ppm. |
| 1-[6-(4-Chloro-phenylamino)-pyrimidin-4-yl]-N3-(2-fluoro-4-morpholin-4-yl-phenyl)-1H-[1,2,4]triazole-3,5-diamine | B | 482 | 4.4 | |
| 1-[6-(2,5-Dimethoxy-phenylamino)-pyrimidin-4-yl]-N3-(2-fluoro-4-methoxy-phenyl)-1H-[1,2,4]triazole-3,5-diamine | B | 453.2 | 3.7 | |
| N3-(2-Fluoro-4-methoxy-phenyl)-1-[6-(5-methoxy-2-methyl-phenylamino)-pyrimidin-4-yl]-1H-[1,2,4]triazole-3,5-diamine | B | 437.2 | 3.7 | |
| N3-(2-Fluoro-4-methoxy-phenyl)-1-(6-phenylamino-pyrimidin-4-yl)-1H-[1,2,4]triazole-3,5-diamine | B | 393.2 | 3.8 | |
| 2(R)-{6-[5-Amino-3-(2-fluoro-4-methoxy-phenylamino)-[1,2,4]triazol-1-yl]-pyrimidin-4-ylamino}-4-methyl-pentan-1-ol | B | 417 | 3.15 | 500MHz DMSO-d6: 8.8(br m, 1H), 8.459br m, 1H), 8.4 (s, 1H), 7.83(t, 1H), 6.9(d, 1H), 6.75(m, 2H), 4.2(m, 1H), 3.75 (s, 3H), 3.4(br d, 2H), 1.65(m, 1H), 1.4(m, 2H), 0.9(d, 6H) |
| 2(S)-{6-[5-Amino-3-(2-fluoro-4-methoxy-phenylamino)-[1,2,4]triazol-1-yl]-pyrimidin-4-ylamino}-4-methyl-pentan-1-ol | B | 417 | 3.15 | 500MHz DMSO-d6: 8.8(br m, 1H), 8.459br m, 1H), 8.4 (s, 1H), 7.83(t, 1H), 6.9(d, 1H), 6.75(m, 2H), 4.2(m, 1H), 3.75 (s, 3H), 3.4(br d, 2H), 1.65(m, 1H), 1.4(m, 2H), 0.9(d, 6H) |
| (1-{6-[5-Amino-3-(2-fluoro-4-methoxy-phenylamino)-[1,2,4]triazol-1-yl]-pyrimidin-4-ylamino}-cyclopentyl)-methanol | B | 415 | 3.07 | 500MHz DMSO-d6: 8.7(br m, 1H), 8.45(br m, 1H), 7.9(t, 1H), 6.9(d, 1H), 6.75(m, 2H), 3.75(s, 3H), 3.6(m, 2H), 1.95(m, 2H), 1.75(m, 2H), 1.65(m, 2H), 1.54(m, 2H) |
| (1-{6-[5-Amino-3-(2-fluoro-4-methoxy-phenylamino)-[1,2,4]triazol-1-yl]-pyrimidin-4-yl]-piperidin-4-yl)- | B | 415 | 2.94 | 500MHz DMSO-d6: 8.65(br m, 1H), 8.4(s, 1H), 7.9(t, 1H), 6.9(d, 1H), 6.77(d, 1H), 6.67(s, 1H), 4.4(m br, 1H), 3.75(s, 3H) 3.3(m, 2H), 3.0(t, 2H), 2.0(d m, 1H), 1.77(d, 2H), 1.7(m, 1H), |

| Name | Substitution Method | MS (M + H) | Retention time(min) | 1H NMR |
|---|---|---|---|---|
| methanol | | | | 1.1(quart, 2H) |
| 2(S)-{6-[5-Amino-3-(2-fluoro-4-morpholin-4-yl-phenylamino)-[1,2,4]triazol-1-yl]-pyrimidin-4-ylamino}-2-phenyl-ethanol | B | 492.2 | 2.73 | 500MHz(dmso)8.25(s, 1H), 8.19(m, 1H), 8.07(m, 1H), 7.83(dd, 1H), 7.67(m, 2H), 7.36(m, 2H), 7.31(dd, 2H), 7.23(dd, 1H), 6.83(dd, 1H), 6.73(m, 1H), 5.22(m, 1H), 3.74(m, 4H), 3.64(m, 2H), 3.08(m, 4H)ppm |
| 4-{6-[5-Amino-3-(2-fluoro-4-morpholin-4-yl-phenylamino)-[1,2,4]triazol-1-yl]-pyrimidin-4-ylamino}-piperidine-1-carboxylic acid ethyl ester | B | 527.3 | 3 | 500MHz(dmso)8.31(s, 1H), 8.18(m, 1H), 7.78(dd, 1H), 7.70(m, 2H), 7.63(d, 1H), 6.82(dd, 1H), 6.70(dd, 1H), 6.54(s, 1H), 4.11–4.02(burried m, 1H), 4.04(q, 2H), 3.90(m, 2H), 3.73(m, 4H), 3.06(m, 4H), 2.98(m, 2H), 1.87(m, 2H), 1.32(m, 2H), 1.18(t, 3H)ppm |
| 2(R)-{6-[5-Amino-3-(2-fluoro-4-morpholin-4-yl-phenylamino)-[1,2,4]triazol-1-yl]-pyrimidin-4-ylamino}-propan-1-ol | B | 430.2 | 2.05 | 500MHz(dmso)8.29(s, 1H), 8.22(br s, 1H), 7.81(dd, 1H), 7.72(m, 2H), 7.54(m, 1H), 6.83(dd, 1H), 6.70(dd, 1H), 6.58(br s, 1H), 4.10(m, 1H), 3.73(m, 4H), 3.45(dd, 1H), 3.34(m, 1H), 3.06(m, 4H), 1.12(d, 3H)ppm |
| 2(S)-{6-[5-Amino-3-(2-fluoro-4-morpholin-4-yl-phenylamino)-[1,2,4]triazol-1-yl]-pyrimidin-4-ylamino}-3-methyl-butan-1-ol | B | 458.3 | 2.51 | 500MHz(dmso)8.27(s, 1H), 7.82(br s, 1H), 7.82(dd, 1H), 7.71(m, 2H), 7.45(m, 1H), 6.83(d, 1H), 6.71(d, 1H), 6.67(br s, 1H), 4.00(m, 1H), 3.73(m, 4H), 3.46(d, 2H), 3.07(m, 4H), 1.92(m, 1H), 0.90(t, 6H)ppm |
| N3-Phenyl-1-(2-phenylamino-pyridin-4-yl)-1H-[1,2,4]triazole-3,5-diamine | B | 344.2 | 2.38 | 500MHz(DMSO)10.27(bs s, 1H), 9.24(s, 1H), 8.09(d, 1H), 7.55(d, 2H), 7.49(m, 4H), 7.33(s, 1H), 7.25(m, 2H), 7.23(t, 2H), 7.09(br s, 2H), 6.86(t, 1H)ppm |
| N3-(2,4-Difluoro-phenyl)-1-[6-(4-methyl-piperazin-1-yl)-pyrimidin-4-yl]-1H-[1,2,4]triazole-3,5-diamine | A | 388.30 | 1.63 | (500MHz, DMSO-d6)8.62(s, 1H), 8.47(d, 1H), , 8.13(m, 1H), 7.82(s, 2H), 7.23(m, 1H), 7.02(m, 1H), , 6.86(s, 1H), 4.55(d, 2H), 3.54(m, 2H), 3.29(t, 2H), , 3.11(m, 2H), 2.86(s, 3H)ppm |
| 1-(6-Diethylamino-pyrimidin-4-yl)-N3-(2,4-difluoro-phenyl)-1H-[1,2,4]triazole-3,5-diamine | A | 361.20 | 3.91 | (500MHz, DMSO-d6)8.66 9s, 1H), 8.36(s, 1H), , 8.04(m, 1H), 7.77(s, 2H), 7.21(m, 1H), 7.01(m, 1H), , 6.56(s, 1H), 3.54(m, 4H), 1.15(t, 6H)ppm |
| N3-(2-Methoxy-phenyl)-1-[6-(2-pyrrolidin-1-yl-ethylamino)-pyrimidin-4-yl]-1H-[1,2,4]triazole-3,5-diamine | A | 396.30 | 1.81 | (500MHz, DMSO-d6)9.48(s, 1H), 8.39(s, 1H), , 8.12(dd, 1H), 7.87(sd, 1H), 7.77(s, 2H), &.38(s, 1H), , 7.01(dd, 1H), 6.91(m, 2H), 6.70(s, 1H), 3.87(s, 3H), , 3.70(m, 2H), 3.62(m, 2H), 3.34(m, 2H), 3.08(m, 2H), , 2.02(m, 2H), 1.87(m, 2H)ppm |
| N3-(2,4-Difluoro-phenyl)-1-[6-(2-pyrrolidin-1-yl-ethylamino)-pyrimidin-4-yl]-1H-[1,2,4]triazole-3,5-diamine | A | 402.30 | 1.85 | (500MHz, DMSO-d6)8.62(s, 1H), 8.39(s, 3H), , 8.06(m, 1H), 7.84(s, 1H), 7.75(s, 2H), 7.24(m, 1H), , 6.99(m, 1H), 6.62(s, 1H), 3.68(m, 2H), 3.61(m, 2H), , 3.34(m, 2H), 3.07(m, 2H), 2.02(m, 2H), 1.86(m, 2H)ppm |
| N3-Indan-4-yl-1-[6-(2-pyrrolidin-1-yl-ethylamino)-pyrimidin-4-yl]-1H[1,2,4]triazole3,5-diamine | A | 406.30 | 2.70 | (500MHz, DMSO-d6)8.39(s, 1H), 8.08(s, 3H), , 7.85(s, 1H), 7.80(d, 1H), 7.71(s, 2H), 7.05(t, 1H), , 6.81(d, 1H), 6.65(s, 1H), 3.69(m, 2H), 3.61(m , 2H), , 3.35(m, 2H), 3.07(m, 2H), 2.86(, m, 4H), 2.01(m, 4H), , 1.86(m, 2H)ppm |
| N3-Indan-4-yl-1-[6-(4-methyl-piperazin-1-yl)-pyrimidin-4-yl]-1H-[1,2,4]triazole-3,5-diamine | A | 392.30 | 2.61 | (500MHz, DMSO-d6)8.48(s, 1H), 8.08(s, 1H), , 7.80(d, 1H), 7.77(s, 2H), 7.08(t, 1H), , 6.84(s, 1H), 6.80(d, 1H), 4.52(m, 2H), 3.54(m, 2H), , 3.30(m, 2H), 3.11(m, 2H), 2.85(m, 7H), 1.99(m, 4H), ppm |
| 1-[6-(4-Cyclopropyl-piperazin-1-yl)-pyrimidin-4-yl]-N3-indan-4-yl-1H-[1,2,4]triazole-3,5-diamine | A | 418.30 | 2.15 | (500MHz, DMSO-d6)8.48(s, 1H), 8.10(s, 1H), , 7.80(d, 1H), 7.77(s, 2H), 7.07(t, 1H), 6.84(s, 1H), , 6.81(d, 1H), 4.53(br m, 2H), 3.59(br m, 2H), , 3.30(br m, 4H), 2.86(m, 5H), 1.99(m, 2H), , 0.97(br m, 2H), 0.84(br m, 2H)ppm |
| 1-[6-(4-Cyclopropyl-piperazin-1-yl)- | A | 408.30 | 1.88 | (500MHz, DMSO-d6)8.48(s, 1H), 8.16(dd, 1H), , 7.84(s, 2H), 7.38(s, 1H), 7.00 |

-continued

| Name | Substitution Method | MS (M + H) | Retention time(min) | 1H NMR |
|---|---|---|---|---|
| pyrimidin-4-yl)-N3-(2-methoxy-phenyl)-1H-[1,2,4]triazole-3,5-diamine | | | | (dd, 1H), , 6.99(m , 3H), 4.6(br m, 2H), 3.87(s, 3H), 3.6(br m, 2H), , 3.30(br m, 4H), 2.9(br m, 1H), , 0.98(br m, 2H), 0.85 (br m, 2H)ppm |
| 1-[6-(4-Cyclopropyl-piperazin-1-yl)-pyrimidin-4-yl]-N3-(2,4-difluoro-phenyl)-1H-[1,2,4]triazole-3,5-diamine | A | 414.30 | 2.45 | (500MHz, DMSO-d6)8.64(s, 1H), 8.47(s, 1H), 8.12(m, 1H), 7.82(s, 2H), 7.23(m, 1H), 7.01(m , 1H), , 6.83(s, 1H), 4.5(br m, 2H), 3.6(br m, 2H), , 3.30(br m, 4H), 2.85 (br m, 1H), , 0.95(br m, 2H), 0.83(br m, 2H)ppm |
| N3-(4-Morpholin-4-yl-phenyl)-1-[6-(2-pyrrolidin-1-yl-ethylamino)-pyrimidin-4-yl]-1H-[1,2,4]triazole-3,5-diamine | A | 451.30 | 0.24 | (500MHz, DMSO-d6)8.91(s, 1H), 8.38(s, 1H), , 7.84(s, 1H), 7.70(s, 2H), 7.50(d, 2H), 6.90(d, 2H), , 6.66(s, 1H), 3.76(m, 4H), 3.69(m, 2H), , 3.62(br m, 2H), 3.35 (m, 2H), 3.04(m , 6H), , 2.02(m, 2H), 1.86 (m , 2H)ppm |
| N3-(4-Morpholin-4-yl-phenyl)-1-(6-piperazin-1-yl-pyrimidin-4-yl)-1H-[1,2,4]triazole-3,5-diamine | A | 423.30 | 1.98 | (500MHz, DMSO-d6)8.93(s, 1H), 8.88(s, 1H), , 8.45(s, 1H), 7.76(s, 2H), 7.53(d, 2H), 6.94(d, 2H), , 6.82(s, 1H), 3.89(m, 4H), 3.76(m, 4H), 3.24(m, 4H), , 3.05(m, 4H)ppm |
| 1-[6-(4-Methyl-piperazin-1-yl)-pyrimidin-4-yl]-N5-(4-morpholin-4-yl-phenyl)-1H-[1,2,4]triazole-3,5-diamine | A | 437.30 | 2.30 | (DMSO-d6, 500MHz)10.85(s, 1H), 8.54 (d, 1H), , 7.58(dd, 2H), 6.96(d, 2H), 6.76 (s, 1H), 5.80(br, 2H), , 4.5(br m, 2H), 3.75 (m, 4H), 3.53(m, 2H), , 3.29(m, 2H), 3.10 (m, 2H), 3.07(m, 4H), 2.85(s, 3H)ppm |
| 1-[6-(4-Cyclopropyl-piperazin-1-yl)-pyrimidin-4-yl]-N3-(4-morpholin-4-yl-phenyl)-1H-[1,2,4]triazole-3,5-diamine | A | 463.40 | 2.07 | (500MHz, DMSO-d6)8.92(s, 1H), 8.47(s, 1H), , 7.76(s, 2H), 7.53(d, 2H), 6.92(d, 2H), 6.86(s, 1H), 4.5(br m, 2H), 3.75(m, 4H), 3.6(br m, 2H), , 3.3(br m, 4H), 3.04 (m, 4H), 2.9(br m, 1H), , 0.98(m, 2H), 0.86(m, 2H)ppm |
| 1-[6-(2-Dimethylamino-ethylamino)-pyrimidin-4-yl]-N3-(2-methoxy-4-morpholin-4-yl-phenyl)-1H-[1,2,4]triazole-3,5-diamine | A | 455.3 | 1.8 | CD3CN: 11.1(s, 1H), 8.3(s, 1H), 8.1(d, 1H), 6.6(s, 1H), 6.4(m, 2H), , 5.9(bs, 1H), 4.4(s, 1H), 3.8(s, 3H), 3.7(m, 4H), 3.2(m, 8H), 3.0(m, 4H), 2.4(m, 2H). |
| 1-[6-(2-Dimethylamino-ethylamino)-pyrimidin-4-yl]-N3-(4-morpholin-4-yl-phenyl)-1H-[1,2,4]triazole-3,5-diamine | A | 425.3 | | DMSO-d6: 8.8(s, 1H), 8.3(s, 1H), 7.65(bs, 2H), 7.5(d, 2H), 6.85(d, 2H), , 6.65(bs, 1H), 3.7(m, 4H), 3.4(bs, 2H), 3.0(m, 4H), 2.4(m, 2H), , 2.2(bs, 6H). |
| 1-[6-(2-Dimethylamino-ethylamino)-pyrimidin-4-yl]-N5-(4-morpholin-4-yl-phenyl)-1H-[1,2,4]triazole-3,5-diamine | A | 425.3 | | DMSO-d6: 8.4(bs, 1H), 7.55(m, 3H), 6.95(d, 2H), , 6.5(bs, 2H), 5.7(bs, 1H), 3.75(m, 4H), 3.5(bs, 2H), 3.05(m, 4H), , 2.4(m, 2H), 2.2(s, 6H). |
| 1-[6-(3-Methyl-piperazin-1-yl)-pyrimidin-4-yl]-N3-(4-morpholin-4-yl-phenyl)-1H-[1,2,4]triazole-3,5-diamine | A | 437.33 | 0.31 | DMSO-d6: 8.82(s, 1H), 8.35(s, 1H), 7.71(bs, 2H), 7.47(d, 2H), , 6.87(d, 2H), 6.68(s, 1H), 4.25(m, 1H), 4.15(m, 1H), 3.72(m, 4H), , 2.97(m, 5H), 2.89(t, 1H), 2.67(m, 2H), 2.53m, 1H), 2.34(m, 1H), , 1.04(d, 3H |
| 1-[6-(3-Dimethylamino-pyrrolidin-1-yl)-pyrimidin-4-yl]-N3-(4-morpholin-4-yl-phenyl)-1H-[1,2,4]triazole-3,5-diamine | A | 451.40 | 0.80 | DMSO-d6: 8.82(s, 1H), 8.34(s, 1H), 7.70(s, 2H), 7.49(d, 2H), 6.87(d, 2H), 6.39(s, 1H), 3.71(m, 4H), 2.99(m, 4H), 2.49(s, 7H), 1.86(bs, 1H), 3.9–2.6 (5H). |
| 1-[6-(4-Methyl-[1,4]diazepan-1-yl)-pyrimidin-4-yl]-N3-(4-morpholin-4-yl-phenyl)-1H-[1,2,4]triazole-3,5-diamine | A | 467.20 | 1.46 | CD3CN: 8.25(s, 1H), 7.43(d, 2H), 6.83(m, 3H0, 6.64(bs, 1H), , 3.66(m, 4H), 3.57(m, 2H), 3.08(s, 3H), 2.98(m, 4H), 2.6–2.4, (m, 6H), 0.95(t, 6H). |

| Name | Substitution Method | MS (M + H) | Retention time(min) | 1H NMR |
|---|---|---|---|---|
| 1-{6-[(2-Diethylamino-ethyl)-methyl-amino]-pyrimidin-4-yl}-N3-(4-morpholin-4-yl-phenyl)-1H-[1,2,4]triazole-3,5-diamine | A | 467.20 | 1.46 | CD3CN: 8.25(s, 1H), 7.43(d, 2H), 6.83(m, 3H0, 6.64(bs, 1H), , 3.66(m, 4H), 3.57(m, 2H), 3.08(s, 3H), 2.98(m, 4H), 2.6–2.4, (m, 6H), 0.95(t, 6H). |
| 1-[6-(4-Isopropyl-piperazin-1-yl)-pyrimidin-4-yl]-N3-(4-morpholin-4-yl-phenyl)-1H-[1,2,4]triazole-3,5-diamine | A | 437.20 | 1.50 | DMSO-d6: 9.9(bs, 1H), 8.9(s, 1H), 8.4(s, 1H), 7.75(bs, 2H), 7.5(d, 2H), 6.9(d, 2H), 6.8(s, 1H), 4.5(m, 2H), 3.75(4H), 3.5(m, 2H), , 3.3(m, 2H), 3.1(m, 6H), 2.8(s, 3H) |
| N3-(2,4-Difluoro-phenyl)-1-[6-(4-methyl-piperazin-1-yl)-pyrimidin-4-yl]-1H-[1,2,4]triazole-3,5-diamine | A | 388.30 | 1.63 | (500MHz, DMSO-d6)8.62(s, 1H), 8.47 (d, 1H), , 8.13(m, 1H), 7.82(s, 2H), 7.23 (m, 1H), 7.02(m, 1H), , 6.86(s, 1H), 4.55 (d, 2H), 3.54(d, 2H), 3.29(t, 2H), , 3.11(m, 2H), 2.86(s, 3H)ppm |
| 1-(6-Diethylamino-pyrimidin-4-yl)-N3-(2,4-difluoro-phenyl)-1H-[1,2,4]triazole-3,5-diamine | A | 361.20 | 3.91 | (500MHz, DMSO-d6)8.66 9s, 1H), 8.36 (s, 1H), , 8.04(m, 1H), 7.77(s, 2H), 7.21 (m, 1H), 7.01(m, 1H), , 6.56(s, 1H), 3.54 (m, 4H), 1.15(t, 6H)ppm |
| N3-(2-Methoxy-phenyl)-1-[6-(2-pyrrolidin-1-yl-ethylamino)-pyrimidin-4-yl]-1H-[1,2,4]triazole-3,5-diamine | A | 396.30 | 1.81 | (500MHz, DMSO-d6)9.48(s, 1H), 8.39(s, 1H), , 8.12(dd, 1H), 7.87(sd, 1H), 7.77(s, 2H), &.38(s, 1H), , 7.01(dd, 1H), 6.91(m, 2H), 6.70(s, 1H), 3.87(s, 3H), , 3.70(m, 2H), 3.62(m, 2H), 3.34(m, 2H), 3.08(m, 2H), , 2.02(m, 2H), 1.87(m, 2H)ppm |
| N3-(2,4-Difluoro-phenyl)-1-[6-(2-pyrrolidin-1-yl-ethylamino)-pyrimidin-4-yl]-1H-[1,2,4]triazole-3,5-diamine | A | 402.30 | 1.85 | (500MHz, DMSO-d6)8.62(s, 1H), 8.39(s, 3H), , 8.06(m, 1H), 7.84(s, 1H), 7.75(s, 2H), 7.24(m, 1H), 6.99(m, 1H), 6.62(s, 1H), 3.68(m, 2H), 3.61(m, 2H), , 3.34(m, 2H), 3.07(m, 2H), 2.02(m, 2H), 1.86(m, 2H)ppm |
| N3-Indan-4-yl-1-[6-(2-pyrrolidin-1-yl-ethylamino)-pyrimidin-4-yl]-1H-[1,2,4]triazole-3,5-diamine | A | 406.30 | 2.70 | (500MHz, DMSO-d6)8.39(s, 1H), 8.08(s, 3H), 7.85(s, 1H), 7.80(d, 1H), 7.71(s, 2H), 7.05(t, 1H), , 6.81(d, 1H), 6.65(s, 1H), 3.69(m, 2H), 3.61(m, 2H), , 3.35(m, 2H), 3.07(m, 2H), 2.86(, m, 4H), 2.01(m, 4H), , 1.86(m, 2H)ppm |
| N3-Indan-4-yl-1-[6-(4-methyl-piperazin-1-yl)-pyrimidin-4-yl]-1H-[1,2,4]triazole-3,5-diamine | A | 392.30 | 2.61 | (500MHz, DMSO-d6)8.48(s, 1H), 8.08(s, 1H), , 7.80(d, 1H), 7.77(s, 2H), 7.08(t, 1H), 6.84(s, 1H), 6.80(d, 1H), 4.52(m, 2H), 3.54(m, 2H), , 3.30(m, 2H), 3.11(m, 2H), 2.85(m, 7H), 1.99(m, 4H), ppm |
| 1-[6-(4-Cyclopropyl-piperazin-1-yl)-pyrimidin-4-yl]-N3-indan-4-yl-1H-[1,2,4]triazole-3,5-diamine | A | 418.30 | 2.15 | (500MHz, DMSO-d6)8.48(s, 1H), 8.10(s, 1H), , 7.80(d, 1H), 7.77(s, 2H), 7.07(t, 1H), 6.84(s, 1H), , 6.81(d, 1H), 4.53(br m, 2H), 3.59(br m, 2H), , 3.30(br m, 4H), 2.86 (m, 5H), 1.99(m, 2H), , 0.97(br m, 2H), 0.84(br m, 2H)ppm |
| 1-[6-(4-Cyclopropyl-piperazin-1-yl)-pyrimidin-4-yl]-N3-(2-methoxy-phenyl)-1H-[1,2,4]triazole-3,5-diamine | A | 408.30 | 1.88 | (500MHz, DMSO-d6)8.48(s, 1H), 8.16 (dd, 1H), , 7.84(s, 2H), 7.38(s, 1H), 7.00 (dd, 1H), , 6.99(m , 3H), 4.6(br m, 2H), 3.87(s, 3H), 3.6(br m, 2H), , 3.30(br m, 4H), 2.9(br m, 1H), , 0.98(br m, 2H), 0.85 (br m, 2H)ppm |
| 1-[6-(4-Cyclopropyl-piperazin-1-yl)-pyrimidin-4-yl]-N3-(2,4-difluoro-phenyl)-1H-[1,2,4]triazole-3,5-diamine | A | 414.30 | 2.45 | (500MHz, DMSO-d6)8.64(s, 1H), 8.47(s, 1H), 8.12(m, 1H), , 7.82(s, 2H), 7.23(m, 1H), 7.01(m, 1H), 6.83(s, 1H), 4.5(br m, 2H), 3.6(br m, 2H), , 3.30(br m, 4H), 2.85 (br m, 1H), , 0.95(br m, 2H), 0.83(br m, 2H)ppm |
| N3-(4-Morpholin-4-yl-phenyl)-1-[6-(2-pyrrolidin-1-yl-ethylamino)-pyrimidin-4-yl]-1H-[1,2,4]triazole-3,5-diamine | A | 451.30 | 0.24 | (500MHz, DMSO-d6)8.91(s, 1H), 8.38(s, 1H), , 7.84(s 1H), 7.70(s, 2H), 7.50(d, 2H), 6.90(d, 2H), , 6.66(s, 1H), 3.76(m, 4H), 3.69(m, 2H), , 3.62(br m, 2H), 3.35 (m, 2H), 3.04(m , 6H), , 2.02(m, 2H), 1.86 (m, 2H)ppm |
| N3-(4-Morpholin-4-yl-phenyl)-1-(6-piperazin-1-yl-pyrimidin-4-yl)- | A | 423.30 | 1.98 | (500MHz, DMSO-d6)8.93(s, 1H), 8.88(s, 1H), , 8.45(s, 1H), 7.76(s, 2H), 7.53(d, 2H), 6.94(d, 2H), , 6.82,(s, 1H), 3.89(m, |

| Name | Substitution Method | MS (M + H) | Retention time(min) | 1H NMR |
|---|---|---|---|---|
| 1H-[1,2,4]triazole-3,5-diamine | | | | 4H), 3.76(m, 4H), 3.24(m, 4H), , 3.05(m, 4H)ppm |
| 1-[6-(4-Methyl-piperazin-1-yl)-pyrimidin-4-yl]-N5-(4-morpholin-4-yl-phenyl)-1H-[1,2,4]triazole-3,5-diamine | A | 437.30 | 2.30 | (DMSO-d6, 500MHz)10.85(s, 1H), 8.54 (d, 1H), , 7.58(dd, 2H), 6.96(d, 2H), 6.76 (s, 1H), 5.80(br, 2H), , 4.5(br m, 2H), 3.75 (m, 4H), 3.53(m, 2H), , 3.29(m, 2H), 3.10 (m, 2H), 3.07(m, 4H), 2.85(s, 3H)ppm |
| 1-[6-(4-Cyclopropyl-piperazin-1-yl)-pyrimidin-4-yl]-N3-(4-morpholin-4-yl-phenyl)-1H-[1,2,4]triazole-3,5-diamine | A | 463.40 | 2.07 | (500MHz, DMSO-d6)8.92(s, 1H), 8.47(s, 1H), , 7.76(s, 2H), 7.53(d, 2H), 6.92(d, 2H), , 6.86(s, 1H), 4.5(br m, 2H), 3.75(m, 4H), 3.6(br m, 2H), , 3.3(br m, 4H), 3.04 (m, 4H), 2.9(br m, 1H), , 0.98(m, 2H), 0.86(m, 2H)ppm |
| 1-[6-(2-Dimethylamino-ethylamino)-pyrimidin-4-yl]-N3-(2-methoxy-4-morpholin-4-yl-phenyl)-1H-[1,2,4]triazole-3,5-diamine | A | 455.3 | 1.8 | CD3CN: 11.1(s, 1H), 8.3(s, 1H), 8.1(d, 1H), 6.6(s, 1H), 6.4(m, 2H), , 5.9(bs, 1H), 4.4(s, 1H), 3.8(s, 3H), 3.7(m, 4H), 3.2(m, 8H), , 3.0(m, 4H), 2.4(m, 2H). |
| 1-[6-(2-Dimethylamino-ethylamino)-pyrimidin-4-yl]-N3-(4-morpholin-4-yl-phenyl)-1H-[1,2,4]triazole-3,5-diamine | A | 425.3 | | DMSO-d6: 8.8(s, 1H), 8.3(s, 1H), 7.65(bs, 2H), 7.5(d, 2H), 6.85(d, 2H), , 6.65(bs, 1H), 3.7(m, 4H), 3.4(bs, 2H), 3.0(m, 4H), 2.4(m, 2H), , 2.2(bs, 6H). |
| 1-[6-(2-Dimethylamino-ethylamino)-pyrimidin-4-yl]-N5-(4-morpholin-4-yl-phenyl)-1H-[1,2,4]triazole-3,5-diamine | A | 425.3 | | DMSO-d6: 8.4(bs, 1H), 7.55(m, 3H), 6.95(d, 2H), , 6.5(bs, 1H), 5.7(bs, 2H), 3.75(m, 4H), 3.5(bs, 2H), 3.05(m, 4H), , 2.4(m, 2H), 2.2(s, 6H). |
| 1-[6-(3-Methyl-piperazin-1-yl)-pyrimidin-4yl]-N3-(4-morpholin-4-yl-phenyl)-1H-[1,2,4]triazole-3,5-diamine | A | 437.33 | 0.31 | DMSO-d6: 8.82(s, 1H), 8.35(s, 1H), 7.71(bs, 2H), 7.47(d, 2H), , 6.87(d, 2H), 6.68(s, 1H), 4.25(m, 1H), 4.15(m, 1H), 3.72(m, 4H), , 2.97(m, 5H), 2.89(t, 1H), 2.67(m, 2H), 2.53m, 1H), 2.34(m, 1H), , 1.04(d, 3H |
| 1-[6-(3-Dimethylamino-pyrrolidin-1-yl)-pyrimidin-4-yl]-N3-(4-morpholin-4-yl-phenyl)-1H-[1,2,4] triazole-3,5-diamine | A | 451.40 | 0.80 | DMSO-d6: 8.82(s, 1H), 8.34(s, 1H), 7.70(s, 2H), 7.49(d, 2H), 6.87(d, 2H), 6.39(s, 1H), 3.71(m, 4H), 2.99(m, 4H), 2.49(s, 7H), 1.86(bs, 1H), 3.9–2.6 (5H). |
| 1-[6-(4-Methyl-[1, 4]diazepan-1-yl)-pyrimidin-4-yl]-N3-(4-morpholin-4-yl-phenyl)-1H-[1,2,4]triazole-3,5-diamine | A | 467.20 | 1.46 | CD3CN: 8.25(s, 1H), 7.43(d, 2H), 6.83(m, 3H0, 6.64(bs, 1H), , 3.66(m, 4H), 3.57(m, 2H), 3.08(s, 3H), 2.98(m, 4H), 2.6–2.4, (m, 6H), 0.95(t, 6H). |
| 1-{6-[(2-Diethylamino-ethyl)-methyl-amino]-pyrimidin-4yl}-N3-(4-morpholin-4-yl-phenyl)-1H-[1,2,4]triazole-3,5-diamine | A | 467.20 | 1.46 | CD3CN: 8.25(s, 1H), 7.43(d, 2H), 6.83(m, 3H0, 6.64(bs, 1H), , 3.66(m, 4H), 3.57(m, 2H), 3.08(s, 3H), 2.98(m, 4H), 2.6–2.4, (m, 6H), 0.95(t, 6H). |
| 1-[6-(4-Isopropyl-piperazin-1-yl)-pyrimidin-4-yl]-N3-(4-morpholin-4-yl-phenyl)-1H-[1,2,4]triazole-3,5-diamine | A | 437.20 | 1.50 | DMSO-d6: 9.9(bs, 1H), 8.9(s, 1H), 8.4(s, 1H), 7.75(bs, 2H), , 7.5(d, 2H), 6.9(d, 2H), 6.8(s, 1H), 4.5(m, 2H), 3.75(4H), 3.5(m, 2H), , 3.3(m, 2H), 3.1(m, 6H), 2.8(s, 3H) |
| 1-(6-Chloro-pyrimidin-4-yl)-N3-(2-fluoro-4-morpholin-4-yl- | | 391.2 | 3.02 | 500MHz(dmso)8.79(s, H), 8.44(s, 1H), 7.87(s, 2H), 7.82 9t, 2H), 7.50(s, 1H), 6.82 (dd, 1H), 6.77(dd, 1H), 3.72(m, 4H), 3.07 |

-continued

| Name | Substitution Method | MS (M + H) | Retention time(min) | 1H NMR |
|---|---|---|---|---|
| phenyl)-1H-[1,2,4]triazole-3,5-diamine | | | | (m, 4H)ppm |
| 1-(6-Chloro-pyrimidin-4-yl)-N3-phenyl-1H-[1,2,4]triazole-3,5-diamine | | 288.15 | 3.31 | ¹H NMR(500MHz, DMSO-d6)δ9.30(1H, s), 8.81(1H, s), 7.91(2H, s), 7.62(3H, m), 7.28(2H, t), 6.87(1H, t)ppm |
| 1-(6-Chloro-pyrimidin-4-yl)-N3-(2-fluoro-4-methoxy-phenyl)-1H-[1,2,4]triazole-3,5-diamine | | | | ¹H NMR(500MHz, DMSO-d6)δ8.80(d, 1H), 8.52(s, 1H), 7.89(m, 3H), 7.52(d, 1H), 6.85(dd, 1H), 6.79(dd, 1H)ppm |

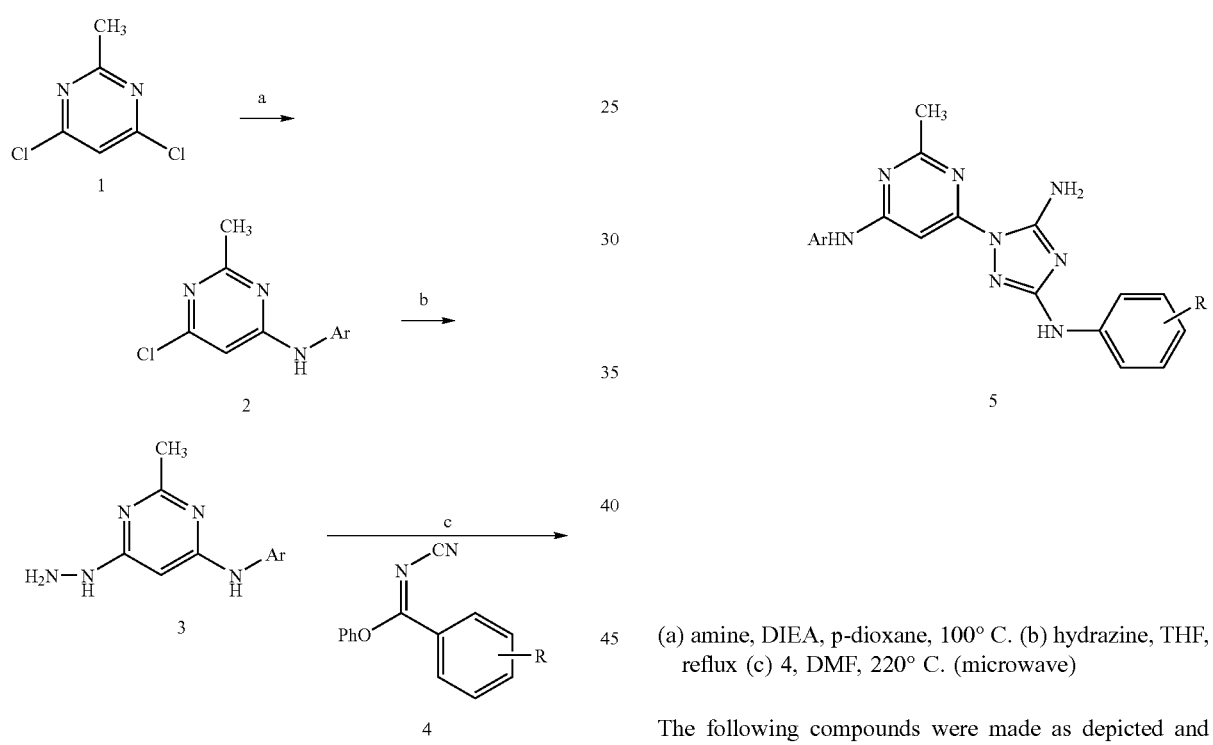

(a) amine, DIEA, p-dioxane, 100° C. (b) hydrazine, THF, reflux (c) 4, DMF, 220° C. (microwave)

The following compounds were made as depicted and described in scheme 29:

| Name | MS (M + H) | Rt (min) | NMR |
|---|---|---|---|
| N3-(3-Methoxy-phenyl)-1-(2-methyl-6-phenylamino-pyrimidin-4-yl)-1H-[1,2,4]triazole-3,5-diamine | 389 | 3.40 | 500MHz DMSO-d6: 9.75(s, 1H), 9.13(s, 1H), 7.8(s, 2H), 7.65(d, 2H), 7.35(t, 2H), 7.3(s, 1H), 7.15(m, 2H), 7.05(t, 1H), 6.79(s, 1H), 6.45(m, 1H), 3.75(s, 3H), 2.52(s, 3H) |
| N3-(3-Dimethylamino-phenyl)-1-(2-methyl-6-phenylamino-pyrimidin-4-yl)-1H-[1,2,4]triazole-3,5-diamine | 402 | 2.86 | 500MHz DMSO-d6: 9.7(s, 1H), 8.9(s, 1H), 7.8(s, 2H), 7.6(d, 2H), 7.35(t, 2H), 7.03(m, 4H), 6.75(s, 1H), 6.25(d, 1H), 2.8(s, 6H), 2.55(s, 3H) |
| N3-(2,4-Dimethoxy-phenyl)-1-(2-methyl-6-phenylamino-pyrimidin-4-yl)-1H-[1,2,4]triazole-3,5- | 419 | 3.52 | 500MMHz DMSO-d6: 9.7(s, 1H), 7.95(d, 1H), 7.8 (s, 2H), 7.68(d, 2H), 7.37(t, 2H), 7.23(s, 1H), 7.03 (t, 1H), 6.8(s, 1H), 6.65(s, 1H), 6.45(d, 1H), 3.85(s, 3H), 3.73(s, 3H), 2.55(s, 3H) |

| Name | MS (M + H) | Rt (min) | NMR |
|---|---|---|---|
| 3,5-diamine | | | |
| N3-[3-Methoxy-4-(2-morpholin-4-yl-ethoxy)-phenyl]-1-(2-methyl-6-phenylamino-pyrimidin-4-yl)-1H-[1,2,4]triazole-3,5-diamine | 518 | 2.82 | 500MHz DMSO-d6: 10.0(br m, 1H), 9.68(s, 1H), 9.03(s, 1H), 7.81(s, 2H), 7.6(d, 2H), 7.38(m, 3H), 7.1(m, 2H), 6.95(d, 1H), 6.75(s, 1H), 4.25(m, 2H), 4.0(m, 2H), 3.8(m, 2H), 3.7(s, 3H), 3.6(m, 2H), 3.55(m, 2H), 3.25(m, 2H), 2.5(s, 3H) |
| N3-(2-Methoxy-phenyl)-1-(2-methyl-6-phenylamino-pyrimidin-4-yl)-1H-[1,2,4]triazole-3,5-diamine | 389 | 3.57 | 500MHz DMSO-d6: 9.7(s, 1H), 8.15(d, 1H), 7.85 (s, 2H), 7.7(d, 2H), 7.4(s, 1H), 7.38(t, 2H), 7.03(t, 1H), 7.01(d, 1H), 6.92(m, 2H), 6.83(m, 2H), 3.83(s, 3H), 2.5(s, 3H) |
| 1-(2-Methyl-6-phenylamino-pyrimidin-4-yl)-N3-phenyl-1H-[1,2,4]triazole-3,5-diamine | 359 | 3.46 | 500MHz DMSO-d6: 9.73(s, 1H), 9.17(s, 1H), 7.8(s, 2H), 7.7(d, 2H), 7.62(d, 2H), 7.35(t, 2H), 7.25(t, 2H), 7.05(t, 1H), 6.83(t, 1H), 6.81(s, 2H), 2.53(s, 3H) |
| N3-(3-Amino-phenyl)-1-(2-methyl-6-phenylamino-pyrimidin-4-yl)-1H-[1,2,4]triazole-3,5-diamine | 374 | 2.80 | 500MHz DMSO-d6: 10.05(s, 1H), 9.7(s, 1H), 8.1(s, 1H), 7.8(m, 3H), 7.5(d, 1H), 7.4(s, 1H), 7.35(m, 2H), 7.05(t, 1H), 6.85(d, 1H), 2.55(s, 3H) |
| 1-(6-Cyclohexylamino-2-methyl-pyrimidin-4-yl)-N3-phenyl-1H-[1,2,4]triazole-3,5-diamine | 365.30 | 3.19 | (dmso)9.10(s, 1H), 7.23(br s, 2H), 7.44(d, 2H), 7.23(d, 1H), 7.23(dd, 2H), 6.83(dd, 1H), 6.47(br s, 1H), 3.91(m, 1H), 2.37(s, 3H), 1..88(m, 2H), 1.72 (m, 2H), 1.58(m, 1H), 1.33(m, 2H), 1.21(m, 3H)ppm |
| 1-(6-Cyclohexylamino-2-methyl-pyrimidin-4-yl)-N3-(2-methoxy-phenyl)-1H-[1,2,4]triazole-3,5-diamine | 395.30 | 3.42 | (dmso)8.14(dd, 1H), 7.77(br s, 2H), 7.45(d, 1H), 7.00(dd, 1H)< 6.90(m, 2H), 6.48(br s, 1H), 3.91(m, 1H), 3.87(s, 3H), 2.37(s, 3H), 1.88(m, 2H), 1.72(m, 2H), 1.58 m, 1H), 1.32(m, 2H), 1.18(m, 3H)ppm |
| 1-[6-(1-Benzyl-piperidin-4-ylamino)-2-methyl-pyrimidin-4-yl]-N3-phenyl-1H-[1,2,4]triazole-3,5-diamine | 456.30 | 2.13 | (dmso)9.11(s, 1H), 7.73(s, 2H), 7.60(d, 2H), 7.49 (d, 1H), 7.323(complex m, 4H), 7.25(m, 3H), 6.84 (dd, 1H), 6.48(s, 1H), 3.92(m, 1H), 3.48(s, 2H), 2.78(m, 2H), 2.37(s, 3H), 2.07(dd, 2H), 1.86(m 2H), 1.45(m, 2H)ppm |
| 1-[6-(1-Benzyl-piperidin-4-ylamino)-2-methyl-pyrimidin-4-yl]-N3-(2-methoxy-phenyl)-1H-[1,2,4]triazole-3,5-diamine | 486.30 | 2.28 | 8.13(dd, 1H), 7.76(br s, 2H), 7.50(d, 1H), 7.31(m, 5H), 7.25(dd, 1H), 6.99(d, 1H), 6.90(m, 1H), 6.49 (s, 1H), 3.91(m, 1H), 3.87(s, 3H), 3.48(s, 2H), 2.78 (m, 2H), 2.38(s, 3H), 2.07(dd, 2H0, 1.85(m, 2H), 1.44(m, 2H)ppm |
| 1-[6-(1-Benzyl-piperidin-4-ylamino)-2-methyl-pyrimidin-4-yl]-N3-[3-methoxy-4-(3-morpholin-4-yl-propoxy)-phenyl]-1H-[1,2,4]triazole-3,5-diamine | 532.40 | 2.20 | (dmso)(9.66(s, 1H), 9.48(m, 1H), 8.98(s, 1H), 7.80 (s, 2H), 7.59(d, 2H), 7.36(m, 3H), 7.08(dd, 2H), 6.86(d, 1H), 6.75(s, 1H), 4.02(d, 2H), 3.97(t, 2H), 3.68(s, 3H), 3.65(t, 2H), 3.51(d, 2H), 3.30(m, 2H), 3.11(dd, 2H), 2.09(m, 2H)ppm |
| 1-[6-(1-Benzyl-piperidin-4-ylamino)-2-methyl-pyrimidin-4-yl]-N3-[3-methoxy-4-(4-morpholin-4-yl-butoxy)-phenyl]-1H-[1,2,4]triazole-3,5-diamine | 546.40 | 2.24 | (dmso)9.66(s, 1H), 9.53(m, 1H), 8.94(s, 1H), 7.79 (s, 2H), 7.59(d, 2H), 7.36(dd, 2H), 7.33(d, 1H), 7.08 (m, 2H), 6.83(d, 1H), 6.75(s, 1H), 3.99(d, 2H), 3.92 (dd, 2H), 3.68(s, 3H), 3.64(t, 2H), 3.45(d, 2H), 3.20 (m, 2H), 3.06(m, 2H), 1.82(m, |
| 1-[2-Methyl-6-(piperidin-4-ylamino)-pyrimidin-4-yl]-N3-phenyl-1H-[1,2,4]triazole-3,5-diamine | 366.30 | 1.52 | (dmso)9.20(s, 1H), 8.74(m, 2H), 8.10–7.70(m, 3H), 7.60(d, 2H), 7.25(dd, 2H), 6.85(dd, 1H), 6.56(s, 1H), 4.24(m, 1H), 3.31(m, 2H), 3.04(m, 2H), 2.46 (s, 3H), 2.05(m, 2H), 1.68(m, 2H)ppm |
| N3-(3-Isopropoxy-phenyl)-1-(2-methyl-6-phenylamino-pyrimidin-4-yl)-1H-[1,2,4]triazole-3,5-diamine | 417.22 | 4.09 | 500MHz(dmso)9.73(s, 1H), 9.08(s, 1H), 7.80(s, 2H), 7.63(d, 2H), 7.35(dd, 2H), 7.21(d, 1H), 7.11–7.03 (complex m, 3H), 6.79(s, 1H), 6.41(dd, 1H), 4.52(m, 1H), 2.47(burried s, 3H), 1.25(d, 6H)ppm |
| N3-(2-Fluoro-phenyl)-1-(2-methyl-6-phenylamino-pyrimidin-4-yl)-1H-[1,2,4]triazole-3,5-diamine | 377.20 | 3.91 | 500MHz(dmso)9.78(s, 1H), 8.57(s, 1H), 8.14(dd, 1H), 7.80(br s, 2H), 7.65(d, 2H), 7.35(dd, 2H), 7.17 (dd, 1H), 7.12(dd, 1H), 7.05(dd, 1H), 6.93(dd, 1H), 6.79(s, 1H), 2.5(obscured s, 3H)ppm, |
| 1-(2-Methyl-6-phenylamino-pyrimidin-4-yl)-N3-(4-morpholin-4-yl-phenyl)-1H- | 444.22 | 2.72 | 500MHz(dmso)9.65(s, 1H), 8.81(s, 1H),(7.72 s, 2H), 7.67(d, 2H), 7.49(d, 2H), 7.35(dd, 2H), 7.04 (dd, 1H), 6.85(dd, 2H), 6.79(s, 1H), 3.74(m, 4H), 3.00(m, 4H), 2.5(obscured s, 3H)ppm |

| Name | MS (M + H) | Rt (min) | NMR |
|---|---|---|---|
| N3-(2-Fluoro-4-morpholin-4-yl-phenyl)-1-(2-methyl-6-phenylamino-pyrimidin-4-yl)-1H-[1,2,4]triazole-3,5-diamine | 462.10 | 3.51 | 500MHz(MeOD)7.59(m, 1H), 7.56(d, 2H), 7.38 (dd, 2H), 7.16(dd, 1H), 6.85(m, 2H), 6.76(m, 1H), 3.85(m, 3H), 3.16(m, 4H), 2.56(s, 3H)ppm |
| 1-(2-Methyl-6-phenylamino-pyrimidin-4-yl)-N3-m-tolyl-1H-[1,2,4]triazole-3,5-diamine | 373.30 | 3.90 | |
| 1-(2-Methyl-6-phenylamino-pyrimidin-4-yl)-N3-p-tolyl-1H-[1,2,4]triazole-3,5-diamine | 373.30 | 3.90 | |

Example 62

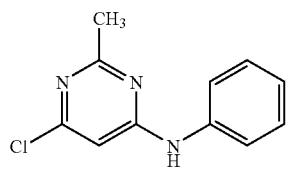

(6-Chloro-2-methyl-pyrimidin-4-yl)-phenyl-amine

2-Methyl-4,6-dichloropyrimidine (430 mg; 2.64 mMol) was refluxed in p-dioxane 10 mL with DIEA (575 uL; 426 mg; 3.3 mMol) and aniline (239 uL; 247 mg; 2.65 mMol) for 48 hrs under N2. The solvent was removed under reduced pressure and the residue partitioned between ethyl acetate and 0.5 N HCl. The organic fraction was washed with water, brine, and dried over $Na_2SO_4$) and the solvent removed under reduced pressure. Crude material was triturated with MTBE, suction filtered to isolate and washed with more MTBE and air dried to afford 375 mg of white solid, 64.5% yield. $^1$H NMR (500 MHz DMSO-d6) d 8.9 (s, 1H), 7.7 (s, 1H), 7.55 (m, 2H), 7.27 (t, 2H), 6.95 (t, 1H), 6.0 (s, 1H) 2.25 (s, 3H) ppm

Example 63

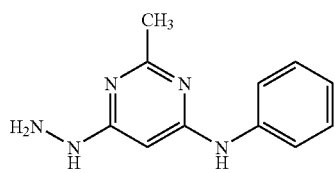

(6-Hydrazino-2-methyl-pyrimidin-4-yl)-phenyl-amine(6-Chloro-2-methyl-pyrimidin-4-yl)-phenyl-amine (2.83 g; 12.9 mMol) was refluxed in THF (35 mL) with anhydrous hydrazine (5 mL; 4.9 gm; 153 mMol) under N2 for 26 hrs. Reaction was cooled and the solvent was removed under reduced pressure. The residue was partitioned between ethyl acetate and water, the organic phase being washed again with water, brined, and dried ($NaSO_4$) and solvent removed under reduced pressure. The crude material was dissolved in a minimum amount of methylene chloride (hot) and added 100 mL of hot hexanes and material was stirred while it cooled to ambient temperature. The solid was isolated via suction filtration and washed with more hexanes and air dried., yielding 2.5 g of white powder, 89% yield. $^1$H NMR (500 MHz—DMSO-d6) d 8.9 (s, 1H), 7.7 (s, 1H), 7.5 (d, 2H), 7.26 (t, 2H), 6.9 (t, 1H), 6.0 (s, 1H), 4.15 (s, 2H), 2.3 (s, 3H) ppm; MS (M+H) 216

Example 64

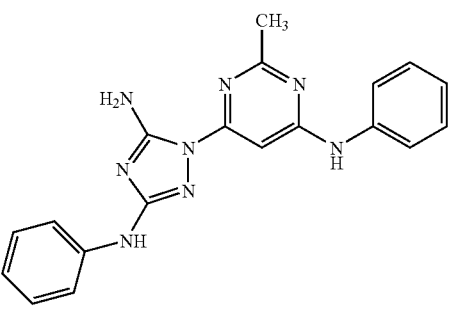

1-(2-Methyl-6-phenylamino-pyrimidin-4-yl)-N-3-phenyl-1H-[1,2,4]triazole-3,5-diamine (6-Hydrazino-2-methyl-pyrimidin-4-yl)-phenyl-amine (50 mg; 0.232 mmoles) was heated in a sealed flask in 2 mL of 2-propanol and 60 mg of N-cyano-N'-phenyl-O-phenyli-sourea for 8 h. Reaction was cooled and quenched with water and suction filtered to isolate solid. Crude material was triturated with warm 2-propanol and collected via suction filtration, to afford 15 mg of white material, 18% yield. $^1$H NMR (500 MHz, DMSO-d6) d 9.73 (s, 1H), 9.17

(s, 1H), 7.8 (s, 2H), 7.7 (d, 2H) 7.62 (d, 2H), 7.35 (t, 2H), 7.25 (t, 2H), 7.05 (t, 1H), 6.83 (t, 1H), 6.81 (s, 1H), 2.53 (s, 3H); MS (M+H) 359

Scheme 30

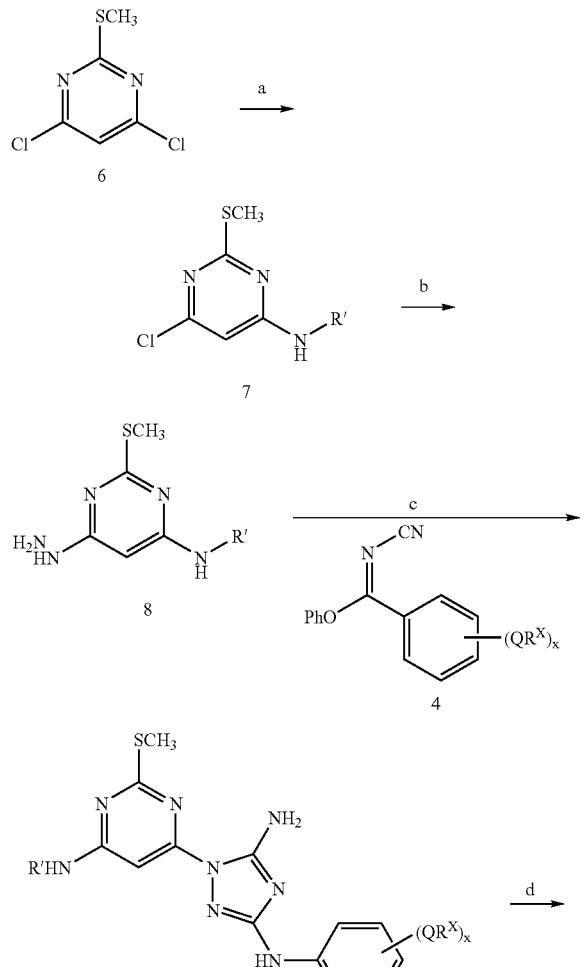

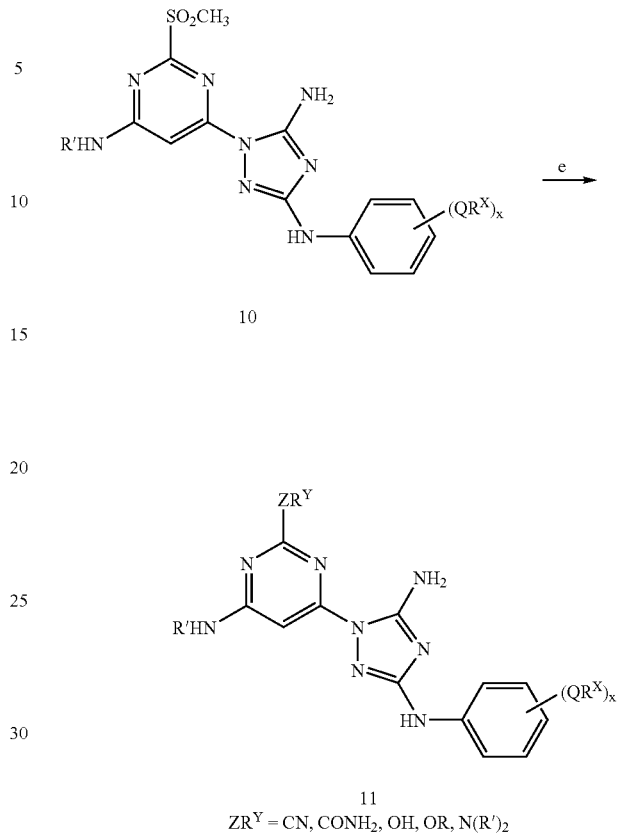

$ZR^Y$ = CN, $CONH_2$, OH, OR, $N(R')_2$ amine, DIEA, p-dioxane, 100° C. (b) hydrazine, THF, reflux (c) 4, DMF, 220° C. (microwave) (d) mCPBA, THF/p-dioxane (e) for $ZR^Y$=CN, $CONH_2$: i) KCN, DMSO ii) $K_2CO_3$, 30% $H_2O_2$, DMSO; for $ZR^Y$=OR: iii) NaOR, DMF; for $ZR^Y$=OH: iv) NaOH, DMF; for $ZR^Y$=$N(R')_2$: v) $HN(R')_2$, THF, 80° C.

The following compounds were made as described in scheme 29:

| Name | MS (M + H) | HPLC Rt (min) | NMR |
|---|---|---|---|
| N3-(2-Methoxy-phenyl)-1-(2-methylsulfanyl-6-phenylamino-pyrimidin-4-yl)-1H-[1,2,4]triazole-3,5-diamine | 421 | 4.17 | 500MHz DMSO-d6: 9.9(s, 1H), 8.12(d, meta spl, 1H), 7.85,(br s, 2H), 7.65(d, 2H), 7.63(s, 1H), 7.35(t, 2H), 7.05t, 1H), , 7.02(d, meta spl, 1H), 6.95(m, 2H), 6.75(s, 1H), 3.85(s, 3H), , 2.55(s, 3H) |
| N3-(3-Methoxy-phenyl)-1-(2-methylsulfanyl-6-phenylamino-pyrimidin-4-yl)-1H-[1,2,4]triazole-3,5-diamine | 421 | 4.08 | 500MHz DMSO-d6; 9, 9(s, 1H), 9.2(s, 1H), 7.73(br s, 1H), , 7.63(d, 2H), 7.33(t, 2H), 7.0(s, 1H), 7.19(m, 2H), 7.07(t, 1H), , 6.7(s, 1H), 6.45(m, 1H), 3.75(s, 3H), 2.55(s, 3H) |
| 1-(2-Methylsulfanyl-6-phenylamino-pyrimidin-4-yl)-N3-phenyl-1H- | 391 | 4.10 | 500MHz DMSO-d6: 10.0(br s, 1H), 9.38(br m, 1H), 7.7,(d, 2H), 7.63(d, 2H), 7.36(t, 2H), 7.27(t, 2H), 7.08(t, 1H), , 6.88(t, 1H), 6.77(s, 1H), |

| Name | MS (M + H) | HPLC Rt (min) | NMR |
|---|---|---|---|
| [1,2,4]triazole-3,5-diamine | | | 2.6(s, 3H) |
| N3-[3-Methoxy-4-(3-morpholin-4-yl-propoxy)-phenyl]-1-(2-methylsulfanyl-pyrimidin-4-yl)-1H-[1,2,4]triazole-3,5-diamine | 473 | 2.80 | 500MHz DMSO-d6: 9.05(s, 1H), 8.6(d, 1H), 7.7(s, 2H), , 7.37(d, 1H) 7.27(d, 1H), 7.1(dd, 1H), 6.85(1H), 3.93(t, 2H), , 3.78(s, 3H), 3.59(m, 4H), 2.55(s, 3H), 2.43–2.35(2m, 6H), , 1.83(m, 2H) |
| 1-(2-Methylsulfanyl-pyrimidin-4-yl)-N3-phenyl-1H-[1,2,4]triazole-3,5-diamine | 300 | 3.40 | 500MHz DMSO-d6: 9.2(s, 1H), 8.6(d, 1H), 7.7(s, 2H), , 7.6(d, 2H), 7.35(d, 1H), 7.25(t, 2H), 6.9(t, 1H), 2.53(s, 3H) |
| 1-(2-Methylsulfanyl-pyrimidin-4-yl)-N3-phenyl-1H-[1,2,4]triazole-3,5-diamine | 315 | 3.05 | 500MHz DMSO-d6: 9.1(s, 1H), 7.6(m, 4H), 7.2(t, 2H), , 7, 15(br m, 2H), 6.83(t, 1H), 6.3(s, 1H), 2.42(s, 3H) |
| 1-(6-Amino-2-methylsulfanyl-pyrimidin-4-yl)-N3-[3-methoxy-4-(3-morpholin-4-yl-propoxy)-phenyl]-1H-[1,2,4]triazole-3,5-diamine | 488 | | 500MHz(DMSO-d6)7.3(s, 1H), 7.1(d, 1H), 6.93(d, 1H), 6.4(1H), 4.03(m, 4H), 3.83(s, 3H), 3.77,(t, 2H), 3.51(d, 2H), 3.32(t, 2H), 3.15(t, 2H), 2.53(s, 3H), 2.15(m, 2H) |
| N3-(3-Amino-phenyl)-1-(2-methylsulfanyl-6-phenylamino-pyrimidin-4-yl)-1H-[1,2,4]triazole-3,5-diamine | 406 | 3.25 | 500MHz(DMSO-d6)10.15(s, 1H), 9.7(s, 1), 8.18(s, 1H, , 7.75(d, 2H), 7.45(s, 1H), 7.44(d, 1H), 7.3(t, 3H), 7.03(t, 1H), 6.85(d, 1H), 2.55(s, 5H)2 exh |
| 6-(5-Amino-3-phenylamino-[1,2,4]triazol-1-yl)-N2-methyl-N4-phenyl-pyrimidine-2,4-diamine | 374 | 3.39 | 500MHz DMSO-d6: 9.6(br s, 1H), 9.15(br s, 1H), 7.72,(d, 2H), 7.6(d, 2H), 7.35(t, 2H), 7.25(t, 2H), 7.03(t, 1H), , 6.85(t, 1H), 6.3(s, 1H), 2.9(s, 3H) |
| 6-(5-Amino-3-phenylamino-[1,2,4]triazol-1-yl)-N2-ethyl-N4-phenyl-pyrimidine-2,4-diamine | 388 | 3.68 | 500MHz DMSO-d6: 9.7(br s, 1H), 9.25(br s, 1H), 7.7,(d, 2H), 7.53(d, 2H), 7.35(t, 2H), 7.25(t, 2H), 7.05(br t, 1H), , 6.85(t, 1H), 6.3(s, 1H), 3.3(br quatr, 2H), 1.15(t, 3H) |
| 6-(5-Amino-3-phenylamino-[1,2,4]triazol-1-yl)-N2-ethyl-N2-methyl-N4-phenyl-pyrimidine-2,4-diamine | 402 | 4.01 | 500MHz DMSO-d6: 9.45(br s, 1H), 9.05(br s, 1H), 7.7,(d, 2H), 7.65(br m, 2H), 7.61(d, 2H), 7.35(t, 2H), 7.25(t, 2H), , 6.97(t, 1H), 6.85(t, 1H), 6.33(s, 1H), 3.6(br quatr, 2H), , 3.1(br s, 3H), 1.15(t, 3H) |
| 6-(5-Amino-3-phenylamino-[1,2,4]triazol-1-yl)-N4-phenyl-N2-propyl-pyrimidine-2,4-diamine | 402 | 4.46 | 500MHz DMSO-d6: 9.5(br s, 1H), 9.1(br s, 1H), 7.7,(d, 2H), 7.61(d, 2H), 7.35(t, 2H), 7.25(t, 2H), 7.0(br t, 1H), , 6.85(t, 1H), 6.33(s, 1H), 3.3(br quatr, 2H), 1/6(m, 2H), , 0.95(t, 3H) |
| 6-(5-Amino-3-phenylamino-[1,2,4]triazol-1-yl)-N2-ethyl-N2-methyl-pyrimidine-2,4-diamine | 326 | 2.79 | 500MHz DMSO-d6: 9.23(br s, 1H), 7.65(br m, 2H). 7.6,(d, 2H), 7.25(t, 2H), 6.86(t, 1H), 6.2(s, 1H), 3.6(quart, 2H), , 3.17(s, 3H), 1.15(t, 3H) |
| 6-(5-Amino-3-phenylamino-[1,2,4]triazol-1-yl)-N2-methyl-pyrimidine-2,4-diamine | 298 | 2.65 | 500MHz DMSO-d6: 9.25(br s, 1H), 7.55(d, 2H), 7.24,(t, 2H), 6.87(t, 1H), 6.15(br s, 1H), 2.9(br m, 3H), |
| 6-(5-Amino-3-phenylamino-[1,2,4]triazol-1-yl)-N2-propyl-pyrimidine-2,4-diamine | 326 | 2.75 | 500MHz MeOD-d4: 7.55(d, 2H), 7.34(t, 2H), 7.05(t, 1H), , 6.5(br s, 1H), 3.4(t, 2H), 3.2(s, 2H), 1.7(quin, 2H), , 1.5(br t, 3H) |
| 6-(5-Amino-3-phenylamino-[1,2,4]triazol-1-yl)-N2-ethyl-pyrimidine-2,4-diamine | 312 | 2.70 | 500MHz DMSO-d: 6:9.25(s, 1H), 8.8(br s, 1H), 8.4(br s, , 2H), 7.9(br s, 2H), 7.6(d, 2H), 7.25(t, 2H), 6.84(t, 1H), 6.2,(s, 1H), 3.38(m, 2H), 1.2(t, 3H) |
| 4-(5-Amino-3-phenylamino-[1,2,4]triazol-1-yl)-6- | | 3.19 | 500MHz DMSO-d6: 10.5(br s, 1H)9.15(s, 1H), 7.9(br s, 2H), 7.66(d, 4H), 7.4(t, 2H), 7.2(t, 2H), 7.18(br s, 1H), 6.8(t, 1H), 6.35(br s, 1H) |

| Name | MS (M + H) | HPLC Rt (min) | NMR |
|---|---|---|---|
| phenylamino-pyrimidin-2-ol | | | |
| 1-(2-Methoxy-6-phenylamino-pyrimidin-4-yl)-N3-phenyl-1H-[1,2,4]triazole-3,5-diamine | 375 | 3.68 | 500MHz DMSO-d6: 9.8(s, 1H)9.15(s, 1H), 7.7(m, 7H), 7.37(t, 2H), 7.25(t, 2H), 7.02(t, 1H), 6.83(t, 1H), 6.64(s, 1H), 3.9(s, 3H) |
| 1-(2-Isopropoxy-6-phenylamino-pyrimidin-4-yl)-N3-phenyl-1H-[1,2,4]triazole-3,5-diamine | 403 | 4.01 | 500MHz DMSO-d6: 9.8(s, 1H)9.15(s, 1H), 7.7(m, 6H), 7.37(t, 2H), 7.25(t, 2H), 7.02(t, 1H), 6.83(t, 1H), 6.64(s, 1H), 5.15(m, 1H), 1.35(d, 6H) |
| N3-Methyl-1-(2-methylsulfanyl-6-phenylamino-pyrimidin-4-yl)-1H-[1,2,4]triazole-3,5-diamine | 329 | 3.30 | 500MHz DMSO-d6: 9.83(s, 1H), 7.93(br m, 2H), 7.68,(d, 2H), 7.35(t, 2H), 7.02(t, 1H), 6.64(s, 1H), 2.77(s, 3H), , 2.52(s, 3H), |
| N3-Cyclohexyl-1-(2-methylsulfanyl-6-phenylamino-pyrimidin-4-yl)-1H-[1,2,4]triazole-3,5-diamine | 397 | 3.86 | 500MHz DMSO-d6: 9.93(s, 1H), 8.2(br m, 1H), 7.65,(d, 2H), 7.35(t, 2H), 7.05(t, 1H), 6.4(s, 1H), 4.35(m, 1H), , 2.55(s, 3H), 1.93(m, 2H), 1.72(m, 2H), 1.55(m, 1H), , 1.25(m, 4H), 1.16(m, 2H) |
| N3-Cyclohexylmethyl-1-(2-methylsulfanyl-6-phenylamino-pyrimidin-4-yl)-1H-[1,2,4]triazole-3,5-diamine | 411 | 4.04 | 500MHz DMSO-d6: 9.7(s, 1H), 7.65(d, 2H), 7.5(s, 2H), , 7.32(t, 2H), 7.05(t, 1H), 6.5(s, 1H), 6.02(m, 1H), 3.3(s, 3H), , 2.95(m, 2H), 1.7(m, 6H), 1.6(m, 1H), 1.2(m, 4H), 0.9(m, 2H) |
| 6-[5-Amino-3-(2-fluoro-4-morpholin-4-yl-phenylamino)-[1,2,4]triazol-1-yl]-N4-phenyl-pyrimidine-2,4-diamine | 494.20 | 4.19 | 500MHz(dmso)9.78(s, 1H), 8.21(s, 1H), 7.75 (dd, 1H), 7.62(d, 2H), 7.59(s, 2H), 7.34(dd, 2H), 7.05(dd, 1H), 7.82(dd, 1H), 7.69(dd, 1H), 6.59(s, 1H), 3.74(m, 4H), 3.07(m, 4H), 2.52(s, 3H)ppm |

Example 65

(6-Chloro-2-methylsulfanyl-pyrimidin-4-yl)-phenyl-amine

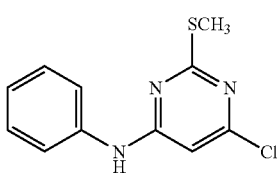

A mixture of 2.00 g (10.2 mMol) of 2-thiomethyl-4,6-dichloropyrimidine was heated to 100 C in 20 mL of p-dioxane along with (1.8 mL; 1.35 g; 10.2 mMol) of DIEA and (0.93 mL; 0.96 g; 10.3 mMol) of aniline under a $N_2$ atmosphere for 24 hr. The reaction was cooled and solvent was removed under reduced pressure. The residue was partitioned between water and ethyl acetate and the organic layer was washed with 0.1N HCl, water, brine, and dried (Na2SO4); the solvent removed under reduced pressure. Material solidifies upon standing to give 2.57 g of white powder, 88% yield. MS m/e (FIA+) 250/252

(6-Hydrazino-2-methylsulfanyl-pyrimidin-4-yl)-phenyl-amine

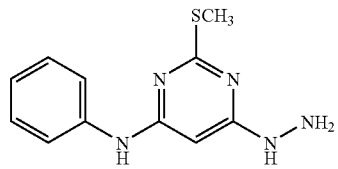

6-Chloro-2-methylsulfanyl-pyrimidin-4-yl)-phenyl-amine (2.7 g; 11 mMol) was heated under reflux in 25 mL of THF with (2.5 mL; 2.44 g; 76 mMol) of anhydrous hydrazine for 5 hrs under a $N_2$ atmosphere. The reaction was cooled and the solvent removed under reduced pressure. The mixture was stirred with 100 mL of water whereupon a white solid formed. The material was collected via suction filtration, washed with more water, and air dried to provide 2.69 g of white powder, a 95% yield.

MS m/e (FIA+) 246; $^1$H NMR (500 MHz DMSO-d6 d 9.05 (s, 1H), 7.8 (s, 1H), 7.5 (d, 2H), 7.25 (2H), 6.9 (t, 1H), 5.85 (s, 1H), 4.26 (br s, 2H) 2.45 (s, 3H) ppm.

1-(2-Methylsulfanyl-6-phenylamino-pyrimidin-4-yl)-N-3-phenyl-1H-[1,2,4]triazole-3,5-diamine

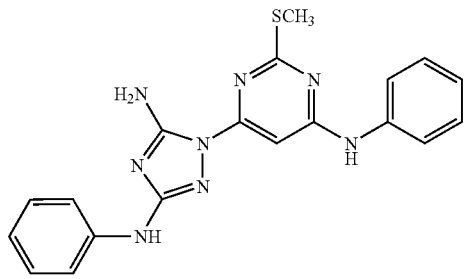

(6-Hydrazino-2-methylsulfanyl-pyrimidin-4-yl)-phenylamine (100 mg; 0.40 mMol) was heated with (96 mg; 0.44 mMol) of N-cyano-N'-phenyl-O-phenylisourea in 0.5 mL of DMSO in a sealed tube for 4 hours at 100° C. The reaction was quenched with water and the resulting solid was isolated via suction filtration. The solid was washed with water and transferred to a round bottom flask with acetonitrile and the solvent removed under reduced pressure. HPLC (gradient: water-acetonitrile, 0.1% TFA eluent) afforded 15 mg of a beige powder, 11% yield.

MS m/e (FIA+) 391, m/e (FIA−) 389; $^1$H NMR (500 MHz DMSO-d6) d 10.0 (br s, 1H), 9.38 (br m, 1H), 7.7 (d, 2H), 7.63 (d, 2H), 7.36 (t, 2H), 7.27 (t, 2H), 7.08 (t, 1H), 6.88 (t, 1H), 6.77(s, 1H), 2.6 (s, 3H) ppm.

1-(2-Methanesulfonyl-6-phenylamino-pyrimidin-4-yl)-N-3-phenyl-1H-[1,2,4]triazole-3,5-diamine

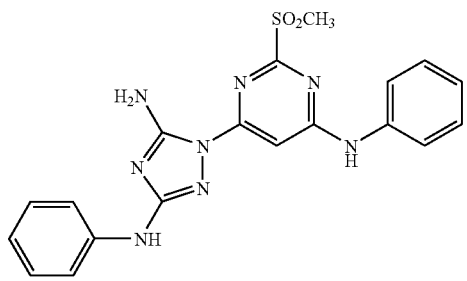

To (240 mg; 0.615 mMol) of 1-(2-methylsulfanyl-6-phenylamino-pyrimidin-4-yl)-N3-phenyl-1H-[1,2,4]triazole-3,5-diamine in 10 mL of p-dioxane and 10 mL THF was added (413 mg; 2.4 mMol) of 77% mCPBA. The reaction was stirred at ambient temperature for 2 hr. Reaction was quenched into water. The resulting solid was isolated via suction filtration and the solid washed with more water. The solid was transferred to a round bottom flask with acetonitrile and the solvent was removed under reduced pressure. The resulting solid was triturated with MTBE and the solid was collected via suction filtration and air-dried to provide 214 mg of off white powder (82.3% yield).

MS m/e (FIA+) 423, m/e (FIA−) 421; $^1$H NMR (500 MHz DMSO-d6) δ10.4 (s, 1H), 9.25 (s, 1H), 7.72 (s, 1H), 7.13 (t, 4H), 7.43 (t, 2H), 7.25 (t, 2H), 7.15 (t, 1H), 7.03 (s, 1H), 6.85 (t, 1H), 3.3 (s, 3H) ppm.

4-(5-Amino-3-phenylamino-[1,2,4]triazol-1-yl)-6-phenylamino-pyrimidine-2-carbonitrile

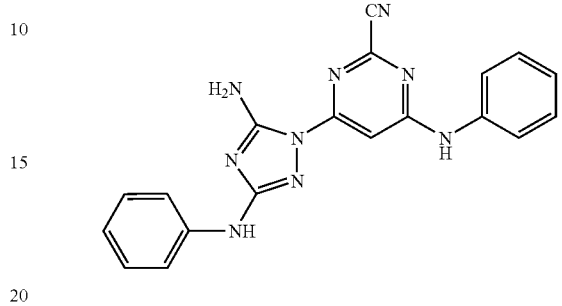

To a solution of (50 mg; 0.12 mMol) of 1-(2-methanesulfonyl-6-phenylamino-pyrimidin-4-yl)-N-3-phenyl-1H-[1,2,4]triazole-3,5-diamine in 2 mL of DMSO was added 8 mg (0.13 mMol) of potassium cyanide and reaction was stirred for 1 hr at ambient temperature. The solvent was removed under reduced pressure. The residue was triturated with water and the solid was isolated via suction filtration. Column chromatography (SiO$_2$, 5% EtOH—CH$_2$Cl$_2$) followed by trituration with diethyl ether affording 5 mg of an off white powder, (11% yield).

MS m/e (FIA+) 370, m/e (FIA−) 368; $^1$H NMR (500 MHz DMSO-d6) δ10.25 (s, 1H), 9.25 (s, 1H), 7.63 m, 6H), 7.4 (t, 2H), 7.25 (t, 2H), 7.15 (t, 1H), 7.07 (s, 1H), 6.88 (t, 1H)ppm.

4-(5-Amino-3-phenylamino-[1,2,4]triazol-1-yl)-6-phenylamino-pyrimidine-2-carboxylic acid amide

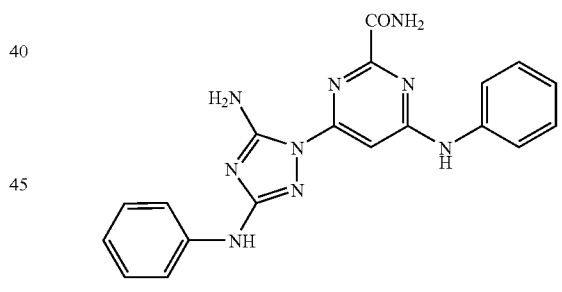

To (20 mg; 0.054 mMol) of 4-(5-amino-3-phenylamino-[1,2,4]triazol-1-yl)-6-phenylamino-pyrimidine-2-carbonitrile in 500 μL of DMSO was added, at ambient temperature, (5 mg; 0.036 mMol) of anhydrous K$_2$CO$_3$, followed by 10 drops of 30% aqueous H$_2$O$_2$. The reaction was stirred for 10 min and quenched with water. The aqueous layer was extracted with EtOAc (2×). The organic fractions were combined and washed with water, brine, and then dried (Na$_2$SO$_4$), filtered and concentrated. The solid was triturated with hot 2-propanol, allowed to cool and the solid was collected via suction filtration, washed with 2-propanol, and MTBE, and air-dried to provide an off white powder (61% yield).

MS m/e (FIA+) 388, 410 (M+Na), m/e (FIA−) 386; $^1$H NMR (500 MHz DMSO-d6) δ10.0 (br s, 1H), 9.2 (s, 1H), 7.83 (d, 4H), 7.68 (d, 2H), 7.63 (d, 2H), 7.4(t, 2H), 7.23 (t, 2H), 7.1 (t, 1H), 6.85 (t, 1H) ppm.

4-(5-Amino-3-phenylamino-[1,2,4]triazol-1-yl)-6-phenylamino-1H-pyrimidin-2-one

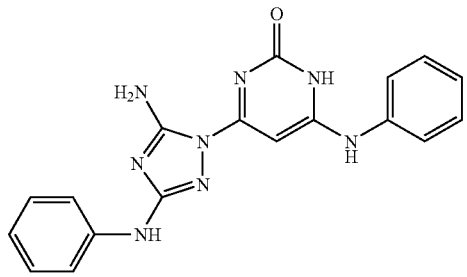

1-(2-Methanesulfonyl-6-phenylamino-pyrimidin-4-yl)-N-3-phenyl-1H-[1,2,4]triazole-3,5-diamine (12 mg, 0.028 mMol) was stirred at ambient temperature in 500 uL of DMF with 200 uL of 1N NaOH for 2 hrs. The reaction was quenched with water and a precipitate allowed come out of solution. The filtrate was decanted off and the solid was resuspended with water, allowed to settle, and again decanted. The solid was transferred to a round bottom flask with acetonitrile and the solvents removed under reduced pressure. The resultant material, a beige yellow solid, resulted in 90% yield.

MS m/e (FIA−) 359; $^1$H NMR (500 mHz DMSO-d6) δ 10.5 (br s, 1H), 9.15 (s, 1H), 7.9 (br s, 2H), 7.66 (d, 4H), 7.4 (t, 2H), 7.2 (t, 2H), 7.18 (br s, 1H), 6.8 (t, 1H), 6.35 (br s, 1H) ppm 1-(2-Methoxy-6-phenylamino-pyrimidin-4-yl)-N-3-phenyl-1H-[1,2,4]triazole-3,5-diamine

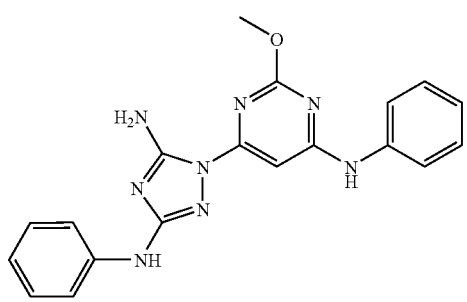

1-(2-Methanesulfonyl-6-phenylamino-pyrimidin-4-yl)-N-3-phenyl-1H-[1,2,4]triazole-3,5-diamine (12 mg, 0.028 mMol) was stirred at ambient temperature in 500 μL of DMF with 200 uL of a freshly prepared sodium methoxide solution for 2 hrs. The reaction was quenched with water and precipitate was allowed to come out of solution. The filtrate was decanted off and material was washed with water, again decanted and the solid transferred to a round bottom flask with acetonitrile and the solvents removed under reduced pressure. Preparative HPLC (gradient: acetonitrile-water, 0.1% TFA eluent) afforded 12 mg of a beige solid, in 90% yield.

MS m/e (FIA+) 375; $^1$H NMR (500 MHz DMSO-d6) δ 9.8 (s, 1H), 9.15 (s, 1H), 7.7 (m, 7H), 7.37 (t, 2H), 7.25 (t, 2H), 7.02 (t, 1H), 6.83 (t, 1H), 6.64 (s, 1H)ppm 6-(5-Amino-3-phenylamino-[1,2,4]triazol-1-yl)-N-2-ethyl-N-2-methyl-N-4-phenyl-pyrimidine-2,4-diamine

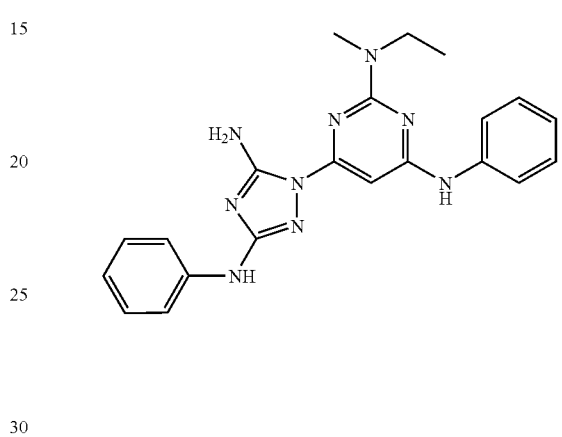

1-(2-Methanesulfonyl-6-phenylamino-pyrimidin-4-yl)-N-3-phenyl-1H-[1,2,4]triazole-3,5-diamine (75 mg, 0.18 mMol) was stirred with (200 uL; 1.5 mMol) of N-ethyl-methylamine in 1 mL of THF in a sealed tube for 10 hr. at 80° C. Quenched with 1N HCl and the resulting precipitate was centrifuged to a pellet. The pellet was suspended in water and again centrifuged to a pellet. Preparative HPLC (gradient: acetonitrile-water, 0.1% TFA eluent) provided the title compound. The purified material was converted into the HCl salt with the addition of 1N HCl, the solvent being removed under reduced pressure. The material was obtained as an off white solid (5 mg, 6% yield).

MS m/e (FIA+) 402, m/e (FIA−) 400; HNMR (500 MHz DMSO-d6) δ9.45 (br s, 1H), 9.05 (br s, 1H), 7.7 (d, 2H), 7.65 (br s, 2H), 7.61 (d, 2H), 7.35 (t, 2 h), 7.25 (t, 2H), 6.97 (t, 1H), 6.85 (t, 1H), 6.33 (s, 1H), 3.6 (br quart, 2H), 3.1 (br s, 3H), 1.15 (t, 3H) ppm Scheme 30

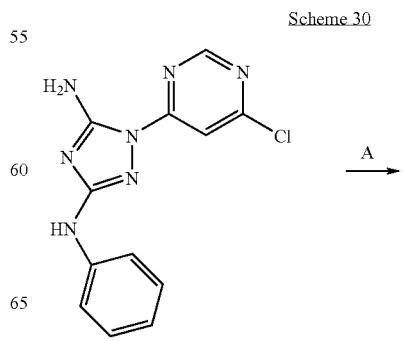

609

-continued

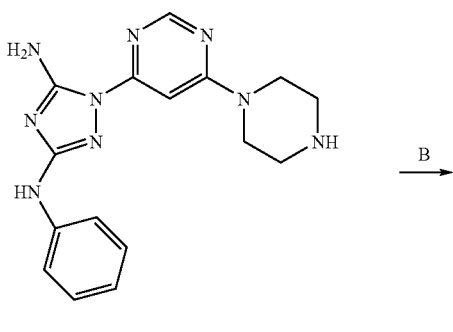

Reaction conditions: A. piperazine, NMP, 220° C., 6 min; B. acid chloride, Hunig's base, $CH_2Cl_2$

Example 66

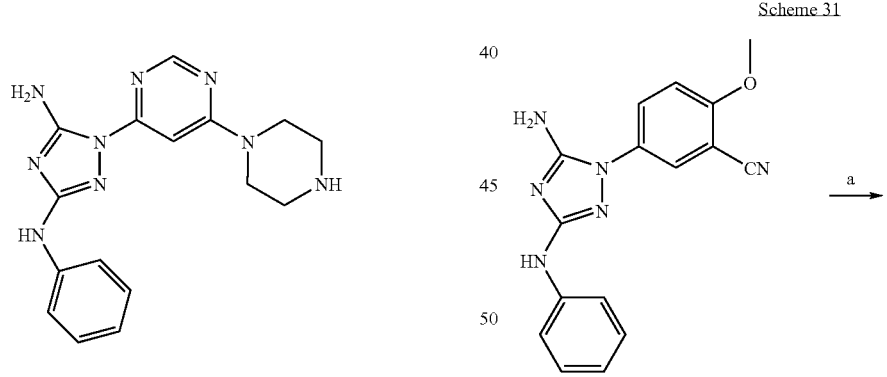

N3-Phenyl-1-(6-piperazin-1-yl-pyrimidin-4-yl)-1H-[1,2,4]triazole-3,5-diamine.

To a solution of 200 mg of 1-(6-chloro-pyrimidin-4-yl)-N-3-phenyl-1H-[1,2,4]triazole-3,5-diamine (0.69 mMol, 1 equiv) in 5 mL of NMP was added 200 mg of piperazine (2.32 mMol, 3.3 equiv). The reaction vessel was sealed and warmed to 220° C. via microwave irradiation for 6 min and allowed to cool. The resulting solution was poured into 50 mL of water and the precipitate was filtered and washed with water (3×20 mL). The resulting waxy solid (150 mg) was used without further purification.

LCMS: Rt=1.35 min, 338.24 (M+H).

610

Example 67

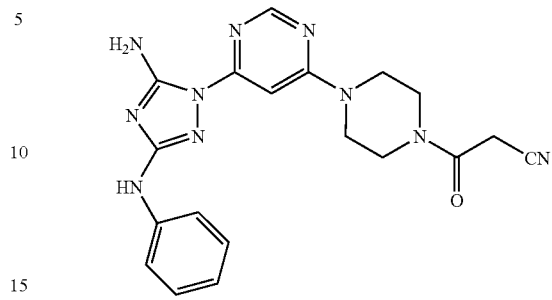

3-{4-[6-(5-Amino-3-phenylamino-[1,2,4]triazol-1-yl)-pyrimidin-4-yl]-piperazin-1-yl}-3-oxo-propionitrile. To a stirred solution of 100 mg of 2-cyanoactetic acid (1.2 mMol, 7.9 equiv) in 10 mL of $CH_2Cl_2$ was added sequentially 300/L of oxalyl chloride (435 mg, 3.45 mMol, 23 equiv) and 1 drop of DMF. The reaction was allowed to stir at 25° C. until effervesence stopped. The reaction was concentrated and azeotroped from $CH_2Cl_2$ (3×10 mL) before being redissolved in 10 mL of $CH_2Cl_2$. To this solution was added 50 mg of N3-phenyl-1-(6-piperazin-1-yl-pyrimidin-4-yl)-1H-[1,2,4]triazole-3,5-diamine (0.148 mMol, 1 equiv) in 5 mL of $CH_2Cl_2$. After the subsequent addition of 200 μL of Hunig's base, the reaction was allowed to stir for 12 h at 25° C. The reaction was then concentrated and purified by silica gel chromatography to yield 2.9 mg (0.007 mMol, 5% yield). LCMS: 2.72 min/405.2 (M+H). $^1$H NMR (500 MHz, $CDCl_3$) δ 8.31 (1H, s), 7.40 (2H, d), 7.25 (2H, t), 6.89 (1H, t), 6.77 (1H, s), 6.65 (2H, br s), 6.45 (1H, s), 3.82 (2H, m), 3.70 (4H, m), 3.52 (2H, m), 3.40 (2H, s) ppm.

Scheme 31

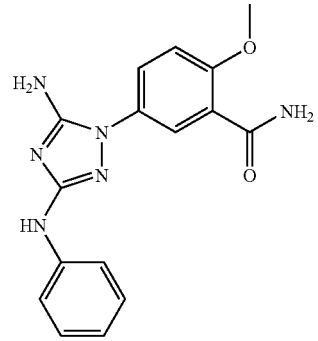

(a) K$_2$CO$_3$, 30% H$_2$O$_2$, DMSO 5-(5-Amino-3-phenylamino-[1,2,4]triazol-1-yl)-2-methoxy-benzamide:

To a stirred solution of 5-(5-amino-3-phenylamino-[1,2,4]triazol-1-yl)-2-methoxy-benzonitrile (20 mg, 0.065 mMol) and K$_2$CO$_3$ (2 mg) in DMSO (0.3 mL), at r.t., add a solution of 30% aq. H$_2$O$_2$, (0.3 mL). After 1 h, add additional 30% aq. H$_2$O$_2$ (0.15 mL). After 40 min, water is added along with 5% aq. Na$_2$CO$_3$ and the mixture is stirred for several minutes. The solid was collected and rinsed with several portions of water and dried in vacuo to provide a white solid (18 mg, 0.055 mMol, 85% yield). $^1$H NMR 500 MHz (dmso) 8.82 (s, 1H), 7.93 (d, 1H), 7.71 (br s, 1H), 7.63 (dd, 1H), 7.60 (br s, 1H), 7.52 (d, 2H), 7.25 (d, 1H), 7.19 (t, 2H), 6.75 (t, 1H), 6.28 (br s, 2H), 3.93 (s, 3H) ppm. LC/MS: Rt=2.27 min, (M+H)=325.2

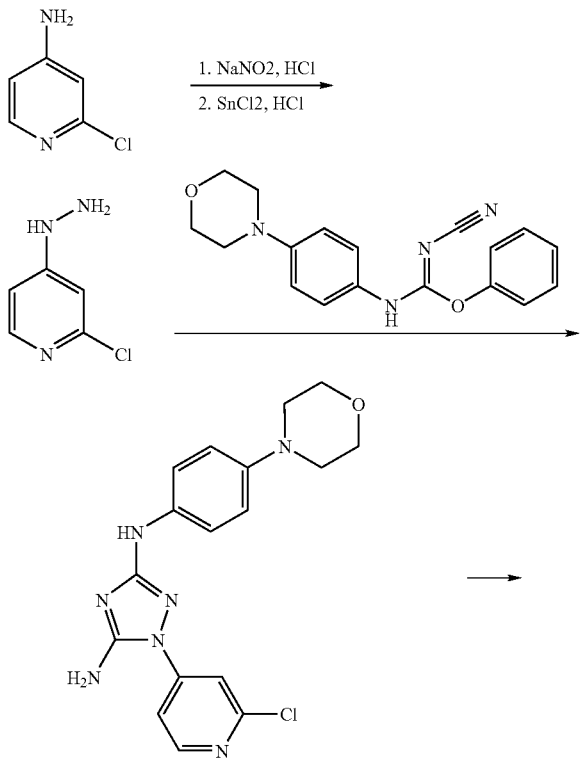

Scheme 32

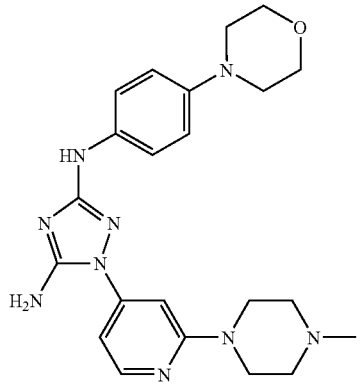

(2-Chloro-pyridin-4-yl)-hydrazine

2-Chloro-pyridin-4-ylamine, (2 g, 15.6 mmol), was dissolved in 20 mL 1M HCl and 4 mL conc. HCl and cooled to 0° C. Sodium nitrite, (1 g, 17 mmol), was dissolved in 2 mL water and added dropwise to the pyridine solution. The mixture was stirred at 0-5° C. for 2 h and then added dropwise to a suspension of SnCl2 in 35 mL conc.HCl at 0° C. The mixture was stirred at 0° C. for 1 h and then the pH carefully raised to pH9-10 with NaOH, using efficient cooling and stirring. The aqueous mixture was extracted with 10% MeOH/chloroform and the organic layer was separated, dried (sodium sulfate), and evaporated. The crude product mixture was purified by column chromatography, (silica, 5% MeOH/DCM), affording 400 mg (2-Chloro-pyridin-4-yl)-hydrazine. MS ES+ 144.0, 146.3

The diaminotriazole 1-(2-Chloro-pyridin-4-yl)-N-3-(4-morpholin-4-yl-phenyl)-1H-[1,2,4]triazole-3,5-diamine, and other diaminotriazoles described in the scheme and table were formed from (2-Chloro-pyridin-4-yl)-hydrazine and imidate esters using procedures described elsewhere in this document.

5-[2-(4-Methyl-piperazin-1-yl)-pyridin-4-yl]-N-2-(4-morpholin-4-yl-phenyl)-5H-imidazole-2,4-diamine: 1-(2-Chloro-pyridin-4-yl)-N-3-(4-morpholin-4-yl-phenyl)-1H [1,2,4]triazole-3,5-diamine, (100 mg, 0.27 mmol), and N-methylpiperazine, (101 mg, 1 mmol) were mixed in 1 mL n-butanol and heated to 230° C. for 360 sec in a Personal Microwave instrument. The solvent was evaporated under vacuum and the residue purified by preparative tlc, (1% NH$_4$OH/10% MeOH/DCM), affording 45 mg 5-[2-(4-Methyl-piperazin-1-yl)-pyridin-4-yl]-N-2-(4-morpholin-4-yl-phenyl)-5H-imidazole-2,4-diamine.

The following compounds were prepared in a similar manner.

| Structure name | MS | NMR |
| --- | --- | --- |
| 5-[2-(4-Methyl-piperazin-1-yl)-pyridin-4-yl]-N2-(4-morpholin-4-yl-phenyl)-5H-imidazole-2,4-diamine | 433.2 | CD3CN: 7.9(d, 1H), 7.5(d, 2H), 7.1(m, 3H), 3.9(m, 4H), , 3.75(m, 2H), 3.25(m, 2H), 3.2(m, 4H), 2.8(s, 6H). |
| 1-[2-(2-Dimethylamino-ethylamino)-pyridin-4-yl]-N3-(4-morpholin-4-yl-phenyl)-1H-[1,2,4]triazole-3,5-diamine | 424.5 | DMSO-d6: 9.8(bs, 1H), 8.85(bs, 1H), 8.2(d, 1H), 7.5(d, 2H), , 7.0(d, 1H), 6.95(s, 1H), 6.90(m, 2H), 6.7(bs, 2H), 4.45(m, 2H), , 3.75(m, 4H), 3.5(m, 2H), 3.2–3.0(m, 8H), 2.85(s, 3H). |

-continued

| Structure name | MS | NMR |
|---|---|---|
| N3-(3-Isopropoxy-4-morpholin-4-yl-phenyl)-1-[2-(4-methyl-piperazin-1-yl)-pyridin-4-yl]-1H-[1,2,4]triazole-3,5-diamine | 494.5 | DMSO-d6: 8.75(s, 1H), 8.10(d, 1H), 7.40(s, 1H), 6.95(d, 1H), , 6.90(d, 1H), 6.85(s, 1H), 6.75(d, 1H), 6.60(bs, 2H), 4.50(m, 1H), , 3.70(m, 4H), 3.50(m, 4H), 2.90(m, 4H), 2.40(m, 4H), , 2.22(s, 3H), 1.32(d, 6H). |

Example 68

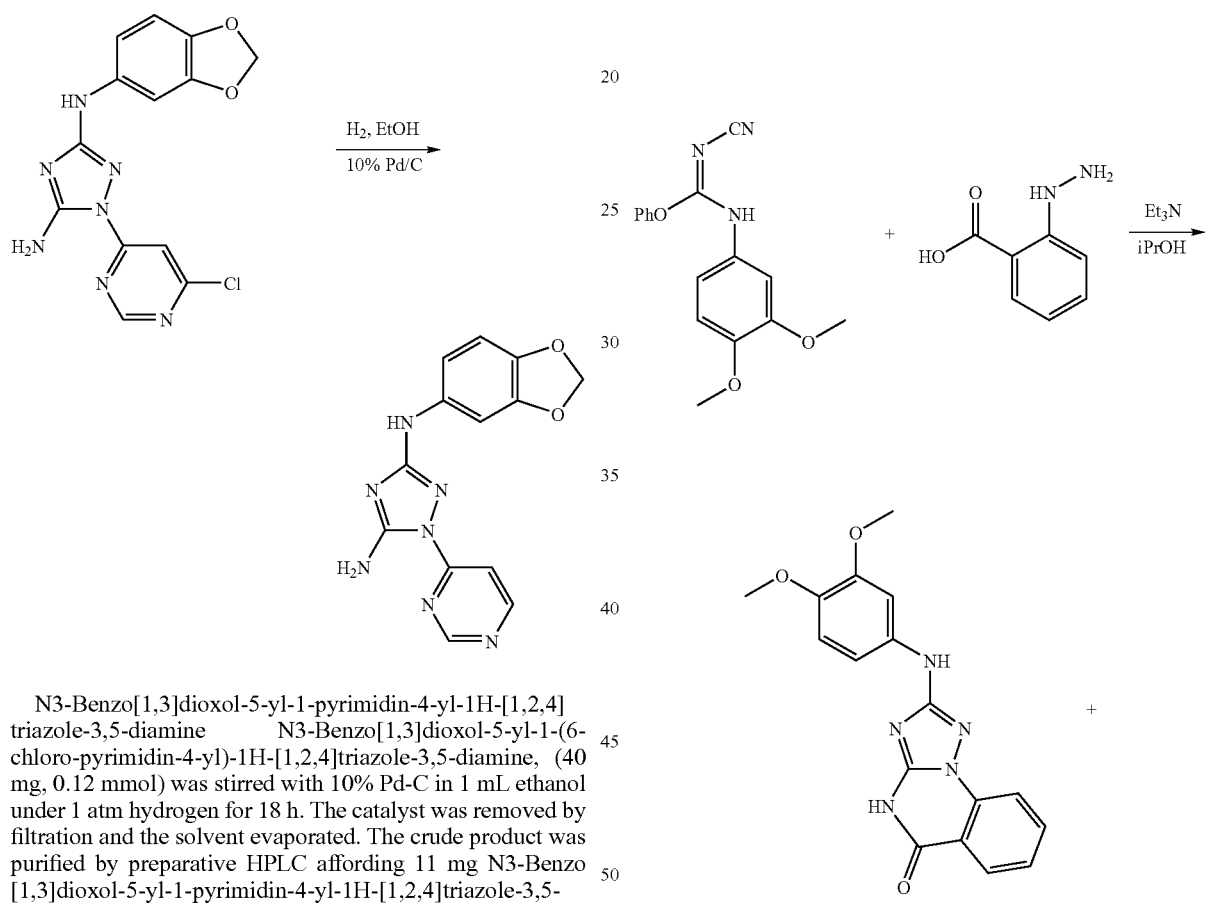

2-(3,4-Dimethoxy-phenylamino)-4H-[1,2,4]triazolo[1,5-a]quinazolin-5-one and 2-Amino-4-(3,4-dimethoxy-phenyl)-4H-[1,2,4]triazolo[1,5-a]quinazolin-5-one N3-Benzo[1,3]dioxol-5-yl-1-pyrimidin-4-yl-1H-[1,2,4]triazole-3,5-diamine N3-Benzo[1,3]dioxol-5-yl-1-(6-chloro-pyrimidin-4-yl)-1H-[1,2,4]triazole-3,5-diamine, (40 mg, 0.12 mmol) was stirred with 10% Pd-C in 1 mL ethanol under 1 atm hydrogen for 18 h. The catalyst was removed by filtration and the solvent evaporated. The crude product was purified by preparative HPLC affording 11 mg N3-Benzo[1,3]dioxol-5-yl-1-pyrimidin-4-yl-1H-[1,2,4]triazole-3,5-diamine as the TFA salt.

$^1$H-NMR acetone-d6: 8.9(s, 1H), 8.8(d, 1H), 8.1(bs, 1H), 7.4(m, 3H), 7.1(d, 1H), 6.8(d, 1H), 5.9(s, 2H)

The following compound was prepared in a similar manner:

| Name | MS (M + H) | HPLC Method A | $^1$H-NMR |
|---|---|---|---|
| N3-(4-Morpholin-4-yl-phenyl)-1-pyrimidin-4-yl-1H-[1,2,4]triazole-3,5-diamine | 339.40 | 1.60 | DMSO-d6: 8.95(s, 1H), 8.90(s, 1H), 7.8(bs, 2H), 7.6(s, 1H), , 7.5(d, 2H), 6.9(d, 2H), 3.75(m, 4H), 3.0(m, 4H). |

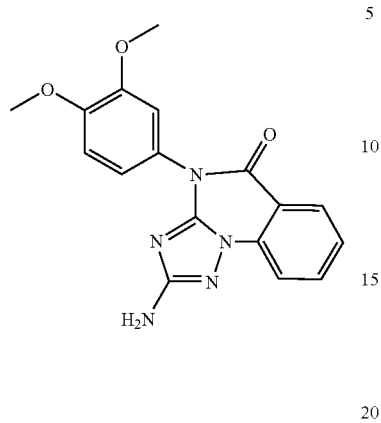

A solution of 1-(3,4-dimethoxy-phenyl)-3-cyano-2-phenyl-isourea (600 mg, 2 mmol), 2-hydrozinobenoic acid hydrochloride (760 mg, 4 mmol) and triethylamine (1.6 mL) in iso-propanol (20 mL) was heated under reflux for 24 h. Evaporation. The residue was suspended in water (50 mL). Filtration. The solid was purified by HPLC to give 2-(3,4-Dimethoxy-phenylamino)-4H-[1,2,4]triazolo[1,5-a]quinazolin-5-one (263 mg) and its isomer (72 mg). Data of 2-(3,4-Dimethoxy-phenylamino)-4H-[1,2,4]triazolo[1,5-a]quinazolin-5-one: FIA-MS; m/e=338.2 (M+H), 336.1 (M−H). Rt=3.09 min (Method A). $^1$H-NMR (500 MHz, DMSO(d6)):12.90 (s, 1H), 9.36 (s, 1H), 8.15 (d, 1H), 7.91 (t, 1H), 7.86 (d, 1H), 7.45 (t, 1H), 7.41 (d, 1H), 7.18 (dd, 1H), 6.90 (d, 1H), 3.80 (s, 3H), 3.71 (s, 3H). Data of 2-Amino-4-(3,4-dimethoxy-phenyl)-4H-[1,2,4]triazolo[1,5-a]quinazolin-5-one: LC-MS; m/e=338.2 (M+H), 336.1 (M−H). Rt=2.34 min. $^1$H-NMR (500 MHz, DMSO(d6)): 8.17 (d, 1H), 7.90 (t, 1H), 7.76 (d, 1H), 7.45 (t, 1H), 7.16 (d, 1H), 7.09 (d, 1H), 7.02 (dd, 1H), 6.04 (s, 2H), 3.82 (s, 3H), 3.70 (s, 3H).

(4,5-Dihydro-[1,2,4]triazolo[1,5-a]quinazolin-2-yl)-(3,4-dimethoxy-phenyl)-amine

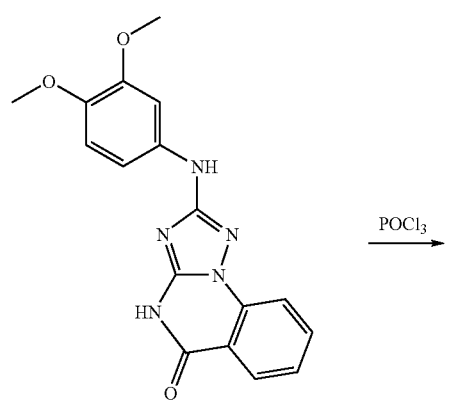

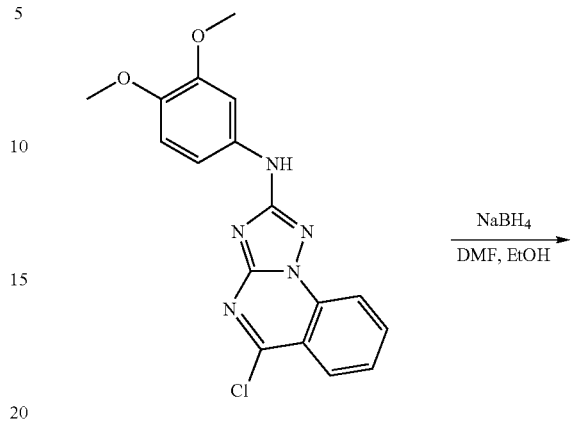

A suspension of 2-(3,4-Dimethoxy-phenylamino)-4H-[1,2,4]triazolo[1,5-a]quinazolin-5-one (57 mg) in phosphorus oxychloride (5 mL) was heated at 90° C. for 2 h. Evaporation. The residue was suspended in dichloromethane, washed with cold sodium bicarbonate, brine and dried (Na$_2$SO$_4$). Filtration and concentration gave crude (5-Chloro-[1,2,4]triazolo[1,5-a]quinazolin-2-yl)-(3,4-dimethoxy-phenyl)-amine (68 mg). LC-MS: m/e=356.1 (M+H), At 0°C, a solution of sodium borohydride (2.0M, 0.25 mL) was added to a solution of the above chloride (38 mg, 0.107 mmol) in chloroform (5 mL) and ethanol (2 mL) (or DMF and MeOH). The reaction mixture was kept at r.t. for 1 h (monitored by analytical HPLC), acidified by trifluoroacetic acid, and purified by HPLC to give the title compound (12 mg). FIA-MS: m/e=324.1 (M+H). R$_t$=3.08 (Method A). $^1$H-NMR (500 MHz, DMSO(d6)): 8.90 (s, 1H), 7.71 (s, 1H), 7.39 (d, 1H), 7.34 (t, 1H), 7.31 (dd, 1H), 7.25 (d, 1H), 7.12 (dd, 1H), 7.08 (td, 1H), 6.84 (d, 1H), 4.50 (s, 2H), 3.77 (s, 3H), 3.68 (s, 3H).

The following compounds were similarly prepared

| Name | MS (M + H) | HPLC Rt (min) Method A | 1H-NMR |
|---|---|---|---|
| (4,5-Dihydro-[1,2,4]triazolo[1,5-a]quinazolin-2-yl)-(3,5-dimethoxy-phenyl)-amine | 324.2 | 3.32 | DMSO(d6)): 7.99(d, 1H), 7.94(br.s, 1H, NH), 7.43(br.s, 1H, NH), 7.34(d, 2H), 7.26(d, 1H), 7.11(ddd, 1H), 6.63 (d, 1H), 6.54(dd, 1H), 4.53(s, 2H), 3.85(s, 3H), 3.74(s, 3H). |
| (4,5-Dihydro-[1,2,4]triazolo[1,5-a]quinazolin-2-yl)-phenyl-amine | 347.1 | 2.71 | DMSO(d6)): 9.15(s, 1H), 7.73(s, 1H), 7.62(d, 2H), 7.36(m, 2H), 7.25(m, 3H), 7.10(ddd, 1H), 6.81(t, 1H), 4.51 (s, 2H). |
| (4,5-Dihydro-[1,2,4]triazolo[1,5-a]quinazolin-2-yl)-(4-morpholin-4-yl-phenyl)-amine | 349.1 | 2.71 | DMSO(d6)): 8.85(s, 1H), 7.68(s, 1H), 7.51(d, 2H), 7.32(m 2H), 7.25(d, 1H), 7.08(td, 1H), 6.88(d, 2H), 4.50 (s, 2H), 3.75(m, 4H), 2.98(m, 4H). |

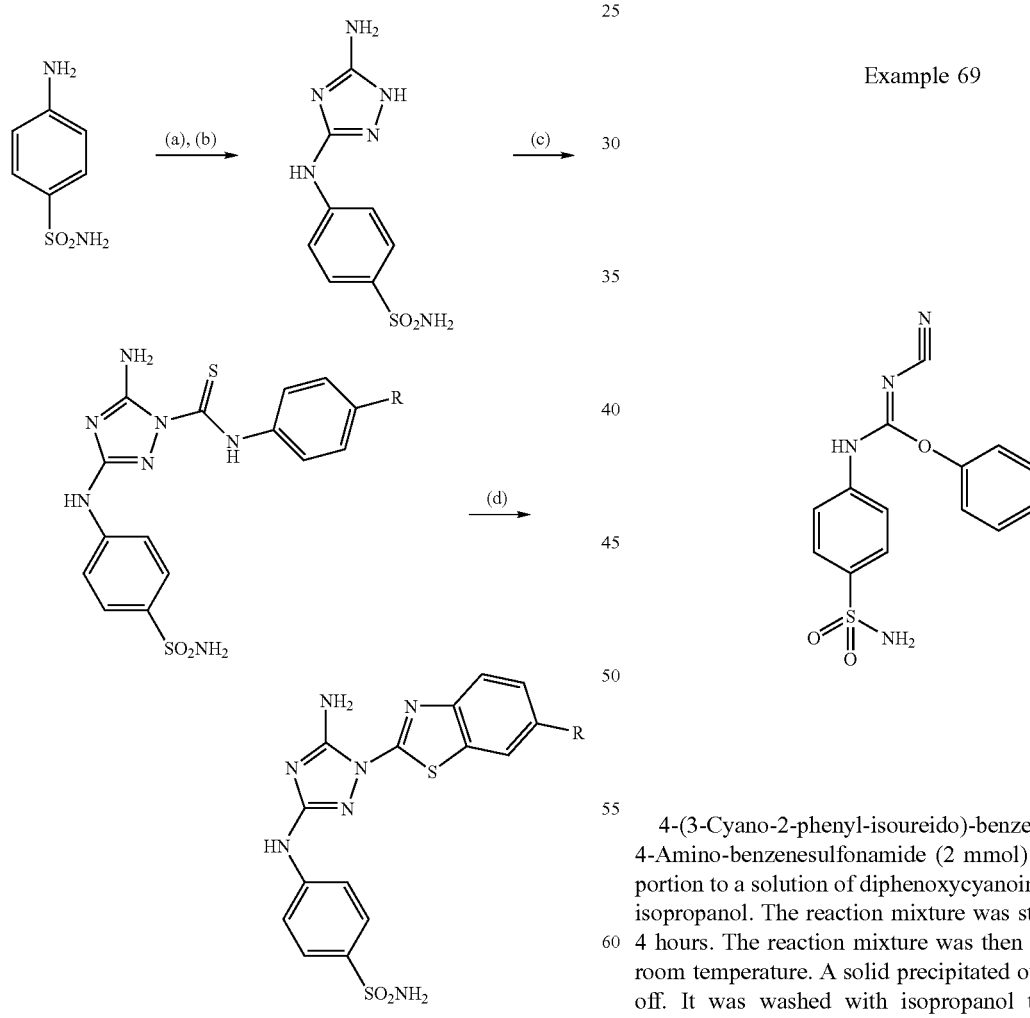

Scheme 33

Reagents: (a) (PhO)$_2$CN(CN), iPrOH, 75° C.; (b) hydrazine monohydrate, iPrOH, 70° C.; (c) Im$_2$CS, imidazole, DMF, RT then aniline, 0° C.; (d) Br$_2$, DMF, RT Scheme 33 above shows a general method for preparing some 6-substituted triazolyl benzothiazoles, where R is either an ether or an amine group, Example 69

4-(3-Cyano-2-phenyl-isoureido)-benzenesulfonamide: 4-Amino-benzenesulfonamide (2 mmol) was added in one portion to a solution of diphenoxycyanoimidate (2 mmol) in isopropanol. The reaction mixture was stirred at 75° C. for 4 hours. The reaction mixture was then allowed to cool to room temperature. A solid precipitated out and was filtered off. It was washed with isopropanol to afford the title compound (0.33 g; 70% yield). $^1$H NMR (400 MHz, DMSO-d6) δ7.30-7.40 (5H, m), 7.45-7.50 (2H, t), 7.65-7.70 (2H, d), 7.80-7.85 (2H, d), 11.20 (1H, s); MS (ES+) m/e=317

Example 70

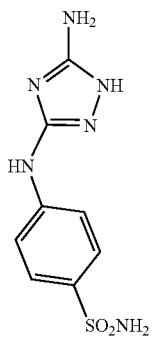

4-(5-Amino-1H-[1,2,4]triazol-3-ylamino)-benzene-sulfonamide: To a solution of 4-(3-cyano-2-phenyl-isoureido)-benzenesulfonamide (1.35 mmol) in TBF (5 ml), was added a solution of hydrazine monohydrate (2 mmol; 1.5 equivalents). The solution was stirred at 70° C. for 16 hours. The reaction mixture was allowed to cool to room temperature. A white solid precipitated out. It was removed by filtration and was washed with ethanol to afford the title compound (300 mg; 87% yield). $^1$H NMR (400 MHz, DMSO-d6) $\delta$5.95-6.00 (2H, s), 7.00-7.05 (2H, s), 7.55-7.65 (4H, m), 9.15-9.20 (1H, s); MS (ES+) m/e=255

Example 71

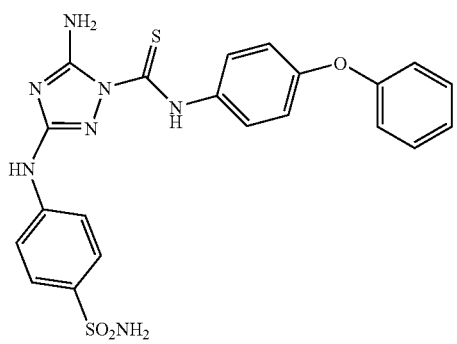

5-Amino-3-(4-sulfamoyl-phenylamino)-[1,2,4]triazole-1-carbothioic acid (4-phenoxy-phenyl)-amide: Thiocarbonyldiimidazole (0.56 mmol, 1.5 equivalent) was added to a solution of 4-phenoxy aniline (0.6 mmol, 1.6 equivalents) and imidazole (0.07 mmol, 0.2 equivalent) in acetonitrile (5 ml). The reaction mixture was stirred at room temperature for three hours. 4-(5-Amino-1H-[1,2,4]triazol-3-ylamino)-benzenesulfonamide (0.37 mM, 1 equivalent) was added in one portion. The reaction mixture was stirred at 50° C. for 16 hours. After addition of DMF (1 ml), the reaction mixture was stirred at 80° C. for one hour. The reaction mixture was concentrated in vacuo. The residue was purified by silica gel chromatography, eluting with EtOAc:pentane (30:70 to 0:100) to afford the title compound (40 mg; 40% yield). $^1$H NMR (400 MHz, DMSO-d6) $\delta$7.05-7.18 (6H, m), 7.20-7.23 (1H, t), 7.40-7.50 (4H, m), 7.70-7.75 (2H, d), 7.80-7.85 (2H, d), 8.45-8.50 (2H, s), 9.80-9.85 (1H, s), 10.90 (1H, s); MS (ES+) m/e=482

Example 72

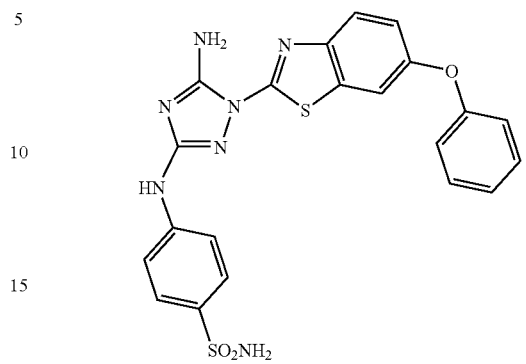

4-[5-Amino-1-(6-phenoxy-benzothiazol-2-yl)-1H-[1,2,4]triazol-3-ylamino]-benzenesulfonamide: Bromine (7 μl, 1 equivalent) was added to a stirred suspension of 5-amino-3-(4-sulfamoyl-phenylamino)-[1,2,4]triazole-1-carbothioic acid (4-phenoxy-phenyl)-amide in dichloromethane (3 ml). The reaction mixture was stirred at room temperature for 18 hours. A solution of bromine (7 μl) in acetic acid (1 ml) was then added to push the reaction to completion: the reaction mixture was stirred for a further four hours. A white solid precipitated and was removed by filtration to afford the title compound (5 mg; 7% yield). $^1$H NMR (400 MHz, DMSO-d6) $\delta$7.05-7.20 (8H, m), 7.35-7.50 (4H, m), 7.70-7.75 (2H, d), 7.80-7.85 (2H, d), 9.90-9.95 (1H, s); MS (ES+) m/e=480

Scheme 34

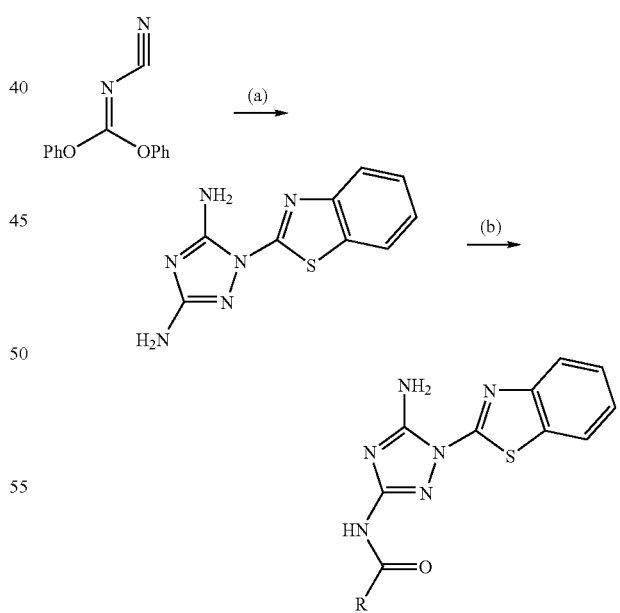

Reagents: (a) NH$_3$, EtOH, 90° C., then benzothiazol-2-yl-hydrazine, NMM, 110° C.; RCOCl, pyridine Scheme 34 above shows a general method for preparing N-(5-Amino-1-benzothiazol-2-yl-1H-[1,2,4]triazol-3-yl)-amides.

Example 73

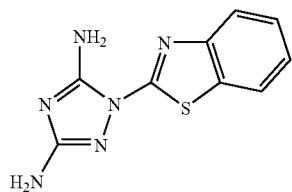

1-Benzothiazol-2-yl-1H-[1,2,4]triazole-3,5-diamine: To a suspension of the diphenoxycyanoimidate (2 mmol) in ethanol (3 ml) in a sealable vial, was added a 2M ammonia ethanolic solution (4 mmol). The reaction mixture was stirred at 90° C. for 48 hours, then concentrated in vacuo. The residue was taken up in N-methylmorpholine (5 ml). To this solution, the benzothiazol-2-yl-hydrazine (2 mmol) was added. The reaction mixture was stirred at 110° C. for 24 hours. Once cooled, distilled water (20 ml) was added to the reaction mixture, which was then partitionned between ethyl acetate and brine (100 ml/100 ml). At this stage, a solid was removed by filtration. This white solid was washed with more ethyl acetate and dried in vacuo to afford the pure title compound (170 mg; 37% yield). $^1$H (400 MHz, DMSO-d6) δ 5.85 (2H, s), 7.30-7.35 (1H, t), 7.45-7.50 (1H, t), 7.60 (2H, s), 7.80-7.85 (1H, d), 7.98-8.02 (1H, d). MS (ES+) m/e=233

Example 74

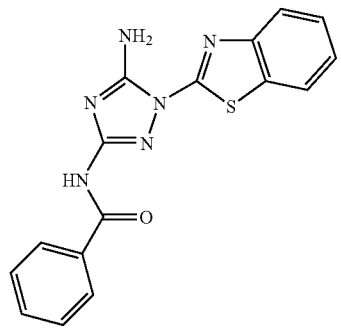

N-(5-Amino-1-benzothiazol-2-yl-1H-[1,2,4]triazol-3-yl)-benzamide: Benzoyl chloride (0.34 mmol) was added dropwise to a stirred solution of 1-benzothiazol-2-yl-1H-[1,2,4]triazole-3,5-diamine (0.34 mmol) in pyridine (3 ml). The reaction mixture was stirred at room temperature for 2 hours then it was concentrated in vacuo. The residue was partitionned between ethyl acetate and 10% aqueous citric acid. At this stage, a white solid was filtered off. The solid was dried in vacuo to afford the pure title compound (10 mg; 15% yield). $^1$H (400 MHz, DMSO-d6) δ 7.40-7.45 (1H, t), 7.50-7.70 (3H, m), 7.85-8.00 (6H, m), 8.1 (1H, d), 10.95 (1H, s). MS (ES+) m/e=337

Scheme 35

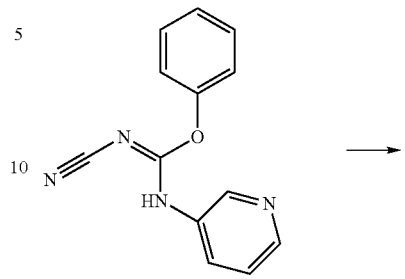

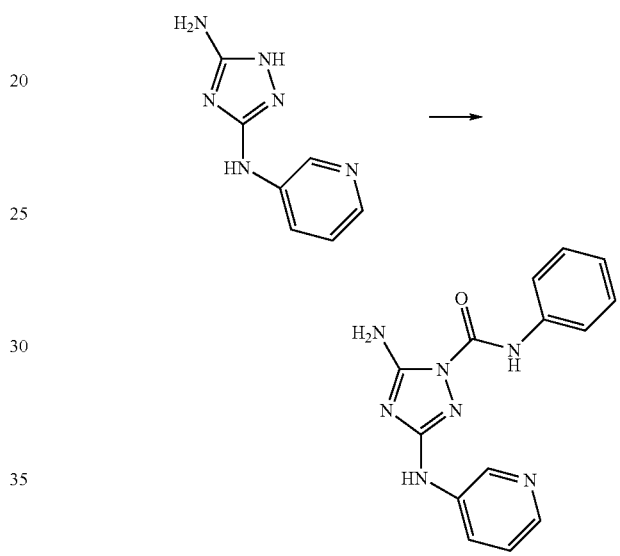

Example 75

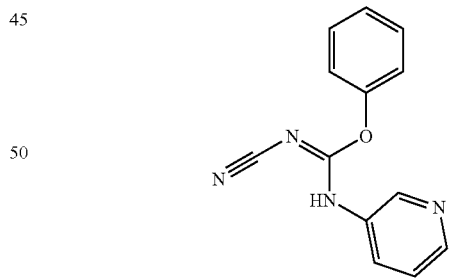

Phenyl-(3-pyridyl)-N-cyanocarbinimidate: To a solution of diphenyl-N-cyanocarbonimidate (1.85 mmol) in tert-butanol (4 mL) was added 3 amino pyridine (1.85 mmol), and the mixture was heated to reflux for 3 hours. Upon cooling to room temperature the resultant white precipitate was collected by filtration under reduced pressure and washed with a little cold Et$_2$O, then dried in vacuo at 40° C. for 3 hours to give the title compound (0.23 g, 54% %). $^1$H NMR (400 MHz, DMSO-d6) δ 7.33 (3H, m), 7.91 (1H, d), 8.43 (1H, d), 8.67 (1H, s), 10.99 (1H, s); MS (ES+): m/e=239.2 (100%).

Example 76

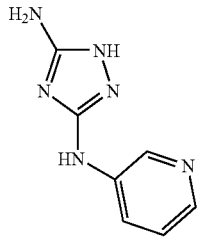

N3-(3-pyridyl)-1H-[1,2,4]triazole-3,5-diamine: To a solution of phenyl-(3-pyridyl)-N-cyanocarbinimidate (1.0 mmol) in isopropanol (10 mL) was added hydrazine hydrate (1 mmol), and the mixture was heated to reflux for 2.5 hours. Upon cooling to room temperature the resultant white precipitate was collected by filtration under reduced pressure and washed with a little cold isopropanol, then dried in vacuuo at 40° C. for 6 hours to give the title compound (0.15 g, 87.5% yield. $^1$H NMR (400 MHz, DMSO-d6) $\delta$5.93 (2H, s), 7.17 (1H, m), 7.94 (2H, m), 8.64 (1H, d), 8.88 (1H, s), 11.24 (1H, s); MS (ES+): m/e=177.2 (100%).

Example 77

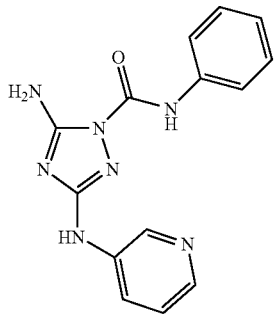

5-Amino-3-(3-pyridylamino)-[1,2,4]triazole-1-carboxylic acid phenylamide: To a solution of N3-(3-pyridyl)-1H-[1,2,4]triazole-3,5-diamine (0.43 mmol) in dry THF (3 mL) and dry DCM (3 mL) was added phenylisocyanate (0.43 mmol) dropwise over 1 minute, and the mixture was stirred at room temperature for 2 hours. The reaction mixture was concentrated in vacuo and the residue purified by column chromatography [Merck silica, eluted with EtOAc and Hexanes (4:1)] to afford compound the title compound (22.0 mg, 17%). $^1$H NMR (400 MHz, DMSO-d6) $\delta$7.17 (1H, t), 7.28 (1H, m), 7.39 (4H, m), 7.65 (2H, d), 8.09 (1H, m), 8.23 (1H, m), 8.79 (1H, d), 9.44 (1H, s), 9.64 (1H, s); MS (ES+): m/e=296.3 (100%).

Additional data for compounds of the invention:

| Compound # | $^1$H NMR | M + 1 (obs) |
|---|---|---|
| I-692 | 3.71(3H, s), 6.89(2H, d), 7.37(1H, t), 7.51 (3H, m), 7.78(2H, s), 7.86(1H, d), 8.06(2H, s), 9.20(1H, s) | 339.2 |
| I-693 | 2.04(3H, s), 7.09(1H, d), 7.17(1H, t), 7.36(1H, t), 7.38(1H, t), 7.42(1H, t), 7.70(1H, s), 7.81 (2H, s), 7.87(1H, d), 8.07(1H, d), 9.40(1H, s), 9.86(1H, s) | 366.3 |
| I-694 | 3.61(3H, s), 3.80(6H, s), 7.04(2H, s), 7.37(1H, t), 7.51(1H, t), 7.80(2H, s), 7.87(1H, d), 8.07 (1H, d), 9.31(1H, s) | 399.3 |
| I-695 | 2.01(3H, s), 7.35(1H, t), 7.47(5H, m), 7.80 (2H, s), 7.87(1H, d), 8.05(1H, d), 9.33(1H, s), 9.78(1H, s) | 366.2 |
| I-696 | 6.33(1H, s), 7.27(3H, m), 7.35(1H, t), 7.48 (1H, t), 7.77(2H, s), 7.84(1H, d), 7.90(1H, s), 8.07(1H, d), 9.09(1H, s), 10.88(1H, s) | 348.3 |
| I-697 | 6.30(1H, m), 7.03(2H, d), 7.07(1H, t), 7.37 (1H, t), 7.48(1H, t), 7.79(2H, s), 7.87(1H, d), 8.07(1H, d), 9.25(1H, s), 9.32(1H, s) | 325.3 |
| I-698 | 3.78(3H, s), 6.46(1H, dd), 7.08(1H, m), 7.17 (1H, t), 7.38(1H, t), 7.40–7.41(1H, m), 7.49 (1H, t), 7.82(2H, br s), 7.86(1H, d). 8.07(1H, d), 9.43(1H, s). | 339 |
| I-699 | 3.88(3H, s), 7.38–7.51(5H, m), 7.87–7.89(3H, m), 8.09(1H, d), 8.31(1H, s), 9.71(1H, s). | 367 |
| I-700 | 7.38(1H, t), 7.52(1H, t), 7.66(1H, d), 7.86–7.93 (6H, m), 8.08(1H, d), 9.94(1H, s), 12.55(1H, br s) | 353 |
| I-701 | 3.46(3H, s), 7.08(1H, t), 7.35(3H, t), 7.49(3H, m), 7.82(2H, s), 7.86(1H, d), 8.04(1H, s) | 323.3 |
| I-702 | 7.18(1H, d), 7.40(1H, t), 7.50(1H, t), 7.58(1H, d), 7.90(4H, m), 8.49(1H, s), 8.64(1H, d), 9.61 (1H, s), 12.81(1H, s) | 349.3 |
| I-703 | 3.01(4H, m), 3.72(4H, m), 6.91(2H, d), 7.37 (1H, t), 7.49(3H, m), 7.78(2H, s), 7.86(1H, d), 8.06(1H, d), 9.15(1H, s) | 394.3 |
| I-704 | 1.47(9H, s), 7.37(4H, m), 7.48(4H, m), 7.79 (2H, s), 7.86(1H, d), 8.05(1H, d), 9.12(1H, s), 9.26(1H, s) | 424.3 |
| I-705 | 3.62(3H, s), 3.79(6H, s), 7.03(2H, s), 7.38 (2H, m), 7.67(1H, m), 7.75(3H, m), 9.22(1H, s) | 383.29 |
| I-706 | 3.63(3H, s), 3.76(6H, s), 5.80(1H, s), 6.55(1H, s), 7.25(2H, m), 7.43(1H, br s), 7.59(1H, d), 7.98(1H, br s), 8.44(1H, d) | 382.32 |
| I-707 | 3.61(3H, s), 3.84(6H, s), 7.00(2H, s), 7.18(2H, m), 7.47(1H, m), 7.56(1H, m), 7.70(1H, s), 9.02(1H, s), 12.4(1H, br s) | 382.31 |
| I-708 | 5.95(2H, s), 6.85(1H, d), 7.01(1H, d.o.d), 7.33 (1H, d), 7.37(1H, t), 7.49(1H, t), 7.80(2H, s), 7.86(1H, d), 8.04(1H, d), 9.31(1H, s) | 353.3 |
| I-709 | 6.51(1H, d), 7.39(1H, t), 7.53(1H, t), 7.70 (5H, m), 7.86(2H, s), 7.88(1H, s), 8.08(1H, d), 8.39(1H, d), 9.62(1H, s) | 375.3 |
| I-710 | 7.08(1H, t), 7.37(1H, t), 7.51(3H, t), 7.54(2H, d), 7.66(1H, s), 7.70(2H, d), 7.86(2H, s), 7.88 (1H, s), 8.08(1H, d), 8.15(1H, s), 9.65(1H, s) | 375.3 |
| I-711 | 7.37(1H, t), 7.49(1H, t), 7.77(2H, d), 7.89 (3H, m), 8.18(3H, m), 9.45(1H, s), 9.76(1H, s) | 393.3 |
| I-712 | 4.64(2H, s), 6.61(2H, s), 7.26(2H, d), 7.39 (1H, t), 7.48(1H, t), 7.72(2H, s), 7.93(1H, d), 8.04(1H, d), 8.86(1H, s) | 324.3 |
| I-713 | 7.33–7.38(2H, m), 7.48–7.52(2H, m), 7.75(1H, d), 7.88(1H, d), 7.93(2H, br s), 8.06(1H, m), 8.10(1H, d), 9.92(1H, s). | 334 |
| I-714 | 6.88(1H, t), 7.28(2H, t), 7.36(1H, t), 7.51(1H, t), 7.59–7.61(2H, m), 7.83(2H, br s), 7.86(1H, d), 8.06(1H, d), 9.45(1H, s). | 309 |
| I-715 | 2.79(3H, s), 7.30(1H, d), 7.33–7.39(2H, m), 7.51(1H, t), 7.78(1H, m), 7.86–7.88(4H, m), 8.00(1H, s), 8.08(1H, d), 8.45(1H, d), 9.57 (1H, s). | 366 |
| I-716 | 2.97(3H, br s), 3.01(3H, br s), 6.89(1H, d), 7.31–7.37 (2H, m), 7.51(1H, t), 7.63–7.64(3H, m), 8.08(1H, d), 9.60(1H, s). | 380 |
| I-717 | 4.42(2H, s), 5.02(1H, t), 7.22(2H, d), 7.36(1H, t), 7.48(1H, t), 7.55(2H, d), 7.82(2H, br s), 7.86 (1H, d), 8.06(1H, d), 9.39(1H, s). | 339 |

| Compound # | ¹H NMR | M + 1 (obs) |
|---|---|---|
| I-718 | 7.06(1H, t), 7.26(1H, t), 7.35–7.40(2H, m), 7.51(1H, t), 7.71(1H, m), 7.87(2H, m), 8.09 (1H, d), 9.67(1H, br s), 12.50(1H, vbr s). | 387 |
| I-719 | 4.47(2H, d), 5.15(1H, t), 6.84(1H, d), 7.23(1H, t), 7.36(1H, t), 7.49–7.52(3H, m), 7.82(2H, br s), 7.86(1H, d), 8.07(1H, d), 9.40(1H, s). | 339 |
| I-720 | 1H NMR(CDCl3)3.24(3H, d J 5.01Hz), 3.89 (3H, s), 4.02(3H, s), 6.63(1H, br), 6.81–6.88 (2H, m), 7.31–7.35(1H, m), 7.45–7.49(1H, m), 7.57–7.58(1H, m), 7.70–7.74(1H, m), 7.80–7.84 (2H, m). | 383.24 |
| I-721 | 3.74(3H, s), 4.29(2H, d, J=6.2Hz), 6.77–6.82 (1H, m), 6.90–7.01(3H, m), 7.20–7.26(1H, m), 7.29–7.35(1H, m), 7.42–7.49(1H, m), 7.68(2H, br s), 7.79–7.81(1H, m), 7.99–8.01(1H, m). | 353.18 |
| I-722 | 4.22(2H, d, J=6.3Hz), 5.98(2H, s), 6.80–6.95 (4H, m), 7.29–7.36(1H, m), 7.41–7.50(1H, m), 7.67(2H, br s), 7.80(1H, d, J=8.0Hz), 8.00(1H, d, J=8.0Hz) | 367.22 |
| I-723 | 3.71(3H, s), 3.74(3H, s), 4.24(2H, d, J=6.2Hz), 5.75–5.78(1H, m), 6.84–6.91(3H, m), 7.00–7.03(1H, m), 7.29–7.36(1H, m), 7.42–7.50 (1H, m), 7.67(2H, br s), 7.79–7.82(1H, m), 7.90–8.11 (1H, m). | 383.23 |
| I-724 | 3.62(3H, s), 3.81(6H, s), 7.03(2H, s), 7.52–7.55 (1H, m), 7.81–7.85(3H, m), 8.22(1H, d), 9.34(1H, s) | 433.16 |
| I-725 | 3.61(3H, s), 3.81(6H, s), 7.03(2H, s), 7.34–7.39 (1H, m), 7.78(2H, m), 7.85–7.88(1H, m), 7.98–8.01(1H, m), 9.32(1H, s) | 417.24 |
| I-726 | (CDCl3/CD3OD): 7.33(1H, t), 7.46(1H, t), 7.62(2H, m), 7.69(2H, m), 7.82(2H, t), 8.08 (1H, s), 8.52(1H, s) | 376.3 |
| I-727 | 3.61(3H, s), 3.81(6H, s), 3.82(3H, s), 7.04(2H, s), 7.07–7.10(1H, m), 7.68–7.76(4H, m), 9.30 (1H, s) | 429.21 |
| I-728 | (CDCl3)3.85–4.97(6H, m), 6.45–6.50(1H, dd), 6.50–6.55(2H, s), 6.8–6.85(1H, d), 7.3–7.4(1H, t), 7.45–7.50(1H, t), 7.8–7.9(2H, m), 8.0(1H, s) | 369 |
| I-729 | (CDCl3)1.25(3H, s), 3.97(3H, s), 6.38–6.4.2 (1H, s), 6.50–6.60(3H, m), 7.05(1H, d), 7.35–7.40 (1H, t), 7.45–7.50 ppm(1H, m), 7.8–7.9 (2H, m), 8.0(1H, s) | 353 |
| I-730 | 7.30–7.60(6H, m), 7.82–7.90(3H, m), 8.08(1H, m), 9.62(1H, s) | 389.09 |
| I-731 | 3.60(3H, s), 3.77(6H, s), 4.21(3H, s), 6.98 (2H, br s), 7.26(2H, m), 7.59(2H, m), 7.72(2H, s), 9.12(1H, br s) | 396.29 |
| I-732 | 3.53(9H, m), 6.20(2H, s), 6.84(2H, s), 7.25 (7H, m), 7.43(1H, m), 7.60(1H, m), 7.88(2H, s), 9.18(1H, s) | 472.42 |
| I-733 | 2.42(3H, s), 3.61(3H, s), 3.81(6H, s), 7.04(2H, br s), 7.32(1H, d), 7.76(3H, m), 7.86(1H, s), 9.30(1H, s) | 413.31 |
| I-734 | 3.27(3H, s), 3.62(6H, s), 3.81(6H, s), 7.06(2H, s), 7.90(2H, br s), 8.02(2H, s), 8.72(1H, s), 9.40(1H, s) | 477.28 |
| I-735 | 0.85–0.90(4H, m), 2.01–2.05(1H, m), 3.59 (3H, s), 3.76(6H, s), 6.93(1H, s), 7.00(2H, s), 7.41(2H, s), 9.17(1H, s) | 389.23 |
| I-736 | 6.95–7.05(1H, m), 7.15–7.25(2H, m), 7.32–7.40 (1H, t), 7.45–7.52(1H, t), 7.8–7.9(3H, m), 8.05–8.10 (1H, d), 8.10–8.14(1H, t), 9.0(1H, s) | 326 |
| I-737 | 3.62(3H, s), 3.81(6H, s), 7.04(2H, s), 7.49(1H, m), 7.82(2H, br s), 7.93(1H, d), 8.21(1H, s), 9.30(1H, s) | 483.22 |
| I-738 | 7.40–7.45(1H, t), 7.50–7.70(3H, m), 7.85–8.00 (6H, m), 8.1(1H, d), 10.95(1H, s) | 337 |
| I-739 | 2.85(2H, t), 3.33(2H, m), 6.52(1H, t), 7.34 (6H, m), 7.46(2H, s), 7.66(2H, s), 7.82(1H, d), 8.01(1H, d), 8.52(1H, s) | 337.3 |
| I-740 | 2.74(2H, m), 3.24(2H, m), 6.46(1H, m), 6.70 (2H, d), 7.05(2H, s), 7.33(1H, t), 7.46(1H, t), 7.65(2H, s), 7.82(1H, d), 8.01(1H, d), 9.17 (1H, s) | 353.3 |
| I-741 | 2.94(2H, m), 3.38(2H, m), 6.55(1H, m), 7.32 (3H, m), 7.49(3H, m), 7.71(2H, s), 7.77(2H, d), 7.82(1H, d), 8.01(1H, d) | 416.3 |
| I-742 | 3.90(2H, s), 7.24(1H, m), 7.39(3H, m), 7.56 (2H, m), 7.63(1H, d), 7.77(2H, m), 7.86(4H, m), 8.08(1H, t), 9.58(1H, s) | 397.4 |
| I-743 | 1.10(3H, t), 2.28(2H, q), 7.34(1H, t), 7.49(5H, m), 7.80(2H, s), 7.87(1H, d), 8.06(1H, d), 9.33 (1H, s), 9.70(1H, s) | 380.3 |
| I-744 | 3.62(3H, s), 3.81(6H, s), 7.05(2H, s), 7.82(1H, dd), 7.89(2H, br s), 8.01(1H, d), 8.58(1H, s), 9.38(1H, s) | 467.22 |
| I-747 | 7.06(1H, d), 7.23(1H, t), 7.35(1H, t), 7.51(2H, m), 7.86(1H, d), 7.91(2H, s), 7.92(1H, m), 8.10 (1H, d), 9.69(1H, s) | 387.2 |
| I-748 | 4.19(4H, m), 6.76(1H, d), 6.95(1H, dd), 7.30 (1H, d), 7.37(1H, t), 7.49(1H, t), 7.78(2H, s), 7.86(1H, d), 8.07(1H, d), 9.20(1H, s) | 367.3 |
| I-749 | 2.29(3H, s), 6.71(1H, d), 7.17(1H, t), 7.29(1H, t), 7.39(1H, m), 7.42(1H, d), 7.48(1H, t), 7.81 (2H, s), 7.87(1H, d), 8.06(1H, d), 9.35(1H, s) | 323.3 |
| I-750 | 7.20(1H, m), 7.37–7.40(1H, t), 7.50–7.55(1H, t), 7.90–8.00(4H, m), 8.1(2H, m) | 343 |
| I-751 | 6.69(2H, d), 7.33–7.41(3H, m), 7.49(1H, t), 7.76(2H, br s), 7.84(1H, d), 8.04(1H, d). 9.06 (1H, s). | 325 |
| I-752 | 7.32(1H, t), 7.40(2H, br s), 7.78(2H, br s), 7.82 (1H, d), 8.03(1H, d), 8.06(1H, s), 9.34(1H, s), 12.84(1H, br s) | 349 |
| I-753 | 7.17(2H, s), 7.40(1H, t), 7.52(1H, t), 7.69–7.74 (4H, m), 7.88(1H, d), 7.91(2H, br s), 8.07(1H, d), 9.95(1H, s). | 388 |
| I-754 | 2.97(6H, s), 7.36–7.38(3H, m), 7.47–7.53(1H, m), 7.62(2H, d), 8.07(1H, d), 9.71(1H, s). | 380 |
| I-755 | 3.17(3H, d), 7.36(1H, t), 7.51(1H, t), 7.62 (2H, d), 7.77(2H, d), 7.87–7.89(3H, m), 8.07 (1H, d), 8.22(1H, m), 9.77(1H, s). | 366 |
| I-756 | 1.36(3H, d), 4.67–4.69(1H, m), 5.13(1H, d), 6.87(1H, d), 7.19(1H, t), 7.36(1H, t), 7.48–7.52 (2H, m), 7.58(1H, s), 7.81(2H, br s), 7.86(1H, d), 8.07(1H, d), 9.37(1H, s). | 353 |
| I-757 | 7.15(1H, t), 7.34–7.39(2H, m), 7.50(1H, t), 7.72–7.73(1H, m), 7.81(2H, br s), 7.85–7.87(2H, m), 8.06(1H, d), 9.25(1H, d). | 353 |
| I-758 | 3.62(3H, s), 3.81(6H, s), 7.04(2H, s), 7.37 (1H, m), 7.60(1H, m), 7.84(2H, s), 8.07(1H, m), 9.40(1H, s) | 433.33 |
| I-759 | 7.31(2H, s), 7.33(1H, t), 7.35(1H, t), 7.48(1H, t), 7.49(1H, t), 7.80(1H, d.o.d), 7.87(1H, d), 7.89(2H, s), 8.07(1H, d), 8.09(1H, s), 9.80(1H, s) | 388.3 |
| I-760 | 2.24(3H, s), 7.09(2H, d), 7.37(1H, t), 7.49 (3H, m), 7.80(2H, s), 7.86(1H, d), 8.07(1H, d), 9.30(1H, s) | 323.3 |
| I-761 | 6.93(1H, d), 7.29(1H, t), 7.39(1H, m), 7.47(1H, d), 7.53(1H, t), 7.78(1H, t), 7.86(1H, d), 7.88 (2H, s), 8.10(1H, d), 9.71(1H, s) | 343.2 |
| I-762 | 4.34(2H, d, J=6.4Hz), 6.93–6.98(1H, m), 7.20–7.24(1H, m), 7.29–7.49(6H, m), 7.65(2H, br s), 7.79–7.82(1H, m), 7.98–8.03(1H, m) | 323.26 |
| I-763 | 2.18(3H, s), 2.21(3H, s), 7.02(1H, d, J=7.8Hz), 7.32–7.39(3H, m), 7.47–7.53(1H, m), 7.78(2H, br s), 7.87(1H, d, J=8.0Hz), 8.07(1H, d, J=7.8Hz), 9.17(1H, s) | 337.24 |
| I-764 | 3.66(3H, s), 3.84(6H, s), 4.01(3H, s), 6.17 (2H, s), 6.99(2H, s), 7.12(1H, d), 7.33(1H, t), 7.62(1H, d), 10.42(1H, s) | 429.39 |
| I-765 | 3.62(3H, s), 3.81(6H, s), 3.97(3H, s), 7.04(2H, br s), 7.10(1H, d), 7.32(1H, t), 7.62(1H, dd), 7.74(2H, br s), 9.28(1H, s) | 429.34 |
| I-766 | 1.37(9H, s), 3.64(3H, s), 3.81(6H, s), 6.00(2H, br s), 6.94(2H, s), 6.99(1H, s), 10.23(1H, s) | 405.39 |
| I-767 | 3.62(3H, s), 3.80(6H, s), 5.28(2H, s), 6.75(1H, dd), 7.02(2H, s), 7.07(1H, d), 7.51(1H, d), 7.59 (2H, s), 9.16(1H, s) | 414.31 |

-continued

| Compound # | ¹H NMR | M + 1 (obs) |
|---|---|---|
| I-768 | 1.52–1.63(4H, m), 3.03–3.08(2H, m), 3.43–3.47 (2H, m), 3.62(3H, s), 3.80(6H, s), 4.40 (1H, t), 5.82(1H, m), 6.78(1H, dd), 7.03(2H, s), 7.07(1H, d), 7.54(1H, d), 7.59(2H, s), 9.17 (1H, s) | 486.37 |
| I-769 | 7.34–7.41(1H, m), 7.44–7.55(3H, m), 7.85–7.92 (3H, m), 7.98(1H, d, J=2.4Hz), 8.10(1H, d, J=7.8Hz), 9.81(1H, s) | 377.20 |
| I-770 | 2.0(2H, m), 2.75–2.9(4H, m), 7.1(1H, d), 7.4 (2H, m), 7.5(2H, m), 7.75(2H, bs), 7.85(1H, d), 8.05(1H, d), 9.2(1H, s) | 349 |
| I-771 | 7.36(1H, m), 7.44(1H, m), 7.5(1H, m), 7.74 (1H, m), 7.84–7.9(3H, m), 8.02(1H, d), 8.07 (1H, d), 9.74(1H, s) | 387 |
| I-772 | 3.79(3H, s), 7.07–7.14(1H, m), 7.21–7.29(1H, m), 7.32–7.49(1H, m), 7.48–7.53(1H, m), 7.56–7.64 (1H, m), 7.81(2H, br s), 7.83–7.89(1H, m), 8.03–8.09(1H, m), 9.40(1H, s) | 357.27 |
| I-773 | 34.39(2H, d, J=6.2Hz), 7.04–7.10(1H, m), 7.29–7.35(1H, m), 7.40–7.51(3H, m), 7.58–7.61 (1H, m), 7.69(2H, br s), 7.79–7.82(1H, m), 7.98–8.08 (1H, m) | 391.25 |
| I-774 | 2.72(3H, s), 3.66(3H, s), 3.83(6H, s), 6.14(2H, bs), 7.06(2H, s), 7.28(1H, t), 7.37(1H, m), 7.88 (1H, d), 10.36(1H, s) | 413.35 |
| I-775 | 2.63(3H, s), 3.62(3H, s), 3.82(6H, s), 7.05(2H, s), 7.27(2H, m), 7.75(2H, bs), 7.87(1H, d), 9.25(1H, s) | 413.36 |
| I-776 | 3.83(3H, s), 6.19(2H, br s), 7.18–7.28(1H, m), 7.35–7.41(1H, m), 7.45–7.58(2H, m), 7.83–7.94 (1H, m), 7.98–8.09(2H, m), 10.15(1H, s) | 357.28 |
| I-777 | 3.65(3H, s), 3.82(6H, s), 6.05(2H, br), 7.12 (2H, s), 7.37–7.39(1H, m), 7.45–7.49(2H, m), 7.66–7.68(2H, m), 8.06(1H, s), 9.77(1H, br) | 425.38 |
| I-778 | 7.33(2H, d), 7.37(1H, t), 7.50(1H, t), 7.62 (2H, d), 7.83(2H, s), 7.88(1H, d), 8.07(1H, d), 9.58(1H, s) | 343.2 |
| I-779 | 2.93(6H, d), 6.27(1H, dd), 6.83(1H, d), 7.07 (1H, t), 7.26(1H, m), 7.35(1H, t), 7.48(1H, t), 7.63(2H, s), 7.87(1H, d), 8.07(1H, d), 9.15 (1H, s) | 352.4 |
| I-780 | 2.50(3H, s), 6.78(1H, d), 7.27(1H, t), 7.29 (1H, m), 7.36(1H, t), 7.49(1H, t), 7.69(1H, s), 7.81(2H, s), 7.88(1H, d), 8.08(1H, d), 9.45 (1H, s) | 355.3 |
| I-781 | 2.44(3H, s), 7.24(2H, d), 7.38(1H, t), 7.50 (1H, t), 7.56(2H, d), 7.80(2H, s), 7.87(1H, d), 8.07(1H, d), 9.43(1H, d) | 355.3 |
| I-782 | 1.49(9H, s), 6.91(1H, d), 7.13(1H, t), 7.38(2H, m), 7.50(1H, t), 7.70(1H, t), 7.77(2H, s), 7.87 (1H, d), 8.03(1H, d), 9.22(1H, s), 9.29(1H, s) | 424.4 |
| I-783 | 3.57(3H, s), 3.65(6H, s), 6.90(2H, s), 7.49(2H, t), 7.62(2H, t), 7.78(2H, s), 8.14(2H, d), 9.14 (1H, s) | 370.4 |
| I-784 | 3.23–3.48(7H, m), 4.00(3H, s), 7.08–7.11(1H, m), 7.35–7.41(1H, m), 7.49–7.55(1H, m), 7.68–7.71 (1H, m), 7.79–7.91(4H, m), 8.05–8.12(2H, m), 9.80(1H, s) | 440.33 |
| I-785 | 3.62(3H, s), 3.81(6H, s), 7.04(2H, s), 7.25(1H, td), 7.68(1H, dd), 7.80(2H, br s), 8.09(1H, dd), 9.30(1H, s) | 417.29 |
| I-786 | 1.98(3H, s), 2.15(3H, s), 7.15(H, d), 7.3(2H, m), 7.4(H, t), 7.5(H, t), 7.75(2H, s), 7.9(H, d), 8.05(H, d), 9.1(H, s), 9.3(H, s) | 380 |
| I-787 | 7.3(2H, m), 7.5(1H, t), 7.85(3H, m), 8.05(3H, m), 8.8(1H, s)and 9.65(1H, s) | 310 |
| I-788 | 4.89(2H, s), 6.14(1H, d), 6.76(1H, s), 6.88 (2H, m), 7.35(1H, t), 7.49(1H, t), 7.74(2H, s), 7.86(1H, d), 8.05(1H, d), 9.03(1H, s) | 324.3 |
| I-789 | 1.70–1.83(2H, m), 3.28(3H, s), 3.30–3.45(4H, m), 4.00(3H, s), 7.06–7.10(1H, m), 7.34–7.41 (1H, m), 7.49–7.55(1H, m), 7.68–7.71(1H, m), 7.76–7.91(4H, m), 8.05–8.12(2H, m), 9.79(1H, s) | 454.31 |

-continued

| Compound # | ¹H NMR | M + 1 (obs) |
|---|---|---|
| I-790 | 4.15(3H, s), 7.10(2H, br), 7.25–7.32(2H, m), 7.60–7.74(8H, m), 9.73(1H, br) | 385.34 |
| I-791 | 4.19(3H, s), 7.24(2H, br), 7.26–7.34(3H, m), 742–7.46(1H, m), 7.58–7.64(3H, m), 7.70(2H, m), 8.39(1H, br), 9.63(1H, br) | 385.32 |
| I-792 | 3.95(3H, s), 4.20(3H, s), 7.25–7.30(1H, d), 7.38–7.45(2H, m), 7.50–7.55(1H, t), 7.70–7.75 (1H, d), 7.85–7.95(3H, m), 8.25(1H, s), 9.75 (1H, s) | |
| I-793 | 4.85(3H, s), 7.12–7.18(1H, d), 7.20–7.30(2H, s), 7.45–7.55(1H, t), 7.70(1H, s), 7.75–7.90(3H, m), 8.12 ppm(1H, s), 8.3–8.5(1H, s), 9.75(1H, s) | |
| I-794 | (CD3OD/CDCl3): 2.93(3H, d), 7.21(2H, d), 7.23(2H, d), 7.44(1H, t), 7.50(1H, t), 7.52(2H, d), 7.81(2H, br) | 403.4 |
| I-795 | 3.62(2H, s), 3.64(3H, s), 6.79(1H, d), 7.23 (1H, t), 7.38(1H, t), 7.48(1H, s), 7.52(1H, t), 7.56(1H, d), 7.80(2H, s), 7.88(1H, d), 8.08 (1H, d), 9.40(1H, s) | 381.3 |
| I-796 | 3.85(3H, s), 7.00(1H, dd), 7.28(2H, br s), 7.35 (1H, d), 7.46–7.49(2H, m), 7.81(1H, d), 7.82 (2H, br s), 7.93(1H, d), 8.09(1H, s), 9.36(1H, s) | 418.23 |
| I-797 | 1.40(9H, s), 1.54–1.66(2H, m), 2.94–3.04(2H, m), 3.24–3.35(2H, m), 4.01(3H, s), 6.82(1H, brt, J=5.5Hz), 7.05–7.62(1H, m), 7.34–7.41 (1H, m), 7.48–7.55(1H, m), 7.68–7.70(1H, m), 7.77–7.81(1H, m), 7.81–7.91(3H, m), 8.05–8.10 (1H, m), 9.80(1H, s) | 539.41 |
| I-798 | 2.38–2.52(6H, m), 3.38–3.48(2H, m), 3.58–3.68 (4H, m), 4.04(3H, s), 7.08–7.12(1H, m), 7.35–7.41 (1H, m), 7.49–7.56(1H, m), 7.70–7.74(1H, m), 7.80–7.92(4H, m), 8.04–8.10(1H, m), 8.23–8.29 (1H, m), 9.80(1H, s) | 495.39 |
| I-800 | 1.62–1.74(2H, m), 2.29–2.41(6H, m), 3.25–3.36 (2H, m), 3.52–3.61(4H, m), 4.00(3H, s), 7.05–7.61 (1H, m), 7.34–7.41(1H, m), 7.48–7.55(1H, m), 7.68–7.71(1H, m), 7.73–7.80(1H, m), 7.81–7.90 (3H, m), 8.00–8.10(2H, m), 9.78(1H, s) | 509.37 |
| I-801 | 2.81(3H, d, J=5.3Hz), 3.99(3H, s), 7.04–7.10 (1H, m), 7.34–7.40(1H, m), 7.69–7.71(1H, m), 7.78–7.91(4H, m), 7.82–7.91(3H, m), 7.95–8.00 (1H, m), 8.06–8.10(1H, m), 9.78(1H, s) | 396.31 |
| I-802 | 3.85(3H, s), 7.12–7.18(3H, m), 7.70–7.85(8H, m), 9.75(1H, s) | |
| I-803 | 6.45–6.50(2H, s), 6.95–7.0(1H, d), 7.30(1H, s), 7.33–7.37(1H, m), 7.4(1H, s), 7.45–7.50(1H, t), 7.65–7.70(1H, d), 7.70–7.75(1H, s), 7.78–7.83 (1H, d), 8.07(1H, s), 9.75(2H, m) | |
| I-804 | 7.40–7.45(1H, t), 7.50–7.55(1H, t), 7.90–7.95 (3H, m), 8.05–8.15(5H, m) | |
| I-805 | 6.60(1H, d), 6.98–7.05(1H, d), 7.25–7.30(2H, s), 7.40 ppm(1H, s), 7.5(1H, d), 7.80–7.90(3H, m), 7.95–8.00(2H, d), 9.8–9.9(1H, s), 10.45(1H, s) | 404 |
| I-806 | 2.32(3H, s), 2.36(3H, s), 3.61(3H, s), 3.77(6H, s), 4.16(3H, s), 6.97(2H, s), 7.36(2H, d), 7.62 (2H, br s), 9.05(1H, br s) | 363.34 |
| I-807 | 2.40(3H, d), 3.61(3H, s), 3.78(6H, s), 7.00(2H, s), 7.27(1H, d), 7.42(2H, br s), 9.11(1H, s) | 363.34 |
| I-808 | 7.04–7.15(1H, m), 7.34–7.41(1H, m), 7.49–7.55 (1H, m), 7.59–7.67(2H, m), 7.70–7.92(6H, m), 8.04–8.11(1H, m), 9.74(1H, s) | 352.27 |
| I-809 | 6.24(2H, s), 7.16–7.29(1H, m), 7.31–7.42(1H, m), 7.49–7.59(1H, m), 7.80–7.99(4H, m), 8.00–8.10 (2H, m), 10.416(1H, s) | 352.23 |
| I-810 | 7.25(1H, m), 7.30–7.40(1H, m), 7.45–7.55(1H, m), 7.75–7.91(4H, m), 7.99–8.02(1H, m), 8.04–8.10 (1H, m), 9.51(1H, s) | 352.23 |
| I-811 | 0.81(3H, t), 1.19–1.45(4H, m), 2.79–2.89(2H, m), 7.25–7.31(1H, m), 7.34–7.40(1H, m), 7.41–7.55 (3H, m), 7.76–7.91(4H, m), 8.05–8.15(2H, m), 9.79(1H, s) | 444.27 |

-continued

| Compound # | ¹H NMR | M + 1 (obs) |
|---|---|---|
| I-812 | 7.05–7.18(6H, m), 7.20–7.23(1H, t), 7.40–7.50 (4H, m), 7.70–7.75(2H, d), 7.80–7.85(2H, d), 8.45–8.50(2H, s), 9.80–9.85(1H, s), 10.9(1H, s) | 482 |
| I-813 | 7.05–7.20(8H, m), 7.35–7.50(4H, m), 7.70–7.75 (2H, d), 7.80–7.85(2H, d), 9.90–9.95(1H, s) | 480 |
| I-814 | 7.14(2H, br s), 7.27(1H, td), 7.69–7.74(5H, m), 7.90(2H, br s), 8.11(1H, dd), 9.92(1H, s) | 406.22 |
| I-815 | 3.51(2H, s), 6.79(1H, s), 7.21(1H, t), 7.36(1H, t), 7.47(1H, s), 7.50(2H, m), 7.80(2H, s), 7.87 (1H, d), 8.07(1H, d), 9.38(1H, s), 12.27(1H, s) | 367.3 |
| I-816 | 3.48(2H, s), 7.20(2H, d), 7.34(1H, t), 7.38(1H, t), 7.48(1H, t), 7.50(2H, d), 7.79(2H, s), 7.87 (1H, d), 8.06(1H, d), 9.35(1H, s), 12.18(1H, s) | 367.3 |
| I-817 | 2.42(3H, s), 7.25(2H, s), 7.29(2H, s), 7.42 (1H, t), 7.49(2H, bs), 7.77(1H, dd), 8.06(1H, s), 9.62(1H, s) | 352.24 |
| I-818 | 1.5–1.6(2H, m), 2.2–2.3(6H, m), 2.8–2.9(2H, m), 3.45–3.5(4H, m), 6.2(2H, s), 7.35–7.7(5H, m), 8.0–8.1(3H, m), 8.25(1H, s)and 10.4(1H, s) | 515 |
| I-819 | 2.91–3.10(4H, m), 3.61–3.71(4H, m), 7.20–7.28 (1H, m), 7.35–7.41(1H, m), 7.49–7.59(2H, m), 7.75–7.60(1H, m), 7.85–7.93(3H, m), 8.08–8.10 (1H, m), 8.19–8.21(1H, m), 9.89(1H, s). | 458.24 |
| I-820 | 3.3(6H, s), 7.4(1H, m), 7.55(1H, m), 7.6–7.7 (2H, m), 7.78–7.8(2H, m), 7.88–7.9(3H, m), 8.1 (1H, m)and 10.5(1H, s) | 416 |
| I-821 | 1.3–1.4(2H, m), 1.5–1.6(4H, m), 2.8–2.9(4H, m), 7.4(1H, m), 7.5(H, m), 7.6–7.65(2H, m), 7.78–7.8(2H, m), 7.9–7.95(3H, m), 8.1(1H, d), 10.05(H, s) | 456 |
| I-822 | 2.22–2.38(6H, m), 2.90–3.00(2H, m), 3.42–3.53 (4H, m), 6.21(2H, br s), 7.35–7.42(1H, m), 7.49–7.68 (4H, m), 7.98–8.12(3H, m), 8.29(1H, br s), 10.40(1H, br s) | 501.28 |
| I-823 | 2.24–2.38(6H, m), 2.91–3.00(2H, m), 3.43–3.50 (4H, m), 7.28–7.56(5H, m), 7.75–7.81(4H, m), 8.04–8.10(1H, m), 8.11–8.18(1H, m), 9.79(1H, s) | 501.29 |
| I-824 | 1.61(6H, d), 5.59(1H, m), 7.16(2H, bs), 7.28 (5H, m), 7.42(1H, t), 7.66(2H, m), 7.81(1H, m), 8.14(1H, t), 9.54(1H, s) | 413.39 |
| I-825 | 3.63(3H, s), 3.79(6H, s), 5.83(2H, s), 7.13(3H, m), 7.36(2H, t), 7.68(2H, d), 9.57(1H, s), 9.68 (1H, s) | 385.4 |
| I-826 | 3.60(3H, s), 3.80(6H, s), 7.00(2H, s), 7.15 (1H, t), 7.37(4H, m), 7.63(2H, d), 9.01(1H, s), 9.40(1H, s) | 385.4 |
| I-827 | 2.8–2.9(4H, m), 3.6–3.7(4H, m), 7.4(H, m), 7.5 (H, m), 7.6–7.7(2H, m), 7.75–7.8(2H, m), 7.9–7.95 (2H, m, NH), 8.1(H, m)and 10.1(H, s) | 458 |
| I-828 | 2.40–2.55(3H, d), 7.25–7.30(1H, m), 7.30–7.41 (2H, m), 7.48–7.55(2H, m), 7.78–7.91(4H, m), 8.06–8.15(1H, m), 9.79(1H, s) | 402.24 |
| I-829 | 7.13(2H, s), 7.35–7.39(3H, m), 7.45–7.48(1H, m), 7.65(2H, br), 7.68–7.74(6H, m), 8.03(1H, br), 9.84(1H, br) | 414 |
| I-830 | 1.20–1.46(6H, m), 2.15–2.39(6H, m), 2.90–3.00 (2H, m), 7.26–7.55(5H, m), 7.76–7.93(4H, m), 8.05–8.18(2H, m), 9.80(1H, s) | 499.33 |
| I-831 | 2.4(3H, d), 7.15(H, m), 7.4(H, m), 7.5(H, m), 7.7(2H, m), 7.75(2H, m), 7.9(3H, m), 8.05(H, m)and 9.95(H, s) | 402, |
| I-832 | 2.14(3H, s), 2.23–2.42(4H, m), 2.92–3.02(4H, m), 6.21(2H, s), 7.34–7.48(2H, m), 7.50–7.58 (1H, m), 7.65–7.71(1H, m), 8.00–8.10(3H, m), 8.28–8.31(1H, m), 10.40(1H, s) | 471.27 |
| I-833 | 2.14(3H, s), 2.33–2.43(4H, m), 2.93–3.03(4H, m), 7.20–7.26(1H, m), 7.34–7.41(1H, m), 7.49–7.58 (2H, m), 7.71–7.79(1H, m), 7.81–7.91(3H, m), 8.09–8.12(1H, m), 8.19–8.24(1H, m), 9.86 (1H, s) | 471.31 |
| I-834 | 2.08(6H, s), 2.25–2.32(2H, m), 2.88–2.98(2H, m), 7.28–7.58(5H, m), 7.78–7.92(4H, m), 8.02–8.16 (2H, m), 9.79(1H, s) | 459.37 |
| I-835 | 7.44(2H, br s), 7.65–7.69(4H, m), 7.74–7.88 (3H, m), 8.05(1H, d), 8.36(1H, ds), 9.22(1H, d) | 382.29 |
| I-836 | 3.65–3.72(2H, m), 3.95–4.00(2H, t), 4.80–4.85 (1H, t), 6.85–6.95(4H, m), 7.55–7.70(4H, dd), 9.0(1H, s) | 448 |
| I-837 | 1.37(3H, t), 4.66(2H, q), 5.91(2H, s), 7.30(2H, m), 7.39(2H, br s), 7.47(1H, d), 7.55(1H, t), 7.69(2H, m), 8.02(1H, d), 8.08(1H, s), 10.75 (1H, s) | 399.29 |
| I-838 | 7.21(2H, s), 7.47(2H, br s), 7.73–7.75(2H, m), 7.83–7.85(2H, m), 8.02–8.06(2H, m), 10.07 (1H, br s), 12.96(1H, s) | 432.20 |
| I-839 | 3.13–3.54(4H, m), 5.02(2H, s), 6.21–6.40(1H, m), 7.00–7.18(2H, m), 7.20–7.50(6H, m), 7.60–8.23 (5H, m), 9.50–9.60(1H, m) | 525.3 |
| I-840 | 2.86(3H, br s), 6.60–6.70(1H, m), 7.15(2H, br s), 7.56–7.93(7H, m), 8.28-8.40(1H, m), 9.69 (1H, s) | 362.32 |
| I-841 | 1.81(4H, m), 2.67–2.72(4H, m), 7.14(2H, s), 7.52(2H, br), 7.63–7.70(4H, m), 9.81(1H, s) | 392.2 |
| I-842 | 7.14–7.16(3H, m), 7.45–7.49(6H, m), 7.67–7.73 (4H, m), 9.68(1H, s), 11.36(1H, br) | 430.3 |
| I-843 | 6.57(2H, s), 7.32(2H, m), 7.82–7.88(4H, m), 9.54(1H, br) | 373.2 |
| I-844 | 3.4–3.7(10H, m), 4.4–4.5(2H, m), 7.1–7.2(4H, m), 7.4–7.5(1H, d), 7.70–7.75(2H, d), 7.80–7.85 (2H, d), 9.45–9.55(2H, s), 10.0(1H, s) | 516 |
| I-845 | 2.8(3H, s), 3.0–3.4(10H, m), 4.2–4.3(2H, s), 7.1–7.2(2H, d), 7.2–7.25(1H, d), 7.4–7.45(2H, d), 7.70–7.75(2H, d), 7.80–7.85(2H, d), 10.0 (1H, s) | 530 |
| I-846 | 4.40(2H, s), 7.05–7.10(2H, m), 7.15(2H, s), 7.35–7.45(2H, m), 7.55(1H, s), 7.70–7.75(2H, d), 7.85–7.90(2H, d), 10.0(1H, s) | 461 |
| I-847 | 7.13(2H, br s), 7.74(4H, m), 7.83(2H, s), 8.06 (1H, d), 8.17(1H, d), 9.78(1H, s) | 367.2 |
| I-848 | 3.15–3.19(2H, m), 3.41–3.47(2H, m), 7.00–7.03 (2H, m), 7.10(2H, m), 7.63–7.68(2H, m), 7.76–7.79(4H, m), 8.30(1H, br s), 9.43(1H, s) | 502.32 |
| I-853 | 7.15(2H, s), 7.54–7.58(1H, m), 7.72–7.80 (5H, m), 7.99–8.04(2H, m), 8.10–8.12(3H, m), 8.64(1H, d), 9.70(1H, s) | 382.32 |
| I-854 | 7.16(2H, s), 7.72(2H, d), 7.79(2H, d), 8.00 (1H, d), 8.29(2H, br s), 8.37(1H, d), 8.86(1H, s), 9.88(1H, s) | 389.24 |
| I-855 | 2.80(3H, d), 7.10(2H, s), 7.42(2H, br s), 7.68–7.74 (2H, m), 7.83–7.85(2H, m), 7.92–7.94 (2H, m), 8.45(1H, br s), 10.00(1H, br s), 11.99 (1H, br s) | 445.32 |
| I-852 | 2.25 ppm(3H, s), 3.95 ppm(3H, s), 7.6–7.8 ppm (4H, m), 7.8–7.9 ppm(2H, s), 7.90–7.95 ppm(2H, d), 10.0 ppm(1H, s) | 436 |
| I-851 | 1.44(3H, t), 4.78(2H, q), 7.29(5H, m), 7.45 (1H, t), 7.62(3H, m), 7.79(1H, bs), 8.19(1H, m), 9.67(1H, s) | |
| I-849 | 5.75(2H, s), 7.21(5H, m), 7.25(1H, t), 7.45 (1H, s), 7.53(1H, d), 7.62(2H, d), 8.00(1H, s), 8.32(1H, d) | 371.4 |
| I-850 | 6.01(2H, s), 7.20(2H, m), 7.28(2H, s), 7.44 (1H, br s), 7.64(1H, br s), 7.76(2H, d), 7.93 (2H, d), 10.98(1H, s), 12.85(1H, s) | 371.4 |
| I-856 | 4.31(2H, s), 7.08(2H, d), 7.20(2H, m), 7.30 (5H, m), 7.72(4H, m), 7.79(1H, m), 8.02(1H, d), 9.78(1H, s) | 423.4 |
| I-857 | 3.07–3.18(2H, m), 3.49–3.51(2H, m), 6.36–6.43 (1H, m), 7.10–7.17(2H, m), 7.60–8.21(8H, m), 9.62(1H, br s). | 391.3 |
| I-858 | 2.45(3H, d), 7.16(2H, s), 7.80(2H, s), 7.86 (2H, d), 8.20–8.21(3H, m), 8.93(1H, s), 9.93 (1H, s) | 403.23 |
| I-859 | 7.14(2H, s), 7.58(3H, d), 7.74(4H, m), 7.94 (2H, s), 8.16(3H, m), 8.45(1H, d), 9.78(1H, s) | 409.3 |
| I-864 | 3.33–3.61(4H, m), 4.76–4.86(1H, m), 6.70–6.76 (1H, m), 7.10–7.20(2H, m), 7.65–7.87(7H, m), 8.28–8.35(1H, m), 9.69(1H, s) | 392.28 |

-continued

| Com-pound # | $^1$H NMR | M + 1 (obs) |
|---|---|---|
| I-860 | 2.86(3H, s), 2.87(3H, s), 3.37–3.41(2H, m), 3.80–3.85(2H, m), 7.16(2H, s), 7.49(2H, s), 7.58–7.60(2H, m), 7.67(1H, t J 5.8Hz), 7.72–7.74 (2H, m), 9.36(1H, br), 9.76(1H, br) | 425.3 |
| I-861 | 2.81(3H, s), 3.12–3.25(4H, m), 3.48–3.51(2H, m), 3.86–3.90(2H, m), 7.00(2H, s), 7.13(2H, s), 7.62–7.64(2H, m), 7.71–7.75(2H, m), 9.65(1H, s), 9.78(1H, br) | 437.3 |
| I-862 | 3.05(3H, d J 5.0Hz), 7.14(2H, s), 7.49(2H, s), 7.57–7.59(2H, m), 7.71–7.74(2H, m), 9.74(1H, br) | 368.3 |
| I-863 | 7.11(2H, s), 7.23(2H, s), 7.69(4H, m), 9.70 (1H, br) | 373.2 |
| I-865 | 3.17–3.20(2H, m), 3.84–3.90(2H, m), 6.85–6.91 (4H, m), 7.64–7.67(2H, m), 7.74–7.76 (2H, m), 9.31(1H, s) | 447.29 |
| I-866 | 1.95(1H, m), 2.2(1H, m), 3.1(1H, m), 3.25 (1H, m), 3.35(1H, m), 3.45(1H, m), 4.6(1H, br s), 6.7(1H, br s, ar), 7.2(2H, br s), 7.7–7.95 (4H, m), 8.1(1H, br s), 8.4(1H, br s), 8.4(1H, s), 9.2(1H, br s)9.45(1H, s) | 417 |
| I-867 | 1.49(3H, brd, J=5.9Hz), 5.20–5.35(1H, m), 6.72–6.80(1H, m), 7.10–7.80(10H, m), 8.09–8.30 (2H, m), 9.68(1H, s) | 452.3 |
| I-868 | 1.86–2.20(2H, m), 3.35–3.60(2H, m), 4.58–4.80 (1H, m), 6.40, 6.80, 1H, br sX2), 7.16–7.58(10H, m), 7.68–7.90(4H, m), 8.12–8.38(2H, m), 9.74 (1H, s) | 482.4 |
| I-869 | 2.64(3H, s), 4.18(2H, t), 6.95(4H, s), 7.66 (2H, d), 7.76(2H, d), 8.42(2H, br s), 9.36(1H, s) | 461.3 |
| I-870 | 0.9–1.9(4H, m), 2.6–3.1(4H, m), 3.8(1H, m, CH), 4.3(,(2H, br s), 6.8(1H, s), 7.1(2H, br s) 7.7–7.9(6H, m), 8.4(1H, s), 9.7(1H, s) | 431 |
| I-871 | 4.39–4.68(2H, m), 6.70–6.83(1H, m), 7.10–7.48 (6H, m), 7.60–7.84(5H, m), 8.09–8.39(2H, m), 9.69(1H, s) | 438 |
| I-872 | 2.69(6H, br s), 4.22(2H, t), 6.96–7.05(4H, m), 7.11(2H, s), 7.67(2H, d), 7.77(2H, d), 9.46 (1H, s) | 475.3 |

B) Biological Data:

Example 1

Inhibition of FLT-3

Compounds were screened for their ability to inhibit FLT-3 activity using a radiometric filter-binding assay. This assay monitors the $^{33}$P incorporation into a substrate poly (Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM MgCl$_2$, 25 mM NaCl, 1 mg/ml pE4Y and 180 µM ATP (containing 0.3 µCi of [γ-$^{33}$P]ATP for each reaction). Solution 2 contains 100 mM HEPES (pH7.5), 10 mM MgCl$_2$, 25 mM NaCl, 2 mM DTT, 0.02% BSA and 3 nM FLT-3. The assay was run on a 96 well plate by mixing 50 µL each of Solution1 and 2.5 mL of the test compounds. The reaction was initiated with Solution2. After incubation for 20 minutes at room temperature, the reaction was stopped with 50/L of 20% TCA containing 0.4 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

In general, compounds of the invention, including compounds in Table 1, are effective for the inhibition of FLT-3.

Example 2

Inhibition of c-KIT

Compounds were screened for their ability to inhibit c-KIT activity using a radiometric filter-binding assay. This assay monitors the $^{33}$P incorporation into a substrate poly (Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 700 µM ATP and 0.5 mg/mL pE4Y (both from Sigma Chemicals, St Louis, Mo.). The final concentration of compounds is generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM MgCl$_2$, 25 mM NaCl, 1 mg/ml pE4Y and 1.4 mM ATP (containing 0.5 µCi of [γ-$^{33}$P]ATP for each reaction). Solution 2 contains 100 mM HEPES (pH7.5), 10 mM MgCl$_2$, 25 mM NaCl, 2 mM DTT, 0.02% BSA and 25 nM c-KIT. The assay was run on a 96 well plate by mixing 33 µL of Solution1 and 1.65 µL of the test compounds. The reaction was initiated with 33 µL of Solution2. After incubation for 20 minutes at room temperature, the reaction was stopped with 50 µL of 10% TCA containing 0.2 mM of ATP. All of the reaction volume was then transferred to a filter plate and washed with 5% TCA by a Harvester9600 from TOMTEC (Hamden, Conn.). The amount of $^{33}$P incorporation into pE4y was analyzed by a Packard TopCount Microplate Scintillation Counter (Meriden, Conn.). The data was fitted using Prism software to get an IC$_{50}$ or K$_i$.

In general, compounds of the invention, including compounds in Table 1, are effective for the inhibition of c-KIT.

Example 3

Inhibition of GSK-3

Compounds were screened for their ability to inhibit GSK-3β (AA 1-420) activity using a standard coupled enzyme system (Fox et al. (1998) Protein Sci. 7, 2249). Reactions were carried out in a solution containing 100 mM HEPES (pH 7.5), 10 mM MgCl$_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

In general, compounds of the invention, including compounds in Table 1, are effective for the inhibition of GSK-3.

Example 4

Inhibition of CDK-2

Compounds were screened for their ability to inhibit CDK-2/Cyclin A using a standard coupled enzyme assay (Fox et al (1998) *Protein Sci* 7, 2249). Reactions were carried out in 100 mM HEPES pH 7.5, 10 mM $MgCl_2$, 25 mM NaCl, 1 mM DTT and 1.5% DMSO. Final substrate concentrations in the assay were 100 µM ATP (Sigma chemicals) and 100 µM peptide (American Peptide, Sunnyvale, Calif.). Assays were carried out at 30° C. and 25 nM CDK-2/Cyclin A. Final concentrations of the components of the coupled enzyme system were 2.5 mM phosphoenolpyruvate, 350 µM NADH, 30 µg/ml pyruvate kinase and 10 µg/ml lactate dehydrogenase.

An assay stock buffer solution was prepared containing all of the reagents listed above, with the exception of CDK-2/Cyclin A, DTT and the test compound of interest. 56/L of the test reaction was placed in a 384 well plate followed by addition of 1 µl of 2 mM DMSO stock containing the test compound (final compound concentration 30 µM). The plate was preincubated for ~10 minutes at 30° C. and the reaction initiated by addition of 10 µl of enzyme (final concentration 25 nM). Rates of reaction were obtained using a BioRad Ultramark plate reader (Hercules, Calif.) over a 5 minute read time at 30° C. $K_i$ values were determined according to standard methods.

In general, compounds of the invention, including compounds in Table 1, are effective for the inhibition of CDK-2.

Example 5

Inhibition of SRC

The compounds are evaluated as inhibitors of human Src kinase using either a radioactivity-based assay or spectrophotometric assay.

Src Inhibition Assay A: Radioactivity-based Assay

The compounds are assayed as inhibitors of full-length recombinant human Src kinase (from Upstate Biotechnology, cat. no. 14-117) expressed and purified from baculo viral cells. Src kinase activity is monitored by following the incorporation of $^{33}P$ from ATP into the tyrosine of a random poly Glu-Tyr polymer substrate of composition, Glu: Tyr=4:1 (Sigma, cat. no. P-0275). The following are the final concentrations of the assay components: 0.05 M HEPES, pH 7.6, 10 mM $MgCl_2$, 2 mM DTT, 0.25 mg/ml BSA, 10 µM ATP (1-2 µCi $^{33}P$-ATP per reaction), 5 mg/ml poly Glu-Tyr, and 1-2 units of recombinant human Src kinase. In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with $^{33}P$-ATP. After 20 min of reaction, the reactions are quenched with 150 µl of 10% trichloroacetic acid (TCA) containing 20 mM $Na_3PO_4$. The quenched samples are then transferred to a 96-well filter plate (Whatman, UNI-Filter GF/F Glass Fiber Filter, cat no. 7700-3310) installed on a filter plate vacuum manifold. Filter plates are washed four times with 10% TCA containing 20 mM $Na_3PO_4$ and then 4 times with methanol. 200 µl of scintillation fluid is then added to each well. The plates were sealed and the amount of radioactivity associated with the filters is quantified on a TopCount scintillation counter. The radioactivity incorporated is plotted as a function of the inhibitor concentration. The data is fitted to a competitive inhibition kinetics model to get the $K_i$ for the compound.

Src Inhibition Assay B: Spectrophotometric Assay

The ADP produced from ATP by the human recombinant Src kinase-catalyzed phosphorylation of poly Glu-Tyr substrate is quantified using a coupled enzyme assay (Fox et al (1998) *Protein Sci* 7, 2249). In this assay one molecule of NADH is oxidised to NAD for every molecule of ADP produced in the kinase reaction. The disappearance of NADH is conveniently followed at 340 nm.

The following are the final concentrations of the assay components: 0.025 M HEPES, pH 7.6, 10 mM $MgCl_2$, 2 mM DTT, 0.25 mg/ml poly Glu-Tyr, and 25 nM of recombinant human Src kinase. Final concentrations of the components of the coupled enzyme system are 2.5 mM phosphoenolpyruvate, 200 µM NADH, 30 µg/ml pyruvate kinase and 10 µg/ml lactate dehydrogenase.

In a typical assay, all the reaction components with the exception of ATP are pre-mixed and aliquoted into assay plate wells. Inhibitors dissolved in DMSO are added to the wells to give a final DMSO concentration of 2.5%. The assay plate is incubated at 30° C. for 10 min before initiating the reaction with 100 µM ATP. The absorbance change at 340 nm with time, the rate of the reaction, is monitored on a molecular devices plate reader. The data of rate as a function of the inhibitor concentration is fitted to competitive inhibition kinetics model to get the $K_i$ for the compound.

In general, compounds of the invention, including compounds in Table 1, are effective for the inhibition of SRC.

Example 6

Inhibition of SYK

Compounds were screened for their ability to inhibit Syk using a standard coupled enzyme assay (Fox et al (1998) *Protein Sci* 7, 2249). Reactions were carried out in 100 mM HEPES pH 7.5, 10 mM MgCl2, 25 mM NaCl, 1 mM DTT and 1.5% DMSO. Final substrate concentrations in the assay were 200 µM ATP (Sigma chemical Co.) and 4 µM poly Gly-Tyr peptide (Sigma Chemical Co.). Assays were carried out at 30° C. and 200 nM Syk. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of Syk, DTT and the test compound of interest. 56 ILI of the test reaction was placed in a 96 well plate followed by the addition of 1 µl of 2 mM DMSO stock containing the test compound (final compound concentration 30 µM). The plate was pre-incubated for ~10 minutes at 30° C. and the reaction initiated by the addition of 10 μl of enzyme (final concentration 25 nM). Rates of reaction were obtained using a BioRad Ultramark plate reader (Hercules, Calif.) over a 5 minute read time at 30° C., and $K_i$ values were determined according to standard methods.

In general, compounds of the invention, including compounds in Table 1, are effective for the inhibition of SYK.

Example 7

Inhibition of FMS

Compounds were screened for their ability to inhibit FMS activity using a radiometric filter-binding assay. This assay monitors the $^{33}P$ incorporation into a substrate poly(Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 μM ATP and 0.5 mg/mL pE4Y (both from Sigma Chemicals, St Louis, Mo.). The final concentration of compounds is generally between 0.01 and 5 μM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH7.5), 10 mM MgCl$_2$, 25 mM NaCl, 1 mg/ml pE4Y and 180 μM ATP (containing 0.3 μCi of [γ-$^{33}$P]ATP for each reaction). Solution 2 contains 100 mM HEPES (pH7.5), 10 mM MgCl$_2$, 25 mM NaCl, 2 mM DTT, 0.02% BSA and 3 nM FMS. The assay was run on a 96 well plate by mixing 50 μL each of Solution1 and 2.5 mL of the test compounds. The reaction was initiated with Solution2. After incubation for 20 minutes at room temperature, the reaction was stopped with 50 μL of 20% TCA containing 0.4 mM of ATP. All of the reaction volume was then transferred to a filter plate and washed with 5% TCA by a Harvester9600 from TOMTEC (Hamden, Conn.). The amount of $^{33}P$ incorporation into pE4y was analyzed by a Packard TopCount Microplate Scintillation Counter (Meriden, Conn.). The data was fitted using Prism software to get an IC$_{50}$ or $K_i$.

In general, compounds of the invention, including compounds in Table 1, are effective for the inhibition of FMS.

Example 8

Rock Inhibition Assay

Compounds were screened for their ability to inhibit ROCK I (AA 6-553) activity using a standard coupled enzyme system (Fox et al. (1998) Protein Sci. 7, 2249). Reactions were carried out in a solution containing 100 mM HEPES (pH 7.5), 10 mM MgCl$_2$, 25 mM NaCl, 2 mM DTT and 1.5% DMSO. Final substrate concentrations in the assay were 45 μM ATP (Sigma Chemicals, St Louis, Mo.) and 200 μM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 μM NADH, 30 μg/ml pyruvate kinase and 10 μg/ml lactate dehydrogenase.

Certain compounds of the invention were found to inhibit ROCK.

Example 9

JAK3 Inhibition Assay

Compound inhibition of JAK was assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), was added 2 μM ATP, 5 mM MgCl$_2$, and a solution of compound in DMSO. The reaction was started with JAK enzyme and the plates incubated for 60 minutes at 30° C. The plates were then washed with PBST, 100 μL HRP-Conjugated 4G10 antibody was added, and the plate incubated for 90 minutes at 30° C. The plate was again washed with PBST, 100 μL TMB solution is added, and the plates were incubated for another 30 minutes at 30° C. Sulfuric acid (100 μL of μM) was added to stop the reaction and the plate is read at 450 nm to obtain the optical densities for analysis to determine $K_i$ values.

Compounds were tested and found to inhibit JAK-3.

PDK-1 Inhibition Assay

Compounds were screened for their ability to inhibit PDK-1 using a radioactive-phosphate incorporation assay (Pitt and Lee, J. Biomol. Screen., (1996) 1, 47). Assays were carried out in a mixture of 100 mM HEPES (pH 7.5), 10 mM MgCl$_2$, 25 mM NaCl, 2 mM DTT. Final substrate concentrations in the assay were 40 μM ATP (Sigma Chemicals) and 65 μM peptide (PDKtide, Upstate, Lake Placid, N.Y.). Assays were carried out at 30° C. and 25 nM PDK-1 in the presence of ~27.5 nCi/μL of [γ-$^{32}$P]ATP (Amersham Pharmacia Biotech, Amersham, UK). An assay stock buffer solution was prepared containing all of the reagents listed above, with the exception of ATP, and the test compound of interest. 15 μl of the stock solution was placed in a 96 well plate followed by addition of 1 μl of 0.5 mM DMSO stock containing the test compound (final compound concentration 25 μM, final DMSO concentration 5%). The plate was preincubated for about 10 minutes at 30° C. and the reaction initiated by addition of 4 μl ATP (final concentration 40 μM).

The reaction was stopped after 10 minutes by the addition of 100 μL 100 mM phosphoric acid, 0.01% Tween-20. A phosphocellulose 96 well plate (Millipore, Cat no. MAPH-NOB50) was pretreated with 100 μL 100 mM phosphoric acid, 0.01% Tween-20 prior to the addition of the reaction mixture (100 μL). The spots were left to soak for at least 5 minutes, prior to wash steps (4×200 μL 100 mM phosphoric acid, 0.01% Tween-20). After drying, 20 μL Optiphase 'SuperMix' liquid scintillation cocktail (Perkin Elmer) was added to the well prior to scintillation counting (1450 Microbeta Liquid Scintillation Counter, Wallac).

Compounds showing greater than 50% inhibition versus standard wells containing the assay mixture and DMSO without test compound were titrated to determine IC$_{50}$ values.

Compounds of the invention were tested and were found to inhibit PDK-1.

The invention claimed is:
1. A compound of formula II or II':

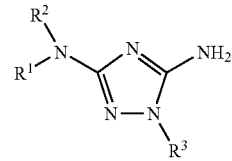

II

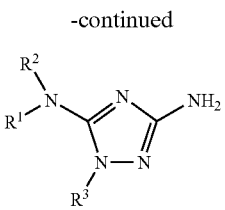

II' or a pharmaceutically acceptable salt thereof, wherein
R¹ is hydrogen;
R² is Ar¹, wherein Ar¹ is a phenyl group substituted with x independent occurrences of Q-R$^X$, wherein x is 1-5; Q is a bond or is a $C_1$-$C_6$ alkylidene chain wherein up to two methylene units of Q are optionally replaced by —NR—, —S—, —O—, —CS—, —$CO_2$—, —OCO—, —CO—, —COCO—, —CONR—, —NRCO—, —$NRCO_2$—, —$SO_2$NR—, —$NRSO_2$—, —CONRNR—, —NRCONR—, —OCONR—, —NRNR—, —$NRSO_2$NR—, —SO—, —$SO_2$—, —PO—, —$PO_2$—, or —POR—; and each occurrence of R$^x$ is independently R', halogen, $NO_2$, CN, OR', SR', N(R')$_2$, NR'COR', NR'CONR'$_2$, NR'$CO_2$R', COR', $CO_2$R', OCOR', CON(R')$_2$, OCON(R')$_2$, SOR', $SO_2$R', $SO_2$N(R')$_2$, NR'$SO_2$R', NR'$SO_2$N(R')$_2$, COCOR', or COCH$_2$COR', wherein at least one Q-R$^X$ is not hydrogen;
R³ is Ar², wherein Ar² is an optionally substituted aryl group selected from pyridyl, pyrimidyl, pyrazinyl, pyridazinyl, triazinyl, imidazolyl, pyrazolyl, triazolyl, furanyl, thiophenyl, oxazolyl, thiazolyl, oxadiazolyl, thiadiazolyl, or an 8-12 membered bicyclic ring having 0-5 heteroatoms independently selected from nitrogen, oxygen, or sulfur; wherein said aryl group is optionally substituted with y occurrences of Z-R$^Y$; wherein y is 0-5, Z is a bond or is a $C_1$-$C_6$ alkylidene chain wherein up to two methylene units of Z are optionally replaced by —NR—, —S—, —O—, —CS—, —$CO_2$—, —OCO—, —CO—, —COCO—, —CONR—, —NRCO—, —$NRCO_2$—, —$SO_2$NR—, —$NRSO_2$—, —CONRNR—, —NRCONR—, —OCONR—, —NRNR—, —$NRSO_2$NR—, —SO—, or —$SO_2$—; and each occurrence of R$^Y$ is independently R', halogen, $NO_2$, CN, OR', SR', N(R')$_2$, NR'COR', NR'CONR'$_2$, NR'$CO_2$R', COR', $CO_2$R', OCOR', CON(R')$_2$, OCON(R')$_2$, SOR', $SO_2$R', $SO_2$N(R')$_2$, NR'$SO_2$R', NR'$SO_2$N(R')$_2$, COCOR', or COCH$_2$COR'; and
each occurrence of R is independently hydrogen or an optionally substituted $C_{1-6}$ aliphatic group; and each occurrence of R' is independently hydrogen or an optionally substituted group selected from a $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that:
a) when R³ is pyridyl, pyrimidinedione, then R² is not phenyl simultaneously substituted with one occurrence of OMe in the meta position, and one occurrence of oxazole in the para position; or
b) when R³ is unsubstituted pyrimidinyl, then R² is not p-OMe substituted phenyl, p-OEt substituted phenyl, or o-OMe substituted phenyl.

2. The compound of claim 1, wherein said compound has the formula II-A-(i) or II-A-(i)':

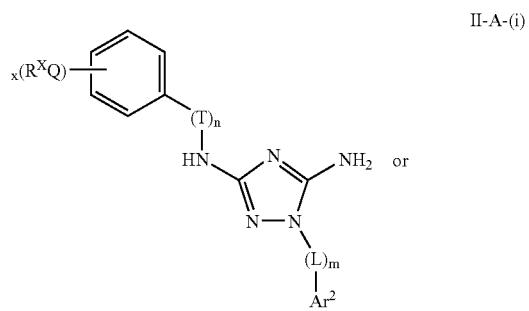

II-A-(i)

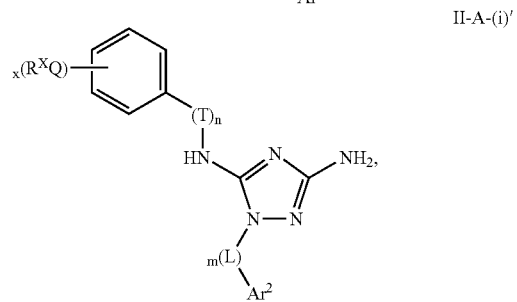

II-A-(i)' wherein each of m and n is 0.

3. The compound of claim 2, wherein Ar² is selected from one of the following groups:

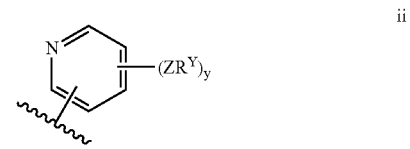

ii

iii

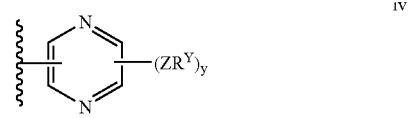

iv

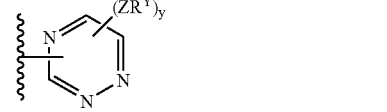

v

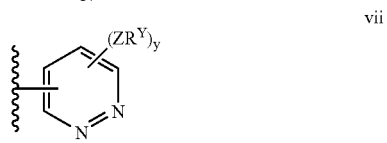

vii

-continued
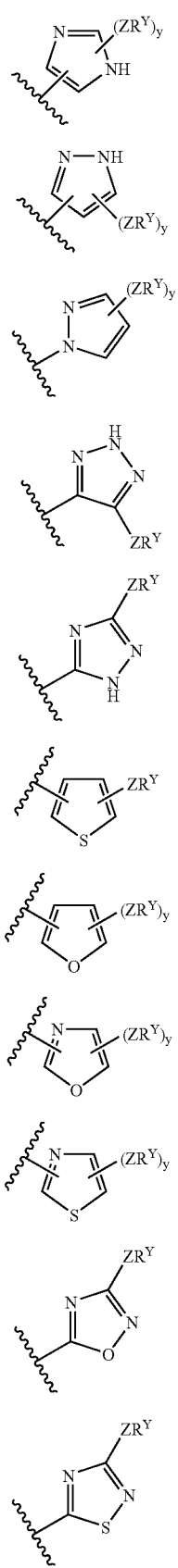
viii
ix
x
xi
xii
xiii
xiv
xv
xvi
xvii
xviii
-continued
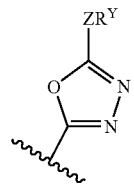
xix
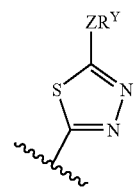
xx
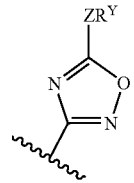
xxi
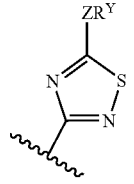
xxii
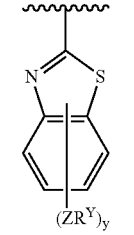
xxiii
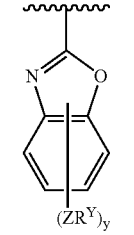
xxiv
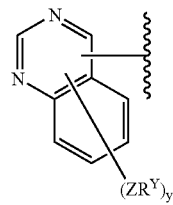
xxv -continued
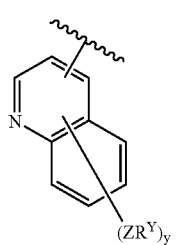
xxvi
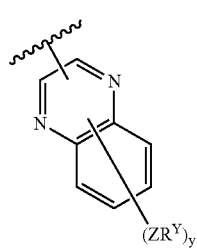
xxvii
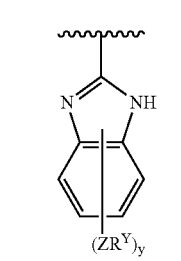
xxviii
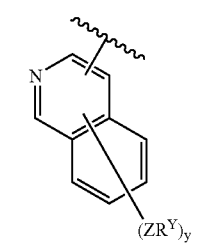
xxix
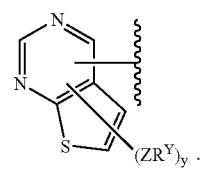
xxxi
wherein any substitutable carbon or nitrogen atom is optionally substituted by $ZR^Y$.
4. The compound of claim 2, wherein Ar is selected from one of the following groups:
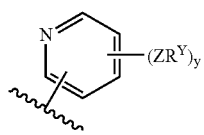
ii
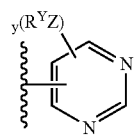
iii
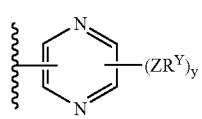
iv
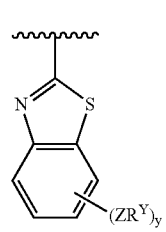
xvi
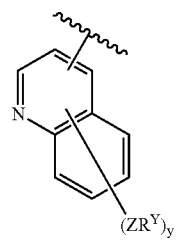
xxiii
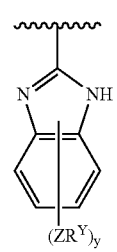
xxvi
xxix -continued

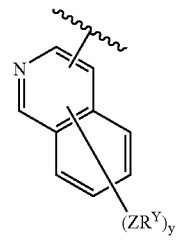
xxx

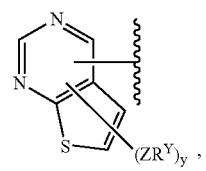
xxxi wherein any substitutable carbon or nitrogen atom is optionally substituted by ZR$^Y$.

5. The compound of claim 1, wherein Ar$^2$ is optionally substituted 2-pyridyl, 2-thiazolyl, 2-pyrimidinyl, 6-pyrimidinyl, 4-pyridyl, benzothiazolyl, or 2-quinolinyl, and said compound has one of the structures II-F-(i), II-G-(i), II-G'-(i), II-H-(i)', II-I-(i), II-I'-(i), II-J-(i), II-F-(i)', II-G-(i)', II-G'-(i)', II-H-(i)', II-I-(i)', II-I'-(i)', or II-J-(i)':

II-F-(i)

II-F-(i)'

II-G-(i)

-continued

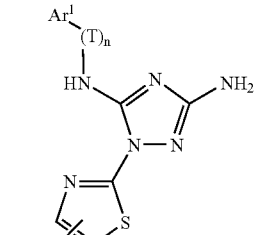
II-G-(i)'

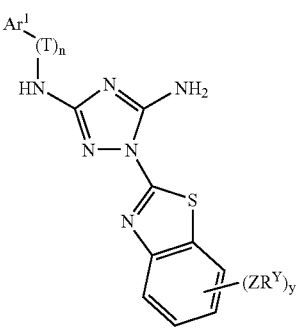
II-G'-(i)

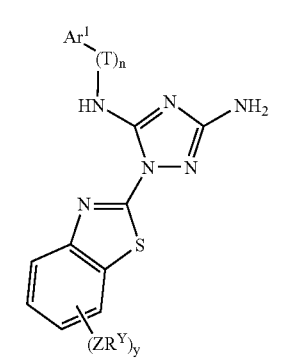
II-G'-(i)'

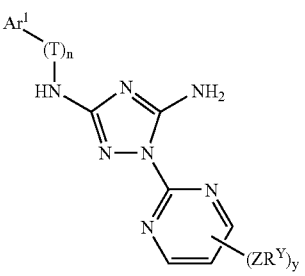
II-H-(i)

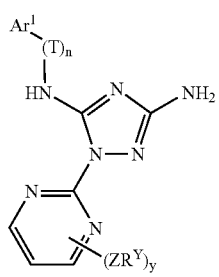
II-H-(i)'

-continued

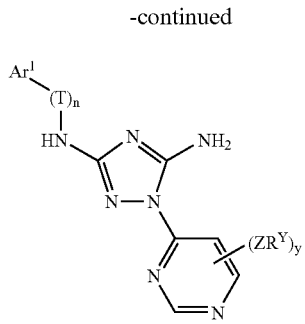

II-I-(i)

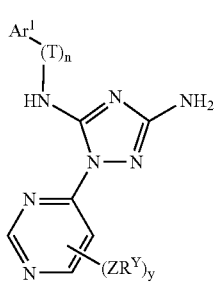

II-I-(i)'

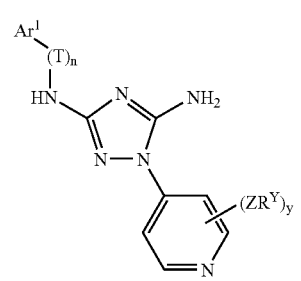

II-I'-(i)

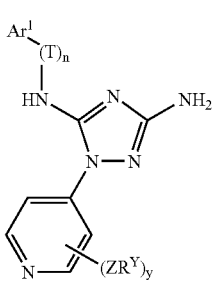

II-I'-(i)'

-continued

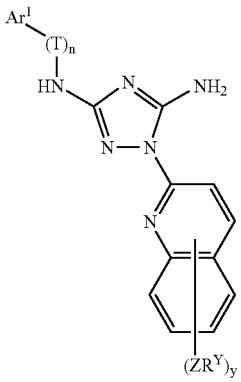

II-J-(i)

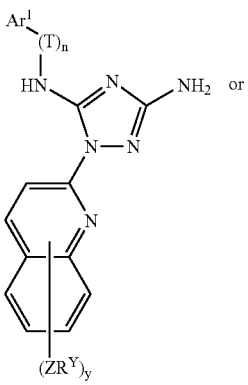

II-J-(i)' or wherein n is 0.

6. The compound of claim 2, wherein $Ar^2$ is pyridyl, pyrimidinyl, quinolinyl, or thiazolyl, each optionally substituted with 0-3 occurrences of $ZR^Y$.

7. The compound of claim 6, wherein x is 1-3; y is 0-3; and each occurrence of $QR^X$ or $ZR^Y$ is independently R', halogen, CN, $NO_2$, —N(R')$_2$, —CH$_2$N(R')$_2$, —OR', —CH$_2$OR', —SR', —CH$_2$SR', —COOR', —NRCOR', —CON(R')$_2$, —SO$_2$N(R')$_2$, —CONR(CH$_2$)$_2$N(R')$_2$, —CONR(CH$_2$)$_3$N(R')$_2$, —CONR(CH$_2$)$_4$N(R')$_2$, —O(CH$_2$)$_2$OR', —O(CH$_2$)$_3$R', —O(CH$_2$)$_4$OR', —O(CH$_2$)$_2$N(R')$_2$, —O(CH$_2$)$_3$N(R')$_2$, or —O(CH$_2$)$_4$N(R')$_2$.

8. The compound of claim 5, wherein x is 1-3; y is 0-3; and each occurrence of $QR^X$ or $ZR^Y$ is independently Cl, Br, F, $CF_3$, Me, Et, CN, —COGH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, methylenedioxy, ethylenedioxy, —O(CH$_2$)$_2$N-morpholino, —O(CH$_2$)$_3$N-morpholino, —O(CH$_2$)$_4$N-morpholino, —O(CH$_2$)$_2$N-piperazinyl, —O(CH$_2$)$_3$N-piperizinyl, —O(CH$_2$)$_4$N-piperizinyl, —NHCH(CH$_2$OH)phenyl, —CONH(CH$_2$)$_2$N-morpholino, —CONH(CH$_2$)$_2$N-piperazinyl, —CONH(CH$_2$)$_3$N-morpholino, —CONH(CH$_2$)$_3$N-piperazinyl, —CONH(CH$_2$)$_4$N-morpholino, —CONH(CH$_2$)$_4$N-piperazinyl, —SO$_2$NH(CH$_2$)$_2$N-morpholino, —SO$_2$NH(CH$_2$)$_2$N-piperazinyl, —SO$_2$NH(CH$_2$)$_3$N-morpholino, —SO$_2$NH(CH$_2$)$_3$N-piperazinyl, —SO$_2$NH(CH$_2$)$_4$N-morpholino, —SO$_2$NH(CH$_2$)$_4$N-piperazinyl, where each of the foregoing phenyl, morpholino, piperazinyl, or piperidinyl groups is optionally substituted, or an optionally substituted group selected from $C_{1-4}$ alkoxy, phenyl, phenyloxy, benzyl, piperidinyl, piperazinyl, morpholino, or benzyloxy.

9. The compound of claim 1, having one of the formulae:
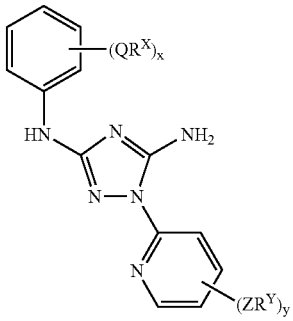
IV
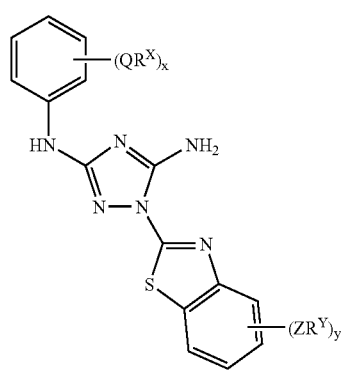
V
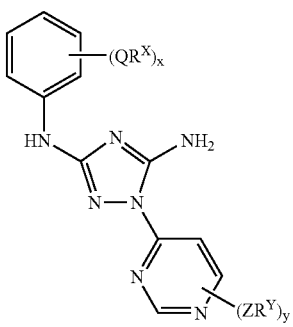
VI
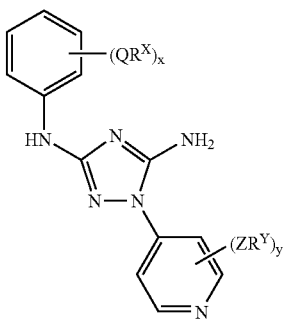
VII
-continued
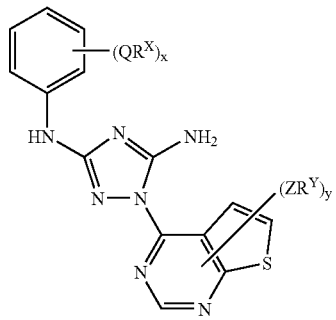
VIII
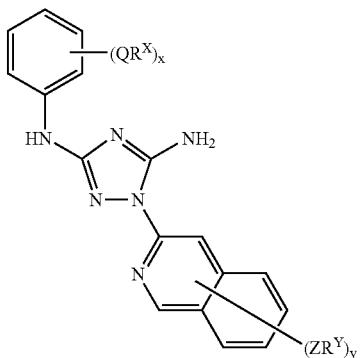
IX
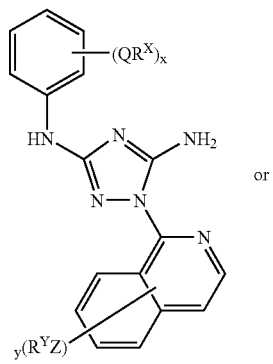
X
or
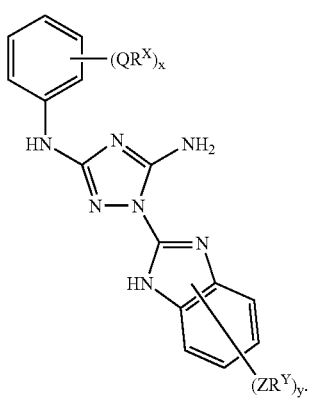
XI 10. The compound of claim 9, wherein x is 1-3; y is 0-3; and each occurrence of $QR^X$ or $ZR^Y$ is independently R', halogen, CN, $NO_2$-N(R')$_2$, —CH$_2$N(R')$_2$, —OR', —CH$_2$OR', —SR', —CH$_2$SR', —COOR', —NRCOR', —CON(R')$_2$, —SO$_2$N(R')$_2$, —CONR(CH$_2$)$_2$N(R')$_2$, —CONR(CH$_2$)$_3$N(R')$_2$, —CONR(CH$_2$)$_4$N(R',)$_2$, —O(CH$_2$)$_2$ OR', —O(CH$_2$)$_3$OR', —O(CH$_2$)$_{40}$R', —O(CH$_2$)$_2$ N(R')$_2$, —O(CH$_2$)$_3$N(R')$_2$, or —O(CH$_2$)$_4$N(R')$_2$.

11. The compound of claim 10, wherein $QR^X$ or $ZR^Y$ groups are each independently Cl, Br, F, CF$_3$, Me, Et, CN, —COOH, —N(CH$_3$)$_2$, —N(Et)$_2$, —N(iPr)$_2$, —O(CH$_2$)$_{20}$CH$_3$, —CONH$_2$, —COOCH$_3$, —OH, —CH$_2$OH, —NHCOCH$_3$, —SO$_2$NH$_2$, methylenedioxy, ethylenedioxy, —O(CH$_2$)$_2$N-morpholino, —O(CH$_2$)$_3$N-morpholino, —O(CH$_2$)$_4$N-morpholino, —O(CH$_2$)$_2$N-piperazinyl, —O(CH$_2$)$_3$N-piperizinyl, —O(CH$_2$)$_4$N-piperizinyl, —NHCH(CH$_2$OH)phenyl, —CONH(CH$_2$)$_2$N-morpholino, —CONH(CH$_2$)$_2$N-piperazinyl, —CONH(CH$_2$)$_3$N-morpholino, —CONH(CH$_2$)$_3$N-piperazinyl, —CONH(CH$_2$)$_4$N-morpholino, —CONH(CH$_2$)$_4$N-piperazinyl, —SO$_2$NH(CH$_2$)$_2$N-morpholino, —SO$_2$NH(CH$_2$)$_2$N-piperazinyl, —SO$_2$NH(CH$_2$)$_3$N-morpholino, —SO$_2$NH(CH$_2$)$_3$N-piperazinyl, —SO$_2$NH(CH$_2$)$_4$N-morpholino, —SO$_2$NH(CH$_2$)$_4$N-piperazinyl, where each of the foregoing phenyl, morpholino, piperazinyl, or piperidinyl groups is optionally substituted, or an optionally substituted group selected from $C_{1-4}$alkoxy, phenyl, phenyloxy, benzyl, piperidinyl, piperazinyl, morpholino, or benzyloxy.

12. A pharmaceutical composition comprising a compound according to claim 1 and a pharmaceutically acceptable carrier, adjuvant, or vehicle.

13. The composition of claim 12, further comprising an additional therapeutic agent selected mechlorethamine, chlorambucil, cyclophosphamide, melphalan, ifosfamide, methotrexate, 6-mercaptopurine, 5-fluorouracil, cytarabile, gemcitabine, vinblastine, vincristine, vinorelbine, paclitaxel, etoposide, irinotecan, topotecan, doxorubicin, bleomycin, mitomycin, carmustine, lomustine, cisplatin, carboplatin, asparaginase, tamoxifen, leuprolide, flutamide, megestrol, imatinib mesylate, adriamycin, dexamethasone, cyclophosphamide, donepezil (Aricept®), rivastigmine (Excelon®)), L-DOPAlcarbidopa, entacapone, ropinrole, pramipexole, bromocriptine, pergolide, trihexephendyl, amantadine, glatiramer (Copaxone®), mitoxantrone, albuterol, montelukast (Singulair®), zyprexa, risperdal, seroquel, haloperidol, a corticosteroid, a TNF blocker, IL-1 RA, azathioprine, cyclophosphamide, sulfasalazine, cyclosporin, tacrolimus, rapamycin, mycophenolate mofetil, an interferon, cyclophosphamide, azathioprine, sulfasalazine, an acetylcholinesterase inhibitor, a monoamine oxidase inhibitor, an interferon, an anti-convulsant, an ion channel blocker, riluzole, a beta-blocker, an acetyl cholinesterase inhibitor, a diuretic, a nitrate, a calcium channel blocker, a statin, cholestyramine, or gamma globulin.

14. A method of inhibiting FLT-3 or c-KIT kinase activity in a biological sample in vitro selected from a cell culture, saliva, urine, feces, semen, tears, or extracts thereof, comprising the step of contacting said biological sample with:
   a) a composition according to claim 12; or
   b) a compound according to claim 1.

15. The compound of claim 1, wherein said compound is selected from the following:

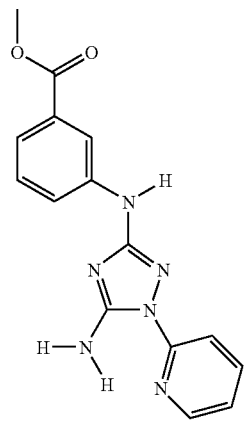

I-3

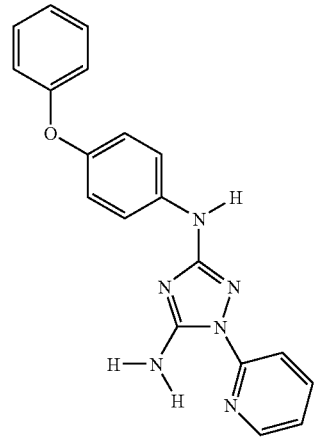

I-22

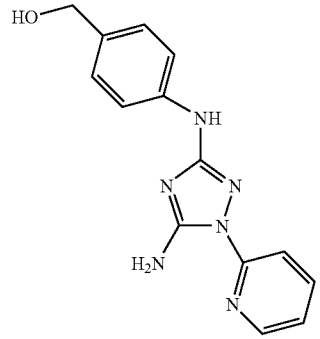

I-23

-continued
I-27
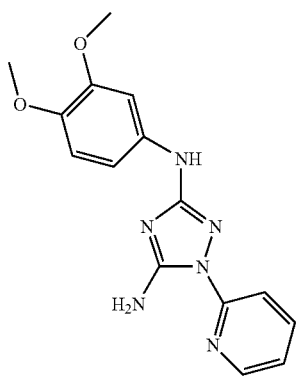
I-28
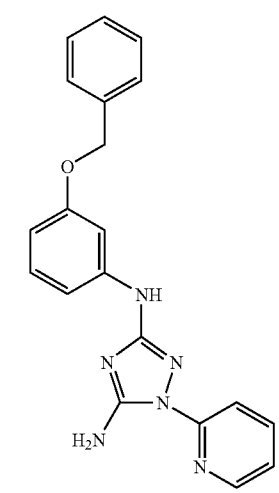
I-29
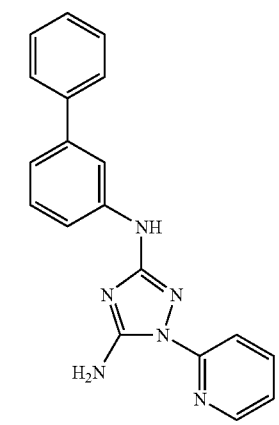
-continued
I-39
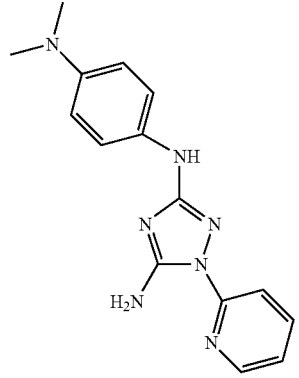
I-49
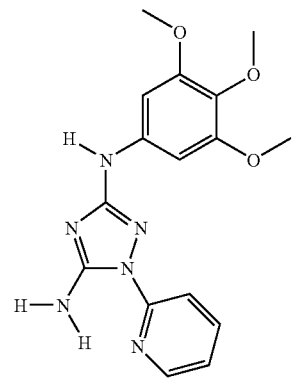
I-51
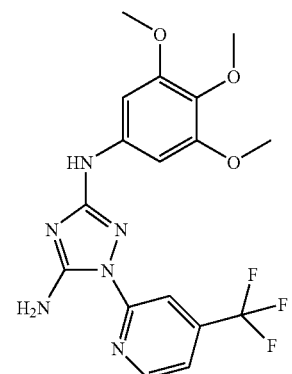
I-52
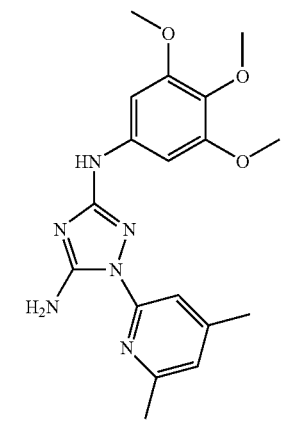

-continued
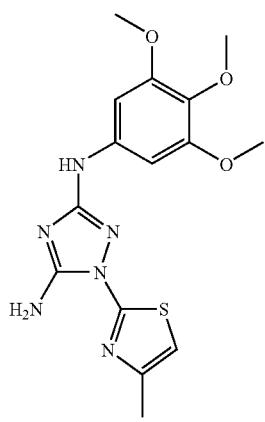
I-53
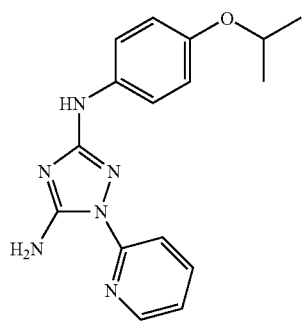
I-57
I-54
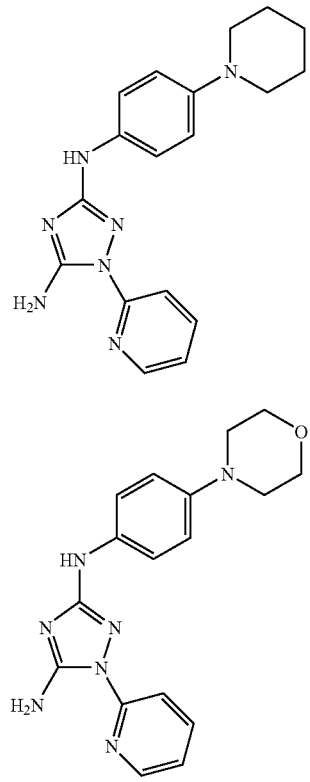
I-55
I-58
I-59
I-56
I-60

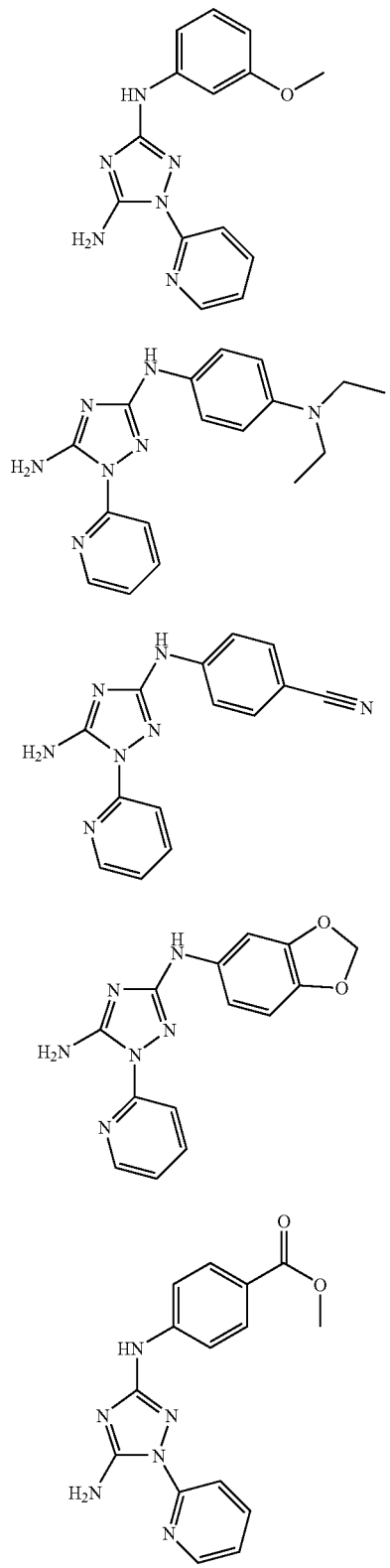
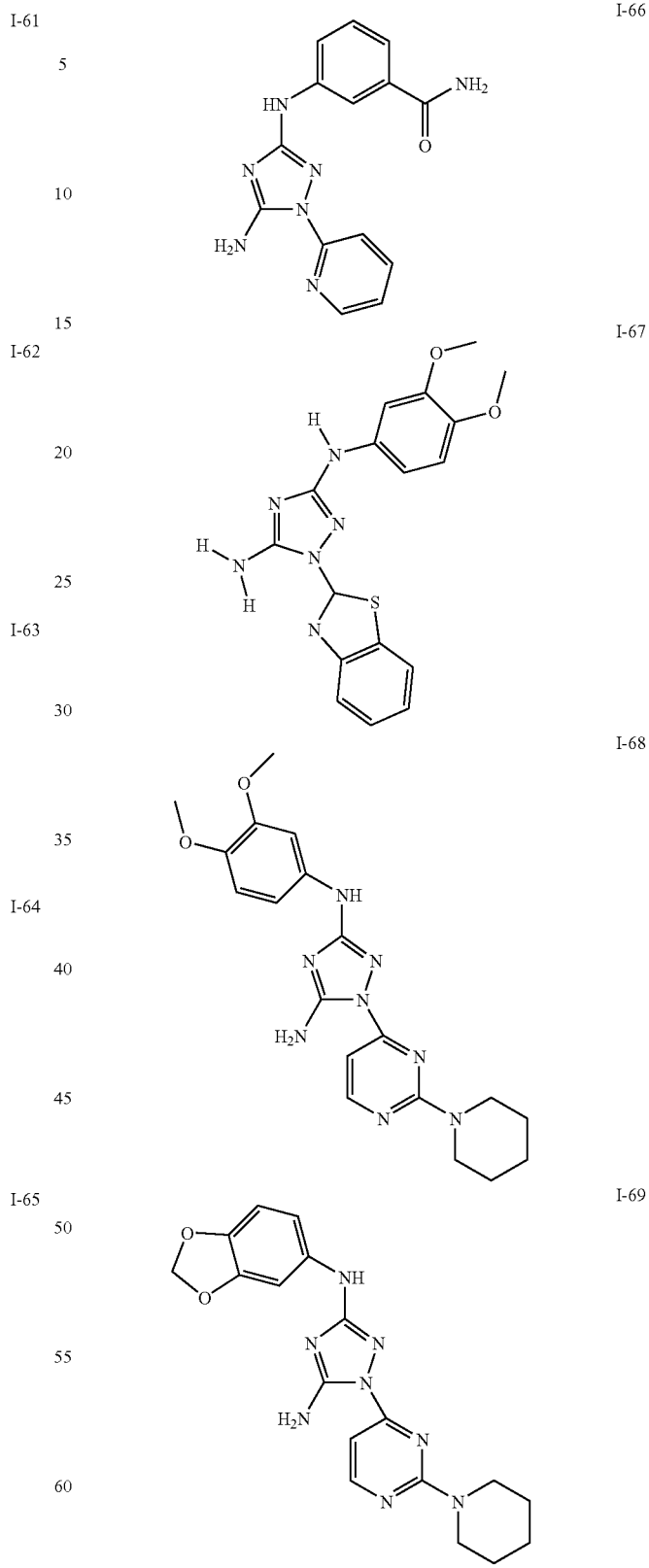

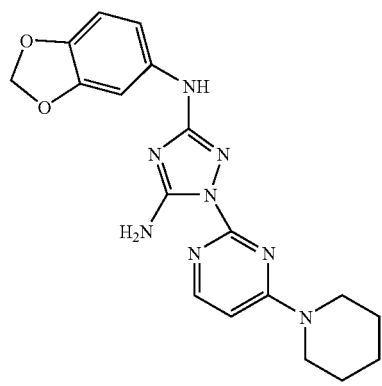
I-70
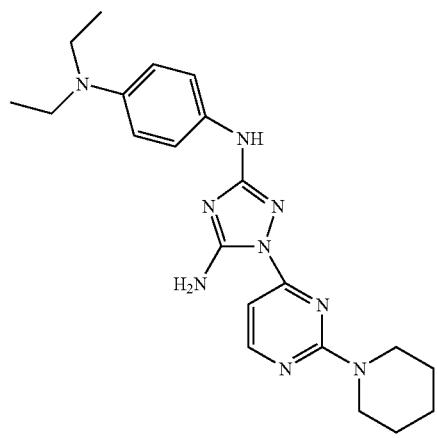
I-71
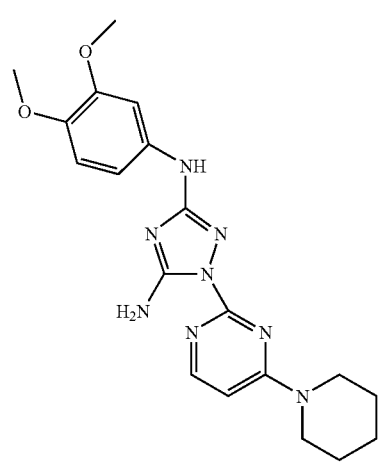
I-72
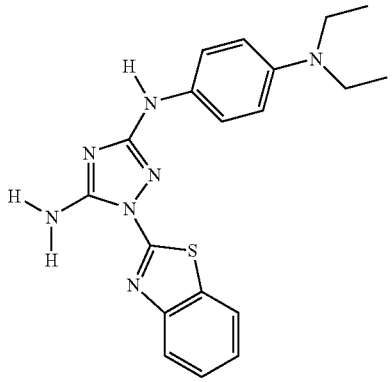
I-73
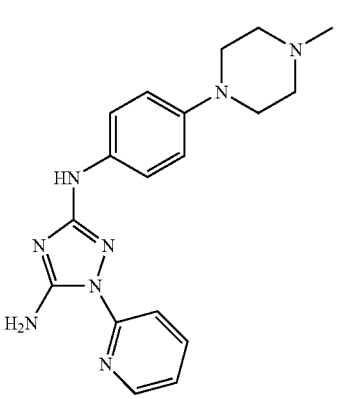
I-74
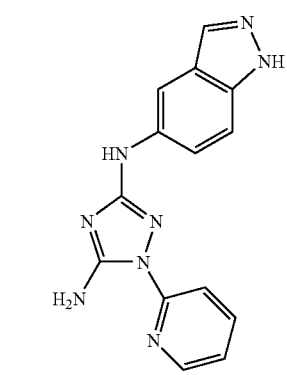
I-75
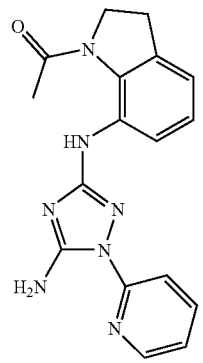
I-76

I-77 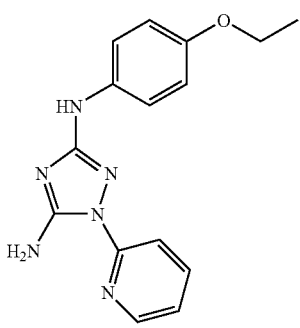
I-78 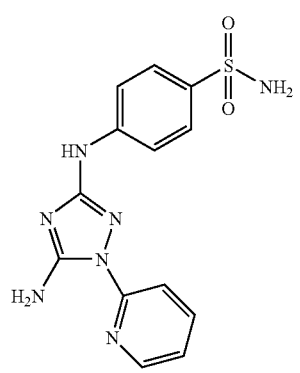
I-79 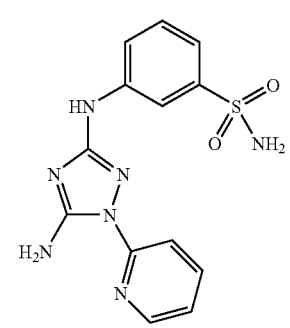
I-80 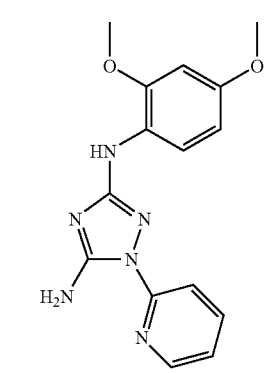
I-82 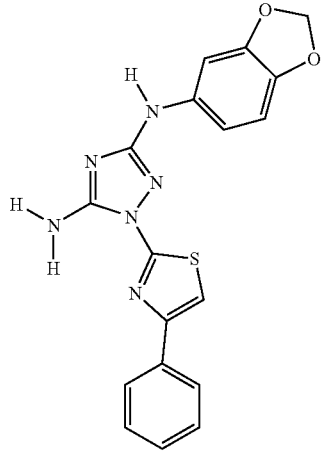
I-83 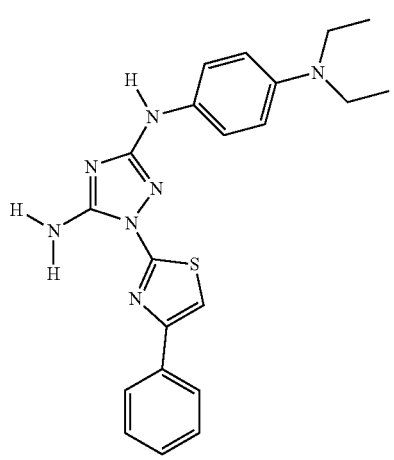
I-84 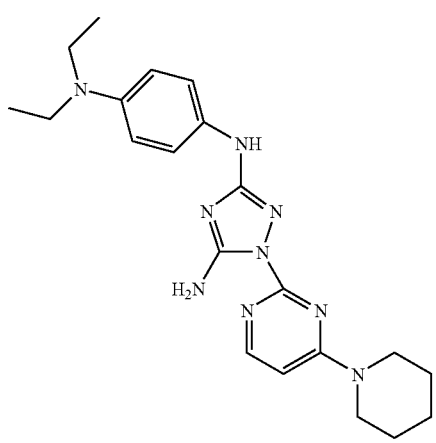

-continued
I-85
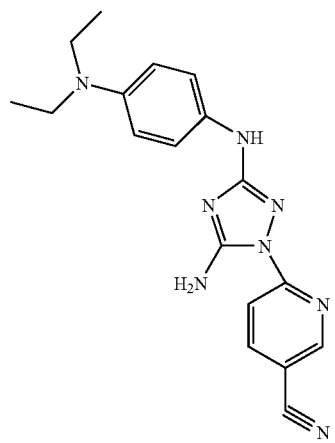
I-86
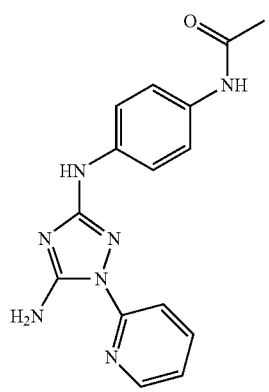
I-87
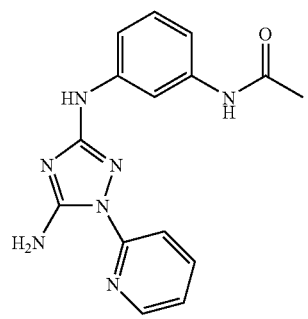
-continued
I-88
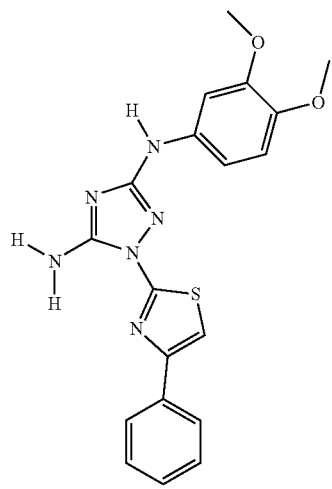
I-89
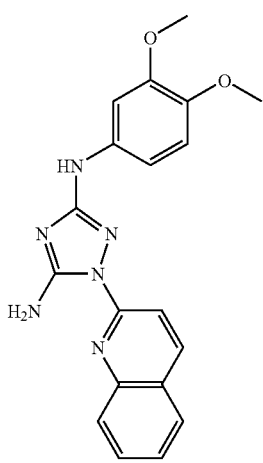
I-91
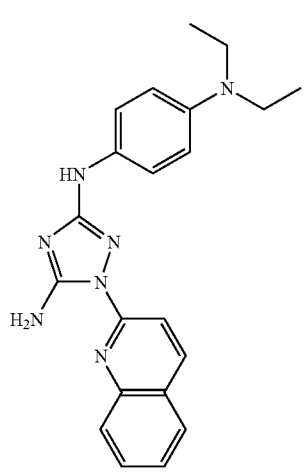

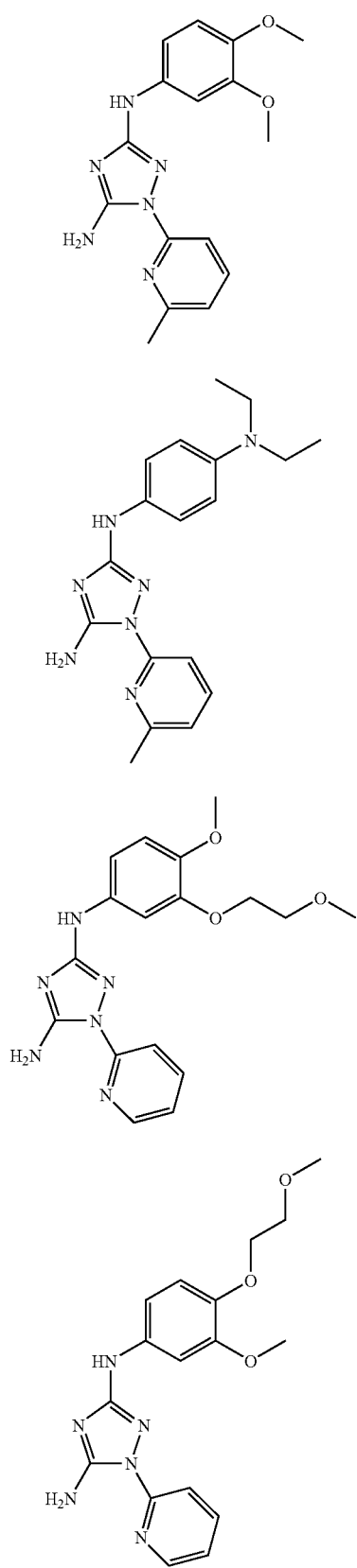
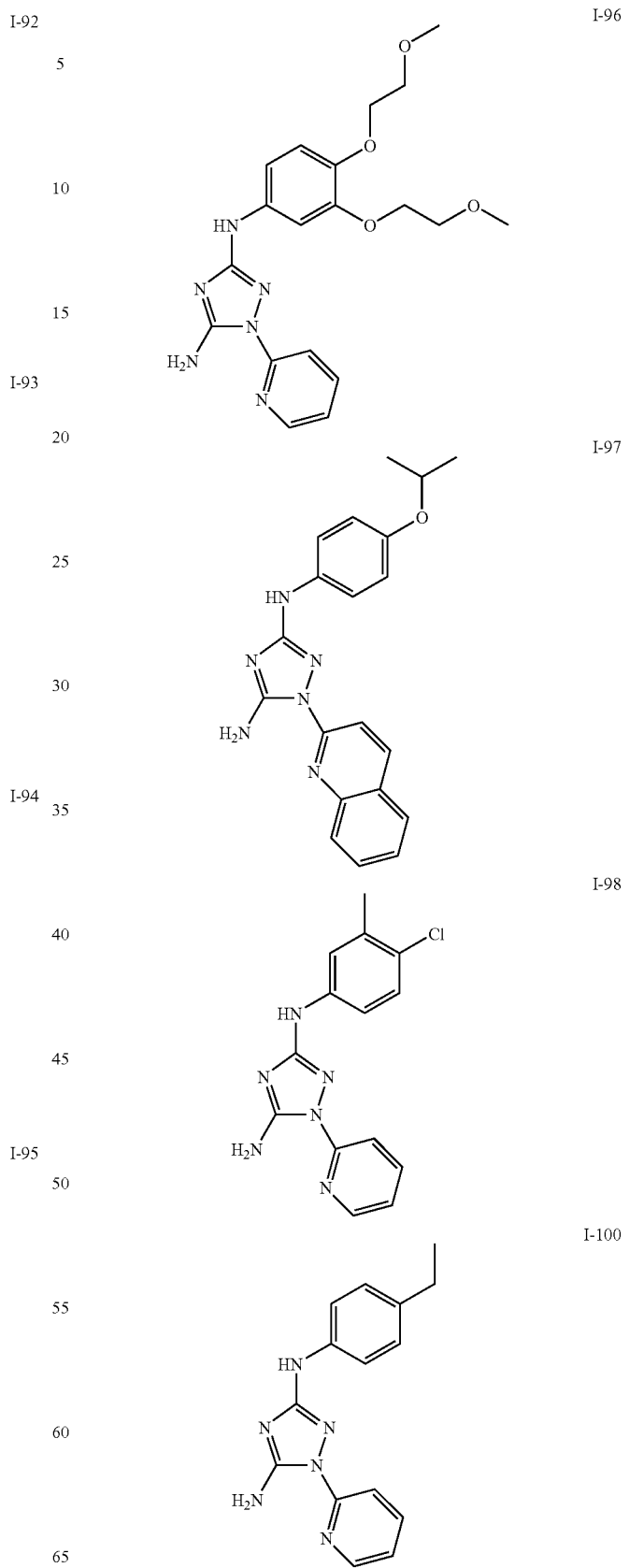

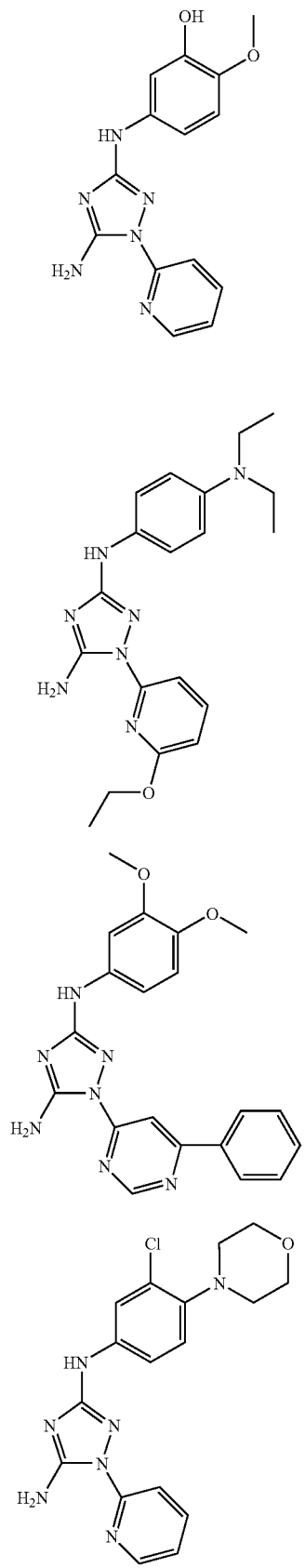

-continued
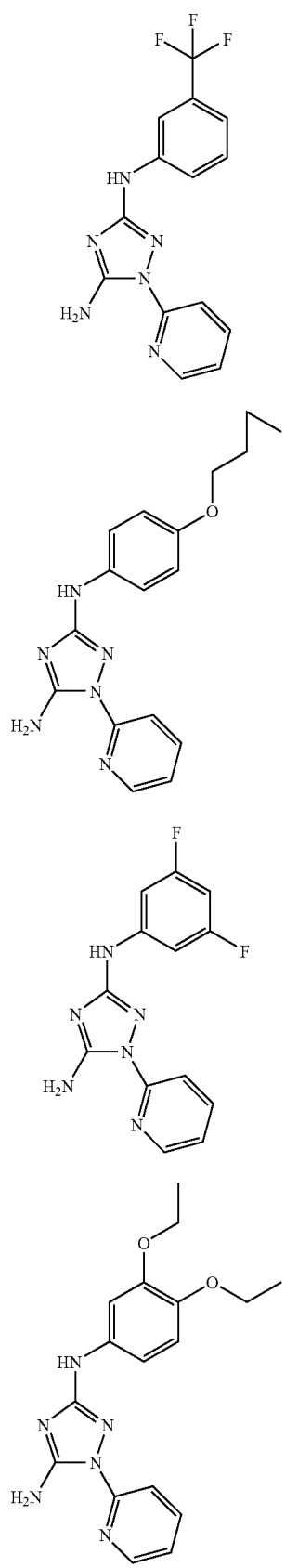
I-109
I-110
I-111
I-117
-continued
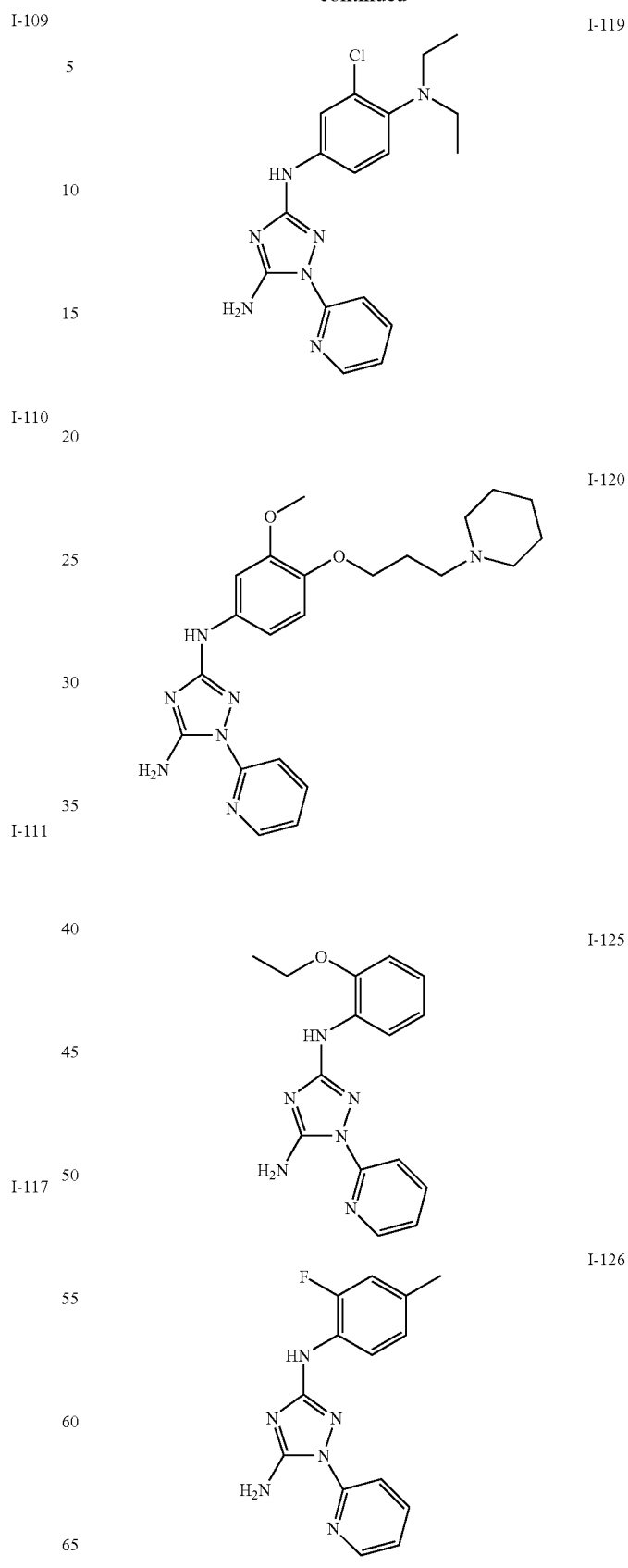
I-119
I-120
I-125
I-126

-continued
I-127
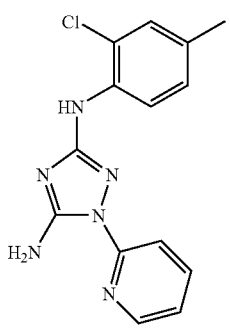
I-128
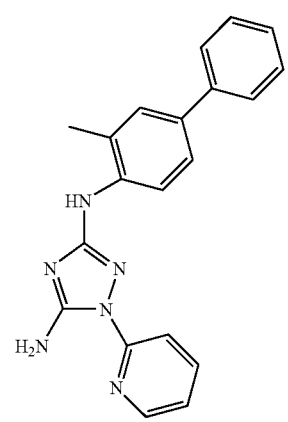
I-130
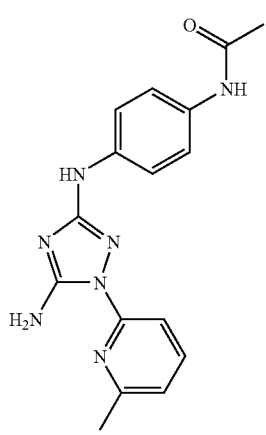
I-131
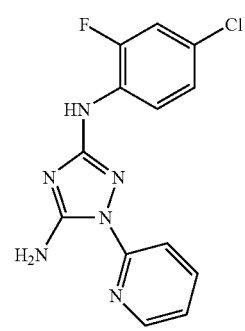
-continued
I-132
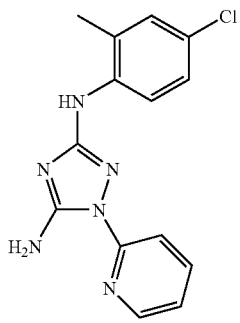
I-133
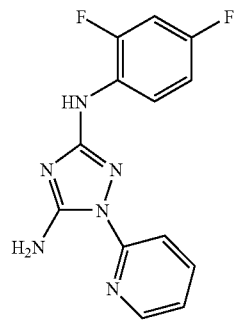
I-134
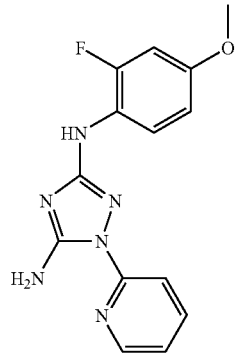
I-137
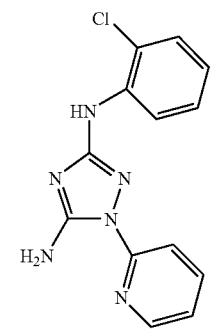

-continued
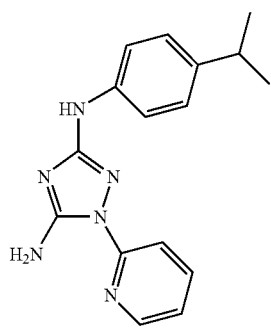
I-138
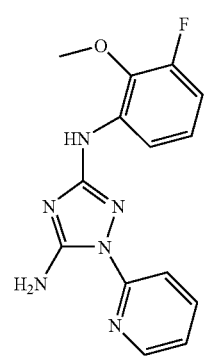
I-139
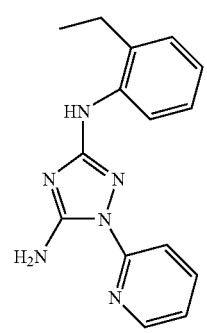
I-140
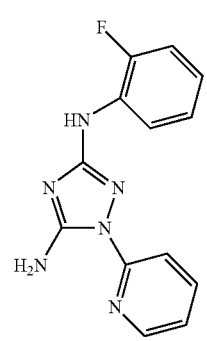
I-141
-continued
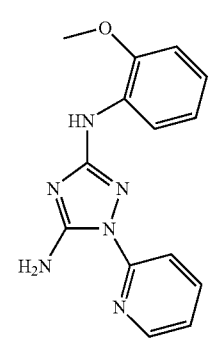
I-142
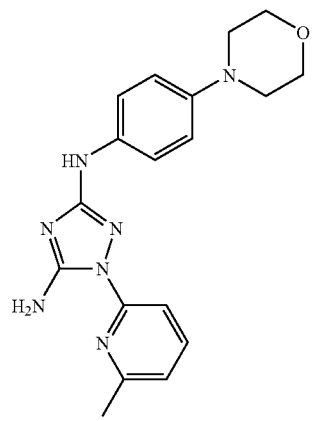
I-144
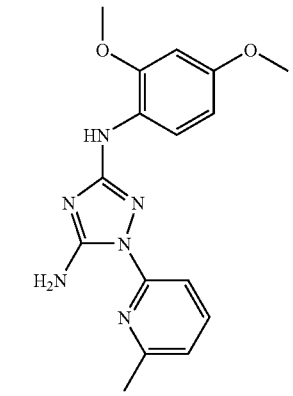
I-145
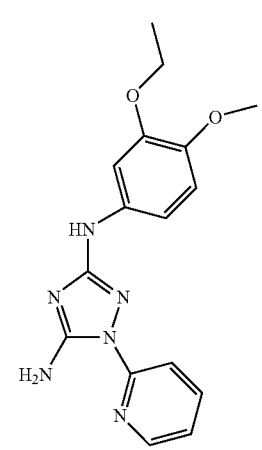
I-147

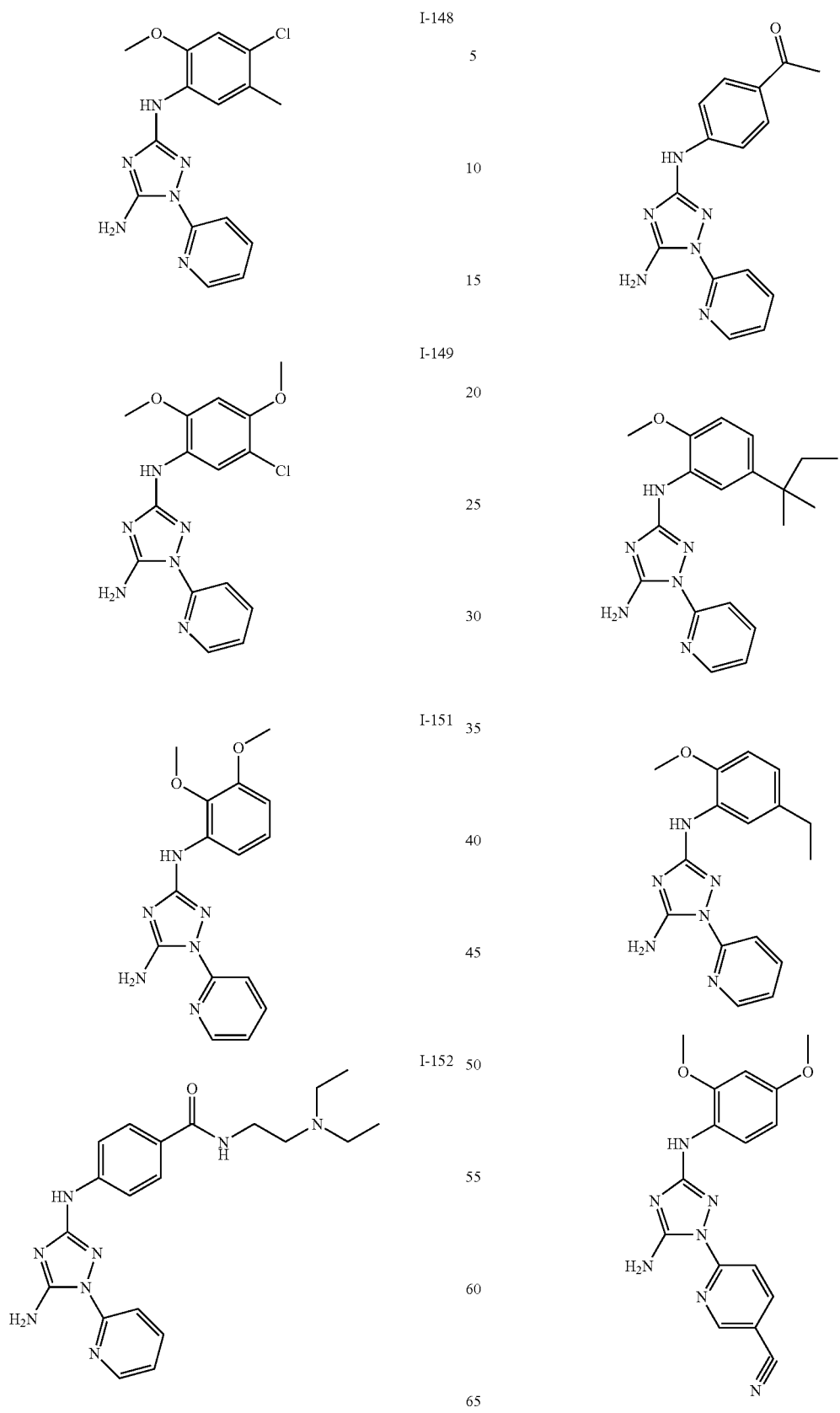

I-159
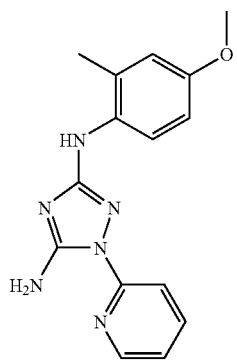
I-160
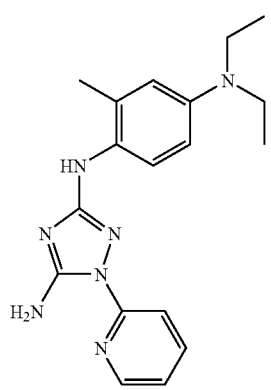
I-162
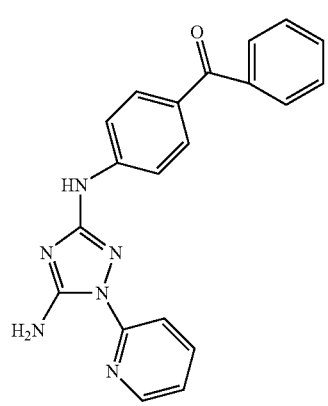
I-163
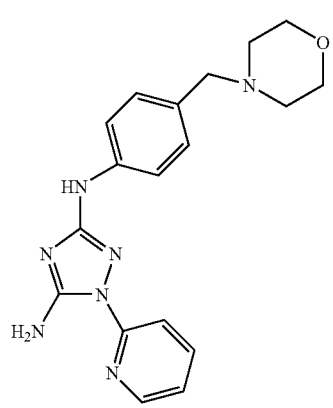
I-165
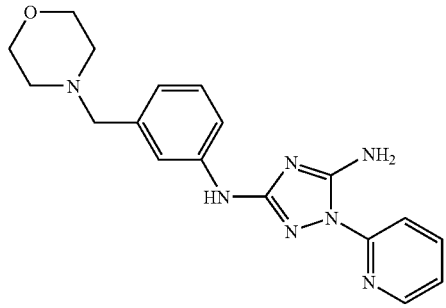
I-167
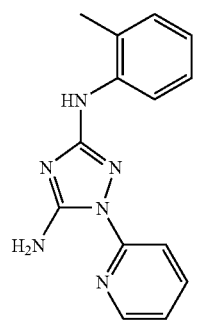
I-168
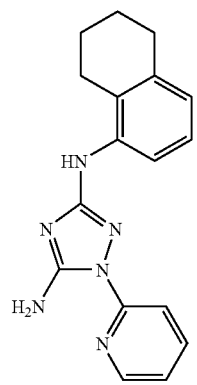
I-169
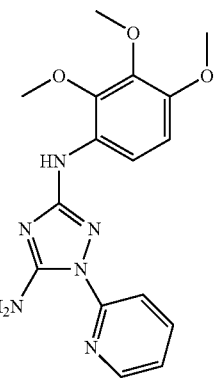

-continued
I-171
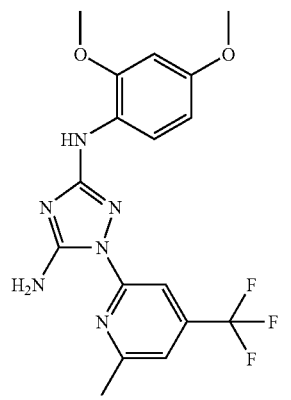
I-175
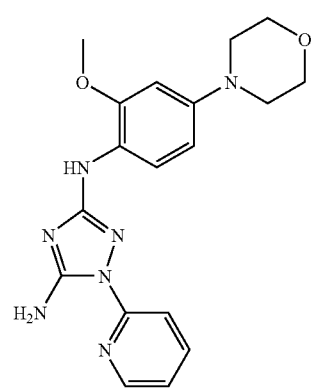
I-176
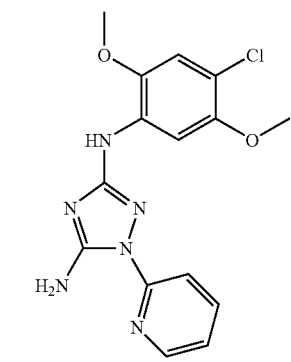
I-177
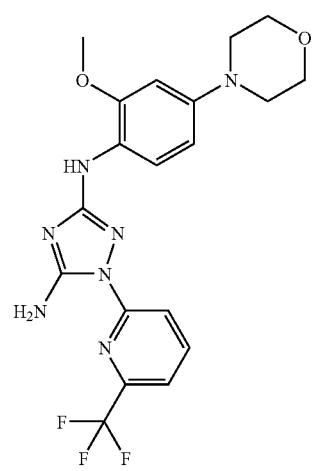
-continued
I-178
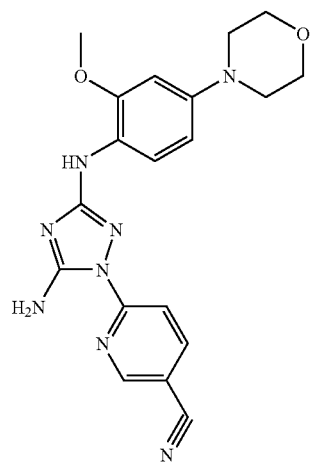
I-179
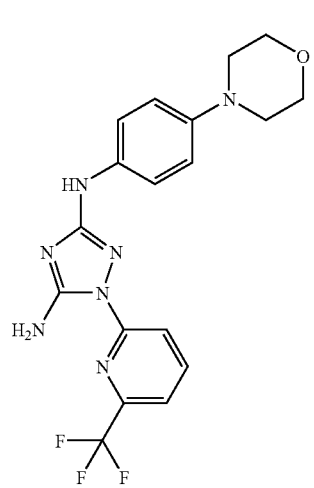
I-180
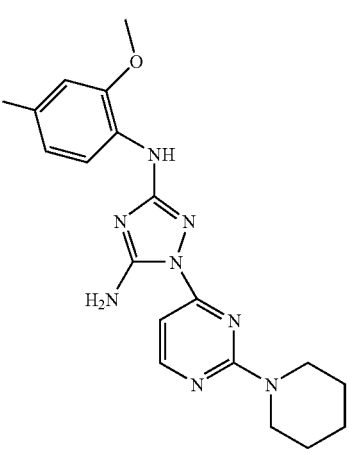

-continued
I-181
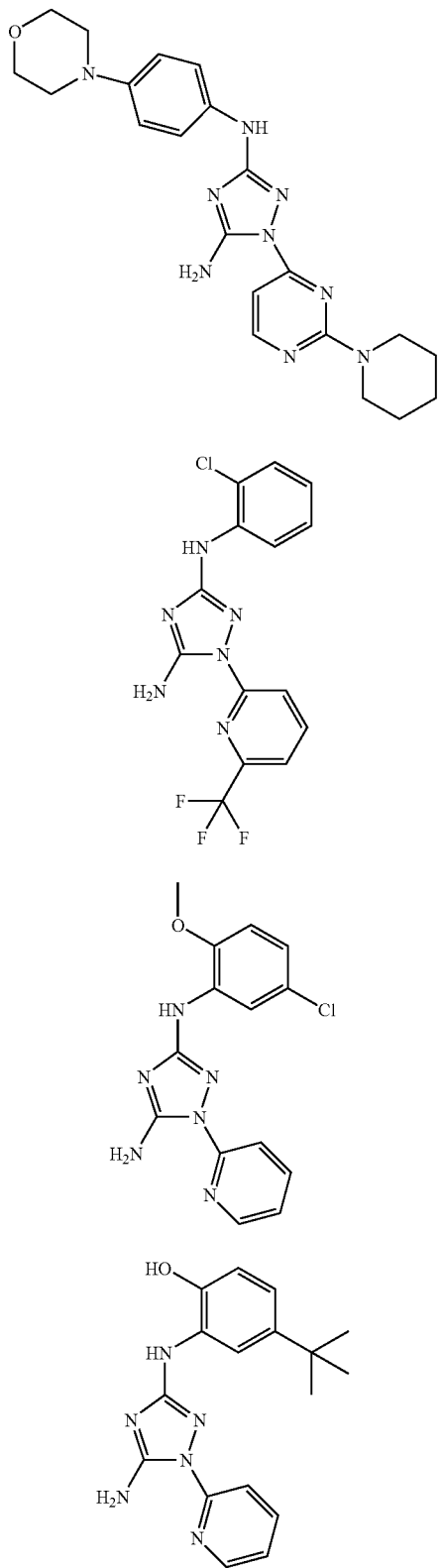
I-182
I-183
I-184
-continued
I-185
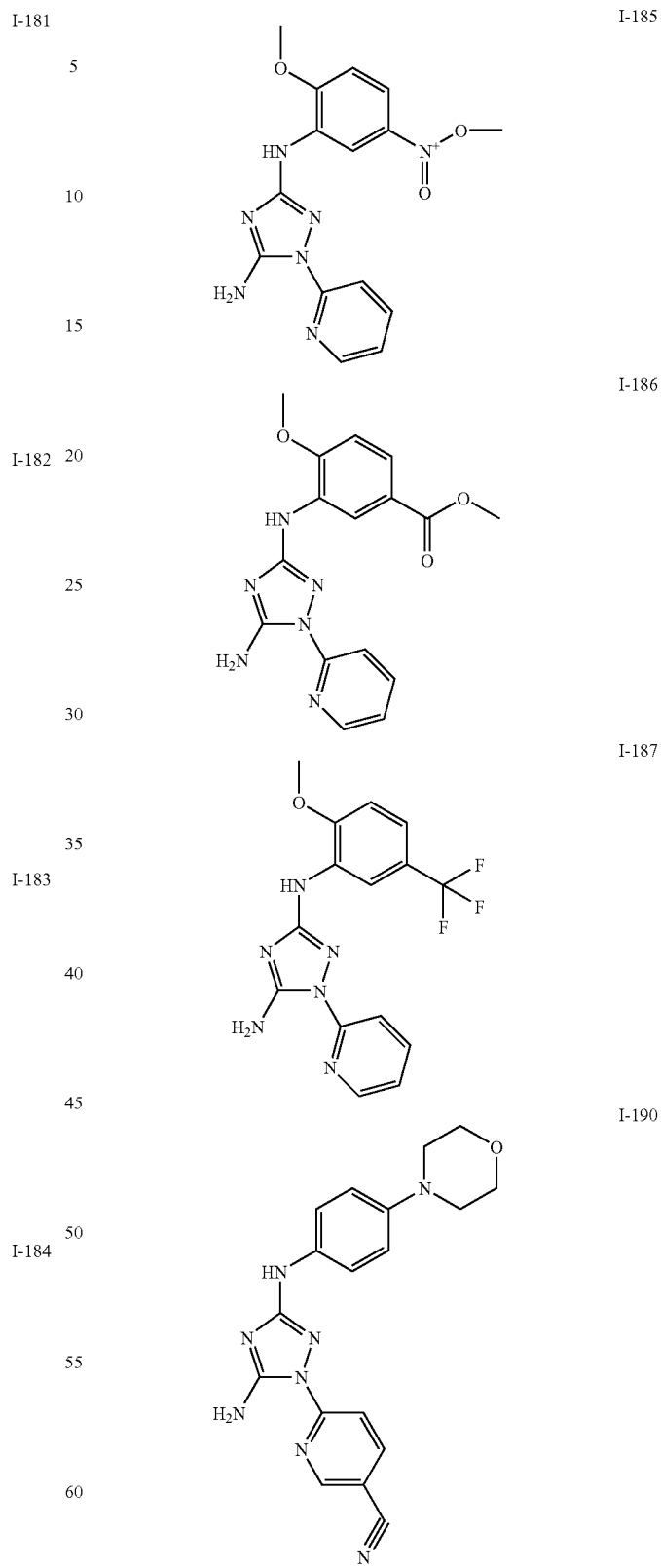
I-186
I-187
I-190

-continued

I-191

I-192

I-193

I-195

I-197

I-198

I-199

I-200

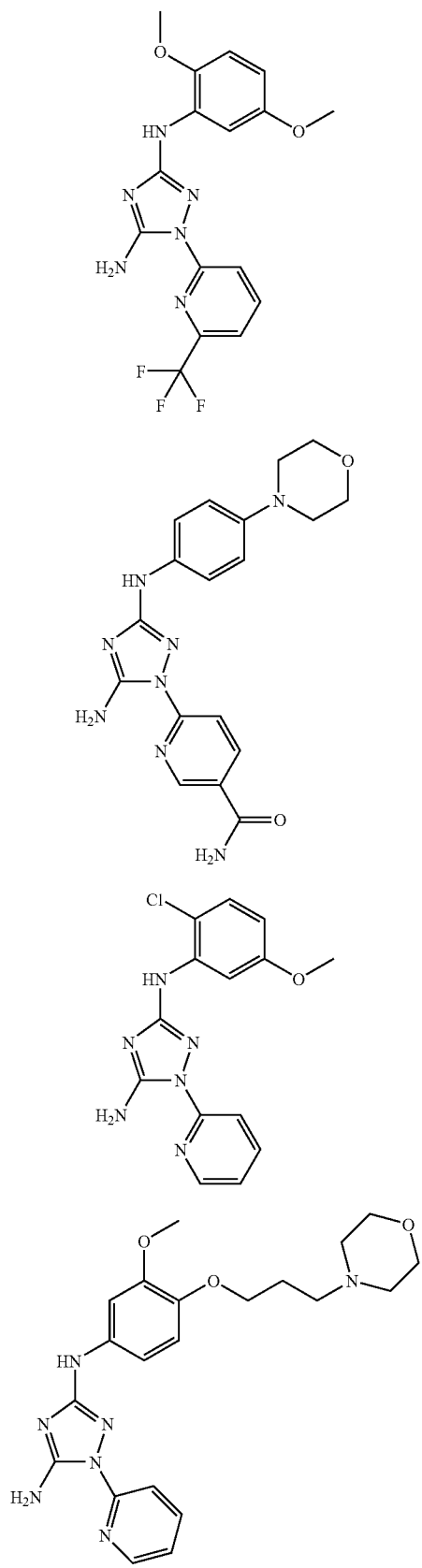

-continued
I-212
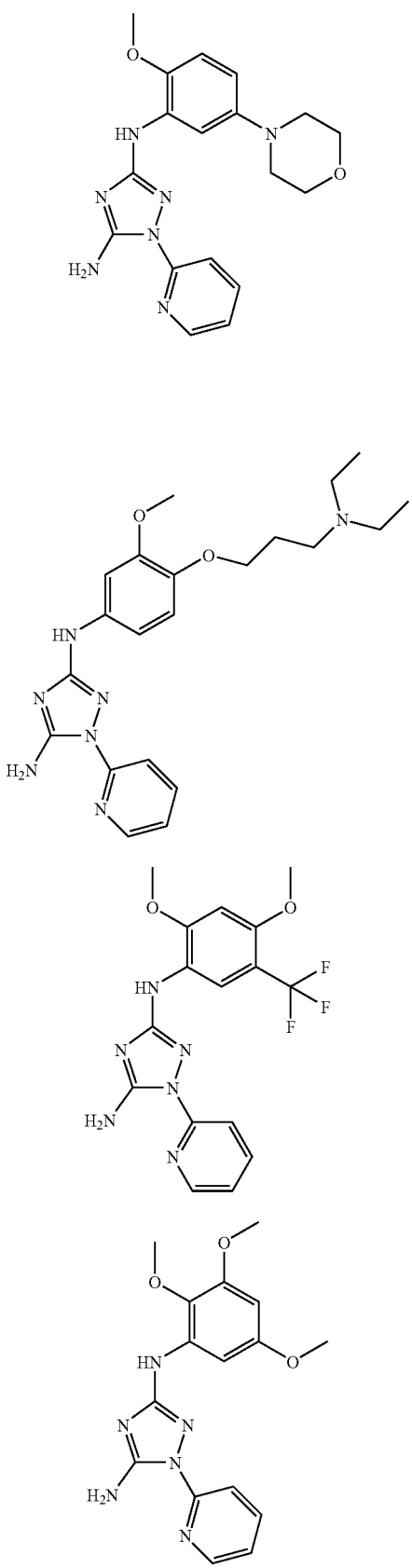
I-215
I-216
I-217
-continued
I-218
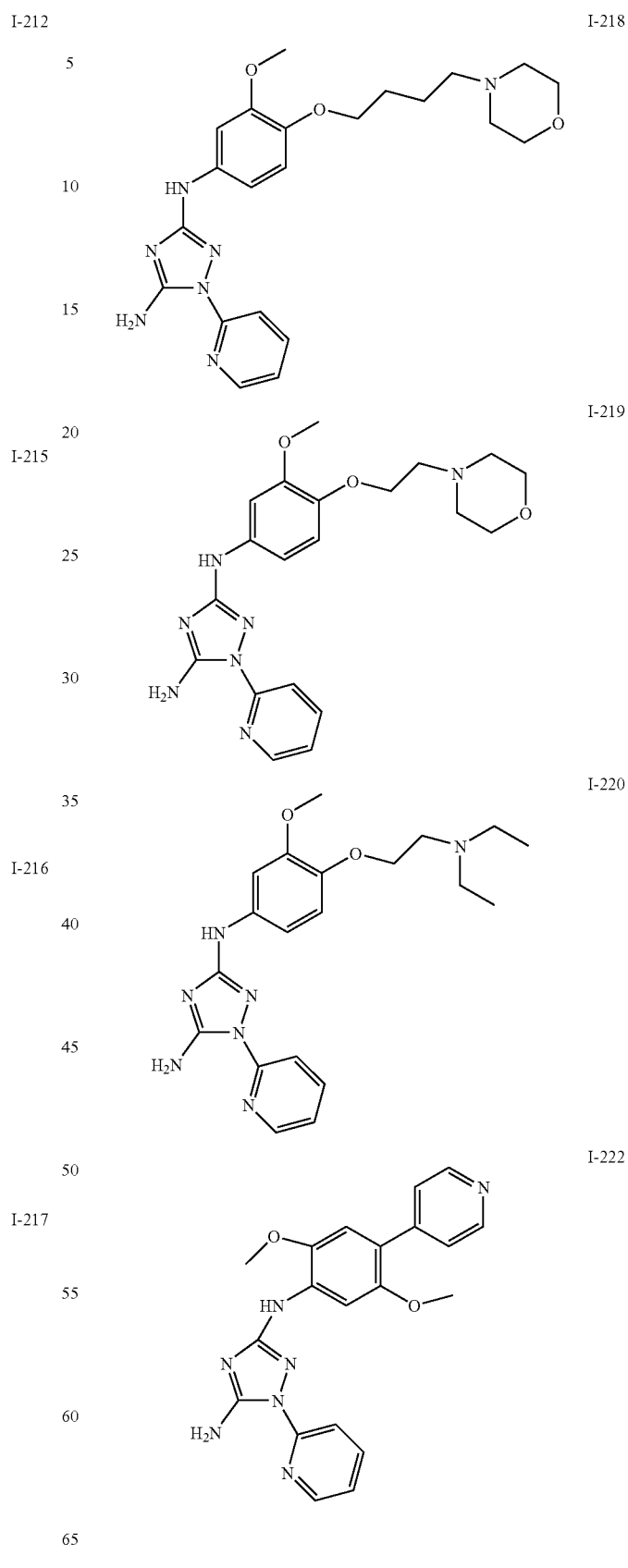
I-219
I-220
I-222

-continued
I-223
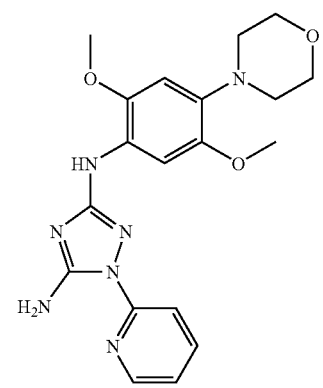
I-224
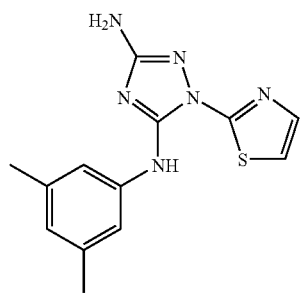
I-225
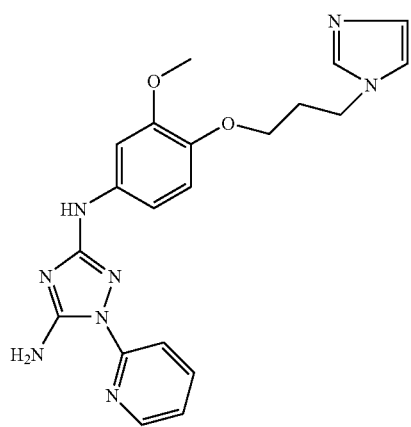
I-226
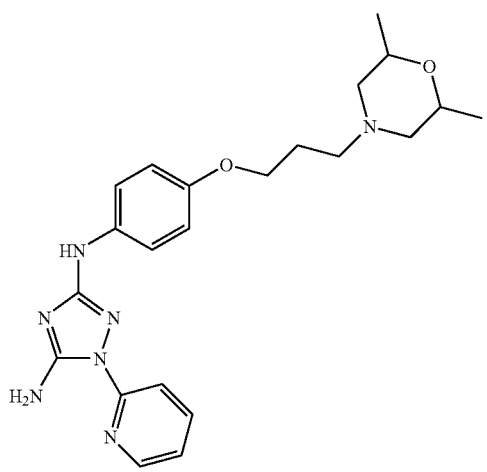
-continued
I-227
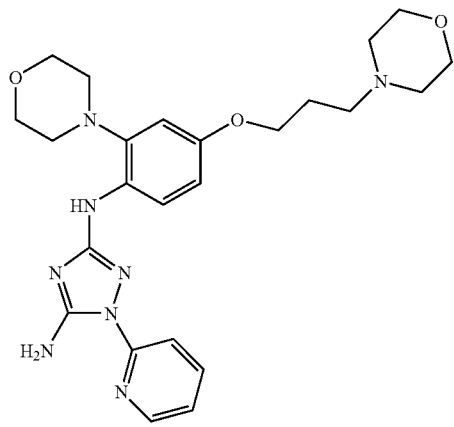
I-228
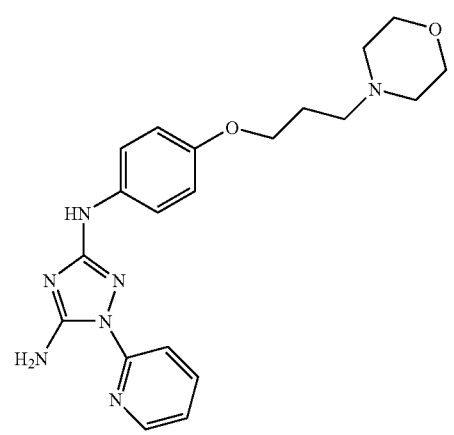
I-229
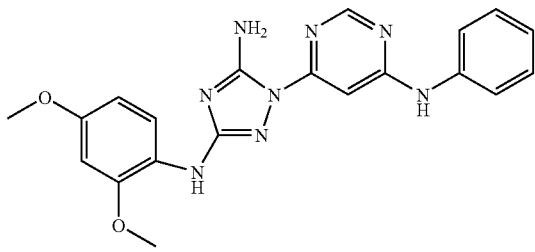
I-230
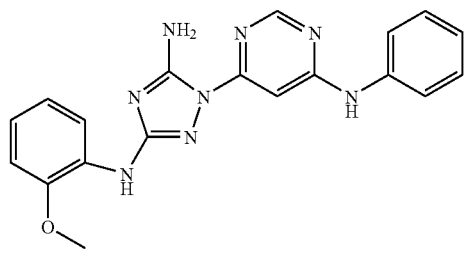
I-231
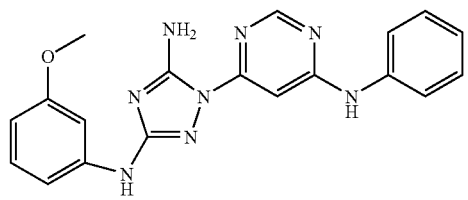

-continued

I-232

I-233

I-234

I-235

I-236

-continued

I-237

I-238

I-239

-continued
I-248
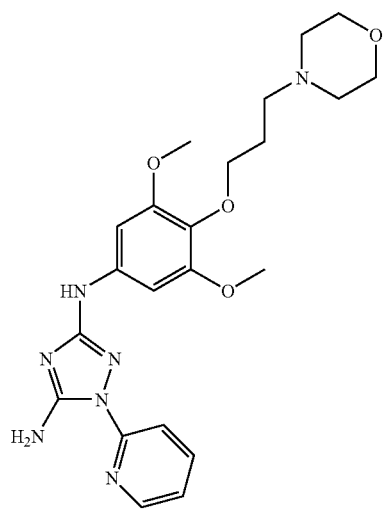
I-249
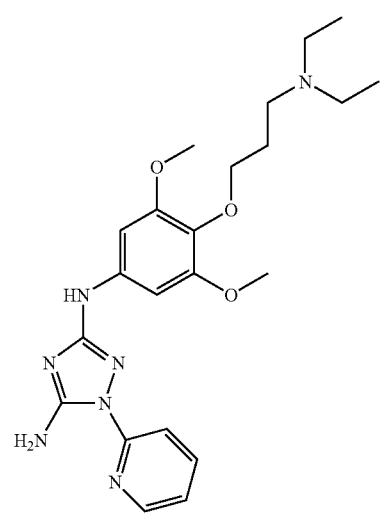
I-250
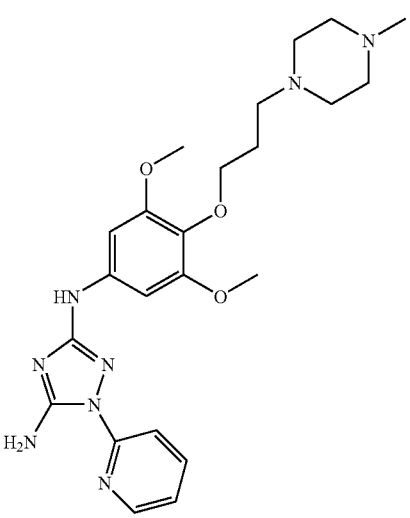
-continued
I-251
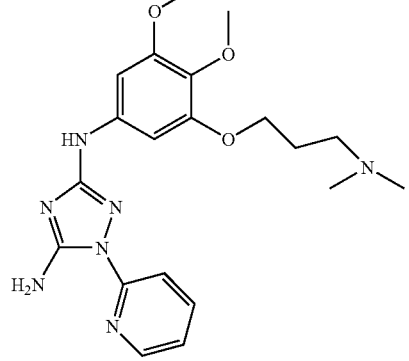
I-254
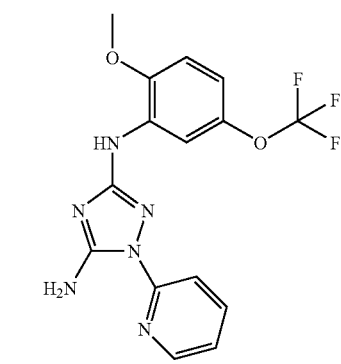
I-255
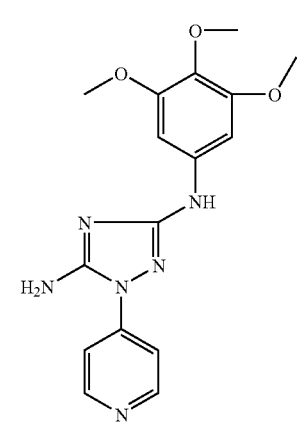
I-256
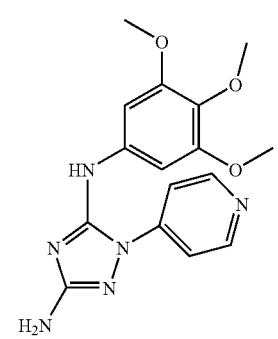

-continued
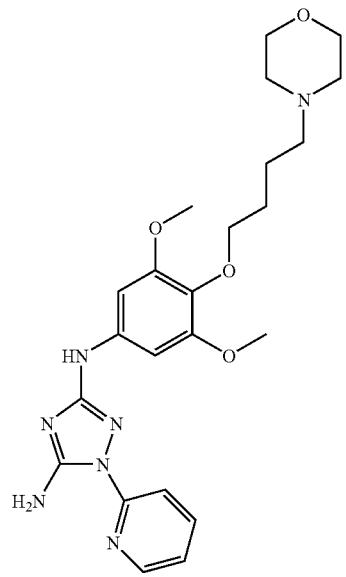
I-257
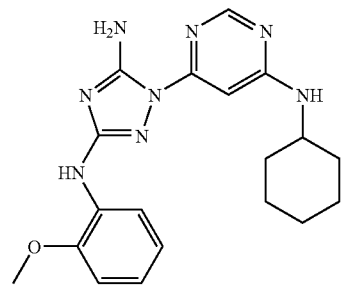
I-258
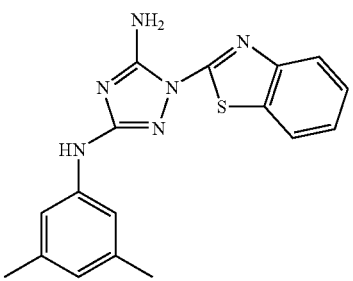
I-262
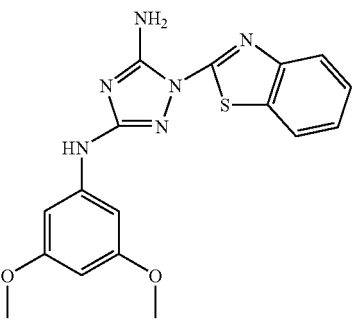
I-263
-continued
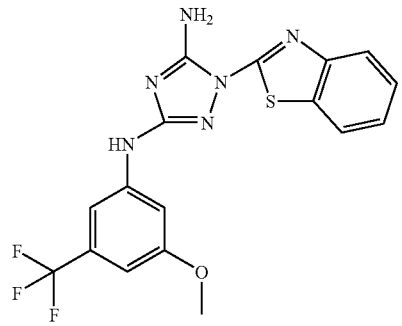
I-264
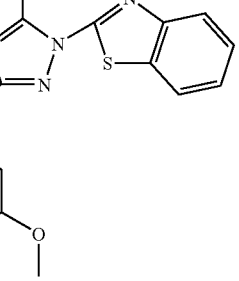
I-265
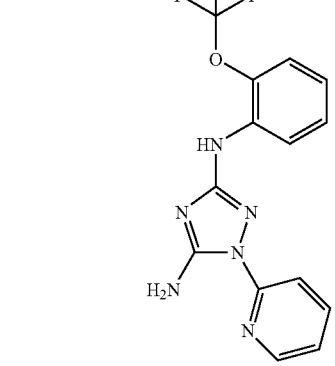
I-266
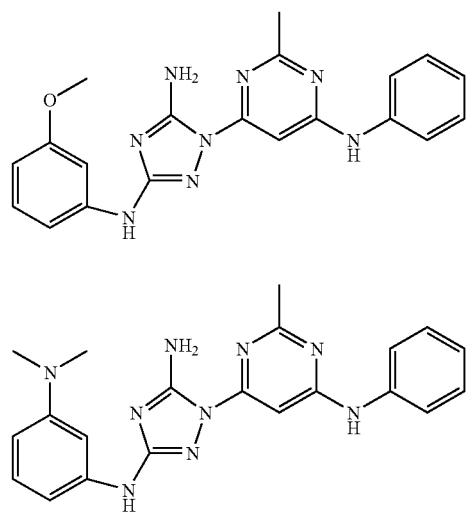
I-267
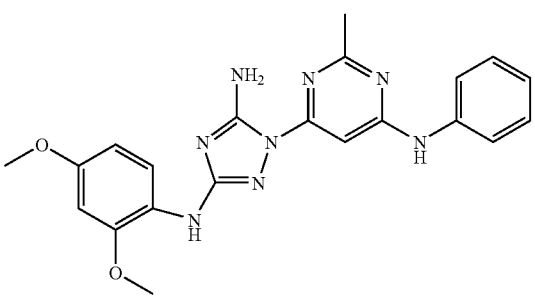
I-269

I-271
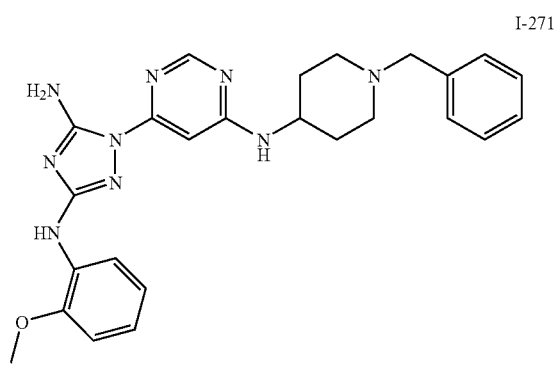
I-282
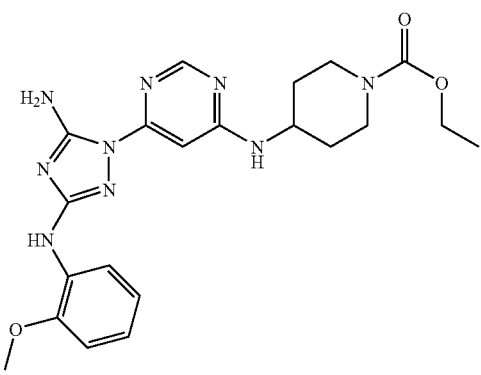
I-272
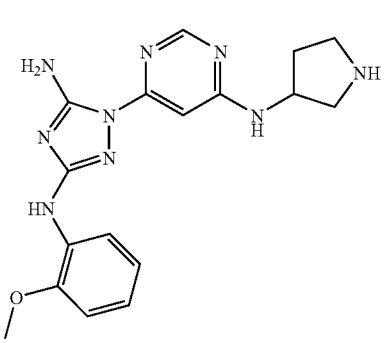
I-283
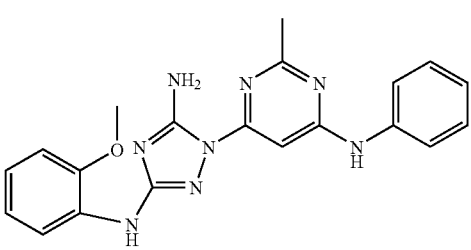
I-280
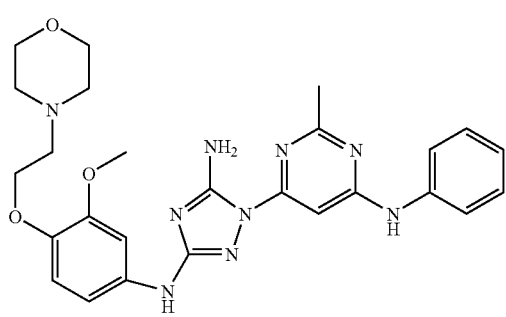
I-284
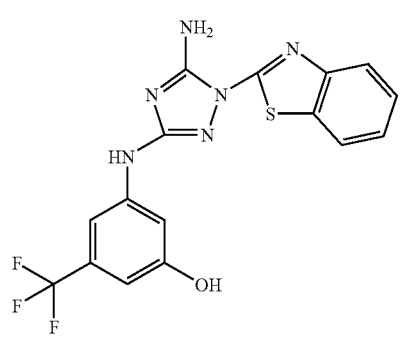
I-281
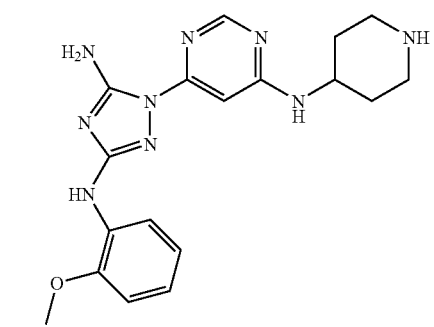
I-286
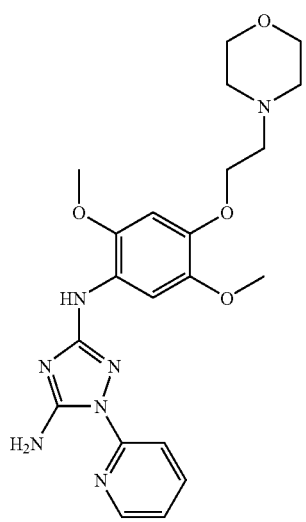

-continued
I-290
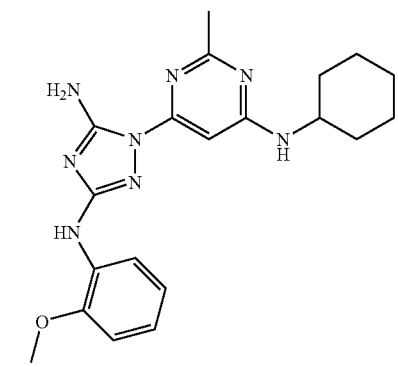
I-292
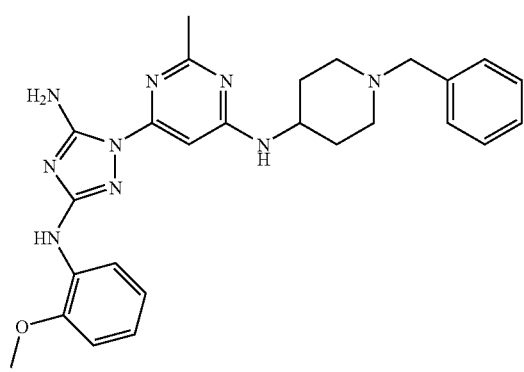
I-293
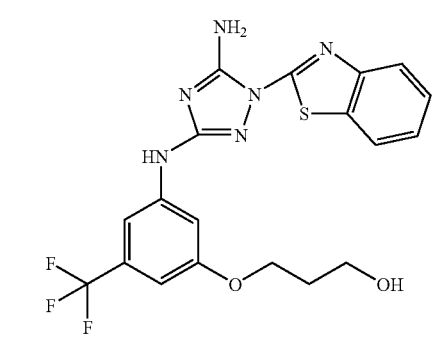
I-294
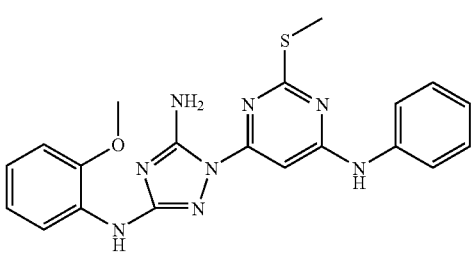
-continued
I-295
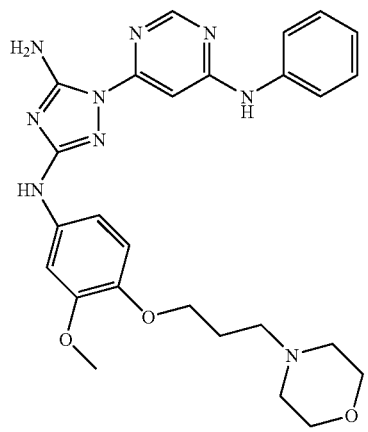
I-296
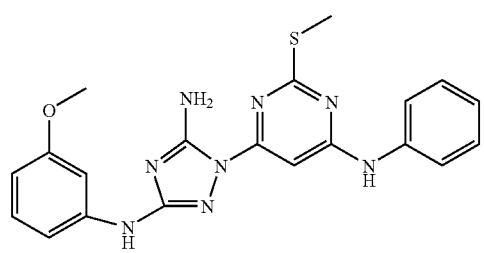
I-297
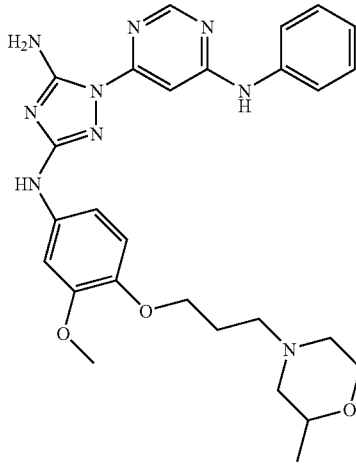
I-302
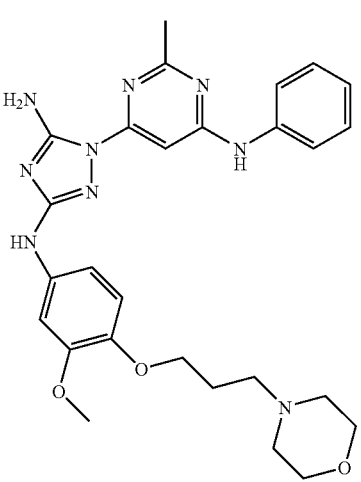

-continued
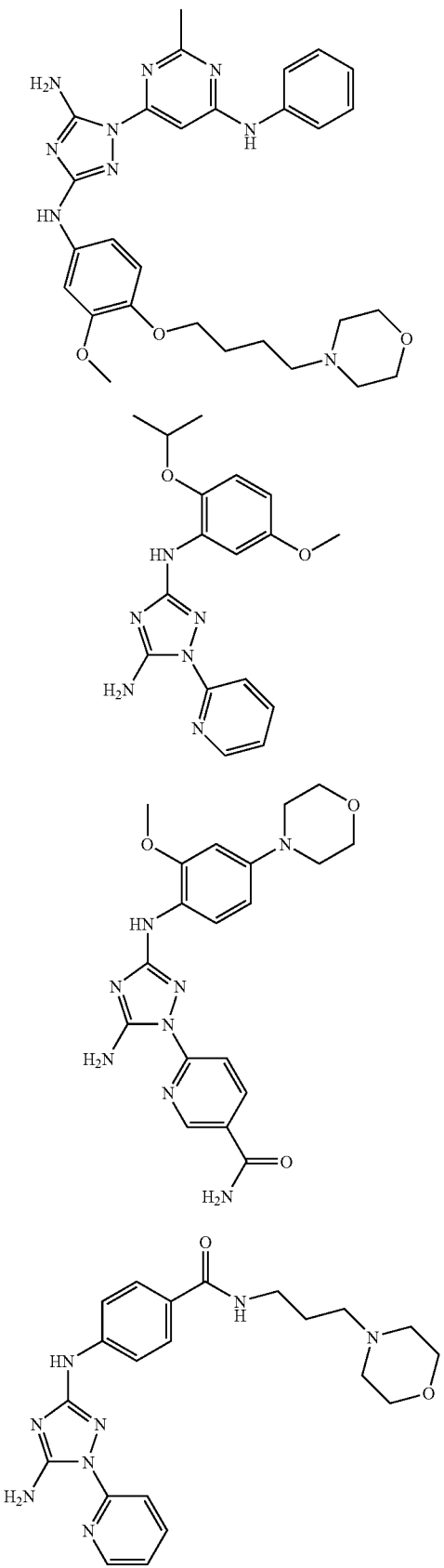
I-309
I-313
I-314
-continued
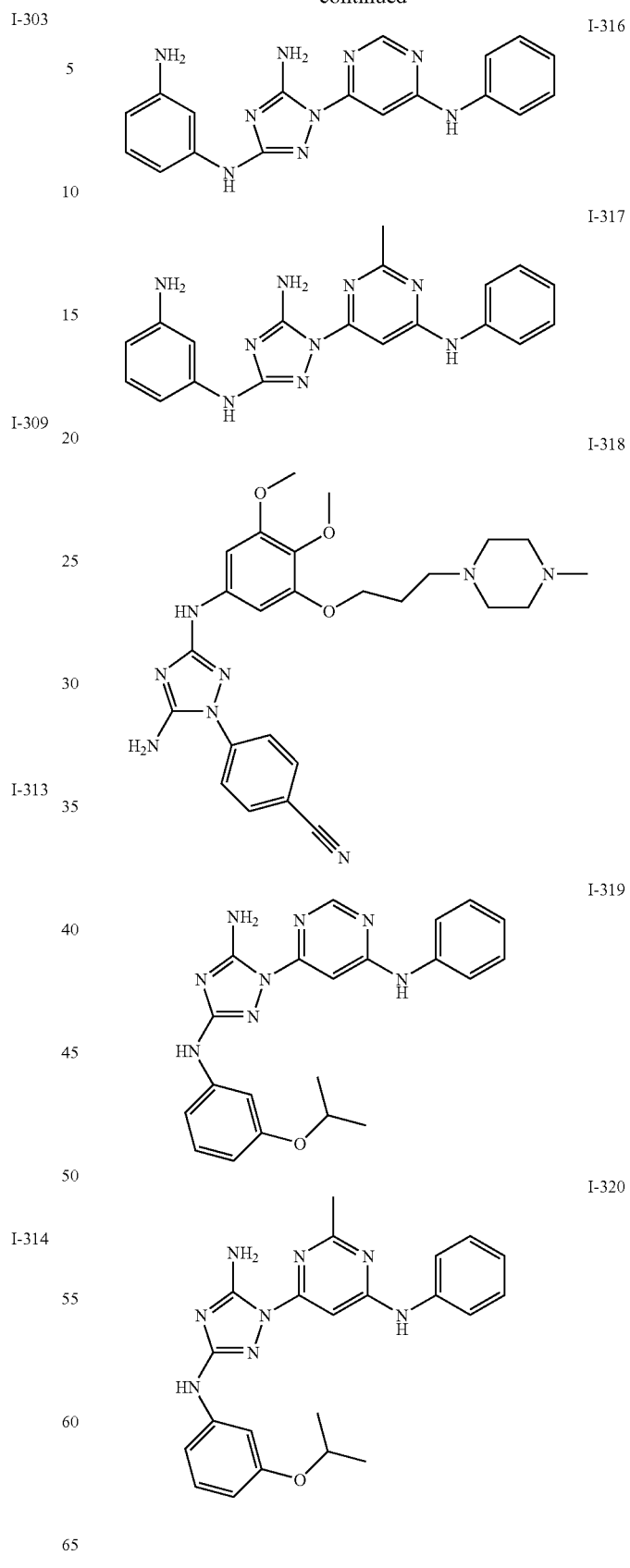
I-303
I-316
I-317
I-318
I-319
I-320

-continued
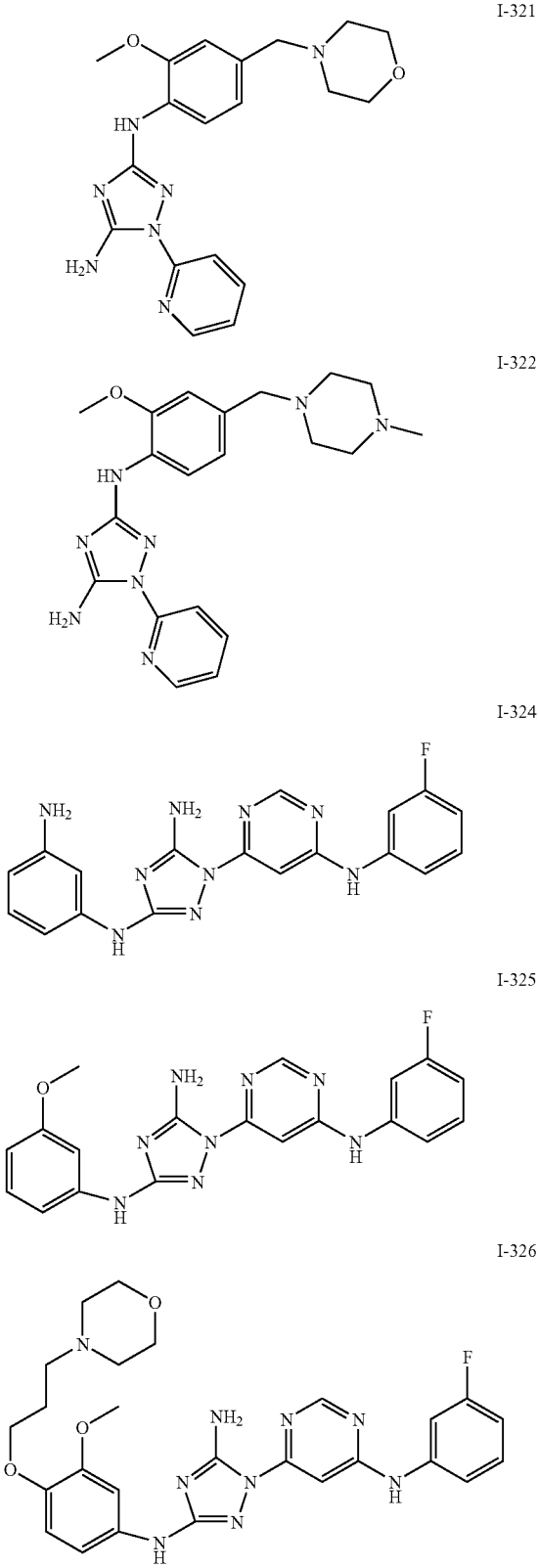
I-321
I-322
I-324
I-325
I-326
-continued
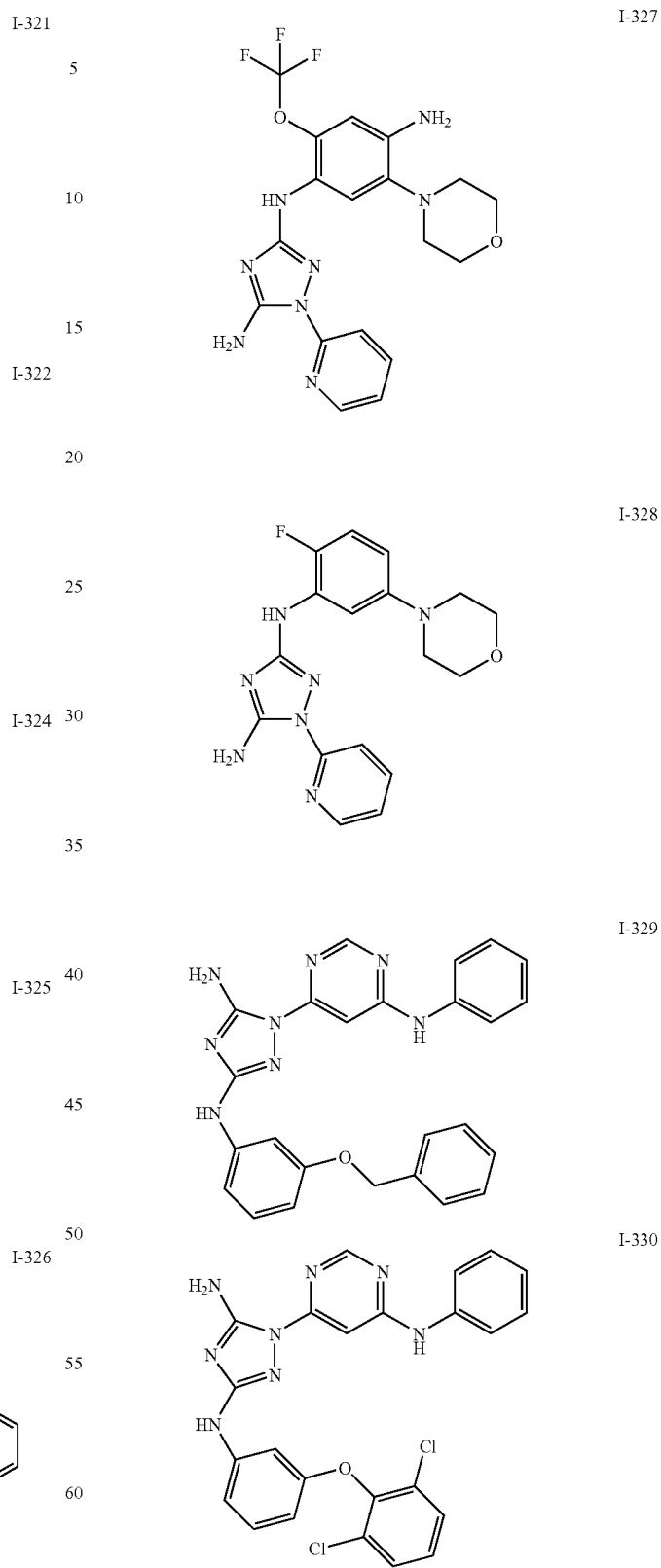
I-327
I-328
I-329
I-330

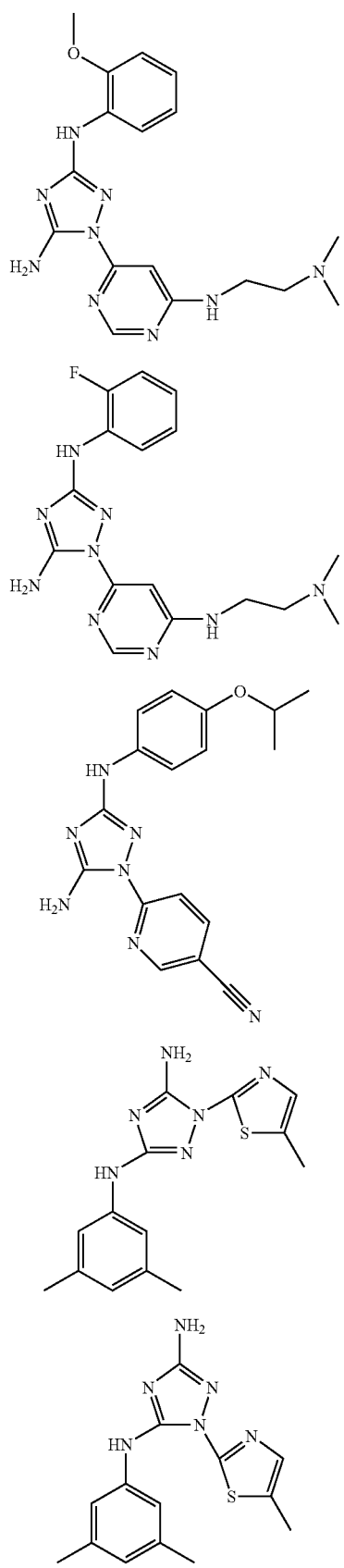

-continued
I-341
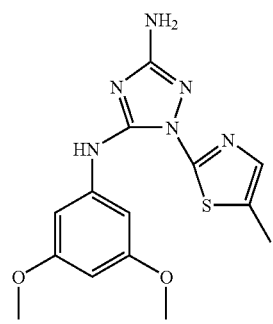
I-342
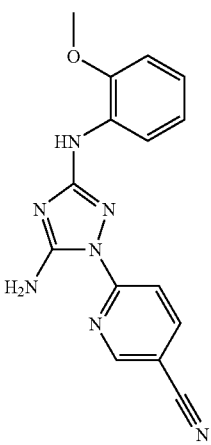
I-343
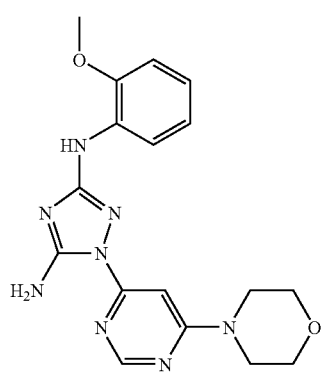
I-346
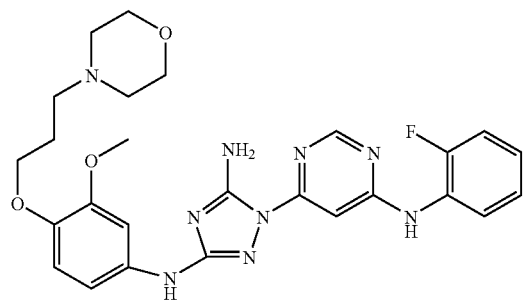
-continued
I-347
I-348
I-351
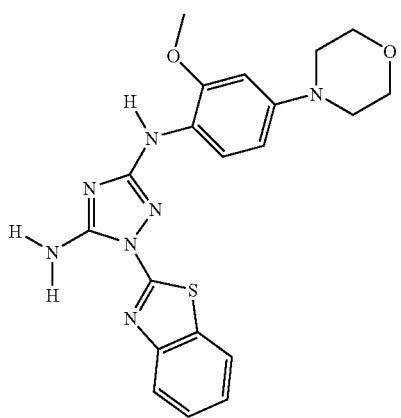

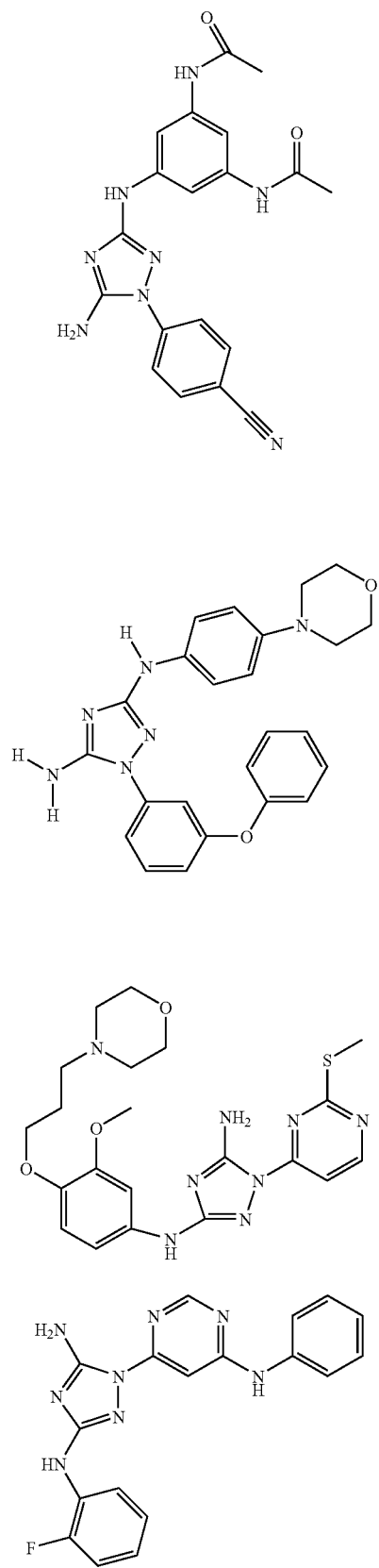
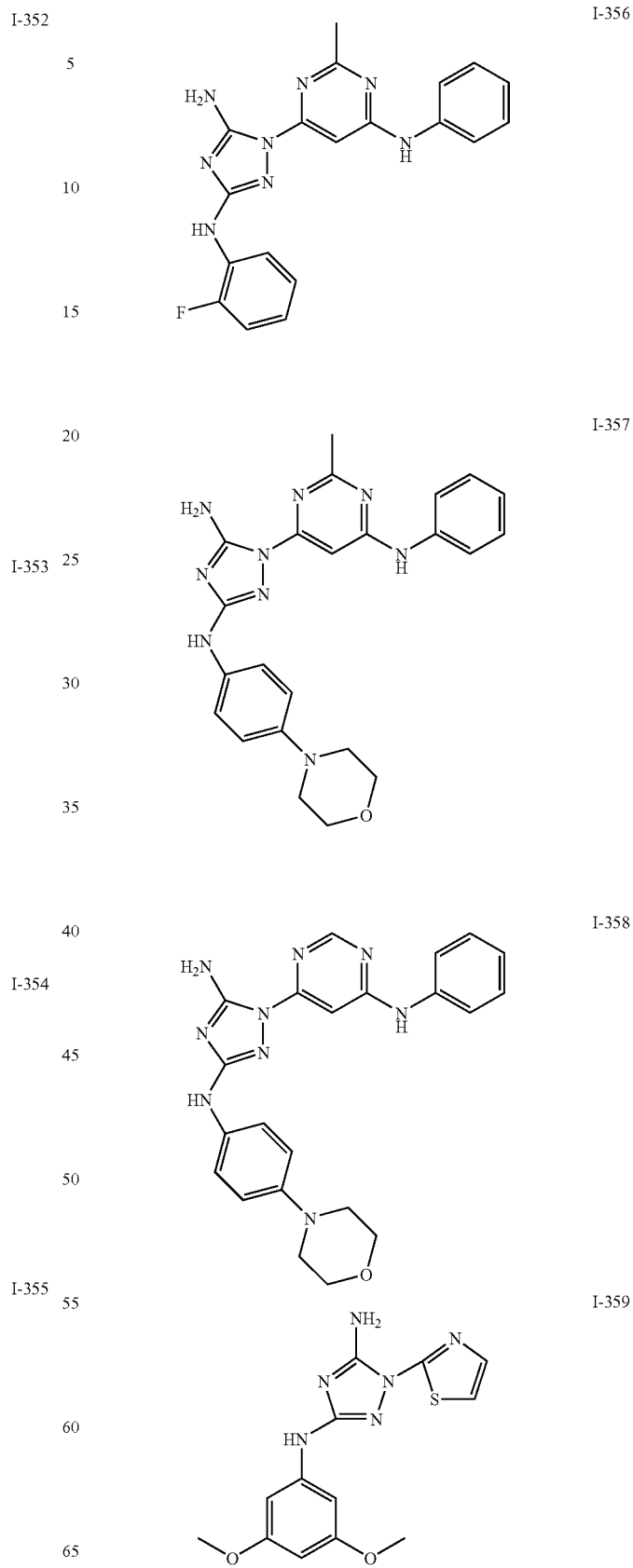

I-360
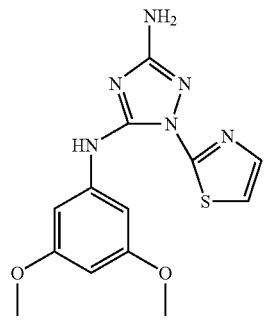
I-361
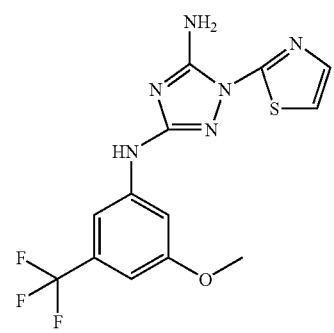
I-362
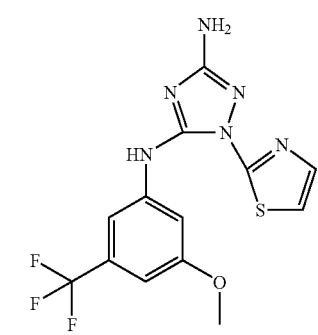
I-366
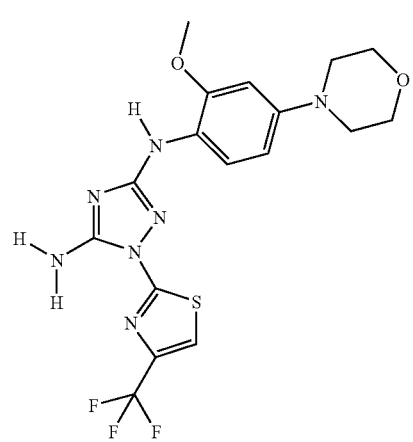
I-367
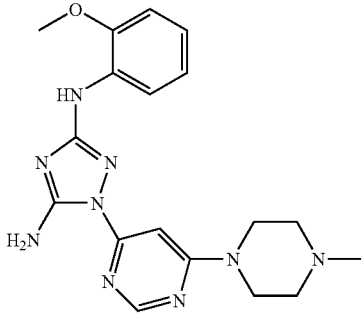
I-368
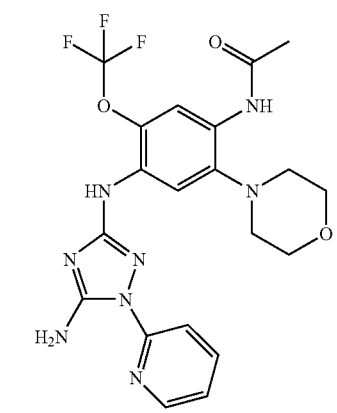
I-369
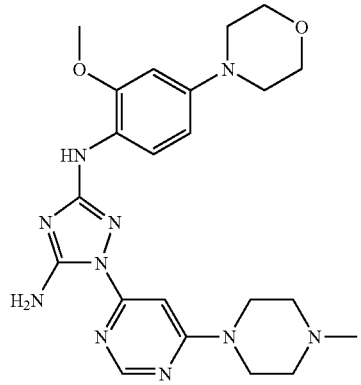
I-370
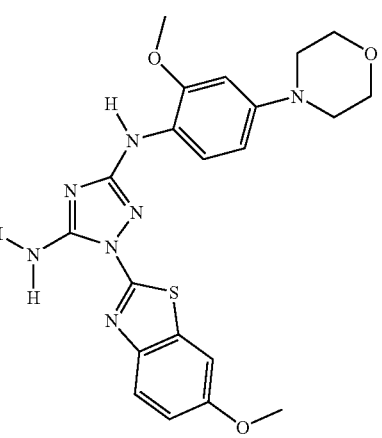

| 711 | 712 |
|---|---|
| -continued | -continued |
I-371
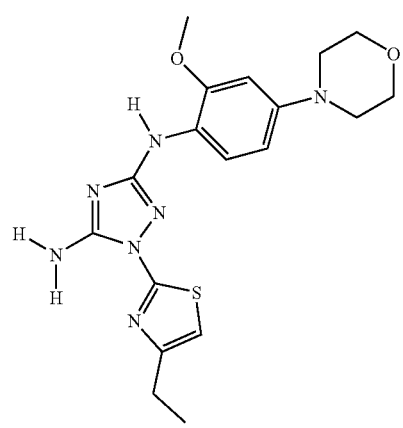
I-375
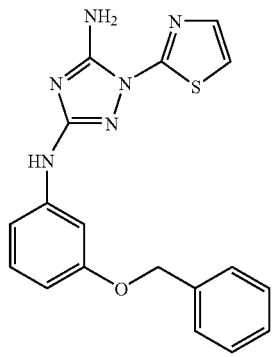
I-372
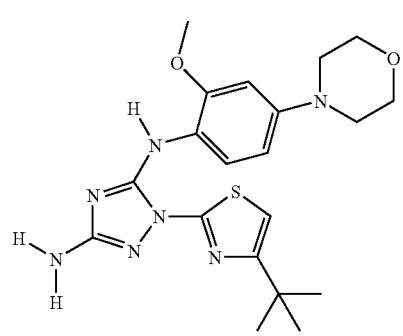
I-381
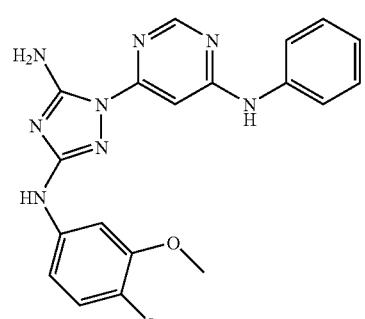
I-373
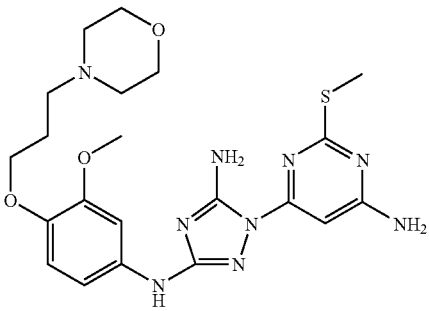
I-382
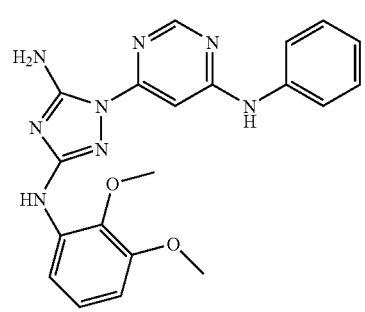
I-374
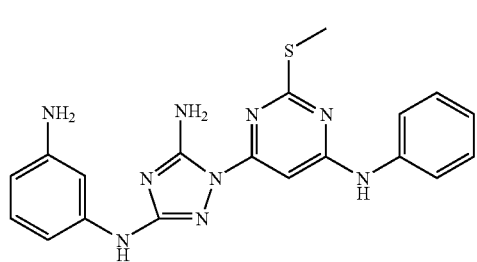
I-383
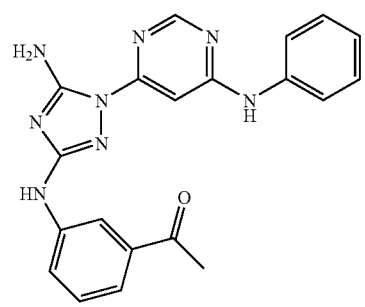

-continued
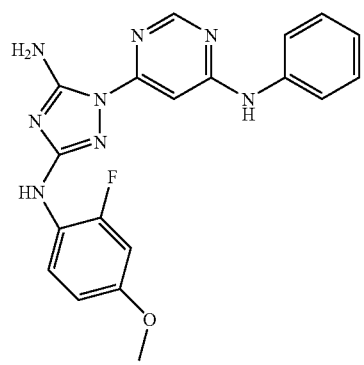
I-384
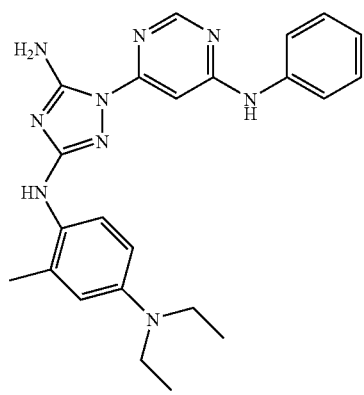
I-385
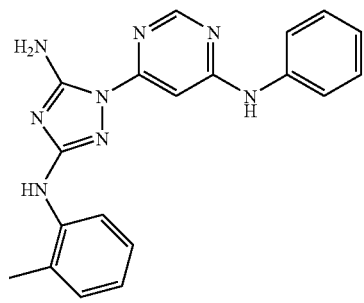
I-386
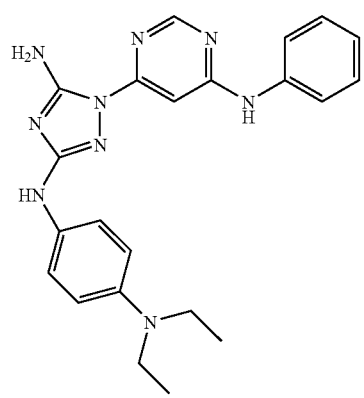
I-387
-continued
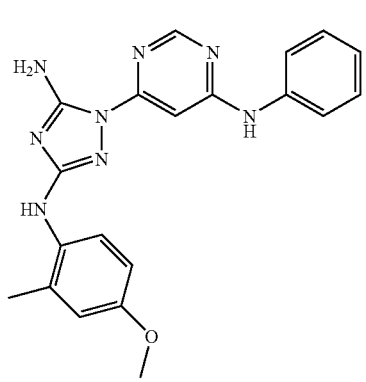
I-388
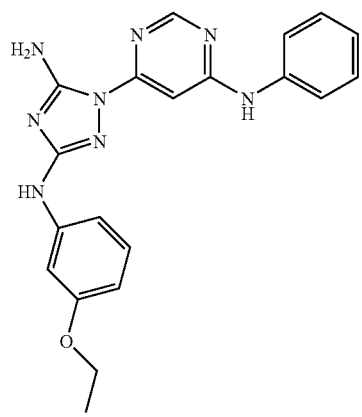
I-389
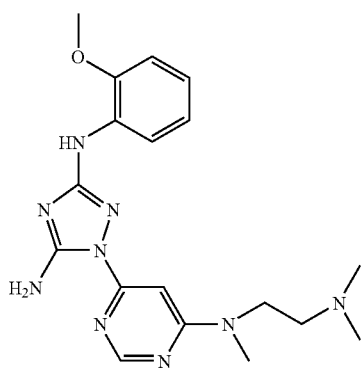
I-390
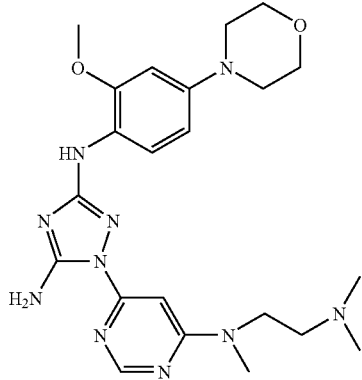
I-391

-continued
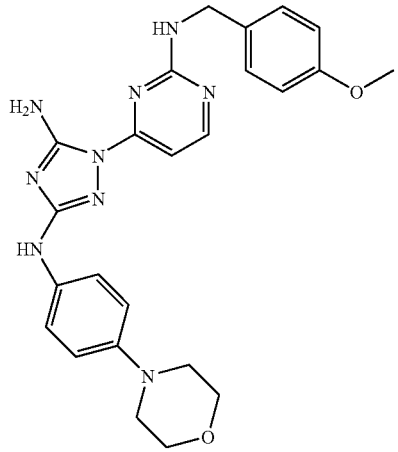
I-394
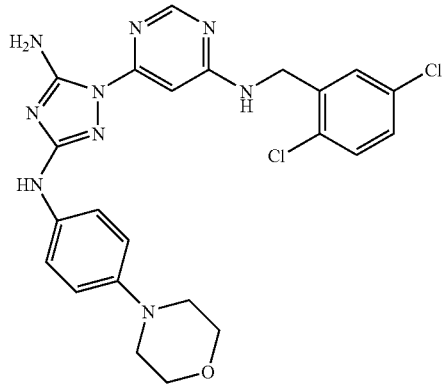
I-399
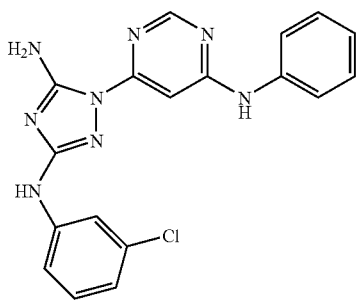
I-400
I-397
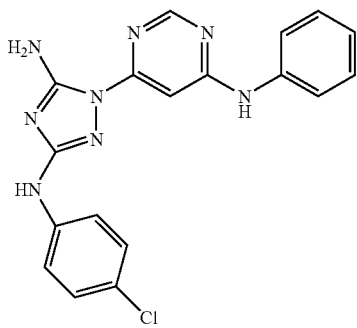
I-401
I-398
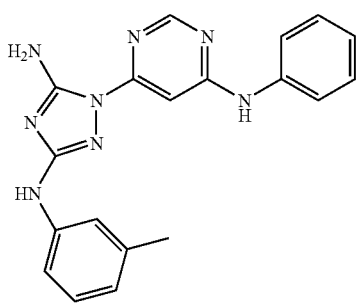
I-402

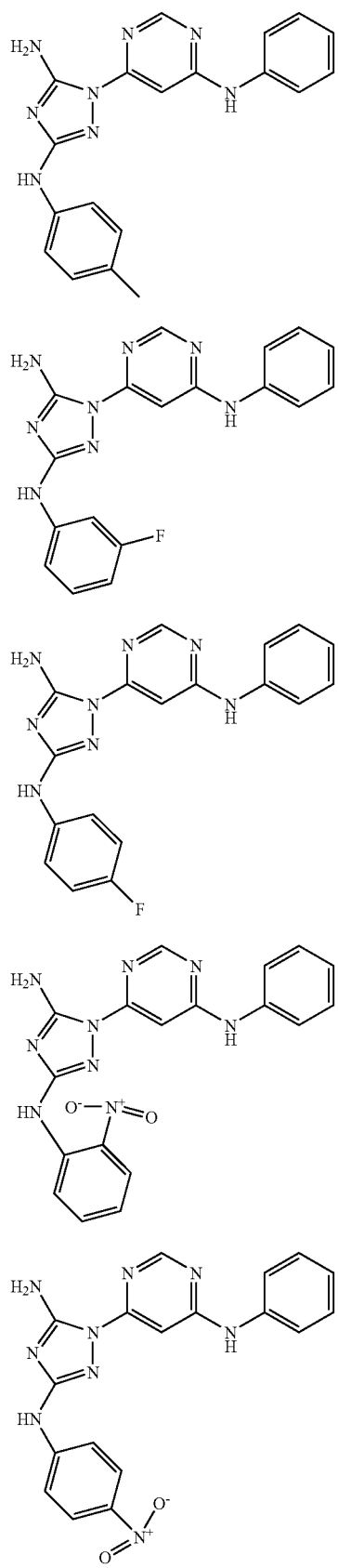
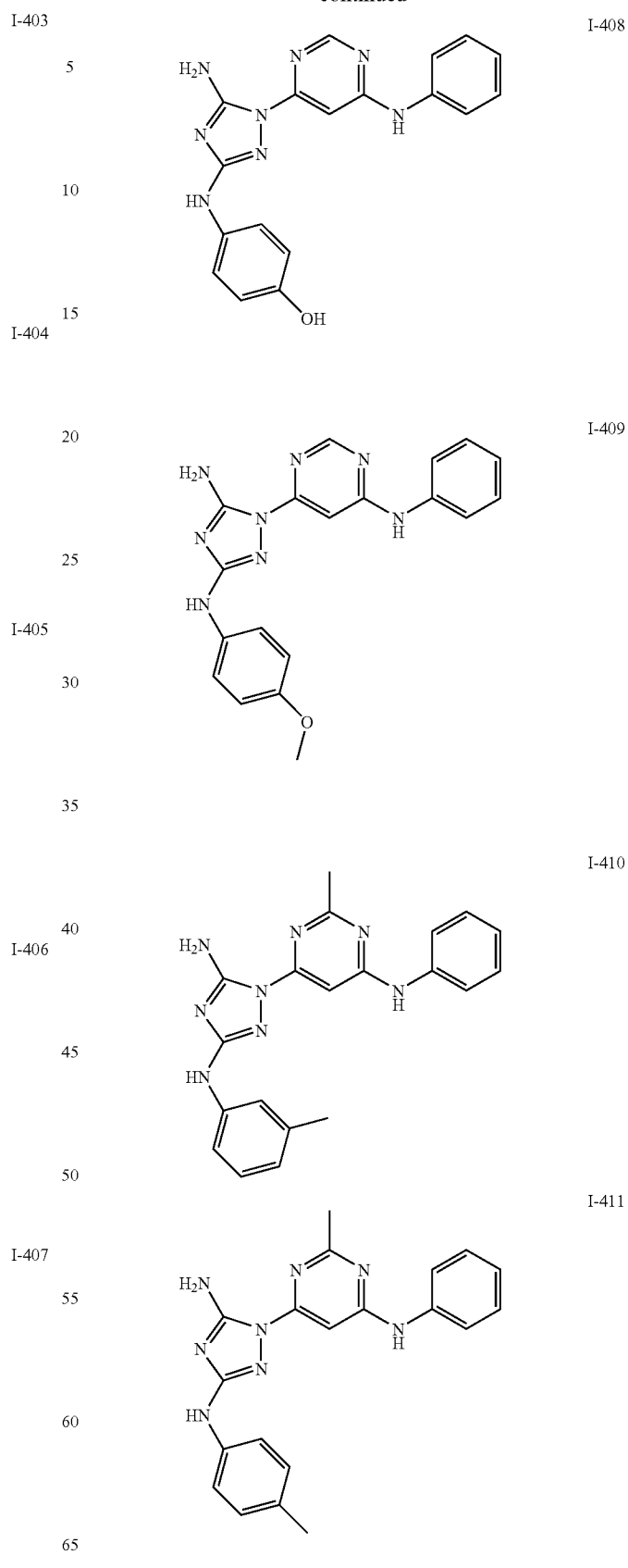

I-417
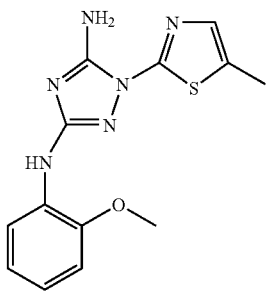
I-429
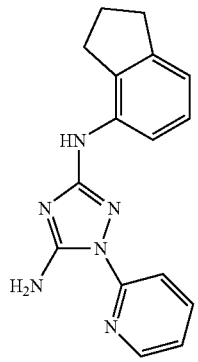
I-418
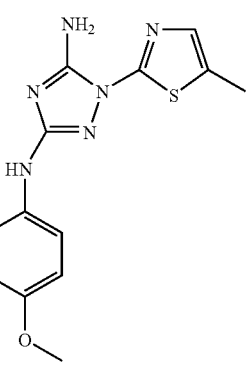
I-431
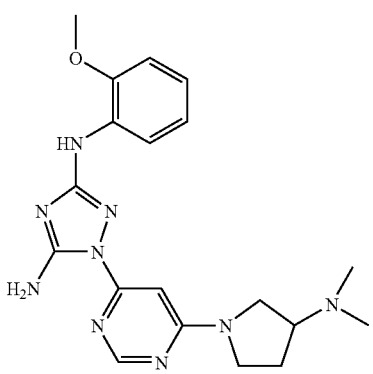
I-419
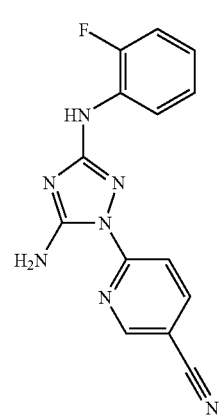
I-432
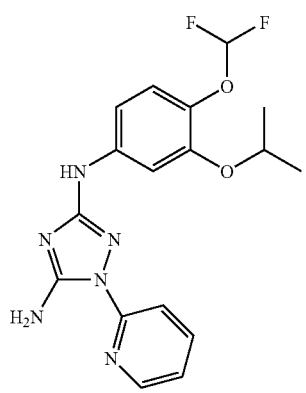
I-421
I-433
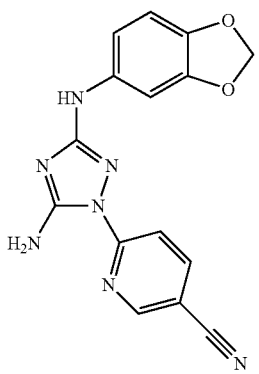

-continued
I-435
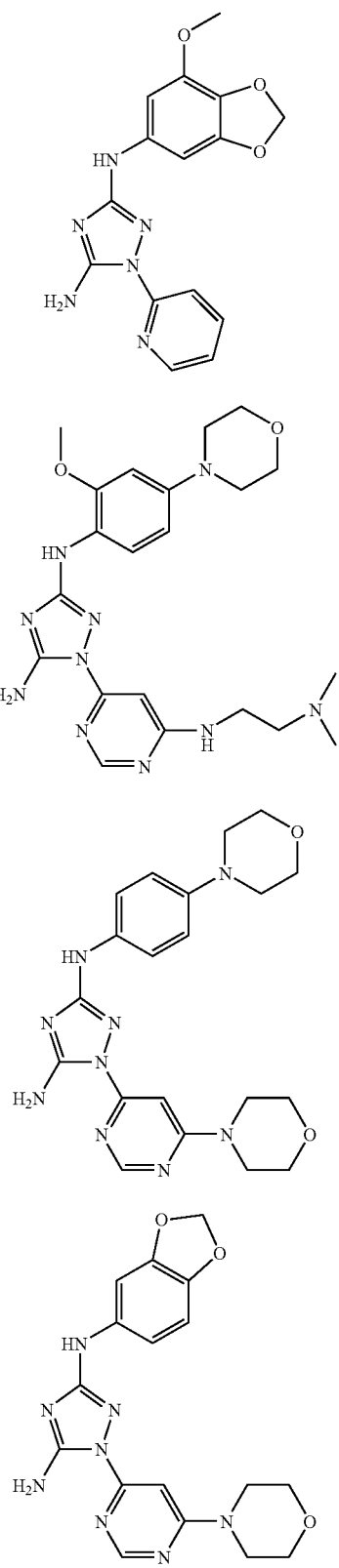
I-436
I-437
I-438
-continued
I-439
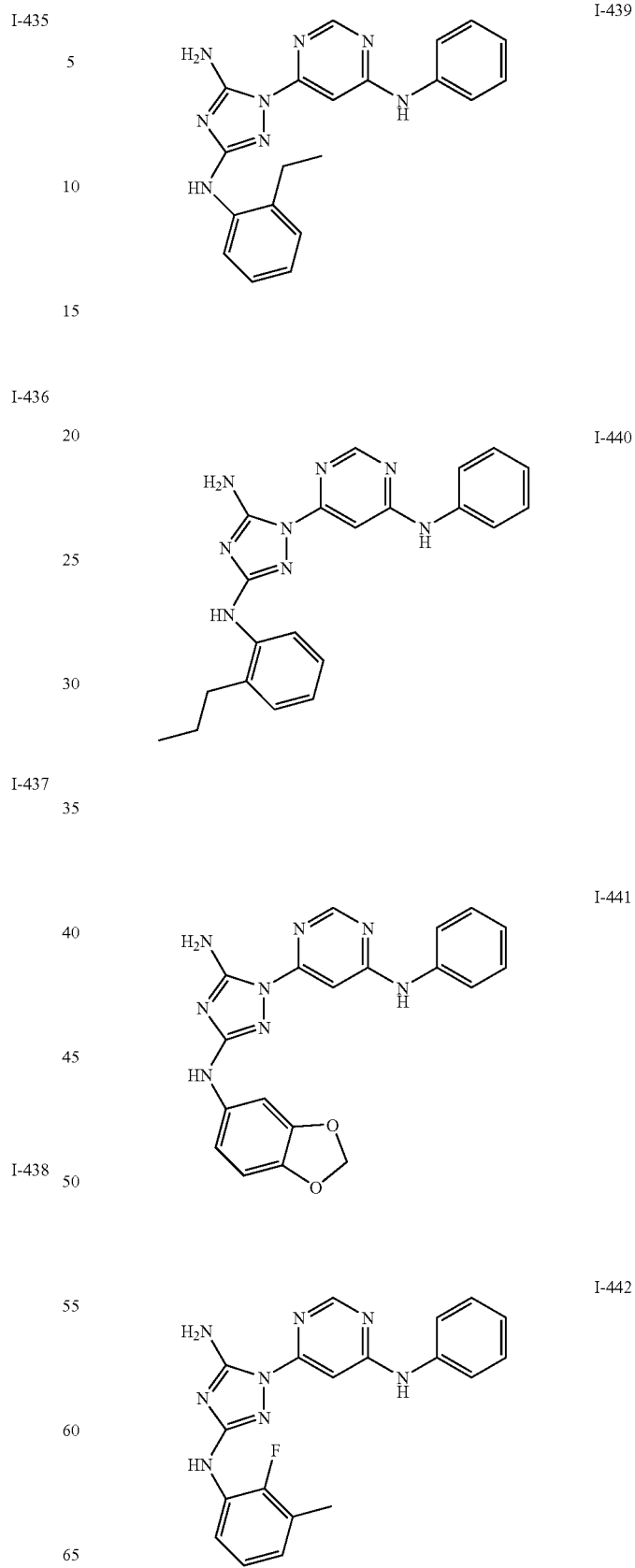
I-440
I-441
I-442

-continued
I-446
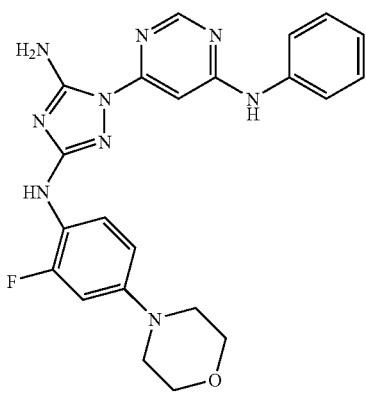
I-447
I-448
-continued
I-449
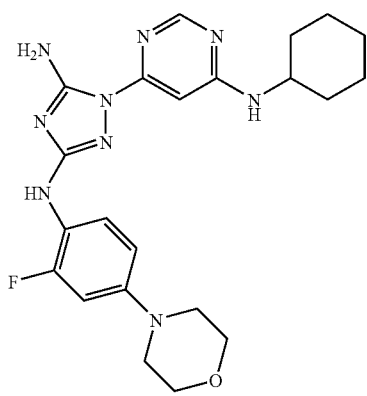
I-450
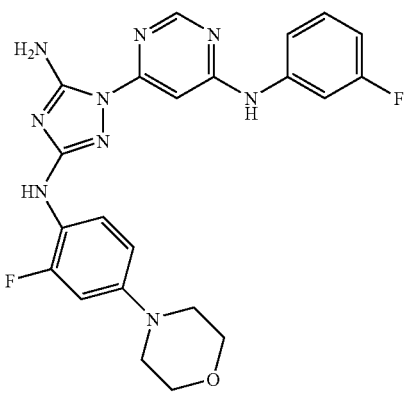
I-451
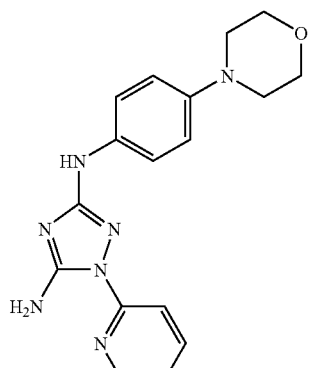
I-452
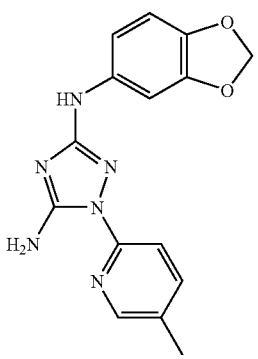

| 725 | 726 |
|---|---|
| -continued | -continued |
I-453
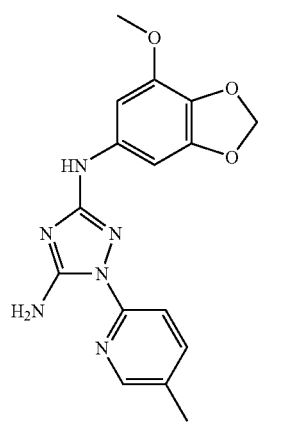
I-457
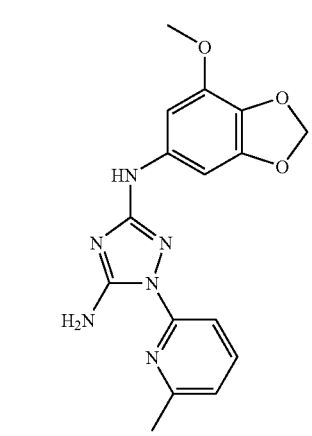
I-454
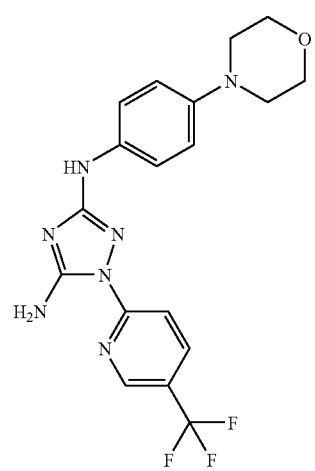
I-462
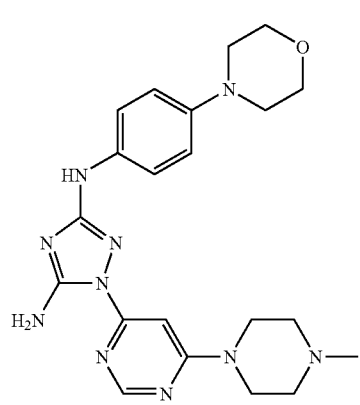
I-455
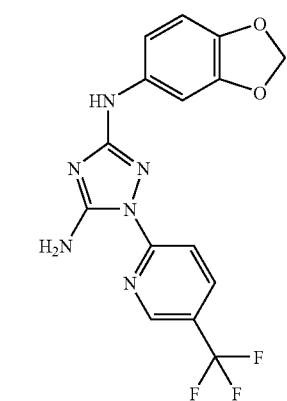
I-463
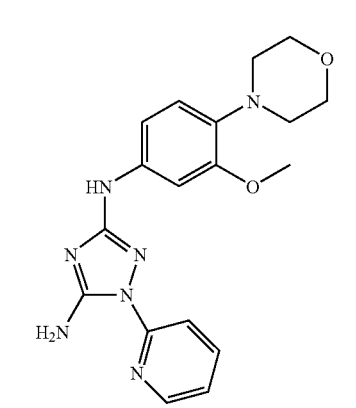
I-456
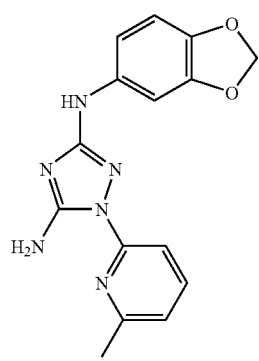
I-465
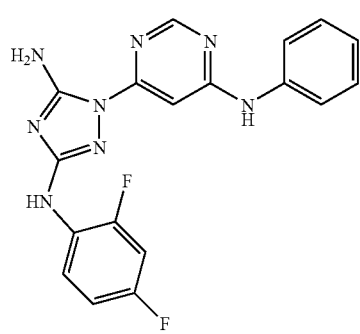

I-466 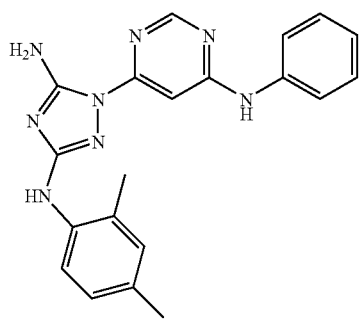
I-467 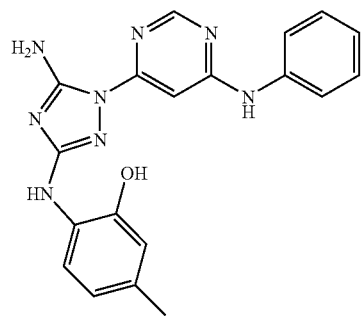
I-468 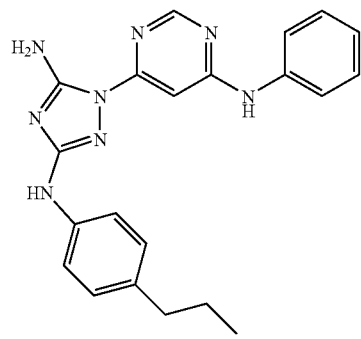
I-469 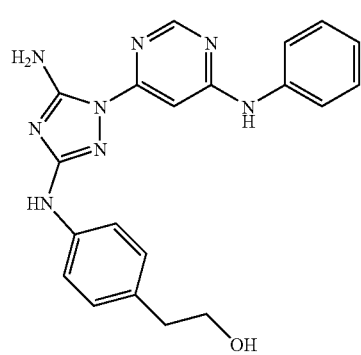
I-470 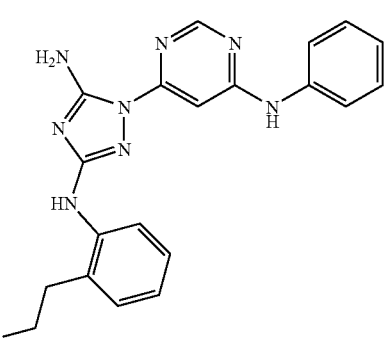
I-471 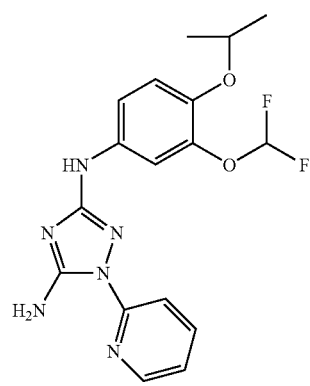
I-472 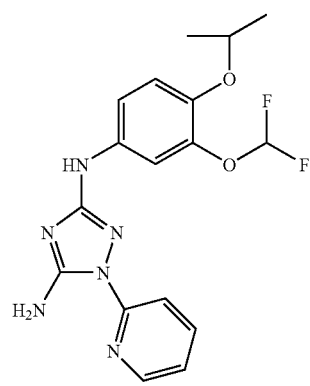
I-474 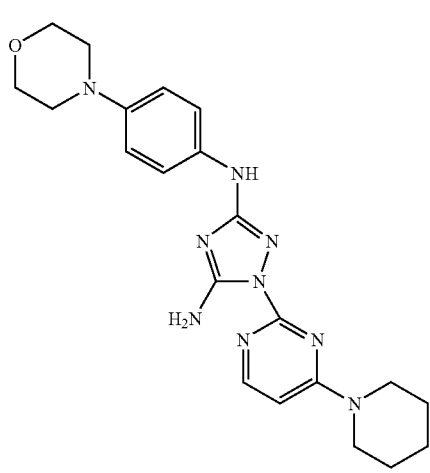

-continued
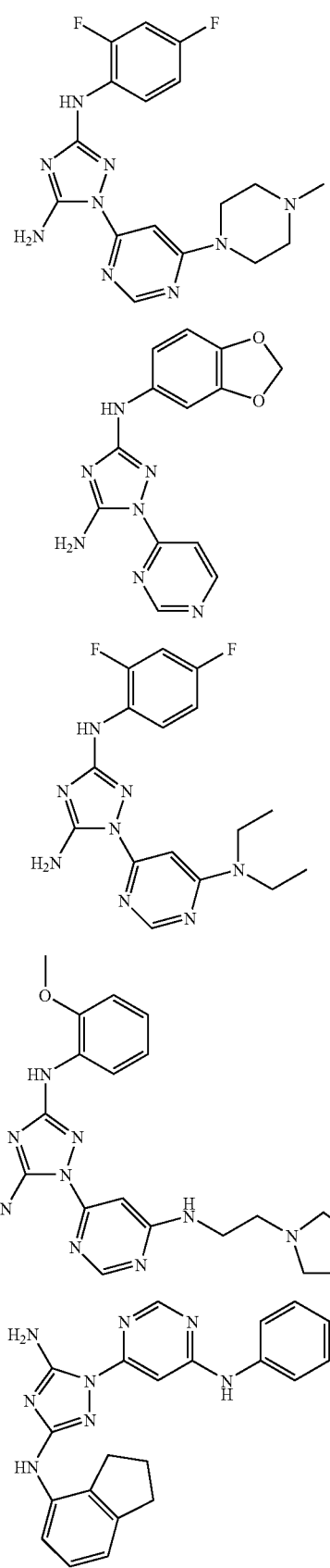
I-476
I-477
I-487
I-488
I-489
-continued
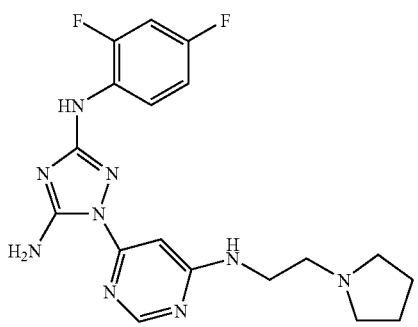
I-491
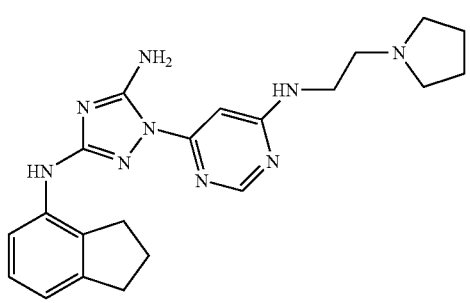
I-492
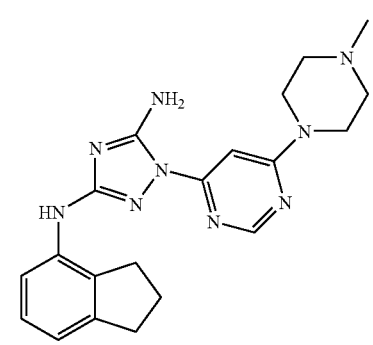
I-493
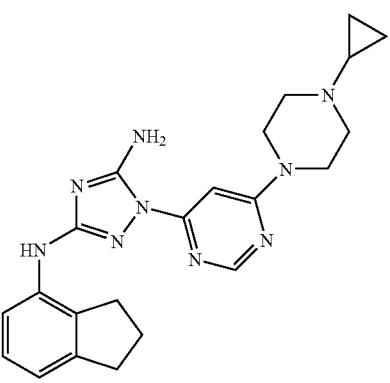
I-494

-continued
I-495
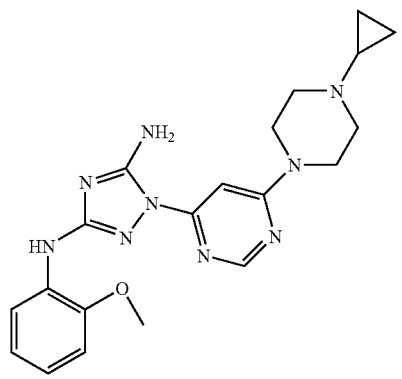
I-496
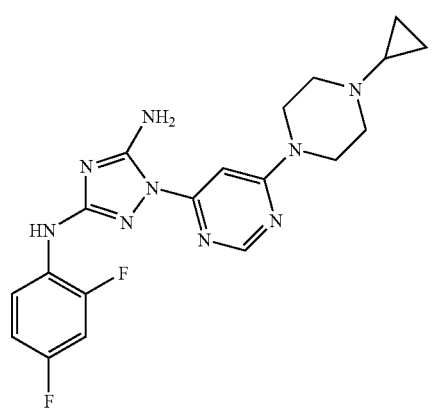
I-497
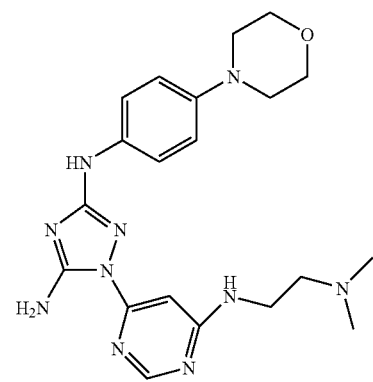
-continued
I-498
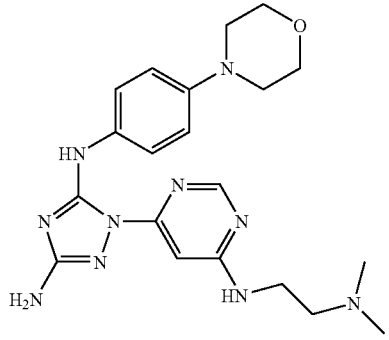
I-499
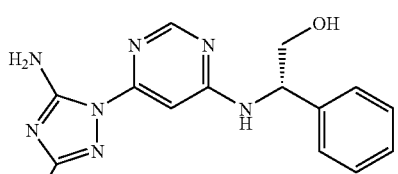
I-500
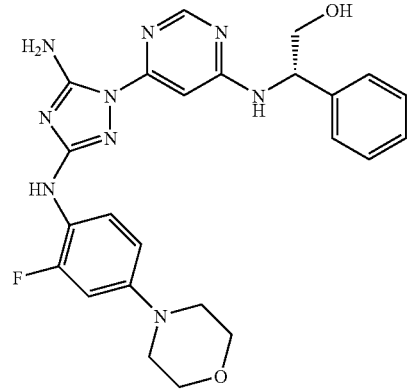
I-501
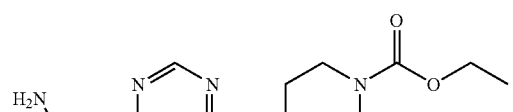

I-502
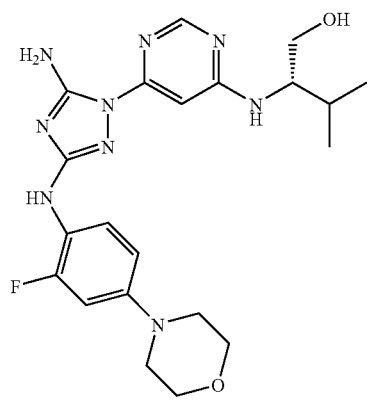
I-515
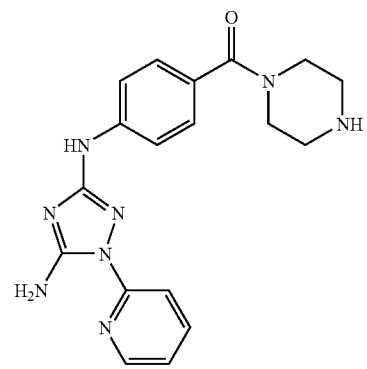
I-516
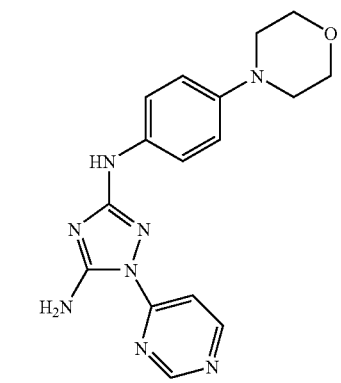
I-520
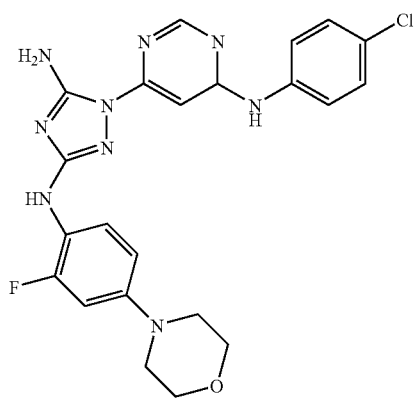
I-528
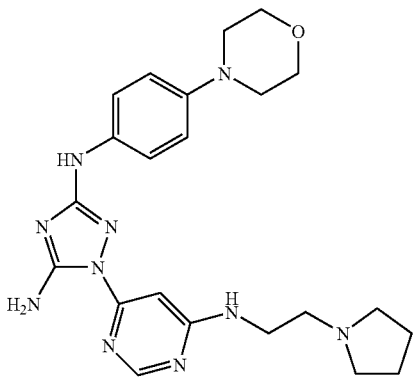
I-529
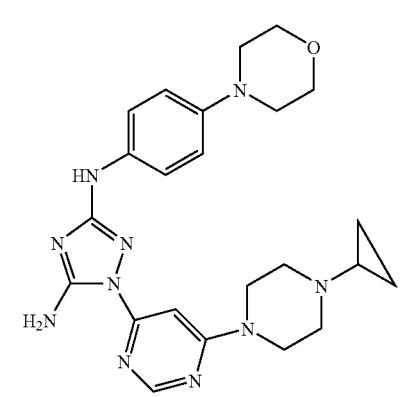
I-531
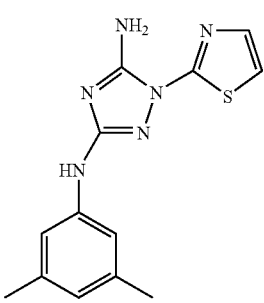
I-532
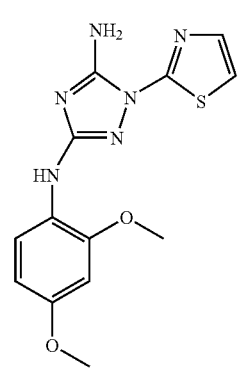

I-533 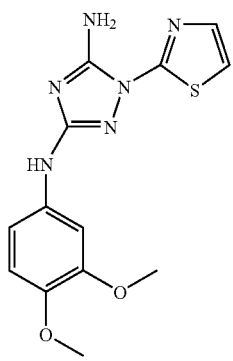
I-534 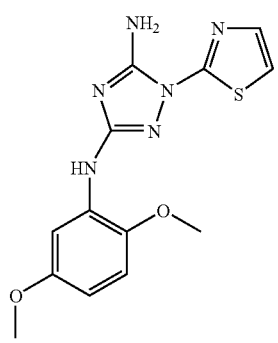
I-535 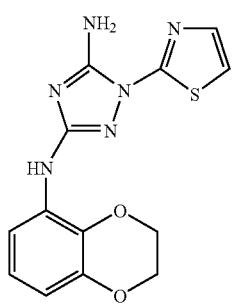
I-536 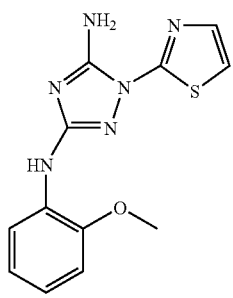
I-537 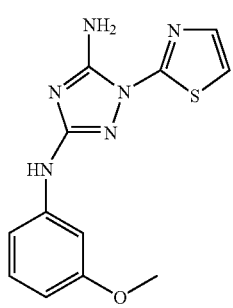
I-538 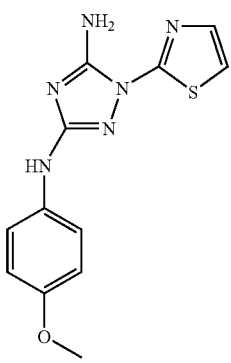
I-539 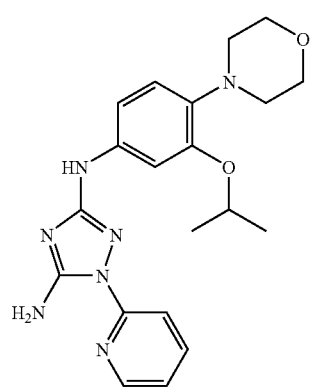
I-543 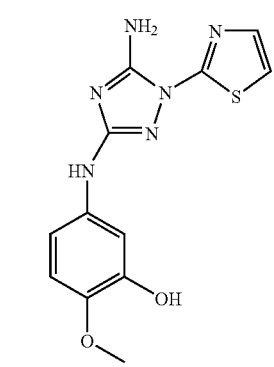
I-544 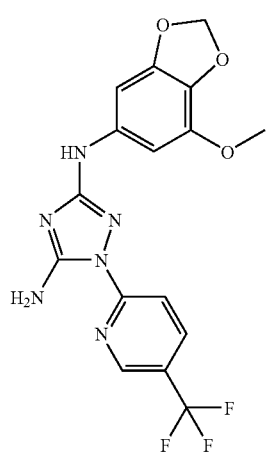

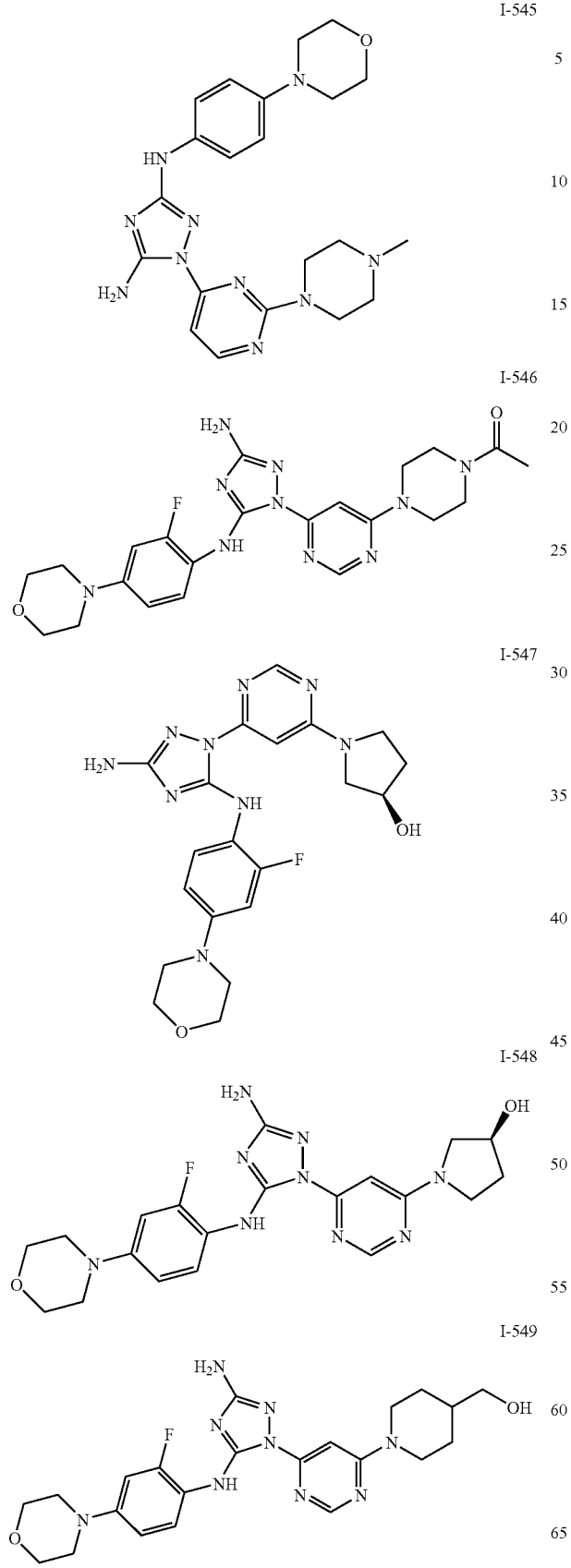
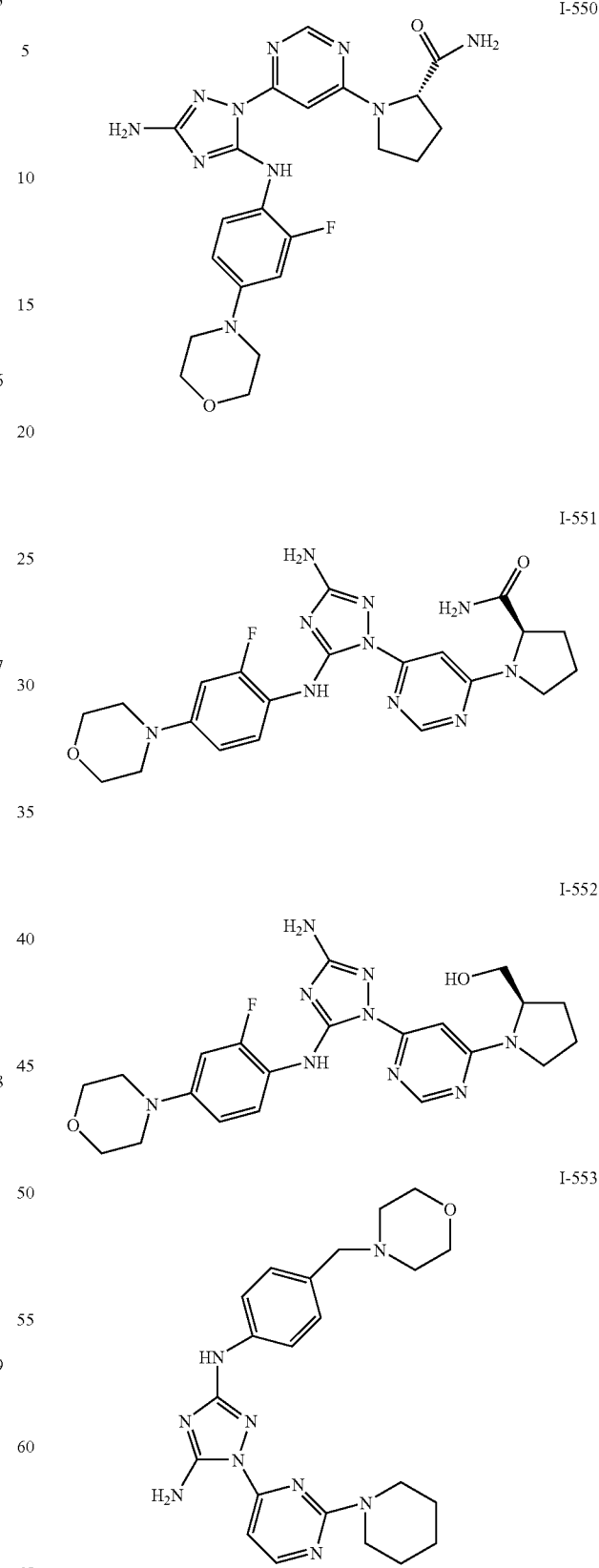

I-554
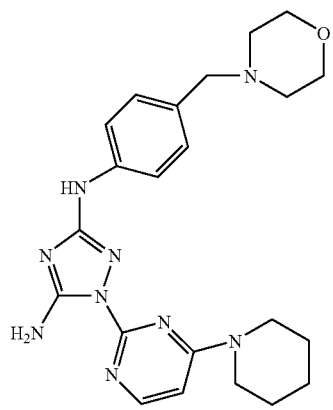
I-555
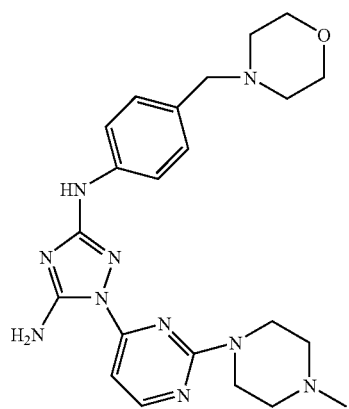
I-558
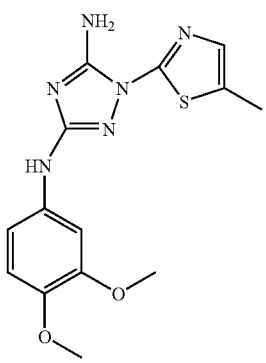
I-599
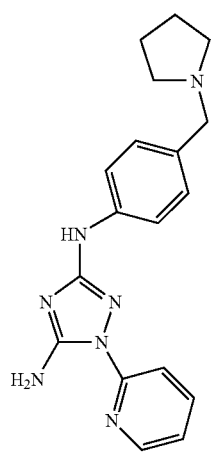
I-560
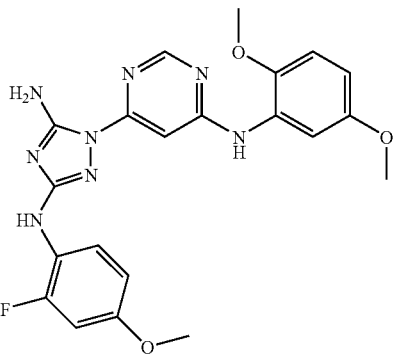
I-561
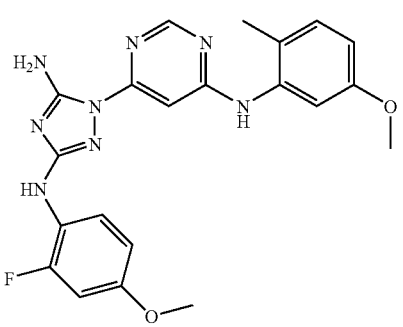
I-562
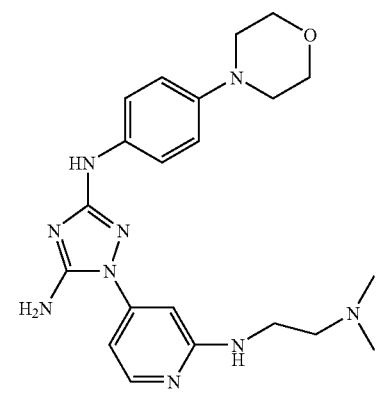
I-563
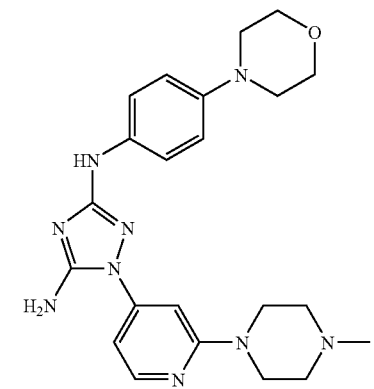

-continued
I-564
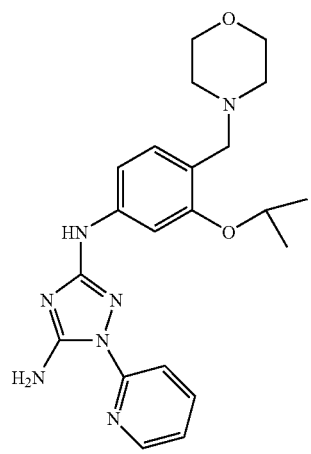
I-565
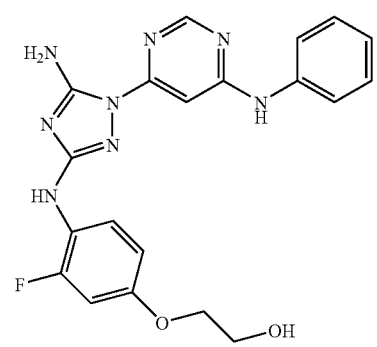
I-566
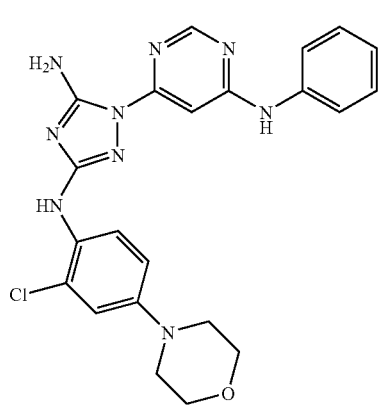
-continued
I-568
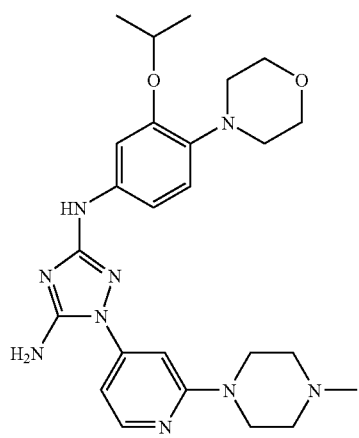
I-569
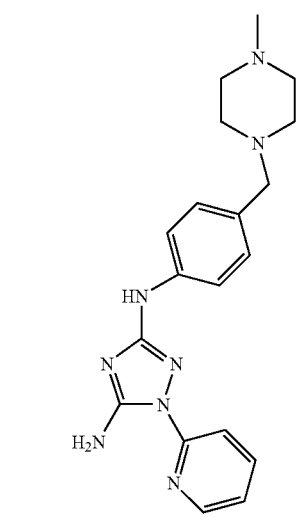
I-572
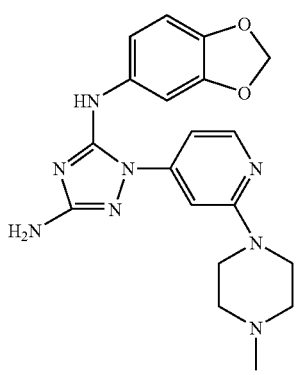

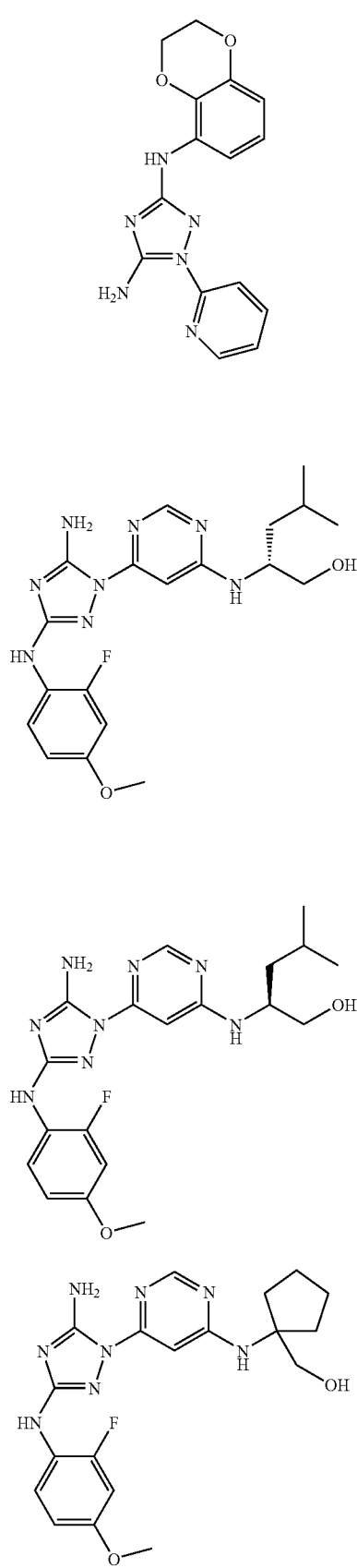
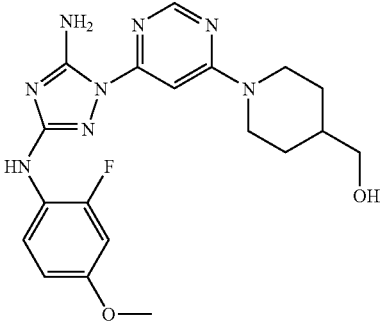
I-574
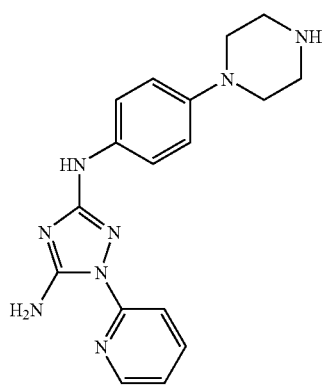
I-575
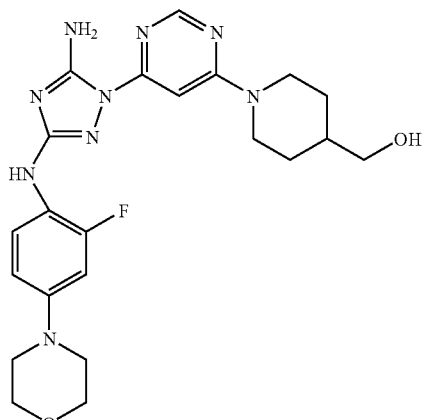
I-576
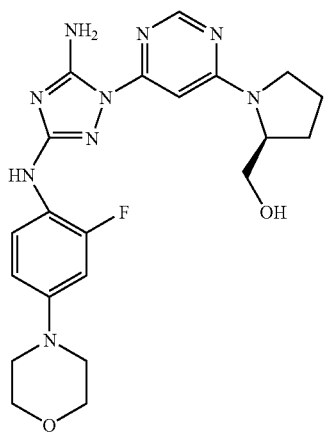
I-577
I-578
I-579
I-582
I-583

I-584
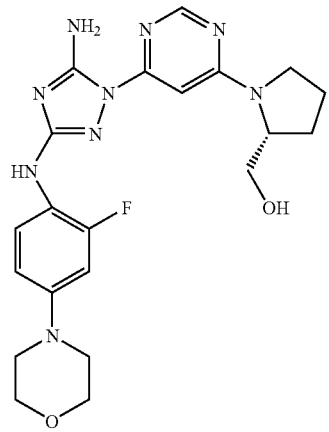
I-585
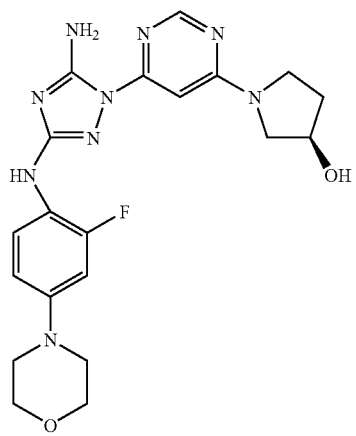
I-586
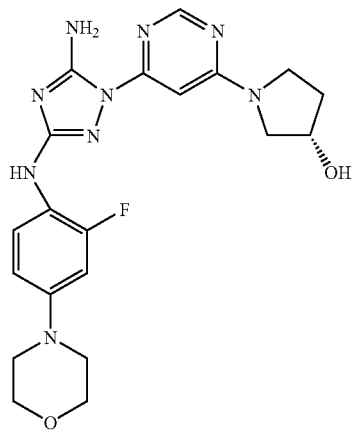
I-587
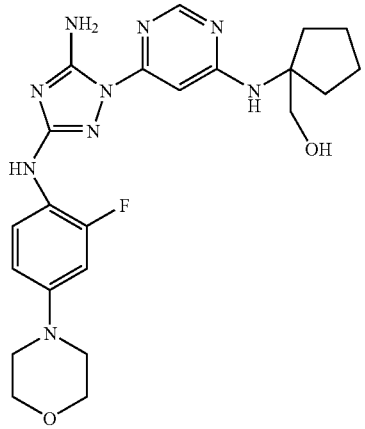
I-588
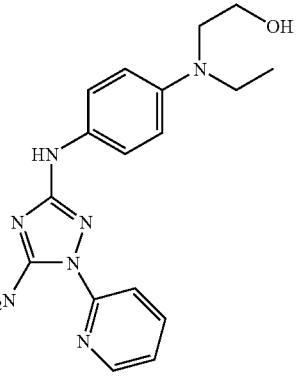
I-589
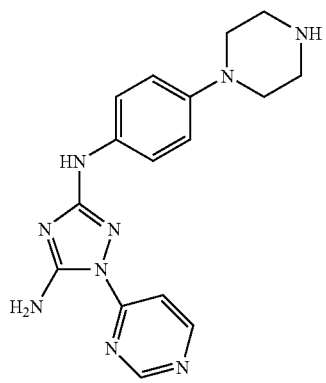
I-590
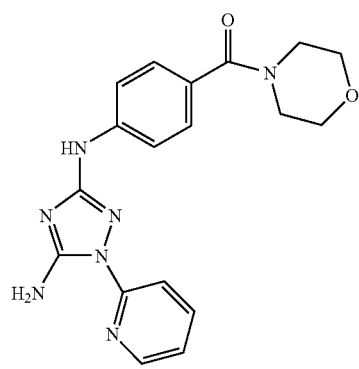

-continued
I-591
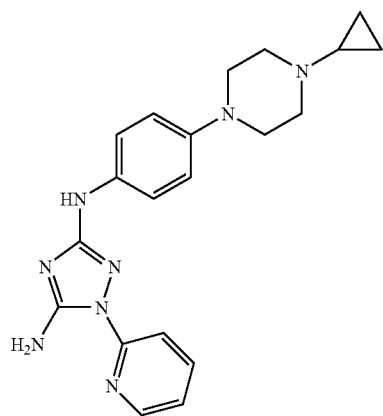
I-592
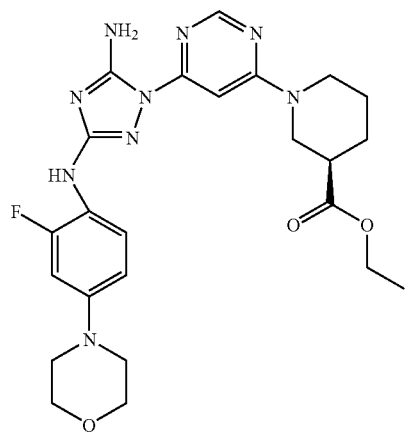
I-593
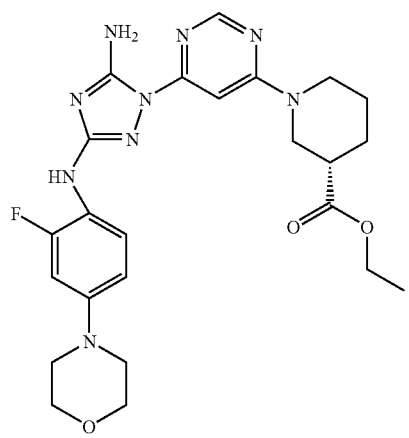
-continued
I-595
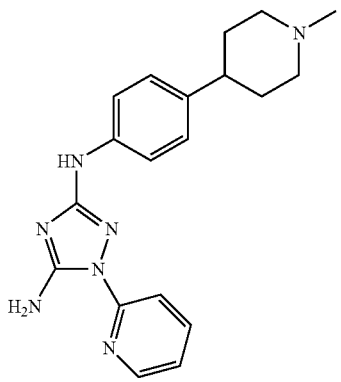
I-596
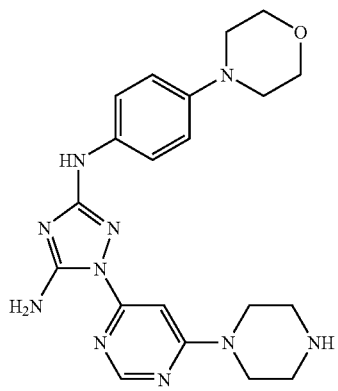
I-597
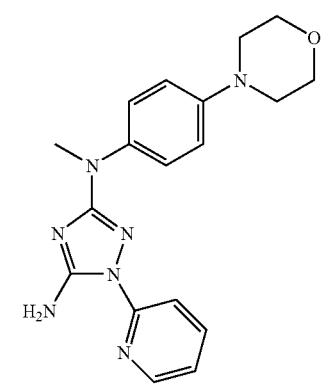
I-598
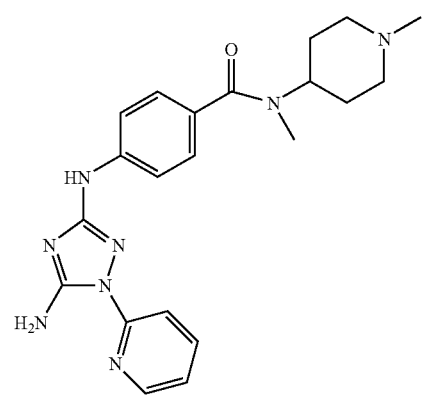

-continued
I-599
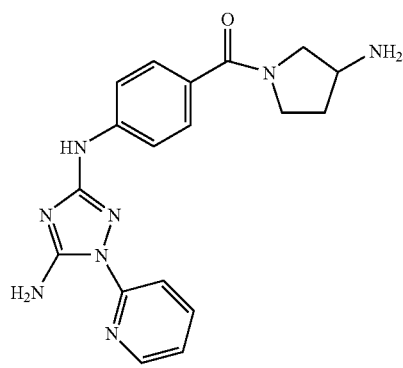
I-600
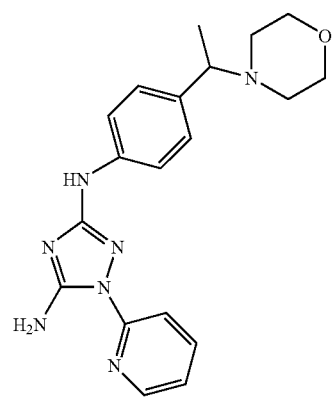
I-601
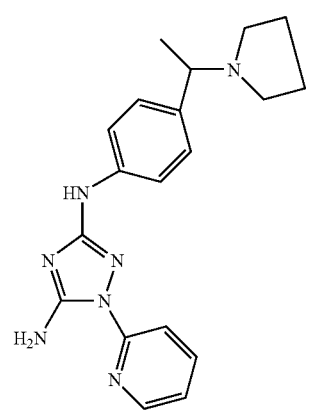
I-602
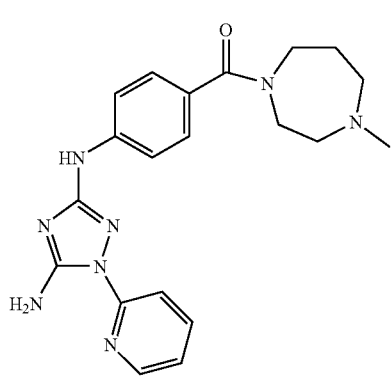
-continued
I-603
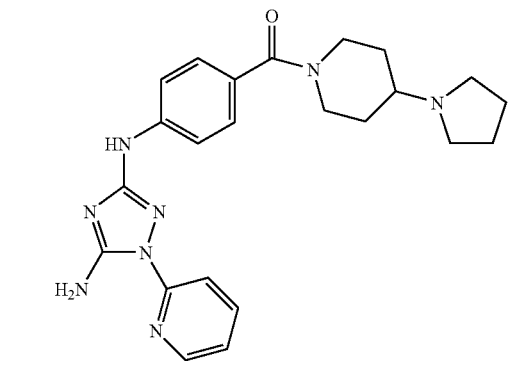
I-604
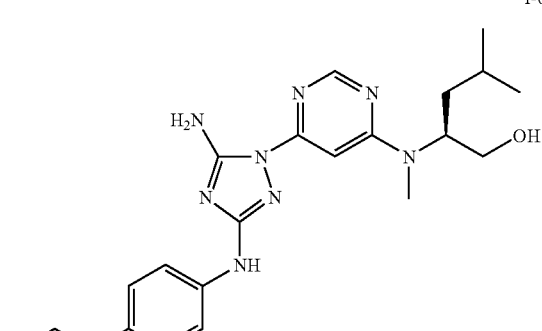
I-605
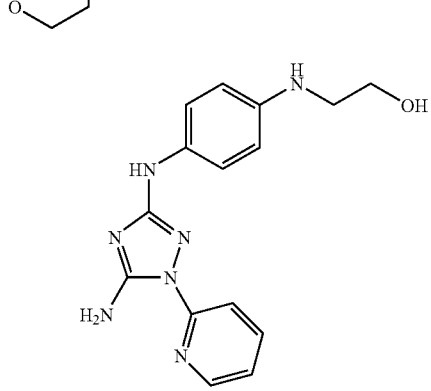
I-606
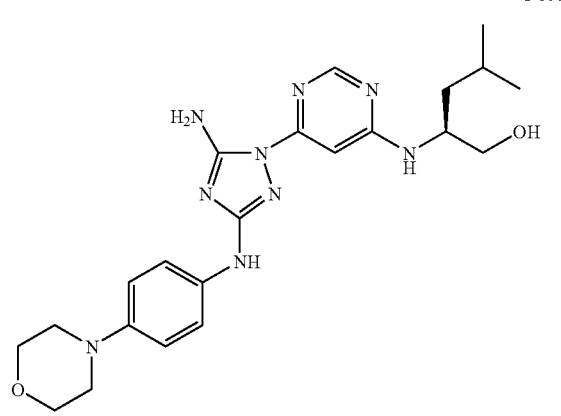

751
-continued
I-607
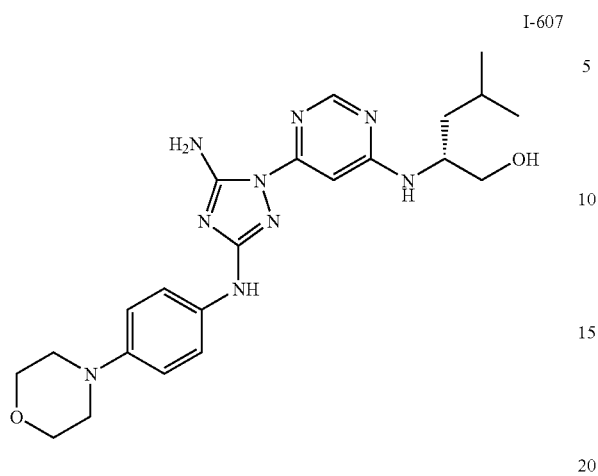
I-608
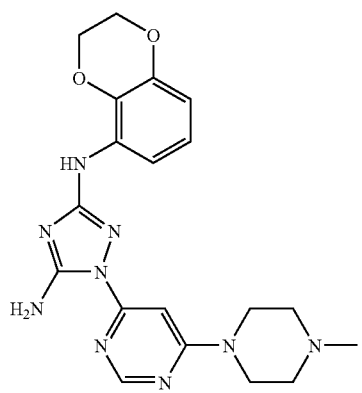
I-609
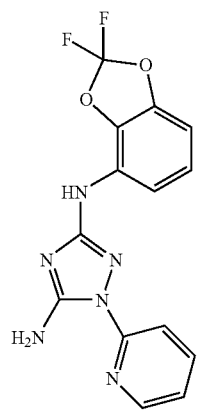
752
-continued
I-610
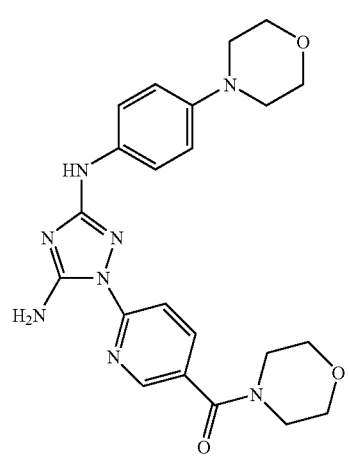
I-611
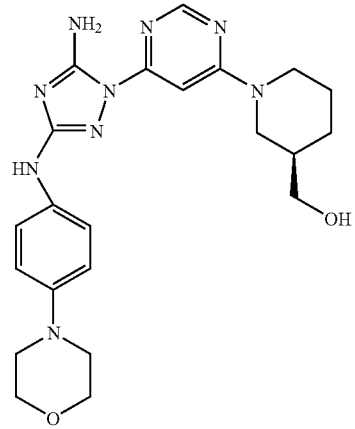
I-612
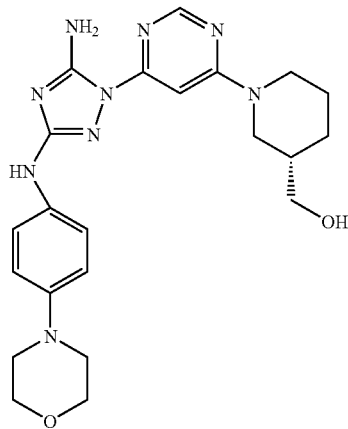

-continued
I-614
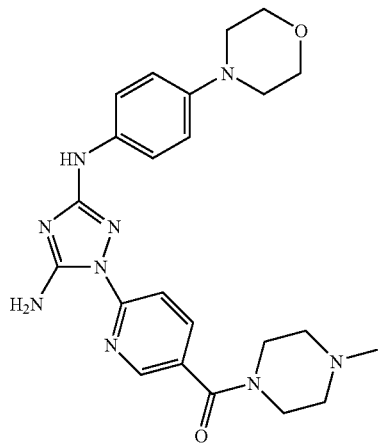
I-615
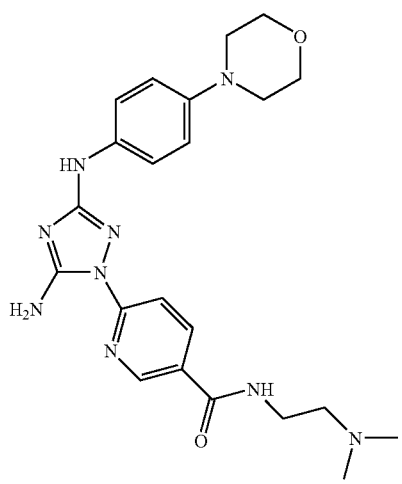
I-616
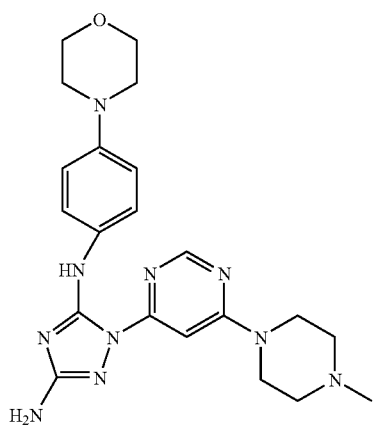
-continued
I-617
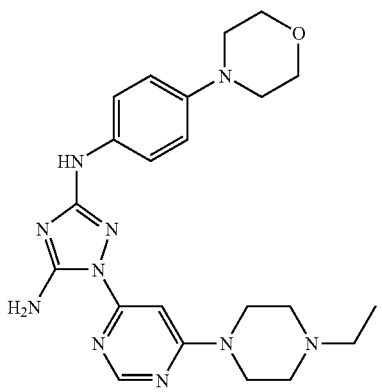
I-618
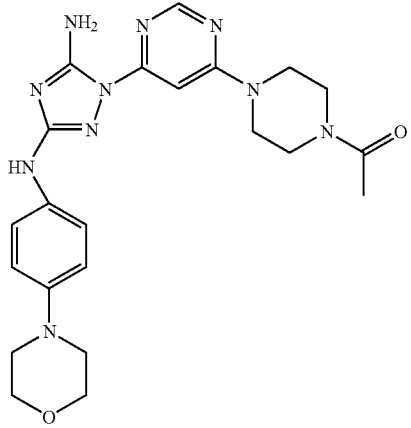
I-619
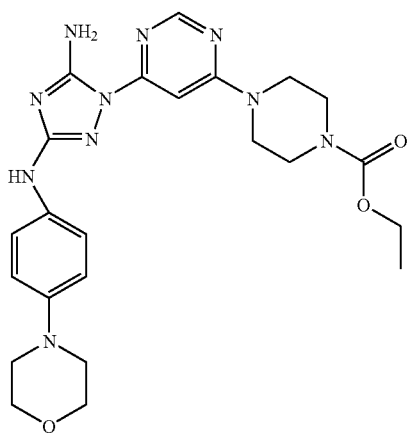

-continued
I-624
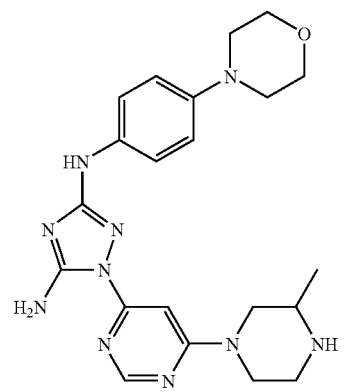
I-625
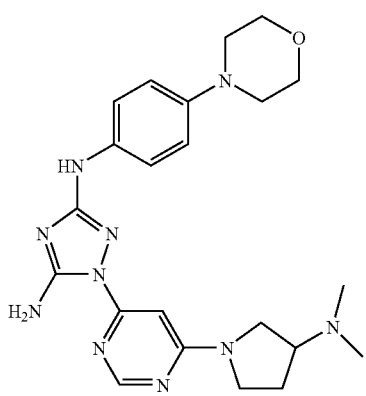
I-626
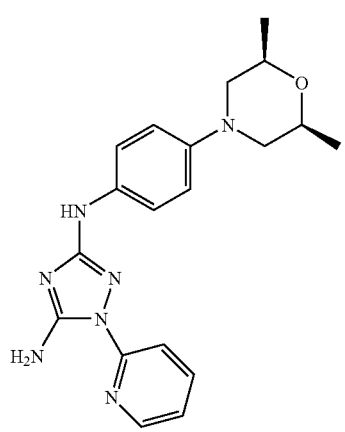
I-627
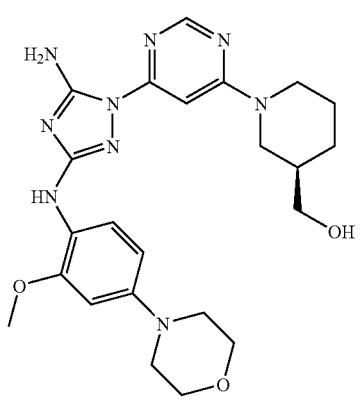
-continued
I-628
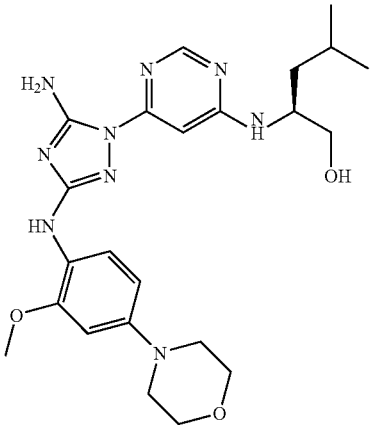
I-629
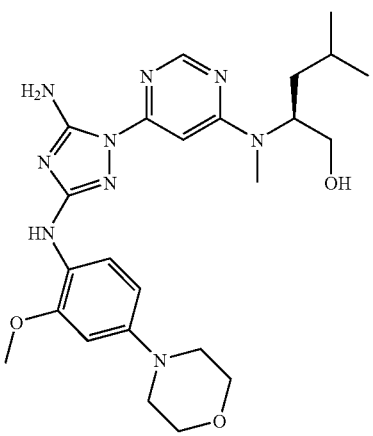
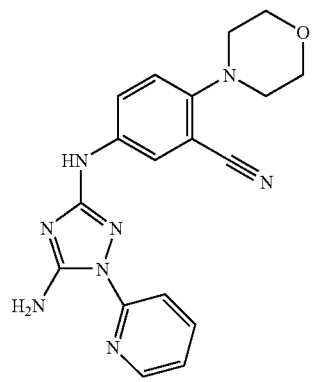
I-631
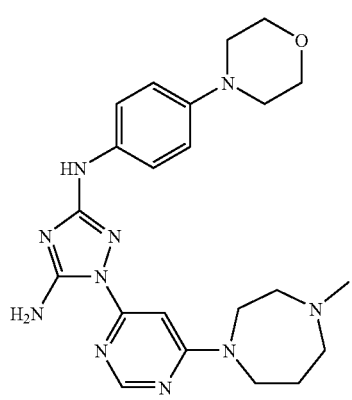

757 -continued
I-632
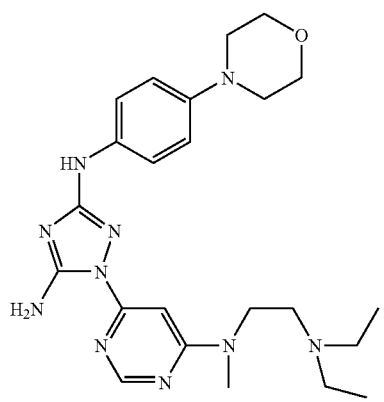
I-637
I-640
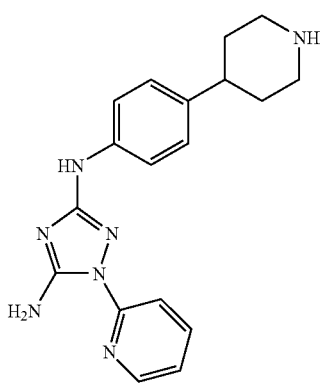
I-641
758 -continued
I-643
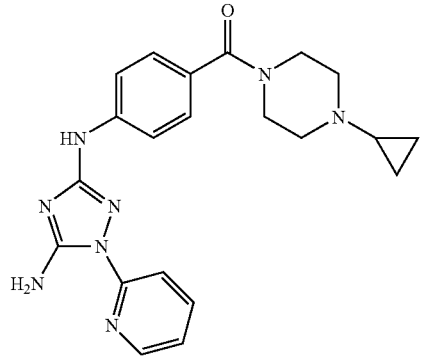
I-645
I-650
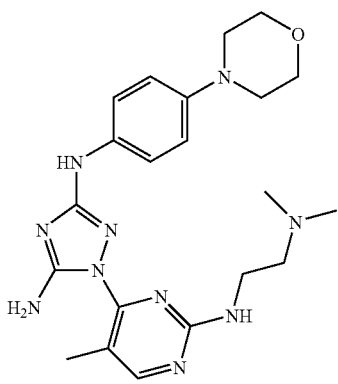
I-653
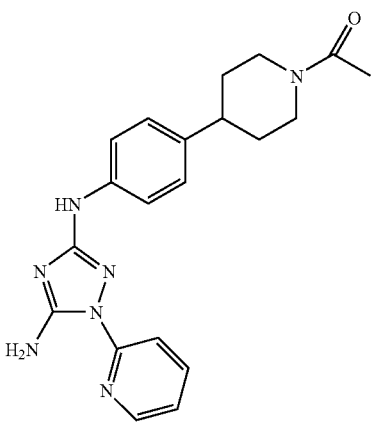

-continued
I-654
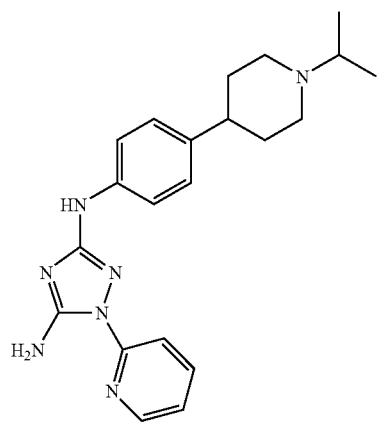
I-656
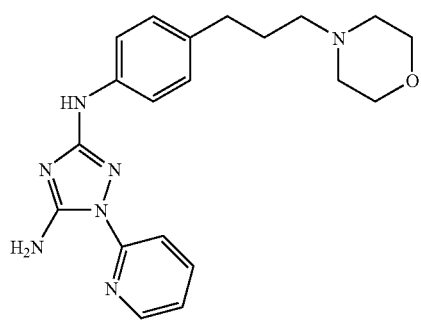
I-659
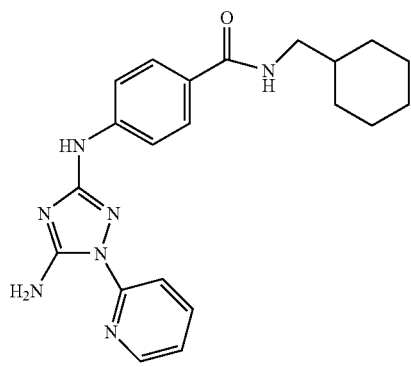
I-660
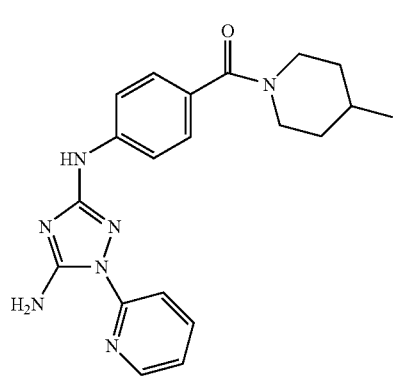
-continued
I-661
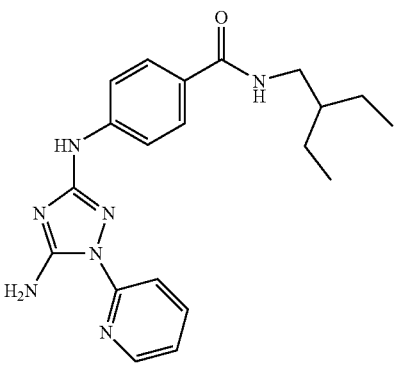
I-662
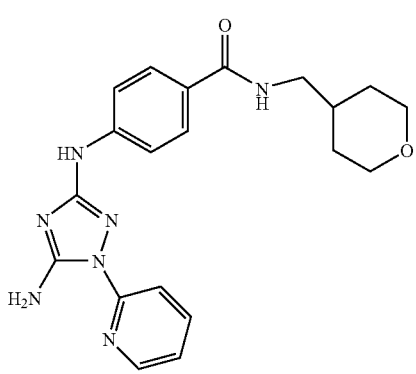
I-663
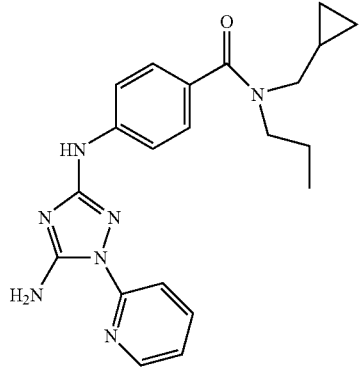
I-664
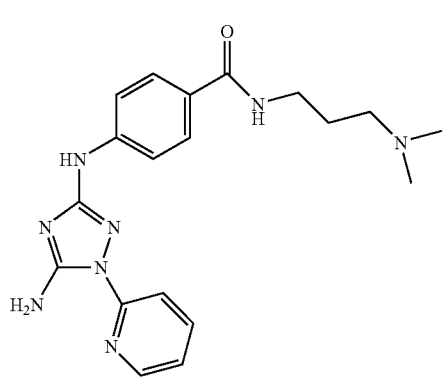

-continued
I-665
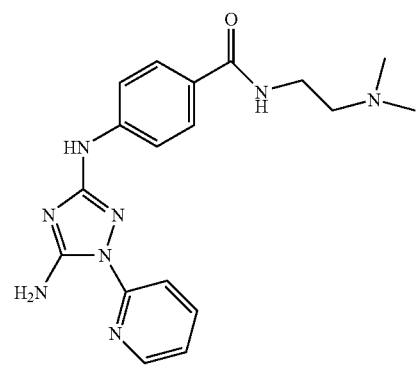
I-666
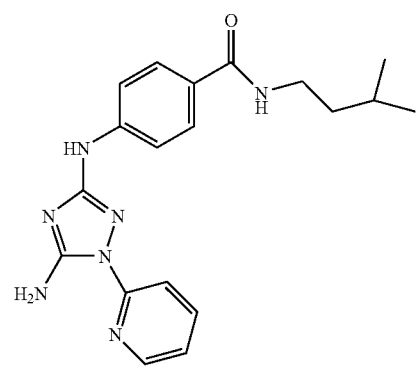
I-667
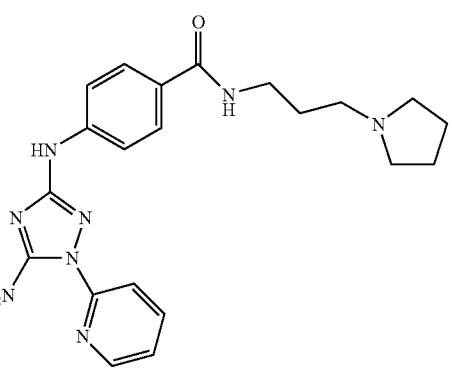
I-668
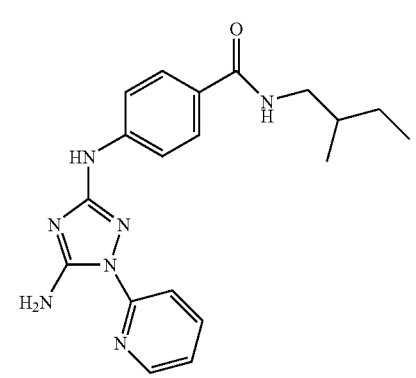
-continued
I-669
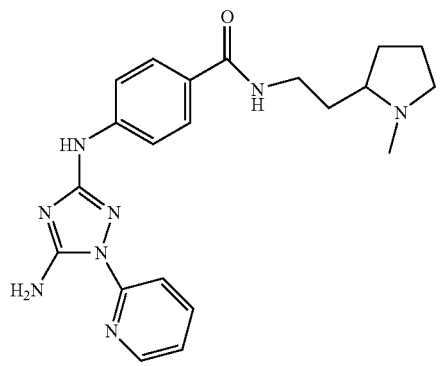
I-670
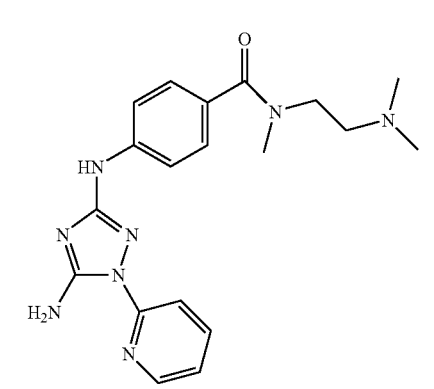
I-676
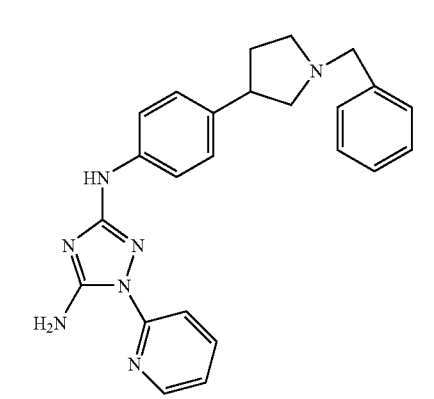
I-677
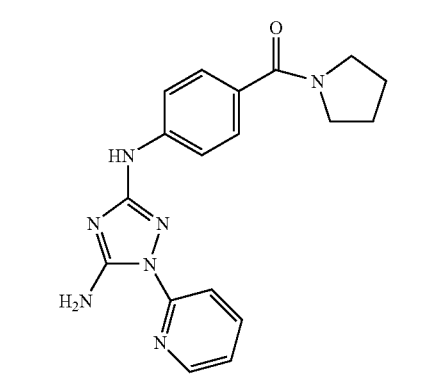

-continued
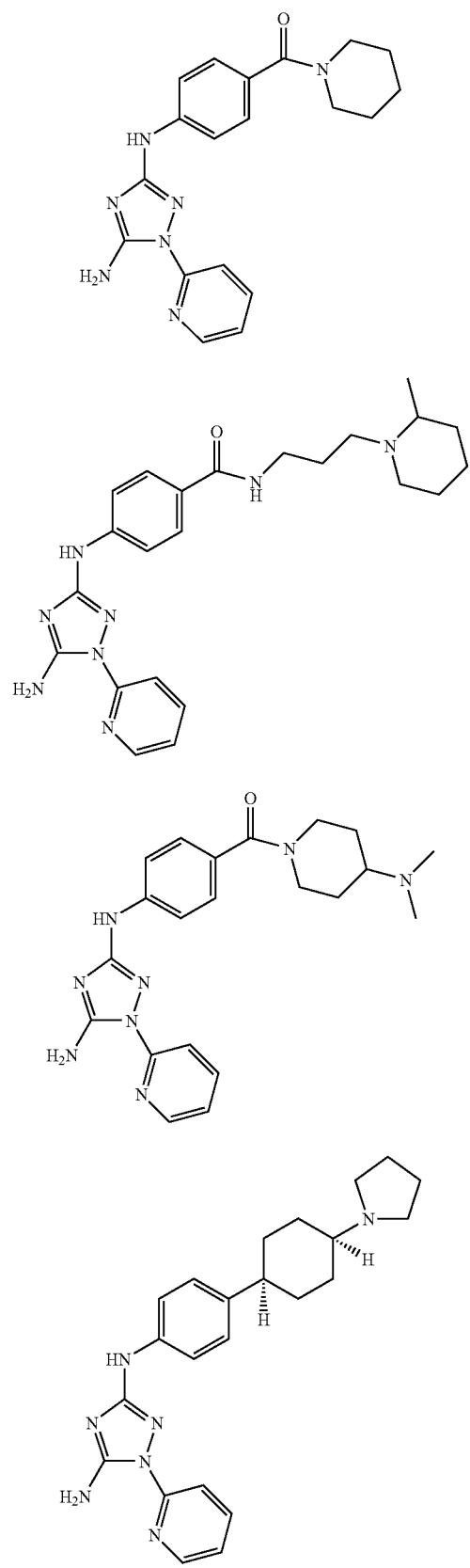
I-678
I-679
I-680
I-681
-continued
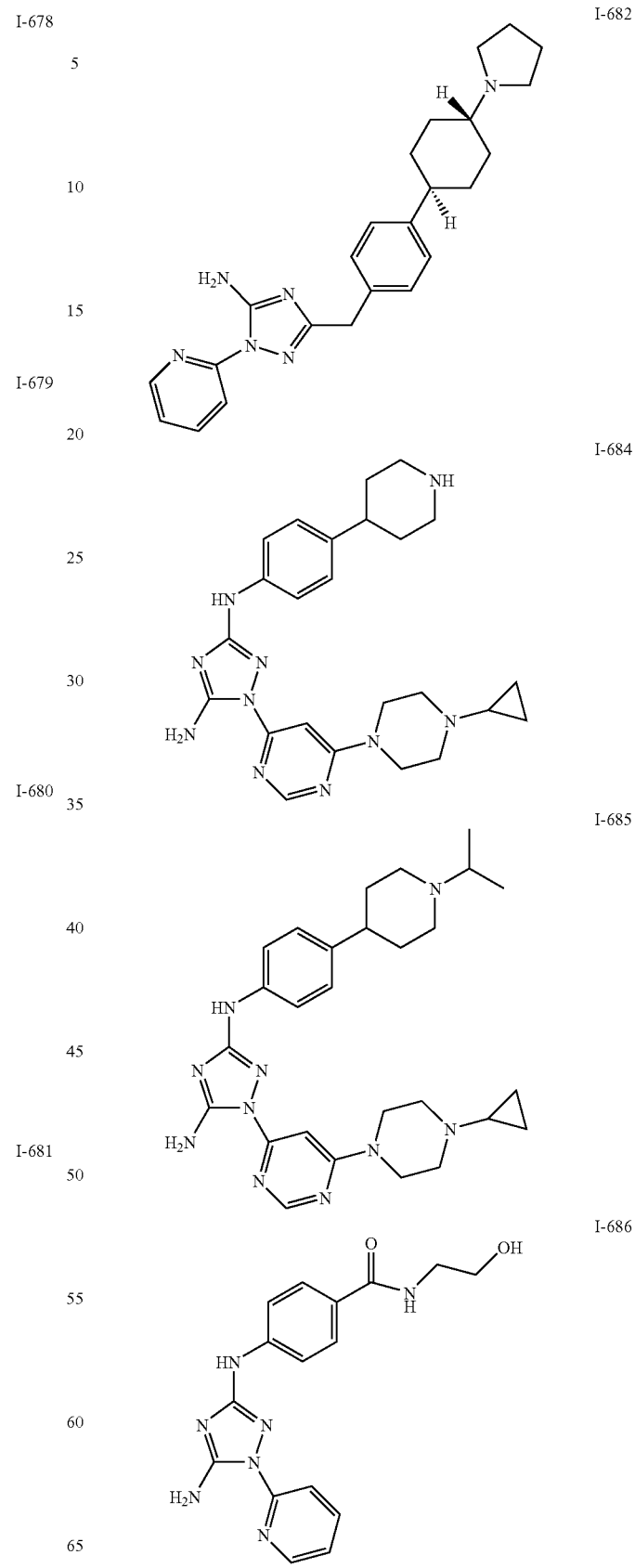
I-682
I-684
I-685
I-686

-continued
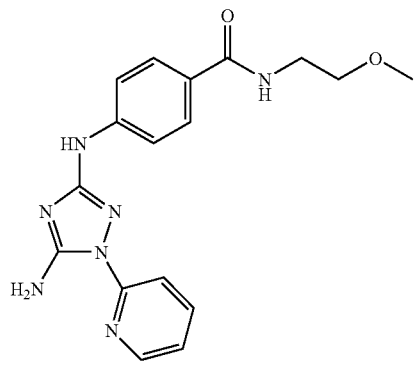
I-687
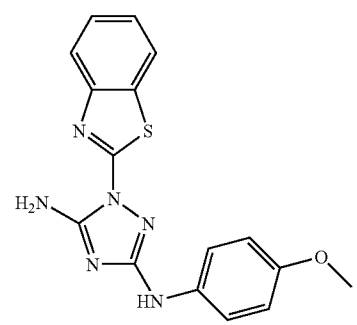
I-692
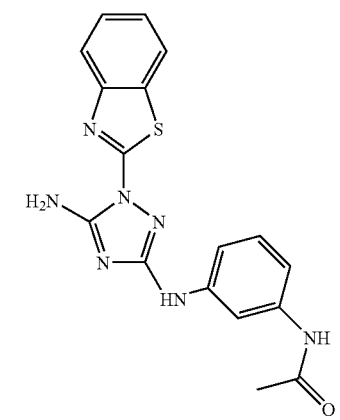
I-693
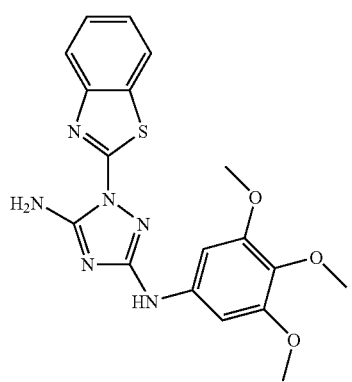
I-694
-continued
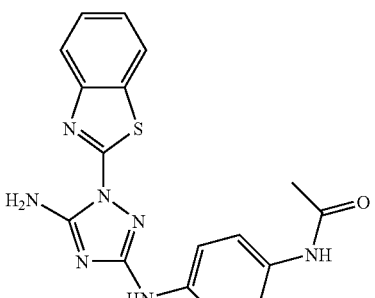
I-695
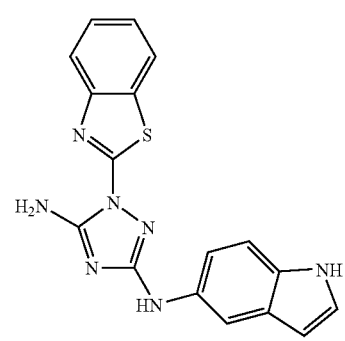
I-696
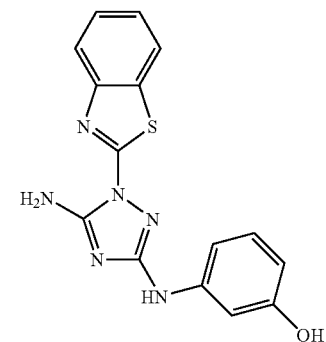
I-697
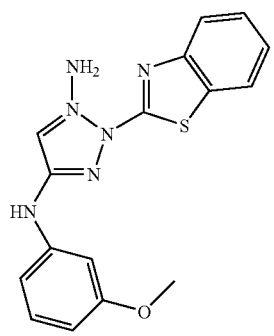
I-698

-continued
I-699
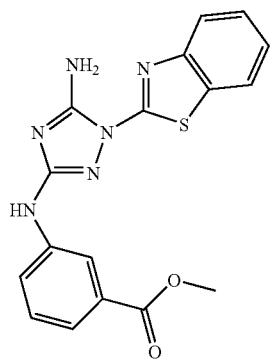
I-700
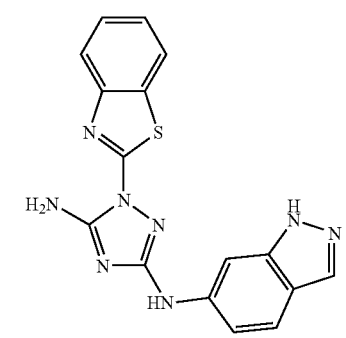
I-702
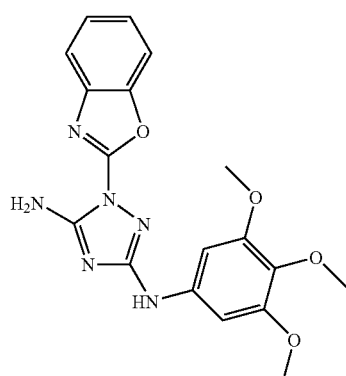
I-703
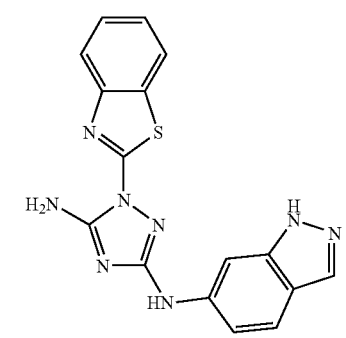
-continued
I-704
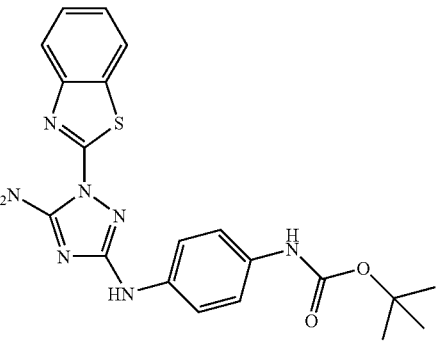
I-705
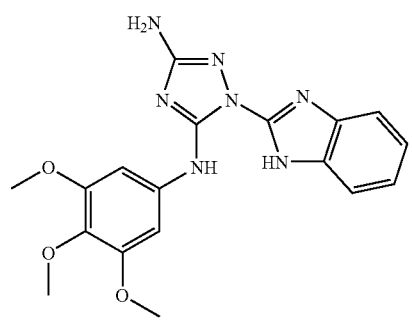
I-706
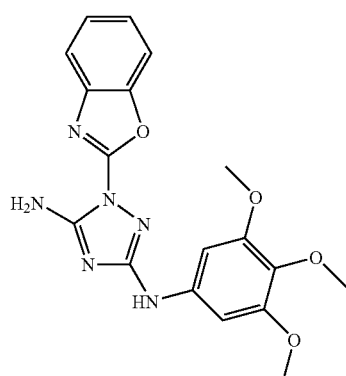
I-707
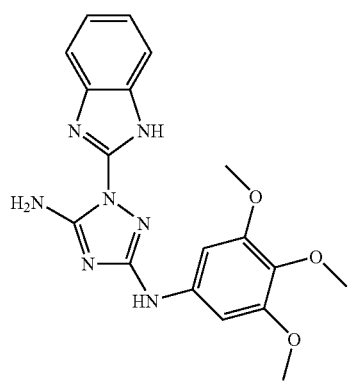

-continued
I-708
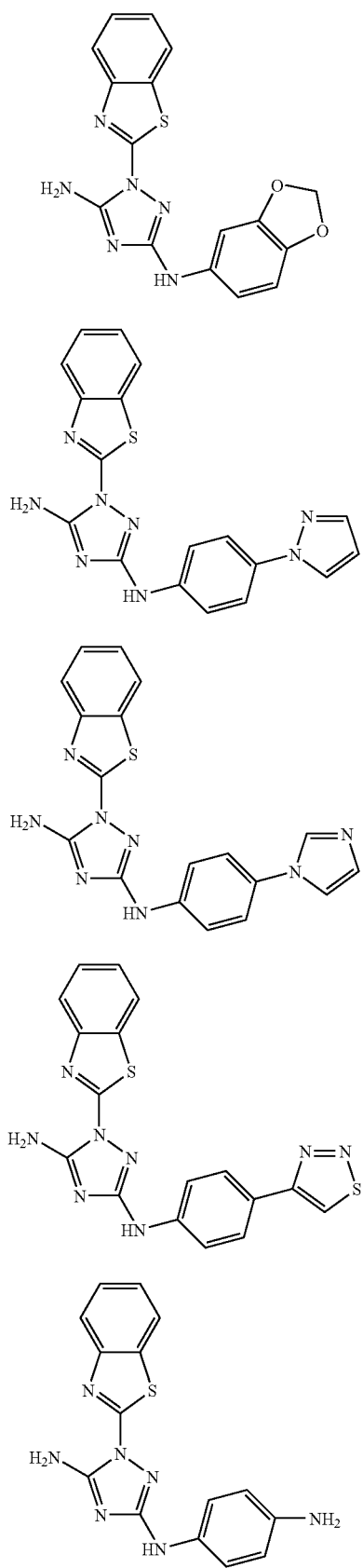
I-709
I-710
I-711
I-712
-continued
I-713
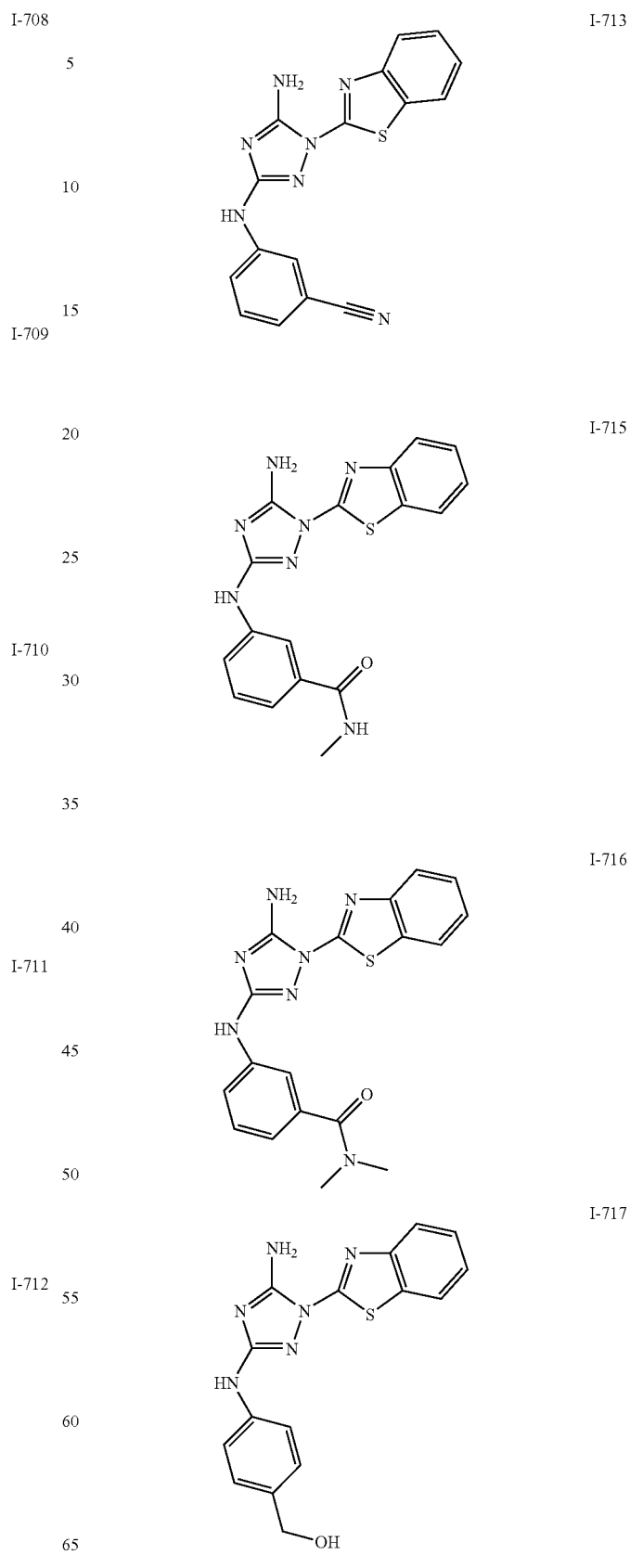
I-715
I-716
I-717

-continued
I-718
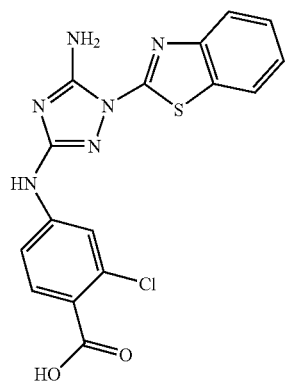
I-719
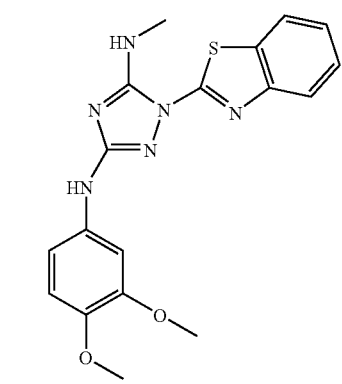
I-720
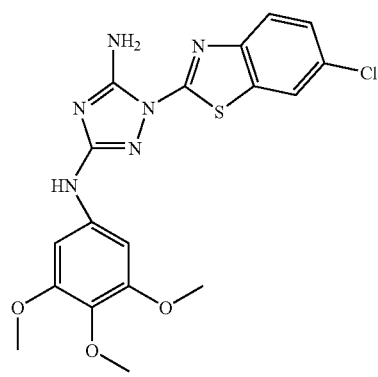
-continued
I-725
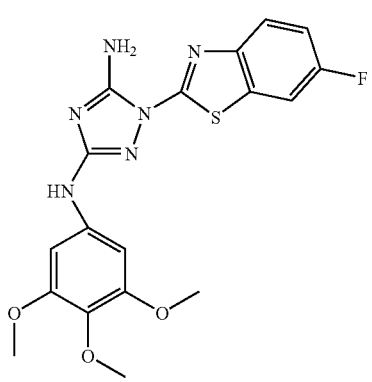
I-726
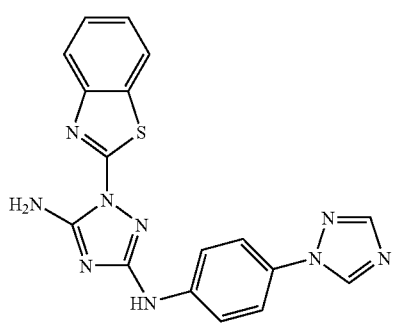
I-727
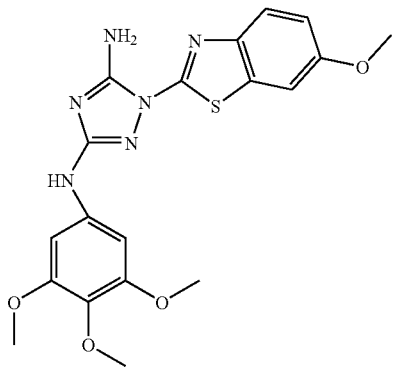
I-724
I-728
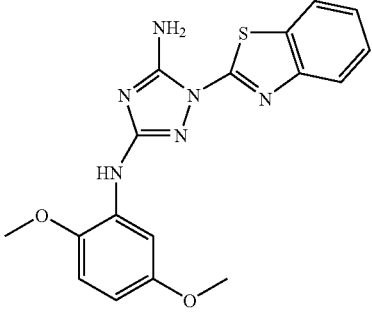

-continued
I-729
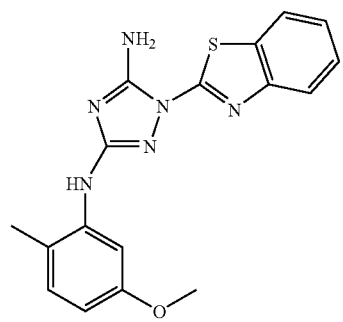
I-730
I-731
I-732
-continued
I-733
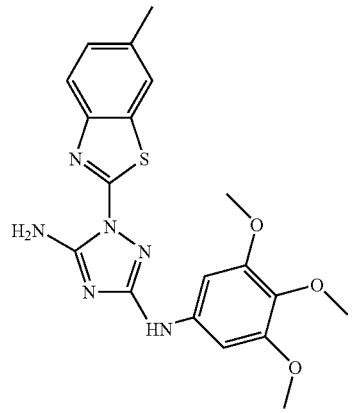
I-734
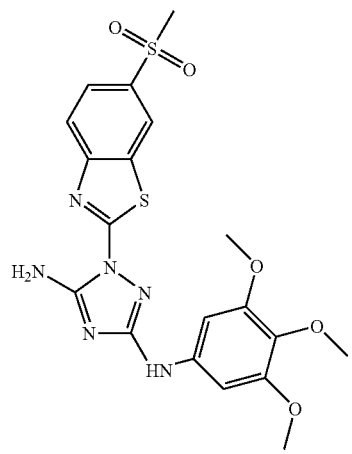
I-735
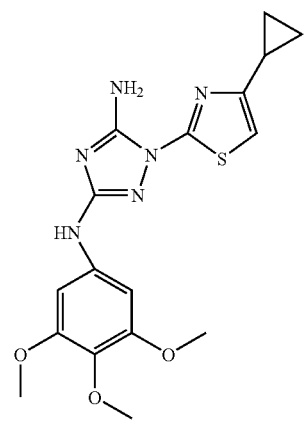
I-736
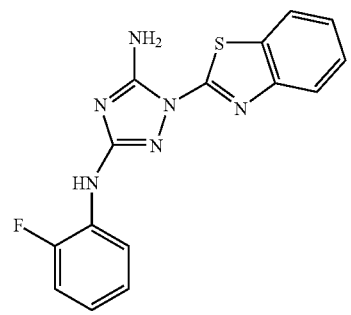

-continued
I-737
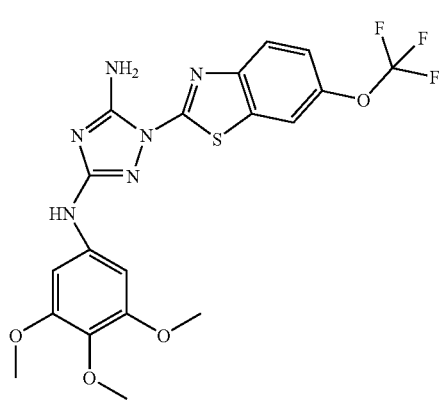
I-743
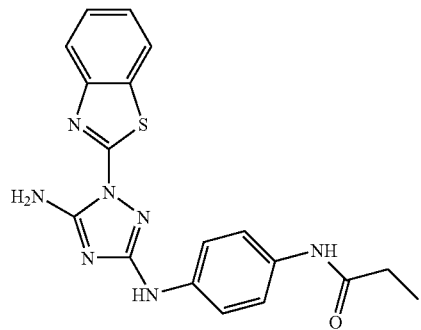
I-744
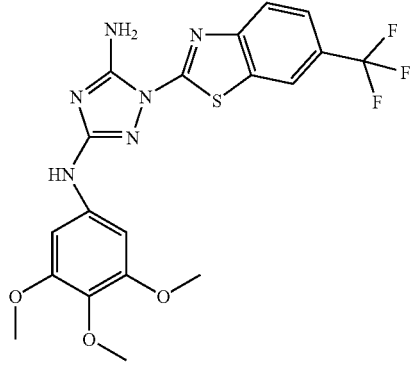
I-745
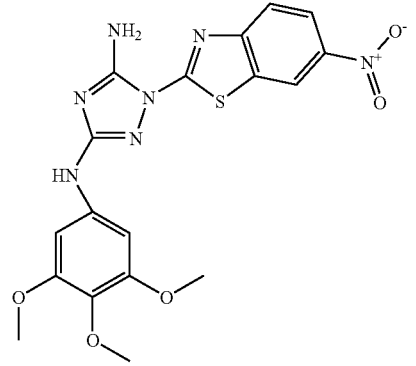
-continued
I-746
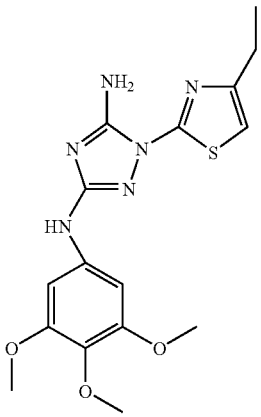
I-747
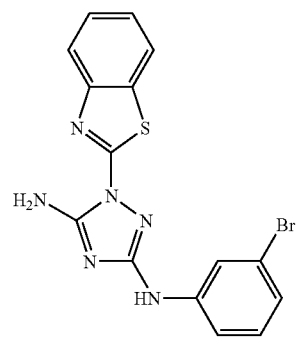
I-748
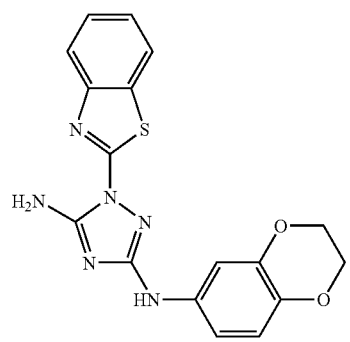
I-749
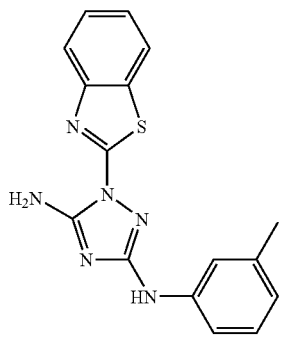

777 778
-continued
I-751
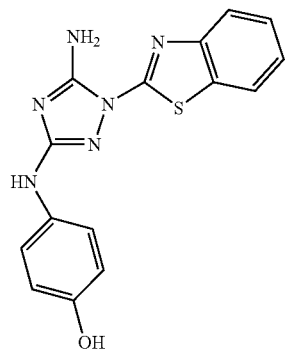
I-752
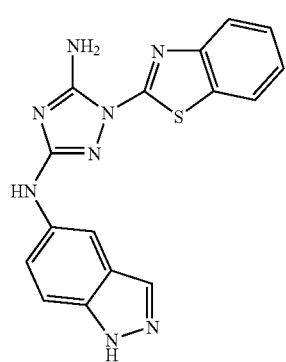
I-756
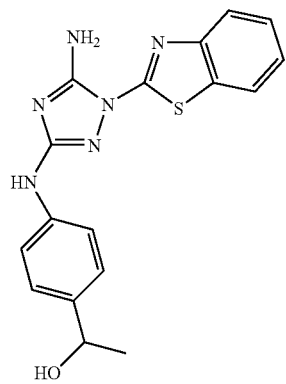
I-757
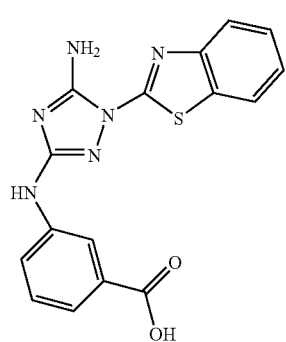
-continued
I-758
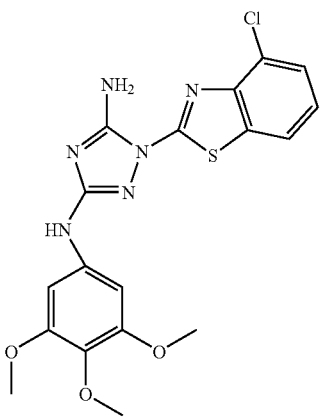
I-759
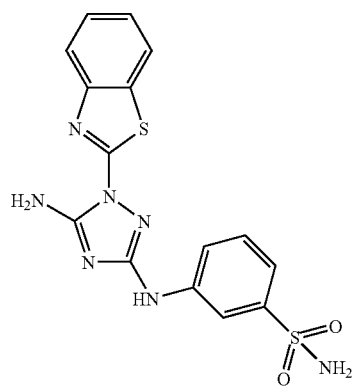
I-760
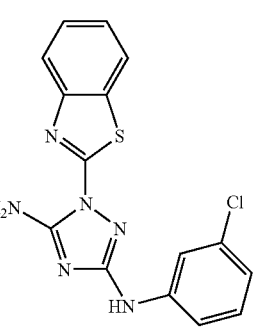
I-761

I-763
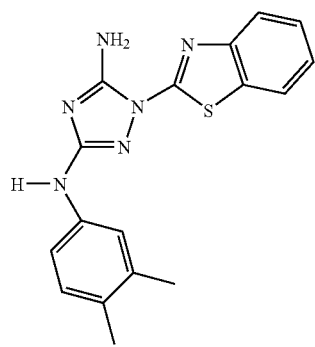
I-764
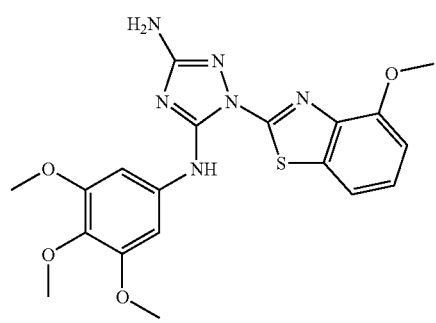
I-765
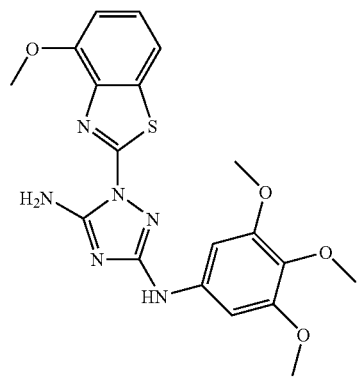
I-766
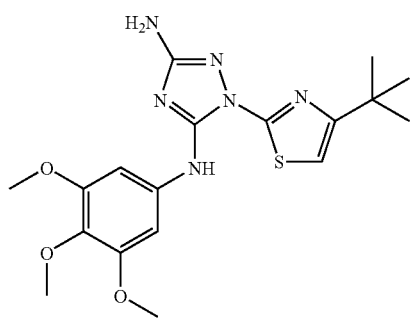
I-767
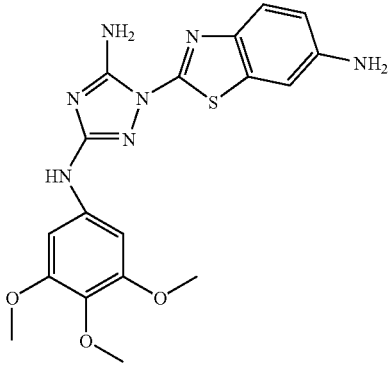
I-768
I-769
I-770
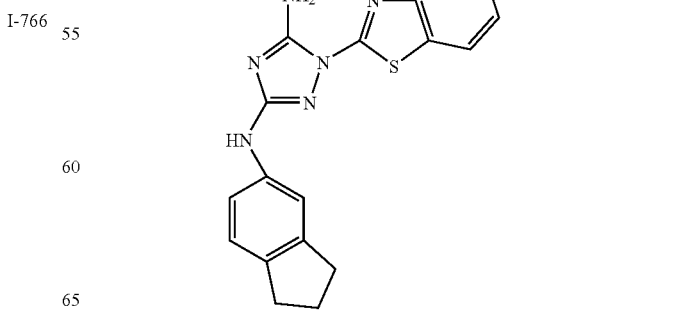

| 781 | 782 |
|---|---|
| -continued | -continued |
I-771
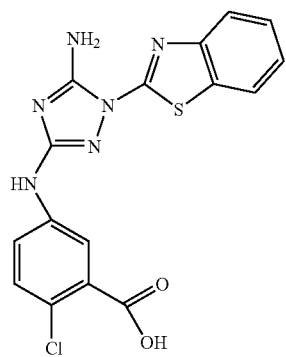
I-776
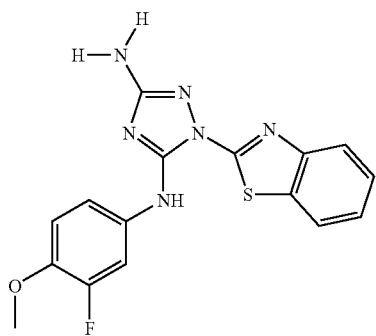
I-772
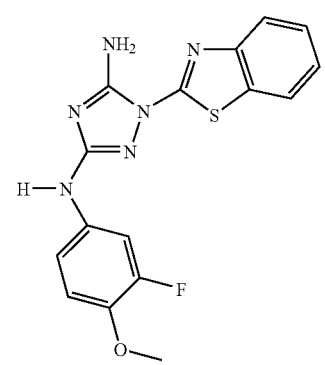
I-777
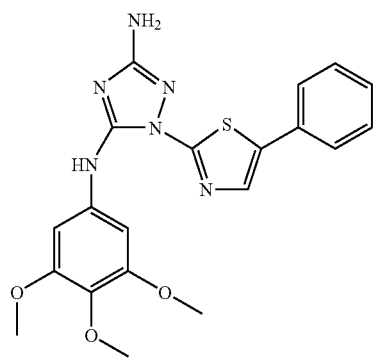
I-774
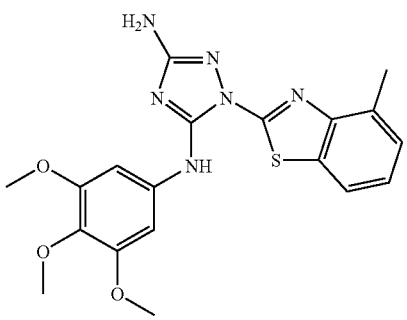
I-778
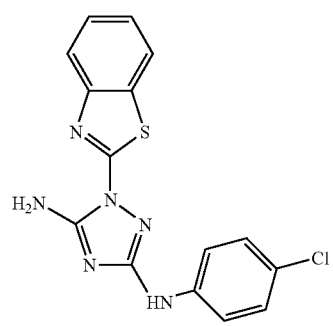
I-775
I-779
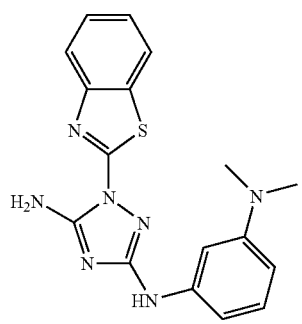

I-780 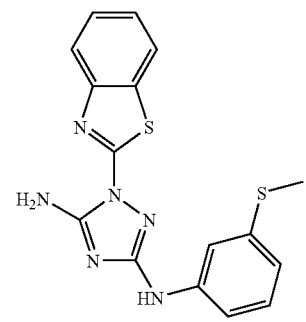
I-781 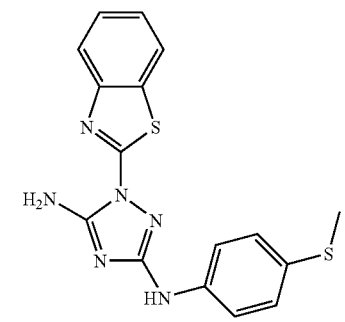
I-782 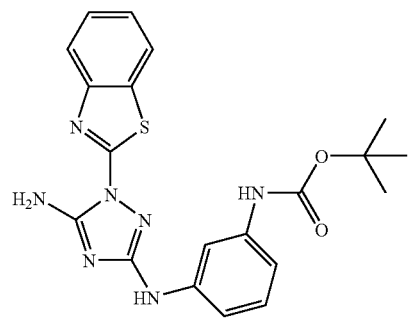
I-784 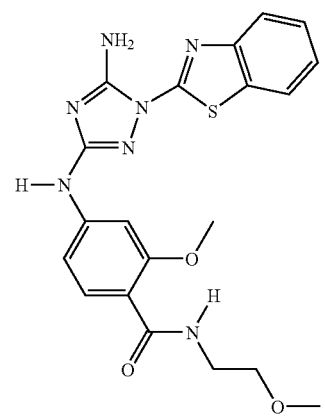
I-785 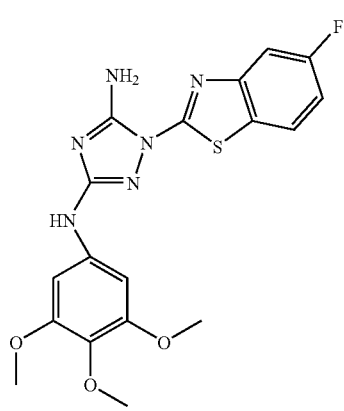
I-786 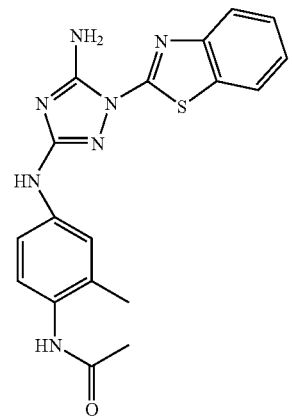
I-788 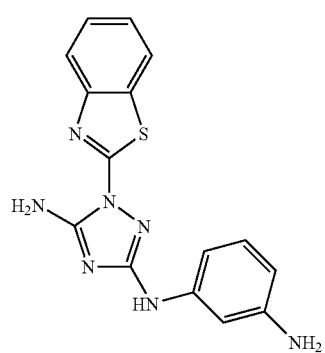
I-789 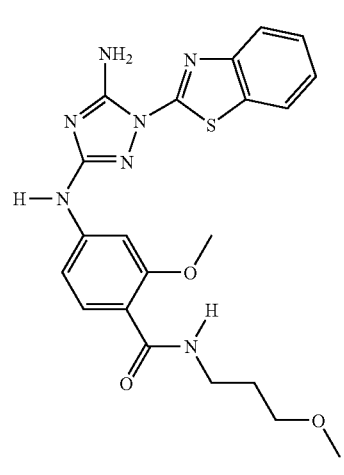

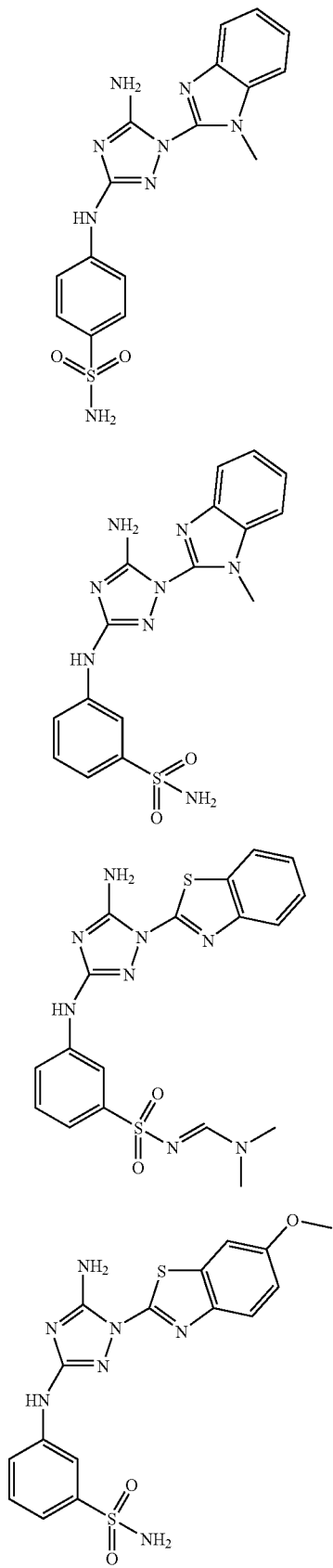
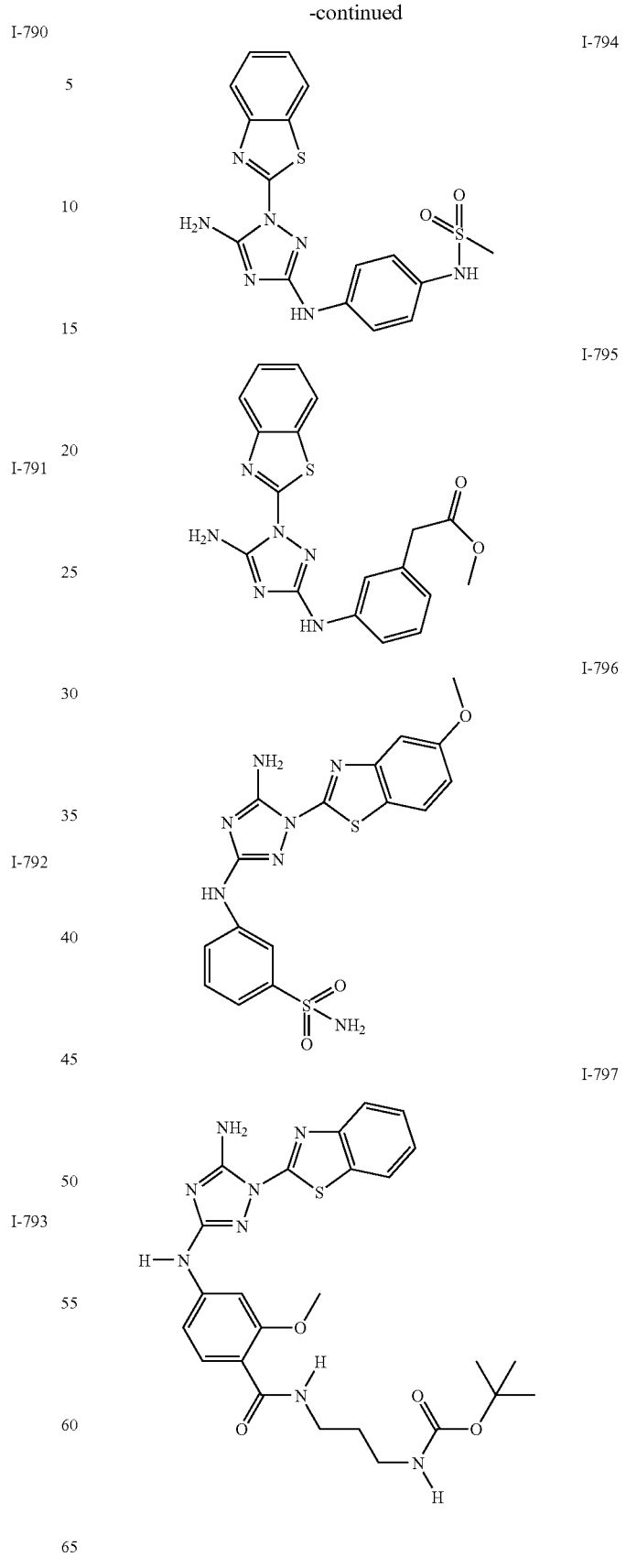

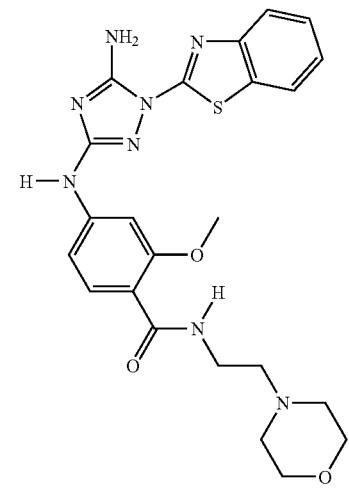
I-798
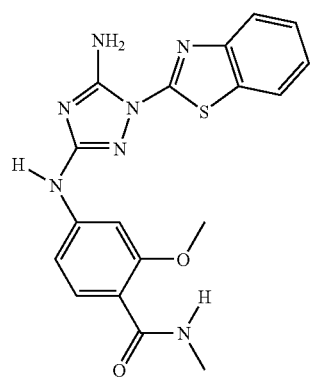
I-801
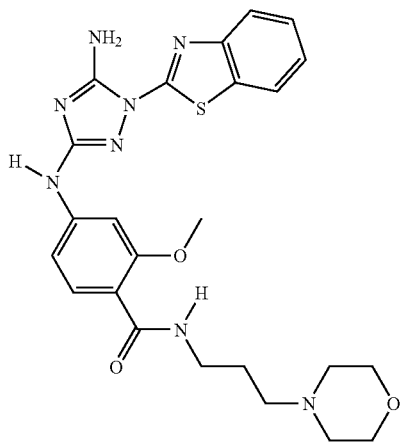
I-799
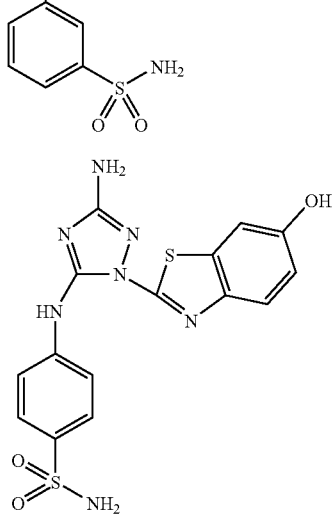
I-802
I-800
I-803
I-805

I-806 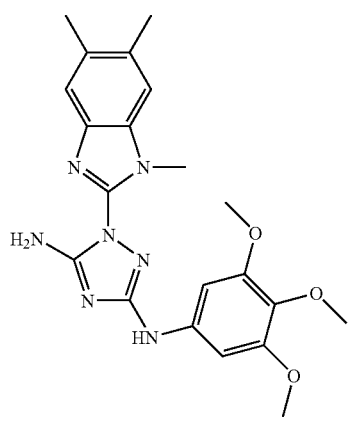
I-807 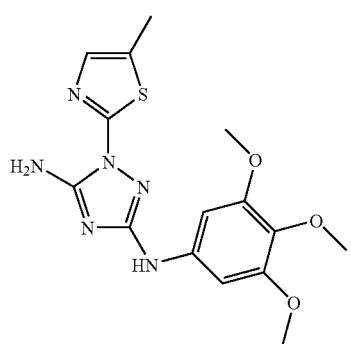
I-808 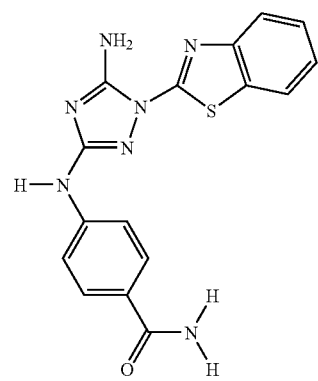
I-809 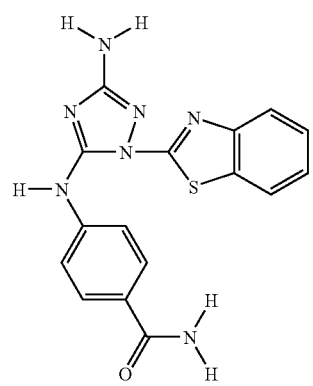
-continued
I-810 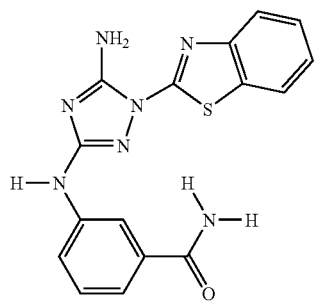
I-811 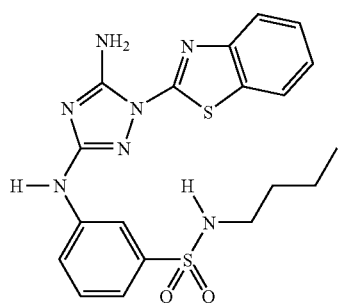
I-813 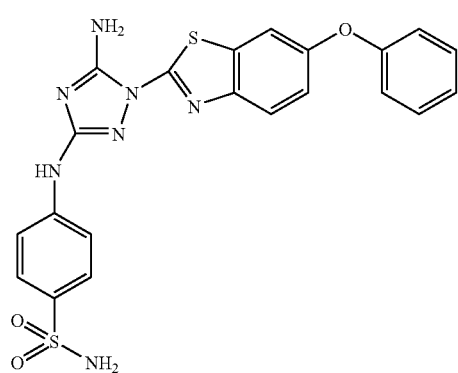
I-814 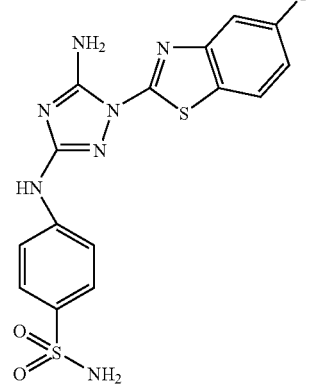

I-815
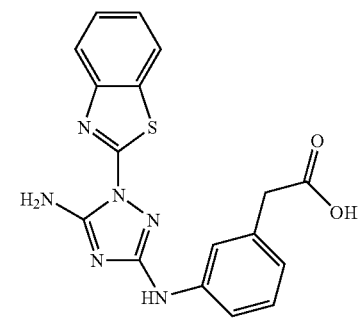
I-816
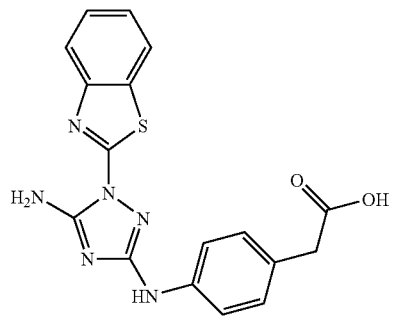
I-817
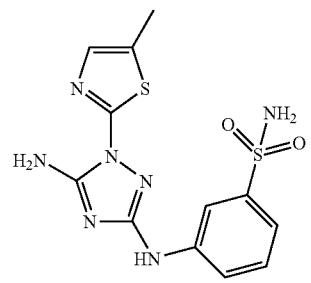
I-818
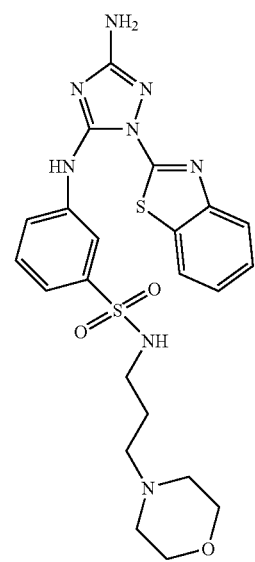
I-819
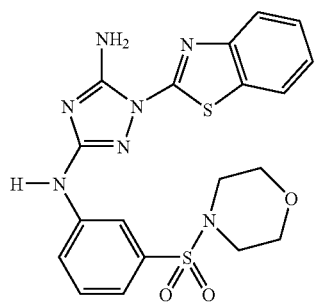
I-820
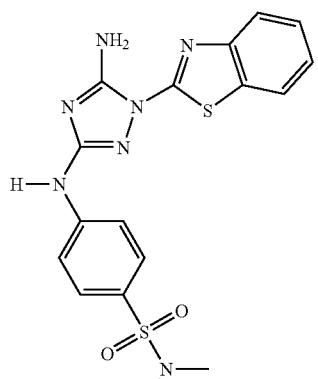
I-821
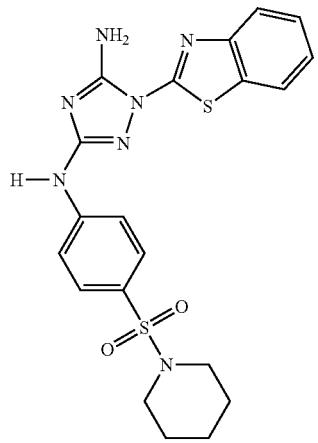
I-822
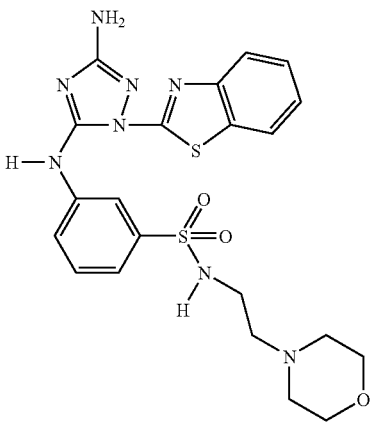

-continued
I-823
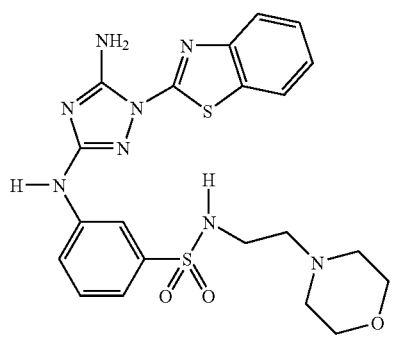
I-824
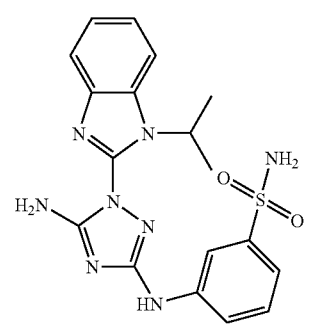
I-827
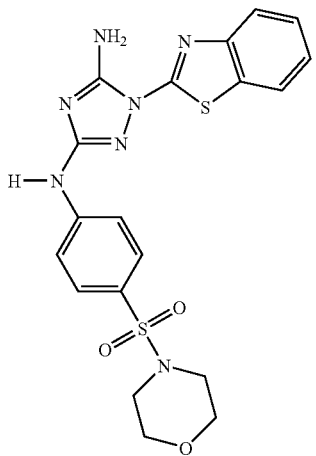
I-828
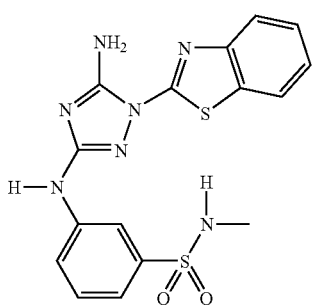
-continued
I-829
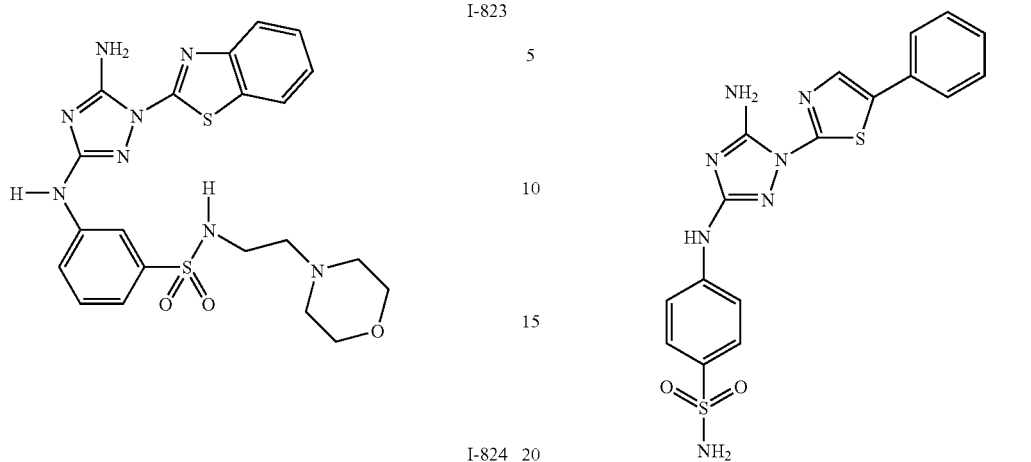
I-830
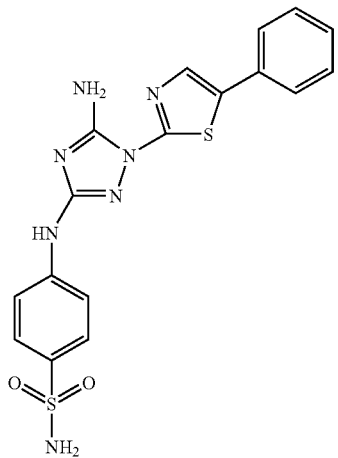
I-831
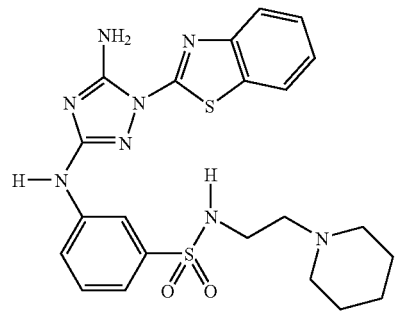
I-832
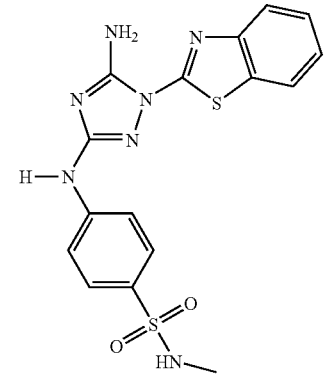

-continued
I-833
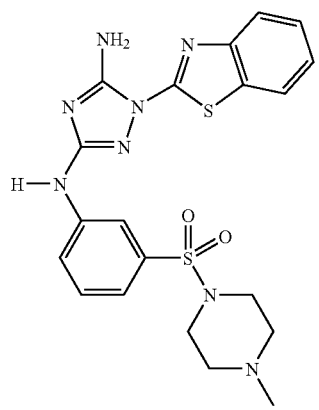
I-834
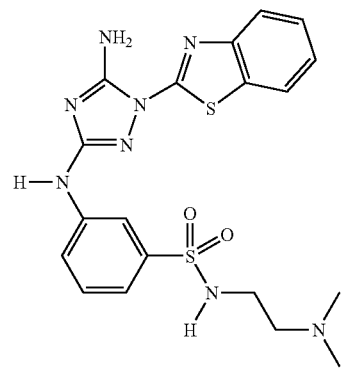
I-835
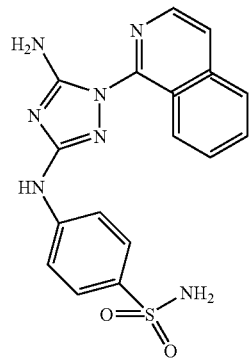
I-836
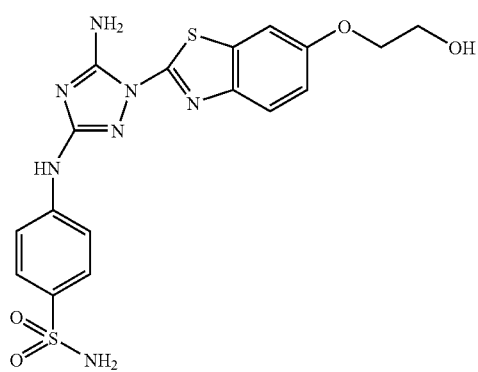
-continued
I-837
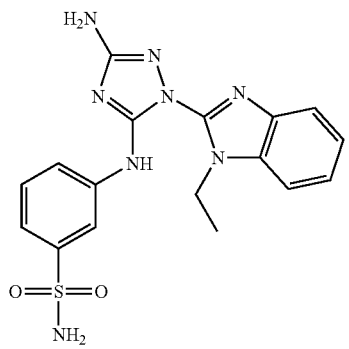
I-838
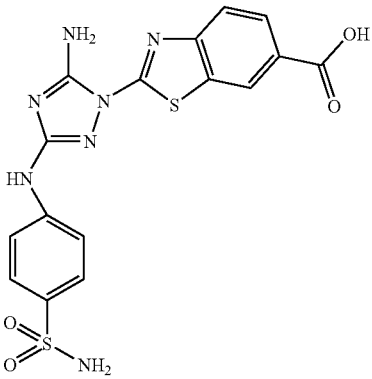
I-839
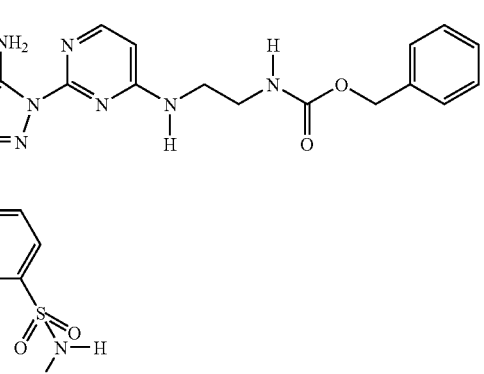
I-840
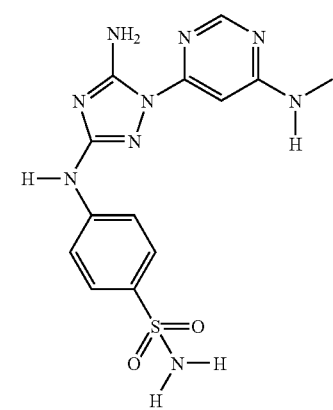

-continued
I-841
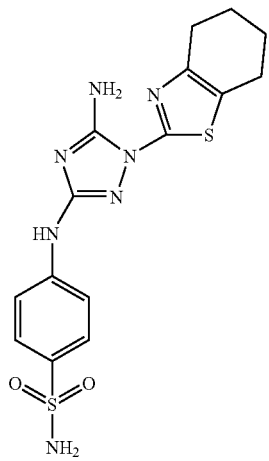
I-843
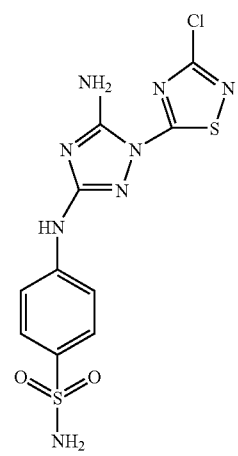
I-844
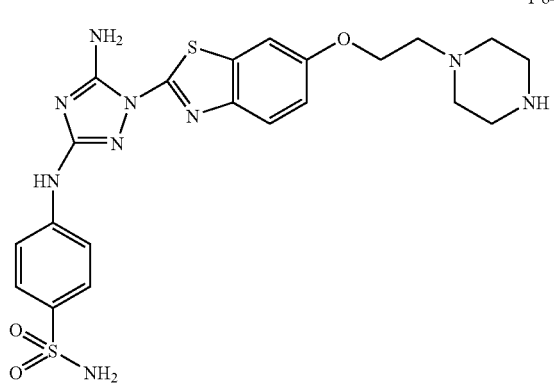
I-845
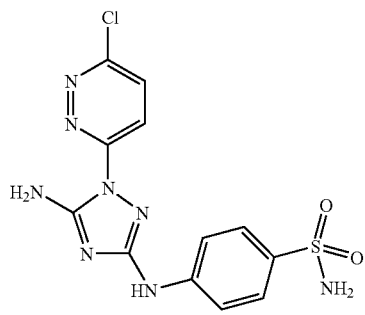
-continued
I-846
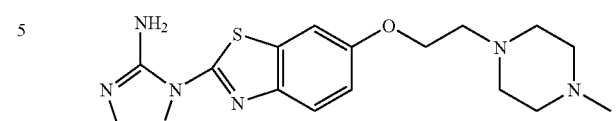
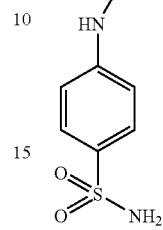
I-847
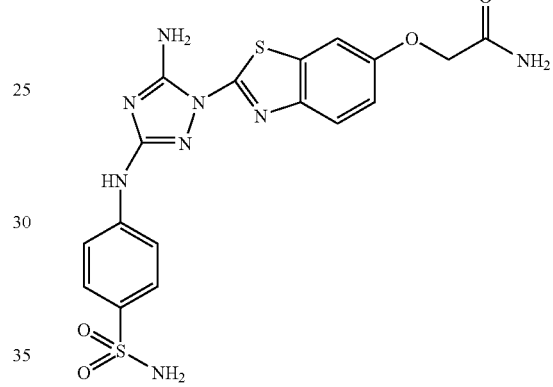
I-848
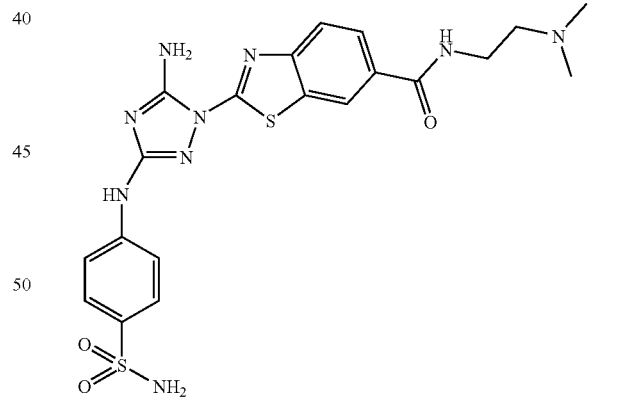
I-849
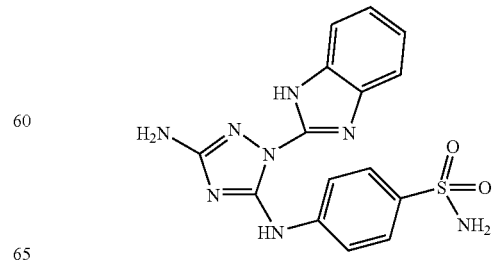

I-850 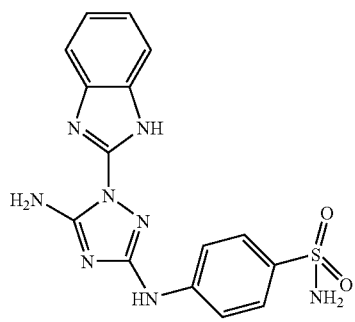
I-851 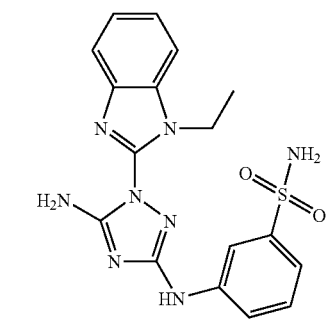
I-852 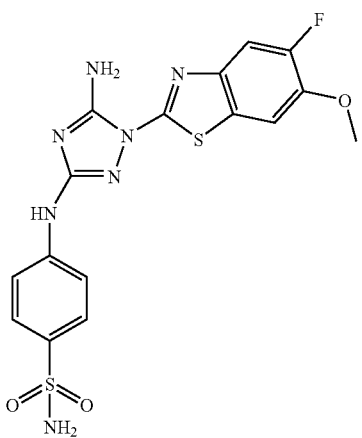
I-853 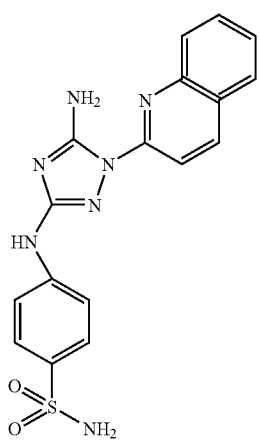
I-854 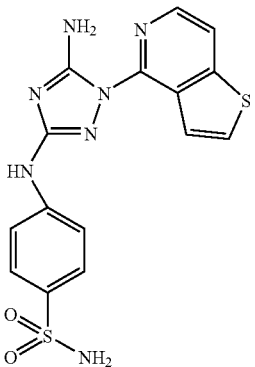
I-855 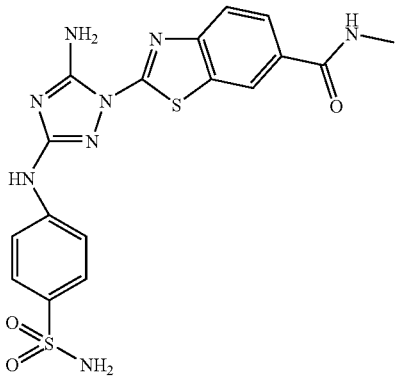
I-856 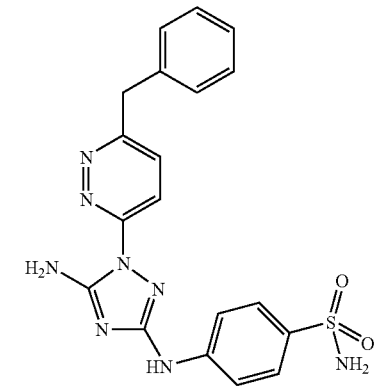
I-857 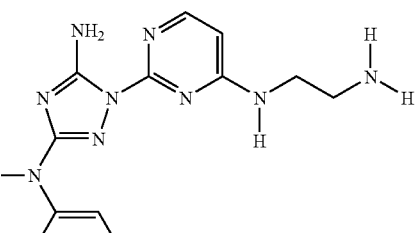

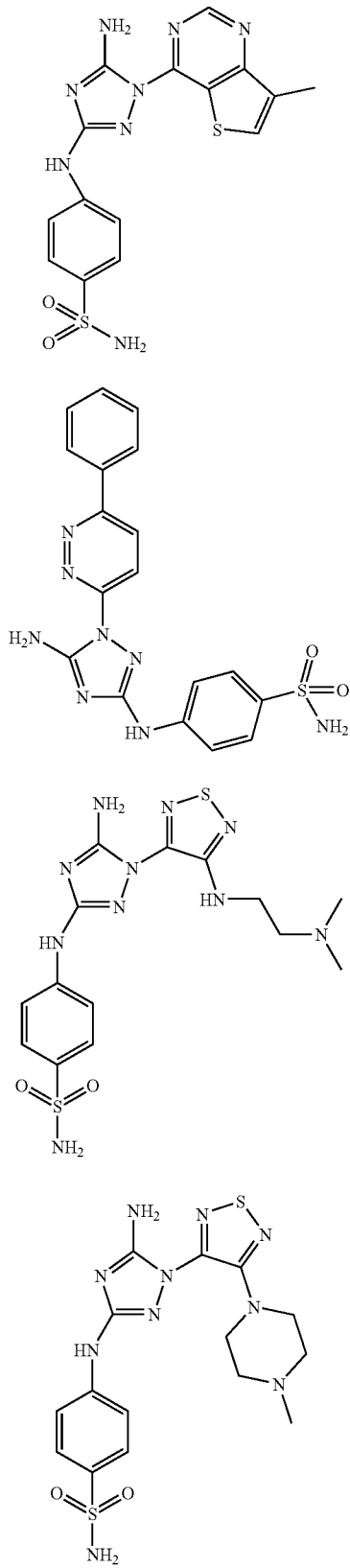

I-866
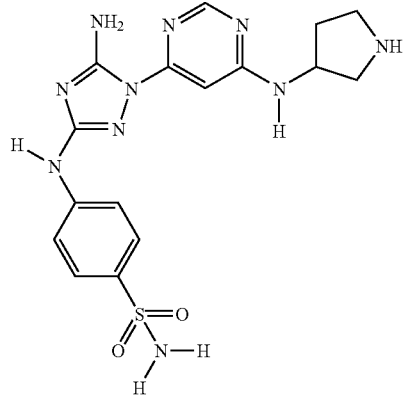
I-869
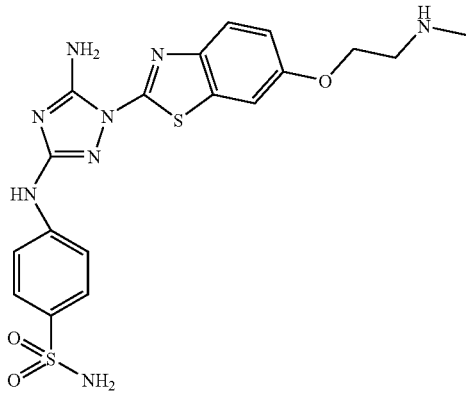
I-867
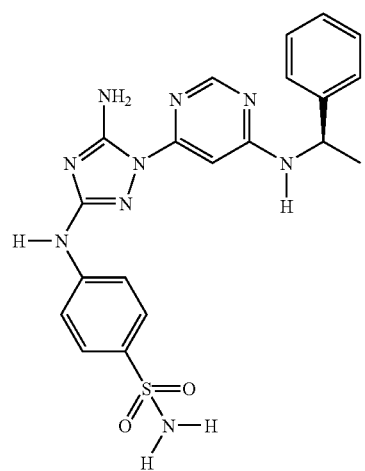
I-870
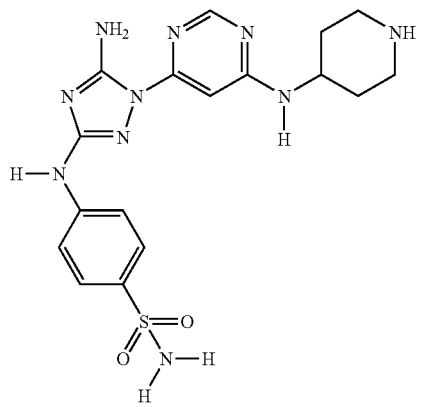
I-868
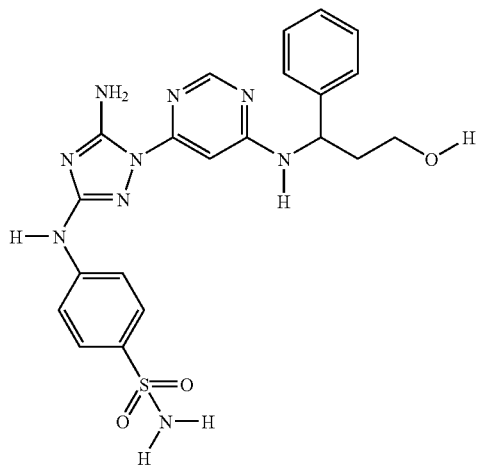
I-871

I-872 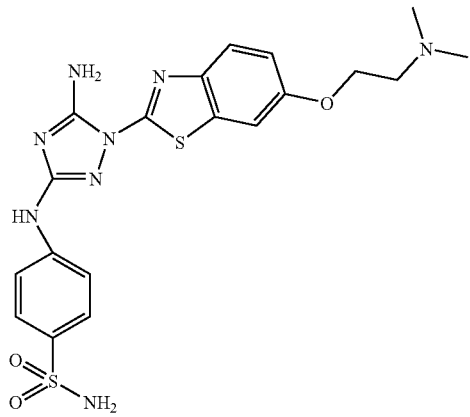
I-873 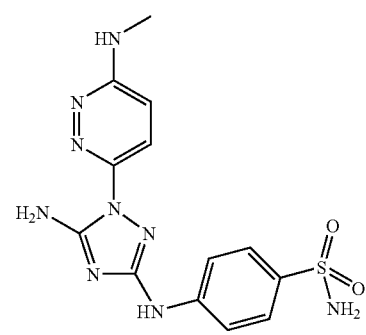
I-874 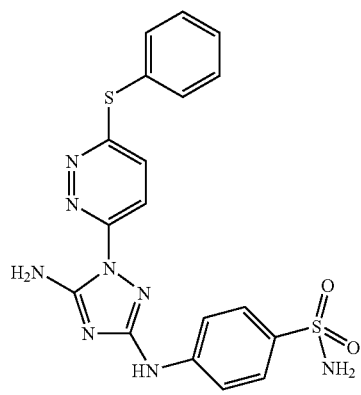
I-875 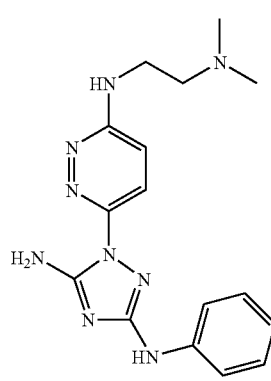
I-876 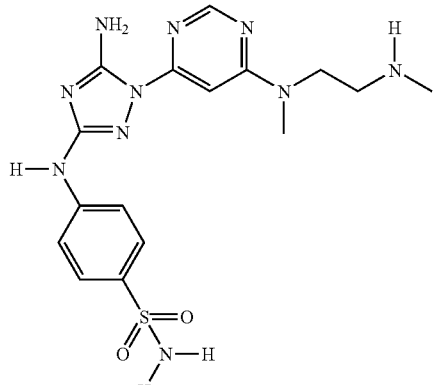
I-877 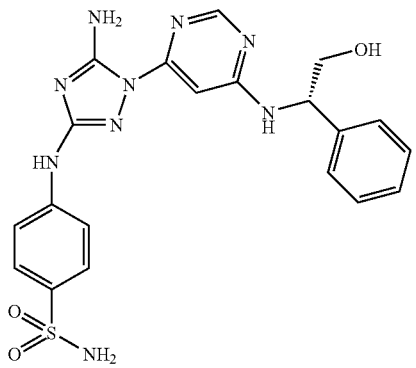
I-878 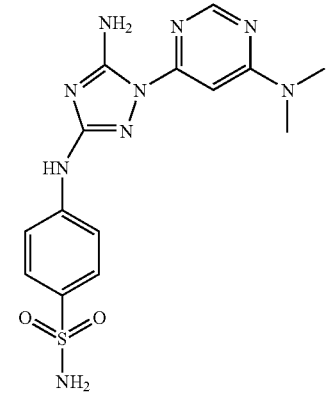
I-879 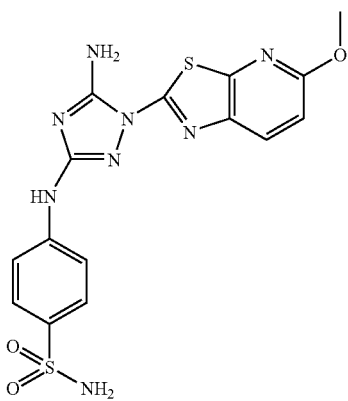

807
-continued
I-880
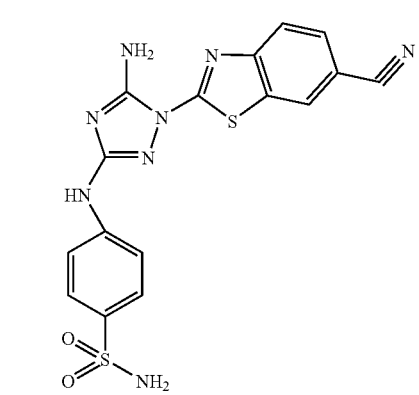
I-881
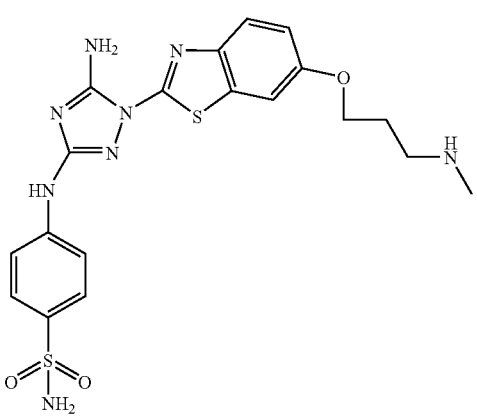
I-882
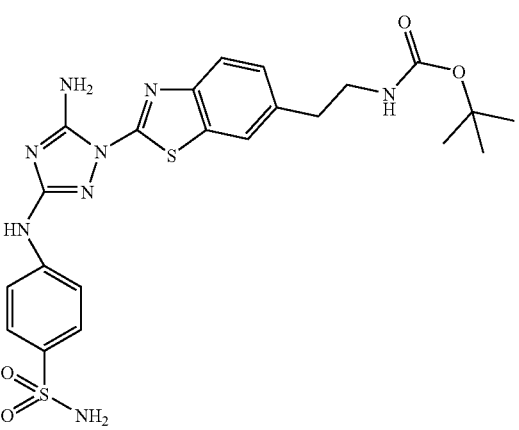
I-883
808
-continued
I-884
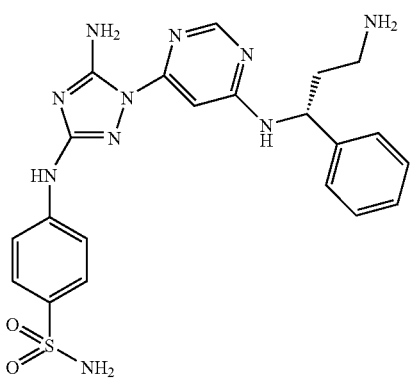
I-885
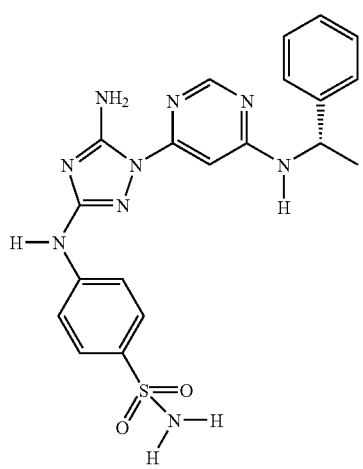
I-892
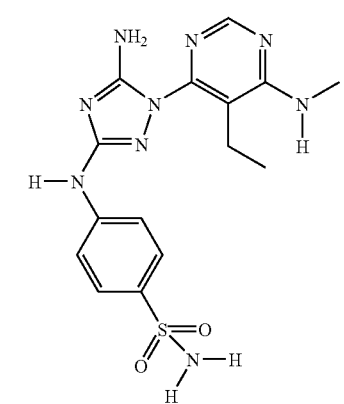

I-893
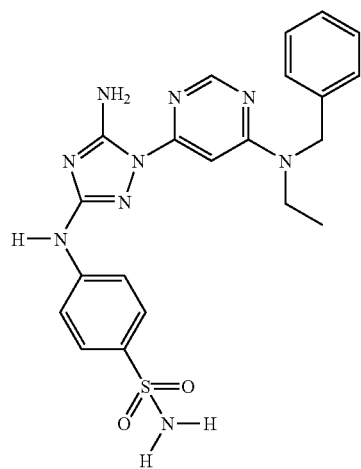
I-894
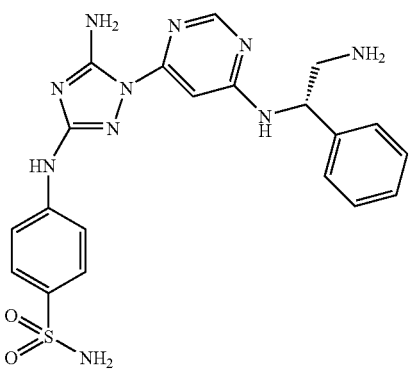
I-895
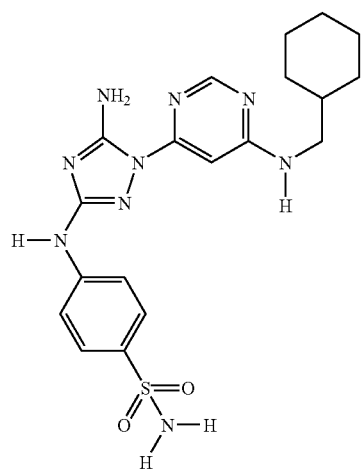
I-896
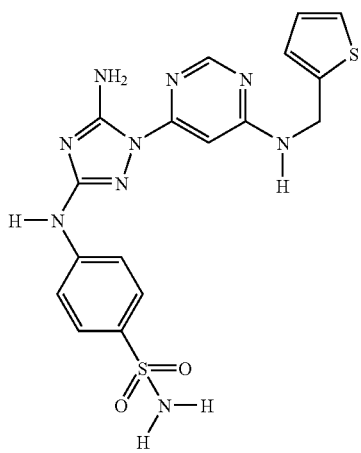
I-897
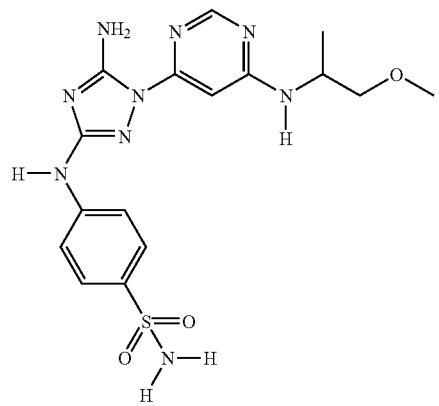
I-898
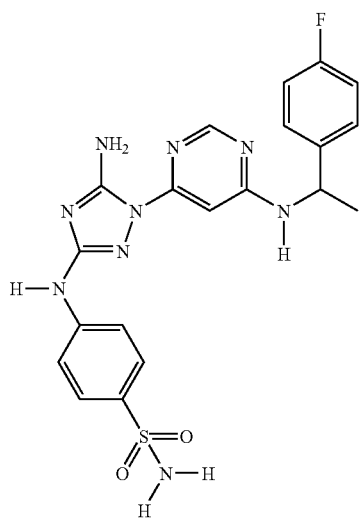

811 812
-continued
I-899
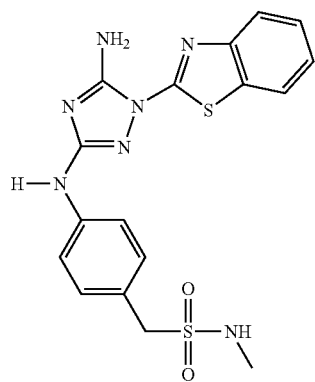
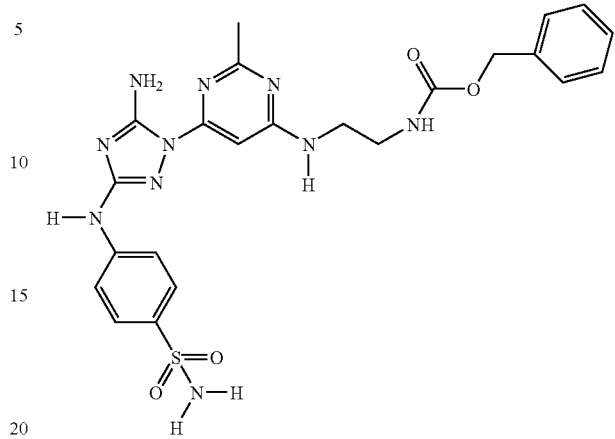
I-900
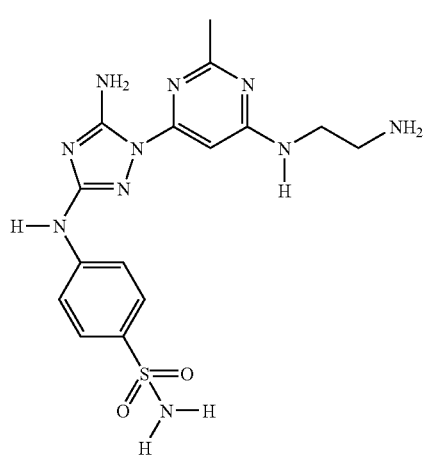
I-903
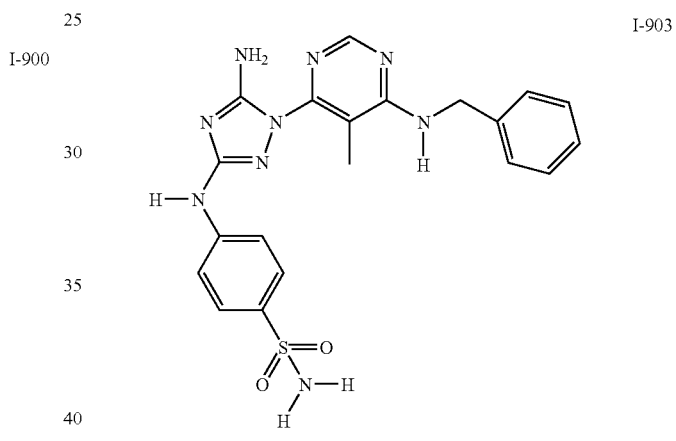
I-901
I-904
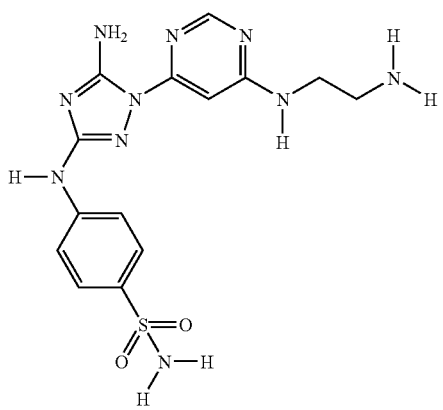

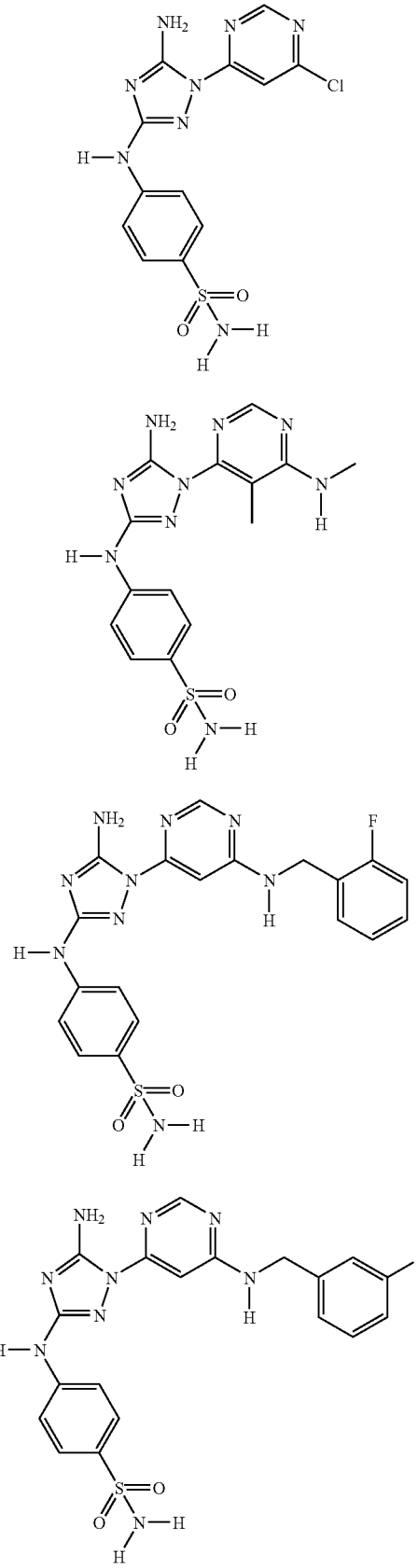
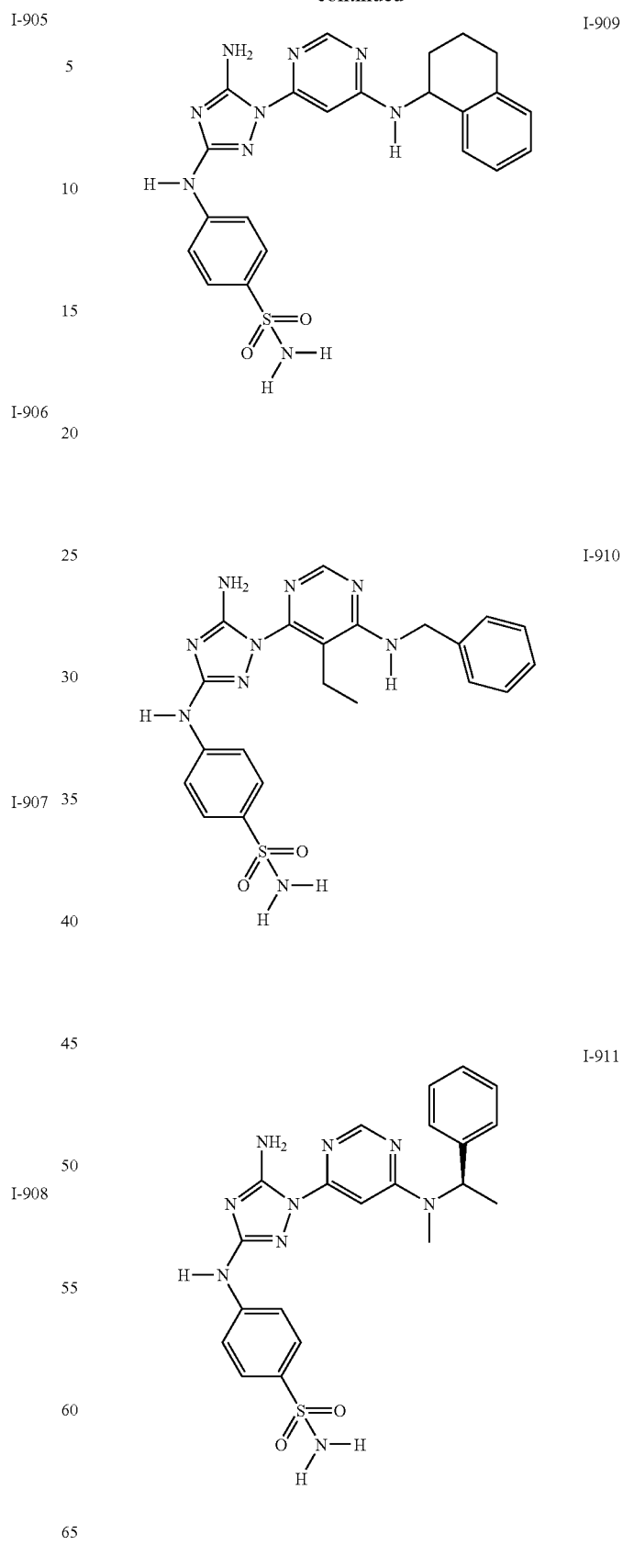

-continued
I-912
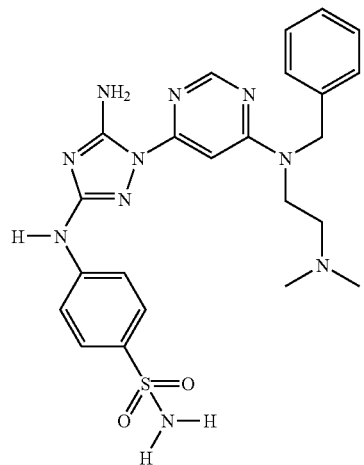
I-913
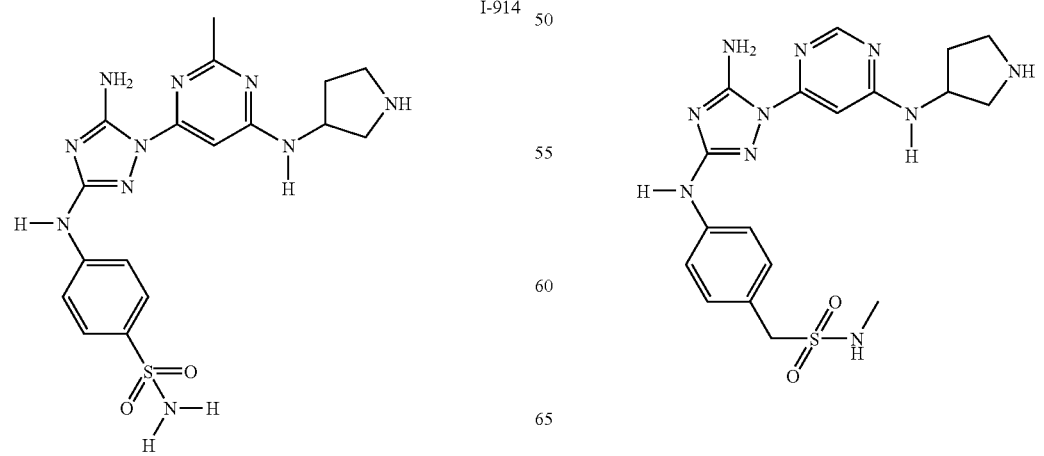
I-914
-continued
I-915
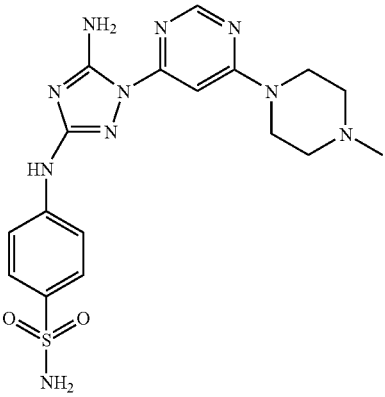
I-916
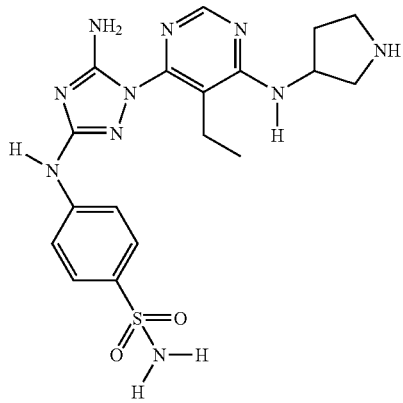
I-917
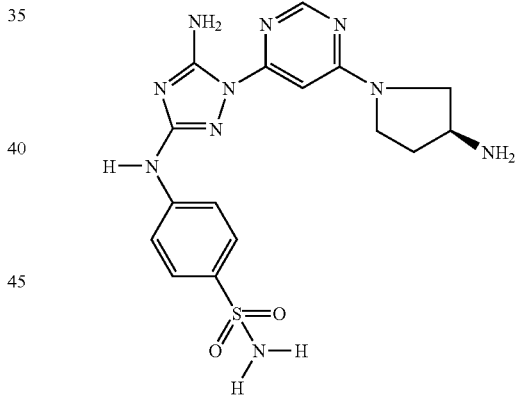
I-918

I-919
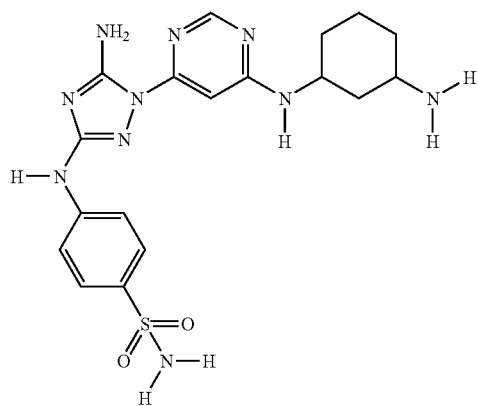
I-922
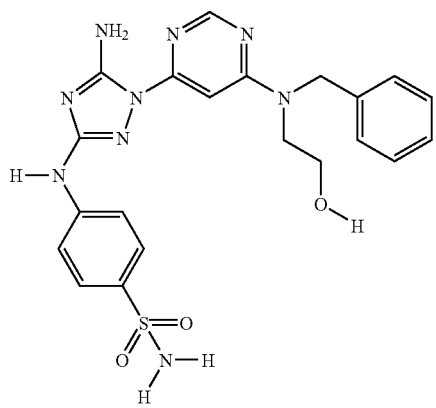
I-920
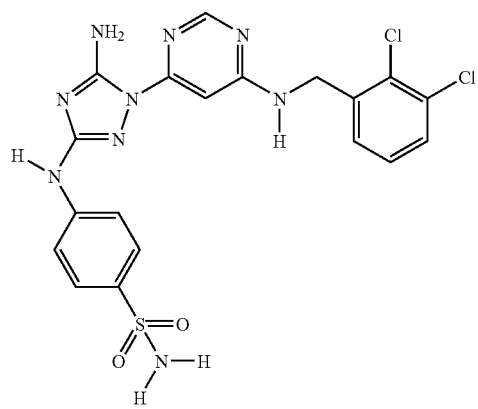
I-923
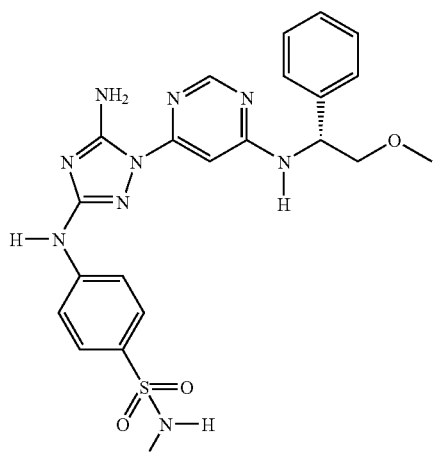
I-921
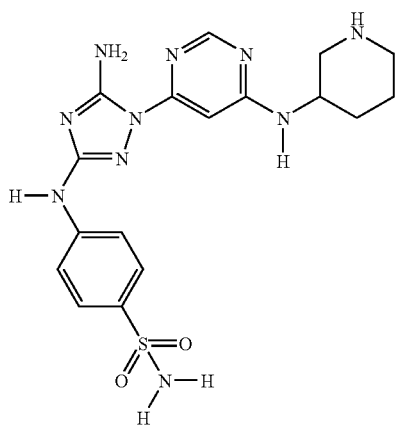
I-924
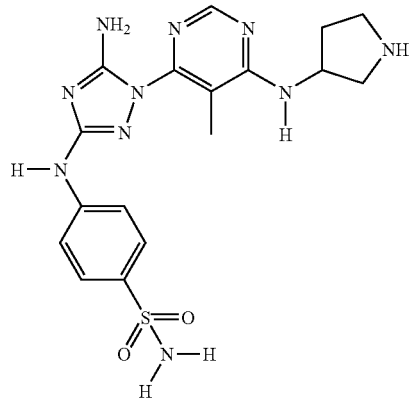

-continued
I-925
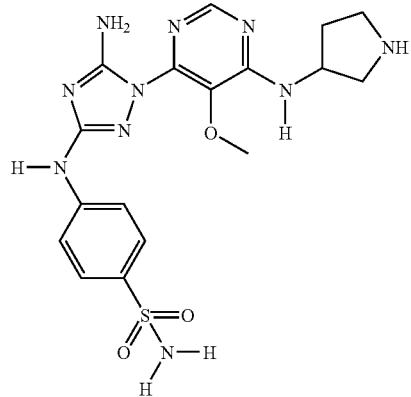
I-926
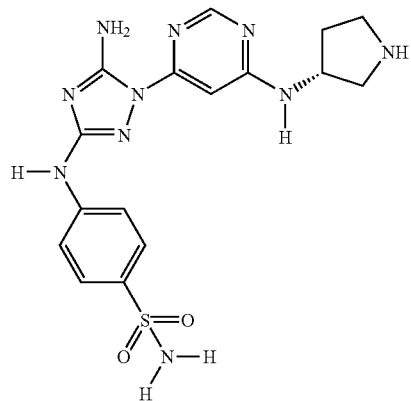
I-927
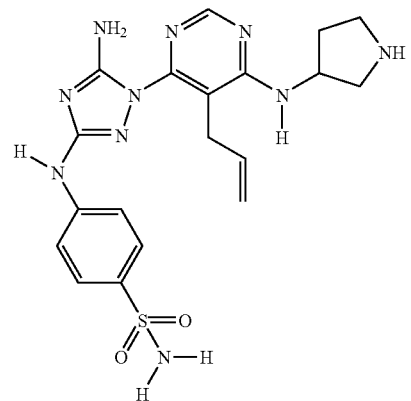
I-928
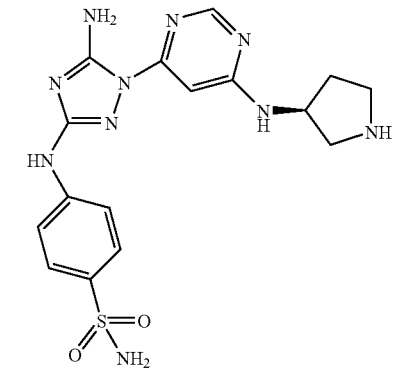
-continued
I-929
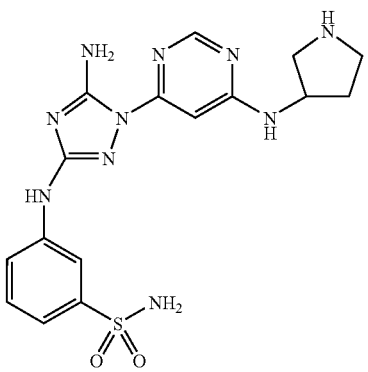
I-930
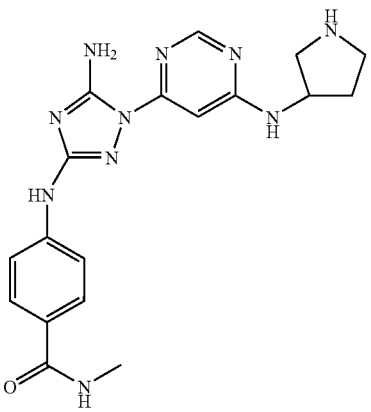
I-931
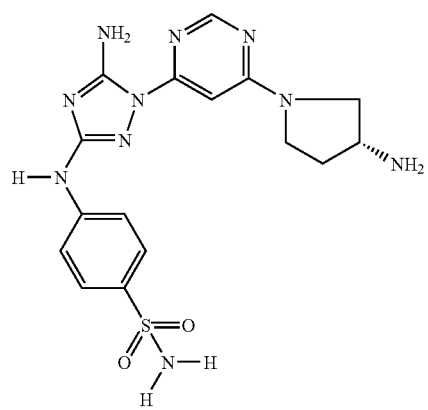
I-932
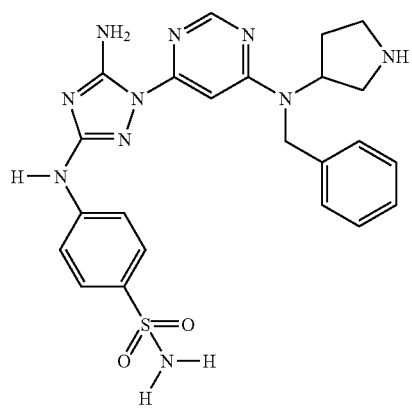

-continued

I-933

I-934

I-935

-continued

I-936

I-937

I-938

823
-continued
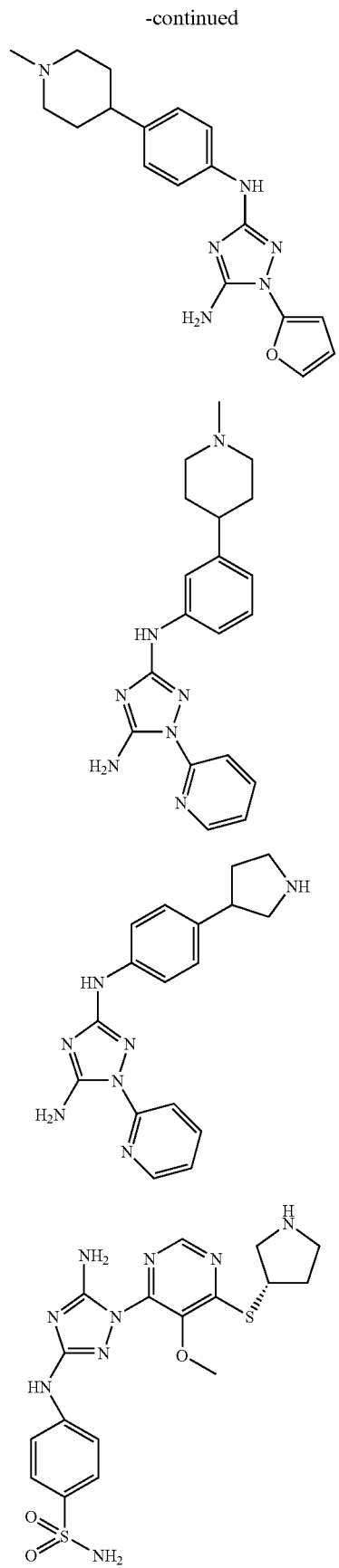
824
-continued
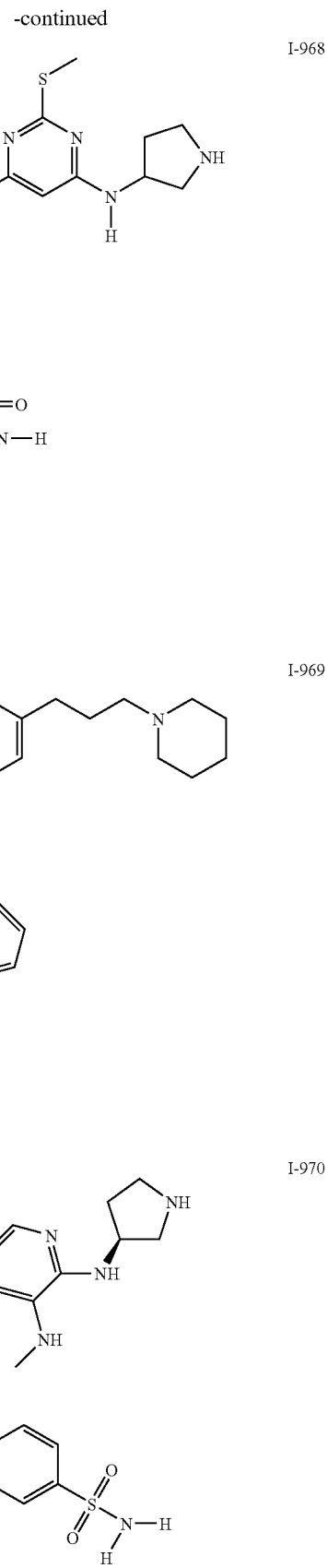

I-971
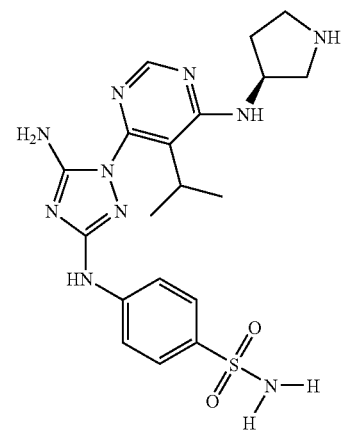
I-975
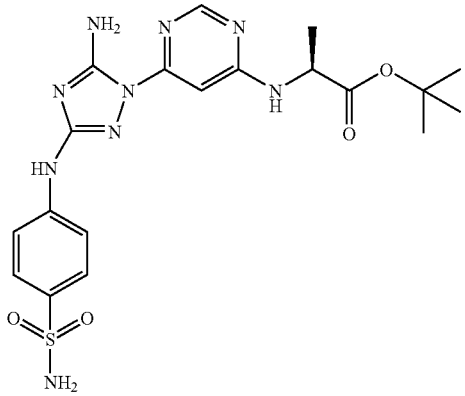
I-972
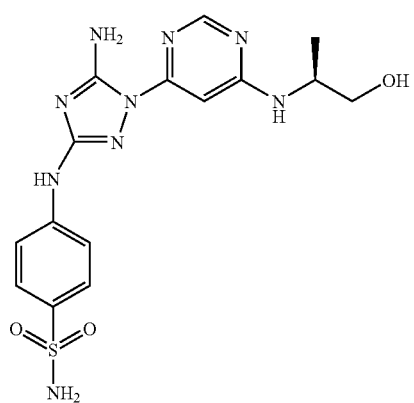
I-973
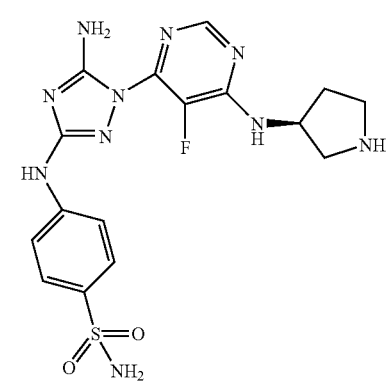
I-976
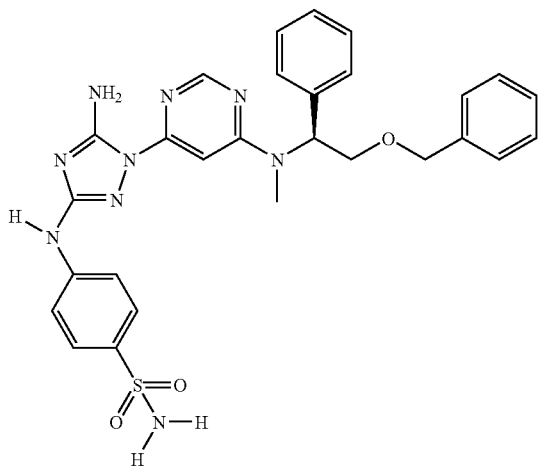
I-974
I-977
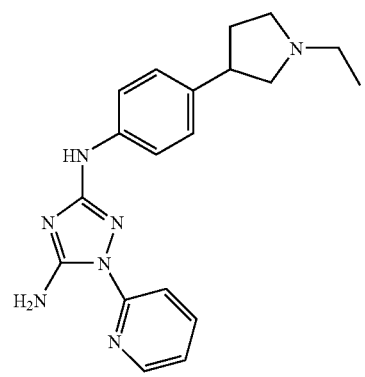

-continued
I-978
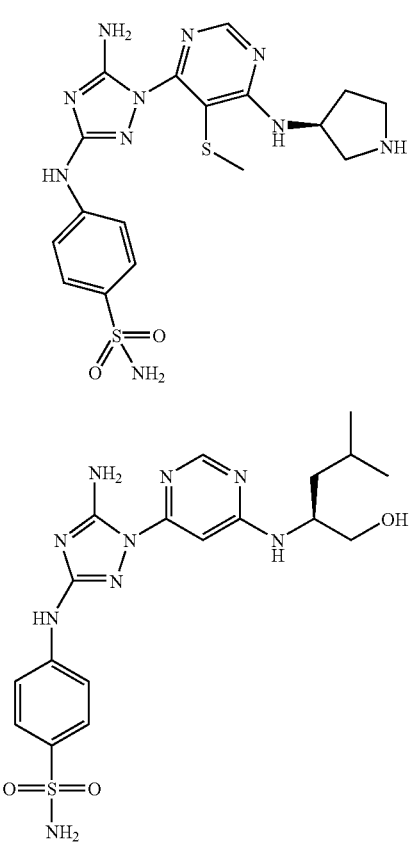
I-979
I-980
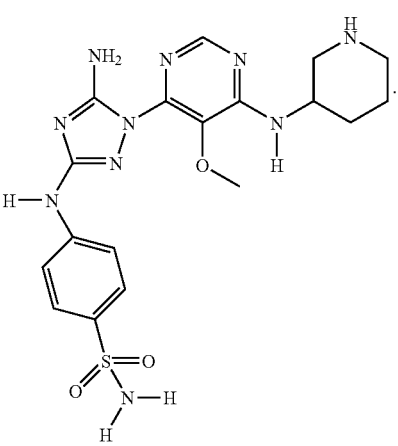
* * * * *